United States Patent
Halperin

(10) Patent No.: US 11,193,123 B2
(45) Date of Patent: Dec. 7, 2021

(54) METHODS AND COMPOSITIONS FOR DIRECTED GENOME EDITING

(71) Applicant: Rewrite Therapeutics, Inc., Emeryville, CA (US)

(72) Inventor: Schaked Omer Halperin, Emeryville, CA (US)

(73) Assignee: Rewrite Therapeutics, Inc., Emeryville, CA (US)

(*) Notice: Subject to any disclaimer, the term of this patent is extended or adjusted under 35 U.S.C. 154(b) by 0 days.

(21) Appl. No.: 17/206,522

(22) Filed: Mar. 19, 2021

(65) Prior Publication Data

US 2021/0292753 A1  Sep. 23, 2021

Related U.S. Application Data

(60) Provisional application No. 63/153,161, filed on Feb. 24, 2021, provisional application No. 63/055,829, filed on Jul. 23, 2020, provisional application No. 62/992,032, filed on Mar. 19, 2020.

(51) Int. Cl.

| | | |
|---|---|---|
| *C12N 15/11* | (2006.01) | |
| *C12N 9/22* | (2006.01) | |
| *C12N 15/90* | (2006.01) | |
| *C12N 9/12* | (2006.01) | |
| *C12N 15/113* | (2010.01) | |
| *C12N 15/52* | (2006.01) | |

(52) U.S. Cl.
CPC ............ *C12N 15/11* (2013.01); *C12N 9/1276* (2013.01); *C12N 9/22* (2013.01); *C12N 15/113* (2013.01); *C12N 15/52* (2013.01); *C12N 15/907* (2013.01); *C12N 2310/122* (2013.01); *C12N 2310/20* (2017.05); *C12N 2310/3519* (2013.01); *C12N 2310/531* (2013.01); *C12N 2800/80* (2013.01)

(58) Field of Classification Search
CPC ........ C12N 15/11; C12N 15/907; C12N 9/22; C12N 2310/20; C12N 2310/122; C12N 2310/3519; C12N 2310/531; C12N 2800/80
See application file for complete search history.

(56) References Cited

U.S. PATENT DOCUMENTS

| 9,161,995 B2 * | 10/2015 | Guschin ................. A61P 19/04 |
| 2002/0192788 A1 | 12/2002 | Ihlenfeldt et al. |
| 2014/0010839 A1 | 1/2014 | Benkirane et al. |
| 2018/0230494 A1 | 8/2018 | Joung et al. |
| 2018/0237770 A1 * | 8/2018 | May ........................ A61P 27/02 |
| 2018/0298414 A1 | 10/2018 | Janulaitis et al. |
| 2018/0313843 A1 | 11/2018 | Keppler et al. |
| 2019/0062409 A1 | 2/2019 | Luban |
| 2019/0350978 A1 | 11/2019 | Beauchesne et al. |
| 2020/0038424 A1 | 2/2020 | Hirano et al. |
| 2020/0248155 A1 | 8/2020 | Halperin |

FOREIGN PATENT DOCUMENTS

| WO | WO-2016196805 A1 | 12/2016 |
| WO | WO-2018049168 A1 | 3/2018 |
| WO | WO-2019051097 A1 | 3/2019 |
| WO | WO-2019070843 A1 | 4/2019 |
| WO | WO-2020012335 A1 | 1/2020 |
| WO | WO-2020047124 A1 | 3/2020 |
| WO | WO-2020051561 A1 | 3/2020 |
| WO | WO-2020191153 A2 | 9/2020 |
| WO | WO-2020191171 A1 | 9/2020 |
| WO | WO-2020191233 A1 | 9/2020 |
| WO | WO-2020191234 A1 | 9/2020 |
| WO | WO-2020191239 A1 | 9/2020 |
| WO | WO-2020191241 A1 | 9/2020 |
| WO | WO-2020191242 A1 | 9/2020 |
| WO | WO-2020191243 A1 | 9/2020 |
| WO | WO-2020191245 A1 | 9/2020 |
| WO | WO-2020191246 A1 | 9/2020 |
| WO | WO-2020191248 A1 | 9/2020 |
| WO | WO-2020191249 A1 | 9/2020 |
| WO | WO-2021188840 | 9/2021 |

OTHER PUBLICATIONS

Anzalone, et al. Search-and-replace genome editing without double-strand breaks or donor DNA. Nature 576, 149-157. (Year: 2019).*
Antczak, et al. New functionality of RNAComposer: application to shape the axis of miR160 precursor structure. Acta Biochim. Pol. 63, 737-744 (2016).
Bajaj, et al. An in vivo genome-wide CRISPR screen identifies the RNA-binding protein Staufen2 as a key regulator of myeloid leukemia. Nature Cancer vol. 1 410-422 (2020).
Co-pending U.S. Appl. No. 17/206,526, inventor Halperin; Schaked Omer, filed Mar. 19, 2021.
Cox, et al. Therapeutic genome editing: prospects and challenges. Nature Medicine vol. 21 121-131 (2015).

(Continued)

*Primary Examiner* — Antonio Galisteo Gonzalez
*Assistant Examiner* — Khaleda B Hasan
(74) *Attorney, Agent, or Firm* — Wilson Sonsini Goodrich & Rosati

(57) ABSTRACT

Provided herein are compositions and methods for increasing editing efficiency of a target nucleic acid. A composition may comprise a guide nucleic acid, a Cas9 nickase, or a reverse transcriptase. The reverse transcriptase may be fused to the Cas9 nickase. The reverse transcriptase may heterodimerize with the Cas9 nickase. The reverse transcriptase may bind to a guide nucleic acid. The reverse transcriptase may be engineered to increase processivity. The guide nucleic acid may be engineered to facilitate synthesis or editing of a sequence. The guide nucleic acid, Cas9 nickase, and reverse transcriptase may be engineered to fit within AAV vectors. The guide nucleic acid may comprise a region that binds to another region on the guide nucleic acid to improve gene editing.

28 Claims, 48 Drawing Sheets

Specification includes a Sequence Listing.

(56) References Cited

OTHER PUBLICATIONS

Gaudelli, et al. Programmable base editing of A•T to G•C in genomic DNA without DNA cleavage. Nature 551, 464-471 (2017).
Grünewald, et al. Transcriptome-wide off-target RNA editing induced by CRISPR-guided DNA base editors. Nature 569, 433-437 (2019).
Haapaniemi, et al. CRISPR-Cas9 genome editing induces a p53-mediated DNA damage response. Nat. Med. 24, 927-930 (2018).
Hrecka, et al. Vpx relieves inhibition of HIV-1 infection of macrophages mediated by the SAMHD1 protein. Nature 474, 658-661 (2011).
Ihry, et al. p53 inhibits CRISPR-Cas9 engineering in human pluripotent stem cells. Nat. Med. 24, 939-946 (2018).
Jinek, et al. A programmable dual-RNA-guided DNA endonuclease in adaptive bacterial immunity. Science 337, 816-821 (2012).
Komor, et al. Programmable editing of a target base in genomic DNA without double-stranded DNA cleavage. Nature 533, 420-424 (2016).
Ledford, H. Crispr Editing Wreaks Chromosomal Mayhem in Human Embryos. Nature. vol. 583. (Jul. 2, 2020): 17-18.
Ledford, H. Crispr gene editing in human embryos wreaks chromosomal mayhem. Nature 583, 17-18 (2020).
Lemmon, et al. Rapid improvement of domestication traits in an orphan crop by genome editing. Nature Plants vol. 4 766-770 (2018).
Maeder, et al. Development of a gene-editing approach to restore vision loss in Leber congenital amaurosis type 10. Nat. Med. 25, 229-233 (2019).
Mali, et al. RNA-guided human genome engineering via Cas9. Science 339, 823-826 (2013).
Middleton, et al. Elexacaftor-Tezacaftor-lvacaftor for Cystic Fibrosis with a Single Phe508del Allele. New England Journal of Medicine vol. 381 1809-1819 (2019).
Ostedgaard, et al. CFTR with a partially deleted R domain corrects the cystic fibrosis chloride transport defect in human airway epithelia in vitro and in mouse nasal mucosa in vivo. Proc. Natl. Acad. Sci. U. S. A. 99, 3093-3098 (2002).
Palikša, et al. Decreased Km to dNTPs is an essential M-MuLV reverse transcriptase adoption required to perform efficient cDNA synthesis in One-Step RT-PCR assay. Protein Eng. Des. Sel. 31, 79-89 (2018).
Xie, et al. Effective and accurate gene silencing by a recombinant AAV-compatible microRNA scaffold.Molecular Therapy 28.2 (2020): 422-430.
Yan, et al. CyclinA2-Cyclin-dependent Kinase Regulates SAMHD1 Protein Phosphohydrolase Domain. Journal of Biological Chemistry vol. 290 13279-13292 (2015).
Yu, et al. The efficiency of Vpx-mediated SAMHD1 antagonism does not correlate with the potency of viral control in HIV-2-infected individuals. Retrovirology 10, 27 (2013).
Zuo, et al. Cytosine base editor generates substantial off-target single-nucleotide variants in mouse embryos. Science 364, 289-292 (2019).
Anzalone, et al. Search-and-replace genome editing without double-strand breaks or donor DNA. Nature 576, 149-157 (2019).
Paliksa et al. Decreased Km to dNTPs is an essential M-MuLV reverse transcriptase adoption required to perform efficient cDNA synthesis in One-Step RT-POR assay, Protein Engineering Design & Selection, Mar. 15, 2018 (Mar. 15, 2018), vol. 31, Iss. 3, pp. 79-89.
PCT International Search Report and Written Opinion, PCT Application No. PCT/US21/23041, dated Jul. 13, 2021, 21 pages.
St. Gelais et al. SAMHD1 restricts HIV-1 infection in dendritic cells (DCs) by dNTP depletion, but its expression in DCs and primary CD4+ T-lymphocytes cannot be upregulated by interferons, Retrovirology, Dec. 11, 2012 (Dec. 11, 2012), vol. 9:105, pp. 1-15.
Zhang et al. Conserved Herpesvirus Protein Kinases Target SAMHD1 to Facilitate Virus Replication, Cell Reports, Jul. 9, 2019 (Jul. 9, 2019), vol. 28, Iss. 2, pp. 449-459.
Ribeiro, et al. Protein Engineering Strategies to Expand CRISPR-Cas9 Applications. International Journal of Genomics, vol. 2018, Aug. 2, 2018, pp. 1-12.
Silas, et al. Direct CRISPR spacer acquisition from RNA by a natural reverse transcriptase-Cas1 fusion protein. Science, New York, N.Y., vol. 351, issue 6276, Feb. 26, 2016.
Toro, et al. The Reverse Transcriptases Associated with CRISPR-Cas Systems. Scientific reports, I vol. 7, issue 7089, Aug. 2, 2017.
U.S. Appl. No. 17/206,526 Office Action dated Sep. 2, 2021.

* cited by examiner

FIG. 4A
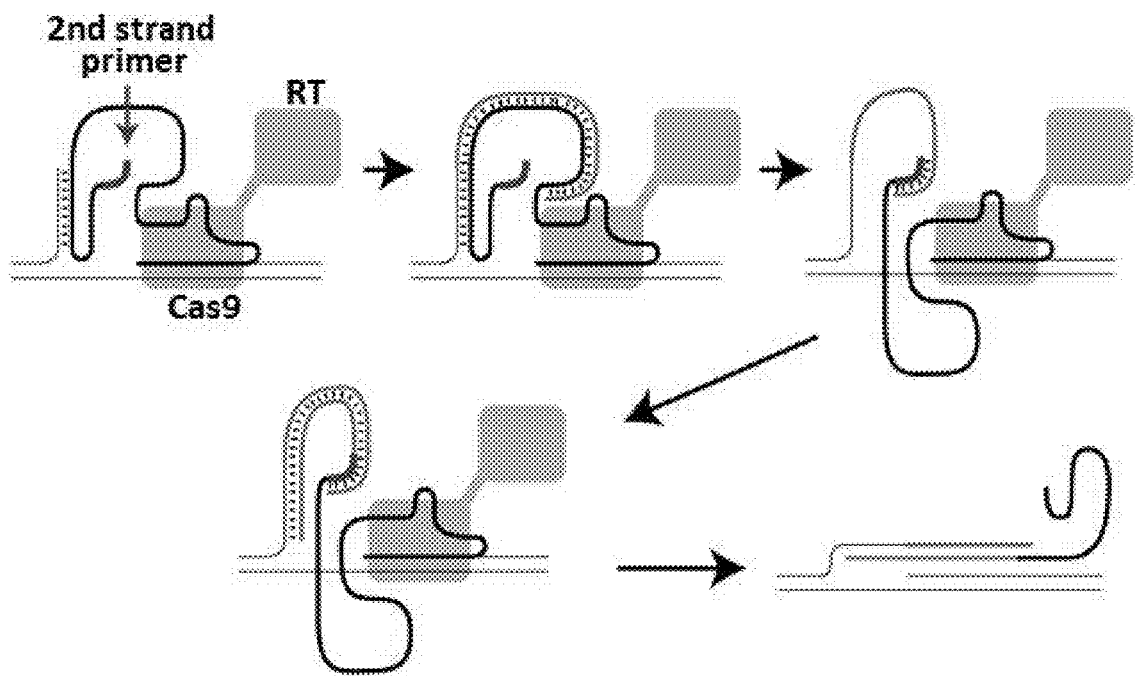
FIG. 4B
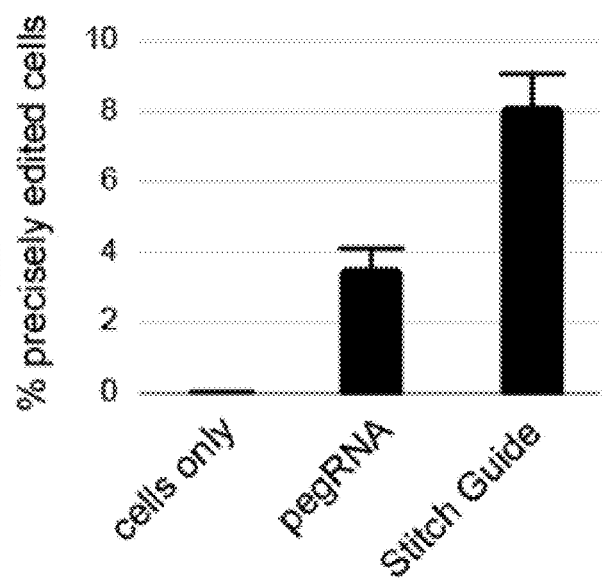

| | Two guides each generate a strand with the edit | Second guide nicks opposite strand |
|---|---|---|
| Two Single Guides | 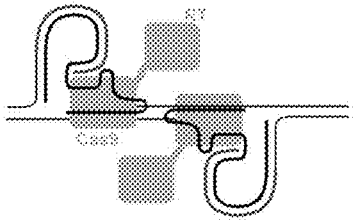 | 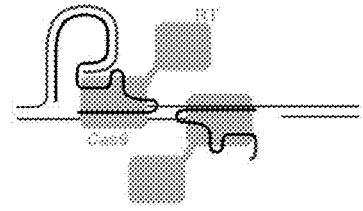 |
| Dual Guide Complex | 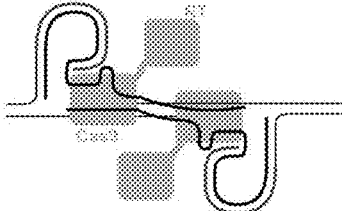 | 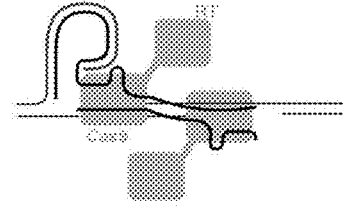 |
FIG. 6

FIG. 25B

| SEQ ID NO | Sequence | % | Mutation |
|---|---|---|---|
| 120 | CTCTGGGCAGTGCGAGTGCAGTGC...AAAAAGAAGC--CAAAAGCACTTGTGACACCTGCAG | 73.5% | (wt) |
| 121 | CTCTGGGCAGTGCGAGTGCAGTGC...AAAAAGAAGC--AAAAAGCACTTCAGTGACACCTGCAG | 18.6% | (2298T>C, 2316C>A) |
| 122 | CTCTGGGCAGTGCGAGTGCAGTGC...AAAAAGAAGC--CAAAAGCACTTCAGTGACACCTGCAG | 3.9% | (2316C>T) |
| 123 | CTCTGGGCAGTGCCAGTGCAGTGC...AAAAAGAAGC--CAAAAGCACTTCAGTGACACCTGCAG | 3.2% | (2298T>C) |
| 124 | CTCTGGGCAGTGCCAGTGCAGTGC...AAAAAGAAGCCAAAAAGCACTTCAGTGACACCTGCAG | 0.4% | (2298T>C, 2315insA, 2316C>A) |
| 125 | CTCTGGGCAGTGCCAGTGCAGTGC...AAAAAGAAGCCAAAAAGCACTTCAGTGACACCTGCAG | 0.2% | (2298T>C, 2304insA, 2316C>A) |

2298T>C    2316C>A    spacer

FIG. 25C genome sequence with PAM bolded (SEQ ID NO: 126) CTCTGGGCAGTGCGAGTGCAGTGTCAAAAAGAAGCCAAAGGACTTCAGTGTGACACCTGCAG
                                                                                                                                              spacer 2316C>A is a silent mutation that was encoded in the RTT to disrupt the PAM site (SEQ ID NO: 127) CTCTGGGCAGTGCGAGTGCAGTGTCAAAAAGAAGCTAAAGGACTTCAGTGTGACACCTGCAG
                                   2298T>C                          2316C>A                          spacer FIG. 27
PE2: nCas9-mlvRT5M
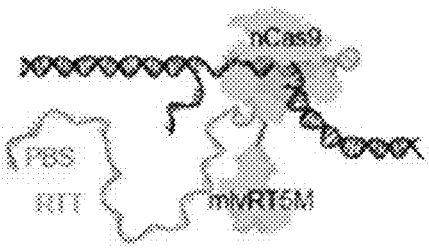
Split PE2: nCas9(1-573)-NpuN + NpuC-nCas9(574-1368)-mlvRT5M
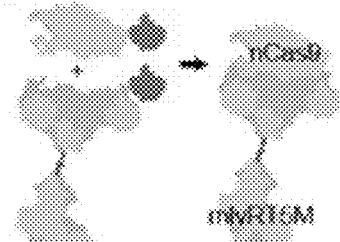
RW1M: nCas9 + MBP-mlvRT5M
RW1L: nCas9-LZ1 + LZ2-mlvRT5M
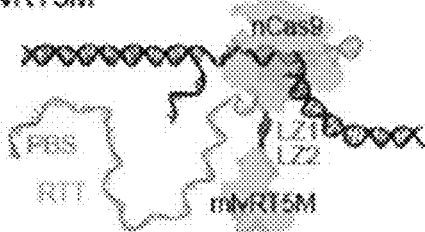
RW1I: nCas9(1-1172)-NpuN + NpuC-nCas9(1173-1368; S1173C)-mlvRT5M
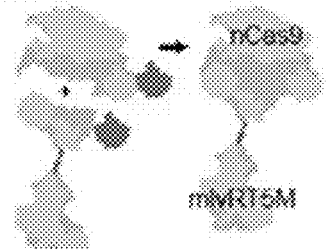
RW1N: nCas9 + mlvRT5M

Ush2a editing with GGTGTCACACACTGAAGTCCTT (SEQ ID NO: 128) spacer extended with 71ntRTT, 15ntPBS, 20ntGPS and AATTCTGCAATCCTCACTCT (SEQ ID NO: 129) spacer nicking the opposite strand

FIG. 30 reference
CTCTGGGCAGTGAGTGCAAAAAAGAAGCCAAAGGACTTCAGTGTGACACCTGCAG  SEQ ID NO: 134 encoding the bolded 6 consecutive A's
in the RTT resulted in undesired edits
CTCTGGGCAGTGCGAGTGCAAAAAAGAAAGCAAAG  SEQ ID NO: 135 breaking up the track of 6 A's with a silent A to
mutation (bolded) eliminated undesired edits
CTCTGGGCAGTGCGAGTGCAAGAAAGAAGCAAAG  SEQ ID NO: 136

FIG. 31A Cells treated with Rewriter HTT components including AGTCCCTCAAGTCCTTCCAG (SEQ ID NO: 137) spacer FIG. 31B Wildtype cells

METHODS AND COMPOSITIONS FOR DIRECTED GENOME EDITING

CROSS-REFERENCE

This application claims the benefit of U.S. Provisional Application No. 62/992,032, filed Mar. 19, 2020, U.S. Provisional Application No. 63/055,829, filed Jul. 23, 2020, and U.S. Provisional Application No. 63/153,161, filed Feb. 24, 2021, all of which are incorporated herein by reference in their entireties.

INCORPORATION BY REFERENCE OF SEQUENCE LISTING

The instant application contains a Sequence Listing which has been submitted electronically in ASCII format and is hereby incorporated by reference in its entirety. Said ASCII copy, created on Mar. 16, 2021, is named 56385-701_201_SL.txt and is 609,554 bytes in size.

BACKGROUND

Cas-directed genome editing techniques that introduce double-strand breaks in a target nucleic acid frequently result in undesired products including sequence translocations, insertions, deletions, and activation of DNA damage repair, cell cycle arrest, or apoptosis functions of p53. Editing techniques that introduce single-strand breaks may be limited in the type and size of permissible mutations or may have limited editing efficiency. There is a need for genome editing techniques with improved accuracy, efficiency, and versatility.

SUMMARY

In various aspects, the present disclosure provides a method of increasing gene editing efficiency in a cell having a low deoxynucleoside triphosphate (dNTP) concentration and comprising a DNA polymerase, the method comprising: increasing the dNTP concentration in the cell, relative to a baseline dNTP concentration. In various aspects, increasing the dNTP concentration in the cell comprises inhibiting a deoxynucleotide triphosphate triphosphohydrolase in the cell. In various aspects, the deoxynucleotide triphosphate triphosphohydrolase comprises SAM domain and HD domain-containing protein 1 (SAMHD1). In various aspects, inhibiting SAMHD1 comprises contacting the SAMHD1 with a Vpx protein, or expressing the Vpx protein in the cell. In various aspects, inhibiting SAMHD1 comprises contacting the SAMHD1 with a BGLF4 protein, or expressing the BGLF4 protein in the cell. In various aspects, inhibiting SAMHD1 comprises contacting an mRNA encoding the SAMHD1 with a microRNA or siRNA that hybridizes to the mRNA, or expressing the microRNA or siRNA in the cell. In various aspects, inhibiting SAMHD1 comprises contacting the SAMHD1 with a small molecule SAMHD1 inhibitor. In various aspects, increasing the dNTP concentration in the cell comprises administering nucleosides or nucleotides (e.g., dNs, dNMPs, or NTPs) to the cell. In various aspects, administering dNTPs to the cell comprises administering the nucleosides or nucleotides to a subject comprising the cell. In various aspects, the administration is oral or by injection. In various aspects, increasing the dNTP concentration in the cell comprises delivering a dNTP synthetic enzyme to the cell. In various aspects, the dNTP synthetic enzyme comprises a kinase. In various aspects, the kinase comprises a nucleoside kinase, deoxynucleoside kinase, deoxynucleoside monophosphase kinase, or deoxynucleotide diphosphate kinase. In various aspects, the DNA polymerase comprises a reverse transcriptase. In various aspects, the cell further comprises a Cas9 programmable nuclease, a guide nucleic acid, or a combination thereof. In various aspects, the low dNTP concentration comprises a dNTP concentration found in a nondividing cell. In various aspects, the low dNTP concentration is less than a dNTP concentration found in an activated peripheral blood mononuclear cell. In various aspects, the low dNTP concentration comprises a dNTP concentration below 1 micromolar. In various aspects, the increasing the dNTP concentration comprises increasing the dNTP concentration by at least 5%, at least 10%, at least 15%, at least 20%, at least 25%, at least 30%, at least 40%, at least 50%, at least 60%, at least 70%, at least 80%, at least 90%, at least 100%, or more, relative to the baseline dNTP measurement. In various aspects, the dNTP concentration comprises a deoxyadenosine triphosphate (dATP) concentration, a deoxycytidine triphosphate (dCTP) concentration, a deoxyguanosine triphosphate (dGTP) concentration, or a deoxythymidine triphosphate (dTTP) concentration, or any combination thereof.

In various aspects, the present disclosure provides a method of increasing genome editing efficiency comprising expressing a Vpx protein in a cell expressing the composition as described herein or the guide nucleic acid as described herein.

In various aspects, the present disclosure provides a method of increasing genome editing efficiency by increasing the dNTP concentration in a cell. In various aspects, the present disclosure provides a method of increasing genome editing efficiency comprising inhibiting SAMHD1 in a cell expressing a Cas9 programmable nuclease, a reverse transcriptase, and a guide nucleic acid. In various aspects, the present disclosure provides a method of increasing genome editing efficiency comprising increasing a dNTP concentration (e.g. by inhibiting SAMHD1) in a cell expressing a Cas9 programmable nuclease, a reverse transcriptase, and a guide nucleic acid.

In some aspects, inhibiting SAMHD1 comprises expressing a Vpx protein in the cell. In some aspects, inhibiting SAMHD1 comprises expressing a microRNA against SAMHD1 in the cell. In some aspects, inhibiting SAMHD1 comprises treating the cell with a small molecule SAMHD1 inhibitor.

In various aspects, the present disclosure provides a composition comprising a Cas nickase and a reverse transcriptase, wherein the Cas nickase and the reverse transcriptase are separate polypeptide chains and the Cas nickase and the reverse transcriptase form a Cas-reverse transcriptase heterodimer.

In some aspects, the Cas-reverse transcriptase heterodimer comprises a first heterodimer domain fused to the Cas nickase and a second heterodimer domain fused to the reverse transcriptase, wherein the first heterodimer domain binds the second heterodimer domain to form a heterodimer. In some aspects, the first heterodimer domain is a leucine zipper and the second heterodimer domain is a leucine zipper. In some aspects, the reverse transcriptase comprises a sequence having at least 80% sequence identity to of any one of SEQ ID NO: 3-SEQ ID NO: 22 or a fragment thereof. In some aspects, the reverse transcriptase comprises a domain from a non-long terminal repeat retrotransposable element fused to a Cas nickase. In some aspects, the reverse transcriptase comprises a sequence from a bacterial group II intron fused to a Cas nickase. In some aspects, the reverse transcriptase comprises a domain from a retroviral gag-pol polyprotein fused to a Cas nickase.

Disclosed herein are compositions comprising a Cas nickase and a reverse transcriptase, wherein the Cas nickase and the reverse transcriptase comprise separate polypeptide chains, and wherein the Cas nickase and reverse transcriptase are not engineered to heterodimerize.

In various aspects, the present disclosure provides a composition comprising a Cas nickase, a reverse transcriptase, and a guide nucleic acid, wherein a first polypeptide comprises the Cas nickase and a second polypeptide comprises the reverse transcriptase and the guide nucleic acid binds to the Cas nickase and the reverse transcriptase.

Some aspects comprise a guide nucleic acid that forms a complex with the Cas nickase, wherein, upon complex formation, the Cas nickase is capable of introducing a single-strand break at a target site in a target nucleic acid. In some aspects, the target nucleic acid comprises a CFTR nucleic acid, a USH2A nucleic acid, an ABCA4 nucleic acid, an ATP7B nucleic acid, or an HTT nucleic acid.

In some aspects, the reverse transcriptase comprises an mcp peptide. In some aspects, the reverse transcriptase comprises a loop region. In some aspects, the loop region is a 2a loop or a 3a loop. In some aspects, the loop region is a 2a loop. In some aspects, the loop region is a 3a loop. In some aspects, the guide nucleic acid comprises a MS2 hairpin.

In various aspects, the present disclosure provides a composition comprising a reverse transcriptase with a sequence having at least 80% sequence identity to of any one of SEQ ID NO: 3-SEQ ID NO: 22 or a fragment thereof fused to a Cas nickase.

In various aspects, the present disclosure provides a composition comprising a reverse transcriptase comprising a domain from a non-long terminal repeat retrotransposable element fused to a Cas nickase.

In various aspects, the present disclosure provides a composition comprising a reverse transcriptase comprising a sequence from a bacterial group II intron fused to a Cas nickase.

In various aspects, the present disclosure provides a composition comprising a reverse transcriptase comprising a domain from a retroviral gag-pol polyprotein fused to a Cas nickase.

In some aspects, the composition comprises a guide nucleic acid that complexes with the Cas nickase and the reverse transcriptase, wherein, upon complex formation, the Cas nickase is capable of introducing a single-strand break at a target site in a target nucleic acid. In some aspects, the composition comprises a nuclear localization signal fused to the Cas nickase or the reverse transcriptase. In some aspects, the reverse transcriptase is a truncated reverse transcriptase. In some aspects, the reverse transcriptase has an increased processivity as compared to a native reverse transcriptase. In some aspects, the reverse transcriptase has increased processivity compared to mlvRT. In some aspects, the reverse transcriptase edits a longer window length in a target sequence compared to mlvRT. In some aspects, the reverse transcriptase has decreased immunogenicity compared to mlvRT. In some aspects, the reverse transcriptase has improved delivery to a cell compared to mlvRT. In some aspects, the reverse transcriptase polymerizes 20 or more, 40 or more, 45 or more, 50 or more, 60 or more, 81 or more, 100 or more, 500 or more, or 1000 or more nucleotides in a single binding event.

In various aspects, the present disclosure provides a composition comprising a Cas nickase and a reverse transcriptase, or at least one polynucleotide encoding the Cas nickase and reverse transcriptase, wherein at least part of the Cas nickase and the reverse transcriptase are included in at least 2 separate polypeptide chains. In some aspects, the at least 2 separate polypeptide chains comprise separate polypeptide chains comprising heterodimer domains that bind one another. In some aspects, the at least 2 separate polypeptide chains comprise separate polypeptide chains comprising inteins that bind one another, and the Cas nickase comprises a mutation at amino acid position 1030 or after amino acid position 1030, the mutation comprising a point mutation to a cysteine, threonine, alanine, or serine, or an insertion of a cysteine, threonine, alanine, or serine. In some aspects, the at least 2 separate polypeptide chains comprise the separate polypeptide chains comprising heterodimer domains that bind one another. In some aspects, the separate polypeptide chains comprise fusion proteins comprising the heterodimer domains. In some aspects, the heterodimer domains comprise leucine zippers, PDZ domains, streptavidin and streptavidin binding protein, foldon domains, hydrophobic polypeptides, an antibody that binds the Cas nickase, or an antibody that binds the reverse transcriptase, or one or more binding fragments thereof. In some aspects, the heterodimer domains comprise a first heterodimer domain and a second heterodimer domain, the Cas nickase comprising the first heterodimer domain and the reverse transcriptase comprising the second heterodimer domain. In some aspects, the first heterodimer domain is fused to an amino or carboxy end of the Cas nickase, and the second heterodimer domain is fused to an amino or carboxy end of the reverse transcriptase. In some aspects, the first heterodimer domain comprises a first leucine zipper, and wherein the second heterodimer domain comprises a second leucine zipper. In some aspects, the at least 2 separate polypeptide chains comprise the separate polypeptide chains comprising the inteins that bind one another, and the Cas nickase comprises the mutation at amino acid position 1030 or after amino acid position 1030, the mutation comprising a point mutation to a cysteine, threonine, alanine, or serine, or an insertion of a cysteine, threonine, alanine, or serine. In some aspects, the point mutation is to a cysteine, or the insertion is of a cysteine. In some aspects, the point mutation is to a threonine, or the insertion is of a threonine. In some aspects, the point mutation is to a alanine, or the insertion is of a alanine. In some aspects, the point mutation is to a serine, or the insertion is of a serine. In some aspects, the mutation comprises the point mutation, wherein the point mutation is at amino acid position D1079, D1125, D1130, G1133, A1140, I1168, S1173, D1180, G1186, L1203, R1212, or a range defined by any two of the aforementioned amino acid positions. In some aspects, the mutation comprises the point mutation, wherein the point mutation is at amino acid position D1079, D1125, D1130, G1133, A1140, I1168, S1173, D1180, G1186, L1203, or R1212. In some aspects, the mutation comprises the insertion mutation, wherein the insertion mutation is immediately upstream or downstream of amino acid position D1079, D1125, D1130, G1133, A1140, I1168, S1173, D1180, G1186, L1203, R1212, or a range defined by any two of the aforementioned amino acid positions. In some aspects, the mutation comprises the insertion mutation, wherein the insertion mutation is immediately upstream or downstream of amino acid position D1079, D1125, D1130, G1133, A1140, I1168, S1173, D1180, G1186, L1203, or R1212. In some aspects, the inteins comprise a first intein and a second intein, and wherein the Cas nickase comprises a first segment comprising the first intein, and a second segment comprising the mutation and the second intein. Some aspects include a guide nucleic acid that binds to the Cas nickase or the reverse transcriptase. In some aspects, the Cas nickase of the complex introduces a single-strand break at a target site in a target nucleic acid. In some aspects, the Cas nickase comprises a Cas9 nickase or a variant thereof. In some aspects, the Cas9 nickase or variant thereof comprises an *S. Pyogenes* Cas9 nickase or a variant thereof. In some aspects, the reverse transcriptase comprises a Moloney leukemia virus reverse transcriptase (mlvRT) or a variant thereof. In some aspects, the reverse transcriptase comprises a point mutation at position P51, S67, Q84, L139, Q221, V223, T197, D653, T664, L671, L435, H204, or D524. In some aspects, the reverse transcriptase comprises a point mutation comprising P51L, S67R, Q84A, L139P, Q221R, V223A, V223M, T197A, D653N, T664N, L671P, L435G, H204R, or D524A. In some aspects, the reverse transcriptase comprises a point mutation at amino acid position Q84, L139, Q221, V223, T664, or L671. In some aspects, the reverse transcriptase comprises a point mutation comprising S67R, Q84A, L139P, Q221R, V223A, V223M, T664N, L671P, or D524A. In some aspects, the composition comprises the Cas nickase and the reverse transcriptase, and wherein the at least 2 separate polypeptide chains are 2 separate polypeptide chains. In some aspects, the composition comprises the Cas nickase and the reverse transcriptase, and wherein the at least 2 separate polypeptide chains comprise a first polypeptide chain comprising a first part of the Cas nickase, and a second polypeptide chain comprising a second part of the Cas nickase and the reverse transcriptase. Some aspects include the at least one polynucleotide encoding the Cas nickase and reverse transcriptase. In some aspects, the at least one polynucleotide encoding the Cas nickase and reverse transcriptase comprises a first polynucleotide encoding a first part of the Cas nickase, and a second polynucleotide encoding a second part of the Cas nickase and the reverse transcriptase. Some aspects include at least one adeno-associated virus comprising the at least one polynucleotide. In some aspects, the composition is produced by a cell.

In various aspects, the present disclosure provides a composition comprising a Cas nickase and a reverse transcriptase, or at least one polynucleotide encoding the Cas nickase and reverse transcriptase, wherein at least part of the Cas nickase and the reverse transcriptase are included in separate polypeptide chains. In some aspects, the Cas nickase or the reverse transcriptase comprise a first leucine zipper. In some aspects, the Cas9 nickase comprises an *S. Pyogenes* Cas9 nickase, or a variant thereof, and a point mutation at amino acid position D1079, D1125, D1130, G1133, A1140, I1168, S1173, D1180, G1186, L1203, or R1212, or an insertion mutation immediately upstream or downstream of amino acid position D1079, D1125, D1130, G1133, A1140, I1168, S1173, D1180, G1186, L1203, or R1212. In some aspects, the reverse transcriptase comprises a Moloney leukemia virus reverse transcriptase (mlvRT), or a variant thereof, and a point mutation at amino acid position Q84, L139, Q221, V223, T664, or L671. In some aspects, the separate polypeptide chains comprise heterodimer domains. In some aspects, the Cas nickase and the reverse transcriptase form a heterodimer comprising a first heterodimer domain fused to the Cas nickase and a second heterodimer domain fused to the reverse transcriptase, wherein the first heterodimer domain binds to the second heterodimer domain to form the heterodimer. In some aspects, the first heterodimer domain comprises the first leucine zipper. In some aspects, the second heterodimer domain comprises a second leucine zipper. In some aspects, the reverse transcriptase comprises a sequence having at least 80% sequence identity to of any one of SEQ ID NO: 3-SEQ ID NO: 22 or SEQ ID NO: 40-SEQ ID NO: 80, or a fragment thereof. In some aspects, the reverse transcriptase comprises a domain from a non-long terminal repeat retrotransposable element fused to part of the Cas nickase, a sequence from a bacterial group II intron fused to part of the Cas nickase, or a domain from a retroviral gag-pol polyprotein fused to part of the Cas nickase. Some aspects include a guide nucleic acid that binds to the Cas nickase or the reverse transcriptase. In some aspects, the Cas nickase of the complex introduces a single-strand break at a target site in a target nucleic acid. In some aspects, the guide nucleic acid comprises a hairpin. In some aspects, the hairpin comprises an MS2 hairpin. In some aspects, the reverse transcriptase comprises a modified reverse transcriptase comprising a hairpin binding domain. In some aspects, the reverse transcriptase comprises a modified reverse transcriptase comprising an MS2 coat protein (MCP) peptide. In some aspects, the reverse transcriptase comprises a loop region. In some aspects, the Cas9 nickase comprises a point mutation or an insertion mutation in a C-terminal half of the Cas9 nickase. In some aspects, the point mutation in the C-terminal half of the Cas9 nickase is to a cysteine, serine, threonine, or alanine; or wherein the insertion mutation is a cysteine insertion serine insertion, threonine insertion, or alanine insertion. In some aspects, the Cas9 nickase comprises the point mutation in the C-terminal half of the Cas9 nickase. In some aspects, the Cas9 nickase comprises the insertion mutation in the C-terminal half of the Cas9 nickase. In some aspects, the Cas9 nickase comprises a first segment comprising a first intein, and a second segment comprising the point mutation or insertion mutation and a second intein. In some aspects, the Cas9 nickase comprises the *S. Pyogenes* Cas9 nickase or variant thereof. In some aspects, the Cas9 nickase comprises the point mutation at amino acid position D1079, D1125, D1130, G1133, A1140, I1168, S1173, D1180, G1186, L1203, or R1212, or the insertion mutation immediately upstream or downstream of amino acid position D1079, D1125, D1130, G1133, A1140, I1168, S1173, D1180, G1186, L1203, or R1212. In some aspects, the Cas nickase or the reverse transcriptase comprises a nuclear localization signal. In some aspects, the reverse transcriptase is a truncated reverse transcriptase. In some aspects, the reverse transcriptase comprises the mlvRT or variant thereof. In some aspects, the reverse transcriptase comprises the point mutation at amino acid position Q84, L139, Q221, V223, T664, or L671 In some aspects, the reverse transcriptase comprises a point mutation comprising P51L, S67R, Q84A, L139P, Q221R, V223A, V223M, T197A, D653N, T664N, L671P, L435G, H204R, or D524A. In some aspects, the reverse transcriptase comprises a point mutation comprising S67R, Q84A, L139P, Q221R, V223A, V223M, T664N, L671P, or D524A. In some aspects, the Cas nickase and the reverse transcriptase comprise separate polypeptide chains. In some aspects, the composition is produced by a cell. Some aspects include the at least one polynucleotide encoding the Cas nickase and reverse transcriptase. Some aspects include at least one adeno-associated virus comprising the at least one polynucleotide.

In various aspects, the present disclosure provides a guide nucleic acid comprising: a spacer reverse complementary to a first region of a target nucleic acid, a scaffold configured to bind to a Cas nickase, a reverse transcriptase template encoding a sequence to be inserted into the target nucleic acid, and a first strand primer binding site reverse complementary to a second region of the target nucleic acid.

In some aspects, the guide nucleic acid further comprises a second strand primer comprising a sequence of a region of the reverse transcriptase template. In some aspects, the first region of the target nucleic acid is on a first strand of the target nucleic acid and the second region of the target nucleic acid is on a second strand of the target nucleic acid. In some aspects, all or part of the first region of the target nucleic acid is reverse complementary to all or part of the second region of the target nucleic acid. In some aspects, the guide nucleic acid further comprises a cleavable sequence at the 3' end of the guide nucleic acid. In some aspects, the cleavable sequence is a ribozyme cleavable sequence. In some aspects, the cleavable sequence is a tRNA cleavable sequence. In some aspects, the first strand primer binding site is configured to hybridize to the second region of the target nucleic acid, and wherein the reverse transcriptase template is configured to serve as a template for reverse transcription from a 3' end of the second region of the target nucleic acid. In some aspects, the second strand primer is configured to serve as a primer for transcription from a template reverse complementary to the reverse transcriptase template. In some aspects, a first synthesized strand serves as a template for synthesis of a second strand from the second strand primer. In some aspects, a Velcro region that hybridizes to a region of the reverse transcriptase template region.

In various aspects, the present disclosure provides a composition comprising a first guide nucleic acid comprising the guide as described herein and a second guide nucleic acid.

In some aspects, the second guide nucleic acid comprises the guide as described herein. In some aspects, the first guide nucleic acid binds to a first Cas nickase, and the second guide nucleic acid binds to a second Cas nickase. In some aspects, a first spacer of the first guide nucleic acid binds a first Cas nickase, a second spacer of the second guide nucleic acid binds a second Cas nickase, a first scaffold of the first guide nucleic acid binds the second Cas nickase, and a second scaffold of the second guide nucleic acid binds the first Cas nickase. In some aspects, the first guide nucleic acid comprises a first linker and the second guide nucleic acid comprises a second linker, wherein the first linker hybridizes to the second linker.

In various aspects, the present disclosure provides a guide nucleic acid comprising: a spacer reverse complementary to a first region of a target nucleic acid; a scaffold configured to bind to a Cas nuclease; a reverse transcriptase template encoding a sequence to be inserted into the target nucleic acid; a first strand primer binding site reverse complementary to a second region of the target nucleic acid; and at least one of: i. a gRNA positioning system (GPS) region and a GPS binding site that hybridizes to the GPS region, ii. a modification in the reverse transcriptase template that disrupts a protospacer adjacent motif (PAM) sequence in the target nucleic acid, iii. a modification in the reverse transcriptase template that disrupts a track of at least 4 consecutive nucleotides of the same base in the target nucleic acid, or iv. a second strand primer comprising a sequence of a region of the reverse transcriptase template. In various aspects, the present disclosure provides a guide nucleic acid comprising: a spacer reverse complementary to a first region of a target nucleic acid; a scaffold configured to bind to a Cas nuclease; a reverse transcriptase template encoding a sequence to be inserted into the target nucleic acid; a first strand primer binding site reverse complementary to a second region of the target nucleic acid; and at least one of: i. a gRNA positioning system (GPS) region and a GPS binding site that hybridizes to the GPS region, ii. a modification in the reverse transcriptase template that disrupts a track of at least 4 consecutive nucleotides of the same base in the target nucleic acid, or iii. a second strand primer comprising a sequence of a region of the reverse transcriptase template. Some aspects include the second strand primer. In some aspects, the second strand primer is configured to serve as a primer for transcription from a template reverse complementary to the reverse transcriptase template. In some aspects, a first synthesized strand serves as a template for synthesis of a second strand from the second strand primer. In some aspects, the first region of the target nucleic acid is on a first strand of the target nucleic acid and the second region of the target nucleic acid is on a second strand of the target nucleic acid. In some aspects, all or part of the first region of the target nucleic acid is reverse complementary to all or part of the second region of the target nucleic acid. Some aspects include a ribozyme cleavable sequence at a 3' end of the guide nucleic acid. Some aspects include a tRNA cleavable sequence at a 3' end of the guide nucleic acid. In some aspects, the first strand primer binding site is configured to hybridize to the second region of the target nucleic acid, and wherein the reverse transcriptase template is configured to serve as a template for reverse transcription from a 3' end of the second region of the target nucleic acid. Some aspects include the GPS region and the GPS binding site. In some aspects, the GPS region and the GPS binding site together comprise a region of the guide nucleic acid that binds to another region on the guide nucleic acid to affect a conformational change in the guide nucleic acid and improve gene editing. In some aspects, the hybridization of the GPS region and the GPS binding site conformationally changes the guide nucleic acid, and improves editing efficiency as compared to a guide nucleic acid without the GPS region or GPS binding site. In some aspects, the reverse transcriptase template region comprises the GPS binding site. In some aspects, the GPS binding site is 5' of the first strand primer binding site. In some aspects, the GPS binding site is 3' of the first strand primer binding site. In some aspects, the GPS region is 5' of the reverse transcriptase template. In some aspects, the GPS region is 3' of the reverse transcriptase template. In some aspects, the GPS region is 5' of the scaffold. In some aspects, the GPS region is 5-100 nucleotides in length. In some aspects, the GPS binding site is at least 50% complementary to the GPS region. In some aspects, the target nucleic acid comprises a CFTR nucleic acid, a USH2A nucleic acid, an ABCA4 nucleic acid, an ATP7B nucleic acid, or an HTT nucleic acid. In some aspects, the spacer comprises a nucleic acid sequence at least 85% identical to any one of SEQ ID NOs: 96-119. Some aspects include the modification in the reverse transcriptase template that disrupts the PAM sequence in the target nucleic acid. In some aspects, the PAM sequence comprises a 2-6 base pair nucleic acid sequence recognized by the Cas nuclease. In some aspects, the modification in the reverse transcriptase template that disrupts the PAM sequence in the target nucleic acid improves gene editing relative to a guide nucleic acid without the modification. Some aspects include the modification in the reverse transcriptase template that disrupts the track of at least 4 consecutive nucleotides of the same base in the target nucleic acid. In some aspects, the track of at least 4 consecutive nucleotides of the same base comprise a polyA track. In some aspects, the modification in the reverse transcriptase template that disrupts the track of at least 4 consecutive nucleotides of the same base in the target nucleic acid improves gene editing relative to a guide nucleic acid without the modification. In some aspects, the Cas nuclease comprises a Cas nickase. In some aspects, the guide nucleic acid comprises a guide RNA. Some aspects include a gene editing method comprising delivering a composition comprising the guide nucleic acid to a cell. In some aspects, the composition comprises a viral vector comprising the guide nucleic acid. Some aspects include the GPS region that hybridizes to the GPS binding site on the second guide nucleic acid.

In various aspects, the present disclosure provides a method of increasing genome editing efficiency comprising delivering an Orflp to a cell expressing the composition as described herein or the guide nucleic acid as described herein.

In various aspects, the present disclosure provides a nucleic acid comprising nucleotide sequence encoding the composition as described herein or the guide nucleic acid as described herein.

In various aspects, the present disclosure provides a viral vector comprising the nucleic acid as described herein.

In various aspects, the present disclosure provides a cell comprising the composition as described herein, the guide nucleic acid as described herein, the nucleic acid as described herein, or the viral vector as described herein.

In some aspects, the cell is a prokaryotic cell. In some aspects, the cell is a eukaryotic cell.

In some aspects, the present disclosure provides a composition comprising a Cas9 programmable nuclease comprising one or more point mutations or insertion mutations that enable or improve intein catalysis. In various aspects, the present disclosure provides a composition comprising a Cas9 programmable nuclease, wherein the Cas9 programmable nuclease comprises a cysteine point mutation located in a C-terminal half of the Cas9 programmable nuclease. In various aspects, the present disclosure provides a composition comprising a Cas9 programmable nuclease, wherein the Cas9 programmable nuclease comprises an insertion mutation (e.g. a cysteine insertion mutation) located in a C-terminal half of the Cas9 programmable nuclease. The point mutation may be a cysteine point mutation, a serine point mutation, a threonine point mutation, or an alanine point mutation. The insertion mutation may be a cysteine insertion mutation, a serine insertion mutation, a threonine insertion mutation, or an alanine insertion mutation.

In some aspects, the Cas9 programmable nuclease is a Cas9 nickase. In some aspects, the Cas9 programmable nuclease is an *S. Pyogenes* Cas9. In some aspects, the point mutation is located at D1079, D1125, D1130, G1133, A1140, I1168, S1173, D1180, G1186, L1203, or R1212 of the *S. Pyogenes* Cas9. In some aspects, the insertion mutation is immediately upstream of D1079, D1125, D1130, G1133, A1140, I1168, S1173, D1180, G1186, L1203, or R1212 of the *S. Pyogenes* Cas9. In some aspects, the cysteine point mutation is located at S1173C, D1079C, or D1180C of the *S. Pyogenes* Cas9. In some aspects, the cysteine insertion mutation is located at 1173C, 1079C, or 1180C of the *S. Pyogenes* Cas9. In some aspects, the Cas9 programmable nuclease comprises a sequence of any one of SEQ ID NO: 85-SEQ ID NO: 87 or SEQ ID NO: 90-SEQ ID NO: 92.

In some aspects, the Cas9 programmable nuclease is expressed as two or more segments. In some aspects, a first segment of the two or more segments comprise an N-terminal portion of the Cas9 programmable nuclease and a first intein, and wherein a second segment of the two or more segments comprise a C-terminal portion of the Cas9 programmable nuclease and a second intein. In some aspects, the cysteine point mutation is located at the N-terminus of the C-terminal portion of the Cas9 programmable nuclease. In some aspects, the cysteine insertion mutation is located at the N-terminus of the C-terminal portion of the Cas9 programmable nuclease. In some aspects, the first intein is fused to the C-terminus of the N-terminal portion of the Cas9 programmable nuclease, and wherein the second intein is fused to the N-terminus of the C-terminal portion of the Cas9 programmable nuclease. In some aspects, the first segment comprises a sequence of SEQ ID NO: 90, and wherein the second segment comprises a sequence of SEQ ID NO: 91. The second segment of the two or more segments may comprise a reverse transcriptase fused to the C-terminal portion of the Cas9 programmable nuclease. The reverse transcriptase may comprise an N-terminus fused to a C-terminus of the C-terminal portion of the Cas9 programmable nuclease. The reverse transcriptase may comprise an mlvRT, or a variant thereof.

Disclosed herein are methods of optimizing genome editing efficiency comprising performing genome editing with a Moloney leukemia virus reverse transcriptase (mlvRT) that is modified to increase its catalytic efficiency in low dNTP concentrations, (e.g. modified to decrease its Km for dNTPs). Disclosed herein are methods of optimizing genome editing efficiency in a limiting dNTP condition, comprising performing genome editing with a Moloney leukemia virus reverse transcriptase (mlvRT), or a variant thereof, comprising a point mutation at position 221 or 223 of the reverse transcriptase. The mlvRT or variant thereof may comprise a point mutation at position 221. The point mutation at position 221 may comprise Q221R. The mlvRT or variant thereof may comprise a point mutation at position 223. The point mutation at position 223 may comprise V223A. The point mutation at position 223 may comprise V223M.

The Cas nickase and RT may be encoded by polynucleotides. Disclosed herein are AAVs comprising the polynucleotides. At least part of the Cas nickase and RT may be encompassed or comprised within separate AAVs. Disclosed herein are AAVs comprising a first AAV comprising a first polynucleotide encoding a Cas or Cas9 component, and a second AAV comprising a second polynucleotide encoding a RT component. The AAVs may comprise AAV1, AAV2, AAV3, AAV4, AAV5, AAV6, AAV7, AAV8, AAV9, AAV10, AAV11, AAV12, AAV-DJ, AAV-DJ/8, AAV-Rh10, AAV-Rh74, AAV-retro, AAV-PHP.B, AAV8-PHP.eB, or AAV-PHP.S, or a combination of thereof.

Disclosed herein are methods for screening or identifying an improved reverse transcriptase (RT), comprising: overexpressing SAMHD1, or expressing a mutant SAMHD1 that has been mutated to prevent phosphorylation of a residue of the mutant SAMHD1, in cells; identifying an RT activity in the cells; and based on the RT activity, identifying the RT as an improved RT.

Disclosed herein are systems comprising an RNA or polynucleotide comprising a spacer, a reverse transcriptase template comprising a desired edit, and a primer binding site, in which the primer binding site binds to a nucleic acid that does not comprise any part of the region of the nucleic acid targeted or bound by the spacer or the nucleic acid reverse complementary to the nucleic acid targeted or bound by the spacer.

Disclosed herein are systems comprising: a first guide nucleic acid comprising: a spacer reverse complementary to a first region of a target nucleic acid; a scaffold configured to bind to a Cas nuclease; a reverse transcriptase template encoding a sequence to be inserted into the target nucleic acid; a first strand primer binding site that binds to a region of the target nucleic acid that does not comprise any part of the first region, and that does not comprise any part of a reverse complement of the first region; and a GPS region that hybridizes to a GPS binding site on a second guide nucleic acid. Disclosed herein are systems comprising: a first guide nucleic acid comprising: a spacer reverse complementary to a first region of a target nucleic acid; a scaffold configured to bind to a Cas nuclease; a reverse transcriptase template encoding a sequence to be inserted into the target nucleic acid; and a first strand primer binding site that binds to a region of the target nucleic acid that does not comprise any part of the first region, and that does not comprise any part of a reverse complement of the first region. Some aspects include a GPS region that hybridizes to a GPS binding site on a second guide nucleic acid. Some aspects include the second guide nucleic acid. The second guide nucleic acid may include the GPS binding site. In some aspects, the second guide nucleic acid comprises a second spacer reverse complementary to another region of the target nucleic acid. The second guide nucleic acid may bring the primer binding site into proximity or contact with a genomic flap.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 4A illustrates a method for genome editing using an engineered gRNA of the present disclosure ("Stitch Guide"). A nCas9-RT construct complexed with a gRNA is recruited to a target site of a target nucleic acid by hybridization of a spacer of the gRNA to the target site. The nCas9 nicks a strand of a target nucleic acid at a target site. A first strand primer binding site of the gRNA hybridizes to a flap 5' of the nick. The RT polymerizes from the 3' end of the flap using a reverse transcriptase template region of the gRNA as a template. A second strand primer ("$2^{nd}$ strand primer") at the 3' end of the gRNA hybridizes to the 3' end of the newly synthesized DNA strand. The 4-200 bp second strand primer region acts as an RNA primer for synthesis of a second DNA strand. The RT polymerizes from the 3' end of the gRNA using the newly synthesized DNA strand as a template. A ribozyme on the 3' end of the gRNA cleaves the gRNA 3' of the second strand primer sequence. The newly synthesized double stranded DNA may be incorporated into the target nucleic acid at the site of the nick.

FIG. 4B shows the editing efficiency of a nCas9-RT construct using a pegRNA or a Stitch Guide gRNA. Schematics of the pegRNA and the Stitch Guide gRNA are shown at left. The fused nCas9-mlvRTv construct was used in this assay.

FIG. 6 illustrates four schemes of genome editing using a two gRNA system with a nCas9-RT. In a two single guide system in which the two guides each generate an edited strand (top left), each gRNA binds to a different nCas9 and the two gRNAs each comprise a reverse transcriptase template region. In a two single guide system in which the second guide nicks the opposite strand (top right), each gRNA binds to a different nCas9 and only one of the gRNAs comprise a reverse transcriptase template region. In a dual guide complex system in which the two guides each generate an edit (bottom left), the spacer of the first gRNA binds the first nCas9, the spacer of the second gRNA binds the second nCas9, the scaffold of the first gRNA binds the second nCas9, and the scaffold of the second gRNA binds the first nCas9; and the two gRNAs each comprise a reverse transcriptase template region and a primer binding site (PBS) region. In a dual guide complex system in which the second guide nicks the opposite strand (bottom right), the spacer of the first gRNA binds the first nCas9, the spacer of the second gRNA binds the second nCas9, the scaffold of the first gRNA binds the second nCas9, and the scaffold of the second gRNA binds the first nCas9; and only one of the gRNAs comprise a reverse transcriptase template region.

FIGS. 25B and 25C illustrate information about some experiments performed using guide RNAs.

FIG. 27 shows components of some editing systems.

FIG. 30 shows components of some editing systems.

DETAILED DESCRIPTION

Figure 1:
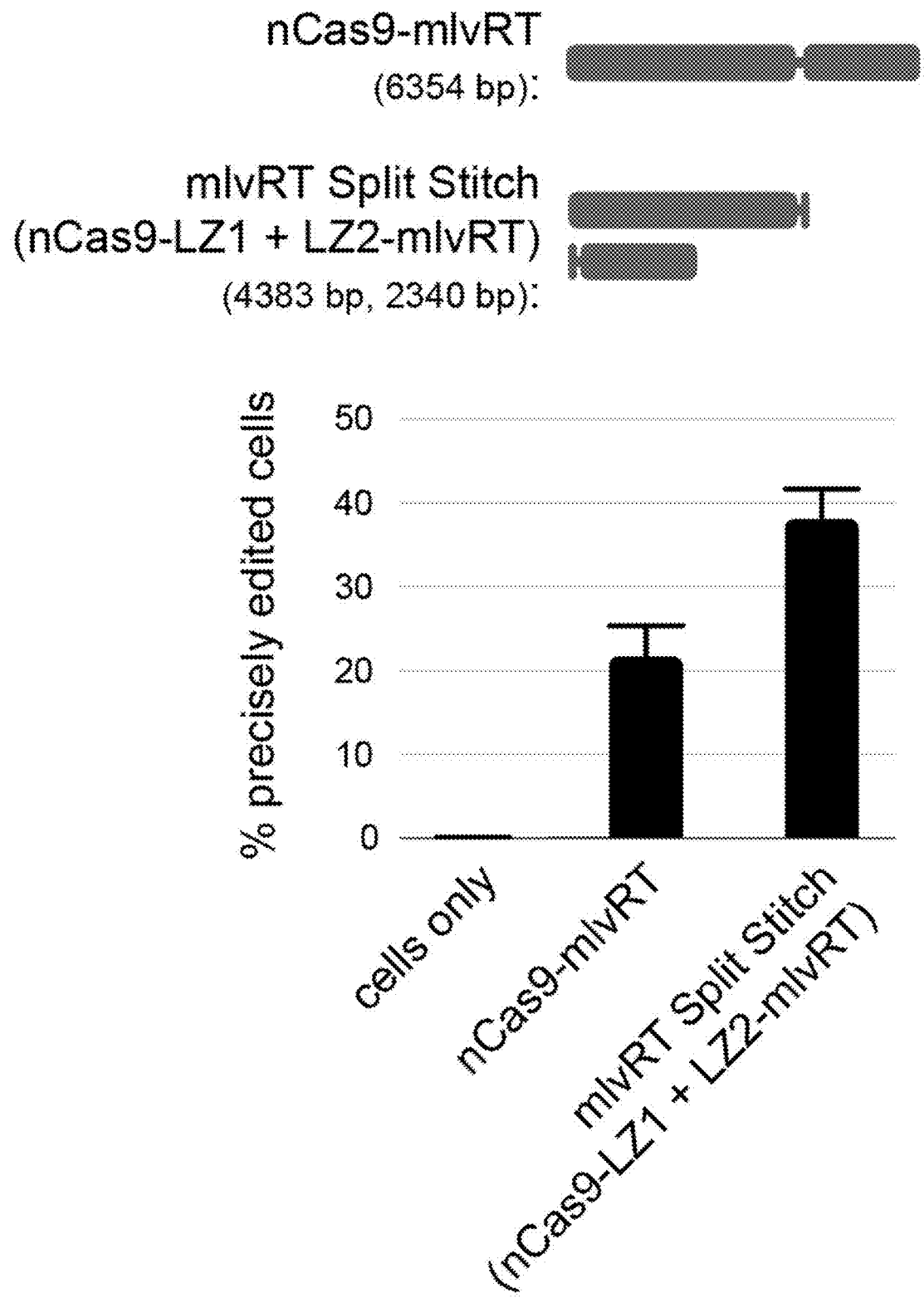
FIG. 1 shows the editing efficiency of a fused Cas9 nickase (nCas9) reverse transcriptase (RT) construct ("nCas9-mlvRT") comprising an nCas9 and a Moloney leukemia virus RT ("mlvRT"), and a split nCas9-LZ1 and LZ2-mlvRT construct ("mlvRT Split Stitch"). The split nCas9-LZ1 and LZ2-mlvRT construct comprises a nCas9-LZ1 (SEQ ID NO: 1, NLS-SpCas9(H840A)-NLS-EE12RR345L(leucine zipper)) and a LZ2-mlvRT (SEQ ID NO: 2, RR12EE345L(leucine zipper)-mlvRTv(nCas9-mlvRT(D200N, L603W, T306K, W313F, T330P)-NLS) on discrete polypeptide chains. The nCas9-LZ1 comprises a SpCas9 (SEQ ID NO: 32) and a C-terminal leucine zipper (SEQ ID NO: 23) that heterodimerizes with the LZ2-mlvRT comprising a mlvRT (SEQ ID NO: 13) and an N-terminal leucine zipper (SEQ ID NO: 24) through the leucine zippers. Schematics of the nCas9-mlvRT constructs are provided at top.

Disclosed herein are methods and compositions for precise and efficient genome editing using CRISPR-Cas systems. Cas9-based base editors comprising a Cas9 nickase (nCas9) linked to a deaminase may be limited to performing transition mutations (e.g., A to G or C to T). Other Cas9-based editors (e.g., "prime editors") comprising a nCas9 linked to a reverse transcriptase (RT) (e.g., a Moloney leukemia virus RT) may be limited to small insertions, deletions, or single nucleotide changes. Provided herein are Cas nickase and reverse transcriptase constructs, engineered guide nucleic acids, and methods of use thereof for improved efficiency, versatility, precision, and deliverability of genome editing.

The methods and compositions described herein may include splitting, dimerizing, or coexpressing a Cas9 and a RT. The splitting, dimerizing, or coexpressing of Cas9 and RT may enable AAV packaging. The splitting, dimerizing, or coexpressing of Cas9 and RT may increase editing efficiency.

Described herein are AAV deliverable precision editing components. Some embodiments include AAV particles that deliver a Cas9 component and a RT component. Various examples are provided for delivering Cas+RT systems with AAV. The examples provided may overcome previous difficulties getting precision editing components to fit within a typical AAV carrying capacity (e.g. of about 4.5 kb).

Also provided are mutations such as point mutations or insertion mutations that improve editing efficiency. For example, Cas nickase or RT (e.g. point mutations or insertion mutations) are included. Some embodiments include an mlvRT for genome editing with an amino acid mutation.

Nicking Cas9 and Reverse Transcriptase Enzymes

Provided herein are compositions comprising a Cas nickase. Provided herein are compositions comprising a reverse transcriptase. Provided herein are compositions comprising a Cas nickase and a reverse transcriptase. At least part of the Cas nickase and the reverse transcriptase may be included in separate polypeptide chains. The Cas nickase and the reverse transcriptase may be completely in separate polypeptide chains. Some embodiments include a functional fragment of the Cas nickase. Some embodiments include a functional fragment of the reverse transcriptase.

The Cas nickase and the reverse transcriptase may form a Cas-reverse transcriptase heterodimer. The Cas-reverse transcriptase heterodimer may include a first heterodimer domain. The first heterodimer domain may be fused to the Cas nickase. The Cas-reverse transcriptase heterodimer may include a second heterodimer domain. The second heterodimer domain may be fused to the reverse transcriptase. The first heterodimer domain may bind the second heterodimer domain. This binding may form the Cas-reverse transcriptase heterodimer. The first heterodimer domain may comprise a leucine zipper. The second heterodimer domain may comprise a leucine zipper. The first or second heterodimer domain may comprise a heterodimer domain other than a leucine zipper, for example a SpyCatcher or SpyTag moiety as described herein.

Provided herein are engineered constructs comprising a Cas programmable nuclease. The Cas programmable nuclease may comprise a Cas9 programmable nuclease. Provided herein are engineered constructs comprising a Cas nickase. The Cas programmable nuclease may include a Cas nickase.

The Cas nickase may comprise a Cas9 nickase (nCas9). The Cas9 programmable nuclease may comprise an nCas9. The Cas nickase may be generated by mutating a Cas9 nuclease domain. The Cas nickase may create a single-strand rather than a double-strand break.

Provided herein are engineered constructs comprising a reverse transcriptase (RT). Provided herein are engineered constructs comprising a Cas nickase and a RT. Provided herein are engineered constructs comprising a Cas9 nickase and a RT. The nCas9 may introduce a single-strand break (SSB) at a target site of a target nucleic acid. The reverse transcriptase may catalyze reverse transcription of a sequence to be inserted at the target site. In some embodiments, a nCas9-RT construct may be fused to a nCas9-RT construct. A fused nCas9-RT construct may comprise a nCas9 and a reverse transcriptase in a single polypeptide chain. In some embodiments, a nCas9-RT construct may be a split nCas9-RT construct. A split nCas9-RT construct may comprise a nCas9 in a first polypeptide chain and a reverse transcriptase in a second polypeptide chain. The nCas9 and the reverse transcriptase of a split nCas9-RT construct may form a heterodimer when co-expressed. In some embodiments, a first dimerization domain may be located N-terminal of the nCas9. In some embodiments, a second dimerization domain that dimerizes with the first dimerization domain may be located C-terminal of the reverse transcriptase. In some embodiments, a first dimerization domain may be located C-terminal of the nCas9. In some embodiments, a second dimerization domain that dimerizes with the first dimerization domain may be located N-terminal of the reverse transcriptase. The first dimerization domain may comprise a leucine zipper, an FKBP, an FRB, a Calcineurin A, a CyP-Fas, a GyrB, a GAI, a GID1, a SNAP tag, a Halo tag, a Bcl-xL, a Fab, or a LOV domain. The second dimerization domain may comprise a leucine zipper, an FKBP, an FRB, a Calcineurin A, a CyP-Fas, a GyrB, a GAI, a GID1, a SNAP tag, a Halo tag, a Bcl-xL, a Fab, or a LOV domain. Dimerization may be induced or spontaneous. Dimerization may be chemically or optically induced. SEQ ID NO:1 provides an example of a nCas9 comprising a leucine zipper at the C-terminus. SEQ ID NO: 2 provides an example of a reverse transcriptase comprising a leucine zipper at the N-terminus.

In some embodiments, a construct of the present disclosure may comprise a nuclear localization signal (NLS). A composition described herein may comprise a nuclear localization signal fused to a Cas nickase. In some embodiments, the Cas nickase fused to an NLS comprises a sequence at least 70%, at least 75%, at least 80%, at least 85%, at least 90%, at least 95%, at least 96%, at least 97%, at least 98%, at least 99%, or 100% identical to SEQ ID NO: 138. A composition described herein may comprise a nuclear localization signal fused to a RT. In some embodiments, the RT fused to an NLS comprises a sequence at least 70%, at least 75%, at least 80%, at least 85%, at least 90%, at least 95%, at least 96%, at least 97%, at least 98%, at least 99%, or 100% identical to SEQ ID NO: 95.

The reverse transcriptase may comprise a domain from a non-long terminal repeat retrotransposable element. The non-long terminal repeat retrotransposable element may be fused to part of a Cas nickase. The reverse transcriptase may comprise a sequence from a bacterial group II intron. The bacterial group II intron may be fused to part of the Cas nickase. The reverse transcriptase may comprise a domain from a retroviral gag-pol polyprotein. The domain from the retroviral gag-pol polyprotein may be fused to part of the Cas nickase.

Dimerization may be achieved using a SpyTag/SpyCatcher or related system. For example, a RT may be conjugated to a SpyTag moiety, and a Cas nickase may be conjugated to a SpyCatcher moiety. Alternatively, a Cas nickase may be conjugated to a SpyTag moiety, and a RT may be conjugated to a SpyCatcher moiety. Dimerization using the SpyTag/SpyCatcher system may include covalent bonds between dimerized molecules (e.g. the Cas nickase may be covalently conjugated to the RT through the SpyTag and SpyCatcher moieties. A Cas nickase conjugated to a SpyTag or SpyCatcher moiety may be provided in a first AAV. A RT conjugated to a SpyCatcher or SpyTag moiety may be provided in a second AAV.

A variety of reverse transcriptases are consistent with the compositions and methods of the present disclosure. A reverse transcriptase as disclosed herein may be a geobacilus stereothermophilus RT (GsI-IICRT, SEQ ID NO: 3), *Eubacterium Rectale* RT (ErRT, SEQ ID NO: 4), marathon RT (SEQ ID NO: 5), BmR2RT (SEQ ID NO: 6), amino acids 116-1016 from the R2 polyprotein (R2(116-1016), SEQ ID NO: 7), BmR2en-RT (SEQ ID NO: 8), humanLlRT (SEQ ID NO: 9), humanLlen-RT (SEQ ID NO: 10), murineLIRT (SEQ ID NO: 11), ltrA (SEQ ID NO: 12), mlvRT5M (SEQ ID NO: 13), mlvRT5M (SEQ ID NO: 40), mlvRT (SEQ ID NO: 14), XMRV3VP35RT (SEQ ID NO: 15), galvRT (SEQ ID NO: 16), sfvRT (SEQ ID NO: 17), foamvRT (SEQ ID NO: 18), HIVP66 (SEQ ID NO: 19), HIVP51 (SEQ ID NO: 20), rsvAlpha (SEQ ID NO: 21), or rsvBeta (SEQ ID NO: 22). A transcriptase of the present disclosure may include an N-terminal methionine, or a transcriptase of the present disclosure may lack an N-terminal methionine. For example, a reverse transcriptase may have a sequence corresponding to any one of SEQ ID NO: 3-SEQ ID NO: 6, SEQ ID NO: 8-SEQ ID NO: 12, SEQ ID NO: 17, SEQ ID NO: 18, or SEQ ID NO: 40-SEQ ID NO: 80 with the N-terminal methionine removed. In another example, a reverse transcriptase may have a sequence corresponding to any one of SEQ ID NO: 7, SEQ ID NO: 13-SEQ ID NO: 16, or SEQ ID NO: 19-SEQ ID NO: 22 with a methionine added to the N-terminus. A reverse transcriptase may comprise a sequence having at least 80%, at least 85%, at least 90%, at least 95%, at least 96%, at least 97%, at least 98%, at least 99%, at least 99.5%, 100% sequence identity, or any percentage therebetween, to any one of SEQ ID NO: 3-SEQ ID NO: 22 or SEQ ID NO: 40-SEQ ID NO: 80, or a fragment thereof.

Disclosed herein are compositions comprising a reverse transcriptase with a sequence having at least 80% sequence identity to of any one of SEQ ID NO: 3-SEQ ID NO: 22 or SEQ ID NO: 40-SEQ ID NO: 80, a fragment thereof. The reverse transcriptase or fragment thereof may be fused to a Cas nickase. Some embodiments include a composition comprising a reverse transcriptase comprising a domain from a non-long terminal repeat retrotransposable element, which may be fused to a Cas nickase. Some embodiments include a reverse transcriptase comprising a sequence from a bacterial group II intron, which may be fused to a Cas nickase. Some embodiments include a reverse transcriptase comprising a domain from a retroviral gag-pol polyprotein, that may be fused to a Cas nickase. The reverse transcriptase may be truncated.

Disclosed are methods of optimizing genome editing efficiency in a limiting dNTP condition. The method may include performing genome editing with a Moloney leukemia virus reverse transcriptase (mlvRT), or a variant thereof. A RT described herein such as a mlvRT may include a mutation such as a point mutation. The point mutation may be at position 221 of the reverse transcriptase. The mlvRT or variant thereof may comprise a point mutation at position 221. The point mutation at position 221 may comprise Q221R. The point mutation may be at position 223 of the reverse transcriptase. The mlvRT or variant thereof may comprise a point mutation at position 223. The point mutation at position 223 may comprise V223A. The point mutation at position 223 may comprise V223M.

Some embodiments include a method of optimizing genome editing efficiency, comprising performing genome editing with a Moloney leukemia virus reverse transcriptase (mlvRT) that is modified to increase its catalytic efficiency in low dNTP concentrations. For example, the mlvRT may be modified to decrease its Km for dNTPs.

A reverse transcriptase of the present disclosure may comprise one or more mutations. For example, a reverse transcriptase may comprise one or more mutations relative to a reference reverse transcriptase sequence (e.g., SEQ ID NO: 81). In some embodiments, a point mutation in a reverse transcriptase may increase the editing efficiency of a Cas9-RT construct relative to a reference sequence lacking the point mutation. A reverse transcriptase may comprise one or more mutations corresponding to D200N, I603W, T330P, T306K, W313F, Y8H, P51L, S56A, S67R, E69K, Q84A, F155Y, T197A, H204R, T246E, N249D, E286R, Q291I, R301L, E302K, F309N, M320L, L435G, D524A, D524G, D524L, E562D, K571R, D583N, Y586S, H594Q, H638G, D653N, T664N, L671P, Q221R, V223A, V223M, or combinations thereof, relative to SEQ ID NO: 81. A reverse transcriptase may comprise one or more mutations (e.g. point mutations) at amino acid position Q84, L139, Q221, V223, T664, L671, D524, P51, or S67. A reverse transcriptase may comprise one or more mutations (e.g. point mutations) corresponding to Q84A, L139P, Q221R, V223A, V223M, T664N, L671P, D524A, P51L, or S67R. The one or more mutations may be in relation to SEQ ID NO: 81 or another sequence identified herein. The one or more mutations may be in relation to an amino acid sequence at least 75%, identical at least 80%, identical at least 85%, identical at least 86%, identical at least 87%, identical at least 88%, identical at least 89%, identical at least 90%, identical at least 91%, identical at least 92%, identical at least 93%, identical at least 94%, identical at least 95%, identical at least 96%, identical at least 97%, identical at least 98%, identical or at least 99% identical, to SEQ ID NO: 81 or another sequence identified herein. In some embodiments, a reverse transcriptase may comprise mutations corresponding to D200N, I603W, T330P, T306K, and W313F (e.g., SEQ ID NO: 13 or SEQ ID NO: 40). In some embodiments, a reverse transcriptase may comprise mutations corresponding to D200N, I603W, T330P, T306K, and W313F and one or more additional mutations (e.g., SEQ ID NO: 41-SEQ ID NO: 80).

Figure 14A:
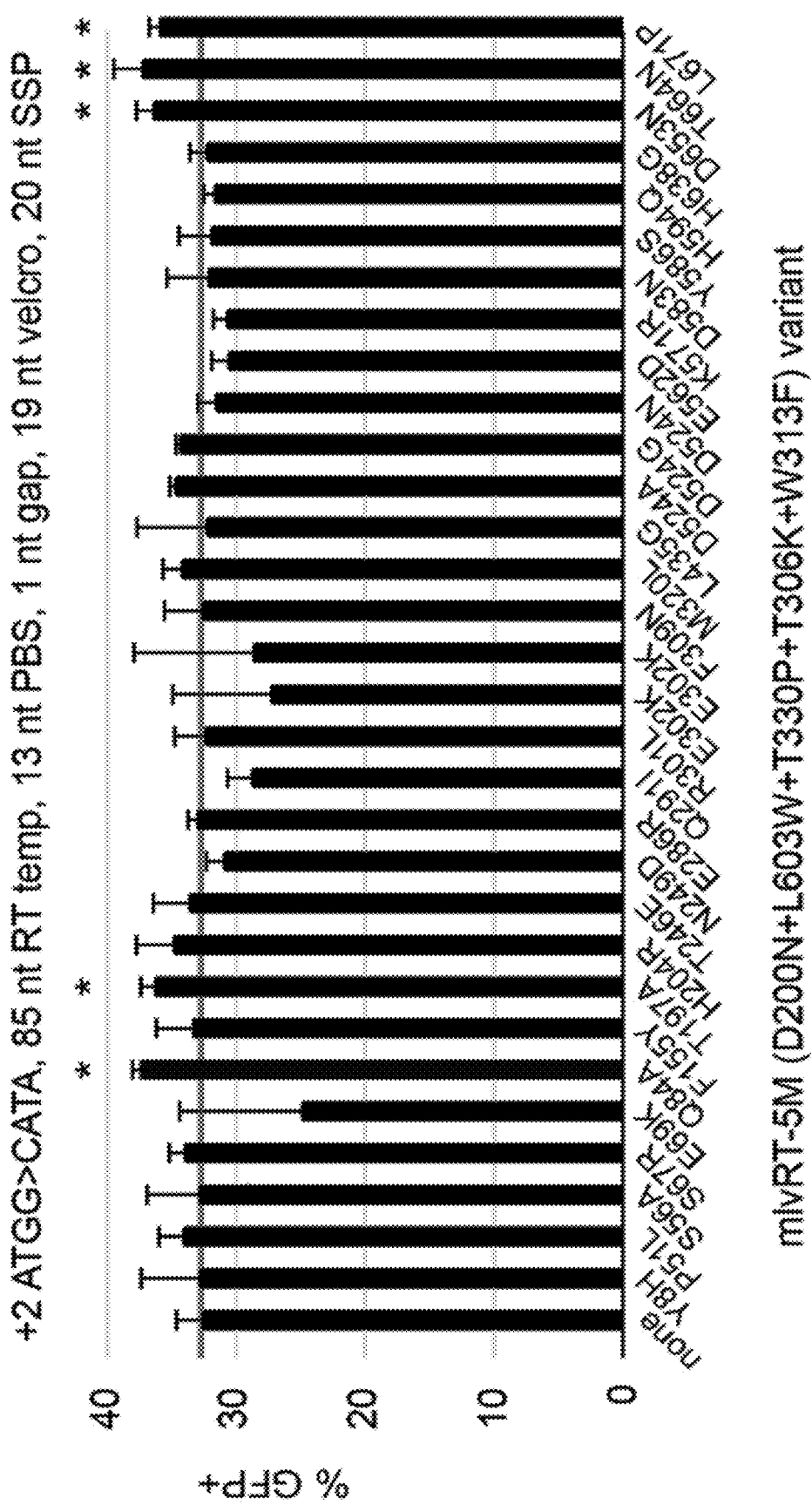
FIG. 14A shows the results of a screen for mutations in a mlvRT reverse transcriptase and their effect on editing efficiency. Mutations were made in a reference mlvRT construct containing five point mutations (D200N, I603W, T330P, T306K, and W313F, SEQ ID NO: 40). Amino acid residues are counted relative to an mlvRT construct lacking an N-terminal methionine (e.g., SEQ ID NO: 14). mlvRT constructs containing a Y8H, P51L, S56A, S67R, E69K, Q84A, F155Y, T197A, H204R, T246E, N249D, E286R, Q291I, R301L, E302K, F309N, M320L, L435G, D524A, D524G, D524N, E562D, K571R, D583N, Y586S, H594Q, H638G, D653N, T664N, or L671P single point mutation (SEQ ID NO: 41-SEQ ID NO: 70, respectively) relative to SEQ ID NO: 40 were tested. Editing efficiency was measured as a percent of cells that were GFP positive (% GFP+). Editing was performed using a gRNA with an 85 nucleotide RT template, a 13 nucleotide primer binding site, a 1 nucleotide gap, a 19 nucleotide Velcro region, and a 20 nucleotide second strand primer to edit a site such that an ATGG sequence, starting 2 nucleotides 3' of the nick, was mutated to CATA. Mutation rate data are shown as mean±one standard deviation from three biologically independent samples.
Figure 14B:
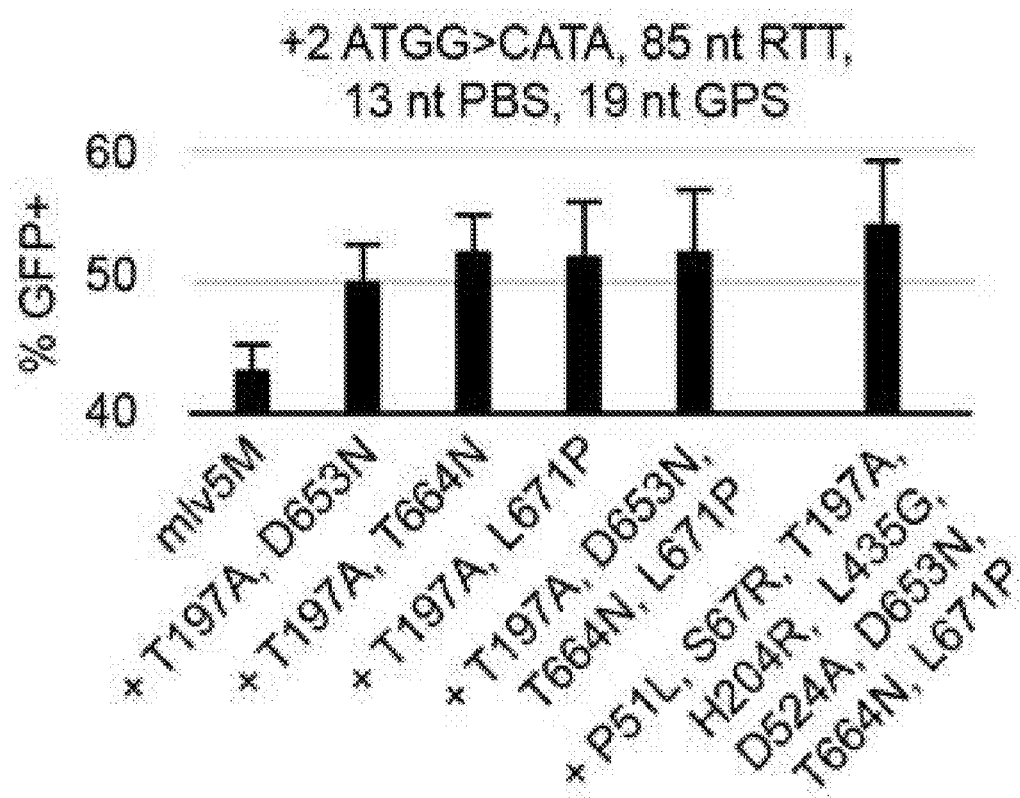
FIG. 14B shows the results of a screen for combinations of mutations in a mlvRT reverse transcriptase and their effect on editing efficiency. Mutations were made in a reference mlvRT construct containing five point mutations (D200N, I603W, T330P, T306K, and W313F, SEQ ID NO: 40). Amino acid residues are counted relative to an mlvRT construct lacking an N-terminal methionine (e.g., SEQ ID NO: 14). mlvRT constructs containing T197A and D653N; T197A and T664N; T197A and L671P; T197A, D653N, T664N and L671P; or P51L, S67R, T197A, H204R, L435G, D524A, D653N, T664N and L671P (SEQ ID NO: 71-SEQ ID NO: 75, respectively) relative to SEQ ID NO: 40 were tested. Editing efficiency was measured as a percent of cells that were GFP positive (% GFP+). Editing was performed using a gRNA with an 85 nucleotide RT template, a 13 nucleotide primer binding site, a 19 nucleotide Velcro region, and a 20 nucleotide second strand primer to edit a site such that an ATGG sequence, starting 2 nucleotides 3' of the nick, was mutated to CATA.

The RT may include one or more mutations included in FIG. 14B. For example, the RT may include a mutation at position 51, 67, 84, 139, 197, 204, 435, 524, 653, 664, or 671, or a combination thereof. The RT may include a mutation at position P51, S67, Q84, L139, Q221, V223, T197, D653, T664, L671, L435, H204, or D524, or a combination thereof. The RT may include mutations at position 51, 67, 84, 139, 197, 204, 435, 524, 653, 664, and 671. The mutation may include at least one point mutation. The at least one point mutation may be at P51L, S67R, Q84A, L139P, Q221R, V223A, V223M, T197A, D653N, T664N, L671P, L435G, H204R, or D524A, or a combination thereof. The RT may include a mutation at position 51. The mutation at position 51 may include P51L. The RT may include a mutation at position 67. The mutation at position 67 may include S67R. The RT may include a mutation at position 84. The mutation at position 84 may include Q84A. The RT may include a mutation at position 139. The mutation at position 139 may include L139P. The RT may include a mutation at position 197. The mutation at position 197 may include T197A. The RT may include a mutation at position 204. The mutation at position 204 may include H204R. The RT may include a mutation at position 435. The mutation at position 435 may include L435G. The RT may include a mutation at position 524. The mutation at position 524 may include D524A. The RT may include a mutation at position 653. The mutation at position 653 may include D653N. The RT may include a mutation at position 664. The mutation at position 664 may include T664N. The RT may include a mutation at position 671. The mutation at position 671 may include L671P. The RT may include, for example, 1, 2, 3, 4, 5, 6, 7, 8, 9, or 10, or more, of said mutations. The RT may include a mlvRT. The RT may include a mlvRT5M. The RT with the one or more mutations may comprise the one or more mutations with reference to a RT sequence provided herein. The one or more mutations may increase editing efficiency of a composition described herein, in relation to a composition without the one or more mutations. The mutation may be or include an insertion mutation. The reverse transcriptase comprises an insertion mutation immediately upstream (e.g. in the amino end direction) of P51, S67, Q84, L139, Q221, V223, T197, D653, T664, L671, L435, H204, or D524, or a combination thereof. The reverse transcriptase comprises an insertion mutation immediately downstream (e.g. in the carboxy end direction) of P51, S67, Q84, L139, Q221, V223, T197, D653, T664, L671, L435, H204, or D524, or a combination thereof. The insertion mutation may comprise an insertion of an amino acid disclosed herein for a point mutation, wherein the point mutation is to an amino acid.

In some embodiments, the reverse transcriptase has a point mutation at position P51, S67, Q84, L139, T197, D200, H204, Q221, V223, T306, W313, T330, L435, D524, D653, T664, L671, or L600, or a combination thereof. In some embodiments, the reverse transcriptase has a point mutation at position P51, S67, Q84, L139, Q221, V223, T197, D653, T664, L671, L435, H204, or D524, or a combination thereof. In some embodiments, the reverse transcriptase has a point mutation at position Q84, L139, Q221, V223, T664, or L671, or a combination thereof.

In some embodiments, the reverse transcriptase has a point mutation comprising P51L, S67R, Q84A, L139P, T197A, D200N, H204R, Q221R, V223A, V223M, T306K, W313F, T330P, L435G, D524A, D653N, T664N, L671P, or L603W, or a combination thereof. In some embodiments, the reverse transcriptase has a point mutation comprising P51L, S67R, Q84A, L139P, Q221R, V223A, V223M, T197A, D653N, T664N, L671P, L435G, H204R, or D524A, or a combination thereof. In some embodiments, the reverse transcriptase has a point mutation comprising S67R, Q84A, L139P, Q221R, V223A, V223M, T664N, L671P, or D524A, or a combination thereof.

A reverse transcriptase of the present disclosure may comprise a loop region (e.g., a 2a loop or a 3a loop). A reverse transcriptase of the present disclosure may transcribe an editing sequence of 20 or more, 40 or more, 45 or more, 50 or more, 60 or more, 81 or more, 100 or more, 500 or more, 1000 or more, 2000 or more, 3000 or more, 4000 or more, 5000 or more, 6000 or more, 7000 or more, 8000 or more, 9000 or more, or 10,000 or more nucleotides. A reverse transcriptase of the present disclosure may transcribe an editing sequence of up to about 20, up to about 40, up to about 45, up to about 50, up to about 60, up to about 81, up to about 100, up to about 500, up to about 1000, up to about 2000, up to about 3000, up to about 4000, up to about 5000, up to about 6000, up to about 7000, up to about 8000, up to about 9000, or up to about 10,000 nucleotides. A reverse transcriptase of the present disclosure may transcribe an editing sequence of from 20 to 10,000 nucleotides.

A reverse transcriptase of the present disclosure can have increased processivity. Processivity may be determined by the number of phosphodiester bonds catalyzed by the reverse transcriptase in a single binding event. The processivity may be compared to a native reverse transcriptase. The reverse transcriptase may comprise increased processivity compared to a mlvRT. A reverse transcriptase with increased processivity may edit longer sequences at a target site of a target nucleic acid. For example, a reverse transcriptase with increased processivity may increase the editing window length of a programmable nuclease. The reverse transcriptase may edit a longer window length in a target sequence compared to a mlvRT. A reverse transcriptase with increased processivity may comprise an insert sequence. In some embodiments, an insertion that increases processivity may be inserted into a reverse transcriptase between domains 2 and 3 or between domains 3 and 4. A reverse transcriptase with increased processivity may comprise a deletion. For example, a reverse transcriptase with increased processivity may lack an RNase domain or may lack a connect domain. A reverse transcriptase with increased processivity may catalyze 20 or more, 40 or more, 45 or more, 50 or more, 60 or more, 81 or more, 100 or more, 500 or more, 1000 or more, 2000 or more, 3000 or more, 4000 or more, 5000 or more, 6000 or more, 7000 or more, 8000 or more, 9000 or more, or 10,000 or more phosphodiester bonds in a single binding event. A reverse transcriptase with increased processivity may catalyze up to about 20, up to about 40, up to about 45, up to about 50, up to about 60, up to about 81, up to about 100, up to about 500, up to about 1000, up to about 2000, up to about 3000, up to about 4000, up to about 5000, up to about 6000, up to about 7000, up to about 8000, up to about 9000, or up to about 10,000 phosphodiester bonds in a single binding event.

In some embodiments, a reverse transcriptase edits a longer sequence at a target site of a target nucleic acid than mlvRT. The reverse transcriptase may increase the editing window length of a programmable nuclease. A reverse transcriptase that edits a longer sequence at a target site may comprise an insert sequence. In some embodiments, an insertion is inserted into a reverse transcriptase that edits a longer sequence at a target site between domains 2 and 3 or between domains 3 and 4. A reverse transcriptase that edits a longer sequence at a target site may comprise a deletion. For example, a reverse transcriptase that edits a longer sequence at a target site may lack an RNase domain or may lack a connect domain. A reverse transcriptase that edits a longer sequence at a target site may catalyze 20 or more, 40 or more, 45 or more, 50 or more, 60 or more, 81 or more, 100 or more, 500 or more, 1000 or more, 2000 or more, 3000 or more, 4000 or more, 5000 or more, 6000 or more, 7000 or more, 8000 or more, 9000 or more, or 10,000 or more phosphodiester bonds in a single binding event. A reverse transcriptase that edits a longer sequence at a target site may catalyze up to about 20, up to about 40, up to about 45, up to about 50, up to about 60, up to about 81, up to about 100, up to about 500, up to about 1000, up to about 2000, up to about 3000, up to about 4000, up to about 5000, up to about 6000, up to about 7000, up to about 8000, up to about 9000, or up to about 10,000 phosphodiester bonds in a single binding event. In some embodiments, the reverse transcriptase that edits a longer sequence at a target site also has increased processivity as described herein.

A reverse transcriptase of the present disclosure may be a small reverse transcriptase. A small reverse transcriptase may have improved delivery to a cell as compared to a larger reverse transcriptase. The reverse transcriptase may comprise improved delivery to a cell compared to a mlvRT. A small reverse transcriptase may have improved expression in a cell as compared to a larger reverse transcriptase. A small reverse transcriptase may comprise no more than about 400, no more than about 420, no more than about 427, no more than about 440, no more than about 450, no more than about 500, no more than about 550, no more than about 560, no more than about 599, no more than about 600, no more than about 650, no more than about 677, no more than about 682, no more than about 700, no more than about 750, no more than about 761, no more than about 762, no more than about 800, no more than about 850, no more than about 900, no more than about 901, no more than about 950, no more than about 1000, no more than about 1100, no more than about 1114, no more than about 1200, no more than about 1275, no more than about 1281, or no more than about 1300 amino acid residues. A construct of the present disclosure may comprise a small reverse transcriptase, a dimerization region, a localization region, or a combination thereof. A small reverse transcriptase may have increased processivity, edit a longer sequence at a target site, or a combination thereof.

A reverse transcriptase of the present disclosure may have a decreased immunogenicity as compared to a Moloney leukemia virus reverse transcriptase. A reverse transcriptase with decreased immunogenicity may also be a small reverse transcriptase, may have increased processivity, edit a longer sequence at a target site, or any combination thereof.

Disclosed herein are compositions comprising a Cas nickase or a Cas9 programmable nuclease. Examples of Cas nickases or Cas9 programmable nucleases that are consistent with the present disclosure include SpCas9 (SEQ ID NO: 32), SaCas9 (SEQ ID NO: 33), CjCas9 (SEQ ID NO: 34), GeoCas9 (SEQ ID NO: 35), HpaCas9 (SEQ ID NO: 36), and NmeCas9 (SEQ ID NO: 37). In some embodiments, the Cas nickase comprises a sequence at least 70%, at least 75%, at least 80%, at least 85%, at least 90%, at least 95%, at least 96%, at least 97%, at least 98%, at least 99%, or 100% identical to any one of SEQ ID NOs: 32-37. A Cas9 programmable nuclease of the present disclosure may comprise mutations, insertions, deletions, or truncations with respect to a native Cas9 programmable nuclease.

The Cas nickase may include a mutation. The mutation may enable or improve intein catalysis. The mutation may be an insertion mutation. The mutation may be a point mutation. The Cas nickase may include a cysteine point mutation. The cysteine point mutation may be located in a C-terminal half of the Cas nickase. A Cas9 described herein may include a cysteine point mutation in a C-terminal half of the Cas9. The cysteine point mutation may be located anywhere after amino acid position 574 of the Cas nickase. The mutation may be in an *S. Pyogenes* Cas9 nickase. The cysteine point mutation may comprise S1173. The cysteine point mutation may comprise D1079. The cysteine point mutation may comprise D1180.

The Cas9 nickase (an *S. Pyogenes* Cas9 nickase) may include a point mutation. The point mutation may enable intein catalysis. The point mutation may improve intein catalysis. In some embodiments, the point mutation comprises a cysteine point mutation, a serine point mutation, a threonine point mutation, or an alanine point mutation. In some embodiments, the point mutation comprises a cysteine point mutation. In some embodiments, the point mutation comprises a serine point mutation. In some embodiments, the point mutation comprises a threonine point mutation. In some embodiments, the point mutation comprises an alanine point mutation. In some embodiments, the point mutation is located at D1079. In some embodiments, the point mutation is located at D1125. In some embodiments, the point mutation is located at D1130. In some embodiments, the point mutation is located at G1133. In some embodiments, the point mutation is located at A1140. In some embodiments, the point mutation is located at I1168. In some embodiments, the point mutation is located at S1173. In some embodiments, the point mutation is located at D1180. In some embodiments, the point mutation is located at G1186. In some embodiments, the point mutation is located at L1203. In some embodiments, the point mutation is located at R1212. In some embodiments, the point mutation is located at D1079, D1125, D1130, G1133, A1140, I1168, S1173, D1180, G1186, L1203, or R1212 of the S. Pyogenes Cas9.

The Cas9 nickase (an S. Pyogenes Cas9 nickase) may include a insertion mutation. The insertion mutation may enable intein catalysis. The insertion mutation may improve intein catalysis. In some embodiments, the insertion mutation comprises a cysteine insertion mutation, a serine insertion mutation, a threonine insertion mutation, or an alanine insertion mutation. In some embodiments, the insertion mutation comprises a cysteine insertion mutation. In some embodiments, the insertion mutation comprises a serine insertion mutation. In some embodiments, the insertion mutation comprises a threonine insertion mutation. In some embodiments, the insertion mutation comprises an alanine insertion mutation. In some embodiments, the insertion mutation is located at amino acid position 1079. In some embodiments, the insertion mutation is located at amino acid position 1125. In some embodiments, the insertion mutation is located at amino acid position 1130. In some embodiments, the insertion mutation is located at amino acid position 1133. In some embodiments, the insertion mutation is located at amino acid position 1140. In some embodiments, the insertion mutation is located at amino acid position 1168. In some embodiments, the insertion mutation is located at amino acid position 1173. In some embodiments, the insertion mutation is located at amino acid position 1180. In some embodiments, the insertion mutation is located at amino acid position 1186. In some embodiments, the insertion mutation is located at amino acid position 1203. In some embodiments, the insertion mutation is located at amino acid position 1212. In some embodiments, the insertion mutation is located immediately before D1079, D1125, D1130, G1133, A1140, I1168, S1173, D1180, G1186, L1203, or R1212 of the S. Pyogenes Cas9.

The Cas nickase may comprise a sequence of any one of SEQ ID NO: 85-SEQ ID NO: 87 or SEQ ID NO: 90-SEQ ID NO: 92. In some embodiments, the Cas nickase comprises a sequence at least 70%, at least 75%, at least 80%, at least 85%, at least 90%, at least 95%, at least 96%, at least 97%, at least 98%, at least 99%, or 100% identical to any one of SEQ ID NO: 85-SEQ ID NO: 87 or SEQ ID NO: 90-SEQ ID NO: 92. The Cas nickase may be expressed as two or more segments. The cysteine point mutation may be located at the N-terminus of a C-terminal portion of the Cas nickase. A first segment may comprise a sequence of SEQ ID NO: 90.

Disclosed herein are compositions comprising a Cas nickase and a reverse transcriptase that do not include heterodimerization domains. For example, the Cas nickase and reverse transcriptase may not be engineered to heterodimerize. And yet, the Cas nickase and reverse transcriptase may heterodimerize and perform nucleic acid editing without said engineering or heterodimerization domains. The Cas nickase and the reverse transcriptase may include separate polypeptide chains.

Disclosed herein are compositions comprising a Cas nickase and a reverse transcriptase, or at least one polynucleotide encoding the Cas nickase and reverse transcriptase, wherein at least part of the Cas nickase and the reverse transcriptase are included in at least 2 separate polypeptide chains, wherein the at least 2 separate polypeptide chains comprise separate polypeptide chains comprising heterodimer domains that bind one another. The separate polypeptide chains may include fusion proteins comprising the heterodimer domains. The heterodimer domains may be fused to the separate polypeptide chains. The heterodimer domains may be fused to amino or carboxy ends of the separate polypeptide chains. A heterodimer domain may include a leucine zipper. A heterodimer domain may include a PDZ domain. A heterodimer domain may include streptavidin. A heterodimer domain may include a streptavidin binding protein. A heterodimer domain may include a foldon domain. A heterodimer domain may include a hydrophobic polypeptide. A heterodimer domain may include an antibody. A heterodimer domain may include a knob, a hole, a leucine zipper, a coiled coil, or a polar amino acid residue capable of forming an electrostatic interaction. A heterodimer domain may include any of heavy chain domain 2 (CH2) of IgM (MHD2) or IgE (EHD2), immunoglobulin Fc region, heavy chain domain 3 (CH3) of IgG or IgA, heavy chain domain 4 (CH4) of IgM or IgE, Fab, $Fab_2$, leucine zipper motifs, barnase-barstar dimers, miniantibodies, or ZIP miniantibodies. A heterodimer domain may include a fibritin foldon domain. A heterodimer domain may include a leucine zipper, foldon domain, fragment X, collagen domain, 2G12 IgG homodimer, mitochondrial antiviral-signaling protein CARD filament, Cardiac phospholamban transmembrane pentamer, parathyroid hormone dimerization domain, Glycophorin A transmembrane, HIV Gp41 trimerisation domain, or HPV45 oncoprotein E7 C-terminal dimer domain. A heterodimer domain may include an Fc domain. A heterodimer domain may include a leucine zipper domain, PSD95-Dlgl-zo-1 (PDZ) domain, streptavidin, streptavidin binding protein (SBP), FKBP binding domain (FRB) of mTOR, Cyclophilin-Fas fusion protein (CyP-Fas), Calcineurin A (CNA) and FK506 binding protein (FKBP), Snap tag, Halo tag, PYL or ABI. A heterodimer domain may include a binding fragment of a heterodimer domain described hererin.

Expression of Split Cas9 Constructs Using Intein Technology

In some embodiments, a Cas9 construct (e.g., a Cas9-RT) may be expressed as split construct as one or more exteins fused to one or more inteins. Intein technology may be used to deliver large proteins into a cell by expressing the protein as two or more shorter peptide segments (exteins). Each extein may be expressed as a fusion with an intein peptide (e.g., an Npu C intein or an Npu N intein). An intein may autocatalyze fusion of two or more exteins and may autocatalyze excision of the intein from its corresponding extein. The result may be a protein complex comprising a first extein fused to a second extein and lacking inteins. An intein may be positioned N-terminal of the extein, or an intein may be positioned C-terminal of the extein. An extein may comprise a cysteine residue positioned adjacent to the intein (e.g., at the C-terminal end of an extein with an intein fused to the C-terminal end of the extein). The Cas nickase may be expressed as two or more segments. A first of the Cas nickase segment may comprise an N-terminal portion of the Cas nickase. A first segment of the Cas nickase may comprise a first intein. A second segment of the Cas nickase may comprise a C-terminal portion of the Cas nickase. A second segment of the Cas nickase may comprise a second intein. An intein may be fused to a C-terminus of an N-terminal portion of the Cas nickase. An intein may be fused to an N-terminus of a C-terminal portion of the Cas nickase.

A nucleic acid sequence encoding an extein-intein fusion may fit into a delivery vector (e.g., an adeno-associated virus (AAV) vector). In some embodiments, a vector encoding a peptide segment extein fused to an intein may be delivered to a cell. In some embodiments, the extein-intein fusion may be expressed in a cell. A first extein-intein fusion peptide may be fused to one or more additional extein-intein fusion peptide, and the inteins may be excised to produce a large protein construct lacking inteins. In some embodiments, a protein may comprise a point mutation to introduce a cysteine residue to facilitate extein fusion and intein excision. In some embodiments, a Cas9-RT of the present disclosure may be expressed as two or more extein-intein fusion peptides. In some embodiments, a Cas9 of the present disclosure (e.g., SEQ ID NO: 32-SEQ ID NO: 37 or SEQ ID NO: 84-SEQ ID NO: 87) may be expressed in conjunction with a reverse transcriptase of the present disclosure (e.g., SEQ ID NO: 3-SEQ ID NO: 22 or SEQ ID NO: 40-SEQ ID NO: 80) as two or more extein-intein fusion peptides to produce a Cas9-RT fusion. For example, a Cas9-RT may be expressed as a first Cas9-RT extein-fusion comprising nCas9 (1-1172) —Npu N intein and a second Cas9-RT extein-fusion comprising Npu C intein—nCas9(1173-1368) —mlvRT5M. nCas9(1-1172) may correspond to residues 1-1172 of a nicking Cas9 (e.g., residues 1-1172 of any one of SEQ ID NO: 84-SEQ ID NO: 87). nCas9(1173-1368) may correspond to residues 1173-1368 of a nicking Cas9 with a cysteine at position 1173 (e.g., residues 1-1172 of SEQ ID NO: 86). mlvRT5M may correspond to a reverse transcriptase comprising 5 point mutations (e.g., SEQ ID NO: 13 or SEQ ID NO: 40). A segment may comprise a sequence of SEQ ID NO: 91. The segment may comprise a reverse transcriptase fused to a Cas nickase (e.g. the C-terminal portion of the Cas nickase). The reverse transcriptase may comprise an N-terminus fused to a C-terminus of the C-terminal portion of the Cas nickase. The reverse transcriptase may comprise an mlvRT, or a variant thereof.

Guide Nucleic Acids

Provided herein are guide nucleic acids (e.g., gRNAs) that direct a programmable nuclease (e.g., a nCas9) to a target nucleic acid. A guide nucleic acid of the present disclosure may facilitate synthesis of a nucleic acid sequence to be inserted into a target site of the target nucleic acid. A guide nucleic acid of the present disclosure may facilitate editing of a nucleic acid sequence at a target site of the target nucleic acid.

In some embodiments, a guide nucleic acid of the present disclosure may comprise a spacer reverse complementary to a first region of a target nucleic acid, a scaffold configured to bind to a Cas nickase, a reverse transcriptase template encoding a sequence to be incorporated into the target nucleic acid (RTT), a first strand primer binding site reverse complementary to a second region of the target nucleic acid, a second strand primer comprising a sequence of a region of the reverse transcriptase template, or a combination thereof. In some embodiments, the first region of the target nucleic acid is on a first strand of the target nucleic acid and the second region of the target nucleic acid is on the second strand of the target nucleic acid. In some embodiments, all or part of the first region of the target nucleic acid is reverse complementary to all or part of the second region of the target nucleic acid. In some embodiments, the first strand primer binding site is configured to hybridize to the second region of the target nucleic acid. In some embodiments, the reverse transcriptase template is configured to serve as a template for reverse transcription from a 3' end of the second region of the target nucleic acid. In some embodiments, the second strand primer is configured to serve as a primer for transcription from a template reverse complementary to the reverse transcriptase template. In some embodiments, the first synthesized strand may be the template for synthesis of a second strand from the second strand primer.

A guide nucleic acid of the present disclosure may comprise an RTT. This way, a nucleic acid sequence that gets inserted may have a mutation in the PAM. This can prevent re-editing of an already inserted nucleic acid sequence. The RTT may comprise a modification that disrupts a protospacer adjacent motif (PAM) sequence. The RTT may comprise two or more modifications that disrupt one or more PAM sequences. The modification may comprise a sequence that is partially complementary with the PAM sequence. The modification may comprise a mismatch with the PAM sequence. The PAM sequence may be disrupted in a target nucleic acid. The target nucleic acid may include a naturally occurring PAM sequence prior to the disruption. The PAM sequence may comprise a 2-6 base pair nucleic acid sequence. An example of PAM sequences is 5'-NGG-3'. Other examples of PAM sequences include 5'-TTTN-3' or 5'-YTN-3'. Any of these PAM sequences may be modified in the RTT. Some examples of such modifications may include an insertion, a deletion, or a point mutation. A PAM sequence may be recognized by a Cas nickase. A modified or disrupted PAM sequence may not be recognized by the Cas nickase in some cases. The modification may comprise a sequence that disrupts or eliminates the PAM in the genome.

The reverse transcriptase template may comprise a modification that disrupts a mononucleotide track in the genome. The modification may comprise a sequence that is partially complementary with the mononucleotide track. The modification may comprise a mismatch with the mononucleotide track. The reverse transcriptase template may comprise two or more modifications that disrupt one or more mononucleotide tracks in the genome. The modification may comprise a sequence that disrupts or eliminates the mononucleotide track in the genome. The guide nucleic acid may comprise one or more modifications in the reverse transcriptase template that eliminate one or more tracks of at least 4 consecutive nucleotides of the same base in the target nucleic acid.

A target nucleic acid may include polyA tracks or long polyA tracks. An RTT may include long of polyA tracks. Introducing a modification in the RTT to disrupt the polyA track may improve an editing efficiency. In some embodiments, the RTT further comprises one or more modifications that eliminate or modify tracks of at least 4 consecutive nucleotides that are the same nucleotide base. The one or more modifications in the reverse transcriptase template may eliminate one or more tracks of consecutive nucleotides (e.g. at least 4 consecutive nucleotides) of the same base in the target nucleic acid. The RTT may comprises a modification that eliminates 4 or more consecutive A nucleotides. The RTT may comprises a modification that eliminates 4 or more consecutive T nucleotides. The RTT may comprises a modification that eliminates 4 or more consecutive G nucleotides. The RTT may comprises a modification that eliminates 4 or more consecutive C nucleotides. The RTT may comprises a modification that eliminates 4 or more consecutive U nucleotides. The RTT may comprises a modification that eliminates 3 or more consecutive nucleotides, wherein the 3 or more consecutive nucleotides all comprise the same nucleobase as each other. The RTT may comprises a modification that eliminates 4 or more consecutive nucleotides, wherein the 4 or more consecutive nucleotides all comprise the same nucleobase as each other. The RTT may comprises a modification that eliminates 5 or more consecutive nucleotides, wherein the 5 or more consecutive nucleotides all comprise the same nucleobase as each other. The RTT may comprises a modification that eliminates 6 or more consecutive nucleotides, wherein the 6 or more consecutive nucleotides all comprise the same nucleobase as each other. The RTT may comprises a modification that eliminates 7 or more consecutive nucleotides, wherein the 7 or more consecutive nucleotides all comprise the same nucleobase as each other. The RTT may comprises a modification that eliminates 8 or more consecutive nucleotides, wherein the 8 or more consecutive nucleotides all comprise the same nucleobase as each other. The RTT may comprises a modification that eliminates 5, 6, 7, 8, 9, 10, or more consecutive nucleotides that include the same base. The RTT may comprises a modification that modifies 4, 5, 6, 7, 8, 9, 10, or more consecutive nucleotides that include the same base in a row to no longer comprise the consecutive nucleotides that include the same base in a row.

The modification may comprise a mutation in relation to an unmodified guide nucleic acid. The mutation may be a silent mutation. In some cases, the mutation is not a silent mutation.

Figure 8A:
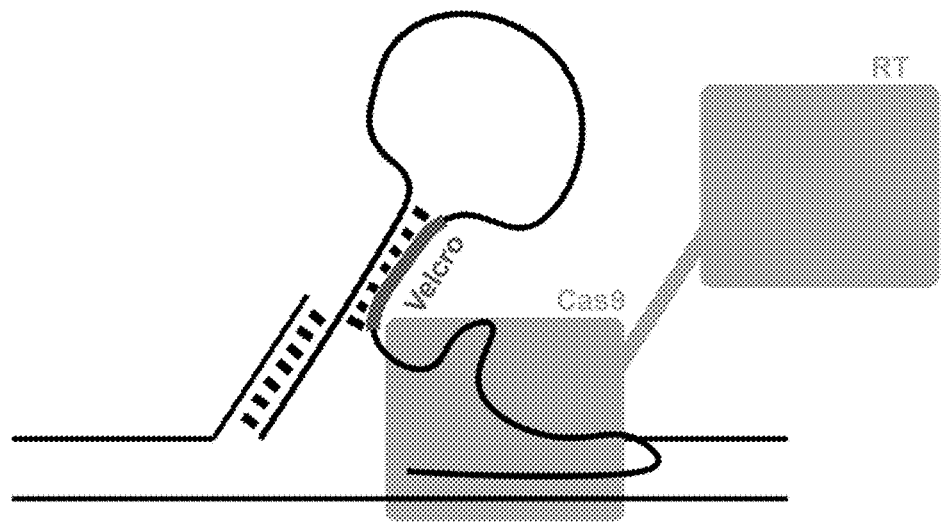
FIG. 8A illustrates a gRNA comprising a Velcro region to accelerate the rate of hybridization of the primer binding site and the flap by creating regions of reverse complementation within the 3' extended guide RNA. The Velcro region comprises 5 to 200 nucleotides positioned 5' of the reverse transcriptase template region that are reverse complementary to the region of the gRNA 5' of the first strand primer binding site.
Figure 8B:
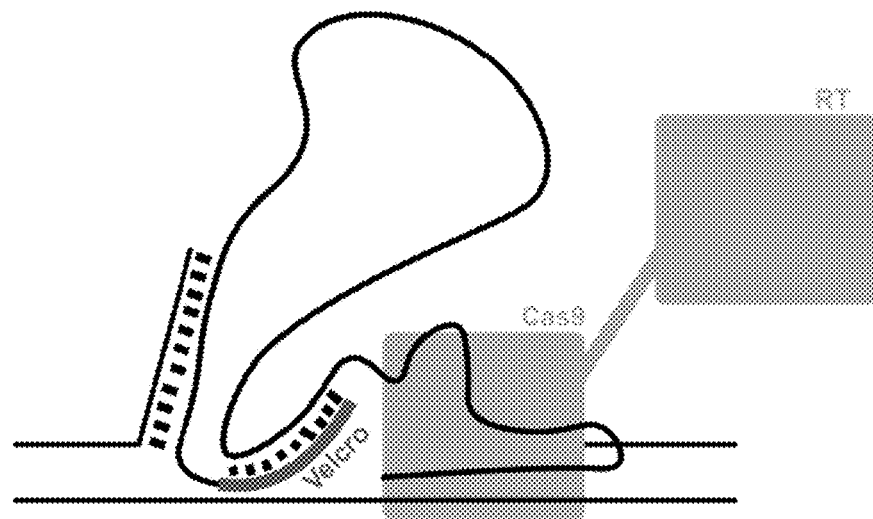
FIG. 8B illustrates a gRNA comprising a Velcro region to accelerate the rate of hybridization of the primer binding site and the flap by creating regions of reverse complementation within the 3' extended guide RNA. The Velcro region comprises 5 to 100 nucleotides positioned 3' of the first strand primer binding site that are reverse complementary to a region of the reverse transcriptase template region.

The guide nucleic acid may comprise a region that binds to itself another region on the guide nucleic acid to improve gene editing. A guide nucleic acid of the present disclosure may comprise a Velcro region. The Velcro region may comprise a region of the guide nucleic acid that binds to another region of the guide nucleic acid referred to as a "Velcro binding site." For example, the Velcro region may comprise a region of the guide nucleic acid that binds to another region of the guide nucleic acid to improve gene editing. The binding of the Velcro region to a Velcro binding site may alter a structure of the guide nucleic acid. The altered structure of the guide nucleic acid by the binding of the Velcro region to the Velcro binding site may improve gene editing. The guide nucleic acid may comprise a gRNA positioning system (GPS). The Velcro region or GPS may hybridize to a region of the gRNA (e.g. a Velcro binding site or a GPS binding site). The Velcro region or GPS may hybridize to a region of the reverse transcriptase template. "Velcro" and "GPS" may be used interchangeably. For example, a "Velcro region" may be referred to as a "GPS region," or vice versa; or a "Velcro binding site" may be referred to as a "GPS binding site," or vice versa. The Velcro region may hybridize to a region of the reverse transcriptase template region. A gRNA comprising a Velcro region may include a second strand primer. A gRNA comprising a Velcro region may comprise a spacer, a scaffold region, a Velcro region, a RT template, a SSP, a ribozyme, or a combination thereof. For example, a gRNA comprising a Velcro region may comprise a spacer, a scaffold region, a Velcro region, a RT template, a SSP, and a ribozyme. A gRNA comprising a Velcro region may comprise a spacer, a scaffold region, a RT template, a Velcro region, a SSP, a ribozyme, or a combination thereof. For example, a gRNA comprising a Velcro region may comprise a spacer, a scaffold region, a RT template, a Velcro region, a SSP, and a ribozyme. A gRNA comprising a Velcro region may comprise a spacer, a scaffold region, a RT template, a Velcro region, a SSP, a ribozyme, or a primer binding site (PBS), or a combination thereof. For example, a gRNA comprising a Velcro region may comprise a spacer, a scaffold region, a RT template, a Velcro region, a SSP, a ribozyme, and a PBS. Examples of gRNAs comprising Velcro regions are shown in FIG. 8A and FIG. 8B and in FIG. 12A and FIG. 12B. The Velcro region may facilitate reverse transcription of a nucleic acid sequence to be inserted into a target nucleic acid at a target site.

The guide nucleic acid comprising a GPS region may comprise a guide RNA. The guide nucleic acid comprising a GPS region may comprise a guide nucleic acid other than a guide RNA. The guide nucleic acid comprising a GPS binding site may comprise a guide RNA. The guide nucleic acid comprising a GPS binding site may comprise a guide nucleic acid other than a guide RNA.

The Velcro region may be synthetic. A Velcro binding site may be synthetic. The Velcro region and the Velcro binding site may be inserted into a gRNA. For example, a synthetic Velcro binding site may be included in a gRNA 5' of a RT template in a gRNA.

Disclosed herein, in some embodiments, are Velcro regions or Velcro binding sites. In some embodiments, a nucleic acid comprises a Velcro region. In some embodiments, one or more viral vectors (e.g. adenoviruses) comprises the nucleic acid comprising the Velcro region. In some embodiments, a cell comprises the nucleic acid comprising the Velcro region. In some embodiments, a guide nucleic acid comprises a Velcro region. The Velcro region may hybridize to a Velcro binding site. In some embodiments, the Velcro binding site is reverse complementary to the Velcro region. In some embodiments, the Velcro binding site is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% reverse complementary to the Velcro region. In some embodiments, the Velcro binding site is at least 50%, at least 55%, at least 60%, at least 65%, at least 70%, or at least 75% reverse complementary to the Velcro region. In some embodiments, the Velcro binding site is at least 50% reverse complementary to the Velcro region. In some embodiments, the Velcro binding site is at least 60% reverse complementary to the Velcro region. In some embodiments, the Velcro binding site is at least 70% reverse complementary to the Velcro region. In some embodiments, the Velcro binding site is at least 80% reverse complementary to the Velcro region. In some embodiments, the Velcro binding site is at least 90% reverse complementary to the Velcro region. In some embodiments, the Velcro binding site is 100% reverse complementary to the Velcro region. In some embodiments, the reverse transcriptase template region comprises the Velcro binding site. In some embodiments, the Velcro binding site is 3' of a primer binding site (e.g. a first strand primer binding site, or a second strand primer binding site). In some embodiments, the Velcro binding site is 5' of a primer binding site. In some embodiments, the Velcro region is 3' of a reverse transcriptase template. In some embodiments, the Velcro region is 5' of a reverse transcriptase template. In some embodiments, the Velcro region is 5' of a scaffold. In some embodiments, the Velcro region is 3' of a scaffold. In some embodiments, the scaffold is complementary to a target nucleic acid (e.g. a CFTR nucleic acid, a USH2A nucleic acid, an ABCA4 nucleic acid, an ATP7B nucleic acid, or an HTT nucleic acid). In some embodiments, a synthetic Velcro sequence is inserted between the scaffold and RTT that binds to a sequence that is rev comp to a synthetic Velcro binding site that is inserted after the PBS. In some embodiments, a Velcro region binds to another Velcro region. In some embodiments, the Velcro region hybridizes to a region of a guide nucleic acid that is not the PAM-proximal 20 nucleotides of the spacer sequence.

In some embodiments, the Velcro binding site is partially reverse complementary to the Velcro region. Perfect complementarity may, in some cases, contribute to truncated AAV genomes, so introducing some bulges or imperfect complementarity may help retain a benefit of GPS without disrupting AAV packaging. AAV genome packaging may in, some instances, be disrupted by secondary structures. GPS may introduce a disruptive secondary structure. Therefore, reducing the degree of complementarity between GPS and the GPS binding site offers a route to eliminate disruption of AAV packaging by GPS. In some embodiments, the Velcro binding site is less than 50%, less than 55%, less than 60%, less than 65%, less than 70%, less than 75%, less than 80%, less than 85%, less than 90%, less than 91%, less than 92%, less than 93%, less than 94%, less than 95%, less than 96%, less than 97%, less than 98%, less than 99%, or less than 100% reverse complementary to the Velcro region. In some embodiments, the Velcro binding site is less than 80%, less than 85%, less than 90%, less than 91%, less than 92%, less than 93%, less than 94%, less than 95%, less than 96%, less than 97%, less than 98%, less than 99%, or less than 100% reverse complementary to the Velcro region. In some embodiments, the Velcro binding site is less than 70% reverse complementary to the Velcro region. In some embodiments, the Velcro binding site is less than 80% reverse complementary to the Velcro region. In some embodiments, the Velcro binding site is less than 90% reverse complementary to the Velcro region. Some embodiments include a range of reverse complementarity defined by any two percentages disclosed herein.

Figure 26:
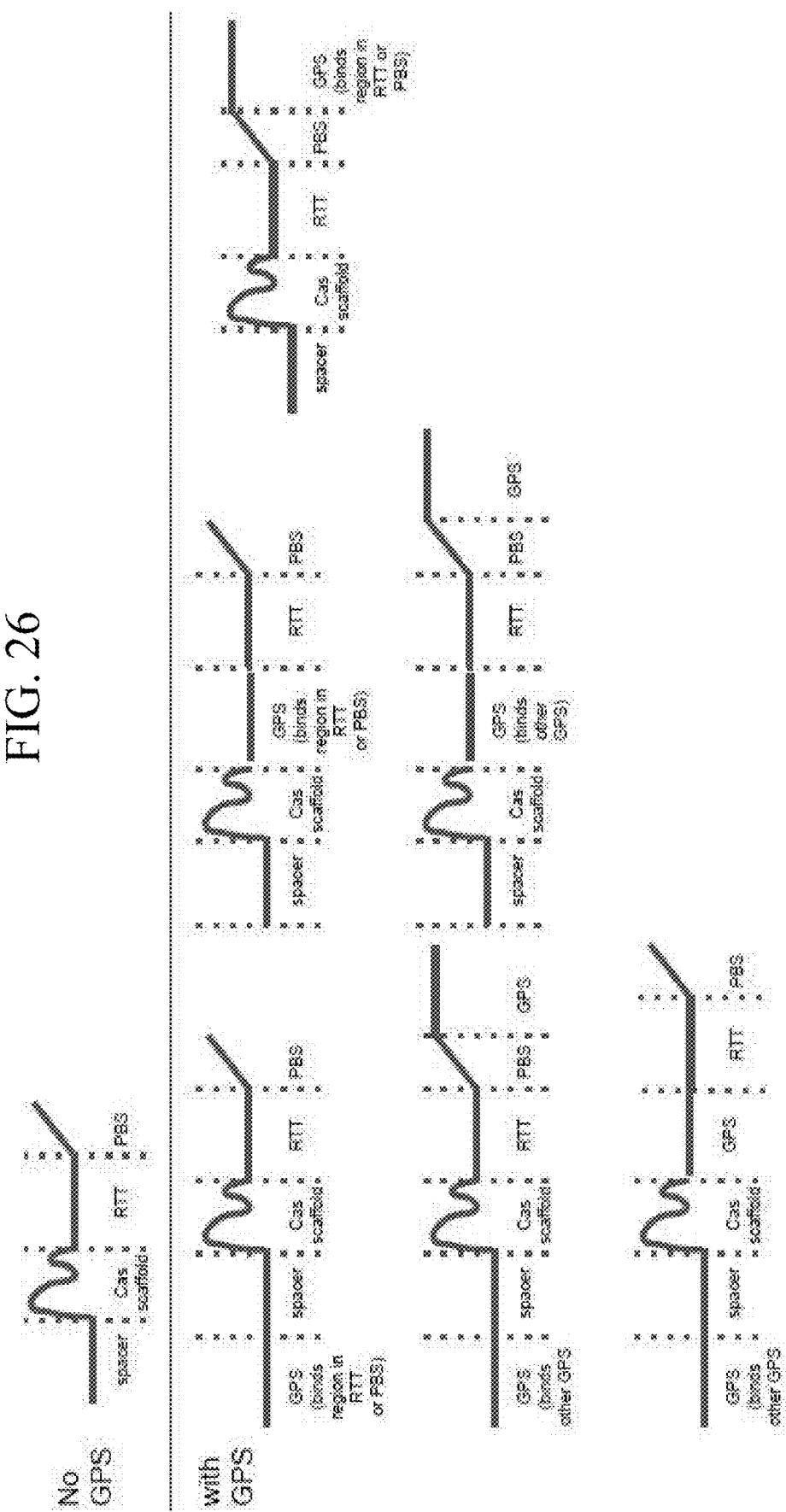
FIG. 26 shows exemplary configurations of Velcro (also referred to as GPS) in a guide nucleic acid.

Non-limiting exemplary configurations of a Velcro region are shown in FIG. 26. The GPS region may be in any configuration within the guide nucleic acid. The GPS region may be at a 5' end of the guide nucleic acid. The GPS region may be 5' to a spacer. The GPS region may be 5' to and adjacent to a spacer. The GPS region may be 5' to a scaffold. The GPS region may be 5' to and adjacent to a scaffold. The GPS region may be 5' to an RTT. The GPS region may be 5' to and adjacent to an RTT. The GPS region may be 5' to a PBS. The GPS region may be 5' to and adjacent to a PBS. The GPS region may be at a 3' end of the guide nucleic acid. The GPS region may be 3' to a spacer. The GPS region may be 3' to and adjacent to a spacer. The GPS region may be 3' to a scaffold. The GPS region may be 3' to and adjacent to a scaffold. The GPS region may be 3' to an RTT. The GPS region may be 3' to and adjacent to an RTT. The GPS region may be 3' to a PBS. The GPS region may be 3' to and adjacent to a PBS. The GPS region may within a scaffold. The GPS region may be within an RTT. The GPS region may be within a PBS. Some embodiments include a second GPS region. The second GPS region may be at any of the aforementioned positions. The second GPS region may hybridize to a second GPS binding site. The GPS region may hybridize to the second GPS region.

A GPS region may comprise a length of nucleotides. For example, the GPS region may be 5-100 nucleotides in length, or about 5-100 nucleotides in length. The GPS region may be 10-50 nucleotides in length, or about 10-50 nucleotides in length. The GPS region may include 5, 10, 15, 20, 25, 30, 35, 40, 45, 50, 55, 60, 65, 70, 75, 80, 85, 90, 95, or 100, or more nucleotides, or a range of nucleotides defined by any two of the aforementioned numbers. The GPS region may include at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, or at least 100 nucleotides. In some cases, the GPS region includes no more than 5, no more than 10, no more than 15, no more than 20, no more than 25, no more than 30, no more than 35, no more than 40, no more than 45, no more than 50, no more than 55, no more than 60, no more than 65, no more than 70, no more than 75, no more than 80, no more than 85, no more than 90, no more than 95, or no more than 100 nucleotides. The GPS region may be 20 nucleotides long. The GPS region may be about 20 nucleotides long.

The GPS region may hybridize to a GPS binding site. The GPS region may be complementary to the GPS binding site. The GPS region may be 100% complementary to the GPS binding site. The GPS region may be at least 50%, at least 60%, at least 70%, at least 80%, at least 85%, at least 90%, at least 91%, at least 92%, at least 93%, at least 94%, at least 95%, at least 96%, at least 97%, at least 98%, or at least 99%, complementary to the GPS binding site. The GPS region may be less than 50%, less than 60%, less than 70%, less than 80%, less than 85%, less than 90%, less than 91%, less than 92%, less than 93%, less than 94%, less than 95%, less than 96%, less than 97%, less than 98%, or less than 99%, complementary to the GPS binding site.

The GPS region may be at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, or 100% complementary to a portion of the GPS binding site. The portion may comprise at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, or at least 100 nucleotides. The portion may comprise less than 5, less than 10, less than 15, less than 20, less than 25, less than 30, less than 35, less than 40, less than 45, less than 50, less than 55, less than 60, less than 65, less than 70, less than 75, less than 80, less than 85, less than 90, less than 95, or less than 100 nucleotides.

The GPS region may be less than 50%, less than 60%, less than 70%, less than 80%, less than 85%, less than 90%, less than 91%, less than 92%, less than 93%, less than 94%, less than 95%, less than 96%, less than 97%, less than 98%, less than 99%, or 100% complementary to a portion (or a second portion) of the GPS binding site. The portion (or second portion) may comprise at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, or at least 100 nucleotides. The portion (or second portion) may comprise less than 5, less than 10, less than 15, less than 20, less than 25, less than 30, less than 35, less than 40, less than 45, less than 50, less than 55, less than 60, less than 65, less than 70, less than 75, less than 80, less than 85, less than 90, less than 95, or less than 100 nucleotides.

In some examples, the GPS region is complementary to 5-10 nucleotides of the GPS binding site. In some examples, the GPS region is at least 80% complementary to 5-10 nucleotides of the GPS binding site. In some examples, the GPS region is complementary to 11-100 nucleotides of the GPS binding site. In some examples, the GPS region is at least 80% complementary to 11-100 nucleotides of the GPS binding site.

Figure 13A:
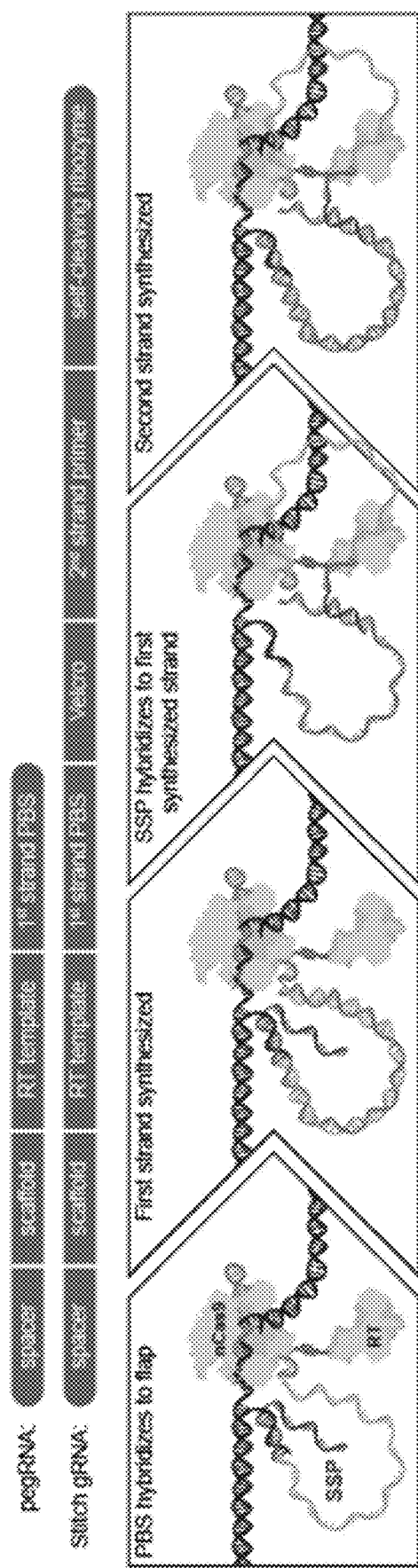
FIG. 13A illustrates schematics of a pegRNA and a Stitch gRNA comprising a Velcro region and a $2^{nd}$ strand primer (top) and a method of genome editing using a Stitch gRNA (bottom). A nCas9-RT construct complexed with a gRNA is recruited to a target site of a target nucleic acid by hybridization of a spacer of the gRNA to the target site. The nCas9 nicks a strand of a target nucleic acid at a target site. A first strand primer binding site of the gRNA hybridizes to a flap 5' of the nick. The RT polymerizes from the 3' end of the flap using a reverse transcriptase template region of the gRNA as a template. A second strand primer ("2$^{nd}$ strand primer") at the 3' end of the gRNA hybridizes to the 3' end of the newly synthesized DNA strand. The 4-200 bp second strand primer region acts as an RNA primer for synthesis of a second DNA strand. The RT polymerizes from the 3' end of the gRNA using the newly synthesized DNA strand as a template. A ribozyme on the 3' end of the gRNA cleaves the gRNA 3' of the second strand primer sequence. The newly synthesized double stranded DNA may be incorporated into the target nucleic acid at the site of the nick.

In some embodiments, a gRNA of the present disclosure may comprise a self-cleaving ribozyme, for example as shown in FIG. 13A. In some embodiments, a second strand primer region of a gRNA may comprise 100% sequence complementarity to a template region positioned on the first synthesized strand. In some embodiments, transcription of the second strand primer may produce a poly-U sequence (e.g., UUUUU) at the 3' end of the gRNA and 3' of the second strand primer. Presence of the poly-U sequence immediately 3' of the second strand primer may inhibit function of the second strand primer. A ribozyme sequence may be included in the gRNA to prevent formation of the poly-U sequence immediately 3' of the second strand primer. The ribozyme may autocatalytically cleave itself off of the gRNA. In some embodiments, the ribozyme may be positioned 3' of the second strand primer. The ribozyme positioned 3' of the second strand primer may autocatalytically cleave itself from the gRNA, leaving an in-tact second strand primer without a poly-U sequence. Inclusion of a ribozyme (e.g., an HDV ribozyme) 3' of the second strand primer may enable 100% complementarity of the second strand primer to the template without formation of a poly-U sequence immediately 3' of the second strand primer that inhibits second strand primer function. In some embodiments, a gRNA comprising a self-cleaving ribozyme may have the self-cleaving ribozyme sequence positioned 3' of the second strand primer. In some embodiments, the ribozyme (e.g., an HDV ribozyme) may leave a 2'3' cyclic phosphate at the 3' end of the gRNA following autocatalytic cleavage of the ribozyme. The 2'3' cyclic phosphate may inhibit function of the second strand primer. The 2'3' cyclic phosphate may be converted to a 3' hydroxyl using a polynucleotide kinase. In some embodiments, the polynucleotide kinase is an endogenous polynucleotide kinase present in a cell expressing a gRNA. In some embodiments, the polynucleotide kinase is exogenously expressed.

In some embodiments, a tRNA may be fused to the gRNA in place of the ribozyme to prevent formation of the poly-U sequence immediately 3' of the second strand primer. In some embodiments, the tRNA may be positioned 3' of the second strand primer. An RNase P enzyme may cleave the tRNA from the rest of the gRNA sequence. In some embodiments, the RNase P may cleave the tRNA from the 3' end of the second strand primer, leaving a 3' hydroxyl at the 3' end of the second strand primer. In some embodiments, the RNase P is an endogenous RNase P present in a cell expressing the gRNA. In some embodiments, the RNase P is exogenously expressed. In some embodiments, a gRNA comprising a tRNA may have the tRNA sequence positioned 3' of the second strand primer. The tRNA may have a sequence corresponding to any tRNA recognized by RNase P. In some embodiments, the tRNA may comprise a sequence of SEQ ID NO: 94.

The guide nucleic acid may include a spacer. The spacer may be reverse complementary to a first region of a target nucleic acid. The guide nucleic acid may include a scaffold. The scaffold may bind a Cas nickase. The guide nucleic acid may include a reverse transcriptase template. The reverse transcriptase template may encode a sequence to be inserted into a target nucleic acid. The guide nucleic acid may include a first strand primer binding site. The first strand primer binding site may be reverse complementary to a second region of the target nucleic acid. The guide nucleic acid may comprise a second strand primer. The second strand primer may include a sequence of a region of the reverse transcriptase template.

Disclosed herein, in some embodiments, are guide nucleic acids comprising a scaffold. The scaffold may bind a nuclease. The scaffold may bind a Cas nuclease. The scaffold may bind a nickase. The scaffold may bind a Cas nickase. The scaffold may bind an *S. Pyogenes* Cas9 nuclease. The scaffold may bind an *S. Pyogenes* Cas9 nickase. The scaffold may include a scaffold nucleic acid sequence. The scaffold nucleic acid sequence may include the sequence of SEQ ID NO: 139. The scaffold nucleic acid sequence may include a sequence that is at least 75% identical, at least 80% identical, at least 85% identical, at least 90% identical, or at least 95% identical, to the sequence of SEQ ID NO: 139.

Disclosed herein, in some embodiments, are guide nucleic acids (e.g. a gRNA). The guide nucleic acid may comprise an extension. The extension may be at a 5' end of the guide nucleic acid. The extension may be at a 3' end of the guide nucleic acid. The guide nucleic acid may comprise a scaffold comprising the extension. The extension may be on a 3' end of the scaffold. The extension may comprise a reverse transcriptase template. The extension may comprise a primer binding site. The extension may contain a reverse transcriptase template and a primer binding site. The primer binding site of the extension may hybridize to a genomic flap generated by a nuclease or nickase. The extension may be oriented using a Velcro region. The extension may be oriented using a Velcro binding site. The extension may be oriented using a Velcro region and a Velcro binding site. The extension may comprise the Velcro region. The Velcro region (and, for example, binding of the Velcro region to the Velcro binding site) may spatially orient the primer binding site to be near the genomic flap. The extension may comprise the Velcro binding region. The guide nucleic acid may include a Velcro region outside of the extension. The guide nucleic acid may include a Velcro binding region outside of the extension.

The first region of the target nucleic acid may be on a first strand of a target nucleic acid. The second region of the target nucleic acid may be on a second strand of the target nucleic acid. All of the first region of the target nucleic acid may be reverse complementary to all of the second region of the target nucleic acid. All of the first region of the target nucleic acid may be reverse complementary to part of the second region of the target nucleic acid. Part of the first region of the target nucleic acid may be reverse complementary to all of the second region of the target nucleic acid. Part of the first region of the target nucleic acid may be reverse complementary to part of the second region of the target nucleic acid.

The guide nucleic acid may comprise a cleavable sequence. The cleavable sequence may be at a 3' end of the guide nucleic acid. The cleavable sequence may be at a 5' end of the guide nucleic acid. The cleavable sequence may comprise a ribozyme cleavable sequence. The cleavable sequence may comprise a tRNA cleavable sequence. The gRNA may include a self cleaving ribozyme such as a HDV ribozyme. The ribozyme may be 3' of a second strand primer (SPP). A tRNA (e.g. a human glutamate tRNA) may be incorporated after the SPP in place of the ribozyme, and this may increase editing efficiency more than with the ribozyme.

The first strand primer binding site may hybridize to the second region of the target nucleic acid. The reverse transcriptase template may serve as a template for reverse transcription. The reverse transcription may be from a 3' end of the second region of the target nucleic acid. The second strand primer may serve as a primer for transcription from a template. The template may be reverse complementary to the reverse transcriptase template. A first synthesized strand may serve as a template for synthesis of a second strand from the second strand primer.

Second strand primers (SPPs) may be included in the gRNA. The SPP may be about 10-30 or about 15-25 nucleotides in length. The SPP may be about 20 nucleotides in length. Including a SPP of, for example 20 nucleotides, may increase the efficiency of editing (by 2×, or from about 20% to about 40%, for example). The SPP may be 20, 40, or 60 nucleotides in length, or a range of nucleotides in length defined by any of the aforementioned numbers of nucleotides. Some embodiments include a nucleic acid (e.g. DNA) strand with a desired edit that is complementary to a first strand. This may allow RT to use the first strand as a template. The terminal 3 nucleotides of the SPP may be complementary to the first strand. The SPP may hybridize to a portion of a first strand that is 3' to an edit site. The SPP may be coded to remove secondary structure, and thereby increase editing efficiency.

A composition described herein may include a first guide nucleic acid. The composition may include a second guide nucleic acid. The second guide nucleic acid may comprise a guide nucleic acid described herein. The first guide nucleic acid may bind to a first Cas nickase. The second guide nucleic acid may bind to a second Cas nickase. A first spacer of the first guide nucleic acid may bind a first Cas nickase. A second spacer of the second guide nucleic acid may bind a second Cas nickase. A first scaffold of the first guide nucleic acid may bind the second Cas nickase. A second scaffold of the second guide nucleic acid may bind the first Cas nickase. The first guide nucleic acid may comprise a first linker. The second guide nucleic acid may comprise a second linker. The first linker may hybridize to the second linker.

The guide nucleic acid may include gRNA 2.0. The guide nucleic acid may include a 13 nucleotide PBS. The guide nucleic acid may include a 10-15 nucleotide PBS. The guide nucleic acid may include a 13 nucleotide RTT. The guide nucleic acid may include a 10-15 nucleotide RTT. The RTT may encode a mutation as compared to the target nucleic acid.

Disclosed herein, in some embodiments, are a first and second guide nucleic acid. In some embodiments, the first guide nucleic acid comprises a reverse transcriptase template (RTT). In some embodiments, the second guide nucleic acid comprises a reverse transcriptase template. The reverse transcriptase templates of the first and second guide nucleic acids may be at least partly complementary. In some embodiments, part of the reverse transcriptase template of the second guide nucleic acid is complementary to part of the reverse transcriptase template of the first guide nucleic acid. In some embodiments, the reverse transcriptase template of the second guide nucleic acid is complementary to part of the reverse transcriptase template of the first guide nucleic acid. In some embodiments, part of the reverse transcriptase template of the second guide nucleic acid is complementary to the reverse transcriptase template of the first guide nucleic acid. In some embodiments, the reverse transcriptase template of the second guide nucleic acid is complementary to the reverse transcriptase template of the first guide nucleic acid. In some embodiments, the reverse transcriptase template of the second guide nucleic acid is complementary (or at least partly complementary) to at least part of the reverse transcriptase template of the first guide nucleic acid. The reverse transcriptase templates of the first and second guide nucleic acids may include overlapping dual extended fRNA's (ODEGs) wherein part of the second gRNA's reverse transcriptase template is reverse complementary to part of the first gRNA's reverse transcriptase template. The parts that are complementary may include at least 5 nucleic acids, at least 10 nucleic acids, at least 20 nucleic acids, at least 30 nucleic acids, at least 40 nucleic acids, at least 50 nucleic acids, at least 60 nucleic acids, at least 70 nucleic acids, at least 80 nucleic acids, at least 90 nucleic acids, at least 100 nucleic acids, or more nucleic acids. The parts that are complementary may in some instances include no more than 5 nucleic acids, no more than 10 nucleic acids, no more than 20 nucleic acids, no more than 30 nucleic acids, no more than 40 nucleic acids, no more than 50 nucleic acids, no more than 60 nucleic acids, no more than 70 nucleic acids, no more than 80 nucleic acids, no more than 90 nucleic acids, no more than 100 nucleic acids, or less nucleic acids.

The guide nucleic acid may comprise gRNA positioning system (GPS). The GPS may include an RNA sequence that binds to a portion of the guide nucleic acid. This may bring the PBS into close proximity with a 5' end of the gRNA. The RNA sequence of the GPS may be 10, 15, 20, 25, or more nucleotides in length, or a range of nucleotides in length defined by any two of the aforementioned integers. A benefit of using GPS may include increasing editing efficiency when using a long RTT (e.g. an RTT of at least 20, 50, or 100 nucleotides).

The RNA sequence of the GPS may be about 20 nucleotides in length. The RNA sequence of the GPS may hybridize to a portion of the RTT. The portion of the RTT that the RNA sequence of the GPS hybridizes to may be 10, 15, 20, 25, or more nucleotides in length, or a range of nucleotides in length defined by any two of the aforementioned integers. The portion of the RTT that the RNA sequence of the GPS hybridizes to may be about 20 nucleotides. The portion of the RTT that the RNA sequence of the GPS hybridizes to may be designed to be the same or about the same length as the GPS, or vice versa.

The GPS may include a version 1 GPS. The guide nucleic acid may include an RNA sequence inserted 5' of the RTT. The RNA sequence may hybridize with the RTT. The RNA sequence may hybridize with a 3' region of the RTT.

The GPS may include a version 2 GPS. The guide nucleic acid may include an RNA sequence inserted 3' of a PBS. The RNA sequence may hybridize with the RTT. The RNA sequence may hybridize with a 5' portion of the RTT.

In some cases, the guide nucleic acid comprises one guide nucleic acid, or one type of guide nucleic acid. In some cases, the guide nucleic acid comprises only one guide nucleic acid, or only one type of guide nucleic acid. In some cases, the guide nucleic acid comprises more than one guide nucleic acid, or more than one type of guide nucleic acid. In some cases, the guide nucleic acid comprises two guide nucleic acids, or two types of guide nucleic acid. In some cases, the guide nucleic acid comprises only two guide nucleic acid, or only two types of guide nucleic acid.

Some aspects of the present disclosure include a single guide nucleic acid system. In some cases, a single guide nucleic acid system might generate a flap containing the desired edit that does not efficiently displace the original genomic strand that doesn't contain the edit. A composition or method for promoting hybridization of the extended flap into the genome may anchor the 3' end of the extended flap in the vicinity of the genomic strand it is intended to replace. GPS-assisted reachover gRNAs (GARGs) may enable this. The GARG may anchor an extended flap. The GARG may anchor a 3' end of an extended flap. In some embodiments, a guide nucleic acid comprises a GARG.

Figure 32:
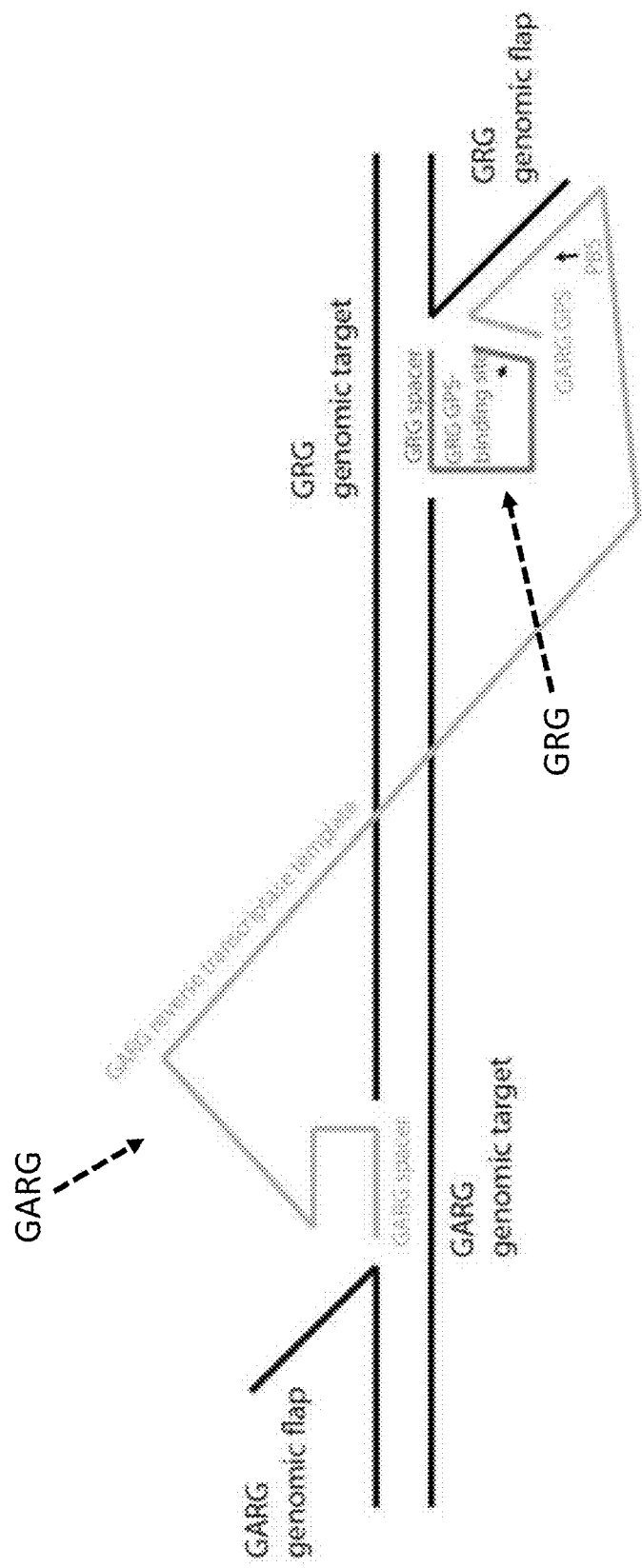
FIG. 32 shows a dual guide system.

An example of a GARG is shown in FIG. 32. FIG. 32 shows a GARG that includes a spacer that targets a first region of a target nucleic acid as well as a primer binding site that hybridizes to a second region of the genome that is targeted by a different guide, called a GPS-recruiting guide (GRG). The GARG contains a GPS component that is designed to hybridize to a GPS-binding site that is part of the GRG. In some embodiments, a guide nucleic acid comprises a GRG. Some embodiments comprise a system including a GARG and GRG. The system may include other gene editing components such as those described herein.

A guide nucleic acid may comprise a GARG. The GARG may include a spacer. The spacer of the GARG may bind a first region of a target nucleic acid. The spacer of the GARG may be reverse complementary to the first region of a target nucleic acid. The GARG may include an RTT. The RTT may encode a sequence to be inserted into the target nucleic acid. The GARG may include a scaffold. The scaffold may bind to a Cas nuclease, or be configured to bind to a Cas nuclease. The GARG may include a primer binding site (e.g. a first primer binding site). The primer binding site of the GARG may bind to a region of the target nucleic acid that does not include any part of the region of the nucleic acid targeted or bound by the spacer or the nucleic acid reverse complementary to the nucleic acid targeted or bound by the spacer. The primer binding site of the GARG may bind to a region of the target nucleic acid that does not comprise any part of a first region of a target nucleic acid complementary to a spacer of the GARG, and that does not comprise any part of a reverse complement of the first region. The primer binding site of the GARG may bind a second region of the target nucleic acid. The primer binding site of the GARG may be reverse complementary to second region of the target nucleic acid. The GARG may include a GRG binding site. The GRG binding site may bind to a second guide nucleic acid (where the GARG comprises a first guide nucleic acid). The second guide nucleic acid may comprise a GRG. The GRG binding site may bind to a GRG. The GRG binding site may be reverse complementary to a portion of a GRG. The portion of the GRG that is reverse complementary to the GRG binding site may be referred to as a GARG-binding portion. The GARG may comprise a GPS region. The GRG binding site may be the GPS region. The GRG may comprise a GPS binding site. The GARG-binding portion may be the GPS binding site. The second guide nucleic acid may bring the primer binding site into proximity with a genomic flap. The second guide nucleic acid may bring the primer binding site into contact with a genomic flap. The second guide nucleic acid may bring the primer binding site into close proximity with a genomic flap. The inclusion of a GPS region and GPS binding site may pull the end of the GARG to where it may bind the genomic flap. The GARG may be encoded by a nucleic acid such as DNA. Any of the components of the GARG may be included in the GRG. The GRG may be encoded by a nucleic acid such as DNA. The GARG and the GRG be encoded by the same nucleic acid, or by separate nucleic acids. The GARG, or a nucleic acid encoding the GARG, may be encompassed by a virus particle such as an AAV. The GRG, or a nucleic acid encoding the GRG, may be encompassed by a virus particle such as an AAV. The GARG and the GRG be encompassed by the same virus particle, or by separate virus particles.

Some embodiments include a dual guide system. The dual guide system may comprise a GARG and a GRG. Some embodiments include a composition comprising a GARG and a GRG. Some embodiments include a method of using a GARG and a GRG, or a method of gene editing with a GARG and a GRG.

Some embodiments include a gene editing method comprising administering a GARG and a GRG to a cell. Some embodiments include a gene editing method comprising administering one or more nucleic acids that express a GARG and a GRG to a cell. Some embodiments include a gene editing method comprising expressing a GARG and a GRG to a cell. Some embodiments include a gene editing method comprising expressing or administering a GARG to a cell comprising a GRG. Some embodiments include a gene editing method comprising expressing or administering a GRG to a cell comprising a GARG. Some embodiments include a gene editing method comprising expressing a GARG or a GRG in a cell comprising a gene editing enzyme. Some embodiments include a gene editing method comprising expressing a GARG and a GRG in a cell comprising a gene editing enzyme. Some embodiments include a gene editing method comprising administering a GARG or a GRG to a cell comprising a gene editing enzyme. Some embodiments include a gene editing method comprising administering a GARG and a GRG to a cell comprising a gene editing enzyme. The administering may be to a subject comprising the cell.

Disclosed herein, in some aspects, are compositions or systems comprising an RNA (or polynucleotide) comprising a spacer, a reverse transcriptase template comprising a desired edit, and a primer binding site, in which the primer binding site binds to a nucleic acid that is targeted by a separate RNA. Disclosed herein are systems comprising an RNA or polynucleotide comprising a spacer, a reverse transcriptase template comprising a desired edit, and a primer binding site, in which the primer binding site binds to a nucleic acid that does not comprise any part of the region of the nucleic acid targeted or bound by the spacer or the nucleic acid reverse complementary to the nucleic acid targeted or bound by the spacer.

Compositions for Genome Editing

Compositions of the present disclosure may facilitate efficient editing of a target nucleic acid at a target site. A composition of the present disclosure may comprise a guide nucleic acid, a nCas9, and a reverse transcriptase. A composition of the present disclosure may comprise a sequence encoding a guide nucleic acid, a nCas9, a reverse transcriptase, or a combination thereof. The nCas9 and the reverse transcriptase may be a fused nCas9-RT construct. The nCas9 and the reverse transcriptase may be a split nCas9-RT construct. A composition of the present disclosure may be introduced into a cell comprising the target nucleic acid, thereby editing the target nucleic acid. In some embodiments, a sequence (e.g., a plasmid) encoding one or more components of the composition may be introduced into a cell comprising the target nucleic acid. The one or more components of the composition may be expressed in the cell. In some embodiments, a composition of the present disclosure may comprise a first guide nucleic acid, a first nCas9s, a first reverse transcriptase, a second guide nucleic acid, a second nCas9s, and a second reverse transcriptase. In some embodiments, the first guide nucleic acid binds to the first nCas9, and the second guide nucleic acid binds to the second nCas9. In some embodiments, a first spacer of the first guide nucleic acid binds the first nCas9, a second spacer of the second guide nucleic acid binds the second nCas9, a first scaffold of the first guide nucleic acid binds the second nCas9, and a second scaffold of the second guide nucleic acid binds the first nCas9. In some embodiments, the first guide nucleic acid comprises a first linker and the second guide nucleic acid comprises a second linker. In some embodiments, the first linker hybridizes to the second linker.

A composition comprising a first guide nucleic acid and a second guide nucleic acid may facilitate synthesis or editing of a sequence. A composition comprising a first guide nucleic acid and a second guide nucleic acid may facilitate editing of a target nucleic acid at a target site. A composition comprising a first guide nucleic acid and a second guide nucleic acid may be a two single guide system. A composition comprising a first guide nucleic acid and a second guide nucleic acid may be a dual guide system. In a two single guide system, each gRNA binds to a different nCas9 and the two gRNAs each comprise a reverse transcriptase template region. In a dual guide system, each gRNA may bind to a different nCas9. In a two single guide system, only one of the gRNAs may comprise a reverse transcriptase template region. In a two single guide system, the second guide may nick the opposite strand. In a dual guide system, only one of the gRNAs may comprise a reverse transcriptase template region. In a dual guide system, the second guide may nick the opposite strand. In a dual guide complex, the spacer of the first gRNA may bind the first nCas9, the spacer of the second gRNA may bind the second nCas9, the scaffold of the first gRNA may bind the second nCas9, and the scaffold of the second gRNA may bind the first nCas9.

The guide nucleic acid may form a complex with a Cas nickase. The guide nucleic acid may form a complex with a reverse transcriptase. Upon complex formation, the Cas nickase may introduce a single-strand break at a target site in a target nucleic acid.

Some non-limiting examples of target nucleic acids include a cystic fibrosis transmembrane conductance regulator (CFTR) nucleic acid, an usherin (USH2A) nucleic acid, an ATP-binding cassette subfamily A member 4 (ABCA4) nucleic acid, a Wilson disease protein (ATP7B) nucleic acid, or a Huntingtin (HTT) nucleic acid. In some embodiments, the target nucleic acid comprises a CFTR gene. In some embodiments, the target nucleic acid comprises a USH2A gene. In some embodiments, the target nucleic acid comprises a ABCA4 gene. In some embodiments, the target nucleic acid comprises a ATP7B gene. In some embodiments, the target nucleic acid comprises a HTT gene.

Disclosed herein are compositions comprising a Cas nickase, a reverse transcriptase, and a guide nucleic acid. A first polypeptide may comprise the Cas nickase. A second polypeptide may comprise the reverse transcriptase. The guide nucleic acid may bind to the Cas nickase. The guide nucleic acid may bind to the reverse transcriptase.

The RT may comprise an MS2 coat protein (MCP) peptide. In some cases, the RT does not include an MS2 coat protein (MCP) peptide. For example, the composition may include RWa1. The guide nucleic acid may comprise a MS2 hairpin. In some cases, the guide nucleic acid does not include a MS2 hairpin. The MCP peptide may bind an MS2 hairpin in the guide nucleic acid. The MS2 hairpin may be between a gRNA scaffold and a RTT. This may bring the RT into close proximity with the gRNA to allow editing. A benefit of using a MCP peptide and MS2 hairpin is to separate the RT and Cas nickase (or a portion of them), and allow them to fit within AAV vectors. The MCP peptide and MS2 hairpin may not be necessary. The composition including the MCP peptide or the MS2 hairpin may have an editing efficiency of at least about 3% or 4%, for example, when transfected into cells. The composition including the MCP peptide or the MS2 hairpin may have an editing efficiency of at least about 10% or 15%, for example, when transfected into cells.

The RT and Cas nickase may include leucine zippers. For example, the composition may include RWb1. The composition including leucine zippers may have an editing efficiency of at least about 35% or 40%, for example, when transfected into cells. The composition including leucine zippers may have an editing efficiency of at least about 3% or 4%, for example, when transduced into cells. A benefit of using leucine zipper is to separate the RT and Cas nickase (or a portion of them), and allow them to fit within AAV vectors. However, the leucine zippers may not be necessary.

The RT or Cas nickase may be split, for example, using intein splitting. In some cases, the RT and Cas nickase are not split using intein splitting. An example of using intein splitting is RWc1. The split may be between residues 1172 and 1173 of the Cas nickase. The composition using the split RT or Cas nickase may have an editing efficiency of at least about 25% or 30%, for example, when transfected into cells. A benefit of using RWc1 or a similar splitting method may be to allow for more space for additional nucleotide sequences such as regulatory elements that may be allowed to fit within an AAV vector with a nucleic acid sequence encoding the RT or Cas nickase. For example, the splitting method may allow for about 500, 600, or 700 (or a range defined by any of the aforementioned integers) more nucleotides for additional nucleotide sequences to fit within an AAV.

The RT or Cas nickase may be separate and not bound together. An example of using non-bound RT and Cas nickase is RWd1.

A composition of the present disclosure may comprise a protein complex or a sequence encoding a protein complex. The protein complex may comprise a protective protein complex. The protein complex may prevent deamination or degradation of a guide nucleic acid. For example, a protective complex may be a Human Orf1p (SEQ ID NO: 38) or a Murine Orf1p (SEQ ID NO: 39).

Disclosed herein are methods of increasing genome editing efficiency. The method may include delivering an Orf1p to a cell. The cell may express a composition or a guide nucleic acid described herein.

Disclosed herein are nucleic acids comprising nucleotide sequences encoding a composition or a guide nucleic acid described herein. Disclosed herein are viral vectors comprising the nucleic acids. Disclosed herein are cells comprising a composition described herein. Disclosed herein are cells comprising a nucleic acid described herein. Disclosed herein are cells comprising a guide nucleic acid described herein. Disclosed herein are cells comprising a viral vector described herein. The cell may be a prokaryotic cell. The cell may be a eukaryotic cell.

Some embodiments include method of increasing genome editing efficiency by increasing the dNTP concentration such as dNTP concentration in a cell. Inhibiting SAMHD1 may increase the dNTP concentration. Administering dNTPs may increase the dNTP concentration in the cell. Some embodiments include a method of increasing genome editing efficiency comprising inhibiting SAMHD1 in a cell. Some embodiments include a method of increasing genome editing efficiency comprising administering dNTPs to a subject or to a cell In some embodiments, a composition of the present disclosure may comprise a protein, a nucleic acid encoding the protein, or a non-coding nucleic acid, for increasing editing efficiency of a Cas9 construct of the present disclosure (e.g., a split Cas9-RT construct). In some embodiments, a protein, a nucleic acid encoding the protein, or a non-coding nucleic acid for increasing editing efficiency of a Cas9 construct may comprise a protein or a nucleic acid that inhibits the dNTP cleavage activity of SAMHD1 or a nucleic acid encoding a protein that inhibits the dNTP cleavage activity of SAMHD1. For example, a nucleic acid that inhibits the dNTP cleavage activity of SAMHD1 may comprise a microRNA that degrades SAMHD1 transcripts.

Some embodiments include increasing the dNTP concentration in the cell, relative to a baseline dNTP concentration. In some embodiments, the dNTP concentration is increased by 5%, 10%, 15%, 20%, 25%, 30%, 40%, 50%, 60%, 70%, 80%, 90%, 100%, or more, or by a range of percentages defined by any two of the aforementioned percentages, relative to the baseline dNTP measurement. In some embodiments, the dNTP concentration is increased by at least 5%, at least 10%, at least 15%, at least 20%, at least 25%, at least 30%, at least 40%, at least 50%, at least 60%, at least 70%, at least 80%, at least 90%, at least 100%, relative to the baseline dNTP measurement. In some embodiments, the dNTP concentration is increased by no more than 5%, no more than 10%, no more than 15%, no more than 20%, no more than 25%, no more than 30%, no more than 40%, no more than 50%, no more than 60%, no more than 70%, no more than 80%, no more than 90%, no more than 100%, relative to the baseline dNTP measurement.

In various aspects, the low dNTP concentration comprises a dNTP concentration of 0.5 micromolar, 0.6 micromolar, 0.7 micromolar, 0.8 micromolar, 0.9 micromolar, 1.0 micromolar, or 1.1 micromolar, or a range defined by any two of the aforementioned dNTP concentrations. In various aspects, the low dNTP concentration comprises a dNTP concentration of about 0.5 micromolar, about 0.6 micromolar, about 0.7 micromolar, about 0.8 micromolar, about 0.9 micromolar, about 1.0 micromolar, or about 1.1 micromolar, or a range defined by any two of the aforementioned dNTP concentrations. In various aspects, the low dNTP concentration comprises a dNTP concentration below about 1.1 micromolar. In various aspects, the low dNTP concentration comprises a dNTP concentration below about 1.0 micromolar. In various aspects, the low dNTP concentration comprises a dNTP concentration below about 0.9 micromolar. In various aspects, the low dNTP concentration comprises a dNTP concentration below about 0.8 micromolar. In various aspects, the low dNTP concentration comprises a dNTP concentration below about 0.7 micromolar. In various aspects, the low dNTP concentration comprises a dNTP concentration below about 0.6 micromolar. In various aspects, the low dNTP concentration comprises a dNTP concentration below about 0.5 micromolar. In various aspects, the low dNTP concentration comprises a dNTP concentration above about 0.9 micromolar. In various aspects, the low dNTP concentration comprises a dNTP concentration above about 0.8 micromolar. In various aspects, the low dNTP concentration comprises a dNTP concentration above about 0.7 micromolar. In various aspects, the low dNTP concentration comprises a dNTP concentration above about 0.6 micromolar. In various aspects, the low dNTP concentration comprises a dNTP concentration above about 0.5 micromolar. In various aspects, the low dNTP concentration comprises a dNTP concentration above about 0.4 micromolar.

In various aspects, the present disclosure provides a method of increasing gene editing efficiency in a cell having a low deoxynucleoside triphosphate (dNTP) concentration and comprising a DNA polymerase, the method comprising: increasing the dNTP concentration in the cell, relative to a baseline dNTP concentration. In various aspects, increasing the dNTP concentration in the cell comprises inhibiting a deoxynucleotide triphosphate triphosphohydrolase in the cell. In various aspects, the deoxynucleotide triphosphate triphosphohydrolase comprises SAM domain and HD domain-containing protein 1 (SAMHD1). In various aspects, inhibiting SAMHD1 comprises contacting the SAMHD1 with a Vpx protein, or expressing the Vpx protein in the cell. In various aspects, inhibiting SAMHD1 comprises contacting the SAMHD1 with a BGLF4 protein, or expressing the BGLF4 protein in the cell. In various aspects, inhibiting SAMHD1 comprises contacting an mRNA encoding the SAMHD1 with a microRNA or siRNA that hybridizes to the mRNA, or expressing the microRNA or siRNA in the cell. In various aspects, inhibiting SAMHD1 comprises contacting the SAMHD1 with a small molecule SAMHD1 inhibitor. In various aspects, increasing the dNTP concentration in the cell comprises administering dNTPs to the cell. In various aspects, administering dNTPs to the cell comprises administering dNTPs to a subject comprising the cell. In various aspects, increasing the dNTP concentration in the cell comprises administering nucleosides or nucleotides to the cell. The nucleosides or nucleotides may include deoxynucleosides (dNs), deoxynucleoside monophosphates (dNMPs), or nucleoside triphosphates (NTPs). In some cases, the nucleosides or nucleotides are not dNTPs, or do not include dNTPs. In various aspects, administering nucleosides or nucleotides to the cell comprises administering the nucleosides or nucleotides to a subject comprising the cell. In various aspects, the administration is oral or by injection. In various aspects, increasing the dNTP concentration in the cell comprises delivering a dNTP synthetic enzyme to the cell. In various aspects, the dNTP synthetic enzyme comprises a kinase. In various aspects, the kinase comprises a nucleoside kinase, deoxynucleoside kinase, deoxynucleoside monophosphase kinase, or deoxynucleotide diphosphate kinase. In various aspects, the DNA polymerase comprises a reverse transcriptase. The DNA polymerase may be adapted for gene editing. The DNA polymerase may be a gene editing polymerase. The DNA polymerase may be a recombinant DNA polymerase. Some embodiments include introducing the DNA polymerase into the cell. Some embodiments include expressing the DNA polymerase in the cell. In various aspects, the cell comprises or further comprises a Cas9 programmable nuclease, a guide nucleic acid, or a combination thereof. Some embodiments include introducing into the cell, or expressing the Cas9 programmable nuclease in the cell. Some embodiments include introducing into the cell, or expressing the guide nucleic acid in the cell. The Cas9 programmable nuclease may be part of the DNA polymerase, or may associate with the DNA polymerase. In various aspects, the low dNTP concentration comprises a dNTP concentration found in a nondividing cell. In various aspects, the low dNTP concentration is less than a dNTP concentration found in an activated peripheral blood mononuclear cell. In various aspects, the low dNTP concentration comprises a dNTP concentration below 1 micromolar. In various aspects, the increasing the dNTP concentration comprises increasing the dNTP concentration by at least 5%, at least 10%, at least 15%, at least 20%, at least 25%, at least 30%, at least 40%, at least 50%, at least 60%, at least 70%, at least 80%, at least 90%, at least 100%, or more, relative to the baseline dNTP measurement. In various aspects, the dNTP concentration comprises a deoxyadenosine triphosphate (dATP) concentration, a deoxycytidine triphosphate (dCTP) concentration, a deoxyguanosine triphosphate (dGTP) concentration, or a deoxythymidine triphosphate (dTTP) concentration, or any combination thereof.

In various aspects, the present disclosure provides a method of increasing gene editing efficiency in a cell having a low deoxynucleoside triphosphate (dNTP) concentration, comprising: increasing the dNTP concentration in the cell, wherein the cell comprises a Cas9 programmable nuclease, a reverse transcriptase, and a guide nucleic acid. In various aspects, the present disclosure provides a method of increasing gene editing efficiency in a cell having a low deoxynucleoside triphosphate (dNTP) concentration, comprising: contacting the cell with a gene editing enzyme modified for efficient catalysis in the low dNTP concentration, or expressing the gene editing enzyme in the cell. In some aspects, increasing the dNTP concentration in the cell comprises inhibiting SAMHD1 in the cell. In some aspects, inhibiting SAMHD1 comprises contacting the SAMHD1 with a Vpx protein, or expressing the Vpx protein in the cell. In some aspects, inhibiting SAMHD1 comprises contacting an mRNA encoding the SAMHD1 with a microRNA or siRNA that hybridizes to the mRNA, or expressing the microRNA or siRNA in the cell. In some aspects, inhibiting SAMHD1 comprises contacting the SAMHD1 with a small molecule SAMHD1 inhibitor. In some aspects, increasing the dNTP concentration in the cell comprises administering dNTPs to the cell. In some aspects, increasing the dNTP concentration in the cell comprises delivering a dNTP synthetic enzyme to the cell. In some aspects, the dNTP synthetic enzyme comprises a deoxynucleoside diphosphate (dNDP) kinase. In some aspects, the gene editing enzyme comprises a Cas9 programmable nuclease or a reverse transcriptase. In some aspects, the reverse transcriptase is modified by introducing a point mutation at position Q84, L139, Q221, V223, T664, or L671. In some embodiments, the method further comprises measuring the dNTP concentration. Some embodiments include measuring a dNTP concentration after increasing the dNTP concentration, and determining an increase relative to a baseline dNTP concentration.

Some embodiments include obtaining determining the increase in dNTP concentration. Some embodiments include measuring the dNTP concentration. In some embodiments, the dNTP concentration is measured using an assay such as an absorbance assay, a colorimetric assay, or an enzyme-linked immunosorbent assay. Some embodiments include measuring the baseline dNTP concentration. In some embodiments, the baseline dNTP concentration is measured using an assay such as an absorbance assay, a colorimetric assay, or an enzyme-linked immunosorbent assay.

Disclosed herein are methods of increasing genome editing efficiency. The method may include inhibiting SAMHD1 in a cell. The cell may express a Cas9 programmable nuclease. The cell may express a Cas nickase. The cell may express a reverse transcriptase. The cell may express a guide nucleic acid. An example of inhibiting SAMHD1 may include treating the cell with a SAMHD1 inhibitor such as a small molecule SAMHD1 inhibitor. An example of inhibiting SAMHD1 may include expressing a microRNA against SAMHD1 in the cell.

A protein for increasing editing efficiency may be a Vpx protein (e.g., SEQ ID NO: 82, SEQ ID NO: 83, or SEQ ID NO: 93). Vpx is in some instances a lentiviral protein. Vpx is in some instances a immunodeficiency virus (SIV) protein which may be used for increasing editing efficiency (e.g. by inhibiting SAMHD1). A Vpx protein may increase editing efficiency of a Cas9-RT construct by increasing the availability of dNTPs in a cell. For example, a Vpx protein may inhibit the dNTP cleavage activity of SAMHD1, thereby increasing availability of dNTPs in the cell. In some embodiments, a Vpx protein may be co-expressed in a cell with a Cas9-RT construct of the present disclosure. The Cas9-RT construct expressed with the Vpx protein may have increased editing efficiency compared to the Cas9-RT construct in the absence of the Vpx protein. A Vpx peptide may be a Hiv2-rod Vpx (e.g., SEQ ID NO: 82). In some embodiments, a Vpx protein may be expressed as its own coding sequence. In some embodiments, a Vpx protein may be expressed in the same coding sequence as the reverse transcriptase. For example, a Vpx protein may be expressed in the same coding sequence as the reverse transcriptase, separated by a p2a self-cleaving peptide (e.g., SEQ ID NON: 83). In some embodiments, a Vpx protein may be a Vpx RH-2-1 D8 protein (e.g., SEQ ID NO: 93). In some embodiments, a Vpx protein may be expressed in the same coding sequence as the Cas9 protein. Inhibiting SAMHD1 may comprise expressing a Vpx protein in the cell.

Disclosed herein are methods of increasing genome editing efficiency comprising expressing a Vpx protein in a cell. The cell may express a composition described herein. The cell may express a guide nucleic acid described herein.

Some embodiments include a method of increasing a dNTP concentration in a cell, or of improving gene editing, by inhibiting a deoxynucleotide triphosphate triphosphohydrolase (dNTPase) such as SAMHD1. Some embodiments relate to a composition for inhibiting SAMHD1. A Vpx protein may be used to inhibit SAMHD1. A BGLF4 protein may be used to inhibit SAMHD1. BGLF4 may phosphorylate SAMHD1 and thereby inhibit a dNTPase activity of SAMHD1. BGLF4 is in some instances an Epstein-Barr virus (EBV)-encoded protein kinase. An EBV-encoded protein kinase may be used for increasing editing efficiency (e.g. by inhibiting SAMHD1). The composition for inhibiting SAMHD1 may include a small molecule SAMHD1 inhibitor. The small molecule SAMHD1 inhibitor may comprise pppCH2dU, or a salt thereof. The small molecule SAMHD1 inhibitor may comprise dGMPNPP, or a salt thereof.

Disclosed herein are methods of increasing genome editing efficiency by increasing the concentration of nucleosides or nucleotides (e.g. dNTPs) in a cell. The cell may express a Cas9 programmable nuclease. The cell may express a Cas nickase. The cell may express a reverse transcriptase. The cell may express a guide nucleic acid. An example of increasing the concentration of dNTPs in a cell comprises delivering nucleotides or nucleosides to a cell. Increasing the concentration of nucleosides or nucleotides in a cell may include delivery of the nucleosides or nucleotides to the cell. The nucleotides or nucleosides may then be converted into dNTPs in the cell. Delivery of the nucleosides or nucleotides may include oral delivery or injection. Conversion of the nucleosides or nucleotides to dNTPs may be through phosphorylation by endogenous kinases or synthesis, for example through endogenous salvage pathways. The method may comprise delivering nucleotides or nucleosides to the cell, resulting in an increased concentration of dNTPs in the cell compared to a cell that did not received the nucleotides or nucleosides. The increased concentration of the dNTPs in the cell may result in increased editing efficiency in the cell comprising the compositions as disclosed herein.

Disclosed here are methods that include using SAMHD1 overexpression to screen for RT mutants that operate better in limiting dNTP concentrations. Also disclosed are methods for screening or identifying improved RTs in cells that are modified to overexpress SAMHD1 or a unphosphorylatable mutant of SAMHD1. Some embodiments include overexpressing SAMHD1 in cells. Some embodiments include expressing a mutant SAMHD1 that has been mutated to prevent phosphorylation of a residue of the mutant SAMHD1 in cells. Some embodiments include identifying an RT activity in the cells. Some embodiments include identifying the RT as an improved RT based on the RT activity. Some embodiments include a method for screening or identifying an improved reverse transcriptase (RT), comprising: overexpressing SAMHD1, or expressing a mutant SAMHD1 that has been mutated to prevent phosphorylation of a residue of the mutant SAMHD1, in cells; identifying an RT activity in the cells; and based on the RT activity, identifying the RT as an improved RT.

AAV and Methods for Delivery of Precision Editing Components

Described herein are precision editing components such as Cas nickases, reverse transcriptases (RTs), or guide RNAs (gRNAs). The nickase and RT may be encoded by polynucleotides. The polynucleotides may be delivered by AAVs. The polynucleotides encoding the nickase and RT may be engineered to fit within the AAVs. Examples are provided herein for engineering the nickase and RT to fit within AAVs. For example, the nickase and RT may be engineered to dimerize. The nickase and RT may be coexpressed. The nickase may be split using an intein system. Part of the nickase may be combined as a fusion protein with the RT. A goal of the exemplary dimerization, coexpression and split intein systems is to be able to deliver the genome editing components using AAVs comprising 4.5 kb carrying capacities.

Figure 24:
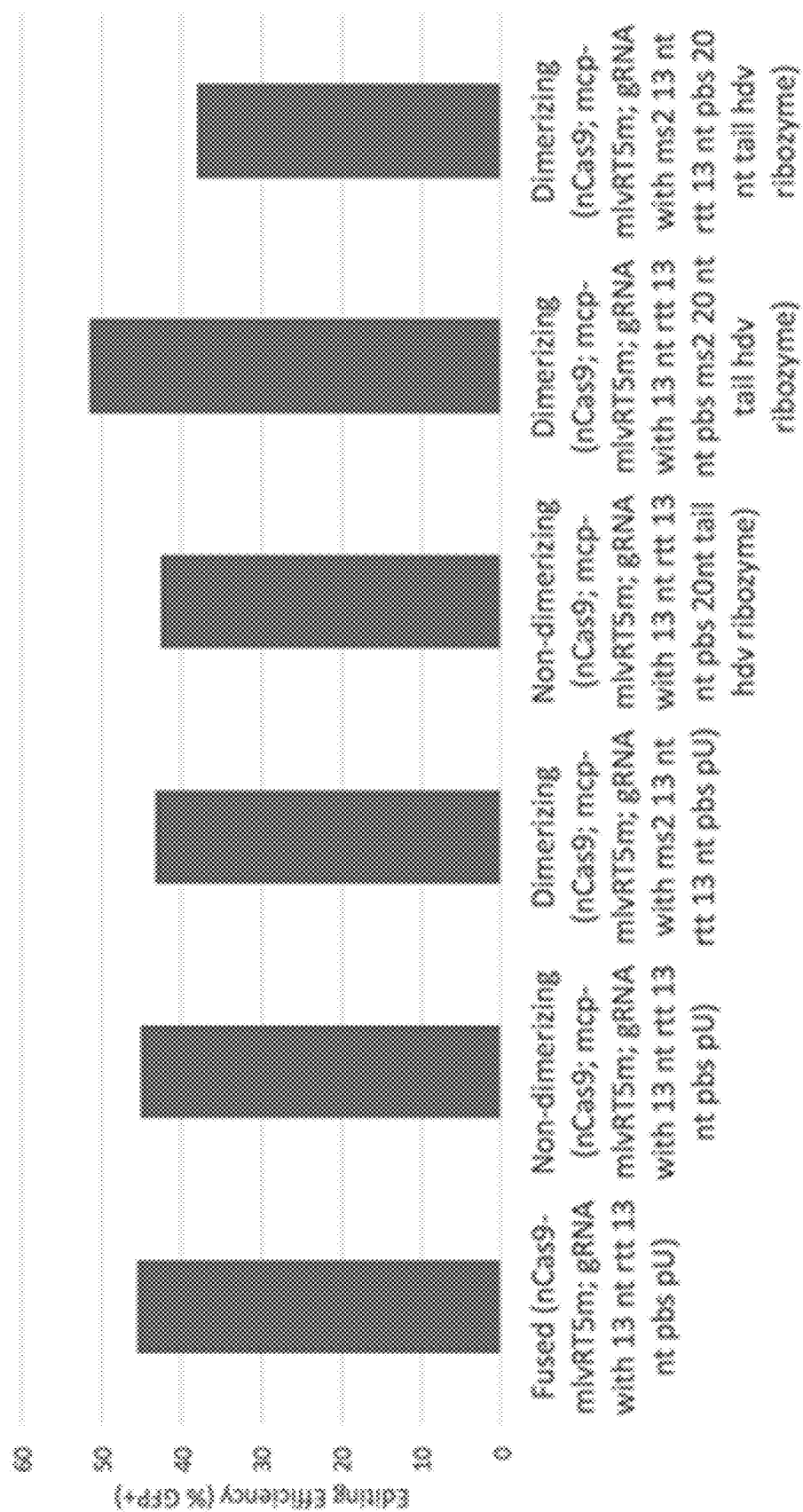
FIG. 24 is a graph showing editing efficiencies of various editing components expressed together in cells.

FIG. 24 shows that when plasmids expressing nCas9 and mcp-mlvRT5m were cotransfected in HEK293T-BFP cells with gRNAs that did and did not include an ms2 hairpin, the same BFP to GFP editing efficiency was achieved. As such, coexpression of unfused and non-dimerizing nCas9 and a reverse transcriptase in the same cell can result in editing. Therefore NLS-nCas9 (SEQ ID NO: 138) and mlvRT5m-NLS (SEQ ID NO: 95) may be coexpressed from separate AAVs to achieve efficient editing. Therefore, coexpression of an unfused and non-dimerizing Cas nickase and a reverse transcriptase in the same cell can result in editing. Therefore a Cas nickase and an RT may be coexpressed from separate AAVs to achieve efficient editing. Likewise, a Cas nickase and an RT that have been engineered to dimerize may be coexpressed from separate AAVs to achieve efficient editing.

A Cas nickase and a RT may be encoded by polynucleotides. The Cas nickase and RT may be encoded by 2 separate polynucleotides, or part of one may be included in the other polynucleotide (for example, as described herein). One or more AAVs may comprising the polynucleotides. At least part of the Cas nickase and RT may be encompassed or comprised within separate AAVs. Part of the Cas nickase and RT may be encompassed or comprised within separate AAVs. All of the Cas nickase and RT may be encompassed or comprised within separate AAVs.

In some cases, a composition is included, which includes a Cas nickase and a reverse transcriptase, wherein at least part of the Cas nickase and the reverse transcriptase are included in separate polypeptide chains, and wherein the Cas nickase and the reverse transcriptase form a Cas-reverse transcriptase heterodimer. The separate polypeptide chains may be encoded by separate polynucleotides. The separate polynucleotides may be included in separate viral vectors such as AAVs. The separate polynucleotides may be divided into 2, 3, 4, 5, 6, 7, 8, 9, or 10, of the separate viral vectors. The separate polynucleotides may be divided into 2 of the separate viral vectors. The separate polynucleotides may be divided into at least 2, at least 3, at least 4, at least 5, at least 6, at least 7, at least 8, at least 9, or at least 10, of the separate viral vectors. The separate polynucleotides may be divided into no more than 2, no more than 3, no more than 4, no more than 5, no more than 6, no more than 7, no more than 8, no more than 9, or no more than 10, of the separate viral vectors. The separate polynucleotides may be divided into no more than 2 of the separate viral vectors. The separate polynucleotides may be divided into no more than 3 of the separate viral vectors. The separate polynucleotides may be divided into no more than 4 of the separate viral vectors.

The separate polynucleotides may be short enough to fit within separate AAV genomes (e.g. each below about 4500 bp). For example, separate polynucleotides may each be about the sizes described in FIG. 19A. Separate polynucleotides may each be less than or no greater than about the sizes described in FIG. 19A. Separate polynucleotides may each be less than or no greater than about 10% less than or greater than the sizes described in FIG. 19A. Separate polynucleotides may each be less than about 4500 bp. Separate polynucleotides may include a range of polynucleotide sizes, such as ranges including any of the sizes in FIG. 19A, or ranges including about the sizes in FIG. 19A.

In some cases, the AAVs include a first AAV. The first AAV may include a first polynucleotide, which may encode a Cas or Cas component such as a Cas nickase described herein. The AAVs may include a second AAV, which may include a second polynucleotide encoding a RT such as a RT described herein.

Examples of AAVs may include AAV1, AAV2, AAV3, AAV4, AAV5, AAV6, AAV7, AAV8, AAV9, AAV10, AAV11, AAV12, AAV-DJ, AAV-DJ/8, AAV-Rh10, AAV-Rh74, AAV-retro, AAV-PHP.B, AAV8-PHP.eB, or AAV-PHP.S, or a combination of thereof. Examples of AAVs may include a serotype such as AAV1, AAV2, AAV3, AAV4, AAV5, AAV6, AAV7, AAV8, AAV9, AAV10, AAV 11, or AAV12. Examples of AAVs may include a pseudotype such as AAV-DJ, AAV-DJ/8, AAV-Rh10, AAV-Rh74, AAV-retro, AAV-PHP.B, AAV8-PHP.eB, or AAV-PHP.S.

The AAV may comprise an AAV genome. The AAV genome may comprise pCMV-NLS-nSpCas9(1-1172)-NpuN-cMycNLS-48 pA, or any combination of components thereof. An AAV genome comprising pCMV-NLS-nSpCas9 (1-1172)-NpuN-cMycNLS-48 pA may include the sequence of SEQ ID NO: 142. The AAV genome may include a sequence at least 75% identical, at least 80% identical, at least 85% identical, at least 90% identical, or at least 95% identical, to the sequence of SEQ ID NO: 142.

The AAV genome may comprise pCMV-NpuC-nSpCas9 (1173-1368;S1173C)-mlvRT14M-SV40 NLS-P2A-VPXrh21-48 pA-pU6-ush2a-gRNA, or any combination of components thereof. An AAV genome comprising pCMV-NpuC-nSpCas9(1173-1368;S1173C)-mlvRT14M-SV40 NLS-P2A-VPXrh21-48 pA-pU6-ush2a-gRNA may include the sequence of SEQ ID NO: 143. The AAV genome may include a sequence at least 75% identical, at least 80% identical, at least 85% identical, at least 90% identical, or at least 95% identical, to the sequence of SEQ ID NO: 143. The AAV may be useful for treatment of Usher syndrome, or restoring a USH2A mutant. The AAV may be administered to a subject with Usher syndrome.

Following administration of the AAVs to a subject, genome editing in the subject may be measured or assessed.

Following administration of the AAVs to one or more cells, genome editing in the one or more cells may be measured or assessed. Genome editing may be measured or assessed by sequencing. Genome editing may be measured or assessed by an assay. The assay may comprise measuring or identifying an edited genome in a subject or cell. The assay may comprise measuring or identifying an RNA resultant from the edited genome in a subject or cell. The assay may comprise measuring or identifying a protein resultant from the edited genome in a subject or cell. Some examples of an assay include a hybridization assay, an immunoassay, a colorimetric assay, a fluorescent assay, or mass spectrometry.

Some embodiments include a method for introducing one or more changes in the nucleotide sequence of a DNA molecule at a target locus, comprising: contacting the DNA molecule with a programmable nuclease and a guide nucleic acid which targets the programmable nuclease to the target locus. The programmable nuclease may form a complex with a reverse transcriptase.

Methods of Treatment Using Precision Editing Components

Some embodiments include treatment of a genetic disorder using a method or composition described herein. For example, some embodiments include administering one or more nucleic acids comprising or encoding gene editing components described herein. For example, a viral vector may be used to deliver the administered nucleic acids.

The administration may include injection. The administration may include administration of a composition comprising the nucleic acids. The administration may include administration of a composition comprising the viral vector. The composition may comprise a pharmaceutical composition. The composition may comprise a pharmaceutical composition. The pharmaceutical composition may include a carrier such as water, a buffer, or a saline solution. The pharmaceutical composition may include liposomes.

The administration may be to a subject in need thereof. For example, the administration may be to a subject having a genetic disorder. The subject may be a vertebrate. The subject may be a mammal. The subject may be a human. In some embodiments, the administration corrects a disease-causing gene mutation in the subject. In some embodiments, the administration corrects a disease-causing gene mutation in a cell of the subject.

Some non-limiting examples of genetic disorders include adenosine deaminase deficiency, alpha-1 antitrypsin deficiency, cystic fibrosis, a muscular dystrophy (e.g. Duchenne muscular dystrophy), galactosemia, hemochromatosis, Huntington's disease, maple syrup urine disease, Marfan syndrome, neurofibromatosis (e.g. Type 1), pachyonychia congenita, phenylkeotnuria, severe combined immunodeficiency, sickle cell disease, Smith-Lemli-Opitz syndrome, or Tay-Sachs disease. In some embodiments, the genetic disorder comprises cystic fibrosis, Stargardt disease, Usher syndrome, or Huntington's disease. In some embodiments, the genetic disorder comprises cystic fibrosis. In some embodiments, the genetic disorder comprises Stargardt disease. In some embodiments, the genetic disorder comprises Usher syndrome. In some embodiments, the genetic disorder comprises Huntington's disease. In some embodiments, the genetic disorder comprises a polygenic disorder such as heart disease, high blood pressure, Alzheimer's disease, arthritis, diabetes, cancer, or obesity.

AAV-Deliverable Precision Editing without Double-Stranded Breaks

Summary

The ability to precisely edit genomes may have profound implications on healthcare, agriculture, or biological sciences, and precise genome editing may cure genetic diseases. While CRISPR nucleases have democratized the ability to target double stranded breaks, generating precise sequence alterations has been difficult due to the inefficiency of homology-directed repair (HDR) at the site of a toxic double-stranded break (DSB) using foreign homologous DNA. Prime Editors have enabled versatile precision editing without relying on HDR but may utilize components that are too large to be delivered with the gene delivery vehicle adeno-associated virus (AAV), have a limited editing window length, break both strands to achieve efficient editing, or have limited efficiency in non-dividing cells. Here these limitations have been overcome with a set of tools called Rewriter. Rewriter's split systems may provide four modular architectures to deliver the gene editing components within two AAV genomes. Rewriter's optimized reverse transcriptase and guide RNA positioning system (GPS) may increase the editing efficiency and editing window length while only generating one single-stranded break. Finally, Rewriter's anti-restriction factor promotes editing in non-dividing cells. Rewriter achieved 75% editing within a 65 nucleotide window, the highest efficiency reported to date for targeted multi-nucleotide changes in mammalian cells without generating DSBs. Finally, Rewriter components were developed that precisely edited a genomic site commonly mutated in patients with inherited deafness and blindness with no detectable off-target mutations.

Described herein are compositions and methods for versatile, efficient, and precise genome editing without homology-directed repair or double-stranded breaks using Rewriter, a dual AAV-deliverable system that utilizes an engineered Cas9 nickase to target an optimized reverse transcriptase for synthesis of defined double stranded DNA contiguous with the genome using a guide RNA positioning system (GPS), a second strand primer, and an anti-restriction factor that provides for efficient editing in nondividing cells. Rewriter installed complex sequence changes with up to 54% efficiency within a 65 nucleotide window. A benefit of this system is that it may be used to correct mutations that cause genetic disorders such as cystic fibrosis or Usher syndrome. Correction of genetic defects in Usher syndrome may be used to prevent or treat deafness or blindness. The safety, efficiency, precision, and versatility of Rewriter may be used to treat diseases, improve foods, or advance basic biologic research.

Introduction

CRISPR nucleases may offer a straightforward approach to create targeted, double-stranded breaks in genomic DNA. However, precisely altering the sequence of a genomic target has been difficult due to inefficiency of homology-directed repair, toxicity of double-stranded breaks, and the challenge of delivering homologous donor DNA. DSBs can lead to long and imprecise deletions that extend beyond the target gene and can even result in the removal of an entire chromosome. Additionally, the vectors encoding the genome editors themselves can be unintentionally integrated at the site of DSBs. Lastly, even a single DSB can activate the p53 pathway, which can lead to apoptosis. CRISPR-guided nucleotide deaminases, or base editors, can avoid double-stranded breaks, and may not rely on homology-directed repair, but may also be limited to making a subset of all substitutions and can cause genomic and transcriptomic off-target mutations. Prime editing may be a more precise and versatile approach for installing insertions, deletions, and complex sequence changes within a 30-nucleotide (nt)

window at the protospacer adjacent motif (PAM)-proximal side of a Cas9 cleavage site. Prime Editors (PEs) may include a nicking Streptococcus pyogenes Cas9 (nSpCas9) that generates a genomic flap that can hybridize to a primer binding site (PBS) in a 3' extension of the CRISPR guide RNA (gRNA). A Moloney leukemia virus reverse transcriptase comprising five point mutations (mlvRT5M), which is fused to the nSpCas9, may utilizes the genomic flap as a primer to synthesize a strand of DNA comprising the desired edit according to the sequence of the RT template (RTT) which is also included in the gRNA's 3' extension. Editing efficiency can be increased by expressing a second gRNA that nicks the other strand. Unfortunately, PEs have generally been too large to be delivered with adeno-associated virus (AAV). Additionally, PEs may suffer from limited efficiency in non-dividing cells, generate unintended insertions or deletions when nicking both strands, or have a short editing window length that may limit the number of pathogenic mutations that can be corrected with a single construct and may require a PAM to be available near the edit site. Described herein is a gene editing system, which in some instances is called Rewriter, that may install any type of mutation within a larger window and with a higher efficiency than prime editors in dividing and non-dividing cells without generating double-stranded breaks. This may be done using components delivered with AAV.

Precision Editors that Fit in AAV

Figure 19A:
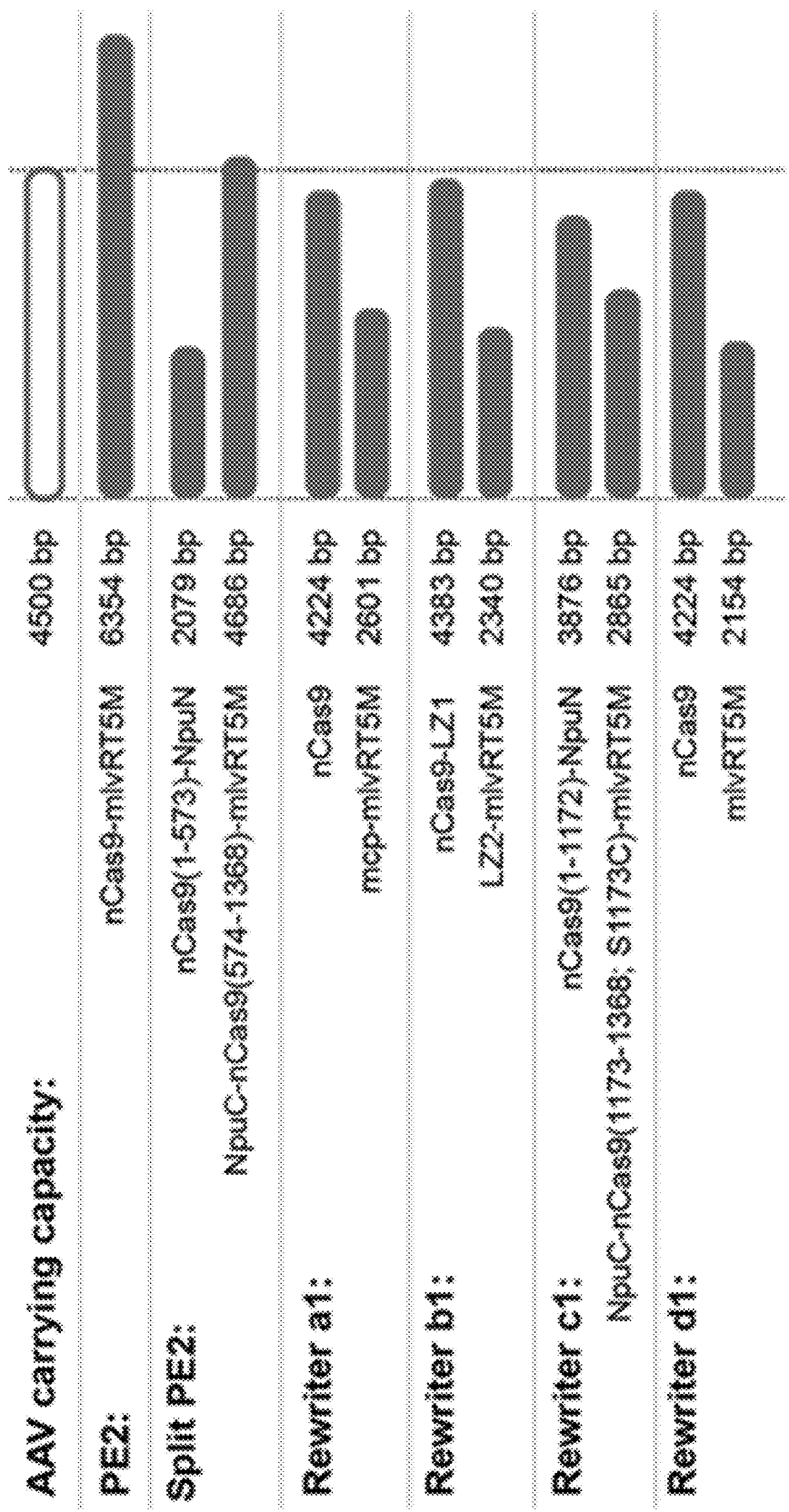
FIG. 19A shows abilities of some precision editing constructs to fit in an AAV, or not to fit within AAV. Both Prime Editor 2 (PE2) and Split PE2 may utilize a nicking Cas9 (nCas9) fused to a Moloney leukemia virus reverse transcriptase pentamutant (mlvRT5M), which may be encoded by ORFs too large to be packaged into AAV. Architectures were developed that can deliver nCas9 and mlvRT5M with AAV, each encoded by two ORFs that are each smaller than the carrying capacity of AAV. Rewriter a1 (RWa1) may utilizes nCas9, a MS2 coat protein (MCP) peptide fused to mlvRT5M and a gRNA comprising the MS2 hairpin to which the MCP peptide may specifically bind. RWb1 may utilize heterodimerizing leucine zippers to colocalize nCas9 and mlvRT5M. RWc1 may utilizes a novel mutant nCas9 that can be split with Npu inteins to produce a nCas9-mlvRT5M protein using ORFs that each fit in AAV. RWd1 may coexpress nCas9 and mlvRT5M without any engineered recruitment components.

While prime editor and a split intein prime editor may install many types of mutations at a target site, their coding sequences alone may be too large to fit into a 4.5 kilobase (kb) carrying capacity of an AAV (FIG. 19A). To provide benefits of precision editing with components that can be delivered within as few as two AAV genomes, Rewriter a1 ("RWa1" or "RW1M") was developed. RWa1 may include nCas9 coexpressed with a MS2 coat protein (MCP) peptide fused to mlvRT5M and a gRNA comprising an MS2 hairpin to which the MCP peptide may specifically bind. RW1M may incorporate an MS2 hairpin into a gRNA bound by nSpCas9 to recruit an MS2-binding peptide (MBP) fused to mlvRT5M. RW1M may allow delivery of nSpCas9 in one AAV, and MBP-mlvRT5M and a gRNA in another AAV (FIG. 27).

As shown in FIG. 27, an editing system comprising PE2 may include a nicking Cas9 (nCas9) fused to a Moloney leukemia virus reverse transcriptase containing 5 point mutations (mlvRT5M). The guide RNA used in PE2 may include an extension on the 3' end of the scaffold sequence containing a reverse transcriptase template (RTT) sequence and a primer binding site (PBS) sequence. The nCas9 may first nick the non-target strand which releases a genomic flap that hybridizes with the PBS. The mlvRT5M may then extend the genomic flap by reverse transcribing the RTT. An editing system comprising split PE2 may utilize an Npu split intein to express two ORFs that catalytically splice together to form the nCas9-mlvRT5M fusion protein. An editing system comprising Rewriter 1M (RW1M) may utilizes nCas9, a MS2-binding peptide (MBP) fused to mlvRT5M and a gRNA containing the MS2 hairpin to which the MBP specifically binds (FIG. 27: Left: the MS2 hairpin may be inserted within the gRNA scaffold; Middle: the MS2 hairpin may be inserted between the gRNA scaffold and the RTT; Right: the MS2 hairpin may be inserted after the PBS). An editing system comprising RW1L may utilize heterodimerizing leucine zippers to colocalize nCas9 and mlvRT5M. An editing system comprising RW1I may utilize a novel mutant nCas9 that can be split with Npu inteins to produce a nCas9-mlvRT5M protein using ORFs that each fit in AAV. An editing system comprising RW1N may coexpress nCas9 and mlvRT5M without any engineered recruitment components.

Precision editing efficiencies were determined using a HEK293 cell line stably expressing BFP, which can be edited to GFP by installing a specific 3-nucleotide (nt) mutation. A plasmid expressing the first protein component (nSpCas9), a second plasmid expressing the second protein component (MBP-mlvRT5M), and a third plasmid expressing a gRNA were transiently cotransfected into the HEK293 cell line. Cotransfection of plasmids expressing RWa1 (nCas9 and MCP-mlvRT5M) with gRNA 2.0, which included MS2 hairpin insertions within the Cas9-binding scaffold, further modified with a 13-nt PBS and a 13-nt RTT encoding a +2 ATGG to CATA mutation that was intended to remove the PAM site and install the GFP mutation resulted in 3.7% GFP+ cells, compared to 19% with PE2 (FIG. 11B). Inserting the MS2 hairpin closer to the site of the genomic flap and PBS may promote initiation of reverse transcription by the recruited MBP-mlvRT5M. The editing efficiency of RWa1 was increased to 15.5% by inserting the MS2 hairpin between an unmodified gRNA scaffold and the RTT.

Rewriter b1 ("RWb1" or "RW1L") may be an alternative approach to deliver editing components within two AAV genomes. The editing components may include a nCas9 fused to a leucine zipper (nSpCas9-LZ1) that heterodimerizes with another leucine zipper fused to an N-terminus of mlvRT5M (LZ2-mlvRT5M) (FIG. 19A). Cotransfection of plasmids expressing RWb1 (nSpCas9-LZ1 and LZ2-mlvRT5M) and gRNA 2.0 comprising a 13-nt PBS and a 13-nt RTT encoding a +2 ATGG to CATA mutation resulted in 38% GFP+ cells (FIG. 11B). As shown in FIG. 11B, HEK293 cells transfected with PE2 and gRNA 2.0, which may contain MS2 hairpin insertions within the Cas9-binding scaffold, further modified with a 13-nt PBS and a 13-nt RTT encoding a +2 ATGG to CATA mutation intended to remove the PAM site and install the GFP mutation, resulted in an editing efficiency of 19%. RWa1 with the same gRNA resulted in 3.7% GFP+ cells. The editing efficiency of RWa1 was increased to 15.5% by inserting the MS2 hairpin between an unmodified gRNA scaffold and the RTT. RWb1 and the gRNA 2.0 construct comprising a 13-nt PBS and a 13-nt RTT encoding a +2 ATGG to CATA mutation resulted in 38% GFP+ cells. RW1L was developed as an alternative design to deliver the editing components within two AAV genomes. RW1L may comprise a nSpCas9 fused to a leucine zipper17 (nSpCas9-LZ1) that heterodimerizes with a complementary leucine zipper fused to the N-terminus of mlvRT5M (LZ2-mlvRT5M). To allow direct comparison to RW1M, RW1L was initially tested with the same gRNA containing the gRNA 2.0 scaffold that was constructed for RW1M, (though the MS2 hairpins in gRNA 2.0 were necessarily not expected to interact with the components of RW1L).

Figure 19B:
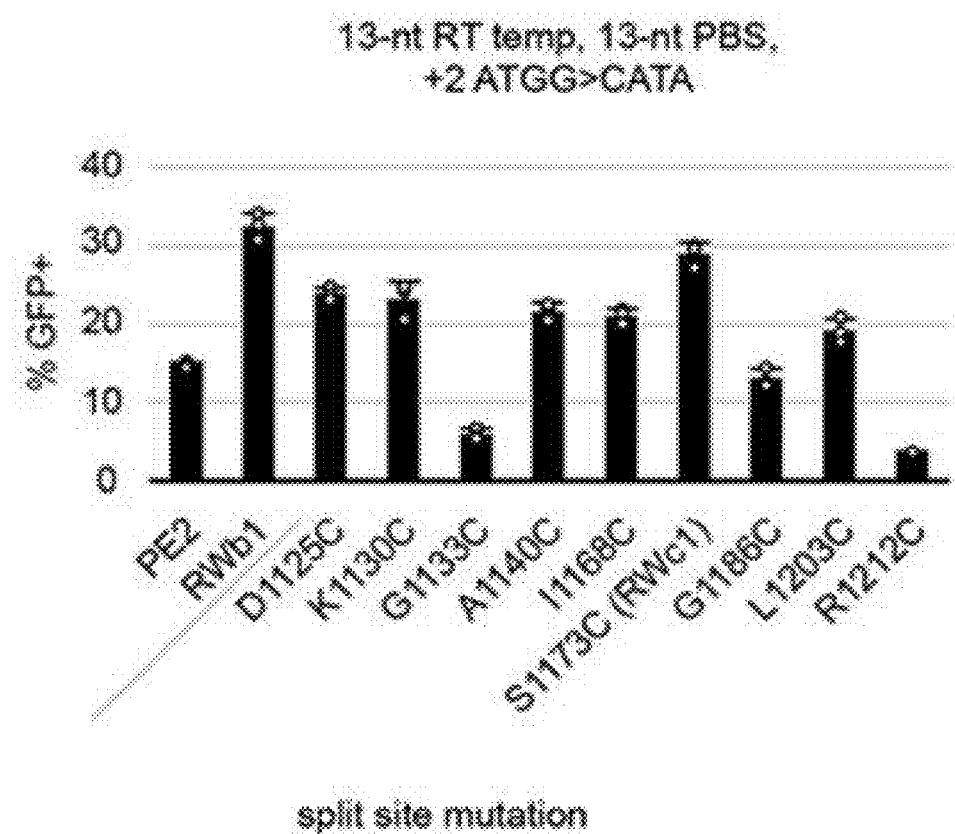
FIG. 19B shows GFP expression in cells comprising some editing constructs. Testing a panel of N-terminal fragments of nCas9 fused to the Npu N-terminal intein paired with an Npu C-terminal intein fused to a C-terminal fragment of nCas9 comprising a cysteine substitution providing for intein catalysis and mlvRT5M revealed that splitting a Ser 173Cys nCas9-mlvRT5M mutant between residues 1172 and 1173 (nCas9(1-1172)-NpuN and nCas9(1173-1368; S1173C)-mlvRT5M) resulted in at least about a 2-fold greater editing efficiency than PE2.

While RWa1 and RWb1 may each include two polypeptides that are within the size constraints permissive to AAV packaging, the size of the nSpCas9 and nSpCas9-LZ1 open reading frames (ORFs) may limit the length of regulatory elements that can be included to control expression. In some instances, due to a possible requirement for a cysteine as a first residue of a Npu C-terminal extein, Split Prime Editor 2 may include inteins to split nSpCas9-mlvRT5M into two fragments at Cys574, the most C-terminal cysteine in nSpCas9. It was considered that if an appropriate intein-flanking sequence could be introduced between residues 700 and 1250 of nSpCas9, then a modified nSpCas9-mlvRT5M fusion protein with two intein-comprising ORFs could be encoded within two recombinant AAV genomes with more room for regulatory elements than RWa1 and RWb1 may otherwise allow. A panel of constructs was tested, which encoded N-terminal fragments of nSpCas9 fused to the Npu N-terminal intein paired with an Npu C-terminal intein fused to a C-terminal fragment of nSpCas9 comprising a cysteine substitution (providing, in some instances, intein catalysis) and mlvRT5M. Splitting a Ser 173Cys nSpCas9-mlvRT5M mutant between residues 1172 and 1173 (nCas9(1-1172)-NpuN and nCas9(1173-1368; S1173C)-mlvRT5M; named "RWc1" or "RW1I") resulted in about a 2-fold greater editing efficiency than PE2 (29% vs 15%, FIG. 19B).

Figure 19C:
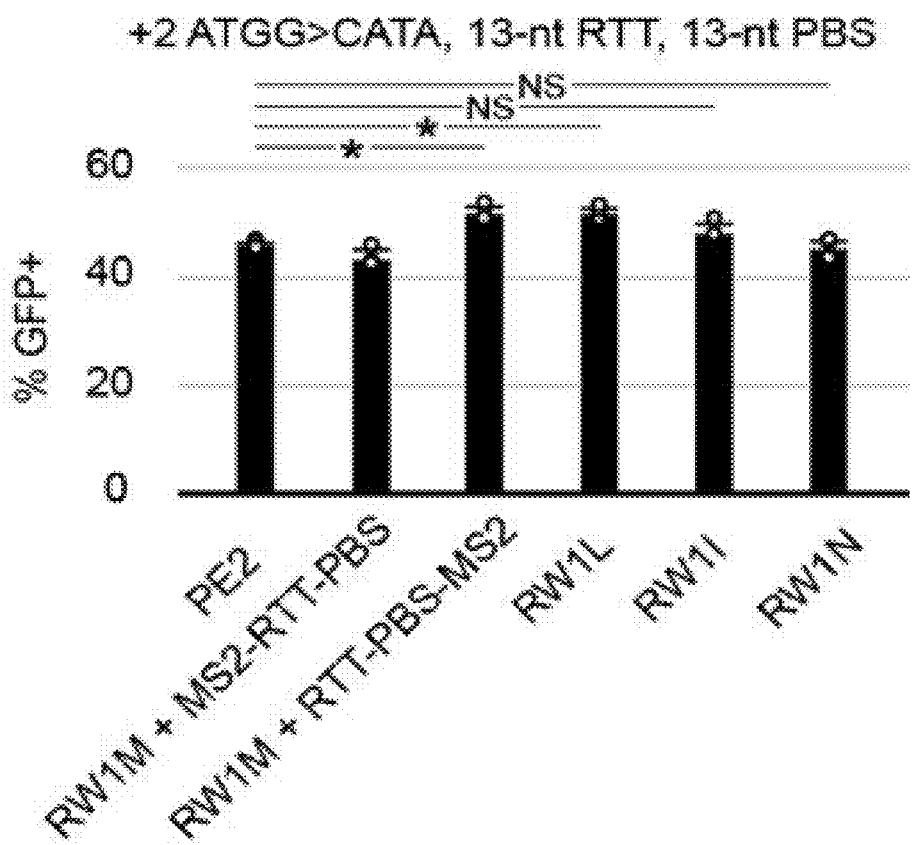
FIG. 19C shows GFP expression in cells comprising some editing constructs. Cotransfecting RWa1, RWb1, and RWc1 with the standard gRNA scaffold all resulted in above 40% editing efficiency. The editing efficiency over 40% was achieved with both RW1M paired with a RTT-PBS-MS2 gRNA extension architecture and RW1L achieving over 50% editing. Coexpression of a gRNA that does not contain the MS2 hairpins with the nCas9 and MCP-mlvRT5M constructs resulted in approximately the same editing efficiency compared to gRNAs that included an MS2 hairpin (RWd1).
Figure 19D:
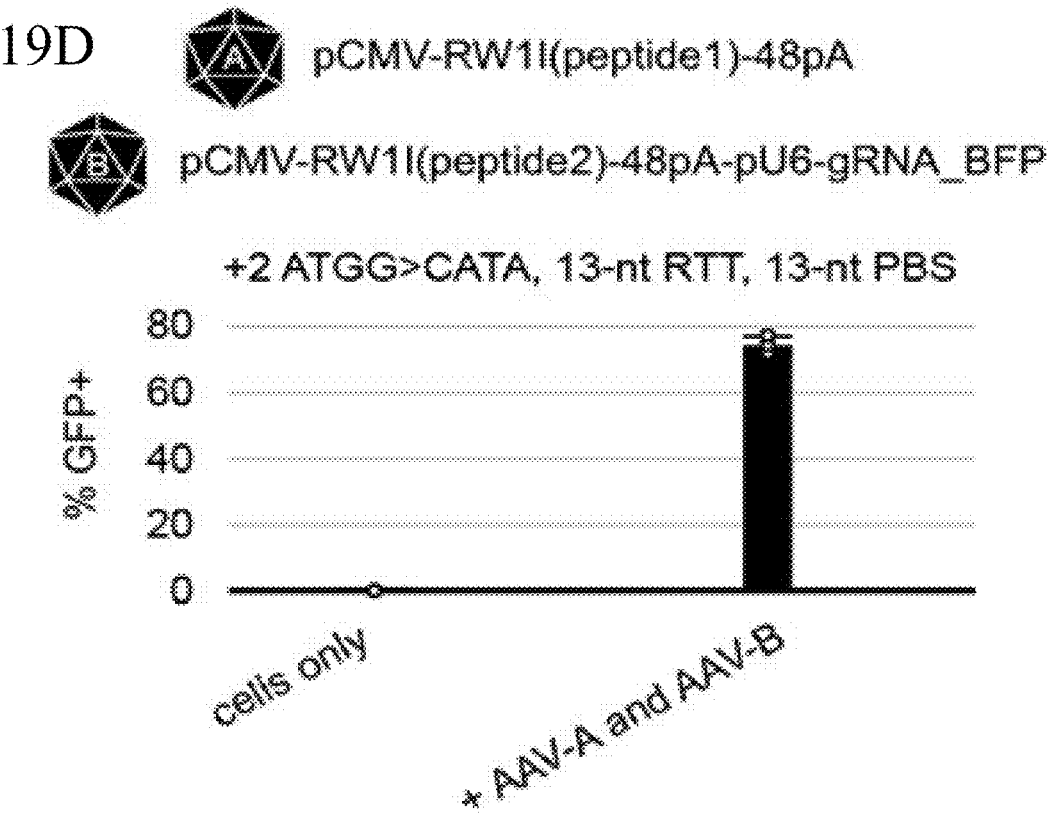
FIG. 19D shows GFP expression in cells transduced with some editing constructs. Transducing HEK293 cells expressing BFP with RWc1 packaged into two separate AAV2 constructs at an MOI of $2.8 \times 10^5$ for each virus resulted in 74.8% GFP+ cells. Mutation rate data are shown as mean±one standard deviation from three biologically independent samples.

Using the standard gRNA scaffold, RWa1, RWb1, and RWc1 were all found to result in above 40% editing efficiency (FIG. 19C). Surprisingly, coexpression of a gRNA not containing the MS2 hairpins with the nCas9 and MCP-mlvRT5M constructs resulted in approximately the same editing efficiency compared to gRNAs including an MS2 hairpin, showing that recruiting or fusing the RT to the site of the nCas9 may not always be necessary, or that simply coexpressing an nCas9 and RT can result in efficient editing. Constructs that did not actively recruit the mlvRT were called Rewriter dl ("RWd1" or "RW1N"). In the context of AAV delivery, RWc1 may be used, as it may accommodate up to approximately 670 nt of regulatory elements. Transducing the HEK293 cells expressing BFP with RWc1 packaged into two separate AAV2 constructs at an MOI of $2.8 \times 10^5$ for each virus resulted in 74.8% GFP+ cells (FIG. 19D).

To demonstrate AAV-mediated delivery of Rewriter, the N-terminal protein component of RW1I, which accommodated a 584-nt CMV promoter, was packaged into an AAV2 vector while packaging both the C-terminal protein component of RW1I (also driven by a CMV promoter) and a gRNA that converts BFP to GFP driven by a U6 promoter, into a separate AAV2 vector. Simultaneous AAV co-transduction of BFP-expressing HEK293 cells at an MOI of 2.8×105 VG/cell for each virus resulted in 74.8% GFP+ cells.

Results indicated that RW1M, RW1L, RW1I, or RW1N may have different editing efficiencies between different gRNAs, so some embodiments include screening several architectures to maximize efficiency with a given gRNA. RW1I may provide the most room for regulatory elements on both AAV genomes, while RW1L and RW1N may accommodate multiple gRNA cassettes in the second AAV genome. Although RW1N surprisingly provided similar editing efficiency as the other architectures when using plasmid transfection, this might require a high enough intracellular concentration of protein components to obviate a possible need for active recruitment. Therefore, RW1N may not provide high editing efficiencies with alternate delivery strategies and expression levels in some cases.

RNA Extension Reorientation

Spatial reorientation of a guide RNA extension may increase editing efficiency or window length. Increasing an editing window length may allow screening more gRNAs for efficient editing of a given mutation, or may correct more pathogenic mutations with a single gRNA. Additionally, Prime Editor 3b may increase editing efficiency by expressing a second gRNA that binds a sequence generated by the RT and nicks the opposite strand, thereby evading nick-mediated mismatch repair of the RT-synthesized edit. The Prime Editor 3b approach may, in some instances, be limited to target sites that have a PAM site within the limited editing window length of prime editors. Increasing the editing window length may require increasing a length of the RTT.

Figure 20A:
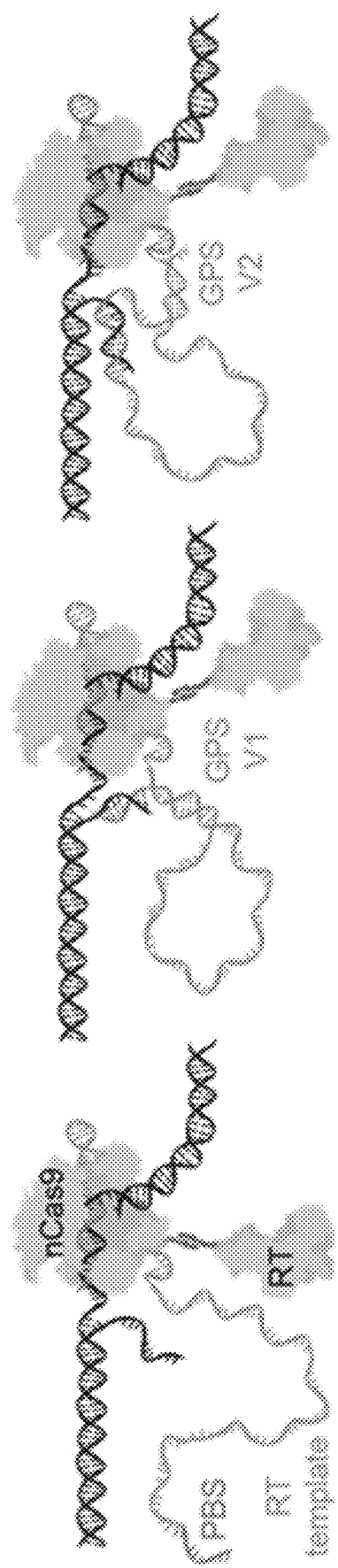
FIG. 20A shows some spatial orientations of enzymes and guide RNAs. Reverse transcription of the RTT can in some cases only be initiated after the PBS hybridizes to the genomic flap. Inserting either a sequence 5' of the RTT that hybridizes with a 3' region of the RTT (GPS V1) or a sequence 3' of the PBS that hybridizes with the 5' portion of the RTT (GPS V2) may reorient the PBS to be in closer proximity to the genomic flap.

It was hypothesized that editing efficiencies of Rewriter and PEs may be limited by a rate of hybridization of the PBS and the genomic flap when using longer RTTs. It was also predicted that if the length of the RTT could be increased, a decrease could be affected in the frequency of reverse transcription of a portion of the gRNA scaffold, which may inadvertently lead to undesirable insertion of a scaffold-templated sequence into the genome. An RNA component was designed, here called the gRNA positioning system (GPS), that may be introduced into the 3' extension of the gRNA to spatially orient the PBS to be near the genomic flap regardless of the length of the RTT. GPS Version 1 (V1) may include an RNA sequence inserted 5' of the RTT that may hybridize with a 3' region of the RTT, and/or GPS Version 2 (V2) may be an RNA sequence inserted 3' of the PBS that may hybridizes with the 5' portion of the RTT (FIG. 20A). Computational RNA folding analysis predicted that GPS V1 and V2 would bring the PBS closer to the 5' end of the gRNA's 3' extension as intended (FIG. 12B). RNA folding analysis predicted that GPS V1 and V2 may alter the structure of the gRNA's 3' extension to bring the PBS closer to the gRNA scaffold.

The GPS may also be referred to as Velcro. Likewise, Velcro may be referred to as GPS. GPS may include Velcro or a component of Velcro. Velcro may include GPS or a component of GPS.

Figure 20B:
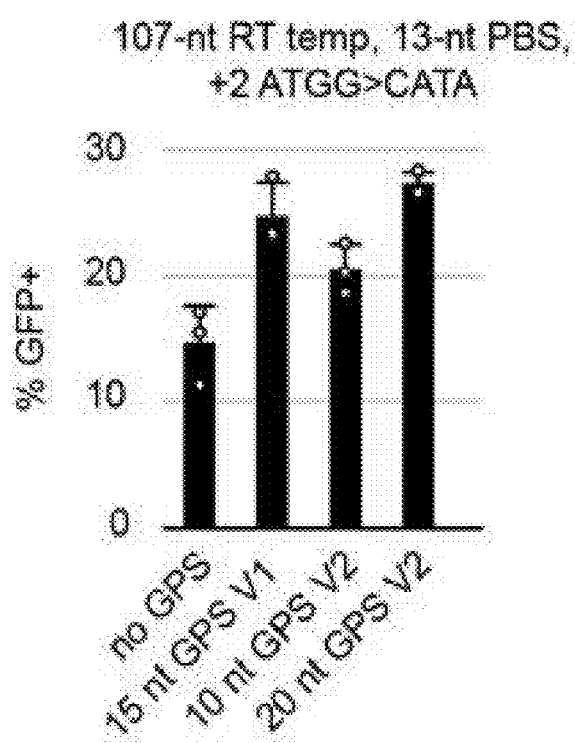
FIG. 20B shows GFP expression in cells comprising some editing constructs. RWb1 and a guide RNA comprising a 107-nt RTT resulted in 14% GFP+ cells, which is significantly lower than the 38% achieved using a shorter 13-nt RTT. Adding a 20-nt GPS V2 (RWb2) increased the editing efficiency to ~27%.
Figure 20C:
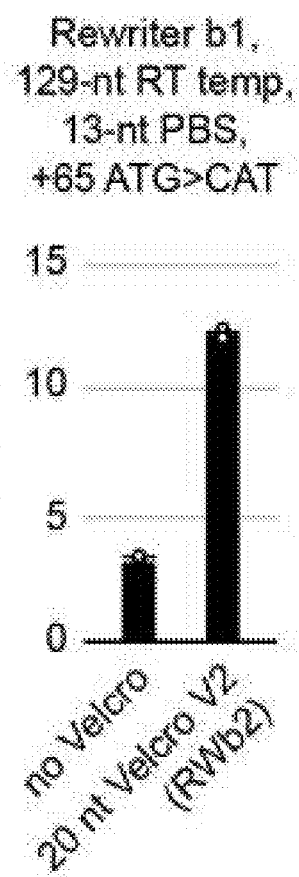
FIG. 20C shows GFP expression in cells comprising some editing constructs. Installing a 3-nt mutation 65-nt from the site of the nick using a 129-nt template was increased 4-fold by incorporating GPS V2.

Cotransfection of RWb1 and a guide RNA comprising a 107-nt RTT resulted in 14% GFP+ cells, which was significantly lower than the 38% achieved using a shorter 13-nt RTT, and thus confirmed that increasing the RTT length to broaden the editing window can decrease editing efficiency. Adding a 20-nt GPS V2 increased the editing efficiency to 27.4%. GPS V1 increased editing efficiency from 14% to 24.8%. GPS V1 may be used to cause reverse transcription and genomic insertion of the GPS sequence. Use of a 20-nt GPS V2, 3' of the PBS, increased the editing efficiency to 27.4% and does not have the potential for genomic insertion of the GPS sequence. GPS V2 was proceeded with, and the Rewriter systems using the GPS V2 component may be referred to as "Rewriter 2.0," or may be denoted with "g" (for example: "RW1I_g"). Next, it was found that installing a 3-nt mutation 65-nt from the site of the nick using a 129-nt template was increased 4-fold by incorporating GPS V2 (FIG. 20B). The efficiency of making this edit was increased to 21% by recoding the RTT to remove secondary structure that might inhibit reverse transcription while maintaining the amino acid sequence of the target site. Finally, a panel of GPSs of various lengths and binding sites was generated, and a 20-nt GPS that hybridized to the first 20-nt of the RTT resulted in the highest editing efficiency among the set (FIG. 12D). A 20-nt GPS that hybridized to the first 20-nt of the RTT resulted in the highest editing efficiency among a panel of GPS V2s of varying lengths and binding sites. Mutation rate data are shown as mean±one standard deviation from three biologically independent samples.

Second Strand Synthesis

Next, it was hypothesized that editing efficiency could be further increased by synthesizing a second strand of DNA comprising a desired edit that is complementary to the first synthesized strand. Second strand primers (SSP) were introduced. An SSP may allow the reverse transcriptase to use the first synthesized strand as a template for second strand synthesis (FIG. 13A). SSP may be inserted into the 3' terminus of the 3' gRNA extension. SSP may hybridize to a portion of the first synthesized strand that is 3' of the edit site. After the PBS hybridizes to the flap and the first strand is reverse transcribed, the SSP may hybridize to the first synthesized strand, allowing the reverse transcriptase to use the first synthesized strand as a template for second strand synthesis.

Figure 21:
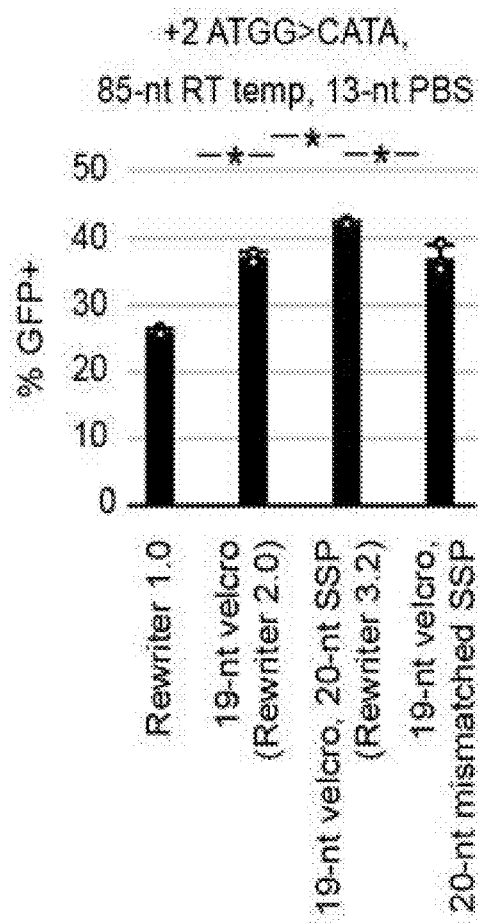
FIG. 21 shows GFP expression in cells comprising some editing constructs. Velcro and SSP may be used simultaneously, resulting in ~41% editing (Rewriter 3.2). The increase in efficiency that SSP provided was abolished when the terminal 3-nt of SSP were not complementary to the first synthesized strand. Mutation rate data are shown as mean±one standard deviation from three biologically independent samples. *=P<0.05; two-sided student's t-test.
Figure 22:
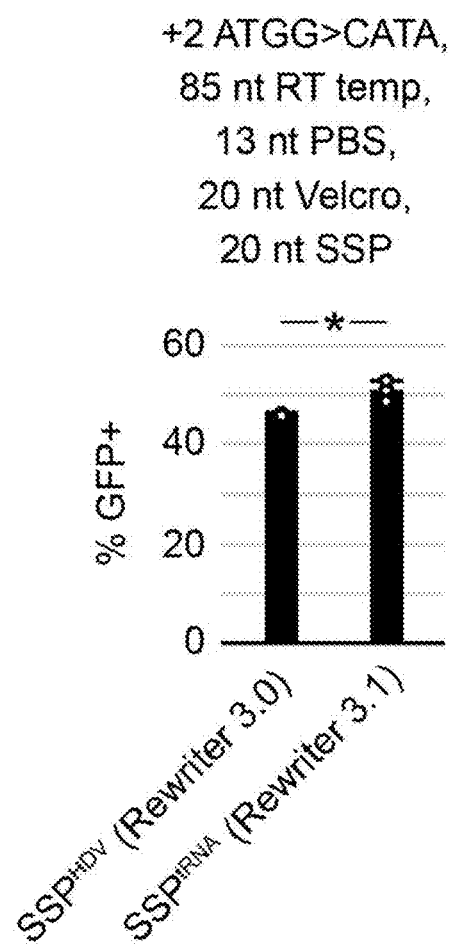
FIG. 22 shows that incorporating a human glutamate tRNA after SSP led to a statistically significant increase in editing efficiency compared to an HDV ribozyme following SSP. Mutation rate data are shown as mean±one standard deviation from three biologically independent samples. *=P<0.05; two-sided student's t-test.

The SSP may hybridize to a portion of the first synthesized strand that is 3' of the edit site. To allow the region from the start of the SSP to the 3' end of the gRNA to be complementary to the first synthesized strand, a self-cleaving hepatitis delta virus (HDV) ribozyme was introduced 3' of the SSP. First tested was whether SSP could improve the editing efficiency of PE2. 20-nt SSPs were found to perform better than 40-nt or 60-nt SSPs (FIG. 13B). 20-nt SSPs performed better than 40- and 60-nt SSPs. Incorporating a 20-nt SSP that hybridized up to 6- and 36-nt from the nick site approximately doubled editing efficiency compared to no SSP. A 20-nt SSP that hybridized up to 55-nt from the nick site did not improve editing efficiency. It was predicted that this was due to a lower efficiency of reverse transcription of the more distal portion of the RTT, thereby limiting the availability of the SSP binding site. The systems that utilize this SSP technology were named Rewriter 3.0. It was then found that SSP could be inserted after Velcro using Rewriter 2.0 to further increase editing efficiency, resulting in ~41% editing (Rewriter 3.2; FIG. 21). It was also demonstrated that the increase in efficiency that SSP provided was abolished when the terminal 3-nt of SSP were not complementary to the first synthesized strand.

Since the HDV ribozyme may leave a 2'3' cyclic phosphate on the 3' terminus, and reverse transcription may use a 3' hydroxyl to initiate synthesis from a primer, an endogenous enzyme such as human polynucleotide kinase may convert the 2'3' cyclic phosphate to a 3' hydroxyl. It was predicted that incorporating a tRNA after the SSP in place of the HDV ribozyme could lead to a more rapid generation of the 3' hydroxyl following RNase P cleavage of the tRNA. Incorporating a human glutamate tRNA led to a statistically significant increase in editing efficiency to 50.9%. The efficiency of making an edit 65-nt from the nick was slightly increased by recoding the RTT to remove secondary structure that might inhibit reverse transcription while maintaining the amino acid sequence of the target site.

Engineering mlvRT

PE2 was developed by introducing mutations into the mlvRT of PE1 that were reported to improve reverse transcriptase activity in vitro. The mlvRT used in PE2 may be improved further by incorporating mutations that increase processivity, thermostability, substrate affinity, or modulate RNaseH activity. Therefore, 31 mutations in mlvRT were screened that may improve mlvRT activity in vitro (FIG. 14A). Five mutations had statistically significant increases in editing. Effects of combinations of these mutations on top of mlvRT5M were tested to determine potential increases in editing efficiency. By adding 9 mutations to mlvRT5M, editing efficiency was increased from ~43% for mlvRT5M to ~54% for mlvRT14M (FIG. 14B). Systems that incorporate mlvRT14M may be referred to as "Rewriter 4" or as "Rewriter 2" (for example: "RW2I_g").

Overcoming Low dNTP Concentrations

Figure 15A:
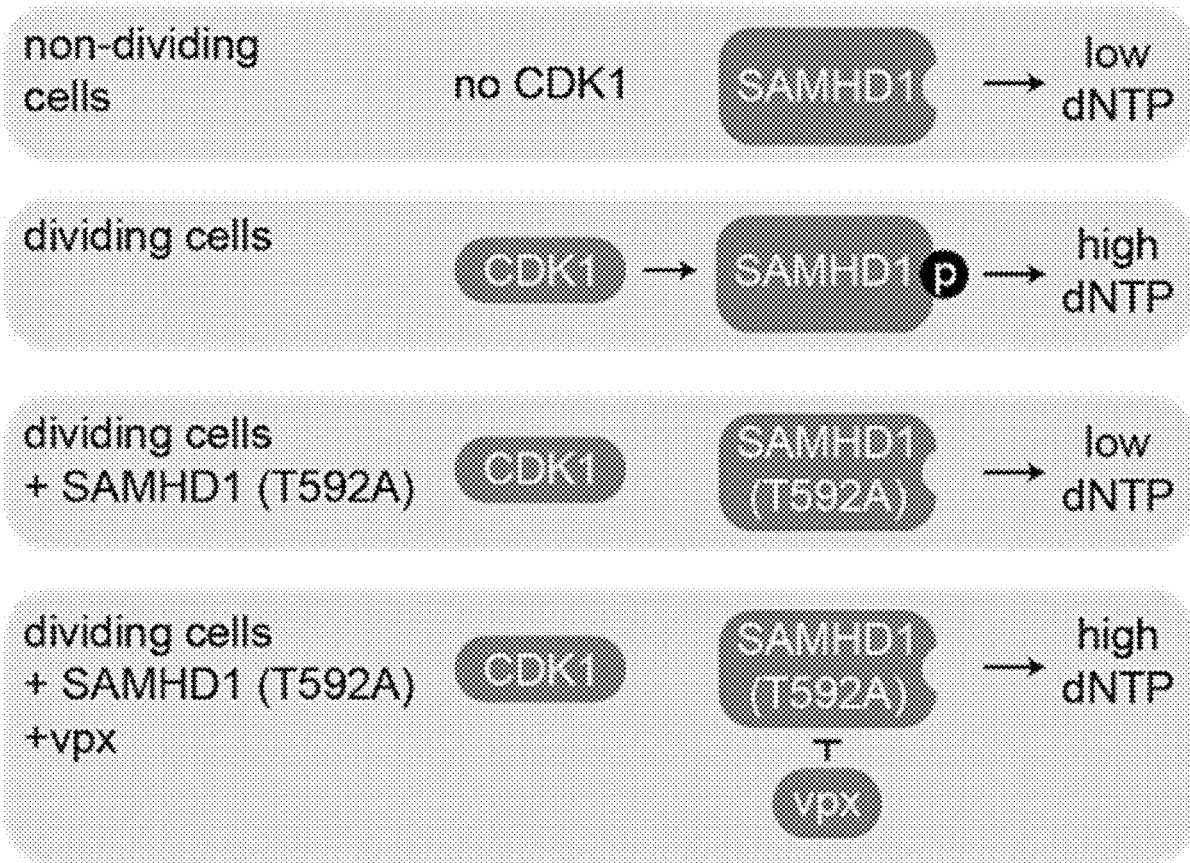
FIG. 15A illustrates a method of increasing availability of dNTPs in a cell to increase editing efficiency. In non-dividing cells lacking CDK1, unphosphorylated SAMHD1 cleaves dNTPs, decreasing the available dNTPs in the cell. In dividing cells, CDK1 phosphorylates SAMHD1, preventing SAMHD1 from cleaving dNTPs and leading to increased availability of dNTPs in the cell. A single point mutation in SAMHD1 (T592A) prevents phosphorylation of SAMHD1 by CDK1, resulting in a constitutively active SAMHD1 and a low availability of dNTPs in the cell. The T592A mutant SAMHD1 was used to induce a low dNTP environment in the assay shown in FIG. 15B, FIG. 15D, and FIG. 15E. Addition of Vpx inhibits SAMHD1, leading to increased availability of dNTPs in the cell.

Genome editors that polymerize DNA using reverse transcriptases, such as PE or some embodiments of Rewriter, may use dNTPs as substrates. It is therefore conceivable that low dNTP concentrations characteristic of non-dividing or slowly dividing cells (such as in the retina and lung) could possibly pose a barrier compared to editing in rapidly dividing cells in culture. SAMHD1 is a triphosphohydrolase that may control cellular dNTP concentrations. In nondividing cells, SAMHD1 may hydrolyze dNTPs. In cycling cells, cyclin dependent kinase 1 (CDK1) may phosphorylate SAMHD1. This may inhibit dNTP hydrolysis. This may lead to a higher dNTP concentration. A SAMHD1 T592A mutant ("SAMHD1$^{P-}$" or "SAMHD1 (T592A)") may in some instances not be phosphorylated, and therefore may deplete dNTP pools regardless of the presence of CDK1. VPX may be a small protein expressed by HIV-2 to specifically target SAMHD1 for degradation. It was predicted that the lower dNTP concentrations of nondividing and slowly dividing cells in HEK293T cells could be modeled by expressing SAMHD1$^{P-}$ (FIG. 15A).

Figure 15B:
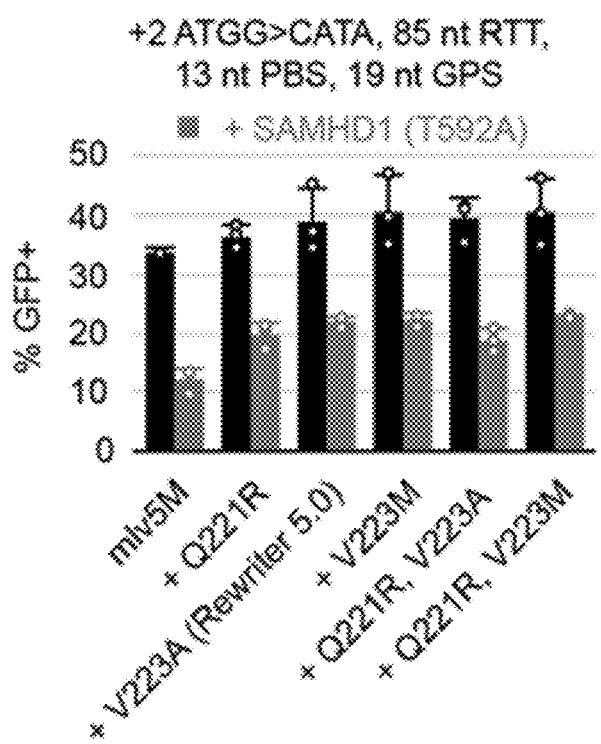
FIG. 15B shows the editing efficiency of mlvRT reverse transcriptase constructs in the presence or absence of a constitutively active SAMHD1 (SAMHD1 (T592A)) to decrease availability of dNTPs in the cell. Mutations were made in a reference mlvRT construct containing five point mutations (D200N, I603W, T330P, T306K, and W313F, SEQ ID NO: 40). Amino acid residues are counted relative to an mlvRT construct lacking an N-terminal methionine (e.g., SEQ ID NO: 14). mlvRT constructs containing Q221R; V223A; V223M; Q221R and V223A; or Q221R and V223M (SEQ ID NO: 76-SEQ ID NO: 80, respectively) relative to SEQ ID NO: 40 were tested. Editing efficiency was measured as a percent of cells that were GFP positive (% GFP+). Editing was performed using a gRNA with an 85 nucleotide RT template, a 13 nucleotide primer binding site, a 19 nucleotide Velcro region, and a 20 nucleotide second strand primer to edit a site such that an ATGG sequence, starting 2 nucleotides 3' of the nick, was mutated to CATA.
Figure 15C:
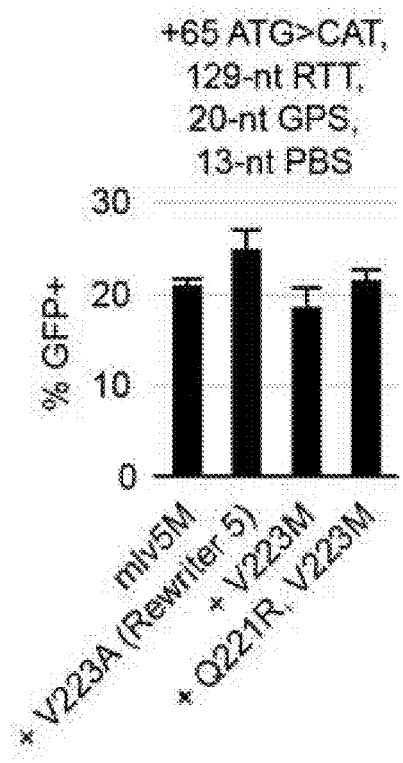
FIG. 15C shows the editing efficiency of mlvRT reverse transcriptase constructs. Mutations were made in a reference mlvRT construct containing five point mutations (D200N, I603W, T330P, T306K, and W313F, SEQ ID NO: 40). Amino acid residues are counted relative to an mlvRT construct lacking an N-terminal methionine (e.g., SEQ ID NO: 14). mlvRT constructs containing V223A; V223M; Q221R and V223A; or Q221R and V223M (SEQ ID NO: 77-SEQ ID NO: 80, respectively) relative to SEQ ID NO: 40 were tested. Editing efficiency was measured as a percent of cells that were GFP positive (% GFP+). Editing was performed using a gRNA with a 129 nucleotide RT template, a 13 nucleotide primer binding site, a 19 nucleotide Velcro region, and a 20 nucleotide second strand primer to edit a site such that an ATG sequence, starting 65 nucleotides 3' of the nick, was mutated to CAT.

FIG. 15B shows that cotransfecting Rewriter 3.2 (which may also be referred to as "RW1L_g") with SAMHD1$^{P-}$ decreased editing efficiency 2.7-fold, supporting the idea that dNTP concentrations may in some instances be limiting for genome editing. Editing efficiency decreased 2.7-fold when SAMHD1 (T592A) was coexpressed. Several mutations to mlvRT5M restored some of the editing efficiency in the presence of SAMHD1 (T592A). Some mutations may lower the $K_m$ of mlvRT for dNTPs. Introducing some such mutations into Rewriter restored some of the editing efficiency in the presence of SAMHD1$^{P-}$ 2-nt away from the nick. It was confirmed that one of these mutations, V223A, did not reduce efficiency. The construct that incorporated V223A was named Rewriter 5.0 (FIG. 15C). Introducing the V223A mutation into mlvRT5M did not reduce the efficiency of installing an edit 65-nt from the nick (Rewriter 5).

Figure 15D:
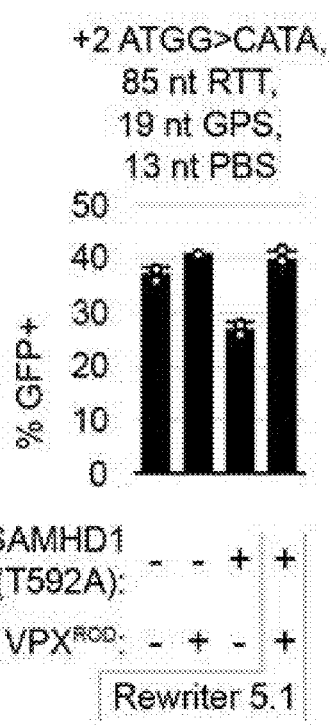
FIG. 15D shows the editing efficiency of a mlvRT reverse transcriptase in the presence or absence of a constitutively active SAMHD1 (SAMHD1 (T592A)) to decrease availability of dNTPs in the cell and with or without Vpx (SEQ ID NO: 82) to inhibit SAMHD1. Editing efficiency was measured as a percent of cells that were GFP positive (% GFP+). Editing was performed using a gRNA with an 85 nucleotide RT template, a 13 nucleotide primer binding site, a 19 nucleotide Velcro region, and a 20 nucleotide second strand primer to edit a site such that an ATGG sequence, starting 2 nucleotides 3' of the nick, was mutated to CATA.

As a complementary approach to increasing editing efficiency in nondividing and slowly dividing cells, VPX was employed. VPX may be a small HIV-2 protein. VPX may specifically target SAMHD1 for degradation. Coexpression of VPX$^{ROD}$ (from the ROD HIV-2 isolate) and SAMHD1$^{P-}$ completely reversed the reduction in editing efficiency caused by expressing SAMHD1$^{P-}$ without VPX (FIG. 15D). The SAMHD1$^{P-}$-induced decrease in editing efficiency was even more drastic when a mutation was installed 65-nt from the nick. Near zero efficiency may be due to the compounding reduction in DNA synthesis efficiency for every dNTP incorporation. Coexpression of VPX$^{ROD}$ restored the editing efficiency to 78% of the efficiency observed without expressing SAMHD1$^{P-}$ (Rewriter 5.1).

Figure 15E:
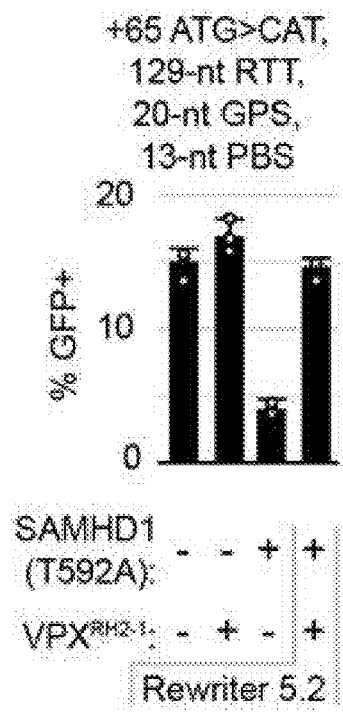
FIG. 15E shows the editing efficiency of a mlvRT reverse transcriptase in the presence or absence of a constitutively active SAMHD1 (SAMHD1 (T592A)) to decrease availability of dNTPs in the cell and with or without Vpx (SEQ ID NO: 82) to inhibit SAMHD1. Editing efficiency was measured as a percent of cells that were GFP positive (% GFP+). Editing was performed using a gRNA with a 129 nucleotide RT template, a 13 nucleotide primer binding site, a 19 nucleotide Velcro region, and a 20 nucleotide second strand primer to edit a site such that an ATG sequence, starting 65 nucleotides 3' of the nick, was mutated to CAT.
Figure 15F:
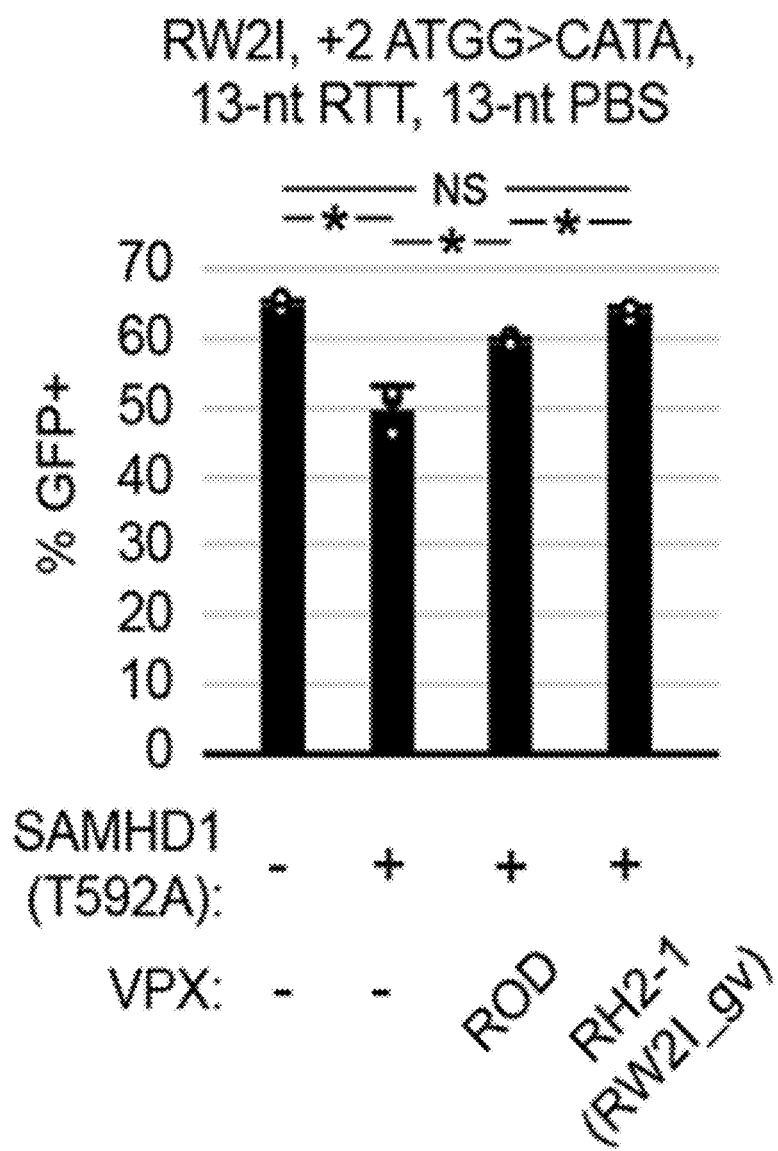
FIG. 15F shows that coexpression of VPX$^{RH2-1}$ and SAMHD1 (T592A) with RW2I completely reversed the reduction in editing efficiency caused by expressing SAMHD1 (T592A) without VPX.
Figure 23:
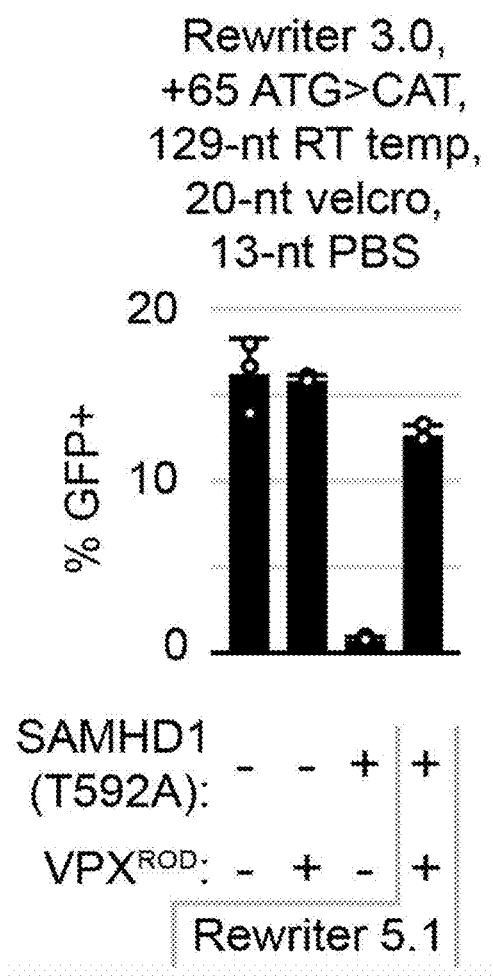
FIG. 23 shows that Coexpression of SAMHD1p− with Rewriter 3.0 drastically decreased the efficiency of installing a mutation 65-nt from the nick. Additional coexpression of VPXROD restored the editing efficiency to 78% of the efficiency observed in the absence of SAMHD1p−. Mutation rate data are mean±one standard deviation from three biologically independent samples.

A variant of VPX was identified from HIV-2 clinical isolate RH2-1 (VPX$^{RH2-1}$) that fully restored the efficiency of installing a mutation 65-nt from the nick in the presence of SAMHD1-(Rewriter 5.2; FIG. 15E). Mutation rate data in FIG. 15E are shown as mean±one standard deviation from three biologically independent samples. VPX$^{RH2-1}$ also outperformed VPX$^{ROD}$ when coexpressing SAMHD1 (T592A) with RW2I and a gRNA that may install a mutation 2-nt from the nick, yielding 64% editing efficiency (FIG. 15F), as well as with RW2I_g and a gRNA installing a mutation 65-nt from the nick (FIG. 23). Rewriter systems that incorporate VPX$^{RH2-1}$ may be designated with "_v" (for example: "RW2I_gv").

Increasing concentration of dNTPs may be an additional complementary approach to increase editing efficiency in a cell. The method may comprise delivering nucleotides or nucleosides to the cell, resulting in an increased concentration of dNTPs in the cell compared to a cell that did not received the nucleotides or nucleosides. The increased concentration of the dNTPs in the cell may result in increased editing efficiency in the cell comprising the compositions as disclosed herein. In some cases, dNTPs are administered to a subject (e.g. a subject comprising the cell). In some embodiments, administering dNTPs to a cell comprises administering the dNTPs to a subject comprising the cell. The administration of dNTPs may include oral administration. The administration of dNTPs may be by injection.

Correcting Cystic Fibrosis Mutations or Other Disease Mutations

Figure 29A:
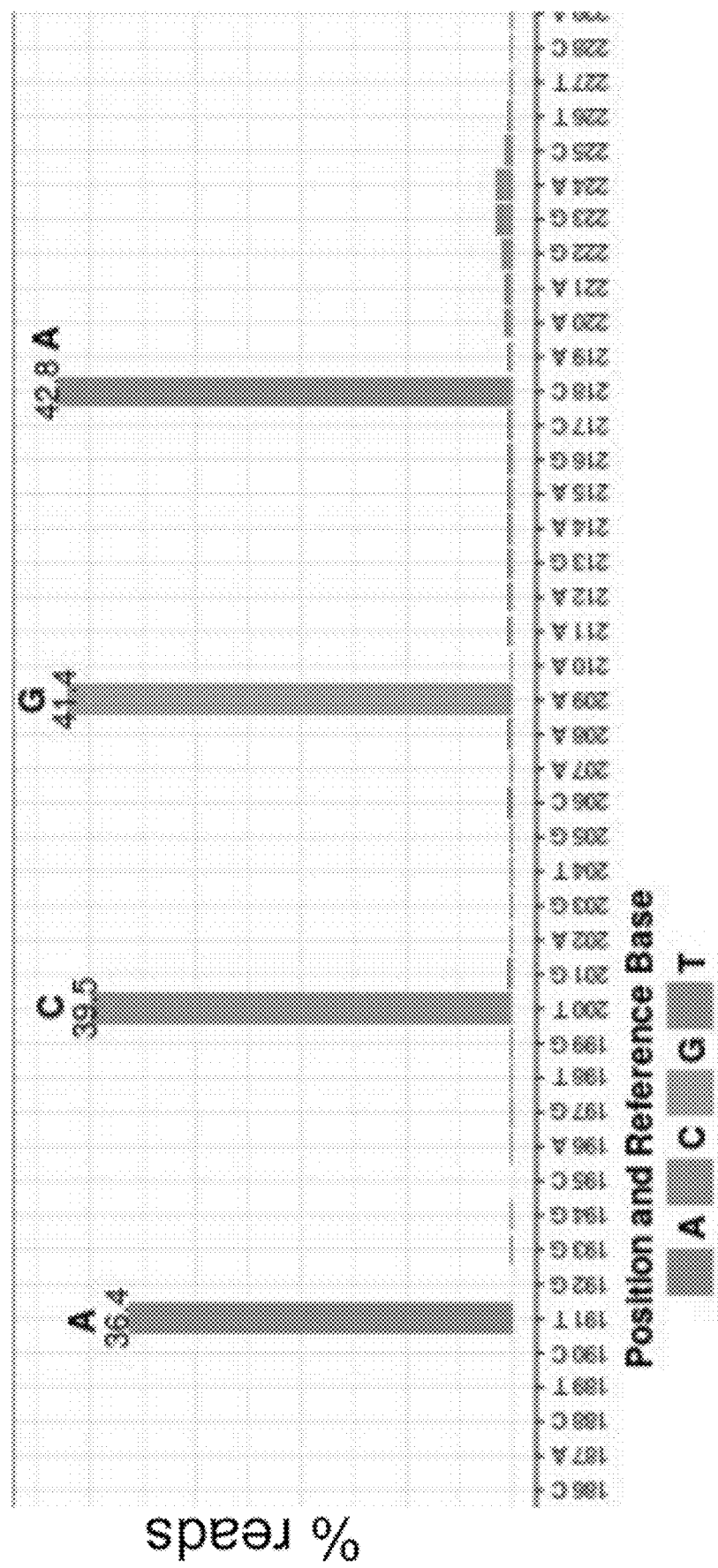
FIGS. 29A-29F show % reads of nucleobases after use of some editing systems.
Figure 29B:
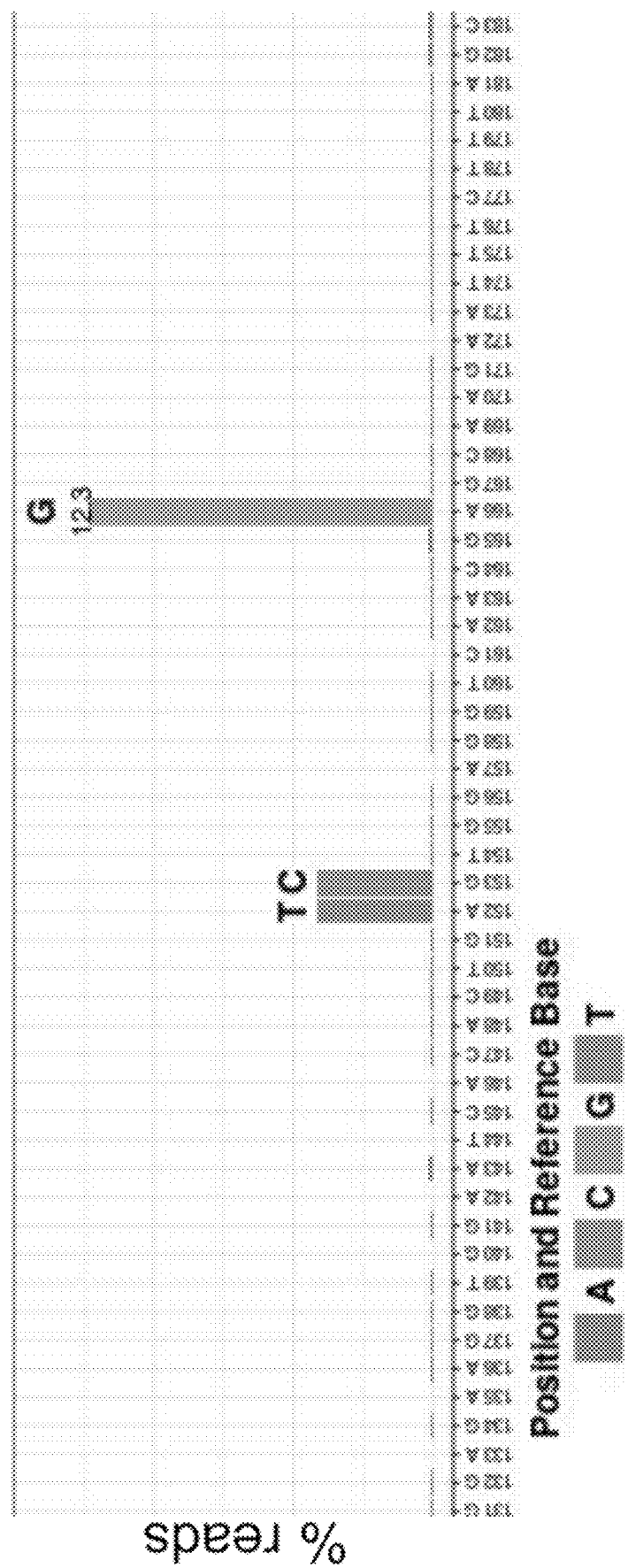
Figure 29C:
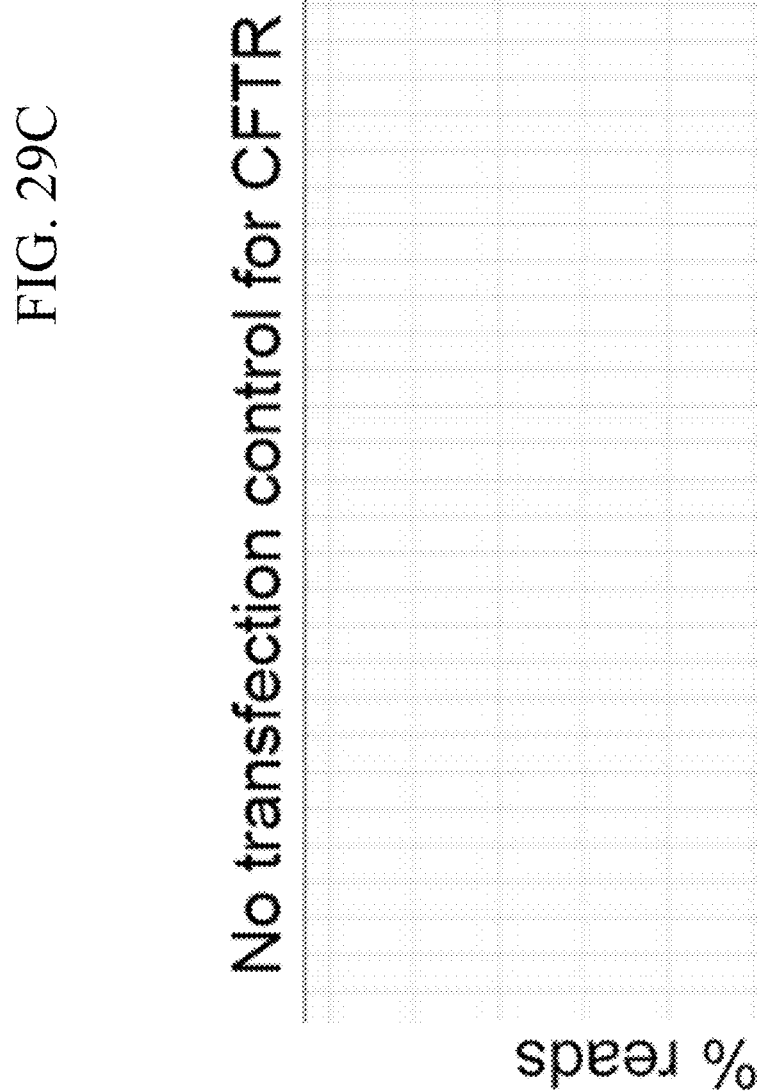

Small-molecule therapies for cystic fibrosis have shown a less than complete functional restoration of sweat chloride, pulmonary complication rate, and forced expiratory volume. Additionally, a majority of cystic fibrosis (CF)-causing mutations in the CFTR gene may not be treatable by these small molecules. Delivering a functional copy of a CFTR gene to affected cells may treat any CF patient, regardless of the CF patient's CFTR genotype. However, gene therapy approaches for treating CF have been limited by transient and synthetic regulation of CFTR expression, as well as the limited packaging capacity of AAV, which may require use of a truncated CFTR that displays incomplete activity. Some data related to CFTR editing are shown in FIG. 29B and FIG. 29C.

As an alternative, editing CF-causing mutations to restore CFTR activity that is controlled by its natural regulatory elements may provide long term and potentially curative therapy. As such, some embodiments of the methods and compositions described herein may be used to treat CF. Some embodiments include administering to a subject in need thereof (e.g. a subject with CF), one or more polynucleotides encoding genome editing components described herein that are configured to correct a mutant CFTR gene, or one or more viruses such as adenoviruses comprising the one or more polynucleotides. An example of such a component includes a guide RNA comprising a spacer that is reverse complementary to a region of a CFTR nucleic acid. The spacer include the nucleic acid sequence of SEQ ID NO: 96. The spacer may include a nucleic acid sequence at least 70%, at least 75%, at least 80%, at least 85%, at least 90%, or at least 95% identical to SEQ ID NO: 96. The spacer include the nucleic acid sequence of SEQ ID NO: 97. The spacer may include a nucleic acid sequence at least 70%, at least 75%, at least 80%, at least 85%, at least 90%, or at least 95% identical to SEQ ID NO: 97. The spacer include the nucleic acid sequence of SEQ ID NO: 98. The spacer may include a nucleic acid sequence at least 70%, at least 75%, at least 80%, at least 85%, at least 90%, or at least 95% identical to SEQ ID NO: 98. The spacer include the nucleic acid sequence of SEQ ID NO: 99. The spacer may include a nucleic acid sequence at least 70%, at least 75%, at least 80%, at least 85%, at least 90%, or at least 95% identical to SEQ ID NO: 99. The spacer include the nucleic acid sequence of SEQ ID NO: 100. The spacer may include a nucleic acid sequence at least 70%, at least 75%, at least 80%, at least 85%, at least 90%, or at least 95% identical to SEQ ID NO: 100. The spacer include the nucleic acid sequence of SEQ ID NO: 101. The spacer may include a nucleic acid sequence at least 70%, at least 75%, at least 80%, at least 85%, at least 90%, or at least 95% identical to SEQ ID NO: 101. The spacer include the nucleic acid sequence of SEQ ID NO: 102. The spacer may include a nucleic acid sequence at least 70%, at least 75%, at least 80%, at least 85%, at least 90%, or at least 95% identical to SEQ ID NO: 102. The spacer include the nucleic acid sequence of SEQ ID NO: 103. The spacer may include a nucleic acid sequence at least 70%, at least 75%, at least 80%, at least 85%, at least 90%, or at least 95% identical to SEQ ID NO: 103. The spacer include the nucleic acid sequence of SEQ ID NO: 104. The spacer may include a nucleic acid sequence at least 70%, at least 75%, at least 80%, at least 85%, at least 90%, or at least 95% identical to SEQ ID NO: 104. The spacer include the nucleic acid sequence of SEQ ID NO: 105. The spacer may include a nucleic acid sequence at least 70%, at least 75%, at least 80%, at least 85%, at least 90%, or at least 95% identical to SEQ ID NO: 105. In some embodiments, the administration improves a therapeutic parameter of CF in the subject.

TABLE 1

| Spacers | | |
|---|---|---|
| Spacer name (gene.mutation.number) | Sequence | Editing efficiency |
| CFTR.F508del.1 | SEQ ID NO: 96 | 6.81% |
| CFTR.F508del.2 | SEQ ID NO: 97 | |
| CFTR.F508del.3 | SEQ ID NO: 98 | |
| CFTR.R553X.1 | SEQ ID NO: 99 | 13.30% |
| CFTR.G542X.NAG.1 | SEQ ID NO: 100 | |
| CFTR.G542X.NAG.2 | SEQ ID NO: 101 | |
| CFTR.G542X.NAG.3 | SEQ ID NO: 102 | |
| CFTR.W1282X.1 | SEQ ID NO: 103 | 18.47% |
| CFTR.W1282X.2 | SEQ ID NO: 104 | |
| CFTR.W1282X.3 | SEQ ID NO: 105 | |
| USH2A.1 | SEQ ID NO: 106 | 41% |
| USH2A.2 | SEQ ID NO: 107 | |
| ABCA4.G1961E.1 | SEQ ID NO: 108 | 37.2% |
| ABCA4.G1961E.2 | SEQ ID NO: 109 | 23.3% |
| ABCA4.G863A.1 | SEQ ID NO: 110 | |
| ABCA4.G863A.2 | SEQ ID NO: 111 | 22.45% |
| ATP7B.H1069Q.1 | SEQ ID NO: 112 | 26.7% |
| ATP7B.H1069Q.2 | SEQ ID NO: 113 | 10.37% |
| ATP7B.R778L.1 | SEQ ID NO: 114 | |
| ATP7B.R778L.2 | SEQ ID NO: 115 | |
| HTT.NAG.1 | SEQ ID NO: 116 | 25% |
| HTT.2 | SEQ ID NO: 117 | |
| HTT.3 | SEQ ID NO: 118 | |
| HTT.4 | SEQ ID NO: 119 | |

Likewise, some embodiments of the methods and compositions described herein may be used to treat other diseases. Editing a disease-causing mutation to restore a correct sequence in a target gene may provide long term and potentially curative therapy for subjects with the disease. Some embodiments include administering to a subject in need thereof (e.g. a subject with a disease), one or more polynucleotides encoding genome editing components described herein that are configured to correct a mutant target gene, or one or more viruses such as adenoviruses comprising the one or more polynucleotides. An example of such a component includes a guide RNA comprising a spacer that is reverse complementary to a region of a target nucleic acid. Some such spacers are included in TABLE 1. The spacer may include a nucleic acid sequence at least 70%, at least 75%, at least 80%, at least 85%, at least 90%, at least 95%, or 100%, identical to a spacer in TABLE 1, or a complementary sequence. In some cases, the spacer includes a similar sequence but includes Us in place of Ts. In some embodiments, the administration improves a therapeutic parameter of the disease in the subject.

Some embodiments of the methods and compositions described herein may be used to treat Usher syndrome. Editing Usher syndrome-causing mutations to restore USH2A may provide long term and potentially curative therapy for subjects with Usher syndrome. Some embodiments include administering to a subject in need thereof (e.g. a subject with Usher syndrome), one or more polynucleotides encoding genome editing components described herein that are configured to correct a mutant USH2A gene, or one or more viruses such as adenoviruses comprising the one or more polynucleotides. An example of such a component includes a guide RNA comprising a spacer that is reverse complementary to a region of a USH2A nucleic acid. The spacer include the nucleic acid sequence of SEQ ID NO: 106. The spacer may include a nucleic acid sequence at least 70%, at least 75%, at least 80%, at least 85%, at least 90%, or at least 95% identical to SEQ ID NO: 106. The spacer include the nucleic acid sequence of SEQ ID NO: 107. The spacer may include a nucleic acid sequence at least 70%, at least 75%, at least 80%, at least 85%, at least 90%, or at least 95% identical to SEQ ID NO: 107. In some embodiments, the administration improves a therapeutic parameter of Usher syndrome in the subject. In some embodiments, the genome editing components correct a mutation shown in FIG. 25B. Some data related to USH2A editing are shown in FIG. 29A.

Figure 25A:
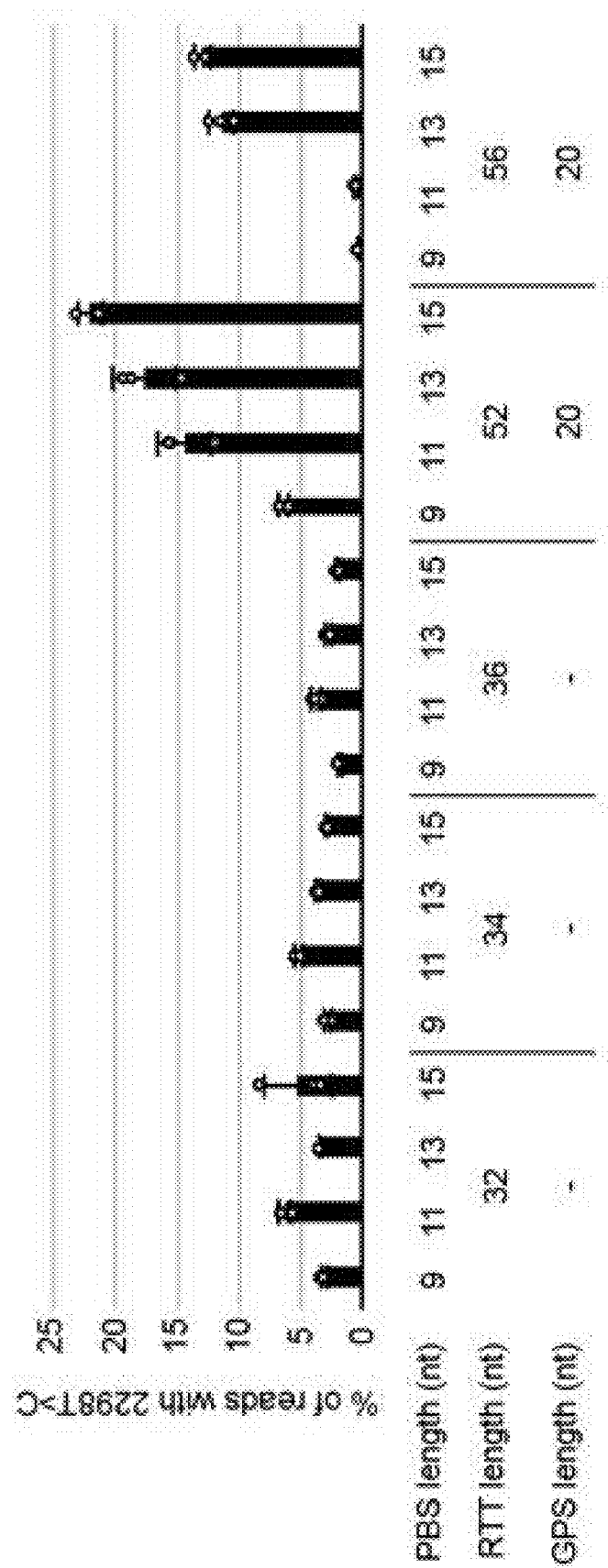
FIG. 25A is a chart showing editing efficiencies using Rewriter constructs.
Figure 25D:
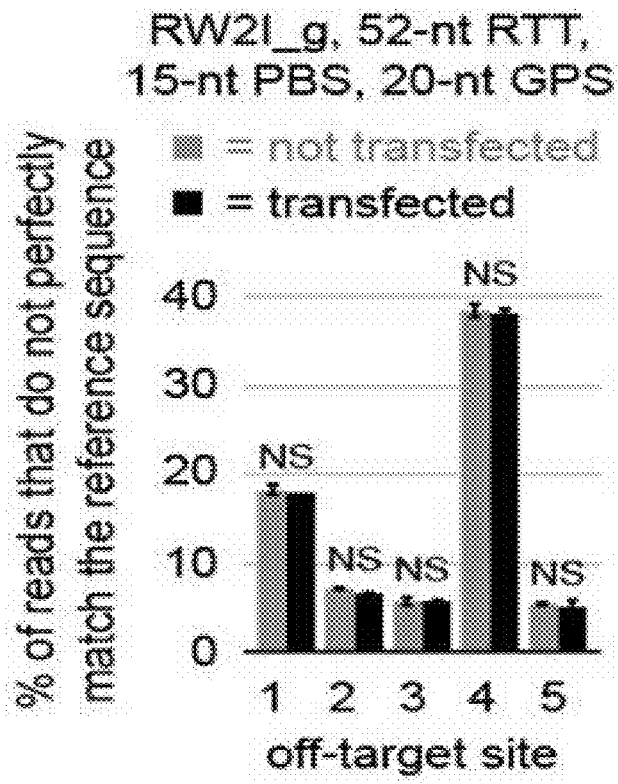
FIG. 25D illustrates that transfecting HEK293T with RW2I and a gRNA to install the 2298T>C mutation did not introduce mutations at the spacer's top five in silico-predicted off-target sites.

The USH2A.1 spacer was used to generate the data in FIG. 25A and FIG. 25B. For the data in FIG. 25A, HEK293T cells were transfected with RW2I using various sequences of PBS, RTT, or GPS. Editing efficiency is displayed as the percentage of reads with the intended 2298T>C mutation. A 15-nt PBS, 52-nt RTT, and 20-nt GPS resulted in 22% editing. Similar experiments were also performed where editing efficiencies are included in TABLE 1. For the data in FIG. 25B, the most frequent mutant allele generated by the 15-nt PBS, 52-nt RTT, 20-nt GPS construct contained both of the 2298T>C and 2316C>A mutations encoded in the RTT (18.8%). An additional 7.1% of reads were represented by either the 2316C>A PAM-disrupting mutation alone or the target 2298T>C mutation alone. A low frequency of adenine insertions were also detected along poly-A tracts within the target sequence. Data shown include mean one standard deviation from three biologically independent samples.

Figure 29D:
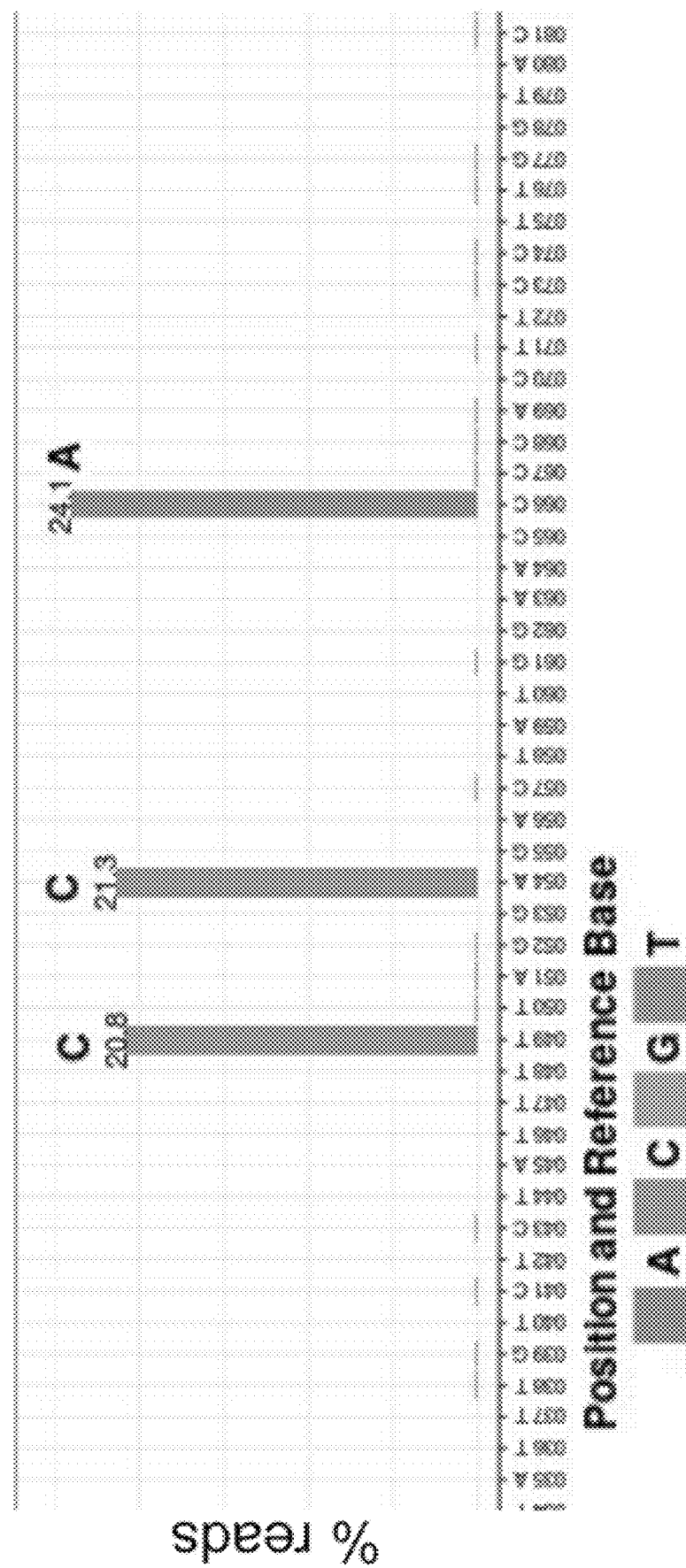
Figure 29E:
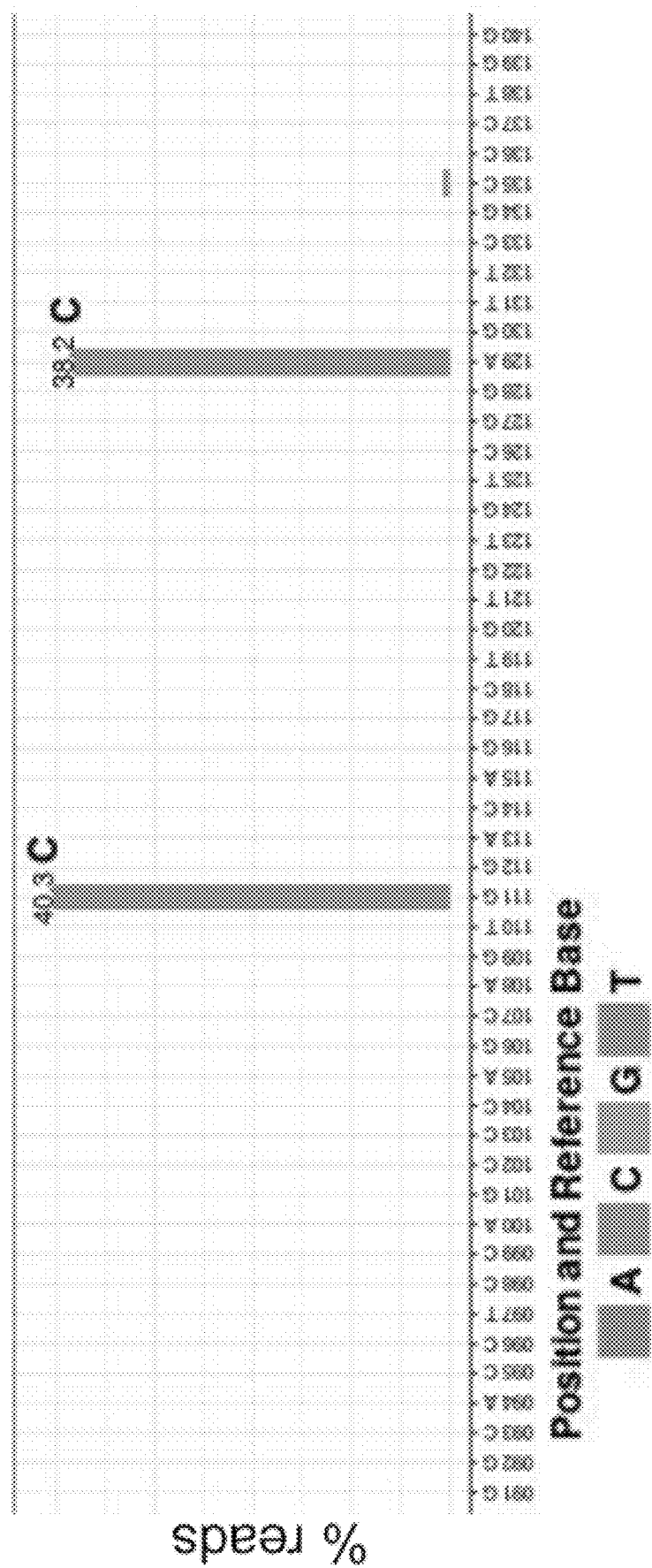
Figure 29F:
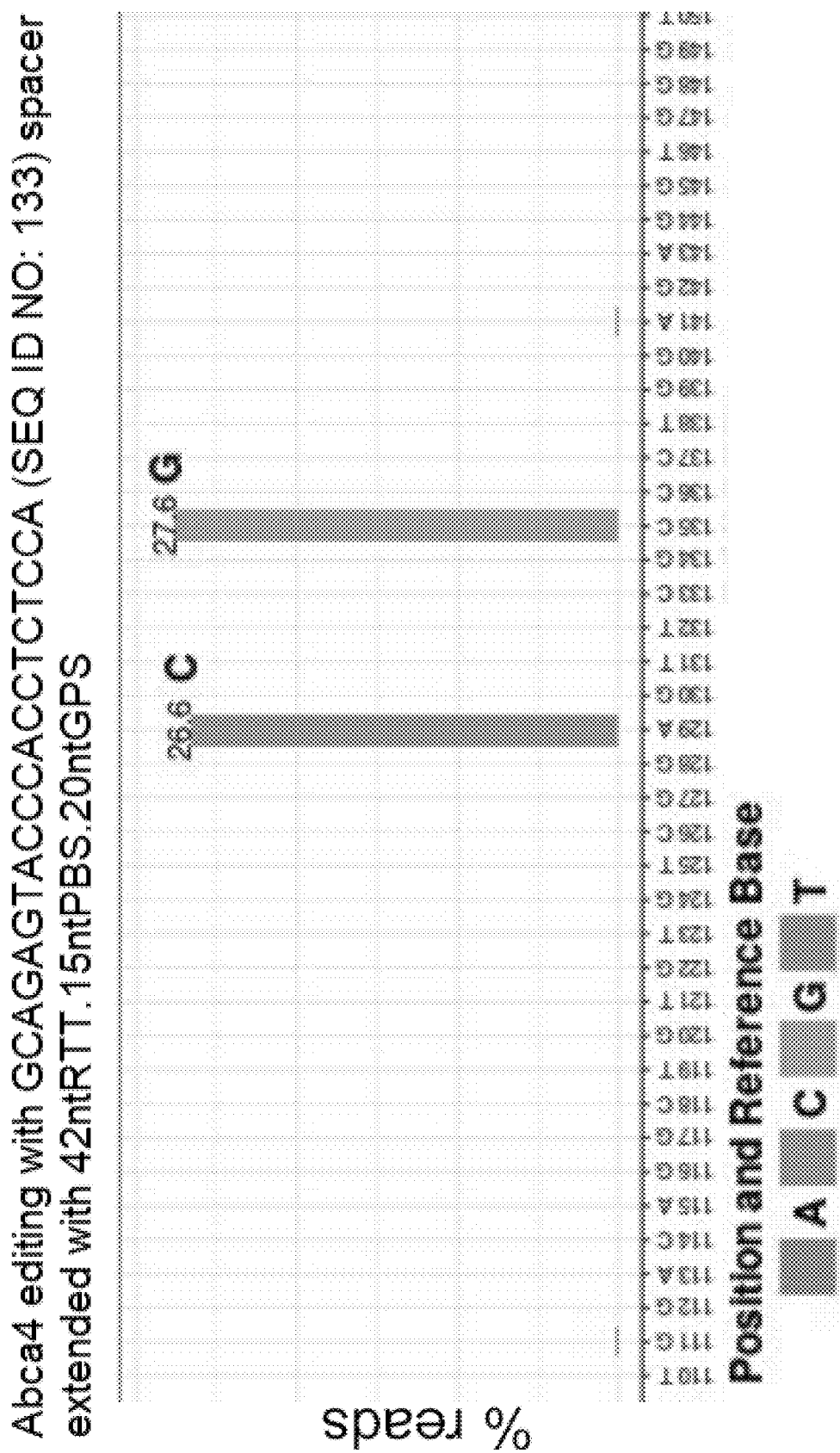

Some embodiments of the methods and compositions described herein may be used to treat Stargardt disease. Editing Stargardt disease-causing mutations to restore ABCA4 may provide long term and potentially curative therapy for subjects with Stargardt disease. Some embodiments include administering to a subject in need thereof (e.g. a subject with Stargardt disease), one or more polynucleotides encoding genome editing components described herein that are configured to correct a mutant ABCA4 gene, or one or more viruses such as adenoviruses comprising the one or more polynucleotides. An example of such a component includes a guide RNA comprising a spacer that is reverse complementary to a region of an ABCA4 nucleic acid. The spacer include the nucleic acid sequence of SEQ ID NO: 108. The spacer may include a nucleic acid sequence at least 70%, at least 75%, at least 80%, at least 85%, at least 90%, or at least 95% identical to SEQ ID NO: 108. The spacer include the nucleic acid sequence of SEQ ID NO: 109. The spacer may include a nucleic acid sequence at least 70%, at least 75%, at least 80%, at least 85%, at least 90%, or at least 95% identical to SEQ ID NO: 109. The spacer include the nucleic acid sequence of SEQ ID NO: 110. The spacer may include a nucleic acid sequence at least 70%, at least 75%, at least 80%, at least 85%, at least 90%, or at least 95% identical to SEQ ID NO: 110. The spacer include the nucleic acid sequence of SEQ ID NO: 111. The spacer may include a nucleic acid sequence at least 70%, at least 75%, at least 80%, at least 85%, at least 90%, or at least 95% identical to SEQ ID NO: 111. In some embodiments, the administration improves a therapeutic parameter of Stargardt disease in the subject. Some data related to ABCA4 editing are shown in FIG. 29D-29F.

Some embodiments of the methods and compositions described herein may be used to treat Wilson disease. Editing Wilson disease-causing mutations to restore ATP7B may provide long term and potentially curative therapy for subjects with Wilson disease. Some embodiments include administering to a subject in need thereof (e.g. a subject with Wilson disease), one or more polynucleotides encoding genome editing components described herein that are configured to correct a mutant ATP7B gene, or one or more viruses such as adenoviruses comprising the one or more polynucleotides. An example of such a component includes a guide RNA comprising a spacer that is reverse complementary to a region of an ATP7B nucleic acid. The spacer include the nucleic acid sequence of SEQ ID NO: 112. The spacer may include a nucleic acid sequence at least 70%, at least 75%, at least 80%, at least 85%, at least 90%, or at least 95% identical to SEQ ID NO: 112. The spacer include the nucleic acid sequence of SEQ ID NO: 113. The spacer may include a nucleic acid sequence at least 70%, at least 75%, at least 80%, at least 85%, at least 90%, or at least 95% identical to SEQ ID NO: 113. The spacer include the nucleic acid sequence of SEQ ID NO: 114. The spacer may include a nucleic acid sequence at least 70%, at least 75%, at least 80%, at least 85%, at least 90%, or at least 95% identical to SEQ ID NO: 114 The spacer include the nucleic acid sequence of SEQ ID NO: 115. The spacer may include a nucleic acid sequence at least 70%, at least 75%, at least 80%, at least 85%, at least 90%, or at least 95% identical to SEQ ID NO: 115. In some embodiments, the administration improves a therapeutic parameter of Wilson disease in the subject.

Some embodiments of the methods and compositions described herein may be used to treat Huntington's disease. Editing Huntington's disease-causing mutations to restore HTT may provide long term and potentially curative therapy for subjects with Huntington's disease. Some embodiments include administering to a subject in need thereof (e.g. a subject with Huntington's disease), one or more polynucleotides encoding genome editing components described herein that are configured to correct a mutant HTT gene, or one or more viruses such as adenoviruses comprising the one or more polynucleotides. An example of such a component includes a guide RNA comprising a spacer that is reverse complementary to a region of an HTT nucleic acid. The spacer include the nucleic acid sequence of SEQ ID NO: 116. The spacer may include a nucleic acid sequence at least 70%, at least 75%, at least 80%, at least 85%, at least 90%, or at least 95% identical to SEQ ID NO: 116. The spacer include the nucleic acid sequence of SEQ ID NO: 117. The spacer may include a nucleic acid sequence at least 70%, at least 75%, at least 80%, at least 85%, at least 90%, or at least 95% identical to SEQ ID NO: 117. The spacer include the nucleic acid sequence of SEQ ID NO: 118. The spacer may include a nucleic acid sequence at least 70%, at least 75%, at least 80%, at least 85%, at least 90%, or at least 95% identical to SEQ ID NO: 118 The spacer include the nucleic acid sequence of SEQ ID NO: 119. The spacer may include a nucleic acid sequence at least 70%, at least 75%, at least 80%, at least 85%, at least 90%, or at least 95% identical to SEQ ID NO: 119. In some embodiments, the administration improves a therapeutic parameter of Huntington's disease in the subject.

Disclosed herein are guide nucleic acids including an extension. The extension may include a extension nucleic acid sequence for editing HTT. The extension nucleic acid sequence for editing HTT may include the sequence of SEQ ID NO: 140. The extension nucleic acid sequence for editing HTT may include a sequence that is at least 75% identical, at least 80% identical, at least 85% identical, at least 90% identical, or at least 95% identical, to the sequence of SEQ ID NO: 140. The extension may include a GPS region. The extension may not include a GPS region. An example of an extension sequence of an extension including a GPS region is included in SEQ ID NO: 141. The extension nucleic acid sequence for editing HTT may include the sequence of SEQ ID NO: 141. The extension nucleic acid sequence for editing HTT may include a sequence that is at least 75% identical, at least 80% identical, at least 85% identical, at least 90% identical, or at least 95% identical, to the sequence of SEQ ID NO: 141.

Rewriting an Usher Syndrome Gene

Usher syndrome may be the most common inherited source of combined deafness and vision loss. While hearing aids and ear implants can treat deafness in some Usher patients, their vision loss is currently untreatable. Possibly the most common mutation that causes Usher syndrome is a single-nucleotide deletion, 2299delG, in the USH2A gene. Rewriter may offer an approach for providing curative treatment for patients with Usher syndrome, as gene therapy involving delivery of functional USH2A may otherwise hampered by a USH2A cDNA size (15.6 kb) beyond the typical AAV and lentivirus packaging capacity, and base editors may otherwise be unable to perform nucleotide insertions.

Components were provided to rewrite the 2299G region in USH2A. Editing efficiency was determined in wildtype HEK293T cells by quantifying the installment of a 2298T>C silent mutation that was encoded in the RTT 23-nt from the nick. Although 2299G is encoded by the RTT, 2298T>C was also included as a surrogate mutation because wildtype HEK293T cells already contain 2299G. Also encoded was a 2316C>A PAM-disabling silent mutation in the RTT 5-nt from the nick that was intended to prevent nSpCas9 from continuing to nick the target site after the intended edit is achieved.

Twenty-two percent editing was achieved through the use of a 15-nt PBS, 52-nt RTT, and 20-nt GPS in a RW2I system (FIG. 25A). For the data in FIG. 25A, HEK293T cells were transfected with RW2I using different sequences of PBS, RTT, and GPS. Editing efficiency is displayed as the percentage of reads with the intended 2298T>C mutation. A 15-nt PBS, 52-nt RTT, and 20-nt GPS resulted in 22% editing.

PBS lengths of 9, 11, 13, and 15-nt were tested; RTT lengths of 32, 34, 36, 52, and 56-nt were assessed; and a 20-nt GPS was included in the 52 and 56-nt RTT constructs. All of the constructs that did not include GPS resulted in under 6.3% editing, while in contrast constructs with a 52-nt RTT and 20-nt GPS gave the highest editing efficiencies with an increase from approximately 6.5% with a 9-nt PBS to 22% with a 15-nt PBS. These results indicate that GPS can significantly improve the efficiency of introducing edits as close as 23-nt from the site of the nick. Deep sequencing of the spacer's top five in silico-predicted off-target genomic sites was performed, and no edits introduced by transfecting the Rewriter components were detected.

Figure 28:
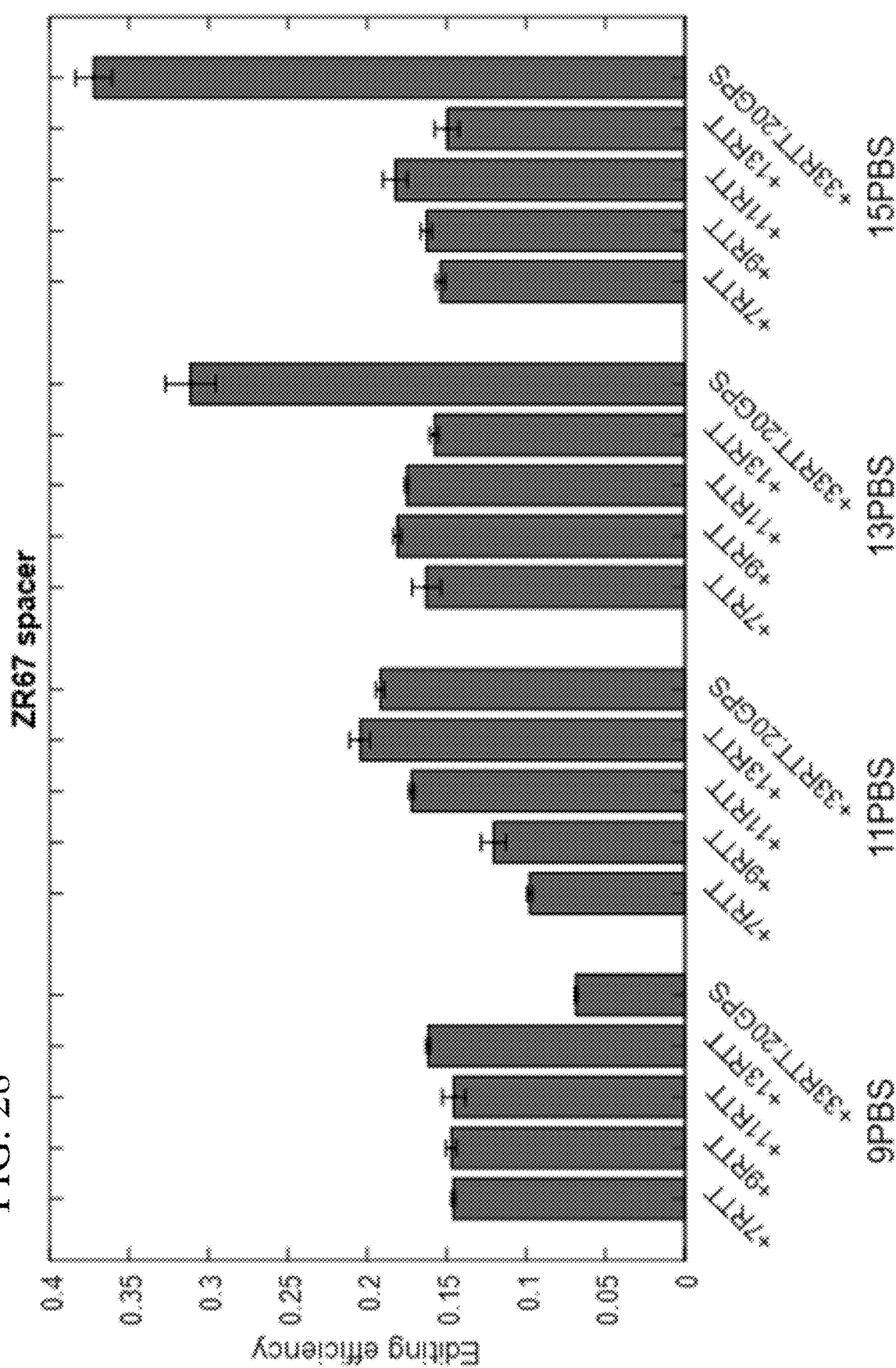
FIG. 28 shows editing efficiencies obtained using some editing system components.

Next, types of allele variants generated by the 15-nt PBS, 52-nt RTT, and 20-nt GPS construct were analyzed, and it was found that the most frequent variant contained both the 2298T>C and 2316C>A mutations (18.8%), followed by the 2316C>A mutation only (3.9%), and then the 2298T>C mutation only (3.2%) (FIG. 25B). FIG. 25B shows that the most frequent mutant allele generated by the 15-nt PBS, 52-nt RTT, 20-nt GPS construct included both the 2298T>C and 2316C>A mutations encoded in the RTT (18.8%). An additional 7.1% of reads were represented by either the 2316C>A PAM-disrupting mutation alone or the target 2298T>C mutation alone. A low frequency of adenine insertions were also detected along poly-A tracts within the target sequence. Some data for some additional aspects are shown in FIG. 28.

Figure 25E:
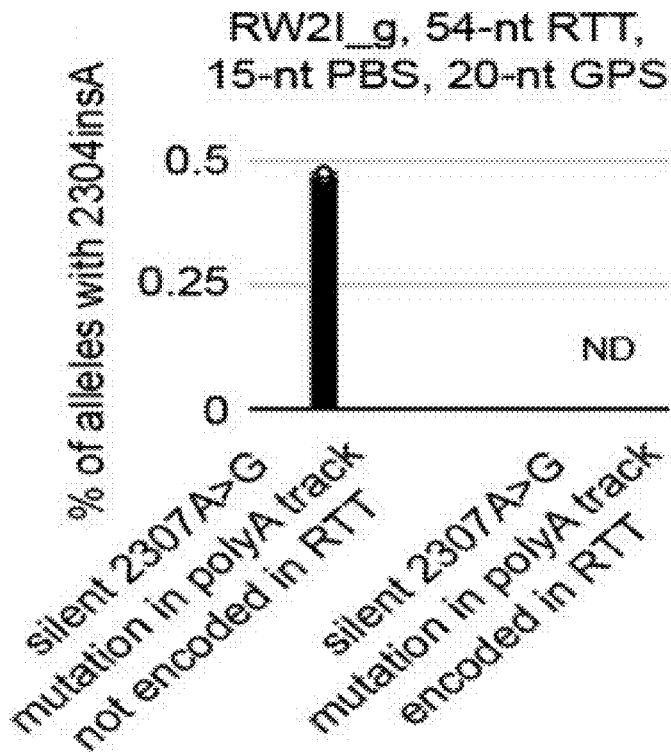
FIG. 25E illustrates that modifying the RTT to include a silent 2307A>G mutation that disrupts a polyA track eliminated an undesirable insertion of an adenine.
Figure 25F:
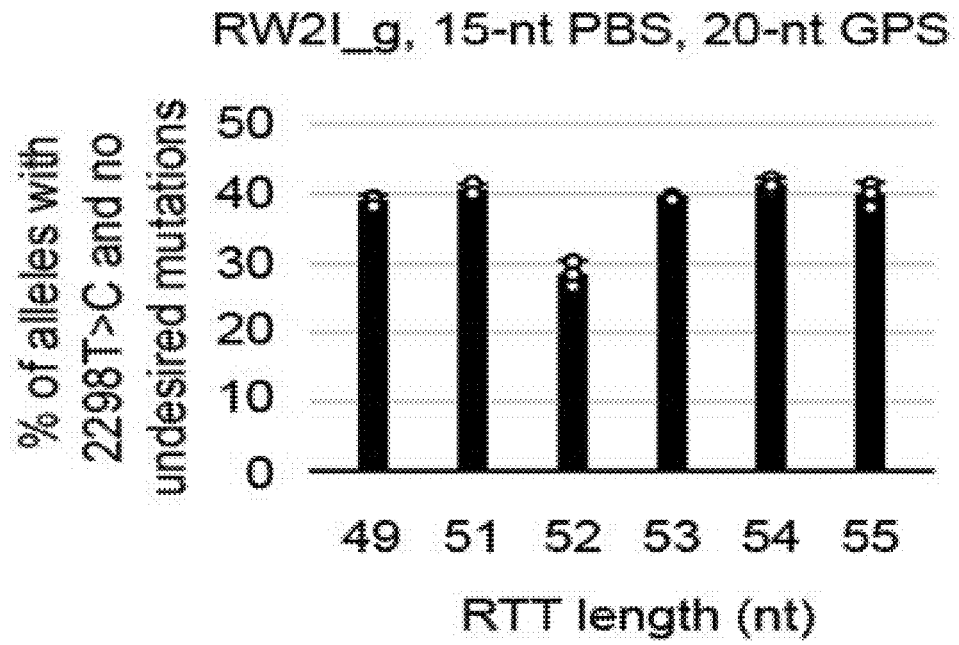
FIG. 25F illustrates that screening additional RTT lengths increased editing efficiency to 41.6%.
Figure 25G:
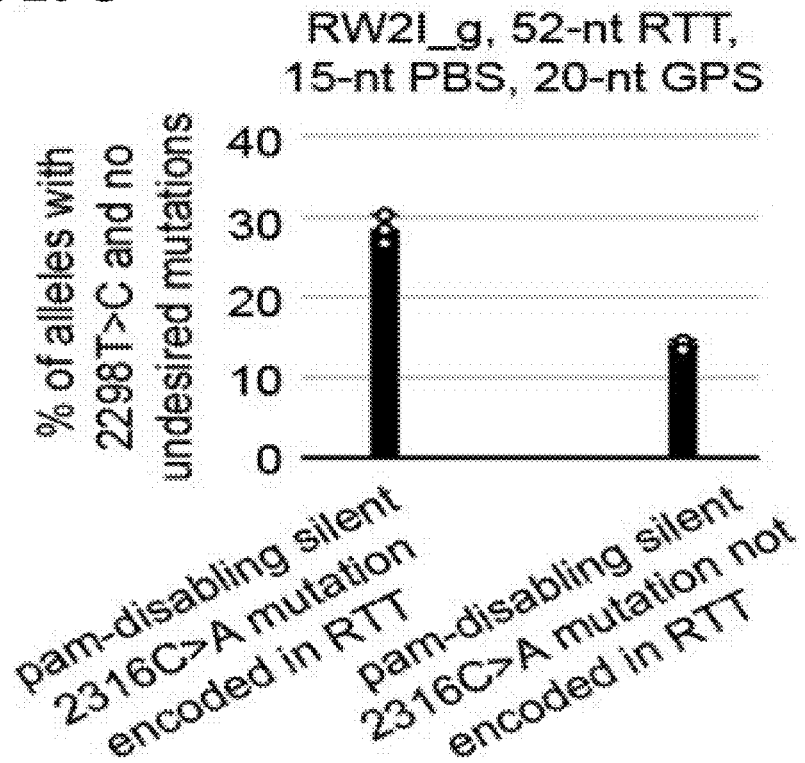
FIG. 25G illustrates that encoding a silent mutation in the RTT that would disrupt the spacer's PAM sequence doubled the efficiency of installing the 2298T>C mutation.

Encoding mutations in the RTT that disrupt the PAM may increase editing efficiency. Encoding mutations in the RTT that disrupt the PAM may increase editing precision. It was found that by encoding a sequence in the RTT that would disrupt the PAM site increased the efficiency of editing and decreases undesirable deletions (FIG. 25C and FIG. 25G).

There were no detectable indels generated by nSpCas9 or scaffold sequence insertion events, as may be for prime editors. Two alleles containing an adenine insertion were identified within the region that was reverse transcribed in addition to the intended 2298T>C and 2316C>A mutations at a frequency of 0.4% and 0.2%, respectively. Each of the adenine insertions was at the end of a poly-A tract, potentially indicating that RT-mediated genome editing approaches can synthesize rare frame-shifting mutations on mononucleotide tracts of RNA templates. It was found that disrupting one of the polyA tracks in the RTT with a silent 2307A>G mutation eliminated the undesirable insertion of an adenine within that polyA track (FIG. 25E). It was also found that the 2298T>C editing efficiency increased to 41.6% by increasing the RTT length to 54-nt (FIG. 25F). Finally, it was found that not including the silent pam-disrupting 2316C>A mutation decreased the efficiency of making the 2298T>C edit 2-fold (FIG. 25G). Graphical data shown in any of FIGS. 25A-25G include a mean±one standard deviation from three biologically independent samples; NS=not significant (P<0.05; two-sided student's t-test); and ND=not detected.

As shown in FIG. 25E and FIG. 30, mutations may be encoded in the RTT to break up tracks of consecutive nucleotides (e.g. 4+ consecutive nucleotides). Undesired insertions were observed on tracks of at least 4 consecutive nucleotides containing the same base. It was considered that the reverse transcriptase was making rare insertions on these mononucleotide tracks relative to it's template sequence in the RTT. It was discovered that by incorporating a mutation to break up the mononucleotide track into tracks of no more than 3 consecutive nucleotides of the same base that the undesirable insertions were no longer detected. As shown in the example in FIG. 25E, without encoding the silent 2307A>G mutation in the polyA track of the RTT, almost 0.5% of reads contained an undesired A insertion at position 2305. The undesirable insertion was not detected with the RTT included the silent 2307A>G mutation in the polyA track of the RTT. of the same base eliminates undesirable edits that were not encoded in the RTT Some highlights of the Usher syndrome data include: GPS improved editing efficiency by about 4-fold, no off target effects were observed, no undesirable mutations were made to USH2A, and over 40% editing efficiency was achieved.

Figure 31:
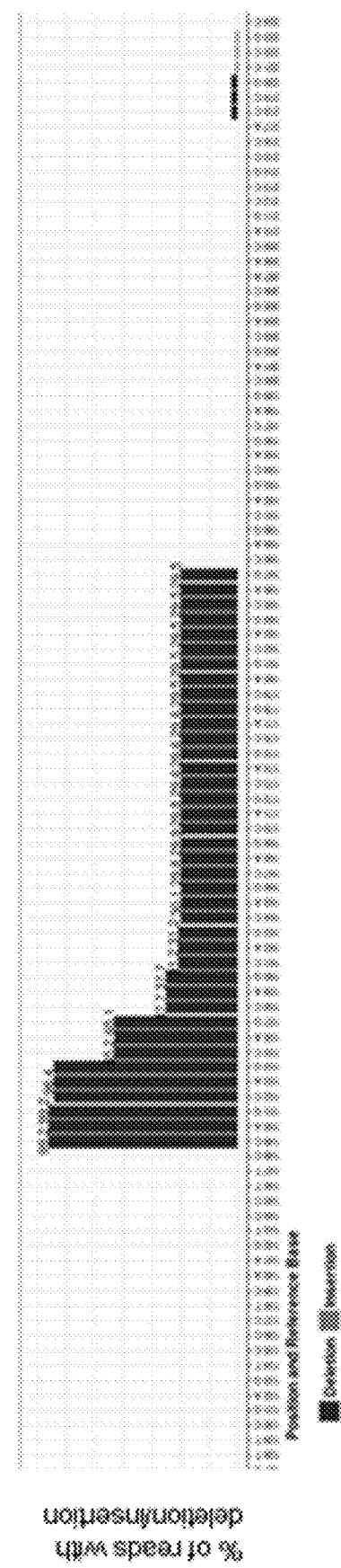
FIG. 31A shows % of reads with mutations after treatment with some editing components described herein.
FIG. 31B shows % of reads with mutations in wildtype cells.

FIG. 31A-31B show that precise shortening of trinucleotide a repeat was achieved in an htt gene, demonstrating applicability of some systems and methods described herein for treating a disease such as Huntington's disease.

Discussion

An editing system such as Rewriter may comprise a targeted and efficient technology for introducing nucleotide substitutions, insertions, deletions, or complex sequence changes within approximately 70-nt of a given Cas9 target site. In addition, the ability to package Rewriter within AAV promises to enable safe and tissue-specific delivery to treat a wide-range of genetic diseases.

Precision genome editing has traditionally relied on generating DSBs, which are in some cases genotoxic lesions that can even cause the loss of an entire chromosome. Rewriter may avoid safety concerns associated with some DSBs by only generating one single-stranded nick, generally a relatively innocuous modification. Additionally, Rewriter's deliverability and safety may not come at the cost of efficiency, as up to 64% editing was achieved, which is the highest efficiency reported to date for targeted multi-nucleotide editing in human cells without generating DSBs.

GPS may include a novel component in the Rewriter platform that may improve editing efficiency and window length by controlling the tertiary structure of the gRNA extension. GPS may relieve a constraint of requiring a PAM immediately adjacent to the site of the edit and may enable correction of multiple pathogenic mutations with a single construct. For example, the second most common USH2A mutation that leads to loss of vision may be 2276G>T, which may be 23-nt from the most common mutation, 2299delG. Some embodiments include use of a gRNA that is capable of treating patients with one of these mutations.

Screening of mlvRT mutants led to identification of the more efficient mlvRT14M, highlighting the potential to further optimize this component. An unbiased library of mlvRT14M mutants may be screened with the BFP to GFP conversion assay in a pooled format to improve editing. Screening a library of RTs in low dNTP concentrations, perhaps through overexpression of SAMHD1 (T592A) may identify a variant with a low enough $K_M$ for dNTPs to obviate a possible need for VPX in order to edit non-dividing cells.

Precise editing in non-dividing cells has traditionally been a significant challenge. The results provided herein using VPX to counteract the restriction in editing caused by SAMHD1 offer a route to edit clinically relevant post-mitotic cells, such as photoreceptors and neurons, or slowly dividing cells that make up many organs. Given the identification of SAMHD1 as a potential restriction factor for editing, SAMHD1-inhibiting small molecules can be evaluated to provide a transient increase in cellular dNTP concentrations.

As the first system that, upon AAV delivery, can precisely generate targeted, complex sequence changes in the genomes of human cells without generating DSBs, Rewriter may be used to advance functional genomic studies and treat human disease.

Methods

General methods: Q5 DNA polymerase (New England Biolabs) was used for DNA amplification. DNA oligonucleotides were obtained from Integrated DNA technologies. Plasmids were constructed by the Golden Gate assembly method. Vectors for mammalian cell experiments were purified using Plasmid Plus midiprep kits (Qiagen) or ZymoPURE miniprep kits (Zymo Research).

General mammalian cell culture: HEK293T cells (ATCC CRL-3216) were cultured and passaged in Dulbecco's modified Eagle's medium (DMEM) plus GlutaMAX (ThermoFisher Scientific) supplemented with 10% (v/v) fetal bovine serum (Gibco) and Antibiotic-Antimycotic (ThermoFisher Scientific) (DMEM+). Cells were cultured at 37° C. with 5% CO2.

Transfection: HEK293T cells were seeded on 96-well poly-d-lysine coated plates (Corning). Approximately 24 hours after seeding, media was replaced with Opti-MEM (Gibco) and each well was transfected with 0.8 ul Lipofectamine 2000 (ThermoFisher Scientific) according to the manufacturer's protocol and 400 ng of total plasmid DNA. Media was replaced with DMEM+ between 6 and 8 hours after transfection.

AAV packaging, harvest, and transduction: HEK293T cells were subjected to a triple-transfection method for production of AAV by co-transfection of three plasmids—a Rep/Cap plasmid, a helper plasmid containing adenoviral genes, and a transfer plasmid containing the cargo intended for packaging flanked by inverted terminal repeats. Transfections were performed using branched polyethylenimine (PEI) with an average molecular weight of 25,000 (Sigma 408727). Three days after transfection, cells were harvested and purified using the AAVpro Purification Kit Maxi (Takara 6666). Titers of purified AAV stocks were determined by qPCR on a CFX96 Real-Time System (Bio-Rad) using SsoAdvanced Universal SYBR Green Supermix (Bio-Rad). BFP-expressing HEK293 cells were co-transduced with equal numbers of AAV-A and AAV-B viral particles, and editing of BFP-to-GFP was determined 96-120 hours after transduction by flow cytometry.

Flow cytometry: 48 hours after transfection, media was removed and cells were detached with 0.05% Trypsin/EDTA (Gibco). Trypsin was neutralized with DMEM+ and suspended cells were placed in round-bottom 96-well plates. An Attune NxT flow cytometer (ThermooFisher Scientific) was used to analyze the fluorescence of 30,000 cells per well.

High-throughput genomic DNA sequencing: Genomic sites of interest were amplified from genomic DNA samples and sequenced on an Illumina MiSeq. Amplification primers comprising Illumina forward and reverse adapters were used for a first round of PCR (PCR 1) to amplify a genomic region of interest. PCR 1 reactions (25 μl) were performed with 0.5 μM of each forward and reverse primer, 1 μl genomic DNA extract and 12.5 μl Phusion U Green Multiplex PCR Master Mix. PCR reactions were carried out as follows: 98° C. for 2 min, then 30 cycles of [98° C. for 10 s, 61° C. for 20 s, and 72° C. for 30 s], followed by a final 72° C. extension for 2 min. Unique Illumina barcoding primer pairs were added to each sample in a secondary PCR reaction (PCR 2). Specifically, 25 μl of a given PCR 2 reaction contained 0.5 μM of each unique forward and reverse Illumina barcoding primer pair, 1 μl unpurified PCR 1 reaction mixture, and 12.5 μl of Phusion U Green Multiplex PCR 2 Master Mix. The barcoding PCR 2 reactions were carried out as follows: 98° C. for 2 min, then 12 cycles of [98° C. for 10 s, 61° C. for 20 s, and 72° C. for 30 s], followed by a final 72° C. extension for 2 min. PCR products were evaluated analytically by electrophoresis in a 1.5% agarose gel. PCR 2 products (pooled by common amplicons) were purified by electrophoresis with a 1.5% agarose gel using a QIAquick Gel Extraction Kit (Qiagen), eluting with 40 μl water. DNA concentration was measured by fluorometric quantification (Qubit, ThermoFisher Scientific) or qPCR (KAPA Library Quantification Kit-Illumina, KAPA Biosystems) and sequenced on an Illumina MiSeq instrument according to the manufacturer's protocols. Sequencing reads were demultiplexed using MiSeq Reporter (Illumina).

Alignment of amplicon sequences to a reference sequence was performed using CRISPResso243. For all prime editing yield quantification, prime editing efficiency was calculated as: percentage of (number of reads with the desired edit that do not contain indels)/(number of total reads). For quantification of point mutation editing, CRISPResso2 was run in standard mode with "discard_indel_reads" on. Prime editing for installation of point mutations was then explicitly calculated as: (frequency of specified point mutation in non-discarded reads) Å~(number of non-discarded reads)/(total reads). For insertion or deletion edits, CRISPResso2 was run in HDR mode using the desired allele as the expected allele (e flag), and with "discard_indel_reads" on. Editing yield was calculated as: (number of HDR-aligned reads)/(total reads). Indel yields were calculated as: (number of indel comprising reads)/(total reads).

36 hours after transfection, cells were detached with 0.05% trypsin, spun down, washed with PBS, and spun down again. Cell pellets were resuspended in 10 ul of QuickExtract (Lucigen) and incubated at 65° C. for 6 minutes. Samples were then vortexed for 15 seconds and incubated at 98° C. for 2 minutes. 10 ul of nuclease-free water was added to each sample. 4 ul of sample was used as a template for PCR with Q5 polymerase and primers that contain Illumina adapters that were designed to amplify the genomic region of interest. Samples were then treated with Exo-CIP (NEB) at 37° C. for 1 hour. DNA concentration was measured with Qubit (ThermoFisher Scientific) and samples were sent to Genewiz for sequencing using the Amplicon-EZ service. PE-Analyzer (www.rgenome.net/pe-analyzer) was used to analyze high-throughput sequencing data. The highest frequency variant in control samples that were not transduced with any genome editing components was set as the detection threshold and any variant below this frequency was discarded. The efficiency of installing the 2298T>C mutation was explicitly calculated as (number of reads containing only the 2298T>C mutation+number of reads containing only the 2298T>C and 2316C>A mutations)/ (total number of reads of alleles that were present at a frequency above the detection threshold).

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," "less than or equal to," or "at most" precedes the first numerical value in a series of two or more numerical values, the term "no more than," "less than" or "less than or equal to," or "at most" applies to each of the numerical values in that series of numerical values. For example, less than or equal to 3, 2, or 1 is equivalent to less than or equal to 3, less than or equal to 2, or less than or equal to 1.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

NUMBERED EMBODIMENTS

Some aspects include any of the following embodiments.
1. A method of increasing gene editing efficiency in a cell having a low deoxynucleoside triphosphate (dNTP) concentration and comprising a DNA polymerase for the gene editing, the method comprising:
increasing the dNTP concentration in the cell, relative to a baseline dNTP concentration.

2. The method of embodiment 1, wherein increasing the dNTP concentration in the cell comprises inhibiting a deoxynucleotide triphosphate triphosphohydrolase in the cell.
3. The method of embodiment 2, wherein the deoxynucleotide triphosphate triphosphohydrolase comprises SAM domain and HD domain-containing protein 1 (SAMHD1).
4. The method of embodiment 3, wherein inhibiting SAMHD1 comprises contacting the SAMHD1 with a Vpx protein, or expressing the Vpx protein in the cell.
5. The method of embodiment 3, wherein inhibiting SAMHD1 comprises contacting the SAMHD1 with a BGLF4 protein, or expressing the BGLF4 protein in the cell.
6. The method of embodiment 3, wherein inhibiting SAMHD1 comprises contacting an mRNA encoding the SAMHD1 with a microRNA or siRNA that hybridizes to the mRNA, or expressing the microRNA or siRNA in the cell.
7. The method of embodiment 3, wherein inhibiting SAMHD1 comprises contacting the SAMHD1 with a small molecule SAMHD1 inhibitor.
8. The method of embodiment 1, wherein increasing the dNTP concentration in the cell comprises administering nucleosides or nucleotides to the cell, wherein the nucleosides or nucleotides optionally comprise deoxynucleosides (dNs), deoxynucleoside monophosphates (dNMPs), or nucleoside triphosphates (NTPs).
9. The method of embodiment 8, wherein administering nucleosides or nucleotides to the cell comprises administering the nucleosides or nucleotides to a subject comprising the cell.
10. The method of embodiment 9, wherein the administration is oral or by injection.
11. The method of embodiment 1, wherein increasing the dNTP concentration in the cell comprises delivering a dNTP synthetic enzyme to the cell.
12. The method of embodiment 11, wherein the dNTP synthetic enzyme comprises a kinase.
13. The method of embodiment 12, wherein the kinase comprises a nucleoside kinase, deoxynucleoside kinase, deoxynucleoside monophosphase kinase, or deoxynucleotide diphosphate kinase.
14. The method of embodiment 1, wherein the DNA polymerase comprises a reverse transcriptase.
15. The method of embodiment 1, wherein the cell further comprises a Cas9 programmable nuclease, a guide nucleic acid, or a combination thereof.
16. The method of embodiment 1, wherein the low dNTP concentration comprises a dNTP concentration found in a nondividing cell.
17. The method of embodiment 1, wherein the low dNTP concentration is less than a dNTP concentration found in an activated peripheral blood mononuclear cell.
18. The method of embodiment 1, wherein the low dNTP concentration comprises a dNTP concentration below 1 micromolar.
19. The method of embodiment 1, wherein the increasing the dNTP concentration comprises increasing the dNTP concentration by at least 5%, at least 10%, at least 15%, at least 20%, at least 25%, at least 30%, at least 40%, at least 50%, at least 60%, at least 70%, at least 80%, at least 90%, at least 100%, or more, relative to the baseline dNTP measurement.
20. The method of any one of embodiments 1-19, wherein the dNTP concentration comprises a deoxyadenosine triphosphate (dATP) concentration, a deoxycytidine triphosphate (dCTP) concentration, a deoxyguanosine triphosphate (dGTP) concentration, or a deoxythymidine triphosphate (dTTP) concentration, or any combination thereof.

21. A composition comprising a Cas nickase and a reverse transcriptase, wherein at least part of the Cas nickase and the reverse transcriptase are included in separate polypeptide chains, and wherein the Cas nickase and the reverse transcriptase form a Cas-reverse transcriptase heterodimer.

22. The composition of embodiment 21, wherein the Cas-reverse transcriptase heterodimer comprises a first heterodimer domain fused to the Cas nickase and a second heterodimer domain fused to the reverse transcriptase, wherein the first heterodimer domain binds the second heterodimer domain to form the Cas-reverse transcriptase heterodimer.

23. The composition of embodiment 22, wherein the first heterodimer domain is a leucine zipper and the second heterodimer domain is a leucine zipper.

24. The composition of any one of embodiments 21-23, wherein the reverse transcriptase comprises a sequence having at least 80% sequence identity to of any one of SEQ ID NO: 3-SEQ ID NO: 22 or SEQ ID NO: 40-SEQ ID NO: 80, or a fragment thereof.

25. The composition of any one of embodiments 21-24, wherein the reverse transcriptase comprises a domain from a non-long terminal repeat retrotransposable element fused to part of the Cas nickase.

26. The composition of any one of embodiments 21-24, wherein the reverse transcriptase comprises a sequence from a bacterial group II intron fused to part of the Cas nickase.

27. The composition of any one of embodiments 21-24, wherein the reverse transcriptase comprises a domain from a retroviral gag-pol polyprotein fused to part of the Cas nickase.

28. A composition comprising a Cas nickase, a reverse transcriptase, and a guide nucleic acid, wherein a first polypeptide comprises the Cas nickase and a second polypeptide comprises the reverse transcriptase and the guide nucleic acid binds to the Cas nickase and the reverse transcriptase.

29. The composition of any one of embodiments 21-28, wherein the reverse transcriptase comprises an mcp peptide.

30. The composition of any one of embodiments 21-29 wherein the reverse transcriptase comprises a loop region.

31. The composition of embodiment 30, wherein the loop region is a 2a loop or a 3a loop.

32. The composition of any one of embodiments 28-31, wherein the guide nucleic acid comprises a MS2 hairpin.

33. A composition comprising a reverse transcriptase with a sequence having at least 80% sequence identity to of any one of SEQ ID NO: 3-SEQ ID NO: 22 or SEQ ID NO: 40-SEQ ID NO: 80, or a fragment thereof fused to a Cas nickase.

34. A composition comprising a reverse transcriptase comprising a domain from a non-long terminal repeat retrotransposable element fused to a Cas nickase.

35. A composition comprising a reverse transcriptase comprising a sequence from a bacterial group II intron fused to a Cas nickase.

36. A composition comprising a reverse transcriptase comprising a domain from a retroviral gag-pol polyprotein fused to a Cas nickase.

37. A composition comprising a Cas nickase and a reverse transcriptase, wherein the Cas nickase and the reverse transcriptase comprise separate polypeptide chains, and wherein the Cas nickase and reverse transcriptase are not engineered to heterodimerize.

38. The composition of any one of embodiments 21-37, comprising a guide nucleic acid that forms a complex with the Cas nickase, wherein, upon complex formation, the Cas nickase is capable of introducing a single-strand break at a target site in a target nucleic acid.

39. The composition of any one of embodiments 21-38, wherein the target nucleic acid comprises a CFTR nucleic acid, a USH2A nucleic acid, an ABCA4 nucleic acid, an ATP7B nucleic acid, or an HTT nucleic acid.

40. The composition of any one of embodiments 21-39, comprising a nuclear localization signal fused to the Cas nickase or the reverse transcriptase.

41. The composition of any one of embodiments 21-40, wherein the reverse transcriptase is a truncated reverse transcriptase.

42. The composition of any one of embodiments 21-41, wherein the reverse transcriptase has an increased processivity as compared to a native reverse transcriptase.

43. The composition of any one of embodiments 21-42, wherein the reverse transcriptase has increased processivity compared to mlvRT.

44. The composition of any one of embodiments 21-43, wherein the reverse transcriptase edits a longer window length in a target sequence compared to mlvRT.

45. The composition of any one embodiments 21-44, wherein the reverse transcriptase has decreased immunogenicity compared to mlvRT.

46. The composition of any one embodiments 21-45, wherein the reverse transcriptase has improved delivery to a cell compared to mlvRT.

47. The composition of any one of embodiments 21-46, wherein the reverse transcriptase polymerizes 20 or more, 40 or more, 45 or more, 50 or more, 60 or more, 81 or more, 100 or more, 500 or more, or 1000 or more nucleotides in a single binding event.

48. A guide nucleic acid comprising:
a spacer reverse complementary to a first region of a target nucleic acid,
a scaffold configured to bind to a Cas nickase,
a reverse transcriptase template encoding a sequence to be inserted into the target nucleic acid, and
a first strand primer binding site reverse complementary to a second region of the target nucleic acid.

49. The guide nucleic acid of embodiment 48, further comprising a second strand primer comprising a sequence of a region of the reverse transcriptase template.

50. The guide nucleic acid of embodiment 48 or embodiment 49, wherein the first region of the target nucleic acid is on a first strand of the target nucleic acid and the second region of the target nucleic acid is on a second strand of the target nucleic acid.

51. The guide nucleic acid of any one of embodiments 48-50, wherein all or part of the first region of the target nucleic acid is reverse complementary to all or part of the second region of the target nucleic acid.

52. The guide nucleic acid of any one of embodiments 48-51, further comprising a cleavable sequence at the 3' end of the guide nucleic acid.

53. The guide nucleic acid of embodiment 52, wherein the cleavable sequence is a ribozyme cleavable sequence.

54. The guide nucleic acid of embodiment 52, wherein the cleavable sequence is a tRNA cleavable sequence.

55. The guide nucleic acid of any one of embodiments 48-54, wherein the first strand primer binding site is configured to hybridize to the second region of the target nucleic acid, and wherein the reverse transcriptase template is configured to serve as a template for reverse transcription from a 3' end of the second region of the target nucleic acid.

56. The guide nucleic acid of any one of embodiments 48-55, wherein the second strand primer is configured to serve as a primer for transcription from a template reverse complementary to the reverse transcriptase template.

57. The guide nucleic acid of any one of embodiments 48-56, wherein a first synthesized strand serves as a template for synthesis of a second strand from the second strand primer.

58. The guide nucleic acid of any one of embodiments 48-57, further comprising a Velcro region that hybridizes to a Velcro binding site.

59. The guide nucleic acid of embodiment 58, wherein the Velcro binding site is 100% reverse complementary to the Velcro region; wherein the Velcro binding site is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% reverse complementary to the Velcro region; and/or wherein the Velcro binding site is no greater than 55%, no greater than 60%, no greater than 65%, no greater than 70%, no greater than 75%, no greater than 80%, no greater than 85%, no greater than 90%, no greater than 91%, no greater than 92%, no greater than 93%, no greater than 94%, no greater than 95%, no greater than 96%, no greater than 97%, no greater than 98%, no greater than 99% reverse complementary to the Velcro region.

60. The guide nucleic acid of embodiment 58 or 59, wherein the reverse transcriptase template region comprises the Velcro binding site.

61. The guide nucleic acid of embodiment 58 or 59, wherein the Velcro binding site is 3' of the first strand primer binding site.

62. The guide nucleic acid of any one of embodiments 48-61, wherein the Velcro region is 3' of the reverse transcriptase template.

63. The guide nucleic acid of any one of embodiments 48-62, wherein the Velcro region is 5' of the scaffold.

64. The guide nucleic acid of any one of embodiments 48-63, wherein the target nucleic acid comprises a CFTR nucleic acid, a USH2A nucleic acid, an ABCA4 nucleic acid, an ATP7B nucleic acid, or an HTT nucleic acid.

65. The guide nucleic acid of any one of embodiments 48-64, wherein the spacer comprises a nucleic acid sequence at least 85% identical to any one of SEQ ID NOs: 96-119.

66. A composition comprising a first guide nucleic acid comprising the guide of any one of embodiments 28-32 or 37-65 and a second guide nucleic acid.

67. The composition of embodiment 66, wherein the second guide nucleic acid comprises the guide nucleic acid any one of embodiments 28, 32 or 37, or 48-65.

68. The composition of embodiment 67, wherein the reverse transcriptase template of the second guide nucleic acid is complementary (or at least partly complementary) to at least part of the reverse transcriptase template of the first guide nucleic acid.

69. The composition of any one of embodiments 66-68, wherein the first guide nucleic acid binds to a first Cas nickase, and the second guide nucleic acid binds to a second Cas nickase.

70. The composition of any one of embodiments 66-68, wherein a first spacer of the first guide nucleic acid binds a first Cas nickase, a second spacer of the second guide nucleic acid binds a second Cas nickase, a first scaffold of the first guide nucleic acid binds the second Cas nickase, and a second scaffold of the second guide nucleic acid binds the first Cas nickase.

71. The composition of any one of any one of embodiments 66-68 or 70, wherein the first guide nucleic acid comprises a first linker and the second guide nucleic acid comprises a second linker, wherein the first linker hybridizes to the second linker.

72. A method of increasing genome editing efficiency comprising delivering an Orflp to a cell expressing the composition of any one of embodiments 21-47 or 66-71 or the guide nucleic acid of any one of embodiments 38-45.

73. One or more nucleic acids encoding the composition of any one of embodiments 21-47 or 66-71, or comprising the guide nucleic acid of any one of embodiments 48-65.

74. A viral vector comprising the nucleic acid of embodiment 73.

75. A cell comprising the composition of any one of embodiments 21-47 or 66-71, the guide nucleic acid of any one of embodiments 48-65, the nucleic acid of embodiment 73, or the viral vector of embodiment 74.

76. The method of embodiment 72 or the cell of embodiment 75, wherein the cell is a prokaryotic cell.

77. The method of embodiment 72 or the cell of embodiment 75, wherein the cell is a eukaryotic cell.

78. A method of increasing genome editing efficiency comprising expressing a Vpx protein in a cell.

79. The method of embodiment 78, wherein the cell expresses the composition of any one of embodiments 21-47 or 66-71 or the guide nucleic acid of any one of embodiments 48-65.

80. A method of increasing genome editing efficiency by increasing the dNTP concentration in a cell, for example a method of increasing genome editing efficiency comprising inhibiting SAMHD1 in a cell.

81. The method of embodiment 80, wherein the cell expresses a Cas9 programmable nuclease, a reverse transcriptase, and a guide nucleic acid.

82. The method of embodiment 80 or 81, wherein inhibiting SAMHD1 comprises expressing a Vpx protein in the cell.

83. The method of embodiment 80 or 81, wherein inhibiting SAMHD1 comprises expressing a microRNA against SAMHD1 in the cell, or comprises treating the cell with a small molecule SAMHD1 inhibitor.

84. A composition comprising a Cas9 programmable nuclease comprising one or more point mutations or insertion mutations that enable or improve intein catalysis.

85. The composition of embodiment 84, wherein the Cas9 programmable nuclease comprises a point mutation or insertion mutation located in a C-terminal half of the Cas9 programmable nuclease, or wherein in the point mutation or insertion mutation is located anywhere after amino acid position 574 of the Cas9 programmable nuclease.

86. The composition of embodiment 85, wherein the point mutation comprises a cysteine point mutation, a serine point mutation, a threonine point mutation, or an alanine point mutation; or wherein the insertion mutation comprises a cysteine insertion mutation, a serine insertion mutation, a threonine insertion mutation, or an alanine insertion mutation.

87. The composition of embodiment 85, wherein the point mutation comprises a cysteine point mutation, or wherein the insertion mutation comprises a cysteine insertion mutation.

88. The composition of any one of embodiments 84-87, wherein the Cas9 programmable nuclease is a Cas9 nickase.

89. The composition of any one of embodiments 84-88, wherein the Cas9 programmable nuclease is an S. Pyogenes Cas9.

90. The composition of embodiment 89, wherein the point mutation is located at D1079, D1125, D1130, G1133, A1140, I1168, S1173, D1180, G1186, L1203, or R1212 of the *S. Pyogenes* Cas9, or wherein the insertion mutation is located immediately upstream of D1079, D1125, D1130, G1133, A1140, I1168, S1173, D1180, G1186, L1203, or R1212 of the *S. Pyogenes* Cas9.

91. The composition of any one of embodiments 84-90, wherein the Cas9 programmable nuclease comprises a sequence of any one of SEQ ID NO: 85-SEQ ID NO: 87 or SEQ ID NO: 90-SEQ ID NO: 92.

92. The composition of any one of embodiments 84-91, wherein the Cas9 programmable nuclease is expressed as two or more segments.

93. The composition of embodiment 92, wherein a first segment of the two or more segments comprise an N-terminal portion of the Cas9 programmable nuclease and a first intein, and wherein a second segment of the two or more segments comprise a C-terminal portion of the Cas9 programmable nuclease and a second intein.

94. The composition of embodiment 93, wherein the cysteine point mutation is located at the N-terminus of the C-terminal portion of the Cas9 programmable nuclease.

95. The composition of embodiment 93 or 94, wherein the first intein is fused to the C-terminus of the N-terminal portion of the Cas9 programmable nuclease, and wherein the second intein is fused to the N-terminus of the C-terminal portion of the Cas9 programmable nuclease.

96. The composition of any one of embodiments 93-95, wherein the first segment comprises a sequence of SEQ ID NO: 90, and wherein the second segment comprises a sequence of SEQ ID NO: 91.

97. The composition of any one of embodiments 93-96, wherein the second segment of the two or more segments comprise a reverse transcriptase fused to the C-terminal portion of the Cas9 programmable nuclease.

98. The composition of embodiment 97, wherein the reverse transcriptase comprises an N-terminus fused to a C-terminus of the C-terminal portion of the Cas9 programmable nuclease.

99. The composition of embodiment 97 or 98, wherein the reverse transcriptase comprises an mlvRT, or a variant thereof.

100. A method of optimizing genome editing efficiency, comprising performing genome editing with a Moloney leukemia virus reverse transcriptase (mlvRT) that is modified to increase its catalytic efficiency in low dNTP concentrations, (e.g. modified to decrease its Km for dNTPs).

101. A method of optimizing genome editing efficiency in a limiting dNTP condition, comprising performing genome editing with a Moloney leukemia virus reverse transcriptase (mlvRT), or a variant thereof, comprising a point mutation at position 221 or 223 of the reverse transcriptase.

102. The method of embodiment 100 or 101, wherein the mlvRT or variant thereof comprises a point mutation at position 221.

103. The method of embodiment 102, wherein the point mutation at position 221 comprises Q221R.

104. The method of embodiment 100 or 101, wherein the mlvRT or variant thereof comprises a point mutation at position 223.

105. The method of embodiment 104, wherein the point mutation at position 223 comprises V223A.

106. The method of embodiment 104, wherein the point mutation at position 223 comprises V223M.

107. The composition of any of embodiments 21-47 or 66-71, wherein the reverse transcriptase comprises a point mutation at position P51, S67, Q84, L139, Q221, V223, T197, D653, T664, L671, L435, H204, or D524.

108. The composition of any of embodiments 21-47 or 66-71, wherein the reverse transcriptase comprises a point mutation comprising P51L, S67R, Q84A, L139P, Q221R, V223A, V223M, T197A, D653N, T664N, L671P, L435G, H204R, or D524A.

109. The composition of any of embodiments 21-47 or 66-71, wherein the reverse transcriptase comprises a point mutation at amino acid position Q84, L139, Q221, V223, T664, or L671.

110. The composition of any of embodiments 21-47 or 66-71, wherein the reverse transcriptase comprises a point mutation comprising S67R, Q84A, L139P, Q221R, V223A, V223M, T664N, L671P, or D524A.

111. The composition of any of embodiments 21-47, wherein the Cas nickase and RT are encoded by polynucleotides.

112. AAVs comprising the polynucleotides of embodiment 111.

113. The AAVs of embodiment 112, wherein at least part of the Cas nickase and RT are encompassed by separate AAVs.

114. Adeno-associated viruses (AAVs) comprising: a first AAV comprising a first polynucleotide encoding at least part of a Cas nickase, and a second AAV comprising a second polynucleotide encoding a reverse transcriptase.

115. The AAVs of any one of embodiments 112-114, wherein the AAVs comprise AAV1, AAV2, AAV3, AAV4, AAV5, AAV6, AAV7, AAV8, AAV9, AAV10, AAV11, AAV12, AAV-DJ, AAV-DJ/8, AAV-Rh10, AAV-Rh74, AAV-retro, AAV-PHP.B, AAV8-PHP.eB, or AAV-PHP.S, or a combination of thereof.

116. The AAVs of embodiment 114 or 115, wherein the Cas nickase and the reverse transcriptase form a heterodimer with each other.

117. The AAVs of any one of embodiments 114-116, wherein the first or second polynucleotide further encodes a guide nucleic acid that binds to the Cas nickase and the reverse transcriptase to form a complex, and wherein the Cas nickase of the complex introduces a single-strand break at a target site in a target nucleic acid.

118. The AAVs of embodiment any one of embodiments 114-117, wherein the Cas nickase comprises a Cas9 nickase such as an *S. Pyogenes* Cas9 nickase, and the reverse transcriptase comprises an mlvRT, or a variant thereof, wherein the reverse transcriptase comprises a point mutation at P51, S67, Q84, L139, Q221, V223, T197, D653, T664, L671, L435, H204, or D524.

119. The AAVs of embodiment 118, wherein the point mutation comprises P51L, S67R, Q84A, L139P, Q221R, V223A, V223M, T197A, D653N, T664N, L671P, L435G, H204R, or D524A.

120. The AAVs of any one of embodiments 114-119, wherein the Cas9 nickase comprises an *S. Pyogenes* Cas9 nickase, and the reverse transcriptase comprises an mlvRT, or a variant thereof, wherein the reverse transcriptase comprises an insertion mutation immediately upstream of P51, S67, Q84, L139, Q221, V223, T197, D653, T664, L671, L435, H204, or D524.

121. A method of genome editing, comprising administering a composition comprising the first or second AAV of any one of embodiments 114-120 to a subject or cell.

122. A method of genome editing, comprising administering a composition comprising the AAVs of any one of embodiments 112-120 to a subject or cell.

123. The method of embodiment 121 or 122, further comprising measuring genome editing in the subject or cell.

124. A method of increasing gene editing efficiency in a cell having a low deoxynucleoside triphosphate (dNTP) concentration, comprising:
contacting the cell with a gene editing enzyme modified for efficient catalysis in the low dNTP concentration, or expressing the gene editing enzyme in the cell.

125. The method of embodiment 124, wherein the gene editing enzyme comprises a reverse transcriptase that is modified by introducing a point mutation at position Q84, L139, Q221, V223, T664, or L671.

126. A method for screening or identifying an improved reverse transcriptase (RT), comprising:
overexpressing SAMHD1, or expressing a mutant SAMHD1 that has been mutated to prevent phosphorylation of a residue of the mutant SAMHD1, in cells;
identifying an RT activity in the cells; and
based on the RT activity, identifying the RT as an improved RT.

127. A system comprising an RNA or polynucleotide comprising a spacer, a reverse transcriptase template comprising a desired edit, and a primer binding site, in which the primer binding site binds to a nucleic acid that does not comprise any part of the region of the nucleic acid targeted or bound by the spacer or the nucleic acid reverse complementary to the nucleic acid targeted or bound by the spacer.

128. A system comprising:
a first guide nucleic acid comprising:
a spacer reverse complementary to a first region of a target nucleic acid;
a scaffold configured to bind to a Cas nuclease;
a reverse transcriptase template encoding a sequence to be inserted into the target nucleic acid;
a first strand primer binding site that binds to a region of the target nucleic acid that does not comprise any part of the first region, and that does not comprise any part of a reverse complement of the first region; and
a GPS region that hybridizes to a GPS binding site on a second guide nucleic acid.

129. The system of embodiment 128, further comprising the second guide nucleic acid comprising the GPS binding site.

130. The system of embodiment 129, wherein the second guide nucleic acid comprises a second spacer reverse complementary to another region of the target nucleic acid.

131. The system of embodiment 129 or 130, wherein the second guide nucleic acid brings the primer binding site into close proximity with a genomic flap.

EXAMPLES

The following examples are illustrative and non-limiting to the scope of the devices, methods, systems, and kits described herein.

Example 1

Genome Editing Efficiency Assays

This example describes genome editing efficiency assays. Precision editing rates of genome editing constructs were determined by measuring the frequency of editing a blue fluorescent protein (BFP) gene to produce green fluorescent protein (GFP). Specifically, 30,000 HEK293T cells with a genomically-integrated BFP gene were seeded in 96-well poly-d-lysine-treated plates in DMEM containing 10% fetal bovine serum (FBS). After 12-24 hours, media was replaced with opti-mem media. Lipofectamine 2000 was used to transfect plasmids encoding genome editing components. 25 microliters of opti-mem containing a total of 400 nanograms of plasmid DNA was added to 25 microliters of opti-mem containing 0.8 microliters of Lipofectamine 2000. After 20 minutes, the 50 microliter mixture was added drop-wise to the well containing cells. After 6 hours, media was replaced with DMEM containing 10% FBS. GFP and BFP levels were measured 36-60 hours later using an Attune NxT flow cytometer.

Example 2

Editing Efficiency of a Split nCas9 Reverse Transcriptase Construct

This example describes the editing efficiency of a split nCas9 reverse transcriptase construct. Plasmids encoding either a fused nCas9-mlvRT or a split nCas9-RT and a gRNA were prepared and transfected as described in EXAMPLE 1. Editing efficiency of each construct was measured. FIG. 1 shows the editing efficiency of a fused Cas9 nickase (nCas9) reverse transcriptase (RT) construct ("nCas9-mlvRT") comprising an nCas9 and a Moloney leukemia virus RT (mlvRT), and a split nCas9-LZ1 and LZ2-mlvRT construct ("mlvRT Split Stitch"). Split Stitch may be referred to as Rewriter (e.g. RWb1), or vice versa. In some cases, a Split Stitch may include a Rewriter (e.g. RWb1) or a Rewriter component. In some cases, a Rewriter may include a Split Stitch or a Split Stitch component. mlvRT Split Stitch may be an example of a component of Rewriter (e.g. RWb1). The split nCas9-LZ1 and LZ2-mlvRT construct comprises a nCas9-LZ1 (SEQ ID NO: 1, NLS-SpCas9(H840A)-NLS-EE12RR345L(leucine zipper)) and a LZ2-mlvRT (SEQ ID NO: 2, RR12EE345L(leucine zipper)-mlvRTv(nCas9-mlvRT(D200N, L603W, T306K, W313F, T330P)-NLS) on discrete polypeptide chains. The nCas9-LZ1 comprises a SpCas9 (SEQ ID NO: 32) and a C-terminal leucine zipper (SEQ ID NO: 23) that heterodimerizes with the LZ2-mlvRT comprising a mlvRT (SEQ ID NO: 13) and an N-terminal leucine zipper (SEQ ID NO: 24) through the leucine zippers. Schematics of the nCas9-mlvRT constructs are provided at the top of the figure. The split nCas9-LZ1 and LZ2-mlvRT construct showed improved editing efficiency (about 38% efficiency) nearly double that of the fused nCas9-RT construct (about 21% efficiency).

Figure 11A:
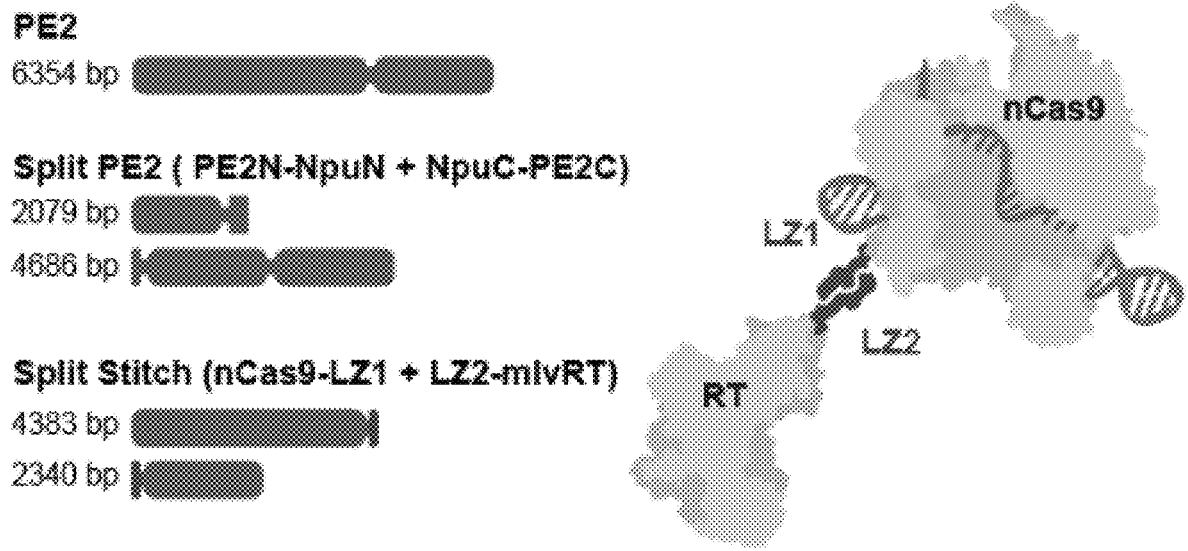
FIG. 11A shows domain arrangements of a prime editor 2 system ("PE2," top), a split prime editor 2 system ("split PE2," middle), and a split stitch construct with two leucine zippers ("Split Stitch," bottom). On the right is a structural schematic of the Split Stitch construct comprising a Cas9 nickase (nCas9) and a reverse transcriptase (RT) linked by two leucine zippers (LZ1 and LZ2) complexed with a guide nucleic acid. The Split Stitch split nCas9-LZ1 and LZ2-mlvRT construct comprises a nCas9-LZ1 (SEQ ID NO: 1, NLS-SpCas9(H840A)-NLS-EE12RR345L(leucine zipper)) and a LZ2-mlvRT (SEQ ID NO: 2, RR12EE345L(leucine zipper)-mlvRTv(nCas9-mlvRT(D200N, L603W, T306K, W313F, T330P)-NLS) on discrete polypeptide chains.
Figure 11B:
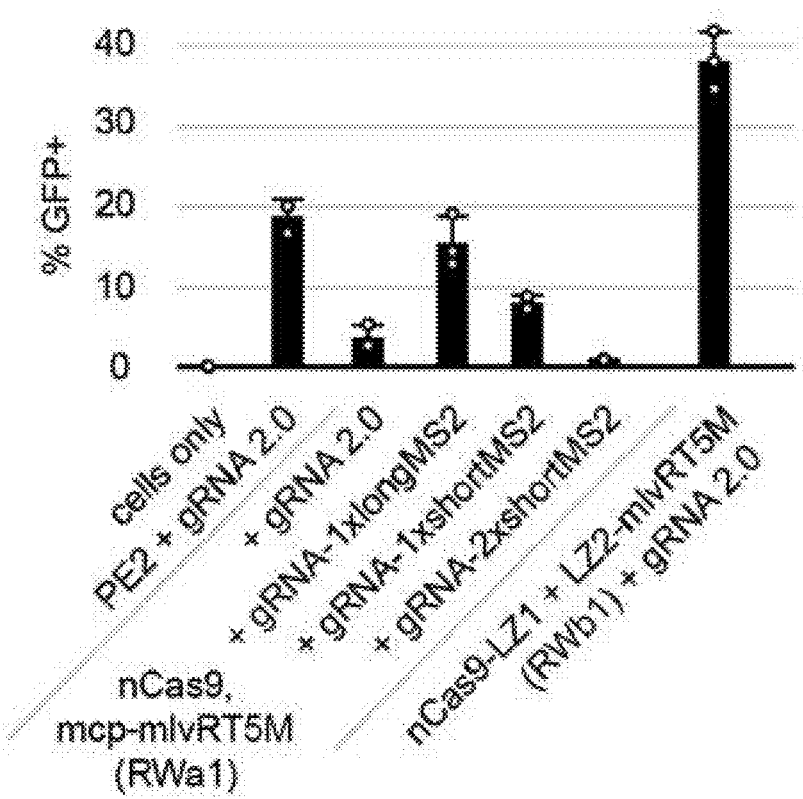
FIG. 11B shows the editing efficiency of the constructs illustrated in FIG. 11A with different gRNAs. Editing efficiency was measured as a percentage of cells that were edited to convert a BFP to a GFP (% GFP+). Editing efficiency was tested with different guide RNA (gRNA) constructs including gRNA 2.0 (SEQ ID NO: 31), a gRNA with a long MS2 hairpin (SEQ ID NO: 28), "gRNA-1× longMS2"), a gRNA with a short MS2 hairpin (SEQ ID NO: 29, "gRNA-1×shortMS2"), or a gRNA with two short MS2 hairpins (SEQ ID NO: 30, "gRNA-2×shortMS2").

FIG. 11A shows domain arrangements of a prime editor 2 system ("PE2," top), a split prime editor 2 system ("split PE2," middle), and a split stitch construct with two leucine zippers ("Split Stitch," bottom). On the right is a structural schematic of the Split Stitch construct comprising a Cas9 nickase (nCas9) and a reverse transcriptase (RT) linked by two leucine zippers (LZ1 and LZ2) complexed with a guide nucleic acid. The Split Stitch split nCas9-LZ1 and LZ2-mlvRT construct comprises a nCas9-LZ1 (SEQ ID NO: 1, NLS-SpCas9(H840A)-NLS-EE12RR345L(leucine zipper)) and a LZ2-mlvRT (SEQ ID NO: 2, RR12EE345L(leucine zipper)-mlvRTv(nCas9-mlvRT(D200N, L603W, T306K, W313F, T330P)-NLS) on discrete polypeptide chains.

Example 3

Effect of gRNA Hairpin Inserts on Reverse Transcriptase Recruitment

Figure 2:
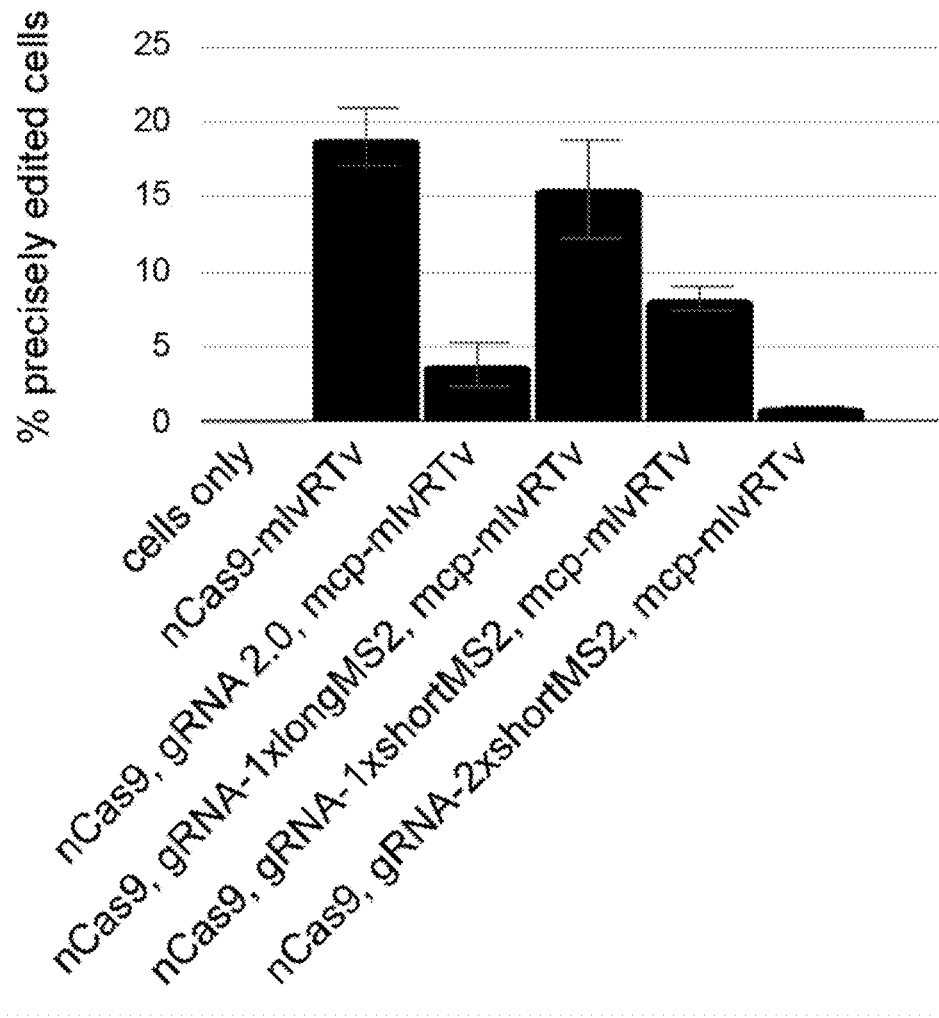
FIG. 2 shows the editing efficiency of a fused nCas9-RT construct ("nCas9-mlvRT") and a split nCas9 and mcp-mlvRT construct ("mcp-mlvRTv") comprising an nCas9 and a mcp peptide fused to reverse transcriptase (SEQ ID NO: 27). The mcp peptide interacts with MS2 RNA hairpins. Efficiency of the split nCas9 and mcp-mlvRT construct was tested with different guide RNA (gRNA) constructs including gRNA 2.0 (SEQ ID NO: 31), a gRNA with a long MS2 hairpin (SEQ ID NO: 28), "gRNA-1×longMS2"), a gRNA with a short MS2 hairpin (SEQ ID NO: 29, "gRNA-1× shortMS2"), or a gRNA with two short MS2 hairpins (SEQ ID NO: 30, "gRNA-2×shortMS2").

This example describes the effect of gRNA hairpin inserts on editing efficiency. Plasmids encoding either a fused nCas9-mlvRT or a split nCas9 and mcp-RT and a gRNA were prepared and transfected as described in EXAMPLE 1. Editing efficiency of the fused nCas9-RT was measured in the presence of pegRNA. Editing efficiency of the split nCas9-RT was measured in the presence of three different gRNAs either with hairpins embedded in the scaffold (gRNA 2.0) or with hairpins of varying lengths (1×longMS2, 1×shortMS2, or 2×shortMS2) positioned after the scaffold. FIG. 2 shows the editing efficiency of a fused nCas9-RT construct ("nCas9-mlvRT") and a split nCas9 and mcp-mlvRT construct ("mcp-mlvRTv") comprising an nCas9 and a mcp peptide fused to reverse transcriptase (SEQ ID NO: 27). The mcp peptide interacts with MS2 RNA hairpins. Efficiency of the split nCas9 and mcp-mlvRT construct was tested with different guide RNA (gRNA) constructs including gRNA 2.0 (SEQ ID NO: 31), a gRNA with a long MS2 hairpin (SEQ ID NO: 28), "gRNA-1× longMS2"), a gRNA with a short MS2 hairpin (SEQ ID NO: 29, "gRNA-1×shortMS2"), or a gRNA with two short MS2 hairpins (SEQ ID NO: 30, "gRNA-2×shortMS2"). The gRNA with the 1×longMS2 hairpin and the gRNA with the 1×shortMS2 hairpin showed improved editing efficiency over gRNA 2.0.

FIG. 11B shows the editing efficiency of the constructs illustrated in FIG. 11A with different gRNAs. Editing efficiency was measured as a percentage of cells that were edited to convert a BFP to a GFP (% GFP+). Editing efficiency was tested with different guide RNA (gRNA) constructs including gRNA 2.0 (SEQ ID NO: 31), a gRNA with a long MS2 hairpin (SEQ ID NO: 28), "gRNA-1× longMS2"), a gRNA with a short MS2 hairpin (SEQ ID NO: 29, "gRNA-1×shortMS2"), or a gRNA with two short MS2 hairpins (SEQ ID NO: 30, "gRNA-2×shortMS2"). The Split Stitch construct (RWb1 in this instance) showed improved editing efficiency over the prime editor 2 (PE2) construct.

Example 4

Split nCas9-RT Construct with Increased Reverse Transcriptase Processivity

This example describes a split nCas9-RT construct with increased reverse transcriptase processivity. The split nCas9-RT construct described in EXAMPLE 2 was further engineered to increase the processivity of the reverse transcriptase polymerase function. The reverse transcriptases with increased processivity was able to catalyze the formation of more sequential phosphodiester bonds in a single binding event than the reverse transcriptase provided in EXAMPLE 2. The increased processivity facilitated the reverse transcription of longer template sequences and may enable editing of longer sequences at a target site of a genome. The editing efficiency of three split nCas9-RT constructs with reverse transcriptases having increased processivity were tested.

Figure 3:
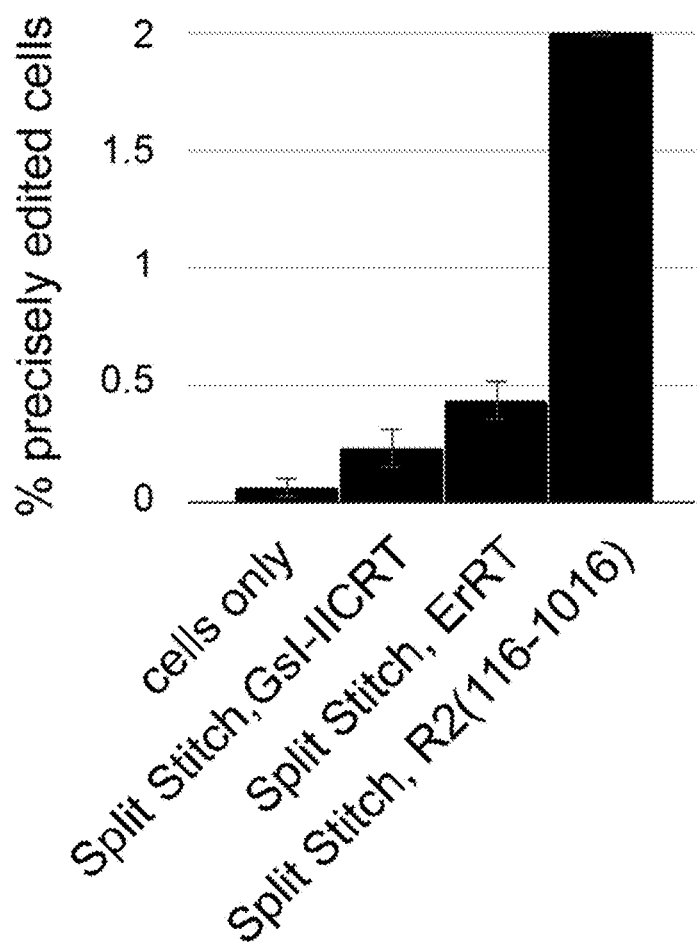
FIG. 3 shows the editing efficiency of different split nCas9-RT constructs comprising modified reverse transcriptases with increased transcriptional processivity. Constructs comprising nCas9 and reverse transcriptases from either geobacilus stereothermophilus (GsI-IICRT, SEQ ID NO: 3), *Eubacterium Rectale* (ErRT, SEQ ID NO: 4), and amino acids 116-1016 from the R2 polyprotein (R2(116-1016), SEQ ID NO: 7) were tested. A schematic of the GsI-IICRT reverse transcriptase ("StitchRT") is shown compared to the mlvRT reverse transcriptase used in FIG. 1 and FIG. 2.

FIG. 3 shows the editing efficiency of different split nCas9-RT constructs comprising modified reverse transcriptases with increased transcriptional processivity. Constructs comprising nCas9 and reverse transcriptases from either geobacilus stereothermophilus (GsI-IICRT, SEQ ID NO: 3), *Eubacterium Rectale* (ErRT, SEQ ID NO: 4), and amino acids 116-1016 from the R2 polyprotein (R2(116-1016), SEQ ID NO: 7) were tested. A schematic of the GsI-IICRT reverse transcriptase ("StitchRT") is shown compared to the mlvRT reverse transcriptase used in FIG. 1 and FIG. 2. Split Stitch R2(116-1016) showed the highest editing efficiency of the three split nCas9 and RT constructs comprising modified reverse transcriptases with increased transcriptional processivity tested.

Example 5 gRNAs for Increased Editing Efficiency at Single-Strand Breaks

This example describes gRNAs for increased editing efficiency at single-strand breaks. gRNAs were designed to increase efficiency of editing at a single-strand break by incorporating a second strand primer at the 3' end of the gRNA. The second strand primer primed the synthesis of the second strand using a newly synthesized first strand as a template. Priming of second strand synthesis facilitated the insertion of the synthesized sequence into the site of a single-strand break without formation of a double-strand break. Formation of double-strand breaks may increase the rate of formation of undesired products.

FIG. 4A illustrates a method for genome editing using an engineered gRNA of the present disclosure ("Stitch Guide"). In some cases, a Stitch Guide may include a Rewriter (e.g. Rewriter 3.0, Rewriter 3.1, or Rewriter 3.2) or a Rewriter component. In some cases, a Rewriter may include a Stitch Guide or a Stitch Guide component. A nCas9-RT construct complexed with a gRNA is recruited to a target site of a target nucleic acid by hybridization of a spacer of the gRNA to the target site. The nCas9 nicks a strand of a target nucleic acid at a target site. A first strand primer binding site of the gRNA hybridizes to a flap 5' of the nick. The RT polymerizes from the 3' end of the flap using a reverse transcriptase template region of the gRNA as a template. A second strand primer ("$2^{nd}$ strand primer") at the 3' end of the gRNA hybridizes to the 3' end of the newly synthesized DNA strand. The 4-300 bp second strand primer region acts as an RNA primer for synthesis of a second DNA strand. The RT polymerizes from the 3' end of the gRNA using the newly synthesized DNA strand as a template. A ribozyme on the 3' end of the gRNA cleaves the gRNA 3' of the second strand primer sequence. The newly synthesized double stranded DNA may be incorporated into the target nucleic acid at the site of the nick.

FIG. 4B shows the editing efficiency of a nCas9-RT construct using a pegRNA gRNA or a Stitch Guide gRNA. Schematics of the pegRNA and the Stitch Guide gRNA are shown at left. The inclusion of the second strand primer in the Stitch Guide gRNA improved the editing efficiency relative to the pegRNA lacking the second strand primer. The fused nCas9-mlvRTv construct was used in this assay.

Figure 5A:
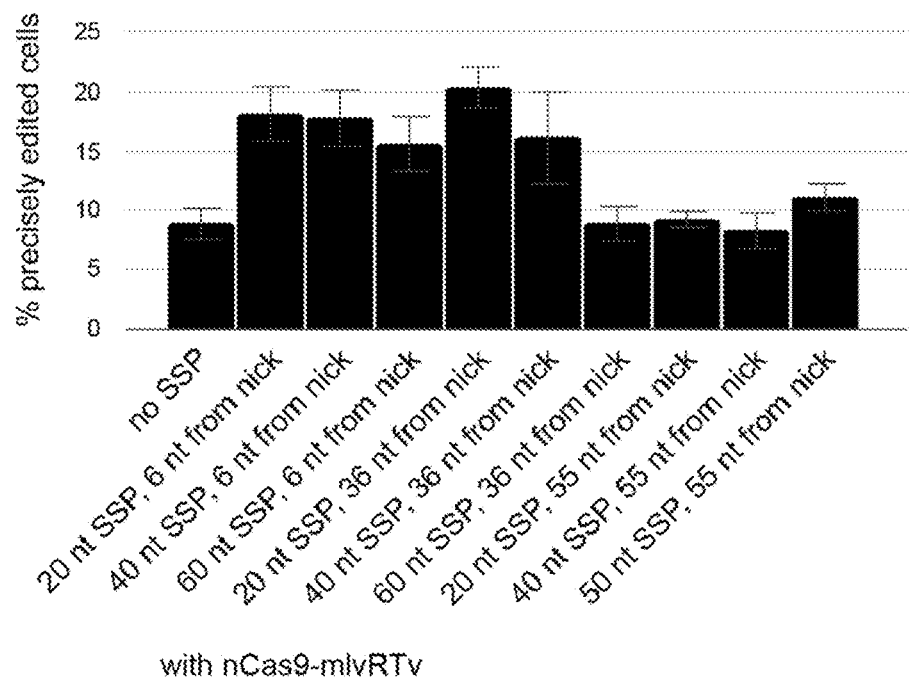
FIG. 5A shows the editing efficiency of a fused nCas9-RT construct ("nCas9-mlvRTv") with different gRNAs comprising second strand primers (SSPs) 20 nucleotides (nt), 40 nt, or 60 nt in length positioned either 6 nt, 36, nt, or 55 nt 3' of the 5' end of the first strand primer binding site ("nt from nick"). A gRNA lacking a second strand primer was tested as a control. All gRNA sequences comprised an HDV ribozyme (SEQ ID NO: 25).
Figure 5B:
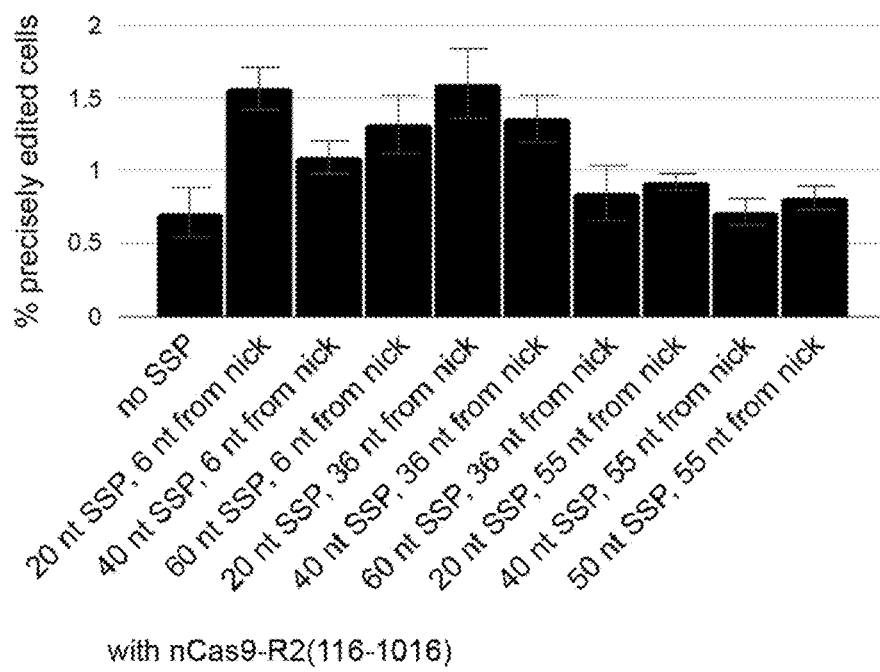
FIG. 5B shows the editing efficiency of a nCas9-RT ("nCas9-R2(116-1016)") with different gRNAs comprising second strand primers (SSPs) 20 nucleotides (nt), 40 nt, or 60 nt in length that positioned either 6 nt, 36, nt, or 55 nt 3' of the 5' end of the first strand primer binding site ("nt from nick"). A gRNA lacking a second strand primer was tested as a control.

In a second assay, the effect of second strand primer length and binding site on editing efficiency of split nCas9-RT constructs was tested. The length of the second strand primer was varied as well as the binding position of the second strand primer relative to the position of the single strand break. FIG. 5A shows the editing efficiency of a fused nCas9-RT construct ("nCas9-mlvRTv") with different gRNAs comprising second strand primers (SSPs) 20 nucleotides (nt), 40 nt, or 60 nt in length positioned either 6 nt, 36, nt, or 55 nt 3' of the 5' end of the first strand primer binding site ("nt from nick"). A gRNA lacking a second strand primer was tested as a control. All gRNA sequences comprise an hdv ribozyme (SEQ ID NO: 25). FIG. 5B shows the editing efficiency of a nCas9-RT ("nCas9-R2(116-1016)") with different gRNAs comprising second strand primers (SSPs) 20 nucleotides (nt), 40 nt, or 60 nt in length that positioned either 6 nt, 36, nt, or 55 nt 3' of the 5' end of the first strand primer binding site ("nt from nick"). A gRNA lacking a second strand primer was tested as a control. With both the nCas9-mlvRTv and the nCas9 and R2 constructs, the gRNAs with shorter (e.g., 20 nt) second strand primers showed improved editing efficiency as compared to the other gRNAs with longer second strand primers.

Example 6

Dual Guide Systems for Improved Editing

This example describes dual guide systems for improved editing. Dual guide systems comprising two gRNAs targeting two target sites on opposite strands in close proximity are introduced into a cell. Each gRNA recruits a nCas9-RT contract to the respective target site, facilitating a single strand break at each target site. The two gRNAs are fused for improved delivery and to ensure co-localization to the two target sites.

FIG. 6 illustrates four schemes of genome editing using a two gRNA system with a nCas9-RT. In a two single guide system in which the two guides each generate an edited strand (top left), each gRNA binds to a different nCas9 and the two gRNAs each comprise a reverse transcriptase template region and a primer binding site (PBS) region. In a two single guide system in which the second guide nicks the opposite strand (top right), each gRNA binds to a different nCas9 and only one of the gRNAs comprise a reverse transcriptase template region and a primer binding site (PBS) region. In a dual guide complex system in which the two guides each comprise a reverse transcriptase template region and a primer binding site (PBS) region (bottom left), the spacer of the first gRNA binds the first nCas9, the spacer of the second gRNA binds the second nCas9, the scaffold of the first gRNA binds the second nCas9, and the scaffold of the second gRNA binds the first nCas9; and the two gRNAs each comprise a reverse transcriptase template region and a PBS region. In a dual guide complex system in which the second guide nicks the opposite strand (bottom right), the spacer of the first gRNA binds the first nCas9, the spacer of the second gRNA binds the second nCas9, the scaffold of the first gRNA binds the second nCas9, and the scaffold of the second gRNA binds the first nCas9; and only one of the gRNAs comprise a reverse transcriptase template region.

Figure 7:
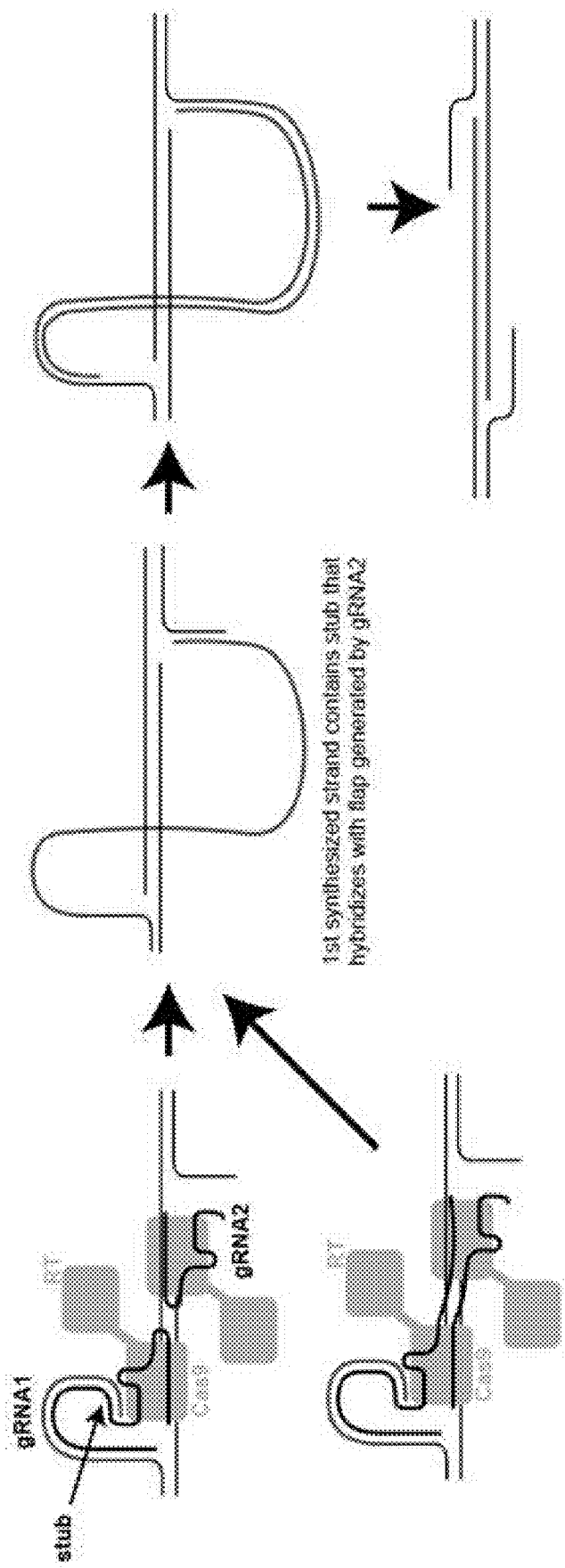
FIG. 7 illustrates a method for increasing the efficiency of gene editing. A two single guide system in which the second guide nicks the opposite strand or a dual guide complex system in which the second guide nicks the opposite strand, the nick on the opposite strand facilitates incorporation of the newly synthesized DNA into the target nucleic acid. The second guide generates a flap that is reverse complementary to a region in the first newly synthesized strand. The first synthesized strand acts as template for second strand synthesis.

FIG. 7 illustrates a method for increasing the efficiency of gene editing. A two single guide system in which the second guide nicks the opposite strand or a dual guide complex system in which the second guide nicks the opposite strand, the nick on the opposite strand facilitates incorporation of the newly synthesized DNA into the target nucleic acid. The second guide generates a flap that is reverse complementary to a region in the of first newly synthesized strand. The first synthesized strand acts as template for second strand synthesis.

Figure 10:
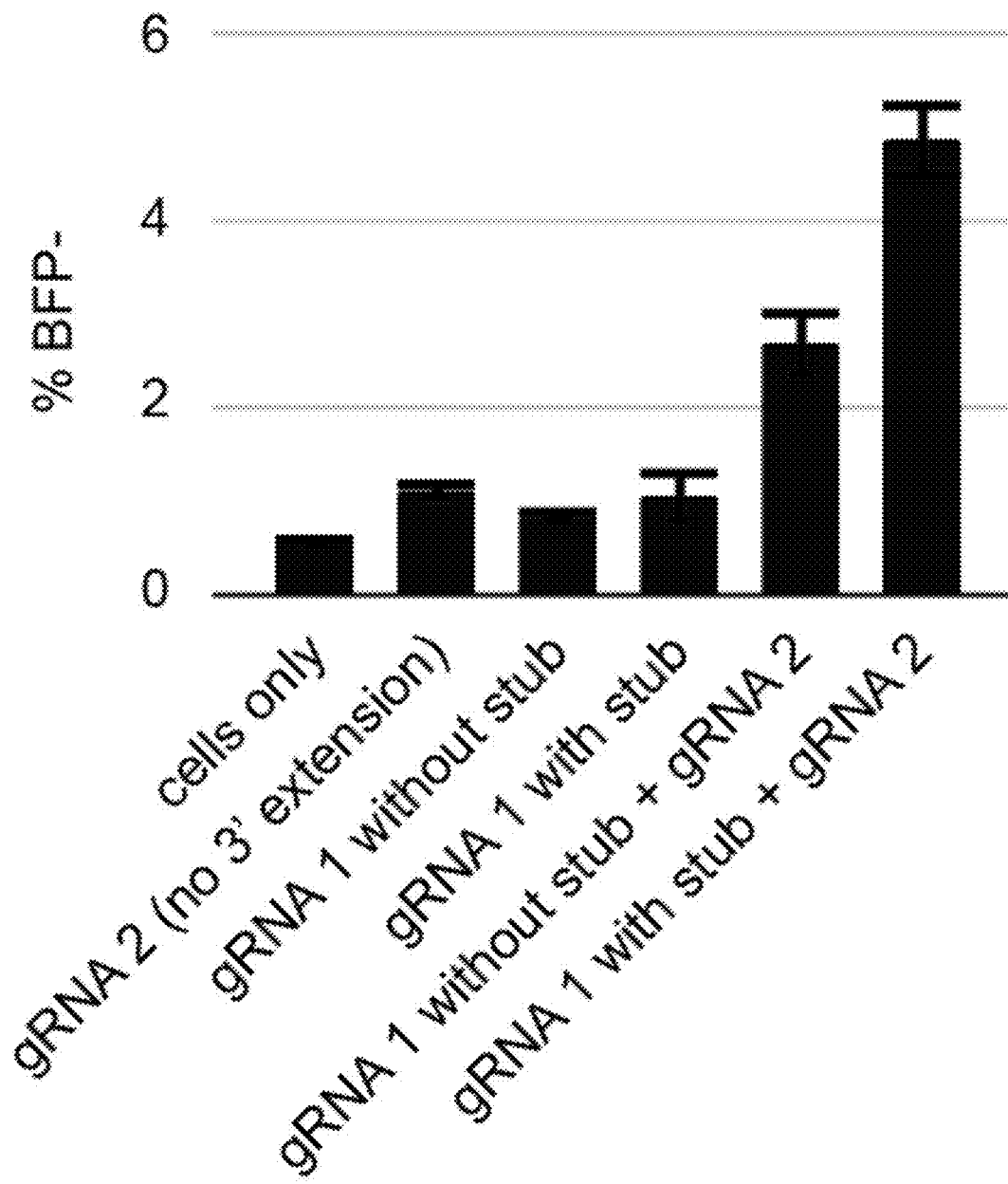
FIG. 10 shows the editing efficiency of a two gRNA system as illustrated in FIG. 7. A target nucleic acid encoding a blue fluorescent protein (BFP) was edited to introduce a stop codon. Lack of BFP fluorescence in a cell was indicative of successful editing. Editing efficiency, as measured by percent of cells negative for BFP ("% BFP−"), was measured for cells only (no gRNA), single gRNAs (gRNA 2 which lacks a 3' extension, gRNA 1 without a stub, gRNA 1 with a stub), and two gRNAs (gRNA 1 without a stub plus gRNA 2 and gRNA 1 with a stub and gRNA 2).

Editing efficiency of a two gRNA system was measured by introducing a stop codon into a target nucleic acid encoding a blue fluorescent protein. Assays were performed as described in EXAMPLE 1 except that successful editing was identified by a lack of BFP fluorescence. FIG. 10 shows the editing efficiency of a two gRNA system as illustrated in FIG. 7. Editing efficiency, as measured by percent of cells negative for BFP ("% BFP−"), was measured for cells only (no gRNA), single gRNAs (gRNA 2 which lacks a 3' extension, gRNA 1 without a stub, and gRNA 1 with a stub), and two gRNAs (gRNA 1 without a stub plus gRNA 2 and gRNA 1 with a stub and gRNA 2). The two gRNA systems increased editing efficiency as compared to the single gRNA systems. Presence of a stub in gRNA 1 in the two gRNA system increased editing efficiency compared to the two gRNA system lacking a stub in gRNA 1.

Example 7 gRNA Velcro for Improved Editing

This example describes gRNA Velcro for improved editing. A gRNA comprising a Velcro region improved the efficiency of strand formation by facilitating an interaction between the gRNA and a flap formed 5' of the nick in the target nucleic acid. The Velcro region was positioned either 5' of the reverse transcriptase template region or 3' of the first strand primer binning site. The gRNA Velcro insertion was compatible with the single guide systems provided in EXAMPLE 2-EXAMPLE 5 or dual guide systems provided in EXAMPLE 6.

FIG. 8A illustrates a gRNA comprising a Velcro region to accelerate the rate of hybridization of the primer binding site and the flap by creating regions of reverse complementation within the 3' extended guide RNA. The Velcro region comprises 5 to 200 nucleotides positioned 5' of the reverse transcriptase template region that are reverse complementary to the region of the gRNA 5' of the first strand primer binding site. FIG. 8B illustrates a gRNA comprising a Velcro region to accelerate the rate of hybridization of the primer binding site and the flap by creating regions of reverse complementation within the 3' extended guide RNA. The Velcro region comprises 5 to 100 nucleotides positioned 3' of the first strand primer binding site that are reverse complementary to the region 5' of the reverse transcriptase template region.

Figure 12A:
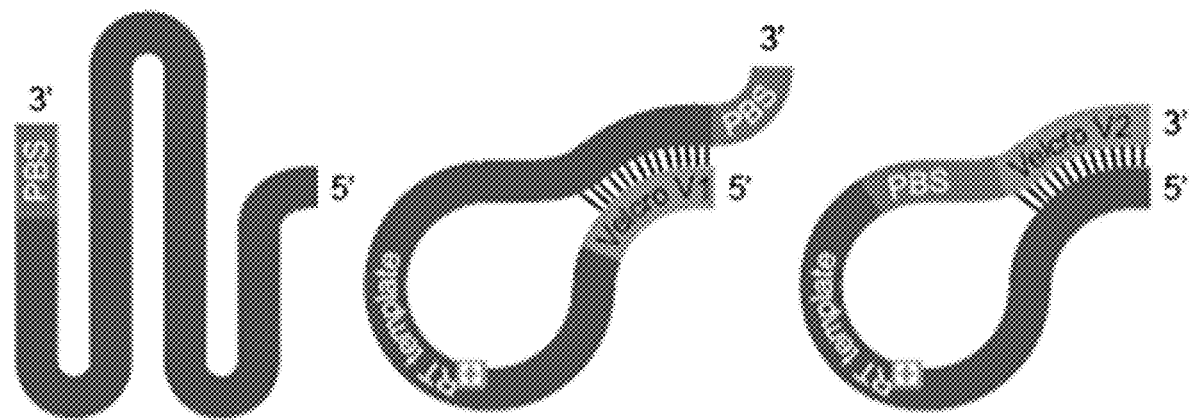
FIG. 12A illustrates gRNA constructs either without (left) or with (middle and right) a Velcro region to accelerate the rate of hybridization of the primer binding site (PBS) to a flap of a target nucleic acid. In a V1 arrangement, the Velcro region may be positioned at or near the 5' end of the gRNA and may hybridize to a region of the gRNA 5' of the primer binding site ("Velcro V1," middle). In a V2 arrangement, the Velcro region may be positioned 3' of the primer binding site and may hybridize to a region at or near the 5' end of the gRNA ("Velcro V2," right).
Figure 12B:
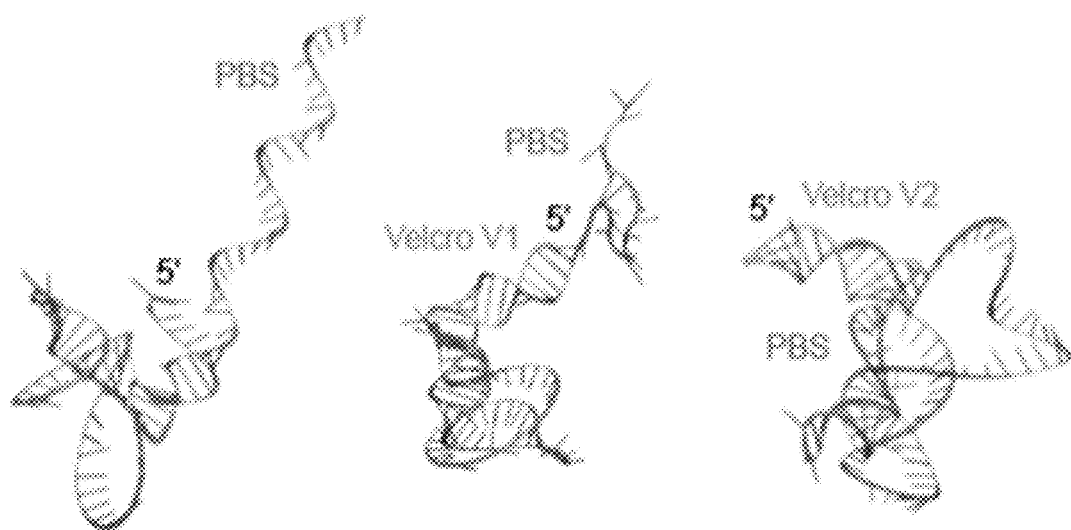
FIG. 12B illustrates predicted three-dimensional structures of the gRNA constructs provided in FIG. 12A. A gRNA lacking a Velcro region is shown in the left. gRNAs comprising a Velcro V1 region or a Velcro V2 region are shown in the middle and right panels, respectively.

FIG. 12A illustrates gRNA constructs either without (left) or with (middle and right) a Velcro region to accelerate the rate of hybridization of the primer binding site (PBS) to a flap of a target nucleic acid. In a V1 arrangement, the Velcro region may be positioned at or near the 5' end of the gRNA and may hybridize to a region of the gRNA 5' of the primer binding site ("Velcro V1," middle). In a V2 arrangement, the Velcro region may be positioned 3' of the primer binding site and may hybridize to a region at or near the 5' end of the gRNA ("Velcro V2," right).

FIG. 12B illustrates predicted three-dimensional structures of the gRNA constructs provided in FIG. 12A. A gRNA lacking a Velcro region is shown in the left. gRNAs comprising a Velcro V1 region or a Velcro V2 region are shown in the middle and right panels, respectively.

Figure 9A:
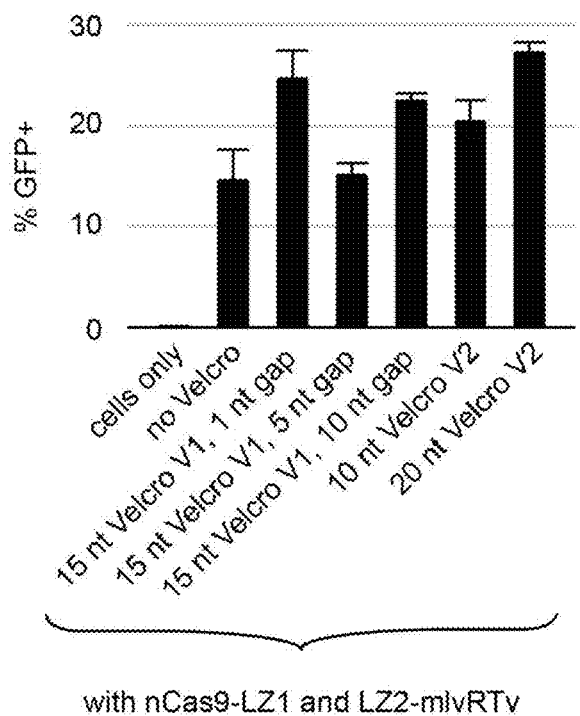
FIG. 9A shows the editing efficiency of a nCas9-LZ1 and LZ2-mlvRTv construct with the gRNA constructs comprising a Velcro region, as illustrated in FIG. 8A and FIG. 8B. Editing efficiency was compared using a gRNA lacking a Velcro region ("no Velcro"), a 15 nt Velcro region positioned 5' of the reverse transcriptase template region ("V1," as illustrated in FIG. 8A) with a gap length of 1, 5, or 10 nts, or a Velcro region positioned 3' of the first strand primer binding site ("V2," as illustrated in FIG. 8B) of either 10 or 20 nt in length. The gRNA contained a 107 nucleotide RT template, and a 13 nucleotide primer binding site. Editing was performed such that an ATCC sequence, starting 2 nucleotides 3' of the nick, was mutated to CATA.
Figure 9B:
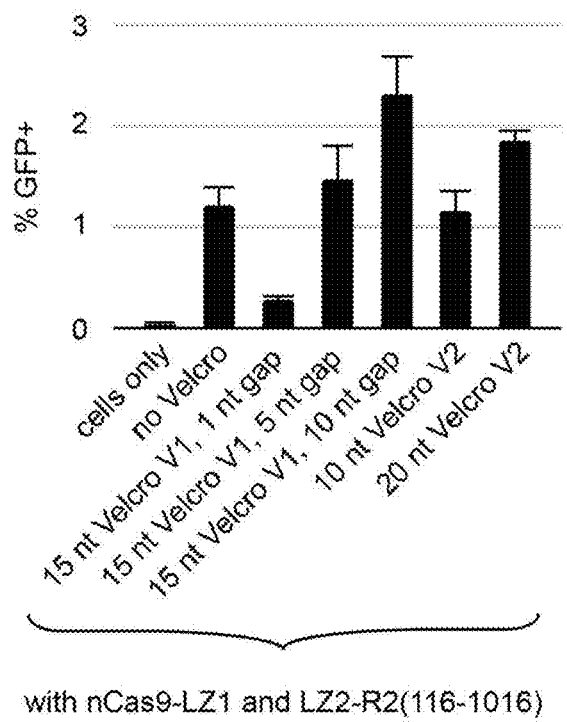
FIG. 9B shows the editing efficiency of a nCas9-LZ1 and LZ2-R2(116-1016) construct with the gRNA constructs comprising a Velcro region, as illustrated in FIG. 8A and FIG. 8B. Editing efficiency was compared using a gRNA lacking a Velcro region ("no Velcro"), a 15 nt Velcro region positioned 5' of the reverse transcriptase template region ("V1," as illustrated in FIG. 8A) with a gap length of 1, 5, or 10 nts between the end of the Velcro binding site and the beginning of the primer binding site, or a Velcro region positioned 3' of the first strand primer binding site ("V2," as illustrated in FIG. 8B) of either 10 or 20 nt in length.

FIG. 9A shows the editing efficiency of a nCas9-LZ1 and LZ2-mlvRTv construct with the gRNA constructs comprising a Velcro region, as illustrated in FIG. 8A and FIG. 8B. Editing efficiency was compared using a gRNA lacking a Velcro region ("no Velcro"), a 15 nt Velcro region positioned 5' of the reverse transcriptase template region ("V1," as illustrated in FIG. 8A) with a gap length of 1, 5, or 10 nts, or a Velcro region positioned 3' of the first strand primer binding site ("V2," as illustrated in FIG. 8B) of either 10 or 20 nt in length. The gRNA contained a 107 nucleotide RT template, and a 13 nucleotide primer binding site. Editing was performed such that an ATGG sequence, starting 2 nucleotides 3' of the nick, was mutated to CATA. FIG. 9B shows the editing efficiency of a nCas9-LZ1 and LZ2-R2 (116-1016) construct with the gRNA constructs comprising a Velcro region, as illustrated in FIG. 8A and FIG. 8B. Editing efficiency was compared using a gRNA lacking a Velcro region ("no Velcro"), a 15 nt Velcro region positioned 5' of the reverse transcriptase template region ("V1," as illustrated in FIG. 8A) with a gap length of 1, 5, or 10 nts between the end of the Velcro binding site and the beginning of the primer binding site, or a Velcro region positioned 3' of the first strand primer binding site ("V2," as illustrated in FIG. 8B) of either 10 or 20 nt in length. With both nCas9-RT constructs, certain gRNAs comprising Velcro regions increased editing efficiency. In particular, the V1 Velcro gRNA with the 1 nt gap and the 20 nt Velcro gRNA improved editing efficiency in the nCas9-mlvRTv construct, and the V1 Velcro gRNA with the 10 nt gap and the 20 nt V2 Velcro gRNA improved editing efficiency in the nCas9-R2 construct.

Figure 12C:
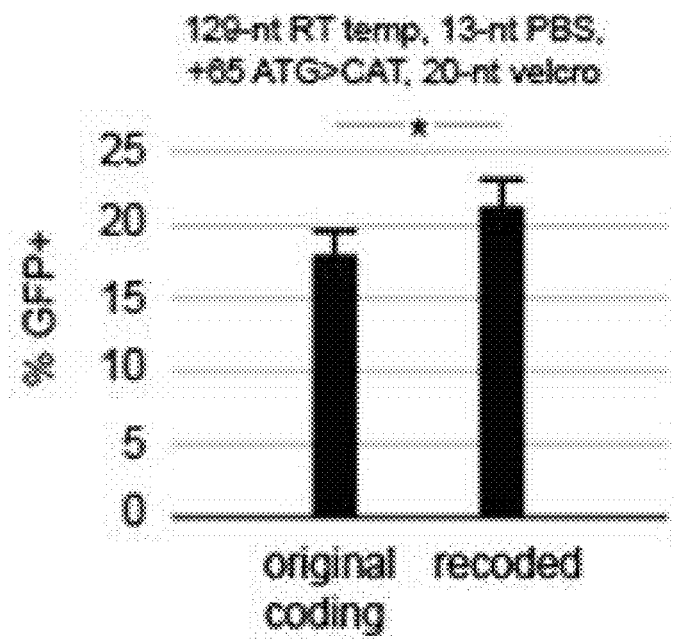
FIG. 12C shows editing efficiency of a gRNA with a 129 nucleotide RT template and a 13 nucleotide primer binding site and a 20 nucleotide Velcro region. Editing was performed such that an ATG sequence, starting 65 nucleotides 3' of the nick, was mutated to CAT. Editing efficiency was compared for the original gRNA ("original coding") or a gRNA recoded with silent mutations in the RT template region of the gRNA extension to remove secondary structure ("recoded").
Figure 12D:
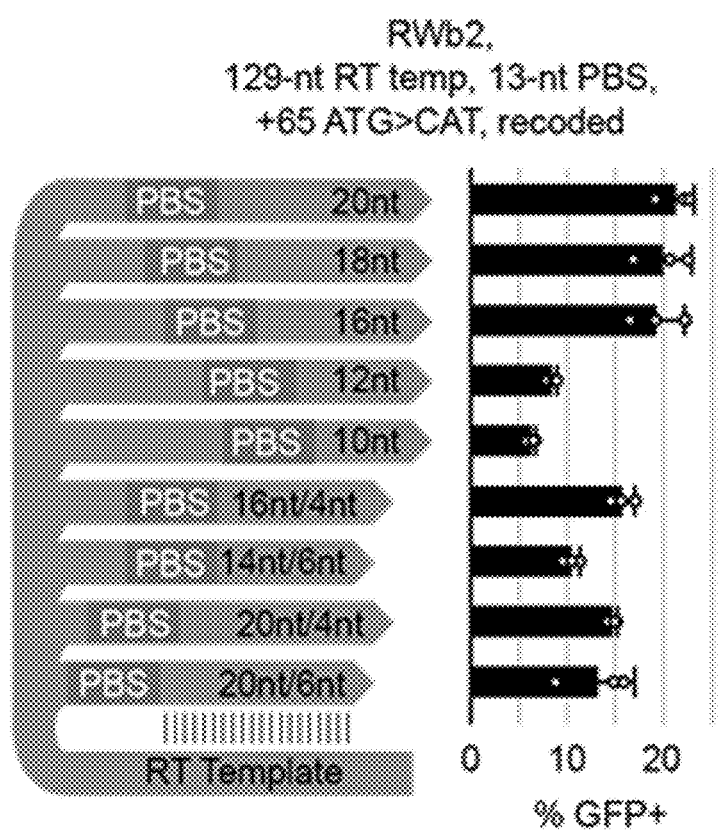
FIG. 12D shows editing efficiency of gRNAs with different lengths of Velcro sequences. Each gRNA contained, in order from 5' to 3', a RT template, a primer binding site, and a Velcro region, as shown in the schematic on the left. Editing efficiency was measured as the percent of cells that were GFP positive (% GFP+). gRNAs had a 129 nucleotide RT template, a 13 nucleotide primer binding site. Editing was performed such that an ATG sequence, starting 65 nucleotides 3' of the nick, was mutated to CAT.

FIG. 12C shows editing efficiency of a gRNA with a 129 nucleotide RT template and a 13 nucleotide primer binding site and a 20 nucleotide Velcro region. Editing was performed such that an ATG sequence, starting 65 nucleotides 3' of the nick, was mutated to CAT. Editing efficiency was compared for the original gRNA ("original coding") or a gRNA recoded with silent mutations in the RT template to remove secondary structure ("recoded"). Removal of secondary structure using silent mutations improved editing efficiency relative to the original RT template. Additionally, use of gRNA comprising a Velcro region allowed efficient editing at a distance of 65 nucleotides from the nicking site.

FIG. 12D shows editing efficiency of gRNAs with different lengths of Velcro sequences. Each gRNA contained, in order from 5' to 3', a RT template, a primer binding site, and a Velcro region, as shown in the schematic on the left. Editing efficiency was measured as the percent of cells that were GFP positive (% GFP+). gRNAs had a 129 nucleotide RT template, a 13 nucleotide primer binding site. Editing was performed such that an ATG sequence, starting 65 nucleotides 3' of the nick, was mutated to CAT. The gRNA with a 20 nucleotide Velcro region positioned at the 3' end with no gap showed higher editing efficiency than the other gRNAs tested.

Example 8

Co-Delivery of Protective Complexes for Improved Editing System Delivery

This example describes co-expression of protective complexes for improved delivery of the editing systems provided herein. A nCas9-RT constructs provided herein and a gRNA provided herein are delivered to a cell. The nCas9-RT and the gRNA are co-expressed with an open reading frame sequence encoding protective protein complexes. The protective protein complexes are expressed in the cell, preventing degradation or deamination of the gRNA, thereby improving delivery of the editing system. The open reading frame sequence is a Human Orflp (SEQ ID NO: 38) or a Murine Orflp (SEQ ID NO: 39).

Example 9

Improved Editing Efficiency with gRNAs with a Velcro Region and a Second Strand Primer This example describes improved editing efficiency with gRNAs with a Velcro region and a second strand primer. gRNAs were designed to increase efficiency of editing at a single-strand break by incorporating a second strand primer at the 3' end of the gRNA and a Velcro region 5' of the second strand primer. The second strand primer primed the synthesis of the second strand using a newly synthesized first strand as a template. Priming of second strand synthesis facilitated the insertion of the synthesized sequence into the site of a single-strand break without formation of a double-strand break. The Velcro region improved the efficiency of strand formation by facilitating an interaction between the gRNA and a flap formed 5' of the nick in the target nucleic acid.

FIG. 13A illustrates schematics of a pegRNA and a Stitch gRNA comprising a Velcro region and a $2^{nd}$ strand primer (top) and a method of genome editing using a Stitch gRNA (bottom). A nCas9-RT construct complexed with a gRNA is recruited to a target site of a target nucleic acid by hybridization of a spacer of the gRNA to the target site. The nCas9 nicks a strand of a target nucleic acid at a target site. A first strand primer binding site of the gRNA hybridizes to a flap 5' of the nick. The RT polymerizes from the 3' end of the flap using a reverse transcriptase template region of the gRNA as a template. A second strand primer ("$2^{nd}$ strand primer") at the 3' end of the gRNA hybridizes to the 3' end of the newly synthesized DNA strand. The 4-200 bp second strand primer region acts as an RNA primer for synthesis of a second DNA strand. The RT polymerizes from the 3' end of the gRNA using the newly synthesized DNA strand as a template. A ribozyme on the 3' end of the gRNA cleaves the gRNA 3' of the second strand primer sequence. The newly synthesized double stranded DNA may be incorporated into the target nucleic acid at the site of the nick.

Figure 13C:
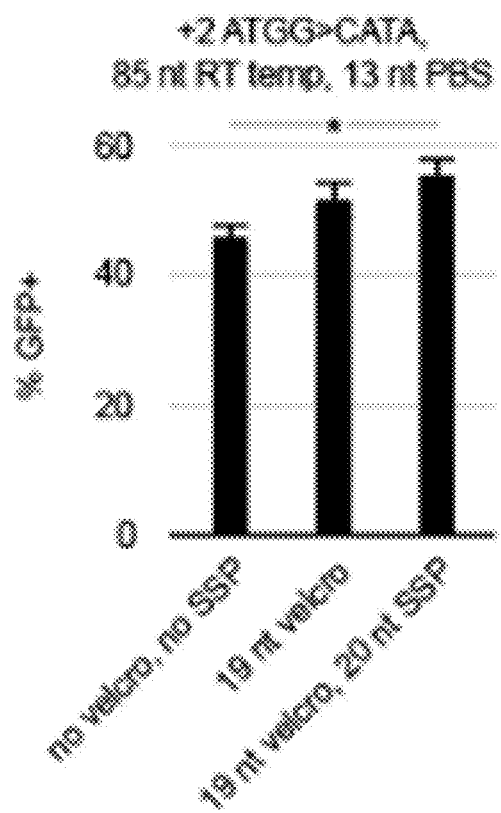
FIG. 13C shows editing efficiency of gRNAs without a Velcro region or a second strand primer ("no velcro, no SSP"), with a 19 nucleotide Velcro region ("19 nt velcro"), or with both a 19 nucleotide Velcro region and a 20 nucleotide second strand primer ("19 nt velcro, 20 nt SSP").
Figure 13B:
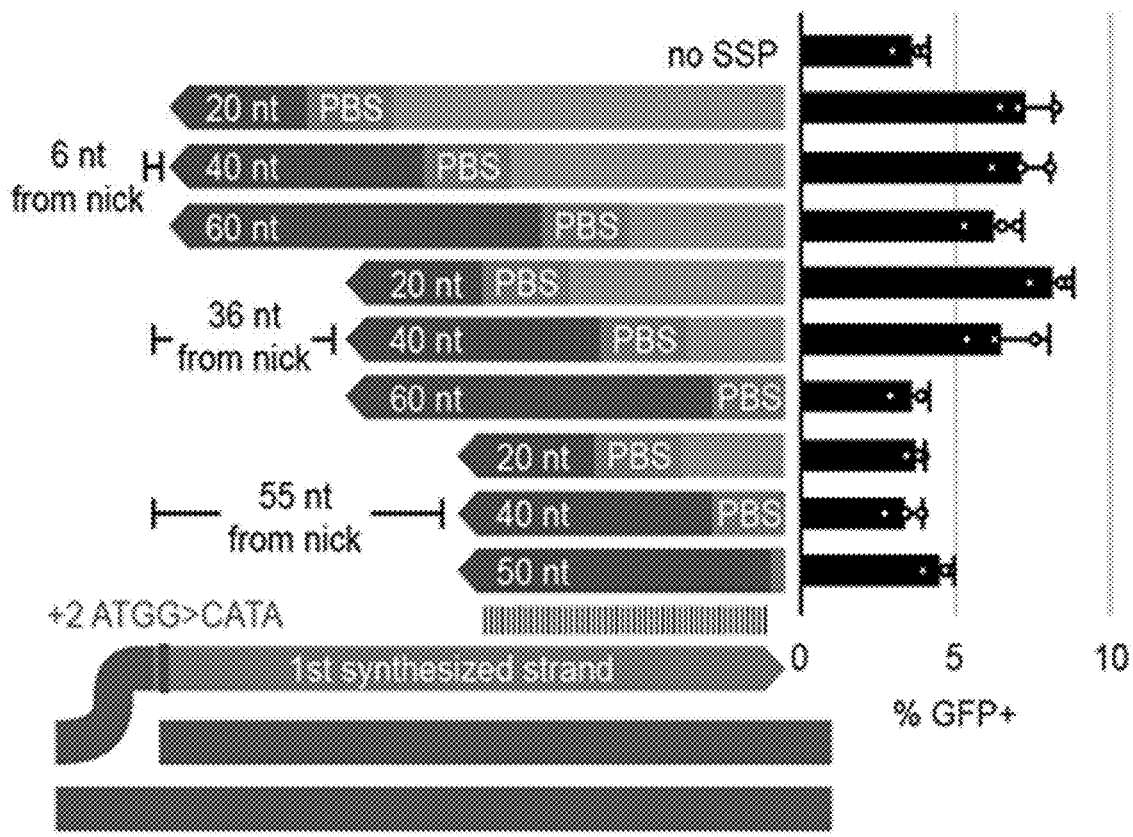
FIG. 13B shows editing efficiency of gRNAs second strand primers (SSPs) of varying lengths and that hybridize at varying distances from the nicking site. Second strand primers 20, 40, or 60 nucleotides (nt) long positioned 6, 36, or 55 nucleotides from the nick were tested. Editing efficiency was measured as the percent of cells that were GFP positive (% GFP+).

FIG. 13B shows editing efficiency of gRNAs second strand primers (SSPs) of varying lengths and that hybridize at varying distances from the nicking site. Second strand primers 20, 40, or 60 nucleotides (nt) long positioned 6, 36, or 55 nucleotides from the nick were tested. Editing efficiency was measured as the percent of cells that were GFP positive (% GFP+).

FIG. 13C shows editing efficiency of gRNAs without a Velcro region or a second strand primer ("no velcro, no SSP"), with a 19 nucleotide Velcro region ("19 nt velcro"), or with both a 19 nucleotide Velcro region and a 20 nucleotide second strand primer ("19 nt velcro, 20 nt SSP"). Editing efficiency was increased when using a gRNA containing both a Velcro region and a second strand primer as compared to a gRNA lacking a Velcro region and a second strand primer or a gRNA containing a Velcro region but no second strand primer. The editing efficiency achieved using the a gRNA containing both a Velcro region and a second strand primer was 54% from a single nick, which was higher than the predicted limit of 50% for editing efficiency from a single nick.

Example 10

Reverse Transcriptase Protein Engineering to Increase Editing Efficiency

This example describes reverse transcriptase protein engineering to increase editing efficiency. Point mutations were made in an mlvRT construct to improve editing efficiency. Editing efficiency was measured using the mutated constructs.

FIG. 14A shows the results of a screen for mutations in a mlvRT reverse transcriptase and their effect on editing efficiency. Mutations were made in a reference mlvRT construct containing five point mutations (D200N, 1603W, T330P, T306K, and W313F, SEQ ID NO: 40). Amino acid residues are counted relative to an mlvRT construct lacking an N-terminal methionine (e.g., SEQ ID NO: 14). mlvRT constructs containing a Y8H, P51L, S56A, S67R, E69K, Q84A, F155Y, T197A, H204R, T246E, N249D, E286R, Q291I, R301L, E302K, F309N, M320L, L435G, D524A, D524G, D524N, E562D, K571R, D583N, Y586S, H594Q, H638G, D653N, T664N, or L671P single point mutation (SEQ ID NO: 41-SEQ ID NO: 70, respectively) relative to SEQ ID NO: 40 were tested. Editing efficiency was measured as a percent of cells that were GFP positive (% GFP+). Editing was performed using a gRNA with an 85 nucleotide RT template, a 13 nucleotide primer binding site, a 1 nucleotide gap, a 19 nucleotide Velcro region, and a 20 nucleotide second strand primer to edit a site such that an ATGG sequence, starting 2 nucleotides 3' of the nick, was mutated to CATA. Mutants containing Q84A (SEQ ID NO: 46), T197A (SEQ ID NO: 48), D653N (SEQ ID NO: 68), T664N (SEQ ID NO: 69), or L671P (SEQ ID NO: 70) showed significantly increased editing efficiency compared to SEQ ID NO: 40.

FIG. 14B shows the results of a screen for combinations of mutations in a mlvRT reverse transcriptase and their effect on editing efficiency. Mutations were made in a reference mlvRT construct containing five point mutations (D200N, 1603W, T330P, T306K, and W313F, SEQ ID NO: 40). Amino acid residues are counted relative to an mlvRT construct lacking an N-terminal methionine (e.g., SEQ ID NO: 14). mlvRT constructs containing T197A and D653N; T197A and T664N; T197A and L671P; T197A, D653N, T664N and L671P; or P51L, S67R, T197A, H204R, L435G, D524A, D653N, T664N and L671P (SEQ ID NO: 71-SEQ ID NO: 75, respectively) relative to SEQ ID NO: 40 were tested. Editing efficiency was measured as a percent of cells that were GFP positive (% GFP+). Editing was performed using a gRNA with an 85 nucleotide RT template, a 13 nucleotide primer binding site, a 19 nucleotide Velcro region, and a 20 nucleotide second strand primer to edit a site such that an ATGG sequence, starting 2 nucleotides 3' of the nick, was mutated to CATA. The construct containing P51L, S67R, T197A, H204R, L435G, D524A, D653N, T664N and L671P point mutations (SEQ ID NO: 75) showed the highest editing efficiency of the constructs tested.

FIG. 15C shows the editing efficiency of mlvRT reverse transcriptase constructs. Mutations were made in a reference mlvRT construct containing five point mutations (D200N, 1603W, T330P, T306K, and W313F, SEQ ID NO: 40). Amino acid residues are counted relative to an mlvRT construct lacking an N-terminal methionine (e.g., SEQ ID NO: 14). mlvRT constructs containing V223A; V223M; Q221R and V223A; or Q221R and V223M (SEQ ID NO: 77-SEQ ID NO: 80, respectively) relative to SEQ ID NO: 40 were tested. Editing efficiency was measured as a percent of cells that were GFP positive (% GFP+). Editing was performed using a gRNA with a 129 nucleotide RT template, a 13 nucleotide primer binding site, a 19 nucleotide Velcro region, and a 20 nucleotide second strand primer to edit a site such that an ATG sequence, starting 65 nucleotides 3' of the nick, was mutated to CAT. The V223A point mutation increased editing efficiency at a distance relative to the nicking site.

Example 11

Increasing Availability of dNTPs to Increase Editing Efficiency

This example describes methods for increasing availability of dNTPs in a cell to increase editing efficiency of a Cas9-RT construct. One factor that may contribute to low editing efficiency in cells is limited availability of dNTPs. FIG. 15A illustrates a method of increasing availability of dNTPs in a cell to increase editing efficiency. In non-dividing cells lacking CDK1, unphosphorylated SAMHD1 cleaves dNTPs, decreasing the available dNTPs in the cell. In dividing cells, CDK1 phosphorylates SAMHD1, preventing SAMHD1 from cleaving dNTPs and leading to increased availability of dNTPs in the cell. A single point mutation in SAMHD1 (T592A) prevents phosphorylation of SAMHD1 by CDK1, resulting in a constitutively active SAMHD1 and a low availability of dNTPs in the cell. The T592A mutant SAMHD1 was used to induce a low dNTP environment in the assay shown in FIG. 15B, FIG. 15D, and FIG. 15E. Addition of Vpx inhibits SAMHD1, leading to increased availability of dNTPs in the cell. To test the effect of low cellular dNTPs on editing efficiency, constitutively active SAMHD1 was co-expressed with Cas9-RT constructs, and editing efficiency was measured.

FIG. 15B shows the editing efficiency of mlvRT reverse transcriptase constructs in the presence or absence of a constitutively active SAMHD1 (SAMHD1 (T592A)) to decrease availability of dNTPs in the cell. Mutations were made in a reference mlvRT construct containing five point mutations (D200N, 1603W, T330P, T306K, and W313F, SEQ ID NO: 40). Amino acid residues are counted relative to an mlvRT construct lacking an N-terminal methionine (e.g., SEQ ID NO: 14). mlvRT constructs containing Q221R; V223A; V223M; Q221R and V223A; or Q221R and V223M (SEQ ID NO: 76-SEQ ID NO: 80, respectively) relative to SEQ ID NO: 40 were tested. Editing efficiency was measured as a percent of cells that were GFP positive (% GFP+). Editing was performed using a gRNA with an 85 nucleotide RT template, a 13 nucleotide primer binding site, a 19 nucleotide Velcro region, and a 20 nucleotide second strand primer to edit a site such that an ATGG sequence, starting 2 nucleotides 3' of the nick, was mutated to CATA. Expression of the constitutively active SAMHD1 decreased editing efficiency of all tested constructs.

To rescue editing efficiency in cells expressing constitutively active SAMHD1, a Vpx peptide (SEQ ID NO: 82) was also expressed in the cells. FIG. 15D shows the editing efficiency of a mlvRT reverse transcriptase in the presence or absence of a constitutively active SAMHD1 (SAMHD1 (T592A)) to decrease availability of dNTPs in the cell and with or without Vpx (SEQ ID NO: 82) to inhibit SAMHD1. Editing efficiency was measured as a percent of cells that were GFP positive (% GFP+). Editing was performed using a gRNA with an 85 nucleotide RT template, a 13 nucleotide primer binding site, a 19 nucleotide Velcro region, and a 20 nucleotide second strand primer to edit a site such that an ATGG sequence, starting 2 nucleotides 3' of the nick, was mutated to CATA.

FIG. 15E shows the editing efficiency of a mlvRT reverse transcriptase in the presence or absence of a constitutively active SAMHD1 (SAMHD1 (T592A)) to decrease availability of dNTPs in the cell and with or without Vpx (SEQ ID NO: 82) to inhibit SAMHD1. Editing efficiency was measured as a percent of cells that were GFP positive (% GFP+). Editing was performed using a gRNA with a 129 nucleotide RT template, a 13 nucleotide primer binding site, a 19 nucleotide Velcro region, and a 20 nucleotide second strand primer to edit a site such that an ATG sequence, starting 65 nucleotides 3' of the nick, was mutated to CAT. Expression of Vpx in the cell increased editing efficiency both in cells expressing constitutively active SAMHD1 and in cells not expressing constitutively active SAMHD1. Additionally, Vpx increased editing efficiency at sites a short distance from the nicking site (FIG. 15D) and at a long distance from the nicking site (FIG. 15E).

Example 12

Inteins for Cellular Expression of Split Cas9 Constructs

This example describes using inteins for cellular expression of Cas9 constructs. In a first assay, a screen of nicking Cas9 (nCas9) point mutations was performed to identify positions in the C-terminal portion of the nCas9 that were conducive to substitution of a cysteine residue. Cysteine point mutations were screened in the context of a nCas9-RT construct linked via a leucine zipper. Cysteines were inserted into the C-terminal portion of the nCas9 at different points to generate constructs with a cysteine residue positioned toward the middle of the nCas9 and reverse transcriptase combined sequence. Cysteine residues were positioned such that each of the portion of the Cas9 protein from the N-terminus up to the inserted cysteine and the portion of the Cas9 protein from and including the inserted cysteine to the C-terminus plus the reverse transcriptase were small enough to fit in an AAV vector when expressed as an intein fusion. Editing efficiency of the leucine zipper linked nCas9-RT cysteine mutants was compared.

Figure 16:
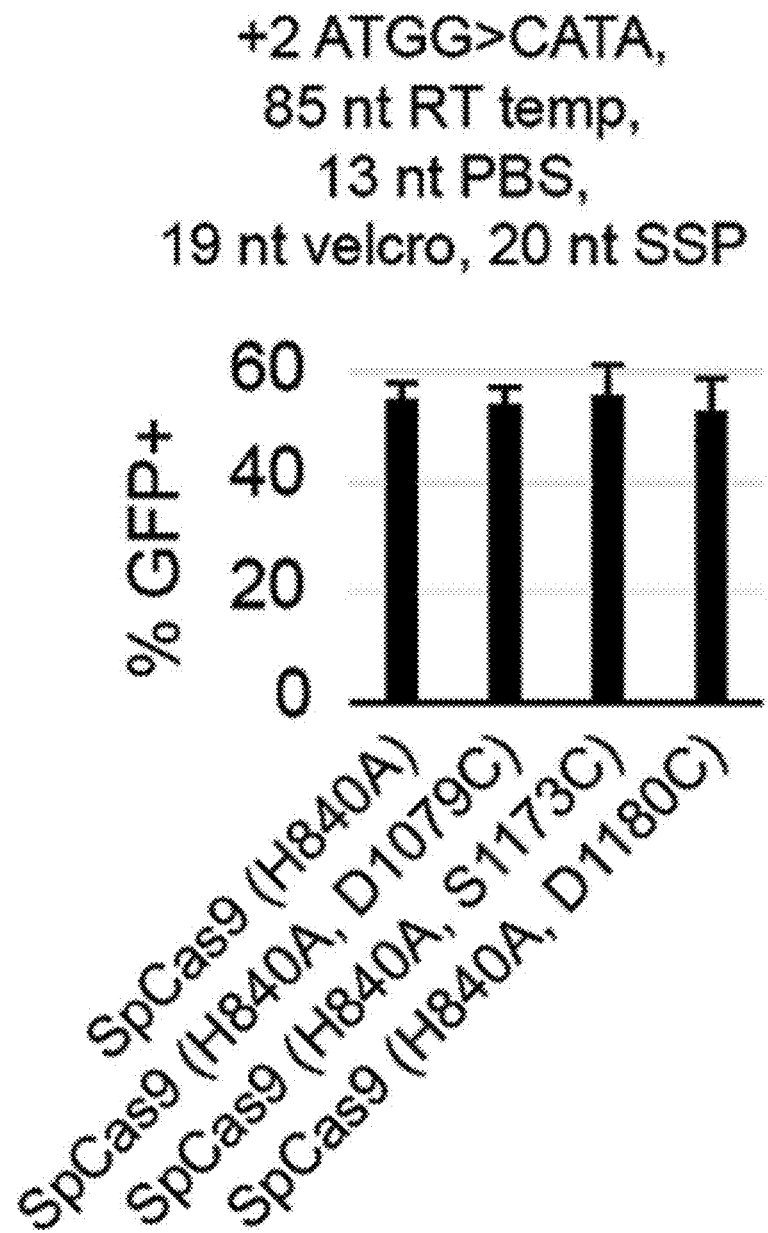
FIG. 16 shows editing efficiency of Cas9 constructs modified for nicking activity and linked to a reverse transcriptase through a leucine zipper. S. Pyogenes Cas9 ("SpCas9") constructs contained an H840A mutation to produce a Cas9 nickase (nCas9). Cysteine residues were introduced into the Cas9 nickase at either D1079C, S1173C, or D1180C to enable splitting of the Cas9 into a split intein Cas9 (iCas9) for expression as extein-intein fusions. Leucine zipper Cas9 constructs containing H840A and D1079C (SEQ ID NO: 85 with a leucine zipper), H840A and S1173C (SEQ ID NO: 86 with a leucine zipper), or H840A and D1180C (SEQ ID NO: 87 with a leucine zipper) point mutations and linked to mlvRT5M (SEQ ID NO: 40 with a leucine zipper) were tested. A Cas9 nickase that contained the H840A mutation but no additional cysteine (SEQ ID NO: 84 with a leucine zipper) linked to mlvRT5M (SEQ ID NO: 40 with a leucine zipper) was used as a control. Editing efficiency was measured as a percent of cells that were GFP positive (% GFP+). Editing was performed using a gRNA with an 85 nucleotide RT template, a 13 nucleotide primer binding site, a 19 nucleotide Velcro region, and a 20 nucleotide second strand primer to edit a site such that an ATGG sequence, starting 2 nucleotides 3' of the nick, was mutated to CATA.

FIG. 16 shows editing efficiency of Cas9 constructs modified for nicking activity and linked to a reverse transcriptase through a leucine zipper. *S. Pyogenes* Cas9 ("SpCas9") constructs contained an H840A mutation to produce a Cas9 nickase (nCas9). Cysteine residues were introduced into the Cas9 nickase at either D1079C, S1173C, or D1180C to enable splitting of the Cas9 into a split intein Cas9 (iCas9) for expression as extein-intein fusions. Leucine zipper Cas9 constructs containing H840A and D1079C (SEQ ID NO: 85 with a leucine zipper), H840A and S1173C (SEQ ID NO: 86 with a leucine zipper), or H840A and D1180C (SEQ ID NO: 87 with a leucine zipper) point mutations and linked to mlvRT5M (SEQ ID NO: 40 with a leucine zipper) were tested. A Cas9 nickase that contained the H840A mutation but no additional cysteine (SEQ ID NO: 84 with a leucine zipper) linked to mlvRT5M (SEQ ID NO: 40 with a leucine zipper) was used as a control. Editing efficiency was measured as a percent of cells that were GFP positive (% GFP+). Editing was performed using a gRNA with an 85 nucleotide RT template, a 13 nucleotide primer binding site, a 19 nucleotide Velcro region, and a 20 nucleotide second strand primer to edit a site such that an ATGG sequence, starting 2 nucleotides 3' of the nick, was mutated to CATA.

In a second assay, the cysteine point mutations identified in the first assay were utilized to generate split intein Cas9 constructs. The editing efficiency of an nCas9-RT fusion comprising the identified S1173C mutation expressed as two extein-intein fusions was tested. The nCas9-RT fusion contained an nCas9 with the S1173C point mutation (SEQ ID NO: 86) fused to mlvRT5M (SEQ ID NO: 40). The first segment of the fusion protein was expressed as a first intein fusion nCas9(1-1172) —Npu N intein (SEQ ID NO: 90) in a first plasmid vector and the second segment of the fusion protein was expressed as a second intein fusion Npu C intein—nCas9(1173-1368 with S1173C) —mlvRT5M (SEQ ID NO: 91) expressed in a second plasmid vector. Autocatalytic activity of the intein domains fused the nCas9(1-1172) extein to the nCas9(1173-1368 with S1173C) —mlvRT5M extein and excised the Npu N (SEQ ID NO: 88) and Npu C (SEQ ID NO: 89) inteins to form the fused nCas9(S1173C) —mlvRT5M construct (SEQ ID NO: 92). Editing efficiency of the split intein nCas9 construct was tested at two positions relative to the nicking site.

Figure 17A:
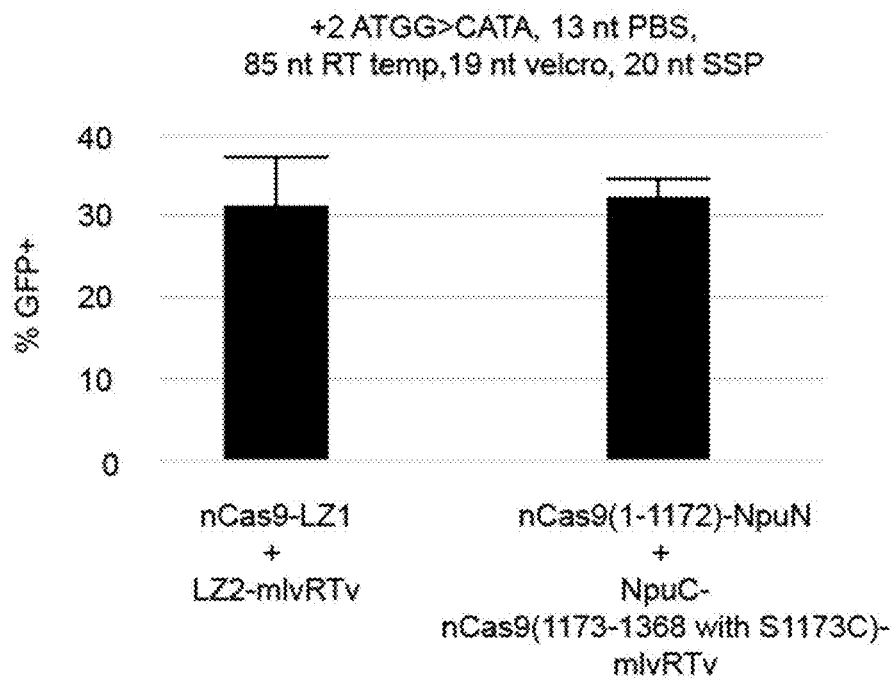
FIG. 17A shows the editing efficiency of a split intein Cas9 (iCas9) S1173C construct modified for nicking activity, fused to a reverse transcriptase, and expressed as two extein-intein fusion proteins. The N-terminal region of the nCas9-RT construct was expressed as nCas9(1-1172)—Npu N intein (SEQ ID NO: 90) and the C-terminal region of the nCas9-RT construct was expressed as Npu C intein—nCas9 (1173-1368 with S1173C)—mlvRT5M (SEQ ID NO: 91). Editing efficiency of the split intein Cas9-RT construct (right bar) was compared to a leucine zipper split Cas9 construct (SEQ ID NO: 1 and SEQ ID NO: 2, left bar). Editing efficiency was measured as a percent of cells that were GFP positive (% GFP+). Editing was performed using a gRNA with an 85 nucleotide RT template, a 13 nucleotide primer binding site, a 19 nucleotide Velcro region, and a 20 nucleotide second strand primer to edit a site such that an ATGG sequence, starting 2 nucleotides 3' of the nick, was mutated to CATA.

FIG. 17A shows the editing efficiency of a split intein Cas9 (iCas9) S1173C construct modified for nicking activity, fused to a reverse transcriptase, and expressed as two extein-intein fusion proteins. The N-terminal region of the nCas9-RT construct was expressed as nCas9(1-1172) —Npu N intein (SEQ ID NO: 90) and the C-terminal region of the nCas9-RT construct was expressed as Npu C intein—nCas9 (1173-1368 with S1173C) —mlvRT5M (SEQ ID NO: 91). Editing efficiency of the split intein Cas9-RT construct (right bar) was compared to a leucine zipper split Cas9 construct (SEQ ID NO: 1 and SEQ ID NO: 2, left bar). Editing efficiency was measured as a percent of cells that were GFP positive (% GFP+). Editing was performed using a gRNA with an 85 nucleotide RT template, a 13 nucleotide primer binding site, a 19 nucleotide Velcro region, and a 20 nucleotide second strand primer to edit a site such that an ATGG sequence, starting 2 nucleotides 3' of the nick, was mutated to CATA.

Figure 17B:
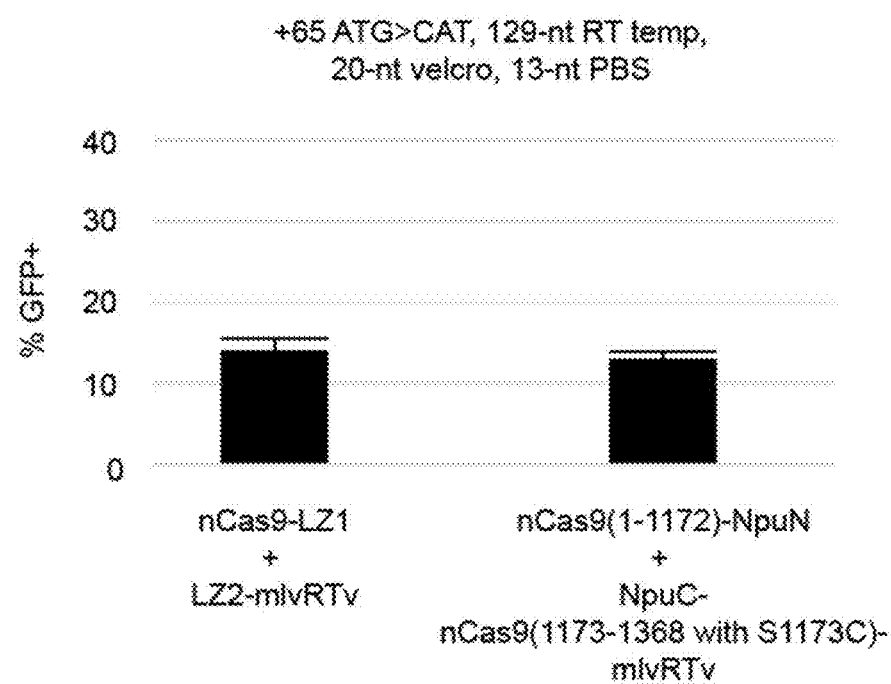
FIG. 17B shows the editing efficiency of a split intein Cas9 (iCas9) S1173C construct modified for nicking activity, fused to a reverse transcriptase, and expressed as two extein-intein fusion proteins. The N-terminal region of the nCas9-RT construct was expressed as nCas9(1-1172)—Npu N intein (SEQ ID NO: 90) and the C-terminal region of the nCas9-RT construct was expressed as Npu C intein—nCas9 (1173-1368 with S1173C)—mlvRT5M (SEQ ID NO: 91). Editing efficiency of the split intein Cas9-RT construct (right bar) was compared to a leucine zipper split Cas9 construct (SEQ ID NO: 1 and SEQ ID NO: 2, left bar). Editing efficiency was measured as a percent of cells that were GFP positive (% GFP+). Editing was performed using a gRNA with an 85 nucleotide RT template, a 13 nucleotide primer binding site, a 19 nucleotide Velcro region, and a 20 nucleotide second strand primer to edit a site such that an ATG sequence, starting 65 nucleotides 3' of the nick, was mutated to CAT.

FIG. 17B shows the editing efficiency of a split intein Cas9 (iCas9) S1173C construct modified for nicking activity, fused to a reverse transcriptase, and expressed as two extein-intein fusion proteins. The N-terminal region of the nCas9-RT construct was expressed as nCas9(1-1172) —Npu N intein (SEQ ID NO: 90) and the C-terminal region of the nCas9-RT construct was expressed as Npu C intein—nCas9 (1173-1368 with S1173C) —mlvRT5M (SEQ ID NO: 91). Editing efficiency of the split intein Cas9-RT construct (right bar) was compared to a leucine zipper split Cas9 construct (SEQ ID NO: 1 and SEQ ID NO: 2, left bar). Editing efficiency was measured as a percent of cells that were GFP positive (% GFP+). Editing was performed using a gRNA with an 85 nucleotide RT template, a 13 nucleotide primer binding site, a 19 nucleotide Velcro region, and a 20 nucleotide second strand primer to edit a site such that an ATG sequence, starting 65 nucleotides 3' of the nick, was mutated to CAT.

The results indicated that the split intein Cas9-RT fusion construct showed robust editing efficiency compared to the leucine zipper split Cas9 constructs.

Example 13

3' Modifications of gRNAs for Improved Editing Efficiency

This example describes 3' modifications of gRNAs for improved editing efficiency. gRNAs with second strand primers 100% complementary to a template region and positioned at the 3' end may be transcribed with a poly-U sequence immediately 3' of the second strand primer, inhibiting priming function. To solve this problem, gRNAs with cleavable RNA sequences positioned 3' of the second strand primer were developed to prevent formation of a poly-U sequence at the 3' end of the second strand primer. gRNAs with either an HDV self-cleaving ribozyme or a tRNA positioned 3' of the second strand primer were tested.

The HDV self-cleaving ribozyme autocatalytically cleaved itself from the 3' end of the gRNA, leaving the second strand primer without a poly-U sequence. The HDV ribozyme left a 2'3' cyclic phosphate at the 3' end of the second strand primer which inhibited primer extension of the second strand primer. Endogenous polynucleotide kinase converted the 2'3' cyclic phosphate to a 3' OH, to enable primer extension. The tRNA was cleaved from the 3' end of the second strand primer by endogenous RNase P, leaving the second strand primer without a poly-U sequence and a 3' OH capable of primer extension.

Figure 18:
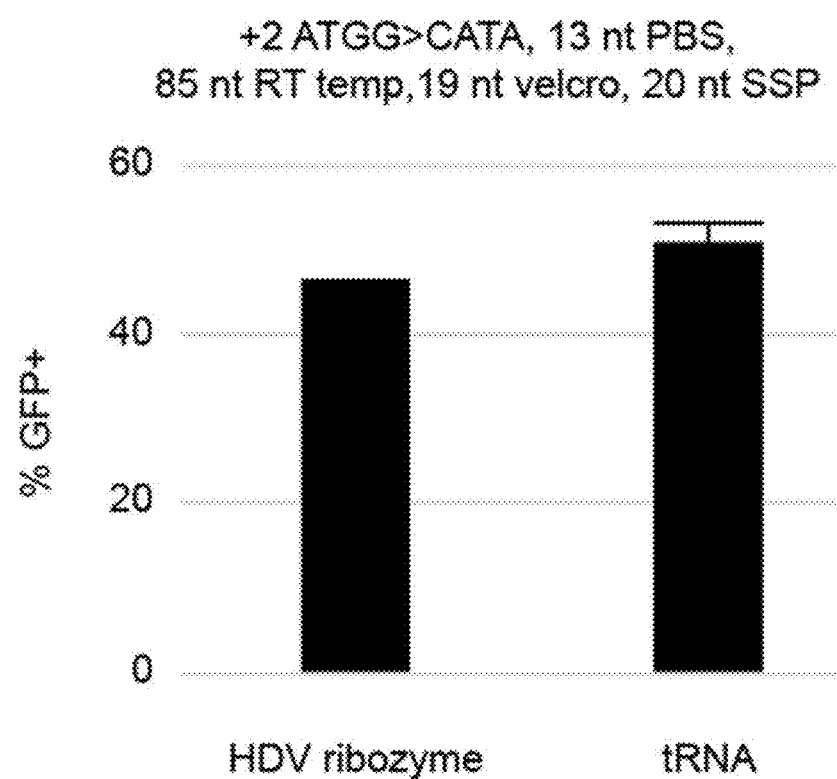
FIG. 18 shows the editing efficiency of a leucine zipper Cas9-RT construct in the presence of a gRNA comprising either an HDV ribozyme (left bar) or a tRNA (right bar) at the 3' end of the gRNA, immediately 3' of the second strand primer. The leucine zipper Cas9-RT construct was expressed as nCas9-LZ1 (SEQ ID NO: 1) and LZ2-mlvRT5M (SEQ ID NO: 2) and linked through a leucine zipper. The tRNA had a sequence corresponding to SEQ ID NO: 94 (GGTCCCATGGTGTAATGGTTAGCACTCTGGACTTT-GAATCCAGCGATCCGAGTTCAA ATCTCGGTGGGACCT). Editing was performed using gRNAs with an 85 nucleotide RT template, a 13 nucleotide primer binding site, a 19 nucleotide Velcro region, a 20 nucleotide second strand primer, and either an HDV ribozyme or a tRNA 3' of the second strand primer to edit a site such that an ATGG sequence, starting 2 nucleotides 3' of the nick, was mutated to CATA.

FIG. 18 shows the editing efficiency of a leucine zipper Cas9-RT construct in the presence of a gRNA comprising either an HDV ribozyme (left bar) or a tRNA (right bar) at the 3' end of the gRNA, immediately 3' of the second strand primer. The leucine zipper Cas9-RT construct was expressed as nCas9-LZ1 (SEQ ID NO: 1) and LZ2-mlvRT5M (SEQ ID NO: 2) and linked through a leucine zipper. The tRNA had a sequence corresponding to SEQ ID NO: 94. Editing was performed using gRNAs with an 85 nucleotide RT template, a 13 nucleotide primer binding site, a 19 nucleotide Velcro region, a 20 nucleotide second strand primer, and either an HDV ribozyme or a tRNA 3' of the second strand primer to edit a site such that an ATGG sequence, starting 2 nucleotides 3' of the nick, was mutated to CATA.

Example 14

GPS-Assisted Reachover gRNAs (GARGs) and GPS-Recruiting Guides (GRGs)

Figure 33:
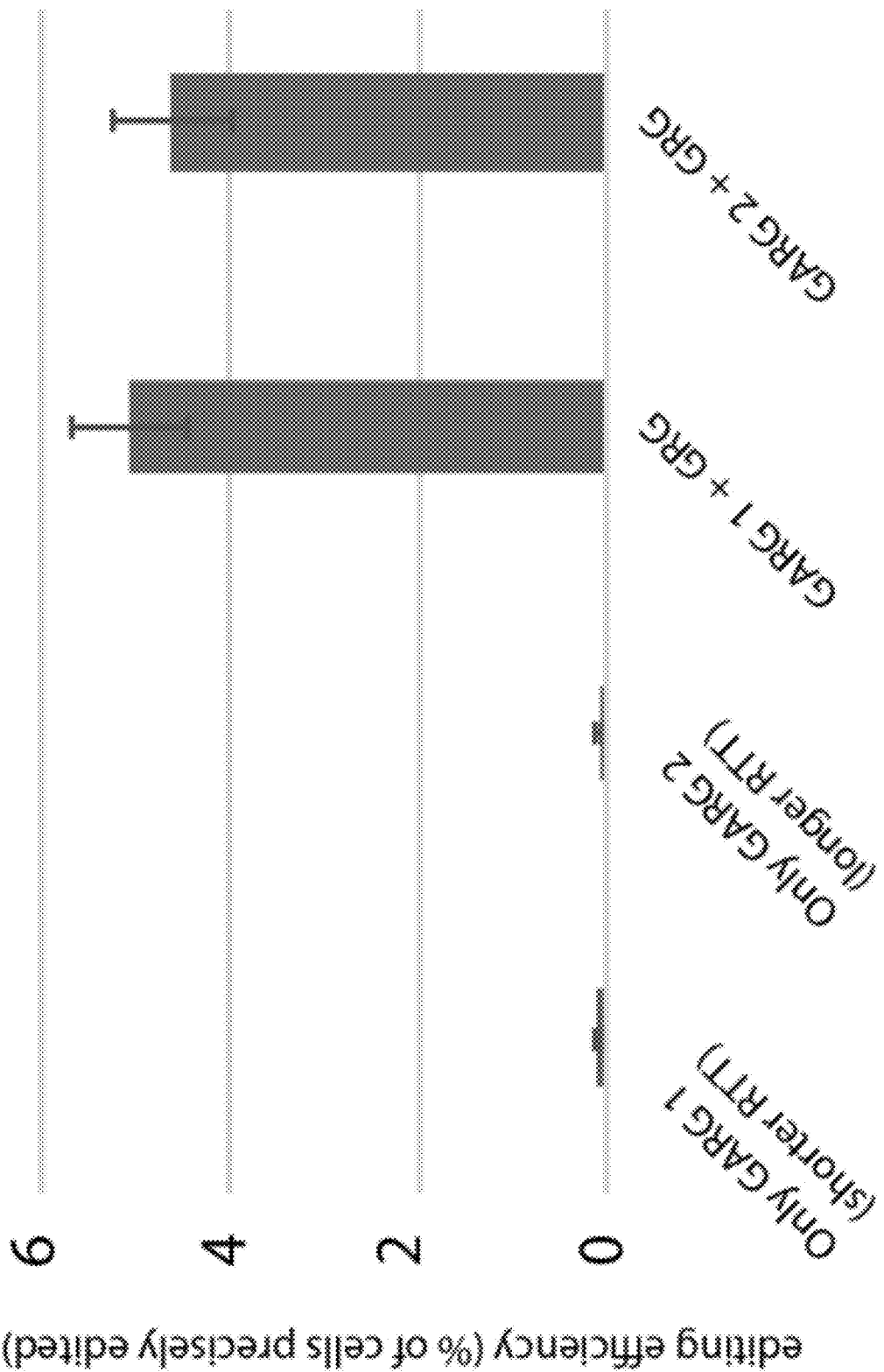
FIG. 33 shows editing efficiencies with a dual guide system.

GPS-assisted reachover gRNAs (GARGs) may improve a gene editing efficiency, for example in a case where a single guide nucleic acid system would otherwise generate a flap containing a desired edit that does not sufficiently displace a genomic strand that doesn't include the edit. A GARGs may be useful for promoting hybridization of the extended flap into the genome, and may anchor the 3' end of the extended flap in the vicinity of the genomic strand it is intended to replace. FIG. 33 depicts data from a dual guide system. Two separate GARGs were tested and successfully led to gene editing in target nucleic acids of mammalian cells. Thus, a method employing a dual guide system comprising a GARG and a GRG may lead to precise genome editing in cells such as mammalian cells.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A guide nucleic acid comprising:

optionally, a spacer reverse complementary to a first region of a target nucleic acid, wherein the spacer is included in the guide nucleic acid, or the spacer is included in a second, different guide nucleic acid when not included in the guide nucleic acid;

a scaffold configured to bind to a Cas nuclease;

a reverse transcriptase template encoding a sequence to be reverse transcribed into a first synthesized strand to be inserted into the target nucleic acid;

a first strand primer binding site reverse complementary to a second region of the target nucleic acid; and at least one of:

(i) a guide nucleic acid positioning system (GPS) region and a GPS binding site that hybridizes to the GPS region, wherein the GPS region and the GPS binding site are at least 10 nucleotides in length and are at least 60% reverse complementary to each other, and wherein hybridization of the GPS region and the GPS binding site positions the first strand primer binding site closer to the second region of the target nucleic acid, (ii) a GPS region that hybridizes to a GPS binding site on the second guide nucleic acid, wherein the GPS region and the GPS binding site are at least 10 nucleotides in length and are at least 60% reverse complementary to each other, wherein the second region of the target nucleic acid does not include any part of the first region of the target nucleic acid, and wherein the second region of the target nucleic acid does not include any part of a reverse complement of the first region of the target nucleic acid, and wherein hybridization of the GPS region and the GPS binding site positions the first strand primer binding site closer to the second region of the target nucleic acid, or (iii) a modification in the reverse transcriptase template that disrupts a track of at least 4 consecutive nucleotides of the same base in the target nucleic acid.

2. The guide nucleic acid of claim 1, further comprising a second strand primer.

3. The guide nucleic acid of claim 2, wherein the second strand primer is configured to serve as a primer for transcription from a template reverse complementary to the reverse transcriptase template.

4. The guide nucleic acid of claim 2, wherein the first synthesized strand serves as a template for synthesis of a second strand from the second strand primer.

5. The guide nucleic acid of claim 2, wherein the first region of the target nucleic acid is on a first strand of the target nucleic acid and the second region of the target nucleic acid is on a second strand of the target nucleic acid.

6. The guide nucleic acid of claim 2, wherein the second strand primer is 10-60 nucleotides in length.

7. The guide nucleic acid of claim 1, further comprising a ribozyme cleavable sequence at a 3' end of the guide nucleic acid.

8. The guide nucleic acid of claim 1, further comprising a tRNA cleavable sequence at a 3' end of the guide nucleic acid.

9. The guide nucleic acid of claim 1, wherein the first strand primer binding site is configured to hybridize to the second region of the target nucleic acid, and wherein the reverse transcriptase template is configured to serve as a template for reverse transcription from a 3' end of the second region of the target nucleic acid.

10. The guide nucleic acid of claim 1, comprising the GPS region and the GPS binding site of (i), or comprising the GPS region of (ii).

11. The guide nucleic acid of claim 10, comprising the GPS region and the GPS binding site of (i), wherein the GPS region and the GPS binding site are separated by at least part of the spacer, scaffold, reverse transcriptase template, or first strand primer binding site.

12. The guide nucleic acid of claim 10, wherein the guide nucleic acid improves editing efficiency as compared to a guide nucleic acid without a GPS region.

13. The guide nucleic acid of claim 10, wherein the reverse transcriptase template region comprises the GPS binding site of (i), or wherein the second guide nucleic acid comprises a reverse transcriptase template region comprising the GPS binding site of (ii).

14. The guide nucleic acid of claim 10, wherein the GPS binding site of (i) is 3' of the first strand primer binding site, or wherein the GPS binding site of (ii) is 3' of a primer binding site of the second guide nucleic acid.

15. The guide nucleic acid of claim 10, wherein the GPS region of (i) or (ii) is 5' of the reverse transcriptase template.

16. The guide nucleic acid of claim 10, wherein the GPS region of (i) or (ii) is 3' of the scaffold.

17. The guide nucleic acid of claim 10, wherein the GPS region of (i) or (ii) is no more than 100 nucleotides in length.

18. The guide nucleic acid of claim 10, wherein the GPS region and the GPS binding site are separated by at least part of the reverse transcriptase template.

19. The guide nucleic acid of claim 1, wherein the target nucleic acid comprises a CFTR nucleic acid, a USH2A nucleic acid, an ABCA4 nucleic acid, an ATP7B nucleic acid, or an HTT nucleic acid.

20. The guide nucleic acid of claim 1, wherein the spacer comprises a nucleic acid sequence at least 85% identical to any one of SEQ ID NOs: 96-119.

21. The guide nucleic acid of claim 1, further comprising a modification in the reverse transcriptase template that disrupts a protospacer adjacent motif (PAM) sequence in the target nucleic acid.

22. The guide nucleic acid of claim 10, wherein the GPS region and GPS binding site of (i) or (ii) do not consist of the first strand primer binding site and the spacer.

23. The guide nucleic acid of claim 1, comprising the modification in the reverse transcriptase template that disrupts the track of at least 4 consecutive nucleotides of the same base in the target nucleic acid.

24. The guide nucleic acid of claim 23, wherein the track of at least 4 consecutive nucleotides of the same base comprise a polyA track.

25. The guide nucleic acid of claim 1, comprising the GPS region of (ii) that hybridizes to the GPS binding site on the second guide nucleic acid.

26. The guide nucleic acid of claim 25, wherein the second guide nucleic acid brings the first strand primer binding site into proximity with a genomic flap.

27. The guide nucleic acid of claim 1, wherein the Cas nuclease comprises a Cas nickase.

28. The guide nucleic acid of claim 1, wherein the guide nucleic acid comprises a guide RNA.

\* \* \* \* \*

SEQUENCE LISTING

```
<160> NUMBER OF SEQ ID NOS: 144

<210> SEQ ID NO 1
<211> LENGTH: 1460
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Lys Arg Thr Ala Asp Gly Ser Glu Phe Glu Ser Pro Lys Lys Lys
1               5                   10                  15

Arg Lys Val Asp Lys Lys Tyr Ser Ile Gly Leu Asp Ile Gly Thr Asn
            20                  25                  30

Ser Val Gly Trp Ala Val Ile Thr Asp Glu Tyr Lys Val Pro Ser Lys
        35                  40                  45

Lys Phe Lys Val Leu Gly Asn Thr Asp Arg His Ser Ile Lys Lys Asn
    50                  55                  60

Leu Ile Gly Ala Leu Leu Phe Asp Ser Gly Glu Thr Ala Glu Ala Thr
65                  70                  75                  80

Arg Leu Lys Arg Thr Ala Arg Arg Arg Tyr Thr Arg Arg Lys Asn Arg
                85                  90                  95

Ile Cys Tyr Leu Gln Glu Ile Phe Ser Asn Glu Met Ala Lys Val Asp
            100                 105                 110

Asp Ser Phe Phe His Arg Leu Glu Glu Ser Phe Leu Val Glu Glu Asp
        115                 120                 125

Lys Lys His Glu Arg His Pro Ile Phe Gly Asn Ile Val Asp Glu Val
    130                 135                 140

Ala Tyr His Glu Lys Tyr Pro Thr Ile Tyr His Leu Arg Lys Lys Leu
145                 150                 155                 160

Val Asp Ser Thr Asp Lys Ala Asp Leu Arg Leu Ile Tyr Leu Ala Leu
                165                 170                 175

Ala His Met Ile Lys Phe Arg Gly His Phe Leu Ile Glu Gly Asp Leu
            180                 185                 190
```

```
Asn Pro Asp Asn Ser Asp Val Asp Lys Leu Phe Ile Gln Leu Val Gln
            195                 200                 205

Thr Tyr Asn Gln Leu Phe Glu Glu Asn Pro Ile Asn Ala Ser Gly Val
    210                 215                 220

Asp Ala Lys Ala Ile Leu Ser Ala Arg Leu Ser Lys Ser Arg Arg Leu
225                 230                 235                 240

Glu Asn Leu Ile Ala Gln Leu Pro Gly Glu Lys Lys Asn Gly Leu Phe
                245                 250                 255

Gly Asn Leu Ile Ala Leu Ser Leu Gly Leu Thr Pro Asn Phe Lys Ser
            260                 265                 270

Asn Phe Asp Leu Ala Glu Asp Ala Lys Leu Gln Leu Ser Lys Asp Thr
    275                 280                 285

Tyr Asp Asp Asp Leu Asp Asn Leu Leu Ala Gln Ile Gly Asp Gln Tyr
    290                 295                 300

Ala Asp Leu Phe Leu Ala Ala Lys Asn Leu Ser Asp Ala Ile Leu Leu
305                 310                 315                 320

Ser Asp Ile Leu Arg Val Asn Thr Glu Ile Thr Lys Ala Pro Leu Ser
                325                 330                 335

Ala Ser Met Ile Lys Arg Tyr Asp Glu His His Gln Asp Leu Thr Leu
            340                 345                 350

Leu Lys Ala Leu Val Arg Gln Gln Leu Pro Glu Lys Tyr Lys Glu Ile
    355                 360                 365

Phe Phe Asp Gln Ser Lys Asn Gly Tyr Ala Gly Tyr Ile Asp Gly Gly
    370                 375                 380

Ala Ser Gln Glu Glu Phe Tyr Lys Phe Ile Lys Pro Ile Leu Glu Lys
385                 390                 395                 400

Met Asp Gly Thr Glu Glu Leu Leu Val Lys Leu Asn Arg Glu Asp Leu
                405                 410                 415

Leu Arg Lys Gln Arg Thr Phe Asp Asn Gly Ser Ile Pro His Gln Ile
            420                 425                 430

His Leu Gly Glu Leu His Ala Ile Leu Arg Arg Gln Glu Asp Phe Tyr
    435                 440                 445

Pro Phe Leu Lys Asp Asn Arg Glu Lys Ile Glu Lys Ile Leu Thr Phe
    450                 455                 460

Arg Ile Pro Tyr Tyr Val Gly Pro Leu Ala Arg Gly Asn Ser Arg Phe
465                 470                 475                 480

Ala Trp Met Thr Arg Lys Ser Glu Glu Thr Ile Thr Pro Trp Asn Phe
                485                 490                 495

Glu Glu Val Val Asp Lys Gly Ala Ser Ala Gln Ser Phe Ile Glu Arg
            500                 505                 510

Met Thr Asn Phe Asp Lys Asn Leu Pro Asn Glu Lys Val Leu Pro Lys
    515                 520                 525

His Ser Leu Leu Tyr Glu Tyr Phe Thr Val Tyr Asn Glu Leu Thr Lys
    530                 535                 540

Val Lys Tyr Val Thr Glu Gly Met Arg Lys Pro Ala Phe Leu Ser Gly
545                 550                 555                 560

Glu Gln Lys Lys Ala Ile Val Asp Leu Leu Phe Lys Thr Asn Arg Lys
                565                 570                 575

Val Thr Val Lys Gln Leu Lys Glu Asp Tyr Phe Lys Lys Ile Glu Cys
            580                 585                 590

Phe Asp Ser Val Glu Ile Ser Gly Val Glu Asp Arg Phe Asn Ala Ser
    595                 600                 605

Leu Gly Thr Tyr His Asp Leu Leu Lys Ile Ile Lys Asp Lys Asp Phe
```

```
              610                 615                 620
Leu Asp Asn Glu Glu Asn Glu Asp Ile Leu Glu Asp Ile Val Leu Thr
625                 630                 635                 640

Leu Thr Leu Phe Glu Asp Arg Glu Met Ile Glu Glu Arg Leu Lys Thr
                645                 650                 655

Tyr Ala His Leu Phe Asp Asp Lys Val Met Lys Gln Leu Lys Arg Arg
                660                 665                 670

Arg Tyr Thr Gly Trp Gly Arg Leu Ser Arg Lys Leu Ile Asn Gly Ile
            675                 680                 685

Arg Asp Lys Gln Ser Gly Lys Thr Ile Leu Asp Phe Leu Lys Ser Asp
690                 695                 700

Gly Phe Ala Asn Arg Asn Phe Met Gln Leu Ile His Asp Asp Ser Leu
705                 710                 715                 720

Thr Phe Lys Glu Asp Ile Gln Lys Ala Gln Val Ser Gly Gln Gly Asp
                725                 730                 735

Ser Leu His Glu His Ile Ala Asn Leu Ala Gly Ser Pro Ala Ile Lys
                740                 745                 750

Lys Gly Ile Leu Gln Thr Val Lys Val Val Asp Glu Leu Val Lys Val
            755                 760                 765

Met Gly Arg His Lys Pro Glu Asn Ile Val Ile Glu Met Ala Arg Glu
770                 775                 780

Asn Gln Thr Thr Gln Lys Gly Gln Lys Asn Ser Arg Glu Arg Met Lys
785                 790                 795                 800

Arg Ile Glu Glu Gly Ile Lys Glu Leu Gly Ser Gln Ile Leu Lys Glu
                805                 810                 815

His Pro Val Glu Asn Thr Gln Leu Gln Asn Glu Lys Leu Tyr Leu Tyr
                820                 825                 830

Tyr Leu Gln Asn Gly Arg Asp Met Tyr Val Asp Gln Glu Leu Asp Ile
            835                 840                 845

Asn Arg Leu Ser Asp Tyr Asp Val Asp Ala Ile Val Pro Gln Ser Phe
850                 855                 860

Leu Lys Asp Asp Ser Ile Asp Asn Lys Val Leu Thr Arg Ser Asp Lys
865                 870                 875                 880

Asn Arg Gly Lys Ser Asp Asn Val Pro Ser Glu Glu Val Val Lys Lys
                885                 890                 895

Met Lys Asn Tyr Trp Arg Gln Leu Leu Asn Ala Lys Leu Ile Thr Gln
                900                 905                 910

Arg Lys Phe Asp Asn Leu Thr Lys Ala Glu Arg Gly Gly Leu Ser Glu
            915                 920                 925

Leu Asp Lys Ala Gly Phe Ile Lys Arg Gln Leu Val Glu Thr Arg Gln
930                 935                 940

Ile Thr Lys His Val Ala Gln Ile Leu Asp Ser Arg Met Asn Thr Lys
945                 950                 955                 960

Tyr Asp Glu Asn Asp Lys Leu Ile Arg Glu Val Lys Val Ile Thr Leu
                965                 970                 975

Lys Ser Lys Leu Val Ser Asp Phe Arg Lys Asp Phe Gln Phe Tyr Lys
            980                 985                 990

Val Arg Glu Ile Asn Asn Tyr His His Ala His Asp Ala Tyr Leu Asn
            995                 1000                1005

Ala Val Val Gly Thr Ala Leu Ile Lys Lys Tyr Pro Lys Leu Glu
    1010                1015                1020

Ser Glu Phe Val Tyr Gly Asp Tyr Lys Val Tyr Asp Val Arg Lys
    1025                1030                1035
```

-continued

```
Met Ile Ala Lys Ser Glu Gln Glu Ile Gly Lys Ala Thr Ala Lys
    1040            1045                1050
Tyr Phe Phe Tyr Ser Asn Ile Met Asn Phe Phe Lys Thr Glu Ile
    1055            1060                1065
Thr Leu Ala Asn Gly Glu Ile Arg Lys Arg Pro Leu Ile Glu Thr
    1070            1075                1080
Asn Gly Glu Thr Gly Glu Ile Val Trp Asp Lys Gly Arg Asp Phe
    1085            1090                1095
Ala Thr Val Arg Lys Val Leu Ser Met Pro Gln Val Asn Ile Val
    1100            1105                1110
Lys Lys Thr Glu Val Gln Thr Gly Gly Phe Ser Lys Glu Ser Ile
    1115            1120                1125
Leu Pro Lys Arg Asn Ser Asp Lys Leu Ile Ala Arg Lys Lys Asp
    1130            1135                1140
Trp Asp Pro Lys Lys Tyr Gly Gly Phe Asp Ser Pro Thr Val Ala
    1145            1150                1155
Tyr Ser Val Leu Val Val Ala Lys Val Glu Lys Gly Lys Ser Lys
    1160            1165                1170
Lys Leu Lys Ser Val Lys Glu Leu Leu Gly Ile Thr Ile Met Glu
    1175            1180                1185
Arg Ser Ser Phe Glu Lys Asn Pro Ile Asp Phe Leu Glu Ala Lys
    1190            1195                1200
Gly Tyr Lys Glu Val Lys Lys Asp Leu Ile Ile Lys Leu Pro Lys
    1205            1210                1215
Tyr Ser Leu Phe Glu Leu Glu Asn Gly Arg Lys Arg Met Leu Ala
    1220            1225                1230
Ser Ala Gly Glu Leu Gln Lys Gly Asn Glu Leu Ala Leu Pro Ser
    1235            1240                1245
Lys Tyr Val Asn Phe Leu Tyr Leu Ala Ser His Tyr Glu Lys Leu
    1250            1255                1260
Lys Gly Ser Pro Glu Asp Asn Glu Gln Lys Gln Leu Phe Val Glu
    1265            1270                1275
Gln His Lys His Tyr Leu Asp Glu Ile Ile Glu Gln Ile Ser Glu
    1280            1285                1290
Phe Ser Lys Arg Val Ile Leu Ala Asp Ala Asn Leu Asp Lys Val
    1295            1300                1305
Leu Ser Ala Tyr Asn Lys His Arg Asp Lys Pro Ile Arg Glu Gln
    1310            1315                1320
Ala Glu Asn Ile Ile His Leu Phe Thr Leu Thr Asn Leu Gly Ala
    1325            1330                1335
Pro Ala Ala Phe Lys Tyr Phe Asp Thr Thr Ile Asp Arg Lys Arg
    1340            1345                1350
Tyr Thr Ser Thr Lys Glu Val Leu Asp Ala Thr Leu Ile His Gln
    1355            1360                1365
Ser Ile Thr Gly Leu Tyr Glu Thr Arg Ile Asp Leu Ser Gln Leu
    1370            1375                1380
Gly Gly Asp Gly Ser Lys Arg Thr Ala Asp Gly Ser Glu Phe Glu
    1385            1390                1395
Pro Lys Lys Lys Arg Lys Val Gly Gly Gly Gly Ser Gly Gly Arg
    1400            1405                1410
Leu Glu Ile Arg Ala Ala Phe Leu Arg Gln Arg Asn Thr Ala Leu
    1415            1420                1425
```

```
Arg Thr Glu Val Ala Glu Leu Glu Gln Glu Val Gln Arg Leu Glu
    1430                1435                1440

Asn Glu Val Ser Gln Tyr Glu Thr Arg Tyr Gly Pro Leu Gly Gly
    1445                1450                1455

Gly Lys
    1460

<210> SEQ ID NO 2
<211> LENGTH: 779
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Leu Glu Ile Glu Ala Ala Phe Leu Glu Arg Glu Asn Thr Ala Leu
1               5                   10                  15

Glu Thr Arg Val Ala Glu Leu Arg Gln Arg Val Gln Arg Leu Arg Asn
            20                  25                  30

Arg Val Ser Gln Tyr Arg Thr Arg Tyr Gly Pro Leu Gly Gly Gly Lys
        35                  40                  45

Ser Gly Gly Ser Ser Gly Gly Ser Gly Ser Glu Thr Pro Gly Thr
    50                  55                  60

Ser Glu Ser Ala Thr Pro Glu Ser Ser Gly Gly Ser Ser Gly Gly Ser
65                  70                  75                  80

Ser Thr Leu Asn Ile Glu Asp Glu Tyr Arg Leu His Glu Thr Ser Lys
                85                  90                  95

Glu Pro Asp Val Ser Leu Gly Ser Thr Trp Leu Ser Asp Phe Pro Gln
            100                 105                 110

Ala Trp Ala Glu Thr Gly Gly Met Gly Leu Ala Val Arg Gln Ala Pro
        115                 120                 125

Leu Ile Ile Pro Leu Lys Ala Thr Ser Thr Pro Val Ser Ile Lys Gln
    130                 135                 140

Tyr Pro Met Ser Gln Glu Ala Arg Leu Gly Ile Lys Pro His Ile Gln
145                 150                 155                 160

Arg Leu Leu Asp Gln Gly Ile Leu Val Pro Cys Gln Ser Pro Trp Asn
                165                 170                 175

Thr Pro Leu Leu Pro Val Lys Lys Pro Gly Thr Asn Asp Tyr Arg Pro
            180                 185                 190

Val Gln Asp Leu Arg Glu Val Asn Lys Arg Val Glu Asp Ile His Pro
        195                 200                 205

Thr Val Pro Asn Pro Tyr Asn Leu Leu Ser Gly Leu Pro Pro Ser His
    210                 215                 220

Gln Trp Tyr Thr Val Leu Asp Leu Lys Asp Ala Phe Phe Cys Leu Arg
225                 230                 235                 240

Leu His Pro Thr Ser Gln Pro Leu Phe Ala Phe Glu Trp Arg Asp Pro
                245                 250                 255

Glu Met Gly Ile Ser Gly Gln Leu Thr Trp Thr Arg Leu Pro Gln Gly
            260                 265                 270

Phe Lys Asn Ser Pro Thr Leu Phe Asn Glu Ala Leu His Arg Asp Leu
        275                 280                 285

Ala Asp Phe Arg Ile Gln His Pro Asp Leu Ile Leu Leu Gln Tyr Val
    290                 295                 300

Asp Asp Leu Leu Leu Ala Ala Thr Ser Glu Leu Asp Cys Gln Gln Gly
305                 310                 315                 320
```

```
Thr Arg Ala Leu Leu Gln Thr Leu Gly Asn Leu Gly Tyr Arg Ala Ser
            325                 330                 335

Ala Lys Lys Ala Gln Ile Cys Gln Lys Gln Val Lys Tyr Leu Gly Tyr
            340                 345                 350

Leu Leu Lys Glu Gly Gln Arg Trp Leu Thr Glu Ala Arg Lys Glu Thr
            355                 360                 365

Val Met Gly Gln Pro Thr Pro Lys Thr Pro Arg Gln Leu Arg Glu Phe
        370                 375                 380

Leu Gly Lys Ala Gly Phe Cys Arg Leu Phe Ile Pro Gly Phe Ala Glu
385                 390                 395                 400

Met Ala Ala Pro Leu Tyr Pro Leu Thr Lys Pro Gly Thr Leu Phe Asn
                405                 410                 415

Trp Gly Pro Asp Gln Gln Lys Ala Tyr Gln Glu Ile Lys Gln Ala Leu
                420                 425                 430

Leu Thr Ala Pro Ala Leu Gly Leu Pro Asp Leu Thr Lys Pro Phe Glu
            435                 440                 445

Leu Phe Val Asp Glu Lys Gln Gly Tyr Ala Lys Gly Val Leu Thr Gln
        450                 455                 460

Lys Leu Gly Pro Trp Arg Arg Pro Val Ala Tyr Leu Ser Lys Lys Leu
465                 470                 475                 480

Asp Pro Val Ala Ala Gly Trp Pro Pro Cys Leu Arg Met Val Ala Ala
                485                 490                 495

Ile Ala Val Leu Thr Lys Asp Ala Gly Lys Leu Thr Met Gly Gln Pro
                500                 505                 510

Leu Val Ile Leu Ala Pro His Ala Val Glu Ala Leu Val Lys Gln Pro
            515                 520                 525

Pro Asp Arg Trp Leu Ser Asn Ala Arg Met Thr His Tyr Gln Ala Leu
        530                 535                 540

Leu Leu Asp Thr Asp Arg Val Gln Phe Gly Pro Val Val Ala Leu Asn
545                 550                 555                 560

Pro Ala Thr Leu Leu Pro Leu Pro Glu Glu Gly Leu Gln His Asn Cys
                565                 570                 575

Leu Asp Ile Leu Ala Glu Ala His Gly Thr Arg Pro Asp Leu Thr Asp
                580                 585                 590

Gln Pro Leu Pro Asp Ala Asp His Thr Trp Tyr Thr Asp Gly Ser Ser
            595                 600                 605

Leu Leu Gln Glu Gly Gln Arg Lys Ala Gly Ala Ala Val Thr Thr Glu
        610                 615                 620

Thr Glu Val Ile Trp Ala Lys Ala Leu Pro Ala Gly Thr Ser Ala Gln
625                 630                 635                 640

Arg Ala Glu Leu Ile Ala Leu Thr Gln Ala Leu Lys Met Ala Glu Gly
                645                 650                 655

Lys Lys Leu Asn Val Tyr Thr Asp Ser Arg Tyr Ala Phe Ala Thr Ala
                660                 665                 670

His Ile His Gly Glu Ile Tyr Arg Arg Gly Trp Leu Thr Ser Glu
            675                 680                 685

Gly Lys Glu Ile Lys Asn Lys Asp Glu Ile Leu Ala Leu Leu Lys Ala
        690                 695                 700

Leu Phe Leu Pro Lys Arg Leu Ser Ile Ile His Cys Pro Gly His Gln
705                 710                 715                 720

Lys Gly His Ser Ala Glu Ala Arg Gly Asn Arg Met Ala Asp Gln Ala
                725                 730                 735
```

```
Ala Arg Lys Ala Ala Ile Thr Glu Thr Pro Asp Thr Ser Thr Leu Leu
            740                 745                 750

Ile Glu Asn Ser Ser Pro Ser Gly Gly Ser Lys Arg Thr Ala Asp Gly
        755                 760                 765

Ser Glu Phe Glu Pro Lys Lys Lys Arg Lys Val
    770                 775

<210> SEQ ID NO 3
<211> LENGTH: 420
<212> TYPE: PRT
<213> ORGANISM: Geobacilus stereothermophilus

<400> SEQUENCE: 3

Met Ala Leu Leu Glu Arg Ile Leu Ala Arg Asp Asn Leu Ile Thr Ala
1               5                   10                  15

Leu Lys Arg Val Glu Ala Asn Gln Gly Ala Pro Gly Ile Asp Gly Val
            20                  25                  30

Ser Thr Asp Gln Leu Arg Asp Tyr Ile Arg Ala His Trp Ser Thr Ile
        35                  40                  45

His Ala Gln Leu Leu Ala Gly Thr Tyr Arg Pro Ala Pro Val Arg Arg
    50                  55                  60

Val Glu Ile Pro Lys Pro Gly Gly Gly Thr Arg Gln Leu Gly Ile Pro
65                  70                  75                  80

Thr Val Val Asp Arg Leu Ile Gln Gln Ala Ile Leu Gln Glu Leu Thr
                85                  90                  95

Pro Ile Phe Asp Pro Asp Phe Ser Ser Ser Phe Gly Phe Arg Pro
            100                 105                 110

Gly Arg Asn Ala His Asp Ala Val Arg Gln Ala Gln Gly Tyr Ile Gln
            115                 120                 125

Glu Gly Tyr Arg Tyr Val Val Asp Met Asp Leu Glu Lys Phe Phe Asp
    130                 135                 140

Arg Val Asn His Asp Ile Leu Met Ser Arg Val Ala Arg Lys Val Lys
145                 150                 155                 160

Asp Lys Arg Val Leu Lys Leu Ile Arg Ala Tyr Leu Gln Ala Gly Val
                165                 170                 175

Met Ile Glu Gly Val Lys Val Gln Thr Glu Gly Thr Pro Gln Gly
            180                 185                 190

Gly Pro Leu Ser Pro Leu Leu Ala Asn Ile Leu Leu Asp Asp Leu Asp
    195                 200                 205

Lys Glu Leu Glu Lys Arg Gly Leu Lys Phe Cys Arg Tyr Ala Asp Asp
    210                 215                 220

Cys Asn Ile Tyr Val Lys Ser Leu Arg Ala Gly Gln Arg Val Lys Gln
225                 230                 235                 240

Ser Ile Gln Arg Phe Leu Glu Lys Thr Leu Lys Leu Lys Val Asn Glu
                245                 250                 255

Glu Lys Ser Ala Val Asp Arg Pro Trp Lys Arg Ala Phe Leu Gly Phe
            260                 265                 270

Ser Phe Thr Pro Glu Arg Lys Ala Arg Ile Arg Leu Ala Pro Arg Ser
        275                 280                 285

Ile Gln Arg Leu Lys Gln Arg Ile Arg Gln Leu Thr Asn Pro Asn Trp
    290                 295                 300

Ser Ile Ser Met Pro Glu Arg Ile His Arg Val Asn Gln Tyr Val Met
305                 310                 315                 320

Gly Trp Ile Gly Tyr Phe Arg Leu Val Glu Thr Pro Ser Val Leu Gln
                325                 330                 335
```

```
Thr Ile Glu Gly Trp Ile Arg Arg Leu Arg Leu Cys Gln Trp Leu
            340                 345                 350

Gln Trp Lys Arg Val Arg Thr Arg Ile Arg Glu Leu Arg Ala Leu Gly
        355                 360                 365

Leu Lys Glu Thr Ala Val Met Glu Ile Ala Asn Thr Arg Lys Gly Ala
    370                 375                 380

Trp Arg Thr Thr Lys Thr Pro Gln Leu His Gln Ala Leu Gly Lys Thr
385                 390                 395                 400

Tyr Trp Thr Ala Gln Gly Leu Lys Ser Leu Thr Gln Arg Tyr Phe Glu
                405                 410                 415

Leu Arg Gln Gly
            420

<210> SEQ ID NO 4
<211> LENGTH: 427
<212> TYPE: PRT
<213> ORGANISM: Eubacterium rectale

<400> SEQUENCE: 4

Met Asp Thr Ser Asn Leu Met Glu Gln Ile Leu Ser Ser Asp Asn Leu
1               5                   10                  15

Asn Arg Ala Tyr Leu Gln Val Val Arg Asn Lys Gly Ala Glu Gly Val
            20                  25                  30

Asp Gly Met Lys Tyr Thr Glu Leu Lys Glu His Leu Ala Lys Asn Gly
        35                  40                  45

Glu Thr Ile Lys Gly Gln Leu Arg Thr Arg Lys Tyr Lys Pro Gln Pro
    50                  55                  60

Ala Arg Arg Val Glu Ile Pro Lys Pro Asp Gly Gly Val Arg Asn Leu
65                  70                  75                  80

Gly Val Pro Thr Val Thr Asp Arg Phe Ile Gln Gln Ala Ile Ala Gln
                85                  90                  95

Val Leu Thr Pro Ile Tyr Glu Glu Gln Phe His Asp His Ser Tyr Gly
            100                 105                 110

Phe Arg Pro Asn Arg Cys Ala Gln Gln Ala Ile Leu Thr Ala Leu Asn
        115                 120                 125

Ile Met Asn Asp Gly Asn Asp Trp Ile Val Asp Ile Asp Leu Glu Lys
    130                 135                 140

Phe Phe Asp Thr Val Asn His Asp Lys Leu Met Thr Leu Ile Gly Arg
145                 150                 155                 160

Thr Ile Lys Asp Gly Asp Val Ile Ser Ile Val Arg Lys Tyr Leu Val
                165                 170                 175

Ser Gly Ile Met Ile Asp Asp Glu Tyr Glu Asp Ser Ile Val Gly Thr
            180                 185                 190

Pro Gln Gly Gly Asn Leu Ser Pro Leu Leu Ala Asn Ile Met Leu Asn
        195                 200                 205

Glu Leu Asp Lys Glu Met Glu Lys Arg Gly Leu Asn Phe Val Arg Tyr
    210                 215                 220

Ala Asp Asp Cys Ile Ile Met Val Gly Ser Glu Met Ser Ala Asn Arg
225                 230                 235                 240

Val Met Arg Asn Ile Ser Arg Phe Ile Glu Glu Lys Leu Gly Leu Lys
                245                 250                 255

Val Asn Met Thr Lys Ser Lys Val Asp Arg Pro Ser Gly Leu Lys Tyr
            260                 265                 270

Leu Gly Phe Gly Phe Tyr Phe Asp Pro Arg Ala His Gln Phe Lys Ala
```

```
                275                 280                 285
Lys Pro His Ala Lys Ser Val Ala Lys Phe Lys Lys Arg Met Lys Glu
    290                 295                 300
Leu Thr Cys Arg Ser Trp Gly Val Ser Asn Ser Tyr Lys Val Glu Lys
305                 310                 315                 320
Leu Asn Gln Leu Ile Arg Gly Trp Ile Asn Tyr Phe Lys Ile Gly Ser
                325                 330                 335
Met Lys Thr Leu Cys Lys Glu Leu Asp Ser Arg Ile Arg Tyr Arg Leu
            340                 345                 350
Arg Met Cys Ile Trp Lys Gln Trp Lys Thr Pro Gln Asn Gln Glu Lys
            355                 360                 365
Asn Leu Val Lys Leu Gly Ile Asp Arg Asn Thr Ala Arg Arg Val Ala
        370                 375                 380
Tyr Thr Gly Lys Arg Ile Ala Tyr Val Cys Asn Lys Gly Ala Val Asn
385                 390                 395                 400
Val Ala Ile Ser Asn Lys Arg Leu Ala Ser Phe Gly Leu Ile Ser Met
                405                 410                 415
Leu Asp Tyr Tyr Ile Glu Lys Cys Val Thr Cys
                420                 425

<210> SEQ ID NO 5
<211> LENGTH: 427
<212> TYPE: PRT
<213> ORGANISM: Unknown
<220> FEATURE:
<223> OTHER INFORMATION: Description of Unknown:
      marathonRT seqeunce

<400> SEQUENCE: 5

Met Asp Thr Ser Asn Leu Met Glu Gln Ile Leu Ser Ser Asp Asn Leu
1               5                   10                  15
Asn Arg Ala Tyr Leu Gln Val Val Arg Asn Lys Gly Ala Glu Gly Val
            20                  25                  30
Asp Gly Met Lys Tyr Thr Glu Leu Lys Glu His Leu Ala Lys Asn Gly
        35                  40                  45
Glu Thr Ile Lys Gly Gln Leu Arg Thr Ala Ala Tyr Ala Pro Gln Pro
    50                  55                  60
Ala Arg Arg Val Glu Ile Pro Lys Pro Asp Gly Gly Val Arg Asn Leu
65                  70                  75                  80
Gly Val Pro Thr Val Thr Asp Arg Phe Ile Gln Gln Ala Ile Ala Gln
                85                  90                  95
Val Leu Thr Pro Ile Tyr Glu Glu Gln Phe His Asp His Ser Tyr Gly
            100                 105                 110
Phe Arg Pro Asn Arg Cys Ala Gln Gln Ala Ile Leu Thr Ala Leu Asn
        115                 120                 125
Ile Met Asn Asp Gly Asn Asp Trp Ile Val Asp Ile Asp Leu Glu Lys
    130                 135                 140
Phe Phe Asp Thr Val Asn His Asp Lys Leu Met Thr Leu Ile Gly Arg
145                 150                 155                 160
Thr Ile Ala Asp Gly Asp Val Ile Ser Ile Val Arg Lys Tyr Leu Val
                165                 170                 175
Ser Gly Ile Met Ile Asp Asp Glu Tyr Glu Asp Ser Ile Val Gly Thr
            180                 185                 190
Pro Gln Gly Gly Asn Leu Ser Pro Leu Leu Ala Asn Ile Met Leu Asn
        195                 200                 205
```

```
Glu Leu Asp Lys Glu Met Glu Ala Ala Gly Leu Asn Phe Val Arg Tyr
        210                 215                 220

Ala Asp Asp Cys Ile Ile Met Val Gly Ser Glu Met Ser Ala Asn Arg
225                 230                 235                 240

Val Met Arg Asn Ile Ser Arg Phe Ile Glu Glu Lys Leu Gly Leu Lys
                245                 250                 255

Val Asn Met Thr Lys Ser Lys Val Asp Arg Pro Ser Gly Leu Lys Tyr
            260                 265                 270

Leu Gly Phe Gly Phe Tyr Phe Asp Pro Arg Ala His Gln Phe Lys Ala
        275                 280                 285

Lys Pro His Ala Lys Ser Val Ala Lys Phe Lys Arg Met Lys Glu
290                 295                 300

Leu Thr Cys Arg Ser Trp Gly Val Ser Asn Ser Tyr Lys Val Glu Lys
305                 310                 315                 320

Leu Asn Gln Leu Ile Arg Gly Trp Ile Asn Tyr Phe Lys Ile Gly Ser
                325                 330                 335

Met Lys Thr Leu Cys Lys Glu Leu Asp Ser Arg Ile Arg Tyr Arg Leu
            340                 345                 350

Arg Met Cys Ile Trp Lys Gln Trp Lys Thr Pro Gln Asn Gln Glu Lys
        355                 360                 365

Asn Leu Val Lys Leu Gly Ile Asp Arg Asn Thr Ala Arg Arg Val Ala
370                 375                 380

Tyr Thr Gly Lys Arg Ile Ala Tyr Val Cys Asn Lys Gly Ala Val Asn
385                 390                 395                 400

Val Ala Ile Ser Asn Lys Arg Leu Ala Ser Phe Gly Leu Ile Ser Met
                405                 410                 415

Leu Asp Tyr Tyr Ile Glu Lys Cys Val Thr Cys
            420                 425

<210> SEQ ID NO 6
<211> LENGTH: 1114
<212> TYPE: PRT
<213> ORGANISM: Bombyx mori

<400> SEQUENCE: 6

Met Met Ala Ser Thr Ala Leu Ser Leu Met Gly Arg Cys Asn Pro Asp
1               5                   10                  15

Gly Cys Thr Arg Gly Lys His Val Thr Ala Ala Pro Met Asp Gly Pro
                20                  25                  30

Arg Gly Pro Ser Ser Leu Ala Gly Thr Phe Gly Trp Gly Leu Ala Ile
            35                  40                  45

Pro Ala Gly Glu Pro Cys Gly Arg Val Cys Ser Pro Ala Thr Val Gly
        50                  55                  60

Phe Phe Pro Val Ala Lys Lys Ser Asn Lys Glu Asn Arg Pro Glu Ala
65                  70                  75                  80

Ser Gly Leu Pro Leu Glu Ser Glu Arg Thr Gly Asp Asn Pro Thr Val
                85                  90                  95

Arg Gly Ser Ala Gly Ala Asp Pro Val Gly Gln Asp Ala Pro Gly Trp
            100                 105                 110

Thr Cys Gln Phe Cys Glu Arg Thr Phe Ser Thr Asn Arg Gly Leu Gly
        115                 120                 125

Val His Lys Arg Arg Ala His Pro Val Glu Thr Asn Thr Asp Ala Ala
    130                 135                 140

Pro Met Met Val Lys Arg Arg Trp His Gly Glu Glu Ile Asp Leu Leu
145                 150                 155                 160
```

```
Ala Arg Thr Glu Ala Arg Leu Leu Ala Glu Arg Gly Gln Cys Ser Gly
            165                 170                 175

Gly Asp Leu Phe Gly Ala Leu Pro Gly Phe Gly Arg Thr Leu Glu Ala
            180                 185                 190

Ile Lys Gly Gln Arg Arg Glu Pro Tyr Arg Ala Leu Val Gln Ala
            195                 200                 205

His Leu Ala Arg Phe Gly Ser Gln Pro Gly Pro Ser Ser Gly Gly Cys
            210                 215                 220

Ser Ala Glu Pro Asp Phe Arg Arg Ala Ser Gly Ala Glu Ala Gly
225                 230                 235                 240

Glu Glu Arg Cys Ala Glu Asp Ala Ala Tyr Asp Pro Ser Ala Val
                245                 250                 255

Gly Gln Met Ser Pro Asp Ala Ala Arg Val Leu Ser Glu Leu Leu Glu
            260                 265                 270

Gly Ala Gly Arg Arg Arg Ala Cys Arg Ala Met Arg Pro Lys Thr Ala
            275                 280                 285

Gly Arg Arg Asn Asp Leu His Asp Asp Arg Thr Ala Ser Ala His Lys
            290                 295                 300

Thr Ser Arg Gln Lys Arg Arg Ala Glu Tyr Ala Arg Val Gln Glu Leu
305                 310                 315                 320

Tyr Lys Lys Cys Arg Ser Arg Ala Ala Ala Glu Val Ile Asp Gly Ala
                325                 330                 335

Cys Gly Gly Val Gly His Ser Leu Glu Glu Met Glu Thr Tyr Trp Arg
                340                 345                 350

Pro Ile Leu Glu Arg Val Ser Asp Ala Pro Gly Pro Thr Pro Glu Ala
            355                 360                 365

Leu His Ala Leu Gly Arg Ala Glu Trp His Gly Asn Arg Asp Tyr
            370                 375                 380

Thr Gln Leu Trp Lys Pro Ile Ser Val Glu Glu Ile Lys Ala Ser Arg
385                 390                 395                 400

Phe Asp Trp Arg Thr Ser Pro Gly Pro Asp Gly Ile Arg Ser Gly Gln
                405                 410                 415

Trp Arg Ala Val Pro Val His Leu Lys Ala Glu Met Phe Asn Ala Trp
            420                 425                 430

Met Ala Arg Gly Glu Ile Pro Glu Ile Leu Arg Gln Cys Arg Thr Val
            435                 440                 445

Phe Val Pro Lys Val Glu Arg Pro Gly Gly Pro Gly Glu Tyr Arg Pro
450                 455                 460

Ile Ser Ile Ala Ser Ile Pro Leu Arg His Phe His Ser Ile Leu Ala
465                 470                 475                 480

Arg Arg Leu Leu Ala Cys Cys Pro Pro Asp Ala Arg Gln Arg Gly Phe
                485                 490                 495

Ile Cys Ala Asp Gly Thr Leu Glu Asn Ser Ala Val Leu Asp Ala Val
                500                 505                 510

Leu Gly Asp Ser Arg Lys Lys Leu Arg Glu Cys His Val Ala Val Leu
            515                 520                 525

Asp Phe Ala Lys Ala Phe Asp Thr Val Ser His Glu Ala Leu Val Glu
530                 535                 540

Leu Leu Arg Leu Arg Gly Met Pro Glu Gln Phe Cys Gly Tyr Ile Ala
545                 550                 555                 560

His Leu Tyr Asp Thr Ala Ser Thr Thr Leu Ala Val Asn Asn Glu Met
                565                 570                 575
```

```
Ser Ser Pro Val Lys Val Gly Arg Gly Val Arg Gln Gly Asp Pro Leu
            580                 585                 590

Ser Pro Ile Leu Phe Asn Val Val Met Asp Leu Ile Leu Ala Ser Leu
        595                 600                 605

Pro Glu Arg Val Gly Tyr Arg Leu Glu Met Glu Leu Val Ser Ala Leu
    610                 615                 620

Ala Tyr Ala Asp Asp Leu Val Leu Leu Ala Gly Ser Lys Val Gly Met
625                 630                 635                 640

Gln Glu Ser Ile Ser Ala Val Asp Cys Val Gly Arg Gln Met Gly Leu
                645                 650                 655

Arg Leu Asn Cys Arg Lys Ser Ala Val Leu Ser Met Ile Pro Asp Gly
            660                 665                 670

His Arg Lys Lys His His Tyr Leu Thr Glu Arg Thr Phe Asn Ile Gly
        675                 680                 685

Gly Lys Pro Leu Arg Gln Val Ser Cys Val Glu Arg Trp Arg Tyr Leu
    690                 695                 700

Gly Val Asp Phe Glu Ala Ser Gly Cys Val Thr Leu Glu His Ser Ile
705                 710                 715                 720

Ser Ser Ala Leu Asn Asn Ile Ser Arg Ala Pro Leu Lys Pro Gln Gln
                725                 730                 735

Arg Leu Glu Ile Leu Arg Ala His Leu Ile Pro Arg Phe Gln His Gly
            740                 745                 750

Phe Val Leu Gly Asn Ile Ser Asp Asp Arg Leu Arg Met Leu Asp Val
        755                 760                 765

Gln Ile Arg Lys Ala Val Gly Gln Trp Leu Arg Leu Pro Ala Asp Val
    770                 775                 780

Pro Lys Ala Tyr Tyr His Ala Ala Val Gln Asp Gly Gly Leu Ala Ile
785                 790                 795                 800

Pro Ser Val Arg Ala Thr Ile Pro Asp Leu Ile Val Arg Arg Phe Gly
                805                 810                 815

Gly Leu Asp Ser Ser Pro Trp Ser Val Ala Arg Ala Ala Lys Ser
            820                 825                 830

Asp Lys Ile Arg Lys Leu Arg Trp Ala Trp Lys Gln Leu Arg Arg
        835                 840                 845

Phe Ser Arg Val Asp Ser Thr Thr Gln Arg Pro Ser Val Arg Leu Phe
850                 855                 860

Trp Arg Glu His Leu His Ala Ser Val Asp Gly Arg Glu Leu Arg Glu
865                 870                 875                 880

Ser Thr Arg Thr Pro Thr Ser Thr Lys Trp Ile Arg Glu Arg Cys Ala
                885                 890                 895

Gln Ile Thr Gly Arg Asp Phe Val Gln Phe Val His Thr His Ile Asn
            900                 905                 910

Ala Leu Pro Ser Arg Ile Arg Gly Ser Arg Gly Arg Gly Gly
        915                 920                 925

Glu Ser Ser Leu Thr Cys Arg Ala Gly Cys Lys Val Arg Glu Thr Thr
    930                 935                 940

Ala His Ile Leu Gln Gln Cys His Arg Thr His Gly Gly Arg Ile Leu
945                 950                 955                 960

Arg His Asn Lys Ile Val Ser Phe Val Ala Lys Ala Met Glu Glu Asn
                965                 970                 975

Lys Trp Thr Val Glu Leu Glu Pro Arg Leu Arg Thr Ser Val Gly Leu
            980                 985                 990

Arg Lys Pro Asp Ile Ile Ala Ser  Arg Asp Gly Val Gly  Val Ile Val
```

```
                995                 1000                1005
Asp Val Gln Val Val Ser Gly Gln Arg Ser Leu Asp Glu Leu His
    1010                1015                1020

Arg Glu Lys Arg Asn Lys Tyr Gly Asn His Gly Glu Leu Val Glu
    1025                1030                1035

Leu Val Ala Gly Arg Leu Gly Leu Pro Lys Ala Glu Cys Val Arg
    1040                1045                1050

Ala Thr Ser Cys Thr Ile Ser Trp Arg Gly Val Trp Ser Leu Thr
    1055                1060                1065

Ser Tyr Lys Glu Leu Arg Ser Ile Ile Gly Leu Arg Glu Pro Thr
    1070                1075                1080

Leu Gln Ile Val Pro Ile Leu Ala Leu Arg Gly Ser His Met Asn
    1085                1090                1095

Trp Thr Arg Phe Asn Gln Met Thr Ser Val Met Gly Gly Gly Val
    1100                1105                1110

Gly

<210> SEQ ID NO 7
<211> LENGTH: 901
<212> TYPE: PRT
<213> ORGANISM: Bombyx mori

<400> SEQUENCE: 7

Phe Cys Glu Arg Thr Phe Ser Thr Asn Arg Gly Leu Gly Val His Lys
1               5                   10                  15

Arg Arg Ala His Pro Val Glu Thr Asn Thr Asp Ala Ala Pro Met Met
            20                  25                  30

Val Lys Arg Arg Trp His Gly Glu Glu Ile Asp Leu Leu Ala Arg Thr
        35                  40                  45

Glu Ala Arg Leu Leu Ala Glu Arg Gly Gln Cys Ser Gly Gly Asp Leu
    50                  55                  60

Phe Gly Ala Leu Pro Gly Phe Gly Arg Thr Leu Glu Ala Ile Lys Gly
65                  70                  75                  80

Gln Arg Arg Arg Glu Pro Tyr Arg Ala Leu Val Gln Ala His Leu Ala
                85                  90                  95

Arg Phe Gly Ser Gln Pro Gly Pro Ser Ser Gly Gly Cys Ser Ala Glu
            100                 105                 110

Pro Asp Phe Arg Arg Ala Ser Gly Ala Glu Ala Gly Glu Glu Arg
            115                 120                 125

Cys Ala Glu Asp Ala Ala Tyr Asp Pro Ser Ala Val Gly Gln Met
    130                 135                 140

Ser Pro Asp Ala Ala Arg Val Leu Ser Glu Leu Leu Glu Gly Ala Gly
145                 150                 155                 160

Arg Arg Arg Ala Cys Arg Ala Met Arg Pro Lys Thr Ala Gly Arg Arg
                165                 170                 175

Asn Asp Leu His Asp Asp Arg Thr Ala Ser Ala His Lys Thr Ser Arg
            180                 185                 190

Gln Lys Arg Arg Ala Glu Tyr Ala Arg Val Gln Glu Leu Tyr Lys Lys
        195                 200                 205

Cys Arg Ser Arg Ala Ala Ala Glu Val Ile Asp Gly Ala Cys Gly Gly
    210                 215                 220

Val Gly His Ser Leu Glu Glu Met Glu Thr Tyr Trp Arg Pro Ile Leu
225                 230                 235                 240

Glu Arg Val Ser Asp Ala Pro Gly Pro Thr Pro Glu Ala Leu His Ala
```

```
            245                 250                 255
Leu Gly Arg Ala Glu Trp His Gly Gly Asn Arg Asp Tyr Thr Gln Leu
            260                 265                 270

Trp Lys Pro Ile Ser Val Glu Ile Lys Ala Ser Arg Phe Asp Trp
        275                 280                 285

Arg Thr Ser Pro Gly Pro Asp Gly Ile Arg Ser Gly Gln Trp Arg Ala
    290                 295                 300

Val Pro Val His Leu Lys Ala Glu Met Phe Asn Ala Trp Met Ala Arg
305                 310                 315                 320

Gly Glu Ile Pro Glu Ile Leu Arg Gln Cys Arg Thr Val Phe Val Pro
                325                 330                 335

Lys Val Glu Arg Pro Gly Gly Pro Gly Glu Tyr Arg Pro Ile Ser Ile
                340                 345                 350

Ala Ser Ile Pro Leu Arg His Phe His Ser Ile Leu Ala Arg Arg Leu
                355                 360                 365

Leu Ala Cys Cys Pro Pro Asp Ala Arg Gln Arg Gly Phe Ile Cys Ala
            370                 375                 380

Asp Gly Thr Leu Glu Asn Ser Ala Val Leu Asp Ala Val Leu Gly Asp
385                 390                 395                 400

Ser Arg Lys Lys Leu Arg Glu Cys His Val Ala Val Leu Asp Phe Ala
                405                 410                 415

Lys Ala Phe Asp Thr Val Ser His Glu Ala Leu Val Glu Leu Leu Arg
                420                 425                 430

Leu Arg Gly Met Pro Glu Gln Phe Cys Gly Tyr Ile Ala His Leu Tyr
            435                 440                 445

Asp Thr Ala Ser Thr Thr Leu Ala Val Asn Asn Glu Met Ser Ser Pro
            450                 455                 460

Val Lys Val Gly Arg Gly Val Arg Gln Gly Asp Pro Leu Ser Pro Ile
465                 470                 475                 480

Leu Phe Asn Val Val Met Asp Leu Ile Leu Ala Ser Leu Pro Glu Arg
                485                 490                 495

Val Gly Tyr Arg Leu Glu Met Glu Leu Val Ser Ala Leu Ala Tyr Ala
            500                 505                 510

Asp Asp Leu Val Leu Leu Ala Gly Ser Lys Val Gly Met Gln Glu Ser
        515                 520                 525

Ile Ser Ala Val Asp Cys Val Gly Arg Gln Met Gly Leu Arg Leu Asn
        530                 535                 540

Cys Arg Lys Ser Ala Val Leu Ser Met Ile Pro Asp Gly His Arg Lys
545                 550                 555                 560

Lys His His Tyr Leu Thr Glu Arg Thr Phe Asn Ile Gly Gly Lys Pro
                565                 570                 575

Leu Arg Gln Val Ser Cys Val Glu Arg Trp Arg Tyr Leu Gly Val Asp
            580                 585                 590

Phe Glu Ala Ser Gly Cys Val Thr Leu Glu His Ser Ile Ser Ser Ala
            595                 600                 605

Leu Asn Asn Ile Ser Arg Ala Pro Leu Lys Pro Gln Gln Arg Leu Glu
        610                 615                 620

Ile Leu Arg Ala His Leu Ile Pro Arg Phe Gln His Gly Phe Val Leu
625                 630                 635                 640

Gly Asn Ile Ser Asp Asp Arg Leu Arg Met Leu Asp Val Gln Ile Arg
                645                 650                 655

Lys Ala Val Gly Gln Trp Leu Arg Leu Pro Ala Asp Val Pro Lys Ala
            660                 665                 670
```

Tyr Tyr His Ala Val Gln Asp Gly Gly Leu Ala Ile Pro Ser Val
            675                 680                 685

Arg Ala Thr Ile Pro Asp Leu Ile Val Arg Arg Phe Gly Gly Leu Asp
        690                 695                 700

Ser Ser Pro Trp Ser Val Ala Arg Ala Ala Lys Ser Asp Lys Ile
705                 710                 715                 720

Arg Lys Lys Leu Arg Trp Ala Trp Lys Gln Leu Arg Arg Phe Ser Arg
                725                 730                 735

Val Asp Ser Thr Thr Gln Arg Pro Ser Val Arg Leu Phe Trp Arg Glu
            740                 745                 750

His Leu His Ala Ser Val Asp Gly Arg Glu Leu Arg Glu Ser Thr Arg
            755                 760                 765

Thr Pro Thr Ser Thr Lys Trp Ile Arg Glu Arg Cys Ala Gln Ile Thr
        770                 775                 780

Gly Arg Asp Phe Val Gln Phe Val His Thr His Ile Asn Ala Leu Pro
785                 790                 795                 800

Ser Arg Ile Arg Gly Ser Arg Gly Arg Gly Gly Glu Ser Ser
                805                 810                 815

Leu Thr Cys Arg Ala Gly Cys Lys Val Arg Glu Thr Thr Ala His Ile
            820                 825                 830

Leu Gln Gln Cys His Arg Thr His Gly Gly Arg Ile Leu Arg His Asn
    835                 840                 845

Lys Ile Val Ser Phe Val Ala Lys Ala Met Glu Glu Asn Lys Trp Thr
850                 855                 860

Val Glu Leu Glu Pro Arg Leu Arg Thr Ser Val Gly Leu Arg Lys Pro
865                 870                 875                 880

Asp Ile Ile Ala Ser Arg Asp Gly Val Gly Val Ile Val Asp Val Gln
                885                 890                 895

Val Val Ser Gly Gln
            900

<210> SEQ ID NO 8
<211> LENGTH: 1114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Met Ala Ser Thr Ala Leu Ser Leu Met Gly Arg Cys Asn Pro Asp
1               5                   10                  15

Gly Cys Thr Arg Gly Lys His Val Thr Ala Ala Pro Met Asp Gly Pro
            20                  25                  30

Arg Gly Pro Ser Ser Leu Ala Gly Thr Phe Gly Trp Gly Leu Ala Ile
        35                  40                  45

Pro Ala Gly Glu Pro Cys Gly Arg Val Cys Ser Pro Ala Thr Val Gly
    50                  55                  60

Phe Phe Pro Val Ala Lys Lys Ser Asn Lys Glu Asn Arg Pro Glu Ala
65                  70                  75                  80

Ser Gly Leu Pro Leu Glu Ser Glu Arg Thr Gly Asp Asn Pro Thr Val
                85                  90                  95

Arg Gly Ser Ala Gly Ala Asp Pro Val Gly Gln Asp Ala Pro Gly Trp
            100                 105                 110

Thr Cys Gln Phe Cys Glu Arg Thr Phe Ser Thr Asn Arg Gly Leu Gly

```
             115                 120                 125
Val His Lys Arg Arg Ala His Pro Val Glu Thr Asn Thr Asp Ala Ala
             130                 135                 140
Pro Met Met Val Lys Arg Arg Trp His Gly Glu Glu Ile Asp Leu Leu
145                 150                 155                 160
Ala Arg Thr Glu Ala Arg Leu Leu Ala Glu Arg Gly Gln Cys Ser Gly
                 165                 170                 175
Gly Asp Leu Phe Gly Ala Leu Pro Gly Phe Gly Arg Thr Leu Glu Ala
                 180                 185                 190
Ile Lys Gly Gln Arg Arg Glu Pro Tyr Arg Ala Leu Val Gln Ala
                 195                 200                 205
His Leu Ala Arg Phe Gly Ser Gln Pro Gly Pro Ser Ser Gly Gly Cys
             210                 215                 220
Ser Ala Glu Pro Asp Phe Arg Arg Ala Ser Gly Ala Glu Glu Ala Gly
225                 230                 235                 240
Glu Glu Arg Cys Ala Glu Asp Ala Ala Ala Tyr Asp Pro Ser Ala Val
                 245                 250                 255
Gly Gln Met Ser Pro Asp Ala Ala Arg Val Leu Ser Glu Leu Leu Glu
                 260                 265                 270
Gly Ala Gly Arg Arg Arg Ala Cys Arg Ala Met Arg Pro Lys Thr Ala
             275                 280                 285
Gly Arg Arg Asn Asp Leu His Asp Asp Arg Thr Ala Ser Ala His Lys
             290                 295                 300
Thr Ser Arg Gln Lys Arg Arg Ala Glu Tyr Ala Arg Val Gln Glu Leu
305                 310                 315                 320
Tyr Lys Lys Cys Arg Ser Arg Ala Ala Ala Glu Val Ile Asp Gly Ala
                 325                 330                 335
Cys Gly Gly Val Gly His Ser Leu Glu Glu Met Glu Thr Tyr Trp Arg
                 340                 345                 350
Pro Ile Leu Glu Arg Val Ser Asp Ala Pro Gly Pro Thr Pro Glu Ala
                 355                 360                 365
Leu His Ala Leu Gly Arg Ala Glu Trp His Gly Gly Asn Arg Asp Tyr
             370                 375                 380
Thr Gln Leu Trp Lys Pro Ile Ser Val Glu Glu Ile Lys Ala Ser Arg
385                 390                 395                 400
Phe Asp Trp Arg Thr Ser Pro Gly Pro Asp Gly Ile Arg Ser Gly Gln
                 405                 410                 415
Trp Arg Ala Val Pro Val His Leu Lys Ala Glu Met Phe Asn Ala Trp
                 420                 425                 430
Met Ala Arg Gly Glu Ile Pro Glu Ile Leu Arg Gln Cys Arg Thr Val
             435                 440                 445
Phe Val Pro Lys Val Glu Arg Pro Gly Gly Pro Gly Glu Tyr Arg Pro
             450                 455                 460
Ile Ser Ile Ala Ser Ile Pro Leu Arg His Phe His Ser Ile Leu Ala
465                 470                 475                 480
Arg Arg Leu Leu Ala Cys Cys Pro Pro Asp Ala Arg Gln Arg Gly Phe
                 485                 490                 495
Ile Cys Ala Asp Gly Thr Leu Glu Asn Ser Ala Val Leu Asp Ala Val
                 500                 505                 510
Leu Gly Asp Ser Arg Lys Lys Leu Arg Glu Cys His Val Ala Val Leu
             515                 520                 525
Asp Phe Ala Lys Ala Phe Asp Thr Val Ser His Glu Ala Leu Val Glu
             530                 535                 540
```

```
Leu Leu Arg Leu Arg Gly Met Pro Glu Gln Phe Cys Gly Tyr Ile Ala
545                 550                 555                 560

His Leu Tyr Asp Thr Ala Ser Thr Thr Leu Ala Val Asn Asn Glu Met
                565                 570                 575

Ser Ser Pro Val Lys Val Gly Arg Gly Val Arg Gln Gly Asp Pro Leu
            580                 585                 590

Ser Pro Ile Leu Phe Asn Val Val Met Asp Leu Ile Leu Ala Ser Leu
        595                 600                 605

Pro Glu Arg Val Gly Tyr Arg Leu Glu Met Glu Leu Val Ser Ala Leu
610                 615                 620

Ala Tyr Ala Asp Asp Leu Val Leu Leu Ala Gly Ser Lys Val Gly Met
625                 630                 635                 640

Gln Glu Ser Ile Ser Ala Val Asp Cys Val Gly Arg Gln Met Gly Leu
                645                 650                 655

Arg Leu Asn Cys Arg Lys Ser Ala Val Leu Ser Met Ile Pro Asp Gly
            660                 665                 670

His Arg Lys Lys His His Tyr Leu Thr Glu Arg Thr Phe Asn Ile Gly
        675                 680                 685

Gly Lys Pro Leu Arg Gln Val Ser Cys Val Glu Arg Trp Arg Tyr Leu
690                 695                 700

Gly Val Asp Phe Glu Ala Ser Gly Cys Val Thr Leu Glu His Ser Ile
705                 710                 715                 720

Ser Ser Ala Leu Asn Asn Ile Ser Arg Ala Pro Leu Lys Pro Gln Gln
                725                 730                 735

Arg Leu Glu Ile Leu Arg Ala His Leu Ile Pro Arg Phe Gln His Gly
            740                 745                 750

Phe Val Leu Gly Asn Ile Ser Asp Asp Arg Leu Arg Met Leu Asp Val
        755                 760                 765

Gln Ile Arg Lys Ala Val Gly Gln Trp Leu Arg Leu Pro Ala Asp Val
770                 775                 780

Pro Lys Ala Tyr Tyr His Ala Ala Val Gln Asp Gly Gly Leu Ala Ile
785                 790                 795                 800

Pro Ser Val Arg Ala Thr Ile Pro Asp Leu Ile Val Arg Arg Phe Gly
                805                 810                 815

Gly Leu Asp Ser Ser Pro Trp Ser Val Ala Arg Ala Ala Ala Lys Ser
            820                 825                 830

Asp Lys Ile Arg Lys Leu Arg Trp Ala Trp Lys Gln Leu Arg Arg
        835                 840                 845

Phe Ser Arg Val Asp Ser Thr Thr Gln Arg Pro Ser Val Arg Leu Phe
850                 855                 860

Trp Arg Glu His Leu His Ala Ser Val Asp Gly Arg Glu Leu Arg Glu
865                 870                 875                 880

Ser Thr Arg Thr Pro Thr Ser Thr Lys Trp Ile Arg Glu Arg Cys Ala
                885                 890                 895

Gln Ile Thr Gly Arg Asp Phe Val Gln Phe Val His Thr His Ile Asn
            900                 905                 910

Ala Leu Pro Ser Arg Ile Arg Gly Ser Arg Gly Arg Gly Gly Gly
        915                 920                 925

Glu Ser Ser Leu Thr Cys Arg Ala Gly Cys Lys Val Arg Glu Thr Thr
930                 935                 940

Ala His Ile Leu Gln Gln Cys His Arg Thr His Gly Gly Arg Ile Leu
945                 950                 955                 960
```

```
Arg His Asn Lys Ile Val Ser Phe Val Ala Lys Ala Met Glu Glu Asn
                965                 970                 975

Lys Trp Thr Val Glu Leu Glu Pro Arg Leu Arg Thr Ser Val Gly Leu
        980                 985                 990

Arg Lys Pro Ala Ile Ile Ala Ser Arg Asp Gly Val Gly Val Ile Val
            995                 1000                1005

Asp Val Gln Val Val Ser Gly Gln Arg Ser Leu Asp Glu Leu His
    1010                1015                1020

Arg Glu Lys Arg Asn Lys Tyr Gly Asn His Gly Glu Leu Val Glu
    1025                1030                1035

Leu Val Ala Gly Arg Leu Gly Leu Pro Lys Ala Glu Cys Val Arg
    1040                1045                1050

Ala Thr Ser Cys Thr Ile Ser Trp Arg Gly Val Trp Ser Leu Thr
    1055                1060                1065

Ser Tyr Lys Glu Leu Arg Ser Ile Ile Gly Leu Arg Glu Pro Thr
    1070                1075                1080

Leu Gln Ile Val Pro Ile Leu Ala Leu Arg Gly Ser His Met Asn
    1085                1090                1095

Trp Thr Arg Phe Asn Gln Met Thr Ser Val Met Gly Gly Gly Val
    1100                1105                1110

Gly

<210> SEQ ID NO 9
<211> LENGTH: 1275
<212> TYPE: PRT
<213> ORGANISM: Homo sapiens

<400> SEQUENCE: 9

Met Thr Gly Ser Asn Ser His Ile Thr Ile Leu Thr Leu Asn Val Asn
1               5                   10                  15

Gly Leu Asn Ser Pro Ile Lys Arg His Arg Leu Ala Ser Trp Ile Lys
            20                  25                  30

Ser Gln Asp Pro Ser Val Cys Cys Ile Gln Glu Thr His Leu Thr Cys
        35                  40                  45

Arg Asp Thr His Arg Leu Lys Ile Lys Gly Trp Arg Lys Ile Tyr Gln
    50                  55                  60

Ala Asn Gly Lys Gln Lys Lys Ala Gly Val Ala Ile Leu Val Ser Asp
65                  70                  75                  80

Lys Thr Asp Phe Lys Pro Thr Lys Ile Lys Arg Asp Lys Glu Gly His
                85                  90                  95

Tyr Ile Met Val Lys Gly Ser Ile Gln Gln Glu Leu Thr Ile Leu
                100                 105                 110

Asn Ile Tyr Ala Pro Asn Thr Gly Ala Pro Arg Phe Ile Lys Gln Val
            115                 120                 125

Leu Ser Asp Leu Gln Arg Asp Leu Asp Ser His Thr Leu Ile Met Gly
    130                 135                 140

Asp Phe Asn Thr Pro Leu Ser Ile Leu Asp Arg Ser Thr Arg Gln Lys
145                 150                 155                 160

Val Asn Lys Asp Thr Gln Glu Leu Asn Ser Ala Leu His Gln Thr Asp
                165                 170                 175

Leu Ile Asp Ile Tyr Arg Thr Leu His Pro Lys Ser Thr Glu Tyr Thr
            180                 185                 190

Phe Phe Ser Ala Pro His His Thr Tyr Ser Lys Ile Asp His Ile Val
        195                 200                 205
```

```
Gly Ser Lys Ala Leu Leu Ser Lys Cys Lys Arg Thr Glu Ile Ile Thr
210                 215                 220
Asn Tyr Leu Ser Asp His Ser Ala Ile Lys Leu Glu Leu Arg Ile Lys
225                 230                 235                 240
Asn Leu Thr Gln Ser Arg Ser Thr Thr Trp Lys Leu Asn Asn Leu Leu
                245                 250                 255
Leu Asn Asp Tyr Trp Val His Asn Glu Met Lys Ala Glu Ile Lys Met
                260                 265                 270
Phe Phe Glu Thr Asn Glu Asn Lys Asp Thr Thr Tyr Gln Asn Leu Trp
                275                 280                 285
Asp Ala Phe Lys Ala Val Cys Arg Gly Lys Phe Ile Ala Leu Asn Ala
                290                 295                 300
Tyr Lys Arg Lys Gln Glu Arg Ser Lys Ile Asp Thr Leu Thr Ser Gln
305                 310                 315                 320
Leu Lys Glu Leu Glu Lys Gln Glu Gln Thr His Ser Lys Ala Ser Arg
                325                 330                 335
Arg Gln Glu Ile Thr Lys Ile Arg Ala Glu Leu Lys Glu Ile Glu Thr
                340                 345                 350
Gln Lys Thr Leu Gln Lys Ile Asn Glu Ser Arg Ser Trp Phe Phe Glu
                355                 360                 365
Arg Ile Asn Lys Ile Asp Arg Pro Leu Ala Arg Leu Ile Lys Lys Lys
                370                 375                 380
Arg Glu Lys Asn Gln Ile Asp Thr Ile Lys Asn Asp Lys Gly Asp Ile
385                 390                 395                 400
Thr Thr Asp Pro Thr Glu Ile Gln Thr Thr Ile Arg Glu Tyr Tyr Lys
                405                 410                 415
His Leu Tyr Ala Asn Lys Leu Glu Asn Leu Glu Glu Met Asp Thr Phe
                420                 425                 430
Leu Asp Thr Tyr Thr Leu Pro Arg Leu Asn Gln Glu Glu Val Glu Ser
                435                 440                 445
Leu Asn Arg Pro Ile Thr Gly Ser Glu Ile Val Ala Ile Ile Asn Ser
                450                 455                 460
Leu Pro Thr Lys Lys Ser Pro Gly Pro Asp Gly Phe Thr Ala Glu Phe
465                 470                 475                 480
Tyr Gln Arg Tyr Lys Glu Glu Leu Val Pro Phe Leu Leu Lys Leu Phe
                485                 490                 495
Gln Ser Ile Glu Lys Glu Gly Ile Leu Pro Asn Ser Phe Tyr Glu Ala
                500                 505                 510
Ser Ile Ile Leu Ile Pro Lys Pro Gly Arg Asp Thr Thr Lys Lys Glu
                515                 520                 525
Asn Phe Arg Pro Ile Ser Leu Met Asn Ile Asp Ala Lys Ile Leu Asn
                530                 535                 540
Lys Ile Leu Ala Asn Arg Ile Gln Gln His Ile Lys Lys Leu Ile His
545                 550                 555                 560
His Asp Gln Val Gly Phe Ile Pro Gly Met Gln Gly Trp Phe Asn Ile
                565                 570                 575
Arg Lys Ser Ile Asn Val Ile Gln His Ile Asn Arg Ala Lys Asp Lys
                580                 585                 590
Asn His Val Ile Ile Ser Ile Asp Ala Glu Lys Ala Phe Asp Lys Ile
                595                 600                 605
Gln Gln Pro Phe Met Leu Lys Thr Leu Asn Lys Leu Gly Ile Asp Gly
                610                 615                 620
Met Tyr Leu Lys Ile Ile Arg Ala Ile Tyr Asp Lys Pro Thr Ala Asn
```

-continued

```
            625                 630                 635                 640
    Ile Ile Leu Asn Gly Gln Lys Leu Glu Ala Phe Pro Leu Lys Thr Gly
                    645                 650                 655

Thr Arg Gln Gly Cys Pro Leu Ser Pro Leu Leu Phe Asn Ile Val Leu
                    660                 665                 670

Glu Val Leu Ala Arg Ala Ile Arg Gln Glu Lys Glu Ile Lys Gly Ile
                    675                 680                 685

Gln Leu Gly Lys Glu Glu Val Lys Leu Ser Leu Phe Ala Asp Asp Met
        690                 695                 700

Ile Val Tyr Leu Glu Asn Pro Ile Val Ser Ala Gln Asn Leu Leu Lys
    705                 710                 715                 720

Leu Ile Ser Asn Phe Ser Lys Val Ser Gly Tyr Lys Ile Asn Val Gln
                    725                 730                 735

Lys Ser Gln Ala Phe Leu Tyr Asn Asn Asn Arg Gln Thr Glu Ser Gln
                    740                 745                 750

Ile Met Gly Glu Leu Pro Phe Thr Ile Ala Ser Lys Arg Ile Lys Tyr
                    755                 760                 765

Leu Gly Ile Gln Leu Thr Arg Asp Val Lys Asp Leu Phe Lys Glu Asn
        770                 775                 780

Tyr Lys Pro Leu Leu Lys Glu Ile Lys Glu Asp Thr Asn Lys Trp Lys
    785                 790                 795                 800

Asn Ile Pro Cys Ser Trp Val Gly Arg Ile Asn Ile Val Lys Met Ala
                    805                 810                 815

Ile Leu Pro Lys Val Ile Tyr Arg Phe Asn Ala Ile Pro Ile Lys Leu
                    820                 825                 830

Pro Met Thr Phe Phe Thr Glu Leu Glu Lys Thr Thr Leu Lys Phe Ile
                    835                 840                 845

Trp Asn Gln Lys Arg Ala Arg Ile Ala Lys Ser Ile Leu Ser Gln Lys
        850                 855                 860

Asn Lys Ala Gly Gly Ile Thr Leu Pro Asp Phe Lys Leu Tyr Tyr Lys
    865                 870                 875                 880

Ala Thr Val Thr Lys Thr Ala Trp Tyr Trp Tyr Gln Asn Arg Asp Ile
                    885                 890                 895

Asp Gln Trp Asn Arg Thr Glu Pro Ser Glu Ile Met Pro His Ile Tyr
                    900                 905                 910

Asn Tyr Leu Ile Phe Asp Lys Pro Glu Lys Asn Lys Gln Trp Gly Lys
                    915                 920                 925

Asp Ser Leu Leu Asn Lys Trp Cys Trp Glu Asn Trp Leu Ala Ile Cys
        930                 935                 940

Arg Lys Leu Lys Leu Asp Pro Phe Leu Thr Pro Tyr Thr Lys Ile Asn
    945                 950                 955                 960

Ser Arg Trp Ile Lys Asp Leu Asn Val Lys Pro Lys Thr Ile Lys Thr
                    965                 970                 975

Leu Glu Glu Asn Leu Gly Ile Thr Ile Gln Asp Ile Gly Val Gly Lys
                    980                 985                 990

Asp Phe Met Ser Lys Thr Pro Lys Ala Met Ala Thr Lys Asp Lys Ile
                    995                1000                1005

Asp Lys Trp Asp Leu Ile Lys Leu Lys Ser Phe Cys Thr Ala Lys
        1010                1015                1020

Glu Thr Thr Ile Arg Val Asn Arg Gln Pro Thr Thr Trp Glu Lys
        1025                1030                1035

Ile Phe Ala Thr Tyr Ser Ser Asp Lys Gly Leu Ile Ser Arg Ile
        1040                1045                1050
```

```
Tyr Asn Glu Leu Lys Gln Ile Tyr Lys Lys Thr Asn Asn Pro
    1055                1060                1065

Ile Lys Lys Trp Ala Lys Asp Met Asn Arg His Phe Ser Lys Glu
1070            1075                1080

Asp Ile Tyr Ala Ala Lys Lys His Met Lys Lys Cys Ser Ser Ser
    1085                1090                1095

Leu Ala Ile Arg Glu Met Gln Ile Lys Thr Thr Met Arg Tyr His
1100                1105                1110

Leu Thr Pro Val Arg Met Ala Ile Ile Lys Lys Ser Gly Asn Asn
1115                1120                1125

Arg Cys Trp Arg Gly Cys Gly Glu Ile Gly Thr Leu Val His Cys
1130                1135                1140

Trp Trp Asp Cys Lys Leu Val Gln Pro Leu Trp Lys Ser Val Trp
1145                1150                1155

Arg Phe Leu Arg Asp Leu Glu Leu Glu Ile Pro Phe Asp Pro Ala
1160                1165                1170

Ile Pro Leu Leu Gly Ile Tyr Pro Lys Asp Tyr Lys Ser Cys Cys
1175                1180                1185

Tyr Lys Asp Thr Cys Thr Arg Met Phe Ile Ala Ala Leu Phe Thr
1190                1195                1200

Ile Ala Lys Thr Trp Asn Gln Pro Asn Cys Pro Thr Met Ile Asp
1205                1210                1215

Trp Ile Lys Lys Met Trp His Ile Tyr Thr Met Glu Tyr Tyr Ala
1220                1225                1230

Ala Ile Lys Asn Asp Glu Phe Ile Ser Phe Val Gly Thr Trp Met
1235                1240                1245

Lys Leu Glu Thr Ile Ile Leu Ser Lys Leu Ser Gln Glu Gln Lys
1250                1255                1260

Thr Lys His Arg Ile Phe Ser Leu Ile Gly Gly Asn
1265                1270                1275

<210> SEQ ID NO 10
<211> LENGTH: 1275
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Thr Gly Ser Asn Ser His Ile Thr Ile Leu Thr Leu Asn Val Asn
1               5                   10                  15

Gly Leu Asn Ser Pro Ile Lys Arg His Arg Leu Ala Ser Trp Ile Lys
            20                  25                  30

Ser Gln Asp Pro Ser Val Cys Cys Ile Gln Glu Thr His Leu Thr Cys
        35                  40                  45

Arg Asp Thr His Arg Leu Lys Ile Lys Gly Trp Arg Lys Ile Tyr Gln
    50                  55                  60

Ala Asn Gly Lys Gln Lys Lys Ala Gly Val Ala Ile Leu Val Ser Asp
65                  70                  75                  80

Lys Thr Asp Phe Lys Pro Thr Lys Ile Lys Arg Asp Lys Glu Gly His
                85                  90                  95

Tyr Ile Met Val Lys Gly Ser Ile Gln Gln Glu Glu Leu Thr Ile Leu
            100                 105                 110

Asn Ile Tyr Ala Pro Asn Thr Gly Ala Pro Arg Phe Ile Lys Gln Val
```

```
            115                 120                 125
Leu Ser Asp Leu Gln Arg Asp Leu Asp Ser His Thr Leu Ile Met Gly
        130                 135                 140

Asp Phe Asn Thr Pro Leu Ser Ile Leu Asp Arg Ser Thr Arg Gln Lys
145                 150                 155                 160

Val Asn Lys Asp Thr Gln Glu Leu Asn Ser Ala Leu His Gln Thr Asp
                165                 170                 175

Leu Ile Asp Ile Tyr Arg Thr Leu His Pro Lys Ser Thr Glu Tyr Thr
            180                 185                 190

Phe Phe Ser Ala Pro His His Thr Tyr Ser Lys Ile Ala His Ile Val
        195                 200                 205

Gly Ser Lys Ala Leu Leu Ser Lys Cys Lys Arg Thr Glu Ile Ile Thr
    210                 215                 220

Asn Tyr Leu Ser Asp Ala Ser Ala Ile Lys Leu Glu Leu Arg Ile Lys
225                 230                 235                 240

Asn Leu Thr Gln Ser Arg Ser Thr Thr Trp Lys Leu Asn Asn Leu Leu
                245                 250                 255

Leu Asn Asp Tyr Trp Val His Asn Glu Met Lys Ala Glu Ile Lys Met
            260                 265                 270

Phe Phe Glu Thr Asn Glu Asn Lys Asp Thr Thr Tyr Gln Asn Leu Trp
        275                 280                 285

Asp Ala Phe Lys Ala Val Cys Arg Gly Lys Phe Ile Ala Leu Asn Ala
    290                 295                 300

Tyr Lys Arg Lys Gln Glu Arg Ser Lys Ile Asp Thr Leu Thr Ser Gln
305                 310                 315                 320

Leu Lys Glu Leu Glu Lys Gln Glu Gln Thr His Ser Lys Ala Ser Arg
                325                 330                 335

Arg Gln Glu Ile Thr Lys Ile Arg Ala Glu Leu Lys Glu Ile Glu Thr
            340                 345                 350

Gln Lys Thr Leu Gln Lys Ile Asn Glu Ser Arg Ser Trp Phe Phe Glu
        355                 360                 365

Arg Ile Asn Lys Ile Asp Arg Pro Leu Ala Arg Leu Ile Lys Lys Lys
    370                 375                 380

Arg Glu Lys Asn Gln Ile Asp Thr Ile Lys Asn Asp Lys Gly Asp Ile
385                 390                 395                 400

Thr Thr Asp Pro Thr Glu Ile Gln Thr Thr Ile Arg Glu Tyr Tyr Lys
                405                 410                 415

His Leu Tyr Ala Asn Lys Leu Glu Asn Leu Glu Glu Met Asp Thr Phe
            420                 425                 430

Leu Asp Thr Tyr Thr Leu Pro Arg Leu Asn Gln Glu Glu Val Glu Ser
        435                 440                 445

Leu Asn Arg Pro Ile Thr Gly Ser Glu Ile Val Ala Ile Ile Asn Ser
    450                 455                 460

Leu Pro Thr Lys Lys Ser Pro Gly Pro Asp Gly Phe Thr Ala Glu Phe
465                 470                 475                 480

Tyr Gln Arg Tyr Lys Glu Glu Leu Val Pro Phe Leu Leu Lys Leu Phe
                485                 490                 495

Gln Ser Ile Glu Lys Glu Gly Ile Leu Pro Asn Ser Phe Tyr Glu Ala
            500                 505                 510

Ser Ile Ile Leu Ile Pro Lys Pro Gly Arg Asp Thr Thr Lys Lys Glu
        515                 520                 525

Asn Phe Arg Pro Ile Ser Leu Met Asn Ile Asp Ala Lys Ile Leu Asn
    530                 535                 540
```

-continued

```
Lys Ile Leu Ala Asn Arg Ile Gln Gln His Ile Lys Leu Ile His
545                 550                 555                 560

His Asp Gln Val Gly Phe Ile Pro Gly Met Gln Gly Trp Phe Asn Ile
                565                 570                 575

Arg Lys Ser Ile Asn Val Ile Gln His Ile Asn Arg Ala Lys Asp Lys
            580                 585                 590

Asn His Val Ile Ile Ser Ile Asp Ala Glu Lys Ala Phe Asp Lys Ile
        595                 600                 605

Gln Gln Pro Phe Met Leu Lys Thr Leu Asn Lys Leu Gly Ile Asp Gly
    610                 615                 620

Met Tyr Leu Lys Ile Ile Arg Ala Ile Tyr Asp Lys Pro Thr Ala Asn
625                 630                 635                 640

Ile Ile Leu Asn Gly Gln Lys Leu Glu Ala Phe Pro Leu Lys Thr Gly
                645                 650                 655

Thr Arg Gln Gly Cys Pro Leu Ser Pro Leu Leu Phe Asn Ile Val Leu
            660                 665                 670

Glu Val Leu Ala Arg Ala Ile Arg Gln Glu Lys Glu Ile Lys Gly Ile
        675                 680                 685

Gln Leu Gly Lys Glu Glu Val Lys Leu Ser Leu Phe Ala Asp Asp Met
    690                 695                 700

Ile Val Tyr Leu Glu Asn Pro Ile Val Ser Ala Gln Asn Leu Leu Lys
705                 710                 715                 720

Leu Ile Ser Asn Phe Ser Lys Val Ser Gly Tyr Lys Ile Asn Val Gln
                725                 730                 735

Lys Ser Gln Ala Phe Leu Tyr Asn Asn Asn Arg Gln Thr Glu Ser Gln
            740                 745                 750

Ile Met Gly Glu Leu Pro Phe Thr Ile Ala Ser Lys Arg Ile Lys Tyr
        755                 760                 765

Leu Gly Ile Gln Leu Thr Arg Asp Val Lys Asp Leu Phe Lys Glu Asn
    770                 775                 780

Tyr Lys Pro Leu Leu Lys Glu Ile Lys Glu Asp Thr Asn Lys Trp Lys
785                 790                 795                 800

Asn Ile Pro Cys Ser Trp Val Gly Arg Ile Asn Ile Val Lys Met Ala
                805                 810                 815

Ile Leu Pro Lys Val Ile Tyr Arg Phe Asn Ala Ile Pro Ile Lys Leu
            820                 825                 830

Pro Met Thr Phe Phe Thr Glu Leu Glu Lys Thr Thr Leu Lys Phe Ile
        835                 840                 845

Trp Asn Gln Lys Arg Ala Arg Ile Ala Lys Ser Ile Leu Ser Gln Lys
    850                 855                 860

Asn Lys Ala Gly Gly Ile Thr Leu Pro Asp Phe Lys Leu Tyr Tyr Lys
865                 870                 875                 880

Ala Thr Val Thr Lys Thr Ala Trp Tyr Trp Tyr Gln Asn Arg Asp Ile
                885                 890                 895

Asp Gln Trp Asn Arg Thr Glu Pro Ser Glu Ile Met Pro His Ile Tyr
            900                 905                 910

Asn Tyr Leu Ile Phe Asp Lys Pro Glu Lys Asn Lys Gln Trp Gly Lys
        915                 920                 925

Asp Ser Leu Leu Asn Lys Trp Cys Trp Glu Asn Trp Leu Ala Ile Cys
    930                 935                 940

Arg Lys Leu Lys Leu Asp Pro Phe Leu Thr Pro Tyr Thr Lys Ile Asn
945                 950                 955                 960
```

Ser Arg Trp Ile Lys Asp Leu Asn Val Lys Pro Lys Thr Ile Lys Thr
                965                 970                 975

Leu Glu Glu Asn Leu Gly Ile Thr Ile Gln Asp Ile Gly Val Gly Lys
            980                 985                 990

Asp Phe Met Ser Lys Thr Pro Lys Ala Met Ala Thr Lys Asp Lys Ile
        995                1000                1005

Asp Lys Trp Asp Leu Ile Lys Leu Lys Ser Phe Cys Thr Ala Lys
    1010                1015                1020

Glu Thr Thr Ile Arg Val Asn Arg Gln Pro Thr Thr Trp Glu Lys
    1025                1030                1035

Ile Phe Ala Thr Tyr Ser Ser Asp Lys Gly Leu Ile Ser Arg Ile
    1040                1045                1050

Tyr Asn Glu Leu Lys Gln Ile Tyr Lys Lys Thr Asn Asn Pro
    1055                1060                1065

Ile Lys Lys Trp Ala Lys Asp Met Asn Arg His Phe Ser Lys Glu
    1070                1075                1080

Asp Ile Tyr Ala Ala Lys Lys His Met Lys Lys Cys Ser Ser Ser
    1085                1090                1095

Leu Ala Ile Arg Glu Met Gln Ile Lys Thr Thr Met Arg Tyr His
    1100                1105                1110

Leu Thr Pro Val Arg Met Ala Ile Ile Lys Lys Ser Gly Asn Asn
    1115                1120                1125

Arg Cys Trp Arg Gly Cys Gly Glu Ile Gly Thr Leu Val His Cys
    1130                1135                1140

Trp Trp Asp Cys Lys Leu Val Gln Pro Leu Trp Lys Ser Val Trp
    1145                1150                1155

Arg Phe Leu Arg Asp Leu Glu Leu Glu Ile Pro Phe Asp Pro Ala
    1160                1165                1170

Ile Pro Leu Leu Gly Ile Tyr Pro Lys Asp Tyr Lys Ser Cys Cys
    1175                1180                1185

Tyr Lys Asp Thr Cys Thr Arg Met Phe Ile Ala Ala Leu Phe Thr
    1190                1195                1200

Ile Ala Lys Thr Trp Asn Gln Pro Asn Cys Pro Thr Met Ile Asp
    1205                1210                1215

Trp Ile Lys Lys Met Trp His Ile Tyr Thr Met Glu Tyr Tyr Ala
    1220                1225                1230

Ala Ile Lys Asn Asp Glu Phe Ile Ser Phe Val Gly Thr Trp Met
    1235                1240                1245

Lys Leu Glu Thr Ile Ile Leu Ser Lys Leu Ser Gln Glu Gln Lys
    1250                1255                1260

Thr Lys His Arg Ile Phe Ser Leu Ile Gly Gly Asn
    1265                1270                1275

<210> SEQ ID NO 11
<211> LENGTH: 1281
<212> TYPE: PRT
<213> ORGANISM: Mus sp.

<400> SEQUENCE: 11

Met Pro Thr Leu Thr Thr Lys Ile Lys Gly Ser Asn Asn Tyr Phe Ser
1               5                   10                  15

Leu Ile Ser Leu Asn Ile Asn Gly Leu Asn Ser Pro Ile Lys Arg His
            20                  25                  30

Arg Leu Thr Asp Trp Leu His Lys Gln Asp Pro Thr Phe Cys Cys Leu
        35                  40                  45

-continued

```
Gln Glu Thr His Leu Arg Glu Lys Asp Arg His Tyr Leu Arg Val Lys
 50                  55                  60
Gly Trp Lys Thr Ile Phe Gln Ala Asn Gly Leu Lys Lys Gln Ala Gly
 65                  70                  75                  80
Val Ala Ile Leu Ile Leu Asp Lys Ile Asp Phe Gln Pro Lys Val Ile
                     85                  90                  95
Lys Lys Asp Lys Glu Gly His Phe Ile Leu Ile Lys Gly Lys Ile Leu
                    100                 105                 110
Gln Glu Glu Leu Ser Ile Leu Asn Ile Tyr Ala Pro Asn Ala Arg Ala
                115                 120                 125
Ala Thr Phe Ile Arg Asp Thr Leu Val Lys Leu Lys Ala Tyr Ile Ala
            130                 135                 140
Pro His Thr Ile Ile Val Gly Asp Phe Asn Thr Pro Leu Ser Ser Lys
145                 150                 155                 160
Asp Arg Ser Trp Lys Gln Lys Leu Asn Arg Asp Thr Val Lys Leu Thr
                165                 170                 175
Glu Val Met Lys Gln Met Asp Leu Thr Asp Ile Tyr Arg Thr Phe Tyr
                180                 185                 190
Pro Lys Thr Lys Gly Tyr Thr Phe Phe Ser Ala Pro His Gly Thr Phe
                195                 200                 205
Ser Lys Ile Asp His Ile Ile Gly His Lys Thr Gly Leu Asn Arg Tyr
210                 215                 220
Lys Asn Ile Glu Ile Val Pro Cys Ile Leu Ser Asp His His Gly Leu
225                 230                 235                 240
Arg Leu Ile Phe Asn Asn Asn Ile Asn Asn Gly Lys Pro Thr Phe Thr
                245                 250                 255
Trp Lys Leu Asn Asn Thr Leu Leu Asn Asp Thr Leu Val Lys Glu Gly
                260                 265                 270
Ile Lys Lys Glu Ile Lys Asp Phe Leu Glu Phe Asn Glu Asn Glu Ala
                275                 280                 285
Thr Thr Tyr Pro Asn Leu Trp Asp Thr Met Lys Ala Phe Leu Arg Gly
                290                 295                 300
Lys Leu Ile Ala Leu Ser Ala Ser Lys Lys Arg Glu Thr Ala His
305                 310                 315                 320
Thr Ser Ser Leu Thr Thr His Leu Lys Ala Leu Glu Lys Lys Glu Ala
                325                 330                 335
Asn Ser Pro Lys Arg Ser Arg Arg Gln Glu Ile Ile Lys Leu Arg Gly
                340                 345                 350
Glu Ile Asn Gln Val Glu Lys Arg Thr Ile Gln Arg Ile Asn Gln
                355                 360                 365
Thr Arg Ser Trp Phe Phe Glu Lys Ile Asn Lys Ile Asp Lys Pro Leu
                370                 375                 380
Ala Arg Leu Thr Lys Gly His Arg Asp Lys Ile Leu Ile Asn Lys Ile
385                 390                 395                 400
Arg Asn Glu Lys Gly Asp Ile Thr Thr Asp Pro Glu Glu Ile Gln Asn
                    405                 410                 415
Thr Ile Arg Ser Phe Tyr Lys Arg Leu Tyr Ser Thr Lys Leu Glu Asn
                420                 425                 430
Leu Asp Glu Met Asp Lys Phe Leu Asp Arg Tyr Gln Val Pro Lys Leu
                435                 440                 445
Asn Gln Asp Gln Val Asp His Leu Asn Ser Pro Ile Ser Pro Lys Glu
                450                 455                 460
```

```
Ile Glu Ala Val Ile Asn Ser Leu Pro Thr Lys Lys Ser Pro Gly Pro
465                 470                 475                 480

Asp Gly Phe Ser Ala Glu Phe Tyr Gln Thr Phe Lys Glu Asp Leu Ile
                485                 490                 495

Pro Ile Leu His Lys Leu Phe His Lys Ile Glu Val Glu Gly Thr Leu
                500                 505                 510

Pro Asn Ser Phe Tyr Glu Ala Thr Ile Thr Leu Ile Pro Lys Pro Gln
                515                 520                 525

Lys Asp Pro Thr Lys Ile Glu Asn Phe Arg Pro Ile Ser Leu Met Asn
                530                 535                 540

Ile Asp Ala Lys Ile Leu Asn Lys Ile Leu Ala Asn Arg Ile Gln Glu
545                 550                 555                 560

His Ile Lys Ala Ile Ile His Pro Asp Gln Val Gly Phe Ile Pro Gly
                565                 570                 575

Met Gln Gly Trp Phe Asn Ile Arg Lys Ser Ile Asn Val Ile His Tyr
                580                 585                 590

Ile Asn Lys Leu Lys Asp Lys Asn His Met Ile Ile Ser Leu Asp Ala
                595                 600                 605

Glu Lys Ala Phe Asp Lys Ile Gln His Pro Phe Met Ile Lys Val Leu
610                 615                 620

Glu Arg Ser Gly Ile Gln Gly Pro Tyr Leu Asn Met Ile Lys Ala Ile
625                 630                 635                 640

Tyr Ser Lys Pro Val Ala Asn Ile Lys Val Asn Gly Glu Lys Leu Glu
                645                 650                 655

Ala Ile Pro Leu Lys Ser Gly Thr Arg Gln Gly Cys Pro Leu Ser Pro
                660                 665                 670

Tyr Leu Phe Asn Ile Val Leu Glu Val Leu Ala Arg Ala Ile Arg Gln
                675                 680                 685

Gln Lys Glu Ile Lys Gly Ile Gln Ile Gly Lys Glu Glu Val Lys Ile
                690                 695                 700

Ser Leu Phe Ala Asp Asp Met Ile Val Tyr Ile Ser Asp Pro Lys Asn
705                 710                 715                 720

Ser Thr Arg Glu Leu Leu Asn Leu Ile Asn Ser Phe Gly Glu Val Ala
                725                 730                 735

Gly Tyr Lys Ile Asn Ser Asn Lys Ser Met Ala Phe Leu Tyr Thr Lys
                740                 745                 750

Asn Lys Gln Ala Glu Lys Glu Ile Trp Glu Thr Thr Pro Phe Ser Ile
                755                 760                 765

Val Thr Asn Asn Ile Lys Tyr Leu Gly Val Thr Leu Thr Lys Glu Val
                770                 775                 780

Lys Asp Leu Tyr Asp Lys Asn Phe Lys Ser Leu Lys Lys Glu Ile Lys
785                 790                 795                 800

Glu Asp Leu Arg Arg Trp Lys Asp Leu Pro Cys Ser Trp Ile Gly Arg
                805                 810                 815

Ile Asn Ile Val Lys Met Ala Ile Leu Pro Lys Ala Ile Tyr Arg Phe
                820                 825                 830

Asn Ala Ile Pro Ile Lys Ile Pro Thr Gln Phe Phe Asn Glu Leu Glu
                835                 840                 845

Gly Ala Ile Cys Lys Phe Val Trp Asn Asn Lys Lys Pro Arg Ile Ala
                850                 855                 860

Lys Ser Leu Leu Lys Asp Lys Arg Thr Ser Gly Gly Ile Thr Met Pro
865                 870                 875                 880

Asp Leu Lys Leu Tyr Tyr Arg Ala Ile Val Ile Lys Thr Ala Trp Tyr
```

```
                885                 890                 895
Trp Tyr Arg Asp Arg Gln Val Asp Gln Trp Asn Arg Ile Glu Asp Pro
            900                 905                 910

Glu Met Asn Pro His Thr Tyr Gly His Leu Ile Phe Asp Lys Gly Asp
            915                 920                 925

Lys Thr Ile Gln Trp Lys Lys Asp Ser Ile Phe Asn Asn Trp Cys Trp
            930                 935                 940

His Asn Trp Leu Leu Ser Cys Arg Arg Met Arg Ile Asp Pro Tyr Leu
945                 950                 955                 960

Ser Pro Cys Thr Lys Val Lys Ser Lys Trp Ile Lys Glu Leu His Ile
                965                 970                 975

Lys Pro Glu Thr Leu Lys Leu Ile Glu Glu Lys Val Gly Lys Ser Leu
            980                 985                 990

Glu Asp Met Gly Thr Gly Glu Lys Phe Leu Asn Arg Thr Ala Met Ala
                995                 1000                1005

Cys Ala Val Arg Ser Arg Ile Asp Lys Trp Asp Leu Met Lys Leu
    1010                1015                1020

Gln Ser Phe Cys Lys Ala Lys Asp Thr Val Asn Lys Thr Lys Arg
    1025                1030                1035

Pro Pro Thr Asp Trp Glu Arg Ile Phe Thr Tyr Pro Lys Ser Asp
    1040                1045                1050

Arg Gly Leu Ile Ser Asn Ile Tyr Lys Glu Leu Lys Lys Val Asp
    1055                1060                1065

Phe Arg Lys Ser Asn Asn Pro Ile Lys Lys Trp Gly Ser Glu Leu
    1070                1075                1080

Asn Lys Glu Phe Ser Pro Glu Glu Tyr Arg Met Ala Glu Lys His
    1085                1090                1095

Leu Lys Lys Cys Ser Thr Ser Leu Ile Ile Arg Glu Met Gln Ile
    1100                1105                1110

Lys Thr Thr Leu Arg Phe His Leu Thr Pro Val Arg Met Ala Lys
    1115                1120                1125

Ile Lys Asn Ser Gly Asp Ser Arg Cys Trp Arg Gly Cys Gly Glu
    1130                1135                1140

Arg Gly Thr Leu Leu His Cys Trp Trp Glu Cys Arg Leu Val Gln
    1145                1150                1155

Pro Leu Trp Lys Ser Val Trp Arg Phe Leu Arg Lys Leu Asp Ile
    1160                1165                1170

Val Leu Pro Glu Asp Pro Ala Ile Pro Leu Leu Gly Ile Tyr Pro
    1175                1180                1185

Glu Asp Ala Pro Thr Gly Lys Lys Asp Thr Cys Ser Thr Met Phe
    1190                1195                1200

Ile Ala Ala Leu Phe Ile Ile Ala Arg Ser Trp Lys Glu Pro Arg
    1205                1210                1215

Cys Pro Ser Thr Glu Glu Trp Ile Gln Lys Met Trp Tyr Ile Tyr
    1220                1225                1230

Thr Met Glu Tyr Tyr Ser Ala Ile Lys Lys Asn Glu Phe Met Lys
    1235                1240                1245

Phe Leu Ala Lys Trp Met Asp Leu Glu Gly Ile Ile Leu Ser Glu
    1250                1255                1260

Val Thr His Ser Gln Arg Asn Ser His Asn Met Tyr Ser Leu Ile
    1265                1270                1275

Ser Gly Tyr
    1280
```

<210> SEQ ID NO 12
<211> LENGTH: 599
<212> TYPE: PRT
<213> ORGANISM: Unknown
<220> FEATURE:
<223> OTHER INFORMATION: Description of Unknown:
      ltrA seqeunce

<400> SEQUENCE: 12

| | | | | | | | | | | | | | | |
|---|---|---|---|---|---|---|---|---|---|---|---|---|---|---|
| Met | Lys | Pro | Thr | Met | Ala | Ile | Leu | Glu | Arg | Ile | Ser | Lys | Asn | Ser | Gln |
| 1 | | | | 5 | | | | | 10 | | | | | 15 | |
| Glu | Asn | Ile | Asp | Glu | Val | Phe | Thr | Arg | Leu | Tyr | Arg | Tyr | Leu | Leu | Arg |
| | | | 20 | | | | | 25 | | | | | 30 | | |
| Pro | Asp | Ile | Tyr | Tyr | Val | Ala | Tyr | Gln | Asn | Leu | Tyr | Ser | Asn | Lys | Gly |
| | | | 35 | | | | | 40 | | | | | 45 | | |
| Ala | Ser | Thr | Lys | Gly | Ile | Leu | Asp | Asp | Thr | Ala | Asp | Gly | Phe | Ser | Glu |
| | | | 50 | | | | | 55 | | | | | 60 | | |
| Glu | Lys | Ile | Lys | Ile | Ile | Gln | Ser | Leu | Lys | Asp | Gly | Thr | Tyr | Tyr | |
| 65 | | | | | 70 | | | | | 75 | | | | | 80 |
| Pro | Gln | Pro | Val | Arg | Arg | Met | Tyr | Ile | Ala | Lys | Lys | Asn | Ser | Lys | Lys |
| | | | | 85 | | | | | 90 | | | | | 95 | |
| Met | Arg | Pro | Leu | Gly | Ile | Pro | Thr | Phe | Thr | Asp | Lys | Leu | Ile | Gln | Glu |
| | | | 100 | | | | | 105 | | | | | 110 | | |
| Ala | Val | Arg | Ile | Ile | Leu | Glu | Ser | Ile | Tyr | Glu | Pro | Val | Phe | Glu | Asp |
| | | | 115 | | | | | 120 | | | | | 125 | | |
| Val | Ser | His | Gly | Phe | Arg | Pro | Gln | Arg | Ser | Cys | His | Thr | Ala | Leu | Lys |
| | | | 130 | | | | | 135 | | | | | 140 | | |
| Thr | Ile | Lys | Arg | Glu | Phe | Gly | Gly | Ala | Arg | Trp | Phe | Val | Glu | Gly | Asp |
| 145 | | | | | 150 | | | | | 155 | | | | | 160 |
| Ile | Lys | Gly | Cys | Phe | Asp | Asn | Ile | Asp | His | Val | Thr | Leu | Ile | Gly | Leu |
| | | | 165 | | | | | 170 | | | | | 175 | | |
| Ile | Asn | Leu | Lys | Ile | Lys | Asp | Met | Lys | Met | Ser | Gln | Leu | Ile | Tyr | Lys |
| | | | 180 | | | | | 185 | | | | | 190 | | |
| Phe | Leu | Lys | Ala | Gly | Tyr | Leu | Glu | Asn | Trp | Gln | Tyr | His | Lys | Thr | Tyr |
| | | | 195 | | | | | 200 | | | | | 205 | | |
| Ser | Gly | Thr | Pro | Gln | Gly | Gly | Ile | Leu | Ser | Pro | Leu | Leu | Ala | Asn | Ile |
| | | | 210 | | | | | 215 | | | | | 220 | | |
| Tyr | Leu | His | Glu | Leu | Asp | Lys | Phe | Val | Leu | Gln | Leu | Lys | Met | Lys | Phe |
| 225 | | | | | 230 | | | | | 235 | | | | | 240 |
| Asp | Arg | Glu | Ser | Pro | Glu | Arg | Ile | Thr | Pro | Glu | Tyr | Arg | Glu | Leu | His |
| | | | 245 | | | | | 250 | | | | | 255 | | |
| Asn | Glu | Ile | Lys | Arg | Ile | Ser | His | Arg | Leu | Lys | Lys | Leu | Glu | Gly | Glu |
| | | | 260 | | | | | 265 | | | | | 270 | | |
| Glu | Lys | Ala | Lys | Val | Leu | Leu | Glu | Tyr | Gln | Glu | Lys | Arg | Lys | Arg | Leu |
| | | | 275 | | | | | 280 | | | | | 285 | | |
| Pro | Thr | Leu | Pro | Cys | Thr | Ser | Gln | Thr | Asn | Lys | Val | Leu | Lys | Tyr | Val |
| | | | 290 | | | | | 295 | | | | | 300 | | |
| Arg | Tyr | Ala | Asp | Asp | Phe | Ile | Ile | Ser | Val | Lys | Gly | Ser | Lys | Glu | Asp |
| 305 | | | | | 310 | | | | | 315 | | | | | 320 |
| Cys | Gln | Trp | Ile | Lys | Glu | Gln | Leu | Lys | Leu | Phe | Ile | His | Asn | Lys | Leu |
| | | | 325 | | | | | 330 | | | | | 335 | | |
| Lys | Met | Glu | Leu | Ser | Glu | Glu | Lys | Thr | Leu | Ile | Thr | His | Ser | Ser | Gln |
| | | | 340 | | | | | 345 | | | | | 350 | | |
| Pro | Ala | Arg | Phe | Leu | Gly | Tyr | Asp | Ile | Arg | Val | Arg | Arg | Ser | Gly | Thr |

```
                355                 360                 365
Ile Lys Arg Ser Gly Lys Val Lys Lys Arg Thr Leu Asn Gly Ser Val
        370                 375                 380

Glu Leu Leu Ile Pro Leu Gln Asp Lys Ile Arg Gln Phe Ile Phe Asp
385                 390                 395                 400

Lys Lys Ile Ala Ile Gln Lys Lys Asp Ser Trp Phe Pro Val His
                405                 410                 415

Arg Lys Tyr Leu Ile Arg Ser Thr Asp Leu Glu Ile Ile Thr Ile Tyr
                420                 425                 430

Asn Ser Glu Leu Arg Gly Ile Cys Asn Tyr Tyr Gly Leu Ala Ser Asn
            435                 440                 445

Phe Asn Gln Leu Asn Tyr Phe Ala Tyr Leu Met Glu Tyr Ser Cys Leu
        450                 455                 460

Lys Thr Ile Ala Ser Lys His Lys Gly Thr Leu Ser Lys Thr Ile Ser
465                 470                 475                 480

Met Phe Lys Asp Gly Ser Gly Ser Trp Gly Ile Pro Tyr Glu Ile Lys
                485                 490                 495

Gln Gly Lys Gln Arg Arg Tyr Phe Ala Asn Phe Ser Glu Cys Lys Ser
                500                 505                 510

Pro Tyr Gln Phe Thr Asp Glu Ile Ser Gln Ala Pro Val Leu Tyr Gly
            515                 520                 525

Tyr Ala Arg Asn Thr Leu Glu Asn Arg Leu Lys Ala Lys Cys Cys Glu
        530                 535                 540

Leu Cys Gly Thr Ser Asp Glu Asn Thr Ser Tyr Glu Ile His His Val
545                 550                 555                 560

Asn Lys Val Lys Asn Leu Lys Gly Lys Glu Lys Trp Glu Met Ala Met
                565                 570                 575

Ile Ala Lys Gln Arg Lys Thr Leu Val Val Cys Phe His Cys His Arg
                580                 585                 590

His Val Ile His Lys His Lys
            595

<210> SEQ ID NO 13
<211> LENGTH: 677
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Thr Leu Asn Ile Glu Asp Glu Tyr Arg Leu His Glu Thr Ser Lys Glu
1               5                   10                  15

Pro Asp Val Ser Leu Gly Ser Thr Trp Leu Ser Asp Phe Pro Gln Ala
                20                  25                  30

Trp Ala Glu Thr Gly Gly Met Gly Leu Ala Val Arg Gln Ala Pro Leu
            35                  40                  45

Ile Ile Pro Leu Lys Ala Thr Ser Thr Pro Val Ser Ile Lys Gln Tyr
        50                  55                  60

Pro Met Ser Gln Glu Ala Arg Leu Gly Ile Lys Pro His Ile Gln Arg
65                  70                  75                  80

Leu Leu Asp Gln Gly Ile Leu Val Pro Cys Gln Ser Pro Trp Asn Thr
                85                  90                  95

Pro Leu Leu Pro Val Lys Lys Pro Gly Thr Asn Asp Tyr Arg Pro Val
                100                 105                 110
```

```
Gln Asp Leu Arg Glu Val Asn Lys Arg Val Glu Asp Ile His Pro Thr
            115                 120                 125
Val Pro Asn Pro Tyr Asn Leu Leu Ser Gly Leu Pro Pro Ser His Gln
        130                 135                 140
Trp Tyr Thr Val Leu Asp Leu Lys Asp Ala Phe Phe Cys Leu Arg Leu
145                 150                 155                 160
His Pro Thr Ser Gln Pro Leu Phe Ala Phe Glu Trp Arg Asp Pro Glu
                165                 170                 175
Met Gly Ile Ser Gly Gln Leu Thr Trp Thr Arg Leu Pro Gln Gly Phe
            180                 185                 190
Lys Asn Ser Pro Thr Leu Phe Asn Glu Ala Leu His Arg Asp Leu Ala
        195                 200                 205
Asp Phe Arg Ile Gln His Pro Asp Leu Ile Leu Leu Gln Tyr Val Asp
210                 215                 220
Asp Leu Leu Leu Ala Ala Thr Ser Glu Leu Asp Cys Gln Gln Gly Thr
225                 230                 235                 240
Arg Ala Leu Leu Gln Thr Leu Gly Asn Leu Gly Tyr Arg Ala Ser Ala
                245                 250                 255
Lys Lys Ala Gln Ile Cys Gln Lys Gln Val Lys Tyr Leu Gly Tyr Leu
            260                 265                 270
Leu Lys Glu Gly Gln Arg Trp Leu Thr Glu Ala Arg Lys Glu Thr Val
        275                 280                 285
Met Gly Gln Pro Thr Pro Lys Thr Pro Arg Gln Leu Arg Glu Phe Leu
        290                 295                 300
Gly Lys Ala Gly Phe Cys Arg Leu Phe Ile Pro Gly Phe Ala Glu Met
305                 310                 315                 320
Ala Ala Pro Leu Tyr Pro Leu Thr Lys Pro Gly Thr Leu Phe Asn Trp
                325                 330                 335
Gly Pro Asp Gln Gln Lys Ala Tyr Gln Glu Ile Lys Gln Ala Leu Leu
            340                 345                 350
Thr Ala Pro Ala Leu Gly Leu Pro Asp Leu Thr Lys Pro Phe Glu Leu
        355                 360                 365
Phe Val Asp Glu Lys Gln Gly Tyr Ala Lys Gly Val Leu Thr Gln Lys
370                 375                 380
Leu Gly Pro Trp Arg Arg Pro Val Ala Tyr Leu Ser Lys Lys Leu Asp
385                 390                 395                 400
Pro Val Ala Ala Gly Trp Pro Pro Cys Leu Arg Met Val Ala Ala Ile
                405                 410                 415
Ala Val Leu Thr Lys Asp Ala Gly Lys Leu Thr Met Gly Gln Pro Leu
            420                 425                 430
Val Ile Leu Ala Pro His Ala Val Glu Ala Leu Val Lys Gln Pro Pro
        435                 440                 445
Asp Arg Trp Leu Ser Asn Ala Arg Met Thr His Tyr Gln Ala Leu Leu
450                 455                 460
Leu Asp Thr Asp Arg Val Gln Phe Gly Pro Val Val Ala Leu Asn Pro
465                 470                 475                 480
Ala Thr Leu Leu Pro Leu Pro Glu Glu Gly Leu Gln His Asn Cys Leu
                485                 490                 495
Asp Ile Leu Ala Glu Ala His Gly Thr Arg Pro Asp Leu Thr Asp Gln
            500                 505                 510
Pro Leu Pro Asp Ala Asp His Thr Trp Tyr Thr Asp Gly Ser Ser Leu
        515                 520                 525
Leu Gln Glu Gly Gln Arg Lys Ala Gly Ala Ala Val Thr Thr Glu Thr
```

```
                530             535             540
Glu Val Ile Trp Ala Lys Ala Leu Pro Ala Gly Thr Ser Ala Gln Arg
545                 550                 555                 560

Ala Glu Leu Ile Ala Leu Thr Gln Ala Leu Lys Met Ala Glu Gly Lys
                565                 570                 575

Lys Leu Asn Val Tyr Thr Asp Ser Arg Tyr Ala Phe Ala Thr Ala His
                580                 585                 590

Ile His Gly Glu Ile Tyr Arg Arg Gly Trp Leu Thr Ser Glu Gly
                595                 600                 605

Lys Glu Ile Lys Asn Lys Asp Glu Ile Leu Ala Leu Leu Lys Ala Leu
                610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
                645                 650                 655

Arg Lys Ala Ala Ile Thr Glu Thr Pro Asp Thr Ser Thr Leu Leu Ile
                660                 665                 670

Glu Asn Ser Ser Pro
            675

<210> SEQ ID NO 14
<211> LENGTH: 677
<212> TYPE: PRT
<213> ORGANISM: Murine leukemia virus

<400> SEQUENCE: 14

Thr Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
                20                  25                  30

Trp Ala Glu Thr Gly Gly Met Gly Leu Ala Val Arg Gln Ala Pro Leu
                35                  40                  45

Ile Ile Pro Leu Lys Ala Thr Ser Thr Pro Val Ser Ile Lys Gln Tyr
50                  55                  60

Pro Met Ser Gln Glu Ala Arg Leu Gly Ile Lys Pro His Ile Gln Arg
65                  70                  75                  80

Leu Leu Asp Gln Gly Ile Leu Val Pro Cys Gln Ser Pro Trp Asn Thr
                85                  90                  95

Pro Leu Leu Pro Val Lys Lys Pro Gly Thr Asn Asp Tyr Arg Pro Val
                100                 105                 110

Gln Asp Leu Arg Glu Val Asn Lys Arg Val Glu Asp Ile His Pro Thr
                115                 120                 125

Val Pro Asn Pro Tyr Asn Leu Leu Ser Gly Leu Pro Pro Ser His Gln
130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
                180                 185                 190

Lys Asn Ser Pro Thr Leu Phe Asp Glu Ala Leu His Arg Asp Leu Ala
                195                 200                 205

Asp Phe Arg Ile Gln His Pro Asp Leu Ile Leu Leu Gln Tyr Val Asp
                210                 215                 220
```

```
Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
            245                 250                 255

Lys Lys Ala Gln Ile Cys Gln Lys Gln Val Lys Tyr Leu Gly Tyr Leu
            260                 265                 270

Leu Lys Glu Gly Gln Arg Trp Leu Thr Glu Ala Arg Lys Glu Thr Val
        275                 280                 285

Met Gly Gln Pro Thr Pro Lys Thr Pro Arg Gln Leu Arg Glu Phe Leu
    290                 295                 300

Gly Thr Ala Gly Phe Cys Arg Leu Trp Ile Pro Gly Phe Ala Glu Met
305                 310                 315                 320

Ala Ala Pro Leu Tyr Pro Leu Thr Lys Thr Gly Thr Leu Phe Asn Trp
                325                 330                 335

Gly Pro Asp Gln Gln Lys Ala Tyr Gln Glu Ile Lys Gln Ala Leu Leu
            340                 345                 350

Thr Ala Pro Ala Leu Gly Leu Pro Asp Leu Thr Lys Pro Phe Glu Leu
        355                 360                 365

Phe Val Asp Glu Lys Gln Gly Tyr Ala Lys Gly Val Leu Thr Gln Lys
    370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
            420                 425                 430

Val Ile Leu Ala Pro His Ala Val Glu Ala Leu Val Lys Gln Pro Pro
        435                 440                 445

Asp Arg Trp Leu Ser Asn Ala Arg Met Thr His Tyr Gln Ala Leu Leu
    450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
            500                 505                 510

Pro Leu Pro Asp Ala Asp His Thr Trp Tyr Thr Asp Gly Ser Ser Leu
        515                 520                 525

Leu Gln Glu Gly Gln Arg Lys Ala Gly Ala Ala Val Thr Thr Glu Thr
    530                 535                 540

Glu Val Ile Trp Ala Lys Ala Leu Pro Ala Gly Thr Ser Ala Gln Arg
545                 550                 555                 560

Ala Glu Leu Ile Ala Leu Thr Gln Ala Leu Lys Met Ala Glu Gly Lys
                565                 570                 575

Lys Leu Asn Val Tyr Thr Asp Ser Arg Tyr Ala Phe Ala Thr Ala His
            580                 585                 590

Ile His Gly Glu Ile Tyr Arg Arg Gly Leu Leu Thr Ser Glu Gly
        595                 600                 605

Lys Glu Ile Lys Asn Lys Asp Glu Ile Leu Ala Leu Leu Lys Ala Leu
    610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
```

```
              645                 650                 655
Arg Lys Ala Ala Ile Thr Glu Thr Pro Asp Thr Ser Thr Leu Leu Ile
            660                 665                 670
Glu Asn Ser Ser Pro
            675

<210> SEQ ID NO 15
<211> LENGTH: 677
<212> TYPE: PRT
<213> ORGANISM: Unknown
<220> FEATURE:
<223> OTHER INFORMATION: Description of Unknown:
      XMRV3VP35RT sequence

<400> SEQUENCE: 15

Thr Leu Asn Ile Glu Asn Lys Tyr Arg Leu His Glu Thr Ser Lys Glu
1               5                   10                  15

Pro Asp Val Pro Leu Gly Ser Thr Trp Leu Ser Asp Phe Pro Gln Ala
            20                  25                  30

Trp Ala Glu Thr Gly Gly Met Gly Leu Ala Val Arg Gln Ala Pro Leu
        35                  40                  45

Ile Ile Pro Leu Lys Ala Thr Ser Thr Pro Val Ser Ile Lys Gln Tyr
 50                 55                  60

Pro Met Ser Gln Glu Ala Arg Leu Gly Ile Lys Pro His Ile Gln Arg
65                  70                  75                  80

Leu Leu Asp Gln Gly Ile Leu Val Pro Cys Gln Ser Pro Trp Asn Thr
                85                  90                  95

Pro Leu Leu Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
        115                 120                 125

Val Pro Asn Pro Tyr Asn Leu Leu Ser Gly Leu Pro Pro Ser His Gln
130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
            180                 185                 190

Lys Asn Ser Pro Thr Leu Phe Asp Glu Ala Leu His Arg Asp Leu Ala
        195                 200                 205

Asp Phe Arg Ile Gln His Pro Asp Leu Ile Leu Leu Gln Tyr Val Asp
    210                 215                 220

Asp Leu Leu Leu Ala Ala Thr Ser Glu Gln Asp Cys Gln Arg Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
            260                 265                 270

Leu Lys Glu Gly Gln Arg Trp Leu Thr Glu Ala Arg Lys Glu Thr Val
        275                 280                 285

Met Gly Gln Pro Thr Pro Lys Thr Pro Arg Gln Leu Arg Glu Phe Leu
    290                 295                 300

Gly Thr Ala Gly Phe Cys Arg Leu Trp Ile Pro Gly Phe Ala Glu Met
305                 310                 315                 320
```

```
Ala Ala Pro Leu Tyr Pro Leu Thr Lys Thr Gly Thr Leu Phe Asn Trp
            325                 330                 335

Gly Pro Asp Gln Gln Lys Ala Tyr Gln Glu Ile Lys Gln Ala Leu Leu
        340                 345                 350

Thr Ala Pro Ala Leu Gly Leu Pro Asp Leu Thr Lys Pro Phe Glu Leu
    355                 360                 365

Phe Val Asp Glu Lys Gln Gly Tyr Ala Lys Gly Val Leu Thr Gln Lys
370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
            420                 425                 430

Val Ile Leu Ala Pro His Ala Val Glu Ala Leu Val Lys Gln Pro Pro
        435                 440                 445

Asp Arg Trp Leu Ser Asn Ala Arg Met Thr His Tyr Gln Ala Met Leu
    450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Lys Glu Ala Pro His Asp Cys Leu
                485                 490                 495

Glu Ile Leu Ala Glu Thr His Gly Thr Arg Pro Asp Leu Thr Asp Gln
            500                 505                 510

Pro Ile Pro Asp Ala Asp Tyr Thr Trp Tyr Thr Asp Gly Ser Ser Phe
        515                 520                 525

Leu Gln Glu Gly Gln Arg Arg Ala Gly Ala Ala Val Thr Thr Glu Thr
    530                 535                 540

Glu Val Ile Trp Ala Arg Ala Leu Pro Ala Gly Thr Ser Ala Gln Arg
545                 550                 555                 560

Ala Glu Leu Ile Ala Leu Thr Gln Ala Leu Lys Met Ala Glu Gly Lys
                565                 570                 575

Lys Leu Asn Val Tyr Thr Asp Ser Arg Tyr Ala Phe Ala Thr Ala His
            580                 585                 590

Val His Gly Glu Ile Tyr Arg Arg Gly Leu Leu Thr Ser Glu Gly
        595                 600                 605

Arg Glu Ile Lys Asn Lys Asn Glu Ile Leu Ala Leu Leu Lys Ala Leu
    610                 615                 620

Phe Leu Pro Lys Arg Leu Ser Ile Ile His Cys Pro Gly His Gln Lys
625                 630                 635                 640

Gly Asn Ser Ala Glu Ala Arg Gly Asn Arg Met Ala Asp Gln Ala Ala
                645                 650                 655

Arg Glu Ala Ala Met Lys Ala Val Leu Glu Thr Ser Thr Leu Leu Ile
            660                 665                 670

Glu Asp Ser Thr Pro
            675

<210> SEQ ID NO 16
<211> LENGTH: 682
<212> TYPE: PRT
<213> ORGANISM: Gibbon ape leukemia virus

<400> SEQUENCE: 16

Val Leu Asn Leu Glu Glu Glu Tyr Arg Leu His Glu Lys Pro Val Pro
1               5                   10                  15
```

```
Ser Ser Ile Asp Pro Ser Trp Leu Gln Leu Phe Pro Thr Val Trp Ala
            20                  25                  30
Glu Arg Ala Gly Met Gly Leu Ala Asn Gln Val Pro Val Val Val
        35                  40                  45
Glu Leu Arg Ser Gly Ala Ser Pro Val Ala Val Arg Gln Tyr Pro Met
50                  55                  60
Ser Lys Glu Ala Arg Glu Gly Ile Arg Pro His Ile Gln Lys Phe Leu
65                  70                  75                  80
Asp Leu Gly Val Leu Val Pro Cys Arg Ser Pro Trp Asn Thr Pro Leu
                85                  90                  95
Leu Pro Val Lys Lys Pro Gly Thr Asn Asp Tyr Arg Pro Val Gln Asp
            100                 105                 110
Leu Arg Glu Ile Asn Lys Arg Val Gln Asp Ile His Pro Thr Val Pro
        115                 120                 125
Asn Pro Tyr Asn Leu Leu Ser Ser Leu Pro Pro Ser Tyr Thr Trp Tyr
    130                 135                 140
Ser Val Leu Asp Leu Lys Asp Ala Phe Phe Cys Leu Arg Leu His Pro
145                 150                 155                 160
Asn Ser Gln Pro Leu Phe Ala Phe Glu Trp Lys Asp Pro Glu Lys Gly
                165                 170                 175
Asn Thr Gly Gln Leu Thr Trp Thr Arg Leu Pro Gln Gly Phe Lys Asn
            180                 185                 190
Ser Pro Thr Leu Phe Asp Glu Ala Leu His Arg Asp Leu Ala Pro Phe
        195                 200                 205
Arg Ala Leu Asn Pro Gln Val Val Leu Leu Gln Tyr Val Asp Asp Leu
    210                 215                 220
Leu Val Ala Ala Pro Thr Tyr Glu Asp Cys Lys Lys Gly Thr Gln Lys
225                 230                 235                 240
Leu Leu Gln Glu Leu Ser Lys Leu Gly Tyr Arg Val Ser Ala Lys Lys
                245                 250                 255
Ala Gln Leu Cys Gln Arg Glu Val Thr Tyr Leu Gly Tyr Leu Leu Lys
            260                 265                 270
Glu Gly Lys Arg Trp Leu Thr Pro Ala Arg Lys Ala Thr Val Met Lys
        275                 280                 285
Ile Pro Val Pro Thr Thr Pro Arg Gln Val Arg Glu Phe Leu Gly Thr
    290                 295                 300
Ala Gly Phe Cys Arg Leu Trp Ile Pro Gly Phe Ala Ser Leu Ala Ala
305                 310                 315                 320
Pro Leu Tyr Pro Leu Thr Lys Glu Ser Ile Pro Phe Ile Trp Thr Glu
                325                 330                 335
Glu His Gln Gln Ala Phe Asp His Ile Lys Lys Ala Leu Leu Ser Ala
            340                 345                 350
Pro Ala Leu Ala Leu Pro Asp Leu Thr Lys Pro Phe Thr Leu Tyr Ile
        355                 360                 365
Asp Glu Arg Ala Gly Val Ala Arg Gly Val Leu Thr Gln Thr Leu Gly
    370                 375                 380
Pro Trp Arg Arg Pro Val Ala Tyr Leu Ser Lys Lys Leu Asp Pro Val
385                 390                 395                 400
Ala Ser Gly Trp Pro Thr Cys Leu Lys Ala Val Ala Ala Val Ala Leu
                405                 410                 415
Leu Leu Lys Asp Ala Asp Lys Leu Thr Leu Gly Gln Asn Val Thr Val
            420                 425                 430
```

```
Ile Ala Ser His Ser Leu Glu Ser Ile Val Arg Gln Pro Asp Arg
            435                 440                 445

Trp Met Thr Asn Ala Arg Met Thr His Tyr Gln Ser Leu Leu Asn
450                 455                 460

Glu Arg Val Ser Phe Ala Pro Pro Ala Val Leu Asn Pro Ala Thr Leu
465                 470                 475                 480

Leu Pro Val Glu Ser Glu Ala Thr Pro Val His Arg Cys Ser Glu Ile
                485                 490                 495

Leu Ala Glu Glu Thr Gly Thr Arg Arg Asp Leu Glu Asp Gln Pro Leu
            500                 505                 510

Pro Gly Val Pro Thr Trp Tyr Thr Asp Gly Ser Ser Phe Ile Thr Glu
        515                 520                 525

Gly Lys Arg Arg Ala Gly Ala Pro Ile Val Asp Gly Lys Arg Thr Val
    530                 535                 540

Trp Ala Ser Ser Leu Pro Glu Gly Thr Ser Ala Gln Lys Ala Glu Leu
545                 550                 555                 560

Val Ala Leu Thr Gln Ala Leu Arg Leu Ala Glu Gly Lys Asn Ile Asn
                565                 570                 575

Ile Tyr Thr Asp Ser Arg Tyr Ala Phe Ala Thr Ala His Ile His Gly
            580                 585                 590

Ala Ile Tyr Lys Gln Arg Gly Leu Leu Thr Ser Ala Gly Lys Asp Ile
        595                 600                 605

Lys Asn Lys Glu Glu Ile Leu Ala Leu Leu Glu Ala Ile His Leu Pro
    610                 615                 620

Arg Arg Val Ala Ile Ile His Cys Pro Gly His Gln Arg Gly Ser Asn
625                 630                 635                 640

Pro Val Ala Thr Gly Asn Arg Arg Ala Asp Glu Ala Ala Lys Gln Ala
                645                 650                 655

Ala Leu Ser Thr Arg Val Leu Ala Gly Thr Thr Lys Pro Gln Glu Pro
            660                 665                 670

Ile Glu Pro Ala Gln Glu Lys Thr Arg Pro
        675                 680

<210> SEQ ID NO 17
<211> LENGTH: 761
<212> TYPE: PRT
<213> ORGANISM: Unknown
<220> FEATURE:
<223> OTHER INFORMATION: Description of Unknown:
      sfvRT sequence

<400> SEQUENCE: 17

Met Asp Pro Leu Gln Leu Leu Gln Pro Leu Glu Ala Glu Ile Lys Gly
1               5                   10                  15

Thr Lys Leu Lys Ala His Trp Asp Ser Gly Ala Thr Ile Thr Cys Val
            20                  25                  30

Pro Glu Ala Phe Leu Glu Asp Glu Arg Pro Ile Gln Thr Met Leu Ile
        35                  40                  45

Lys Thr Ile His Gly Glu Lys Gln Gln Asp Val Tyr Tyr Leu Thr Phe
    50                  55                  60

Lys Val Gln Gly Arg Lys Val Glu Ala Glu Val Leu Ala Ser Pro Tyr
65                  70                  75                  80

Asp Tyr Ile Leu Leu Asn Pro Ser Asp Val Pro Trp Leu Met Lys Lys
                85                  90                  95

Pro Leu Gln Leu Thr Val Leu Val Pro Leu His Glu Tyr Gln Glu Arg
            100                 105                 110
```

-continued

```
Leu Leu Gln Gln Thr Ala Leu Pro Lys Glu Gln Lys Glu Leu Leu Gln
            115                 120                 125
Lys Leu Phe Leu Lys Tyr Asp Ala Leu Trp Gln His Trp Glu Asn Gln
        130                 135                 140
Val Gly His Arg Arg Ile Lys Pro His Asn Ile Ala Thr Gly Thr Leu
145                 150                 155                 160
Ala Pro Arg Pro Gln Lys Gln Tyr Pro Ile Asn Pro Lys Ala Lys Pro
                    165                 170                 175
Ser Ile Gln Ile Val Ile Asp Asp Leu Leu Lys Gln Gly Val Leu Ile
                180                 185                 190
Gln Gln Asn Ser Thr Met Asn Thr Pro Val Tyr Pro Val Pro Lys Pro
            195                 200                 205
Asp Gly Lys Trp Arg Met Val Leu Asp Tyr Arg Glu Val Asn Lys Thr
        210                 215                 220
Ile Pro Leu Ile Ala Ala Gln Asn Gln His Ser Ala Gly Ile Leu Ser
225                 230                 235                 240
Ser Ile Tyr Arg Gly Lys Tyr Lys Thr Thr Leu Asp Leu Thr Asn Gly
                    245                 250                 255
Phe Trp Ala His Pro Ile Thr Pro Glu Ser Tyr Trp Leu Thr Ala Phe
                260                 265                 270
Thr Trp Gln Gly Lys Gln Tyr Cys Trp Thr Arg Leu Pro Gln Gly Phe
            275                 280                 285
Leu Asn Ser Pro Ala Leu Phe Thr Ala Asp Val Val Asp Leu Leu Lys
        290                 295                 300
Glu Ile Pro Asn Val Gln Ala Tyr Val Asp Asp Ile Tyr Ile Ser His
305                 310                 315                 320
Asp Asp Pro Gln Glu His Leu Glu Gln Leu Glu Lys Ile Phe Ser Ile
                    325                 330                 335
Leu Leu Asn Ala Gly Tyr Val Val Ser Leu Lys Lys Ser Glu Ile Ala
                340                 345                 350
Gln Arg Glu Val Glu Phe Leu Gly Phe Asn Ile Thr Lys Glu Gly Arg
            355                 360                 365
Gly Leu Thr Asp Thr Phe Lys Gln Lys Leu Leu Asn Ile Thr Pro Pro
        370                 375                 380
Lys Asp Leu Lys Gln Leu Gln Ser Ile Leu Gly Leu Leu Asn Phe Ala
385                 390                 395                 400
Arg Asn Phe Ile Pro Asn Tyr Ser Glu Leu Val Lys Pro Leu Tyr Thr
                    405                 410                 415
Ile Val Ala Asn Ala Asn Gly Lys Phe Ile Ser Trp Thr Glu Asp Asn
                420                 425                 430
Ser Asn Gln Leu Gln His Ile Ile Ser Val Leu Asn Gln Ala Asp Asn
            435                 440                 445
Leu Glu Glu Arg Asn Pro Glu Thr Arg Leu Ile Lys Val Asn Ser
        450                 455                 460
Ser Pro Ser Ala Gly Tyr Ile Arg Tyr Tyr Asn Glu Gly Ser Lys Arg
465                 470                 475                 480
Pro Ile Met Tyr Val Asn Tyr Ile Phe Ser Lys Ala Glu Ala Lys Phe
                    485                 490                 495
Thr Gln Thr Glu Lys Leu Leu Thr Thr Met His Lys Gly Leu Ile Lys
                500                 505                 510
Ala Met Asp Leu Ala Met Gly Gln Glu Ile Leu Val Tyr Ser Pro Ile
            515                 520                 525
```

```
Val Ser Met Thr Lys Ile Gln Arg Thr Pro Leu Pro Glu Arg Lys Ala
    530                 535                 540
Leu Pro Val Arg Trp Ile Thr Trp Met Thr Tyr Leu Glu Asp Pro Arg
545                 550                 555                 560
Ile Gln Phe His Tyr Asp Lys Ser Leu Pro Glu Leu Gln Gln Ile Pro
                565                 570                 575
Asn Val Thr Glu Asp Val Ile Ala Lys Thr Lys His Pro Ser Glu Phe
            580                 585                 590
Ala Met Val Phe Tyr Thr Asp Gly Ser Ala Ile Lys His Pro Asp Val
        595                 600                 605
Asn Lys Ser His Ser Ala Gly Met Gly Ile Ala Gln Val Gln Phe Ile
    610                 615                 620
Pro Glu Tyr Lys Ile Val His Gln Trp Ser Ile Pro Leu Gly Asp His
625                 630                 635                 640
Thr Ala Gln Leu Ala Glu Ile Ala Ala Val Glu Phe Ala Cys Lys Lys
                645                 650                 655
Ala Leu Lys Ile Ser Gly Pro Val Leu Ile Val Thr Asp Ser Phe Tyr
            660                 665                 670
Val Ala Glu Ser Ala Asn Lys Glu Leu Pro Tyr Trp Lys Ser Asn Gly
        675                 680                 685
Phe Leu Asn Asn Lys Lys Pro Leu Arg His Val Ser Lys Trp Lys
    690                 695                 700
Ser Ile Ala Glu Cys Leu Gln Leu Lys Pro Asp Ile Ile Met His
705                 710                 715                 720
Glu Lys Gly His Gln Gln Pro Met Thr Thr Leu His Thr Glu Gly Asn
                725                 730                 735
Asn Leu Ala Asp Lys Leu Ala Thr Gln Gly Ser Tyr Val Val His Cys
            740                 745                 750
Asn Thr Thr Pro Ser Leu Asp Ala Glu
        755                 760

<210> SEQ ID NO 18
<211> LENGTH: 762
<212> TYPE: PRT
<213> ORGANISM: Unknown
<220> FEATURE:
<223> OTHER INFORMATION: Description of Unknown:
      foamyRT sequence

<400> SEQUENCE: 18

Met Asn Pro Leu Gln Leu Leu Gln Pro Leu Pro Ala Glu Ile Lys Gly
1               5                   10                  15
Thr Lys Leu Leu Ala His Trp Asp Ser Gly Ala Thr Ile Thr Cys Ile
            20                  25                  30
Pro Glu Ser Phe Leu Glu Asp Gln Pro Ile Lys Lys Thr Leu Ile
        35                  40                  45
Lys Thr Ile His Gly Glu Lys Gln Gln Asn Val Tyr Tyr Val Thr Phe
    50                  55                  60
Lys Val Lys Gly Arg Lys Val Glu Ala Glu Val Ile Ala Ser Pro Tyr
65                  70                  75                  80
Glu Tyr Ile Leu Leu Ser Pro Thr Asp Val Pro Trp Leu Thr Gln Gln
                85                  90                  95
Pro Leu Gln Leu Thr Ile Leu Val Pro Leu Gln Glu Tyr Gln Glu Lys
            100                 105                 110
Ile Leu Ser Lys Thr Ala Leu Pro Glu Asp Gln Lys Gln Gln Leu Lys
        115                 120                 125
```

```
Thr Leu Phe Val Lys Tyr Asp Asn Leu Trp Gln His Trp Glu Asn Gln
        130                 135                 140

Val Gly His Arg Lys Ile Arg Pro His Asn Ile Ala Thr Gly Asp Tyr
145                 150                 155                 160

Pro Pro Arg Pro Gln Lys Gln Tyr Pro Ile Asn Pro Lys Ala Lys Pro
                165                 170                 175

Ser Ile Gln Ile Val Ile Asp Asp Leu Leu Lys Gln Gly Val Leu Thr
                180                 185                 190

Pro Gln Asn Ser Thr Met Asn Thr Pro Val Tyr Pro Val Pro Lys Pro
                195                 200                 205

Asp Gly Arg Trp Arg Met Val Leu Asp Tyr Arg Glu Val Asn Lys Thr
210                 215                 220

Ile Pro Leu Thr Ala Ala Gln Asn Gln His Ser Ala Gly Ile Leu Ala
225                 230                 235                 240

Thr Ile Val Arg Gln Lys Tyr Lys Thr Thr Leu Asp Leu Ala Asn Gly
                245                 250                 255

Phe Trp Ala His Pro Ile Thr Pro Glu Ser Tyr Trp Leu Thr Ala Phe
                260                 265                 270

Thr Trp Gln Gly Lys Gln Tyr Cys Trp Thr Arg Leu Pro Gln Gly Phe
                275                 280                 285

Leu Asn Ser Pro Ala Leu Phe Thr Ala Asp Val Val Asp Leu Leu Lys
290                 295                 300

Glu Ile Pro Asn Val Gln Val Tyr Val Asp Asp Ile Tyr Leu Ser His
305                 310                 315                 320

Asp Asp Pro Lys Glu His Val Gln Gln Leu Lys Val Phe Gln Ile
                325                 330                 335

Leu Leu Gln Ala Gly Tyr Val Val Ser Leu Lys Lys Ser Glu Ile Gly
                340                 345                 350

Gln Lys Thr Val Glu Phe Leu Gly Phe Asn Ile Thr Lys Glu Gly Arg
                355                 360                 365

Gly Leu Thr Asp Thr Phe Lys Thr Lys Leu Leu Asn Ile Thr Pro Pro
                370                 375                 380

Lys Asp Leu Lys Gln Leu Gln Ser Ile Leu Gly Leu Leu Asn Phe Ala
385                 390                 395                 400

Arg Asn Phe Ile Pro Asn Phe Ala Glu Leu Val Gln Pro Leu Tyr Asn
                405                 410                 415

Leu Ile Ala Ser Ala Lys Gly Lys Tyr Ile Glu Trp Ser Glu Glu Asn
                420                 425                 430

Thr Lys Gln Leu Asn Met Val Ile Glu Ala Leu Asn Thr Ala Ser Asn
                435                 440                 445

Leu Glu Glu Arg Leu Pro Glu Gln Arg Leu Val Ile Lys Val Asn Thr
450                 455                 460

Ser Pro Ser Ala Gly Tyr Val Arg Tyr Asn Glu Thr Gly Lys Lys
465                 470                 475                 480

Pro Ile Met Tyr Leu Asn Tyr Val Phe Ser Lys Ala Glu Leu Lys Phe
                485                 490                 495

Ser Met Leu Glu Lys Leu Leu Thr Thr Met His Lys Ala Leu Ile Lys
                500                 505                 510

Ala Met Asp Leu Ala Met Gly Gln Glu Ile Leu Val Tyr Ser Pro Ile
                515                 520                 525

Val Ser Met Thr Lys Ile Gln Lys Thr Pro Leu Pro Glu Arg Lys Ala
530                 535                 540
```

```
Leu Pro Ile Arg Trp Ile Thr Trp Met Thr Tyr Leu Glu Asp Pro Arg
545                 550                 555                 560

Ile Gln Phe His Tyr Asp Lys Thr Leu Pro Glu Leu Lys His Ile Pro
            565                 570                 575

Asp Val Tyr Thr Ser Ser Gln Ser Pro Val Lys His Pro Ser Gln Tyr
        580                 585                 590

Glu Gly Val Phe Tyr Thr Asp Gly Ser Ala Ile Lys Ser Pro Asp Pro
    595                 600                 605

Thr Lys Ser Asn Asn Ala Gly Met Gly Ile Val His Ala Thr Tyr Lys
610                 615                 620

Pro Glu Tyr Gln Val Leu Asn Gln Trp Ser Ile Pro Leu Gly Asn His
625                 630                 635                 640

Thr Ala Gln Met Ala Glu Ile Ala Ala Val Glu Phe Ala Cys Lys Lys
            645                 650                 655

Ala Leu Lys Ile Pro Gly Pro Val Leu Val Ile Thr Asp Ser Phe Tyr
        660                 665                 670

Val Ala Glu Ser Ala Asn Lys Glu Leu Pro Tyr Trp Lys Ser Asn Gly
    675                 680                 685

Phe Val Asn Asn Lys Lys Lys Pro Leu Lys His Ile Ser Lys Trp Lys
690                 695                 700

Ser Ile Ala Glu Cys Leu Ser Met Lys Pro Asp Ile Thr Ile Gln His
705                 710                 715                 720

Glu Lys Gly Ile Ser Leu Gln Ile Pro Val Phe Ile Leu Lys Gly Asn
            725                 730                 735

Ala Leu Ala Asp Lys Leu Ala Thr Gln Gly Ser Tyr Val Val Asn Cys
        740                 745                 750

Asn Thr Lys Lys Pro Asn Leu Asp Ala Glu
755                 760

<210> SEQ ID NO 19
<211> LENGTH: 560
<212> TYPE: PRT
<213> ORGANISM: Human immunodeficiency virus

<400> SEQUENCE: 19

Pro Ile Ser Pro Ile Glu Thr Val Pro Val Lys Leu Lys Pro Gly Met
1               5                   10                  15

Asp Gly Pro Lys Val Lys Gln Trp Pro Leu Thr Glu Glu Lys Ile Lys
            20                  25                  30

Ala Leu Val Glu Ile Cys Thr Glu Met Glu Lys Glu Gly Lys Ile Ser
        35                  40                  45

Lys Ile Gly Pro Glu Asn Pro Tyr Asn Thr Pro Val Phe Ala Ile Lys
    50                  55                  60

Lys Lys Asp Ser Thr Lys Trp Arg Lys Leu Val Asp Phe Arg Glu Leu
65                  70                  75                  80

Asn Lys Arg Thr Gln Asp Phe Trp Glu Val Gln Leu Gly Ile Pro His
            85                  90                  95

Pro Ala Gly Leu Lys Lys Lys Ser Val Thr Val Leu Asp Val Gly
        100                 105                 110

Asp Ala Tyr Phe Ser Val Pro Leu Asp Glu Asp Phe Arg Lys Tyr Thr
    115                 120                 125

Ala Phe Thr Ile Pro Ser Ile Asn Asn Glu Thr Pro Gly Ile Arg Tyr
130                 135                 140

Gln Tyr Asn Val Leu Pro Gln Gly Trp Lys Gly Ser Pro Ala Ile Phe
145                 150                 155                 160
```

```
Gln Ser Ser Met Thr Lys Ile Leu Glu Pro Phe Arg Lys Gln Asn Pro
                165                 170                 175

Asp Ile Val Ile Tyr Gln Tyr Met Asp Asp Leu Tyr Val Gly Ser Asp
            180                 185                 190

Leu Glu Ile Gly Gln His Arg Thr Lys Ile Glu Glu Leu Arg Gln His
        195                 200                 205

Leu Leu Arg Trp Gly Leu Thr Thr Pro Asp Lys Lys His Gln Lys Glu
    210                 215                 220

Pro Pro Phe Leu Trp Met Gly Tyr Glu Leu His Pro Asp Lys Trp Thr
225                 230                 235                 240

Val Gln Pro Ile Val Leu Pro Glu Lys Asp Ser Trp Thr Val Asn Asp
                245                 250                 255

Ile Gln Lys Leu Val Gly Lys Leu Asn Trp Ala Ser Gln Ile Tyr Pro
            260                 265                 270

Gly Ile Lys Val Arg Gln Leu Cys Lys Leu Leu Arg Gly Thr Lys Ala
        275                 280                 285

Leu Thr Glu Val Ile Pro Leu Thr Glu Glu Ala Glu Leu Glu Leu Ala
    290                 295                 300

Glu Asn Arg Glu Ile Leu Lys Glu Pro Val His Gly Val Tyr Tyr Asp
305                 310                 315                 320

Pro Ser Lys Asp Leu Ile Ala Glu Ile Gln Lys Gln Gly Gln Gly Gln
                325                 330                 335

Trp Thr Tyr Gln Ile Tyr Gln Glu Pro Phe Lys Asn Leu Lys Thr Gly
            340                 345                 350

Lys Tyr Ala Arg Met Arg Gly Ala His Thr Asn Asp Val Lys Gln Leu
        355                 360                 365

Thr Glu Ala Val Gln Lys Ile Thr Thr Glu Ser Ile Val Ile Trp Gly
    370                 375                 380

Lys Thr Pro Lys Phe Lys Leu Pro Ile Gln Lys Glu Thr Trp Glu Thr
385                 390                 395                 400

Trp Trp Thr Glu Tyr Trp Gln Ala Thr Trp Ile Pro Glu Trp Glu Phe
                405                 410                 415

Val Asn Thr Pro Pro Leu Val Lys Leu Trp Tyr Gln Leu Glu Lys Glu
            420                 425                 430

Pro Ile Val Gly Ala Glu Thr Phe Tyr Val Asp Gly Ala Ala Asn Arg
        435                 440                 445

Glu Thr Lys Leu Gly Lys Ala Gly Tyr Val Thr Asn Arg Gly Arg Gln
    450                 455                 460

Lys Val Val Thr Leu Thr Asp Thr Thr Asn Gln Lys Thr Glu Leu Gln
465                 470                 475                 480

Ala Ile Tyr Leu Ala Leu Gln Asp Ser Gly Leu Glu Val Asn Ile Val
                485                 490                 495

Thr Asp Ser Gln Tyr Ala Leu Gly Ile Ile Gln Ala Gln Pro Asp Gln
            500                 505                 510

Ser Glu Ser Glu Leu Val Asn Gln Ile Ile Glu Gln Leu Ile Lys Lys
        515                 520                 525

Glu Lys Val Tyr Leu Ala Trp Val Pro Ala His Lys Gly Ile Gly Gly
    530                 535                 540

Asn Glu Gln Val Asp Lys Leu Val Ser Ala Gly Ile Arg Lys Val Leu
545                 550                 555                 560

<210> SEQ ID NO 20
<211> LENGTH: 440
```

```
<212> TYPE: PRT
<213> ORGANISM: Human immunodeficiency virus

<400> SEQUENCE: 20
```

| | | | | | | | | | | | | | | |
|---|---|---|---|---|---|---|---|---|---|---|---|---|---|---|
| Pro | Ile | Ser | Pro | Ile | Glu | Thr | Val | Pro | Val | Lys | Leu | Lys | Pro | Gly | Met |
| 1 | | | | 5 | | | | | 10 | | | | | 15 | |

| Asp | Gly | Pro | Lys | Val | Lys | Gln | Trp | Pro | Leu | Thr | Glu | Glu | Lys | Ile | Lys |
|---|---|---|---|---|---|---|---|---|---|---|---|---|---|---|---|
| | | | 20 | | | | | 25 | | | | | 30 | | |

| Ala | Leu | Val | Glu | Ile | Cys | Thr | Glu | Met | Glu | Lys | Glu | Gly | Lys | Ile | Ser |
| | | | 35 | | | | | 40 | | | | | 45 | | |

| Lys | Ile | Gly | Pro | Glu | Asn | Pro | Tyr | Asn | Thr | Pro | Val | Phe | Ala | Ile | Lys |
| 50 | | | | | 55 | | | | | 60 | | | | | |

| Lys | Lys | Asp | Ser | Thr | Lys | Trp | Arg | Lys | Leu | Val | Asp | Phe | Arg | Glu | Leu |
| 65 | | | | | 70 | | | | | 75 | | | | | 80 |

| Asn | Lys | Arg | Thr | Gln | Asp | Phe | Trp | Glu | Val | Gln | Leu | Gly | Ile | Pro | His |
| | | | | 85 | | | | | 90 | | | | | 95 | |

| Pro | Ala | Gly | Leu | Lys | Lys | Lys | Ser | Val | Thr | Val | Leu | Asp | Val | Gly |
| | | | 100 | | | | | 105 | | | | | 110 | | |

| Asp | Ala | Tyr | Phe | Ser | Val | Pro | Leu | Asp | Glu | Asp | Phe | Arg | Lys | Tyr | Thr |
| | | | 115 | | | | | 120 | | | | | 125 | | |

| Ala | Phe | Thr | Ile | Pro | Ser | Ile | Asn | Asn | Glu | Thr | Pro | Gly | Ile | Arg | Tyr |
| 130 | | | | | 135 | | | | | 140 | | | | | |

| Gln | Tyr | Asn | Val | Leu | Pro | Gln | Gly | Trp | Lys | Gly | Ser | Pro | Ala | Ile | Phe |
| 145 | | | | | 150 | | | | | 155 | | | | | 160 |

| Gln | Ser | Ser | Met | Thr | Lys | Ile | Leu | Glu | Pro | Phe | Arg | Lys | Gln | Asn | Pro |
| | | | | 165 | | | | | 170 | | | | | 175 | |

| Asp | Ile | Val | Ile | Tyr | Gln | Tyr | Met | Asp | Asp | Leu | Tyr | Val | Gly | Ser | Asp |
| | | | 180 | | | | | 185 | | | | | 190 | | |

| Leu | Glu | Ile | Gly | Gln | His | Arg | Thr | Lys | Ile | Glu | Glu | Leu | Arg | Gln | His |
| | | | 195 | | | | | 200 | | | | | 205 | | |

| Leu | Leu | Arg | Trp | Gly | Leu | Thr | Thr | Pro | Asp | Lys | Lys | His | Gln | Lys | Glu |
| 210 | | | | | 215 | | | | | 220 | | | | | |

| Pro | Pro | Phe | Leu | Trp | Met | Gly | Tyr | Glu | Leu | His | Pro | Asp | Lys | Trp | Thr |
| 225 | | | | | 230 | | | | | 235 | | | | | 240 |

| Val | Gln | Pro | Ile | Val | Leu | Pro | Glu | Lys | Asp | Ser | Trp | Thr | Val | Asn | Asp |
| | | | | 245 | | | | | 250 | | | | | 255 | |

| Ile | Gln | Lys | Leu | Val | Gly | Lys | Leu | Asn | Trp | Ala | Ser | Gln | Ile | Tyr | Pro |
| | | | 260 | | | | | 265 | | | | | 270 | | |

| Gly | Ile | Lys | Val | Arg | Gln | Leu | Cys | Lys | Leu | Leu | Arg | Gly | Thr | Lys | Ala |
| | | | 275 | | | | | 280 | | | | | 285 | | |

| Leu | Thr | Glu | Val | Ile | Pro | Leu | Thr | Glu | Glu | Ala | Glu | Leu | Glu | Leu | Ala |
| | 290 | | | | | 295 | | | | | 300 | | | | |

| Glu | Asn | Arg | Glu | Ile | Leu | Lys | Glu | Pro | Val | His | Gly | Val | Tyr | Tyr | Asp |
| 305 | | | | | 310 | | | | | 315 | | | | | 320 |

| Pro | Ser | Lys | Asp | Leu | Ile | Ala | Glu | Ile | Gln | Lys | Gln | Gly | Gln | Gly | Gln |
| | | | 325 | | | | | 330 | | | | | 335 | | |

| Trp | Thr | Tyr | Gln | Ile | Tyr | Gln | Glu | Pro | Phe | Lys | Asn | Leu | Lys | Thr | Gly |
| | | | 340 | | | | | 345 | | | | | 350 | | |

| Lys | Tyr | Ala | Arg | Met | Arg | Gly | Ala | His | Thr | Asn | Asp | Val | Lys | Gln | Leu |
| | | | 355 | | | | | 360 | | | | | 365 | | |

| Thr | Glu | Ala | Val | Gln | Lys | Ile | Thr | Thr | Glu | Ser | Ile | Val | Ile | Trp | Gly |
| | 370 | | | | | 375 | | | | | 380 | | | | |

| Lys | Thr | Pro | Lys | Phe | Lys | Leu | Pro | Ile | Gln | Lys | Glu | Thr | Trp | Glu | Thr |
| 385 | | | | | 390 | | | | | 395 | | | | | 400 |

```
Trp Trp Thr Glu Tyr Trp Gln Ala Thr Trp Ile Pro Glu Trp Glu Phe
                405                 410                 415

Val Asn Thr Pro Pro Leu Val Lys Leu Trp Tyr Gln Leu Glu Lys Glu
                420                 425                 430

Pro Ile Val Gly Ala Glu Thr Phe
            435                 440

<210> SEQ ID NO 21
<211> LENGTH: 572
<212> TYPE: PRT
<213> ORGANISM: Rous sarcoma virus

<400> SEQUENCE: 21

Thr Val Ala Leu His Leu Ala Ile Pro Leu Lys Trp Lys Pro Asp His
1               5                   10                  15

Thr Pro Val Trp Ile Asp Gln Trp Pro Leu Pro Glu Gly Lys Leu Val
                20                  25                  30

Ala Leu Thr Gln Leu Val Glu Lys Glu Leu Gln Leu Gly His Ile Glu
            35                  40                  45

Pro Ser Leu Ser Cys Trp Asn Thr Pro Val Phe Val Ile Arg Lys Ala
50                  55                  60

Ser Gly Ser Tyr Arg Leu Leu His Asp Leu Arg Ala Val Asn Ala Lys
65                  70                  75                  80

Leu Val Pro Phe Gly Ala Val Gln Gln Gly Ala Pro Val Leu Ser Ala
                85                  90                  95

Leu Pro Arg Gly Trp Pro Leu Met Val Leu Asp Leu Lys Asp Cys Phe
            100                 105                 110

Phe Ser Ile Pro Leu Ala Glu Gln Asp Arg Glu Ala Phe Ala Phe Thr
        115                 120                 125

Leu Pro Ser Val Asn Asn Gln Ala Pro Ala Arg Arg Phe Gln Trp Lys
130                 135                 140

Val Leu Pro Gln Gly Met Thr Cys Ser Pro Thr Ile Cys Gln Leu Val
145                 150                 155                 160

Val Gly Gln Val Leu Glu Pro Leu Arg Leu Lys His Pro Ser Leu Cys
                165                 170                 175

Met Leu His Tyr Met Asp Asp Leu Leu Leu Ala Ala Ser Ser His Asp
            180                 185                 190

Gly Leu Glu Ala Ala Gly Glu Glu Val Ile Ser Thr Leu Glu Arg Ala
        195                 200                 205

Gly Phe Thr Ile Ser Pro Asp Lys Val Gln Arg Glu Pro Gly Val Gln
    210                 215                 220

Tyr Leu Gly Tyr Lys Leu Gly Ser Thr Tyr Val Ala Pro Val Gly Leu
225                 230                 235                 240

Val Ala Glu Pro Arg Ile Ala Thr Leu Trp Asp Val Gln Lys Leu Val
                245                 250                 255

Gly Ser Leu Gln Trp Leu Arg Pro Ala Leu Gly Ile Pro Pro Arg Leu
            260                 265                 270

Met Gly Pro Phe Tyr Glu Gln Leu Arg Gly Ser Asp Pro Asn Glu Ala
        275                 280                 285

Arg Glu Trp Asn Leu Asp Met Lys Met Ala Trp Arg Glu Ile Val Arg
    290                 295                 300

Leu Ser Thr Thr Ala Ala Leu Glu Arg Trp Asp Pro Ala Leu Pro Leu
305                 310                 315                 320

Glu Gly Ala Val Ala Arg Cys Glu Gln Gly Ala Ile Gly Val Leu Gly
```

```
                    325                 330                 335
Gln Gly Leu Ser Thr His Pro Arg Pro Cys Leu Trp Leu Phe Ser Thr
                340                 345                 350

Gln Pro Thr Lys Ala Phe Thr Ala Trp Leu Glu Val Leu Thr Leu Leu
            355                 360                 365

Ile Thr Lys Leu Arg Ala Ser Ala Val Arg Thr Phe Gly Lys Glu Val
        370                 375                 380

Asp Ile Leu Leu Leu Pro Ala Cys Phe Arg Glu Asp Leu Pro Leu Pro
385                 390                 395                 400

Glu Gly Ile Leu Leu Ala Leu Lys Gly Phe Ala Gly Lys Ile Arg Ser
                405                 410                 415

Ser Asp Thr Pro Ser Ile Phe Asp Ile Ala Arg Pro Leu His Val Ser
            420                 425                 430

Leu Lys Val Arg Val Thr Asp His Pro Val Pro Gly Pro Thr Val Phe
        435                 440                 445

Thr Asp Ala Ser Ser Ser Thr His Lys Gly Val Val Val Trp Arg Glu
450                 455                 460

Gly Pro Arg Trp Glu Ile Lys Glu Ile Ala Asp Leu Gly Ala Ser Val
465                 470                 475                 480

Gln Gln Leu Glu Ala Arg Ala Val Ala Met Ala Leu Leu Leu Trp Pro
                485                 490                 495

Thr Thr Pro Thr Asn Val Val Thr Asp Ser Ala Phe Val Ala Lys Met
            500                 505                 510

Leu Leu Lys Met Gly Gln Glu Gly Val Pro Ser Thr Ala Ala Ala Phe
        515                 520                 525

Ile Leu Glu Asp Ala Leu Ser Gln Arg Ser Ala Met Ala Ala Val Leu
    530                 535                 540

His Val Arg Ser His Ser Glu Val Pro Gly Phe Phe Thr Glu Gly Asn
545                 550                 555                 560

Asp Val Ala Asp Ser Gln Ala Thr Phe Gln Ala Tyr
                565                 570

<210> SEQ ID NO 22
<211> LENGTH: 859
<212> TYPE: PRT
<213> ORGANISM: Rous sarcoma virus

<400> SEQUENCE: 22

Thr Val Ala Leu His Leu Ala Ile Pro Leu Lys Trp Lys Pro Asp His
1               5                   10                  15

Thr Pro Val Trp Ile Asp Gln Trp Pro Leu Pro Glu Gly Lys Leu Val
            20                  25                  30

Ala Leu Thr Gln Leu Val Glu Lys Glu Leu Gln Leu Gly His Ile Glu
        35                  40                  45

Pro Ser Leu Ser Cys Trp Asn Thr Pro Val Phe Val Ile Arg Lys Ala
    50                  55                  60

Ser Gly Ser Tyr Arg Leu Leu His Asp Leu Arg Ala Val Asn Ala Lys
65                  70                  75                  80

Leu Val Pro Phe Gly Ala Val Gln Gln Gly Ala Pro Val Leu Ser Ala
                85                  90                  95

Leu Pro Arg Gly Trp Pro Leu Met Val Leu Asp Leu Lys Asp Cys Phe
            100                 105                 110

Phe Ser Ile Pro Leu Ala Glu Gln Asp Arg Glu Ala Phe Ala Phe Thr
        115                 120                 125
```

-continued

```
Leu Pro Ser Val Asn Asn Gln Ala Pro Ala Arg Arg Phe Gln Trp Lys
    130                 135                 140

Val Leu Pro Gln Gly Met Thr Cys Ser Pro Thr Ile Cys Gln Leu Val
145                 150                 155                 160

Val Gly Gln Val Leu Glu Pro Leu Arg Leu Lys His Pro Ser Leu Cys
                165                 170                 175

Met Leu His Tyr Met Asp Asp Leu Leu Leu Ala Ala Ser Ser His Asp
            180                 185                 190

Gly Leu Glu Ala Ala Gly Glu Val Ile Ser Thr Leu Glu Arg Ala
        195                 200                 205

Gly Phe Thr Ile Ser Pro Asp Lys Val Gln Arg Glu Pro Gly Val Gln
210                 215                 220

Tyr Leu Gly Tyr Lys Leu Gly Ser Thr Tyr Val Ala Pro Val Gly Leu
225                 230                 235                 240

Val Ala Glu Pro Arg Ile Ala Thr Leu Trp Asp Val Gln Lys Leu Val
                245                 250                 255

Gly Ser Leu Gln Trp Leu Arg Pro Ala Leu Gly Ile Pro Pro Arg Leu
            260                 265                 270

Met Gly Pro Phe Tyr Glu Gln Leu Arg Gly Ser Asp Pro Asn Glu Ala
        275                 280                 285

Arg Glu Trp Asn Leu Asp Met Lys Met Ala Trp Arg Glu Ile Val Arg
290                 295                 300

Leu Ser Thr Thr Ala Ala Leu Glu Arg Trp Asp Pro Ala Leu Pro Leu
305                 310                 315                 320

Glu Gly Ala Val Ala Arg Cys Glu Gln Gly Ala Ile Gly Val Leu Gly
                325                 330                 335

Gln Gly Leu Ser Thr His Pro Arg Pro Cys Leu Trp Leu Phe Ser Thr
            340                 345                 350

Gln Pro Thr Lys Ala Phe Thr Ala Trp Leu Glu Val Leu Thr Leu Leu
        355                 360                 365

Ile Thr Lys Leu Arg Ala Ser Ala Val Arg Thr Phe Gly Lys Glu Val
370                 375                 380

Asp Ile Leu Leu Leu Pro Ala Cys Phe Arg Glu Asp Leu Pro Leu Pro
385                 390                 395                 400

Glu Gly Ile Leu Leu Ala Leu Lys Gly Phe Ala Gly Lys Ile Arg Ser
                405                 410                 415

Ser Asp Thr Pro Ser Ile Phe Asp Ile Ala Arg Pro Leu His Val Ser
            420                 425                 430

Leu Lys Val Arg Val Thr Asp His Pro Val Pro Gly Pro Thr Val Phe
        435                 440                 445

Thr Asp Ala Ser Ser Ser Thr His Lys Gly Val Val Val Trp Arg Glu
450                 455                 460

Gly Pro Arg Trp Glu Ile Lys Glu Ile Ala Asp Leu Gly Ala Ser Val
465                 470                 475                 480

Gln Gln Leu Glu Ala Arg Ala Val Ala Met Ala Leu Leu Leu Trp Pro
                485                 490                 495

Thr Thr Pro Thr Asn Val Val Thr Asp Ser Ala Phe Val Ala Lys Met
            500                 505                 510

Leu Leu Lys Met Gly Gln Glu Gly Val Pro Ser Thr Ala Ala Ala Phe
        515                 520                 525

Ile Leu Glu Asp Ala Leu Ser Gln Arg Ser Ala Met Ala Ala Val Leu
530                 535                 540

His Val Arg Ser His Ser Glu Val Pro Gly Phe Phe Thr Glu Gly Asn
```

545                 550                 555                 560
    Asp Val Ala Asp Ser Gln Ala Thr Phe Gln Ala Tyr Pro Leu Arg Glu
                        565                 570                 575

Ala Lys Asp Leu His Thr Ala Leu His Ile Gly Pro Arg Ala Leu Ser
                        580                 585                 590

Lys Ala Cys Asn Ile Ser Met Gln Gln Ala Arg Glu Val Val Gln Thr
                        595                 600                 605

Cys Pro His Cys Asn Ser Ala Pro Ala Leu Glu Ala Gly Val Asn Pro
                    610                 615                 620

Arg Gly Leu Gly Pro Leu Gln Ile Trp Gln Thr Asp Phe Thr Leu Glu
    625                 630                 635                 640

Pro Arg Met Ala Pro Arg Ser Trp Leu Ala Val Thr Val Asp Thr Ala
                        645                 650                 655

Ser Ser Ala Ile Val Val Thr Gln His Gly Arg Val Thr Ser Val Ala
                        660                 665                 670

Val Gln His His Trp Ala Thr Ala Ile Ala Val Leu Gly Arg Pro Lys
                        675                 680                 685

Ala Ile Lys Thr Asp Asn Gly Ser Cys Phe Thr Ser Lys Ser Thr Arg
                    690                 695                 700

Glu Trp Leu Ala Arg Trp Gly Ile Ala His Thr Thr Gly Ile Pro Gly
    705                 710                 715                 720

Asn Ser Gln Gly Gln Ala Met Val Glu Arg Ala Asn Arg Leu Leu Lys
                        725                 730                 735

Asp Arg Ile Arg Val Leu Ala Glu Gly Asp Gly Phe Met Lys Arg Ile
                        740                 745                 750

Pro Thr Ser Lys Gln Gly Glu Leu Leu Ala Lys Ala Met Tyr Ala Leu
                        755                 760                 765

Asn His Phe Glu Arg Gly Glu Asn Thr Lys Thr Pro Ile Gln Lys His
                        770                 775                 780

Trp Arg Pro Thr Val Leu Thr Glu Gly Pro Pro Val Lys Ile Arg Ile
    785                 790                 795                 800

Glu Thr Gly Glu Trp Glu Lys Gly Trp Asn Val Leu Val Trp Gly Arg
                        805                 810                 815

Gly Tyr Ala Ala Val Lys Asn Arg Asp Thr Asp Lys Val Ile Trp Val
                        820                 825                 830

Pro Ser Arg Lys Val Lys Pro Asp Ile Thr Gln Lys Asp Glu Val Thr
                        835                 840                 845

Lys Lys Asp Glu Ala Ser Pro Leu Phe Ala Gly
                850                 855

<210> SEQ ID NO 23
    <211> LENGTH: 47
    <212> TYPE: PRT
    <213> ORGANISM: Artificial Sequence
    <220> FEATURE:
    <223> OTHER INFORMATION: Description of Artificial Sequence: Synthetic
          polypeptide

<400> SEQUENCE: 23

Leu Glu Ile Arg Ala Ala Phe Leu Arg Gln Arg Asn Thr Ala Leu Arg
    1               5                   10                  15

Thr Glu Val Ala Glu Leu Glu Gln Glu Val Gln Arg Leu Glu Asn Glu
                    20                  25                  30

Val Ser Gln Tyr Glu Thr Arg Tyr Gly Pro Leu Gly Gly Gly Lys
                35                  40                  45

<210> SEQ ID NO 24
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Leu Glu Ile Glu Ala Ala Phe Leu Glu Arg Glu Asn Thr Ala Leu Glu
1               5                   10                  15

Thr Arg Val Ala Glu Leu Arg Gln Arg Val Gln Arg Leu Arg Asn Arg
            20                  25                  30

Val Ser Gln Tyr Arg Thr Arg Tyr Gly Pro Leu Gly Gly Gly Lys
        35                  40                  45

<210> SEQ ID NO 25
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ggccggcatg gtcccagcct cctcgctggc gccggctggg caacatgctt cggcatggcg      60
aatgggacac ag                                                          72

<210> SEQ ID NO 26
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
gctgaagcac tgcacgccat gtttaagagc tatgctggaa acagcatagc aagtttaaat      60
aaggctagtc cgttatcaac ttgaaaaagt ggcaccgagt cggtgctgaa ggcgagggcg     120
atgccaccta cggcaagctg accctgaagt tcatctgcac caccggcaag ctgccggtgc     180
cctggcccac cctcgtgacc accctgacat acggcgtgca gtgcttcacc ctcgtgacca     240
ccctgaggcc ggcatggtcc cagcctcctc gctggcgccg gctgggcaac atgcttcggc     300
atggcgaatg ggacacag                                                   318

<210> SEQ ID NO 27
<211> LENGTH: 866
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Lys Arg Thr Ala Asp Gly Ser Glu Phe Glu Ser Pro Lys Lys Lys
1               5                   10                  15

Arg Lys Val Ala Ser Asn Phe Thr Gln Phe Val Leu Val Asp Asn Gly
            20                  25                  30

Gly Thr Gly Asp Val Thr Val Ala Pro Ser Asn Phe Ala Asn Gly Ile
        35                  40                  45

Ala Glu Trp Ile Ser Ser Asn Ser Arg Ser Gln Ala Tyr Lys Val Thr

```
            50                  55                  60
Cys Ser Val Arg Gln Ser Ser Ala Gln Asn Arg Lys Tyr Thr Ile Lys
 65                  70                  75                  80

Val Glu Val Pro Lys Gly Ala Trp Arg Ser Tyr Leu Asn Met Glu Leu
                 85                  90                  95

Thr Ile Pro Ile Phe Ala Thr Asn Ser Asp Cys Glu Leu Ile Val Lys
            100                 105                 110

Ala Met Gln Gly Leu Leu Lys Asp Gly Asn Pro Ile Pro Ser Ala Ile
                115                 120                 125

Ala Ala Asn Ser Gly Ile Tyr Ser Gly Gly Ser Ser Gly Ser Ser
130                 135                 140

Gly Ser Glu Thr Pro Gly Thr Ser Glu Ser Ala Thr Pro Glu Ser Ser
145                 150                 155                 160

Gly Gly Ser Ser Gly Gly Ser Ser Thr Leu Asn Ile Glu Asp Glu Tyr
                165                 170                 175

Arg Leu His Glu Thr Ser Lys Glu Pro Asp Val Ser Leu Gly Ser Thr
            180                 185                 190

Trp Leu Ser Asp Phe Pro Gln Ala Trp Ala Glu Thr Gly Gly Met Gly
                195                 200                 205

Leu Ala Val Arg Gln Ala Pro Leu Ile Ile Pro Leu Lys Ala Thr Ser
210                 215                 220

Thr Pro Val Ser Ile Lys Gln Tyr Pro Met Ser Gln Glu Ala Arg Leu
225                 230                 235                 240

Gly Ile Lys Pro His Ile Gln Arg Leu Leu Asp Gln Gly Ile Leu Val
                245                 250                 255

Pro Cys Gln Ser Pro Trp Asn Thr Pro Leu Leu Pro Val Lys Lys Pro
                260                 265                 270

Gly Thr Asn Asp Tyr Arg Pro Val Gln Asp Leu Arg Glu Val Asn Lys
                275                 280                 285

Arg Val Glu Asp Ile His Pro Thr Val Pro Asn Pro Tyr Asn Leu Leu
290                 295                 300

Ser Gly Leu Pro Pro Ser His Gln Trp Tyr Thr Val Leu Asp Leu Lys
305                 310                 315                 320

Asp Ala Phe Phe Cys Leu Arg Leu His Pro Thr Ser Gln Pro Leu Phe
                325                 330                 335

Ala Phe Glu Trp Arg Asp Pro Glu Met Gly Ile Ser Gly Gln Leu Thr
                340                 345                 350

Trp Thr Arg Leu Pro Gln Gly Phe Lys Asn Ser Pro Thr Leu Phe Asn
                355                 360                 365

Glu Ala Leu His Arg Asp Leu Ala Asp Phe Arg Ile Gln His Pro Asp
370                 375                 380

Leu Ile Leu Leu Gln Tyr Val Asp Asp Leu Leu Leu Ala Ala Thr Ser
385                 390                 395                 400

Glu Leu Asp Cys Gln Gln Gly Thr Arg Ala Leu Leu Gln Thr Leu Gly
                405                 410                 415

Asn Leu Gly Tyr Arg Ala Ser Ala Lys Lys Ala Gln Ile Cys Gln Lys
                420                 425                 430

Gln Val Lys Tyr Leu Gly Tyr Leu Leu Lys Glu Gly Gln Arg Trp Leu
                435                 440                 445

Thr Glu Ala Arg Lys Glu Thr Val Met Gly Gln Pro Thr Pro Lys Thr
450                 455                 460

Pro Arg Gln Leu Arg Glu Phe Leu Gly Lys Ala Gly Phe Cys Arg Leu
465                 470                 475                 480
```

```
Phe Ile Pro Gly Phe Ala Glu Met Ala Ala Pro Leu Tyr Pro Leu Thr
                485                 490                 495

Lys Pro Gly Thr Leu Phe Asn Trp Gly Pro Asp Gln Gln Lys Ala Tyr
            500                 505                 510

Gln Glu Ile Lys Gln Ala Leu Leu Thr Ala Pro Ala Leu Gly Leu Pro
        515                 520                 525

Asp Leu Thr Lys Pro Phe Glu Leu Phe Val Asp Glu Lys Gln Gly Tyr
    530                 535                 540

Ala Lys Gly Val Leu Thr Gln Lys Leu Gly Pro Trp Arg Arg Pro Val
545                 550                 555                 560

Ala Tyr Leu Ser Lys Lys Leu Asp Pro Val Ala Ala Gly Trp Pro Pro
                565                 570                 575

Cys Leu Arg Met Val Ala Ala Ile Ala Val Leu Thr Lys Asp Ala Gly
            580                 585                 590

Lys Leu Thr Met Gly Gln Pro Leu Val Ile Leu Ala Pro His Ala Val
        595                 600                 605

Glu Ala Leu Val Lys Gln Pro Pro Asp Arg Trp Leu Ser Asn Ala Arg
    610                 615                 620

Met Thr His Tyr Gln Ala Leu Leu Leu Asp Thr Asp Arg Val Gln Phe
625                 630                 635                 640

Gly Pro Val Val Ala Leu Asn Pro Ala Thr Leu Leu Pro Leu Pro Glu
                645                 650                 655

Glu Gly Leu Gln His Asn Cys Leu Asp Ile Leu Ala Glu Ala His Gly
            660                 665                 670

Thr Arg Pro Asp Leu Thr Asp Gln Pro Leu Pro Asp Ala Asp His Thr
        675                 680                 685

Trp Tyr Thr Asp Gly Ser Ser Leu Leu Gln Glu Gly Gln Arg Lys Ala
    690                 695                 700

Gly Ala Ala Val Thr Thr Glu Thr Glu Val Ile Trp Ala Lys Ala Leu
705                 710                 715                 720

Pro Ala Gly Thr Ser Ala Gln Arg Ala Glu Leu Ile Ala Leu Thr Gln
                725                 730                 735

Ala Leu Lys Met Ala Glu Gly Lys Lys Leu Asn Val Tyr Thr Asp Ser
            740                 745                 750

Arg Tyr Ala Phe Ala Thr Ala His Ile His Gly Glu Ile Tyr Arg Arg
        755                 760                 765

Arg Gly Trp Leu Thr Ser Glu Gly Lys Glu Ile Lys Asn Lys Asp Glu
    770                 775                 780

Ile Leu Ala Leu Leu Lys Ala Leu Phe Leu Pro Lys Arg Leu Ser Ile
785                 790                 795                 800

Ile His Cys Pro Gly His Gln Lys Gly His Ser Ala Glu Ala Arg Gly
                805                 810                 815

Asn Arg Met Ala Asp Gln Ala Ala Arg Lys Ala Ala Ile Thr Glu Thr
            820                 825                 830

Pro Asp Thr Ser Thr Leu Leu Ile Glu Asn Ser Ser Pro Ser Gly Gly
        835                 840                 845

Ser Lys Arg Thr Ala Asp Gly Ser Glu Phe Glu Pro Lys Lys Lys Arg
    850                 855                 860

Lys Val
865

<210> SEQ ID NO 28
<211> LENGTH: 157
```

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
gctgaagcac tgcacgccat gtttaagagc tatgctggaa acagcatagc aagtttaaat    60
aaggctagtc cgttatcaac ttgaaaaagt ggcaccgagt cggtgcgcgc acatgaggat   120
cacccatgtg caccctgaca tacggcgtgc agtgctt                            157

<210> SEQ ID NO 29
<211> LENGTH: 182
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
gctgaagcac tgcacgccat gtttaagagc tatgctggaa acagcatagc aagtttaaat    60
aaggctagtc cgttatcaac ttgaaaaagt ggcaccgagt cggtgcgcgc acatgaggat   120
cacccatgtg cgcgcacatg aggatcaccc atgtgcaccc tgacatacgg cgtgcagtgc   180
tt                                                                 182

<210> SEQ ID NO 30
<211> LENGTH: 166
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
gctgaagcac tgcacgccat gtttaagagc tatgctggaa acagcatagc aagtttaaat    60
aaggctagtc cgttatcaac ttgaaaaagt ggcaccgagt cggtgcggcc aacatgagga   120
tcacccatgt ctgcagggcc accctgacat acggcgtgca gtgctt                  166

<210> SEQ ID NO 31
<211> LENGTH: 182
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
gctgaagcac tgcacgccat gttttagagc taggccaaca tgaggatcac ccatgtctgc    60
agggcctagc aagttaaaat aaggctagtc cgttatcaac ttggccaaca tgaggatcac   120
ccatgtctgc agggccaagt ggcaccgagt cggtgcaccc tgacatacgg cgtgcagtgc   180
tt                                                                 182

<210> SEQ ID NO 32
<211> LENGTH: 1368
<212> TYPE: PRT
<213> ORGANISM: Streptococcus pyogenes

<400> SEQUENCE: 32

Met Asp Lys Lys Tyr Ser Ile Gly Leu Asp Ile Gly Thr Asn Ser Val
1               5                   10                  15
```

-continued

Gly Trp Ala Val Ile Thr Asp Glu Tyr Lys Val Pro Ser Lys Lys Phe
         20                  25                  30
Lys Val Leu Gly Asn Thr Asp Arg His Ser Ile Lys Lys Asn Leu Ile
             35                  40                  45
Gly Ala Leu Leu Phe Asp Ser Gly Glu Thr Ala Glu Ala Thr Arg Leu
 50                  55                  60
Lys Arg Thr Ala Arg Arg Tyr Thr Arg Arg Lys Asn Arg Ile Cys
 65                  70                  75                  80
Tyr Leu Gln Glu Ile Phe Ser Asn Glu Met Ala Lys Val Asp Asp Ser
                 85                  90                  95
Phe Phe His Arg Leu Glu Glu Ser Phe Leu Val Glu Glu Asp Lys Lys
                100                 105                 110
His Glu Arg His Pro Ile Phe Gly Asn Ile Val Asp Glu Val Ala Tyr
            115                 120                 125
His Glu Lys Tyr Pro Thr Ile Tyr His Leu Arg Lys Lys Leu Val Asp
        130                 135                 140
Ser Thr Asp Lys Ala Asp Leu Arg Leu Ile Tyr Leu Ala Leu Ala His
145                 150                 155                 160
Met Ile Lys Phe Arg Gly His Phe Leu Ile Glu Gly Asp Leu Asn Pro
                165                 170                 175
Asp Asn Ser Asp Val Asp Lys Leu Phe Ile Gln Leu Val Gln Thr Tyr
            180                 185                 190
Asn Gln Leu Phe Glu Glu Asn Pro Ile Asn Ala Ser Gly Val Asp Ala
        195                 200                 205
Lys Ala Ile Leu Ser Ala Arg Leu Ser Lys Ser Arg Arg Leu Glu Asn
    210                 215                 220
Leu Ile Ala Gln Leu Pro Gly Glu Lys Lys Asn Gly Leu Phe Gly Asn
225                 230                 235                 240
Leu Ile Ala Leu Ser Leu Gly Leu Thr Pro Asn Phe Lys Ser Asn Phe
                245                 250                 255
Asp Leu Ala Glu Asp Ala Lys Leu Gln Leu Ser Lys Asp Thr Tyr Asp
            260                 265                 270
Asp Asp Leu Asp Asn Leu Leu Ala Gln Ile Gly Asp Gln Tyr Ala Asp
        275                 280                 285
Leu Phe Leu Ala Ala Lys Asn Leu Ser Asp Ala Ile Leu Leu Ser Asp
    290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
            340                 345                 350
Asp Gln Ser Lys Asn Gly Tyr Ala Gly Tyr Ile Asp Gly Gly Ala Ser
        355                 360                 365
Gln Glu Glu Phe Tyr Lys Phe Ile Lys Pro Ile Leu Glu Lys Met Asp
    370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
            420                 425                 430

-continued

```
Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp His Ile Val Pro Gln Ser Phe Leu Lys
            835                 840                 845

Asp Asp Ser Ile Asp Asn Lys Val Leu Thr Arg Ser Asp Lys Asn Arg
```

-continued

```
            850                 855                 860
Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
            930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
        1025                1030                1035

Tyr Ser Asn Ile Met Asn Phe Phe Lys Thr Glu Ile Thr Leu Ala
        1040                1045                1050

Asn Gly Glu Ile Arg Lys Arg Pro Leu Ile Glu Thr Asn Gly Glu
        1055                1060                1065

Thr Gly Glu Ile Val Trp Asp Lys Gly Arg Asp Phe Ala Thr Val
        1070                1075                1080

Arg Lys Val Leu Ser Met Pro Gln Val Asn Ile Val Lys Lys Thr
        1085                1090                1095

Glu Val Gln Thr Gly Gly Phe Ser Lys Glu Ser Ile Leu Pro Lys
        1100                1105                1110

Arg Asn Ser Asp Lys Leu Ile Ala Arg Lys Lys Asp Trp Asp Pro
        1115                1120                1125

Lys Lys Tyr Gly Gly Phe Asp Ser Pro Thr Val Ala Tyr Ser Val
        1130                1135                1140

Leu Val Val Ala Lys Val Glu Lys Gly Lys Ser Lys Lys Leu Lys
        1145                1150                1155

Ser Val Lys Glu Leu Leu Gly Ile Thr Ile Met Glu Arg Ser Ser
        1160                1165                1170

Phe Glu Lys Asn Pro Ile Asp Phe Leu Glu Ala Lys Gly Tyr Lys
        1175                1180                1185

Glu Val Lys Lys Asp Leu Ile Ile Lys Leu Pro Lys Tyr Ser Leu
        1190                1195                1200

Phe Glu Leu Glu Asn Gly Arg Lys Arg Met Leu Ala Ser Ala Gly
        1205                1210                1215

Glu Leu Gln Lys Gly Asn Glu Leu Ala Leu Pro Ser Lys Tyr Val
        1220                1225                1230

Asn Phe Leu Tyr Leu Ala Ser His Tyr Glu Lys Leu Lys Gly Ser
        1235                1240                1245

Pro Glu Asp Asn Glu Gln Lys Gln Leu Phe Val Glu Gln His Lys
        1250                1255                1260
```

```
His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 33
<211> LENGTH: 1053
<212> TYPE: PRT
<213> ORGANISM: Staphylococcus aureus

<400> SEQUENCE: 33

Met Lys Arg Asn Tyr Ile Leu Gly Leu Asp Ile Gly Ile Thr Ser Val
1               5                   10                  15

Gly Tyr Gly Ile Ile Asp Tyr Glu Thr Arg Asp Val Ile Asp Ala Gly
                20                  25                  30

Val Arg Leu Phe Lys Glu Ala Asn Val Glu Asn Asn Glu Gly Arg Arg
            35                  40                  45

Ser Lys Arg Gly Ala Arg Arg Leu Lys Arg Arg Arg His Arg Ile
    50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Glu Phe Ser Ala Ala Leu Leu His Leu
            100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala
    130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Leu Glu Thr Arg
        195                 200                 205

Arg Thr Tyr Tyr Glu Gly Pro Gly Glu Gly Ser Pro Phe Gly Trp Lys
    210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
```

```
                260                 265                 270
Glu Lys Leu Glu Tyr Tyr Glu Lys Phe Gln Ile Ile Glu Asn Val Phe
            275                 280                 285
Lys Gln Lys Lys Lys Pro Thr Leu Lys Gln Ile Ala Lys Glu Ile Leu
        290                 295                 300
Val Asn Glu Glu Asp Ile Lys Gly Tyr Arg Val Thr Ser Thr Gly Lys
305                 310                 315                 320
Pro Glu Phe Thr Asn Leu Lys Val Tyr His Asp Ile Lys Asp Ile Thr
                325                 330                 335
Ala Arg Lys Glu Ile Ile Glu Asn Ala Glu Leu Leu Asp Gln Ile Ala
            340                 345                 350
Lys Ile Leu Thr Ile Tyr Gln Ser Ser Glu Asp Ile Gln Glu Glu Leu
        355                 360                 365
Thr Asn Leu Asn Ser Glu Leu Thr Gln Glu Glu Ile Glu Gln Ile Ser
    370                 375                 380
Asn Leu Lys Gly Tyr Thr Gly Thr His Asn Leu Ser Leu Lys Ala Ile
385                 390                 395                 400
Asn Leu Ile Leu Asp Glu Leu Trp His Thr Asn Asp Asn Gln Ile Ala
                405                 410                 415
Ile Phe Asn Arg Leu Lys Leu Val Pro Lys Lys Val Asp Leu Ser Gln
            420                 425                 430
Gln Lys Glu Ile Pro Thr Thr Leu Val Asp Asp Phe Ile Leu Ser Pro
        435                 440                 445
Val Val Lys Arg Ser Phe Ile Gln Ser Ile Lys Val Ile Asn Ala Ile
    450                 455                 460
Ile Lys Lys Tyr Gly Leu Pro Asn Asp Ile Ile Ile Glu Leu Ala Arg
465                 470                 475                 480
Glu Lys Asn Ser Lys Asp Ala Gln Lys Met Ile Asn Glu Met Gln Lys
                485                 490                 495
Arg Asn Arg Gln Thr Asn Glu Arg Ile Glu Glu Ile Ile Arg Thr Thr
            500                 505                 510
Gly Lys Glu Asn Ala Lys Tyr Leu Ile Glu Lys Ile Lys Leu His Asp
        515                 520                 525
Met Gln Glu Gly Lys Cys Leu Tyr Ser Leu Glu Ala Ile Pro Leu Glu
    530                 535                 540
Asp Leu Leu Asn Asn Pro Phe Asn Tyr Glu Val Asp His Ile Ile Pro
545                 550                 555                 560
Arg Ser Val Ser Phe Asp Asn Ser Phe Asn Asn Lys Val Leu Val Lys
                565                 570                 575
Gln Glu Glu Asn Ser Lys Lys Gly Asn Arg Thr Pro Phe Gln Tyr Leu
            580                 585                 590
Ser Ser Ser Asp Ser Lys Ile Ser Tyr Glu Thr Phe Lys Lys His Ile
        595                 600                 605
Leu Asn Leu Ala Lys Gly Lys Gly Arg Ile Ser Lys Thr Lys Lys Glu
    610                 615                 620
Tyr Leu Leu Glu Glu Arg Asp Ile Asn Arg Phe Ser Val Gln Lys Asp
625                 630                 635                 640
Phe Ile Asn Arg Asn Leu Val Asp Thr Arg Tyr Ala Thr Arg Gly Leu
                645                 650                 655
Met Asn Leu Leu Arg Ser Tyr Phe Arg Val Asn Asn Leu Asp Val Lys
            660                 665                 670
Val Lys Ser Ile Asn Gly Gly Phe Thr Ser Phe Leu Arg Arg Lys Trp
        675                 680                 685
```

Lys Phe Lys Lys Glu Arg Asn Lys Gly Tyr Lys His His Ala Glu Asp
            690                 695                 700

Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Glu Lys
                725                 730                 735

Gln Ala Glu Ser Met Pro Glu Ile Glu Thr Glu Gln Glu Tyr Lys Glu
            740                 745                 750

Ile Phe Ile Thr Pro His Gln Ile Lys His Ile Lys Asp Phe Lys Asp
            755                 760                 765

Tyr Lys Tyr Ser His Arg Val Asp Lys Lys Pro Asn Arg Glu Leu Ile
            770                 775                 780

Asn Asp Thr Leu Tyr Ser Thr Arg Lys Asp Asp Lys Gly Asn Thr Leu
785                 790                 795                 800

Ile Val Asn Asn Leu Asn Gly Leu Tyr Asp Lys Asp Asn Asp Lys Leu
                805                 810                 815

Lys Lys Leu Ile Asn Lys Ser Pro Glu Lys Leu Leu Met Tyr His His
            820                 825                 830

Asp Pro Gln Thr Tyr Gln Lys Leu Lys Leu Ile Met Glu Gln Tyr Gly
            835                 840                 845

Asp Glu Lys Asn Pro Leu Tyr Lys Tyr Tyr Glu Glu Thr Gly Asn Tyr
            850                 855                 860

Leu Thr Lys Tyr Ser Lys Lys Asp Asn Gly Pro Val Ile Lys Lys Ile
865                 870                 875                 880

Lys Tyr Tyr Gly Asn Lys Leu Asn Ala His Leu Asp Ile Thr Asp Asp
                885                 890                 895

Tyr Pro Asn Ser Arg Asn Lys Val Val Lys Leu Ser Leu Lys Pro Tyr
            900                 905                 910

Arg Phe Asp Val Tyr Leu Asp Asn Gly Val Tyr Lys Phe Val Thr Val
            915                 920                 925

Lys Asn Leu Asp Val Ile Lys Lys Glu Asn Tyr Tyr Glu Val Asn Ser
930                 935                 940

Lys Cys Tyr Glu Glu Ala Lys Lys Leu Lys Lys Ile Ser Asn Gln Ala
945                 950                 955                 960

Glu Phe Ile Ala Ser Phe Tyr Asn Asn Asp Leu Ile Lys Ile Asn Gly
                965                 970                 975

Glu Leu Tyr Arg Val Ile Gly Val Asn Asn Asp Leu Leu Asn Arg Ile
            980                 985                 990

Glu Val Asn Met Ile Asp Ile Thr Tyr Arg Glu Tyr Leu Glu Asn Met
            995                 1000                1005

Asn Asp Lys Arg Pro Pro Arg Ile Ile Lys Thr Ile Ala Ser Lys
            1010                1015                1020

Thr Gln Ser Ile Lys Lys Tyr Ser Thr Asp Ile Leu Gly Asn Leu
            1025                1030                1035

Tyr Glu Val Lys Ser Lys Lys His Pro Gln Ile Ile Lys Lys Gly
            1040                1045                1050

<210> SEQ ID NO 34
<211> LENGTH: 984
<212> TYPE: PRT
<213> ORGANISM: Campylobacter jejuni

<400> SEQUENCE: 34

Met Ala Arg Ile Leu Ala Phe Asp Ile Gly Ile Ser Ser Ile Gly Trp

-continued

```
1               5                   10                  15
Ala Phe Ser Glu Asn Asp Glu Leu Lys Asp Cys Gly Val Arg Ile Phe
            20                  25                  30

Thr Lys Val Glu Asn Pro Lys Thr Gly Glu Ser Leu Ala Leu Pro Arg
            35                  40                  45

Arg Leu Ala Arg Ser Ala Arg Lys Arg Leu Ala Arg Lys Ala Arg
            50                  55                  60

Leu Asn His Leu Lys His Leu Ile Ala Asn Glu Phe Lys Leu Asn Tyr
65                  70                  75                  80

Glu Asp Tyr Gln Ser Phe Asp Glu Ser Leu Ala Lys Ala Tyr Lys Gly
                85                  90                  95

Ser Leu Ile Ser Pro Tyr Glu Leu Arg Phe Arg Ala Leu Asn Glu Leu
                100                 105                 110

Leu Ser Lys Gln Asp Phe Ala Arg Val Ile Leu His Ile Ala Lys Arg
                115                 120                 125

Arg Gly Tyr Asp Asp Ile Lys Asn Ser Asp Asp Lys Glu Lys Gly Ala
        130                 135                 140

Ile Leu Lys Ala Ile Lys Gln Asn Glu Glu Lys Leu Ala Asn Tyr Gln
145                 150                 155                 160

Ser Val Gly Glu Tyr Leu Tyr Lys Glu Tyr Phe Gln Lys Phe Lys Glu
                165                 170                 175

Asn Ser Lys Glu Phe Thr Asn Val Arg Asn Lys Lys Glu Ser Tyr Glu
                180                 185                 190

Arg Cys Ile Ala Gln Ser Phe Leu Lys Asp Glu Leu Lys Leu Ile Phe
        195                 200                 205

Lys Lys Gln Arg Glu Phe Gly Phe Ser Phe Ser Lys Lys Phe Glu Glu
        210                 215                 220

Glu Val Leu Ser Val Ala Phe Tyr Lys Arg Ala Leu Lys Asp Phe Ser
225                 230                 235                 240

His Leu Val Gly Asn Cys Ser Phe Phe Thr Asp Glu Lys Arg Ala Pro
                245                 250                 255

Lys Asn Ser Pro Leu Ala Phe Met Phe Val Ala Leu Thr Arg Ile Ile
                260                 265                 270

Asn Leu Leu Asn Asn Leu Lys Asn Thr Glu Gly Ile Leu Tyr Thr Lys
                275                 280                 285

Asp Asp Leu Asn Ala Leu Leu Asn Glu Val Leu Lys Asn Gly Thr Leu
        290                 295                 300

Thr Tyr Lys Gln Thr Lys Lys Leu Leu Gly Leu Ser Asp Asp Tyr Glu
305                 310                 315                 320

Phe Lys Gly Glu Lys Gly Thr Tyr Phe Ile Glu Phe Lys Lys Tyr Lys
                325                 330                 335

Glu Phe Ile Lys Ala Leu Gly Glu His Asn Leu Ser Gln Asp Asp Leu
        340                 345                 350

Asn Glu Ile Ala Lys Asp Ile Thr Leu Ile Lys Asp Glu Ile Lys Leu
        355                 360                 365

Lys Lys Ala Leu Ala Lys Tyr Asp Leu Asn Gln Asn Gln Ile Asp Ser
        370                 375                 380

Leu Ser Lys Leu Glu Phe Lys Asp His Leu Asn Ile Ser Phe Lys Ala
385                 390                 395                 400

Leu Lys Leu Val Thr Pro Leu Met Leu Glu Gly Lys Lys Tyr Asp Glu
                405                 410                 415

Ala Cys Asn Glu Leu Asn Leu Lys Val Ala Ile Asn Glu Asp Lys Lys
                420                 425                 430
```

```
Asp Phe Leu Pro Ala Phe Asn Glu Thr Tyr Tyr Lys Asp Glu Val Thr
        435                 440                 445

Asn Pro Val Val Leu Arg Ala Ile Lys Glu Tyr Arg Lys Val Leu Asn
    450                 455                 460

Ala Leu Leu Lys Lys Tyr Gly Lys Val His Lys Ile Asn Ile Glu Leu
465                 470                 475                 480

Ala Arg Glu Val Gly Lys Asn His Ser Gln Arg Ala Lys Ile Glu Lys
                485                 490                 495

Glu Gln Asn Glu Asn Tyr Lys Ala Lys Lys Asp Ala Glu Leu Glu Cys
            500                 505                 510

Glu Lys Leu Gly Leu Lys Ile Asn Ser Lys Asn Ile Leu Lys Leu Arg
            515                 520                 525

Leu Phe Lys Glu Gln Lys Glu Phe Cys Ala Tyr Ser Gly Lys Ile
        530                 535                 540

Lys Ile Ser Asp Leu Gln Asp Glu Lys Met Leu Glu Ile Asp His Ile
545                 550                 555                 560

Tyr Pro Tyr Ser Arg Ser Phe Asp Asp Ser Tyr Met Asn Lys Val Leu
                565                 570                 575

Val Phe Thr Lys Gln Asn Gln Gly Lys Leu Asn Gln Thr Pro Phe Glu
        580                 585                 590

Ala Phe Gly Asn Asp Ser Ala Lys Trp Gln Lys Ile Glu Val Leu Ala
        595                 600                 605

Lys Asn Leu Pro Thr Lys Lys Gln Lys Arg Ile Leu Asp Lys Asn Tyr
        610                 615                 620

Lys Asp Lys Glu Gln Lys Asn Phe Lys Asp Arg Asn Leu Asn Asp Thr
625                 630                 635                 640

Arg Tyr Ile Ala Arg Leu Val Leu Asn Tyr Thr Lys Asp Tyr Leu Asp
                645                 650                 655

Phe Leu Pro Leu Ser Asp Asp Glu Asn Thr Lys Leu Asn Asp Thr Gln
            660                 665                 670

Lys Gly Ser Lys Val His Val Glu Ala Lys Ser Gly Met Leu Thr Ser
            675                 680                 685

Ala Leu Arg His Thr Trp Gly Phe Ser Ala Lys Asp Arg Asn Asn His
        690                 695                 700

Leu His His Ala Ile Asp Ala Val Ile Ile Ala Tyr Ala Asn Asn Ser
705                 710                 715                 720

Ile Val Lys Ala Phe Ser Asp Phe Lys Lys Glu Gln Glu Ser Asn Ser
                725                 730                 735

Ala Glu Leu Tyr Ala Lys Lys Ile Ser Glu Leu Asp Tyr Lys Asn Lys
            740                 745                 750

Arg Lys Phe Phe Glu Pro Phe Ser Gly Phe Arg Gln Lys Val Leu Asp
        755                 760                 765

Lys Ile Asp Glu Ile Phe Val Ser Lys Pro Glu Arg Lys Lys Pro Ser
770                 775                 780

Gly Ala Leu His Glu Glu Thr Phe Arg Lys Glu Glu Phe Tyr Gln
785                 790                 795                 800

Ser Tyr Gly Gly Lys Glu Gly Val Leu Lys Ala Leu Glu Leu Gly Lys
                805                 810                 815

Ile Arg Lys Val Asn Gly Lys Ile Val Lys Asn Gly Asp Met Phe Arg
            820                 825                 830

Val Asp Ile Phe Lys His Lys Lys Thr Asn Lys Phe Tyr Ala Val Pro
835                 840                 845
```

Ile Tyr Thr Met Asp Phe Ala Leu Lys Val Leu Pro Asn Lys Ala Val
850                 855                 860

Ala Arg Ser Lys Lys Gly Glu Ile Lys Asp Trp Ile Leu Met Asp Glu
865                 870                 875                 880

Asn Tyr Glu Phe Cys Phe Ser Leu Tyr Lys Asp Ser Leu Ile Leu Ile
                885                 890                 895

Gln Thr Lys Asp Met Gln Glu Pro Glu Phe Val Tyr Tyr Asn Ala Phe
                900                 905                 910

Thr Ser Ser Thr Val Ser Leu Ile Val Ser Lys His Asp Asn Lys Phe
                915                 920                 925

Glu Thr Leu Ser Lys Asn Gln Lys Ile Leu Phe Lys Asn Ala Asn Glu
930                 935                 940

Lys Glu Val Ile Ala Lys Ser Ile Gly Ile Gln Asn Leu Lys Val Phe
945                 950                 955                 960

Glu Lys Tyr Ile Val Ser Ala Leu Gly Glu Val Thr Lys Ala Glu Phe
                965                 970                 975

Arg Gln Arg Glu Asp Phe Lys Lys
                980

<210> SEQ ID NO 35
<211> LENGTH: 1087
<212> TYPE: PRT
<213> ORGANISM: Geobacilus stereothermophilus

<400> SEQUENCE: 35

Met Arg Tyr Lys Ile Gly Leu Asp Ile Gly Ile Thr Ser Val Gly Trp
1               5                   10                  15

Ala Val Met Asn Leu Asp Ile Pro Arg Ile Glu Asp Leu Gly Val Arg
                20                  25                  30

Ile Phe Asp Arg Ala Glu Asn Pro Gln Thr Gly Glu Ser Leu Ala Leu
            35                  40                  45

Pro Arg Arg Leu Ala Arg Ser Ala Arg Arg Arg Leu Arg Arg Arg Lys
50                  55                  60

His Arg Leu Glu Arg Ile Arg Arg Leu Val Ile Arg Glu Gly Ile Leu
65                  70                  75                  80

Thr Lys Glu Glu Leu Asp Lys Leu Phe Glu Glu Lys His Glu Ile Asp
                85                  90                  95

Val Trp Gln Leu Arg Val Glu Ala Leu Asp Arg Lys Leu Asn Asn Asp
            100                 105                 110

Glu Leu Ala Arg Val Leu Leu His Leu Ala Lys Arg Arg Gly Phe Lys
        115                 120                 125

Ser Asn Arg Lys Ser Glu Arg Ser Asn Lys Glu Asn Ser Thr Met Leu
130                 135                 140

Lys His Ile Glu Glu Asn Arg Ala Ile Leu Ser Ser Tyr Arg Thr Val
145                 150                 155                 160

Gly Glu Met Ile Val Lys Asp Pro Lys Phe Ala Leu His Lys Arg Asn
                165                 170                 175

Lys Gly Glu Asn Tyr Thr Asn Thr Ile Ala Arg Asp Asp Leu Glu Arg
            180                 185                 190

Glu Ile Arg Leu Ile Phe Ser Lys Gln Arg Glu Phe Gly Asn Met Ser
        195                 200                 205

Cys Thr Glu Glu Phe Glu Asn Glu Tyr Ile Thr Ile Trp Ala Ser Gln
    210                 215                 220

Arg Pro Val Ala Ser Lys Asp Asp Ile Glu Lys Lys Val Gly Phe Cys
225                 230                 235                 240

```
Thr Phe Glu Pro Lys Glu Lys Arg Ala Pro Lys Ala Thr Tyr Thr Phe
                245                 250                 255
Gln Ser Phe Ile Ala Trp Glu His Ile Asn Lys Leu Arg Leu Ile Ser
            260                 265                 270
Pro Ser Gly Ala Arg Gly Leu Thr Asp Glu Arg Arg Leu Leu Tyr
        275                 280                 285
Glu Gln Ala Phe Gln Lys Asn Lys Ile Thr Tyr His Asp Ile Arg Thr
    290                 295                 300
Leu Leu His Leu Pro Asp Asp Thr Tyr Phe Lys Gly Ile Val Tyr Asp
305                 310                 315                 320
Arg Gly Glu Ser Arg Lys Gln Asn Glu Asn Ile Arg Phe Leu Glu Leu
                325                 330                 335
Asp Ala Tyr His Gln Ile Arg Lys Ala Val Asp Lys Val Tyr Gly Lys
            340                 345                 350
Gly Lys Ser Ser Ser Phe Leu Pro Ile Asp Phe Asp Thr Phe Gly Tyr
        355                 360                 365
Ala Leu Thr Leu Phe Lys Asp Asp Ala Asp Ile His Ser Tyr Leu Arg
    370                 375                 380
Asn Glu Tyr Glu Gln Asn Gly Lys Arg Met Pro Asn Leu Ala Asn Lys
385                 390                 395                 400
Val Tyr Asp Asn Glu Leu Ile Glu Leu Leu Asn Leu Ser Phe Thr
                405                 410                 415
Lys Phe Gly His Leu Ser Leu Lys Ala Leu Arg Ser Ile Leu Pro Tyr
            420                 425                 430
Met Glu Gln Gly Glu Val Tyr Ser Ser Ala Cys Glu Arg Ala Gly Tyr
        435                 440                 445
Thr Phe Thr Gly Pro Lys Lys Lys Gln Lys Thr Met Leu Leu Pro Asn
    450                 455                 460
Ile Pro Pro Ile Ala Asn Pro Val Val Met Arg Ala Leu Thr Gln Ala
465                 470                 475                 480
Arg Lys Val Val Asn Ala Ile Ile Lys Lys Tyr Gly Ser Pro Val Ser
                485                 490                 495
Ile His Ile Glu Leu Ala Arg Asp Leu Ser Gln Thr Phe Asp Glu Arg
            500                 505                 510
Arg Lys Thr Lys Lys Glu Gln Asp Glu Asn Arg Lys Lys Asn Glu Thr
        515                 520                 525
Ala Ile Arg Gln Leu Met Glu Tyr Gly Leu Thr Leu Asn Pro Thr Gly
    530                 535                 540
His Asp Ile Val Lys Phe Lys Leu Trp Ser Glu Gln Asn Gly Arg Cys
545                 550                 555                 560
Ala Tyr Ser Leu Gln Pro Ile Glu Ile Glu Arg Leu Leu Glu Pro Gly
                565                 570                 575
Tyr Val Glu Val Asp His Val Ile Pro Tyr Ser Arg Ser Leu Asp Asp
            580                 585                 590
Ser Tyr Thr Asn Lys Val Leu Val Leu Thr Arg Glu Asn Arg Glu Lys
        595                 600                 605
Gly Asn Arg Ile Pro Ala Glu Tyr Leu Gly Val Gly Thr Glu Arg Trp
    610                 615                 620
Gln Gln Phe Glu Thr Phe Val Leu Thr Asn Lys Gln Phe Ser Lys Lys
625                 630                 635                 640
Lys Arg Asp Arg Leu Leu Arg Leu His Tyr Asp Glu Asn Glu Glu Thr
                645                 650                 655
```

```
Glu Phe Lys Asn Arg Asn Leu Asn Asp Thr Arg Tyr Ile Ser Arg Phe
            660                 665                 670

Phe Ala Asn Phe Ile Arg Glu His Leu Lys Phe Ala Glu Ser Asp Asp
        675                 680                 685

Lys Gln Lys Val Tyr Thr Val Asn Gly Arg Val Thr Ala His Leu Arg
    690                 695                 700

Ser Arg Trp Glu Phe Asn Lys Asn Arg Glu Glu Ser Asp Leu His His
705                 710                 715                 720

Ala Val Asp Ala Ala Ile Val Ala Cys Thr Thr Pro Ser Asp Ile Ala
                725                 730                 735

Lys Val Thr Ala Phe Tyr Gln Arg Arg Glu Gln Asn Lys Glu Leu Ala
            740                 745                 750

Lys Lys Thr Glu Pro His Phe Pro Gln Pro Trp Pro His Phe Ala Asp
        755                 760                 765

Glu Leu Arg Ala Arg Leu Ser Lys His Pro Lys Glu Ser Ile Lys Ala
    770                 775                 780

Leu Asn Leu Gly Asn Tyr Asp Asp Gln Lys Leu Glu Ser Leu Gln Pro
785                 790                 795                 800

Val Phe Val Ser Arg Met Pro Lys Arg Ser Val Thr Gly Ala Ala His
                805                 810                 815

Gln Glu Thr Leu Arg Arg Tyr Val Gly Ile Asp Glu Arg Ser Gly Lys
            820                 825                 830

Ile Gln Thr Val Val Lys Thr Lys Leu Ser Glu Ile Lys Leu Asp Ala
        835                 840                 845

Ser Gly His Phe Pro Met Tyr Gly Lys Glu Ser Asp Pro Arg Thr Tyr
    850                 855                 860

Glu Ala Ile Arg Gln Arg Leu Leu Glu His Asn Asn Asp Pro Lys Lys
865                 870                 875                 880

Ala Phe Gln Glu Pro Leu Tyr Lys Pro Lys Lys Asn Gly Glu Pro Gly
                885                 890                 895

Pro Val Ile Arg Thr Val Lys Ile Ile Asp Thr Lys Asn Gln Val Ile
            900                 905                 910

Pro Leu Asn Asp Gly Lys Thr Val Ala Tyr Asn Ser Asn Ile Val Arg
        915                 920                 925

Val Asp Val Phe Glu Lys Asp Gly Lys Tyr Tyr Cys Val Pro Val Tyr
    930                 935                 940

Thr Met Asp Ile Met Lys Gly Ile Leu Pro Asn Lys Ala Ile Glu Pro
945                 950                 955                 960

Asn Lys Pro Tyr Ser Glu Trp Lys Glu Met Thr Glu Asp Tyr Thr Phe
                965                 970                 975

Arg Phe Ser Leu Tyr Pro Asn Asp Leu Ile Arg Ile Glu Leu Pro Arg
            980                 985                 990

Glu Lys Thr Val Lys Thr Ala Ala Gly Glu Glu Ile Asn Val Lys Asp
        995                 1000                1005

Val Phe Val Tyr Tyr Lys Thr Ile Asp Ser Ala Asn Gly Gly Leu
    1010                1015                1020

Glu Leu Ile Ser His Asp His Arg Phe Ser Leu Arg Gly Val Gly
    1025                1030                1035

Ser Arg Thr Leu Lys Arg Phe Glu Lys Tyr Gln Val Asp Val Leu
    1040                1045                1050

Gly Asn Ile Tyr Lys Val Arg Gly Glu Lys Arg Val Gly Leu Ala
    1055                1060                1065

Ser Ser Ala His Ser Lys Thr Gly Glu Thr Val Arg Pro Leu Gln
```

```
                    1070                1075                1080

Ser Thr Arg Asp
        1085

<210> SEQ ID NO 36
<211> LENGTH: 1052
<212> TYPE: PRT
<213> ORGANISM: Haemophilus parainfluenzae

<400> SEQUENCE: 36

Met Glu Asn Lys Asn Leu His Tyr Ile Leu Gly Leu Asp Leu Gly Ile
1               5                   10                  15

Ala Ser Val Gly Trp Ala Val Val Glu Ile Asp Glu Lys Glu Asn Pro
            20                  25                  30

Leu Arg Leu Ile Asp Val Gly Val Arg Thr Phe Glu Arg Ala Glu Thr
        35                  40                  45

Gln Lys Gly Glu Ser Leu Ala Leu Ser Arg Arg Ser Ala Arg Ser Ala
    50                  55                  60

Arg Arg Leu Thr Gln Arg Val Ala Arg Leu Lys Lys Ala Lys Arg
65                  70                  75                  80

Leu Leu Lys Ser Glu Asn Ile Leu Leu Ser Thr Asp Glu Arg Leu Pro
                85                  90                  95

His Gln Val Trp Gln Leu Arg Val Glu Gly Leu Asp Arg Lys Leu Glu
            100                 105                 110

Arg Gln Glu Trp Ala Ala Val Leu Leu His Leu Ile Lys His Arg Gly
        115                 120                 125

Tyr Leu Ser Gln Arg Lys Asn Glu Ser Lys Ser Glu Asn Lys Glu Leu
    130                 135                 140

Gly Ala Leu Leu Ser Gly Val Ala Ser Asn His Glu Leu Leu Gln Gln
145                 150                 155                 160

Ala Thr Tyr Arg Thr Pro Ala Glu Leu Ala Val Lys Lys Phe Glu Val
                165                 170                 175

Glu Glu Gly His Ile Arg Asn Gln Gln Gly Ala Tyr Thr His Thr Phe
            180                 185                 190

Ser Arg Leu Asp Leu Leu Ala Glu Met Glu Leu Leu Phe Ser Arg Gln
        195                 200                 205

Gln His Phe Gly Asn Pro Phe Ala Ser Glu Lys Leu Leu Glu Asn Leu
    210                 215                 220

Thr Ala Leu Leu Met Trp Gln Lys Pro Ala Leu Ser Gly Glu Asp Ile
225                 230                 235                 240

Leu Lys Met Leu Gly Lys Cys Thr Phe Glu Asp Tyr Lys Ala Ala
                245                 250                 255

Lys Asn Thr Tyr Thr Ala Glu Arg Phe Val Trp Ile Thr Lys Leu Asn
            260                 265                 270

Asn Leu Arg Ile Gln Glu Asn Gly Leu Glu Arg Ala Leu Ser Asp Asn
        275                 280                 285

Glu Arg Leu Met Leu Ile Glu Gln Pro Tyr Glu Lys Ala Lys Leu Thr
    290                 295                 300

Tyr Ala Gln Val Arg Ser Ile Leu Asn Leu Ser Asp Asp Ala Ile Phe
305                 310                 315                 320

Lys Gly Val Arg Tyr Ser Gly Glu Asp Lys Lys Ala Ile Glu Thr Lys
                325                 330                 335

Thr Thr Leu Met Glu Met Lys Ala Tyr His Gln Ile Arg Lys Val Leu
            340                 345                 350
```

```
Glu Gly Asn Asn Leu Lys Ala Glu Trp Val Ala Leu Lys Ala Asn Pro
            355                 360                 365

Thr Leu Leu Asp Glu Ile Gly Thr Ala Phe Ser Leu Tyr Lys Thr Asp
    370                 375                 380

Glu Asp Ile Ser Ala Tyr Leu Ala Gly Lys Leu Ser Gln Pro Val Leu
385                 390                 395                 400

Asn Ala Leu Leu Glu Asn Leu Ser Phe Asp Lys Phe Ile Gln Leu Ser
                405                 410                 415

Leu Lys Ala Leu Tyr Lys Leu Leu Pro Leu Met Gln Gln Gly Leu Arg
            420                 425                 430

Tyr Asp Glu Ala Cys Arg Glu Ile Tyr Gly Asp His Tyr Gly Lys Lys
            435                 440                 445

Thr Glu Glu Thr His His Phe Leu Pro Gln Ile Pro Ala Asp Glu Ile
    450                 455                 460

Arg Asn Pro Val Val Leu Arg Thr Leu Thr Gln Ala Arg Lys Val Ile
465                 470                 475                 480

Asn Gly Val Val Arg Leu Tyr Gly Ser Pro Ala Arg Ile His Ile Glu
                485                 490                 495

Thr Gly Arg Glu Val Gly Lys Ser Tyr Lys Asp Arg His Glu Leu Lys
            500                 505                 510

Lys Arg Gln Glu Glu Asn Arg Lys Gln Arg Glu Lys Thr Ile Ser Glu
            515                 520                 525

Ile Lys Thr Leu Phe Pro Asn Phe Ser Gly Glu Pro Lys Gly Lys Asp
545         530                 535                 540

Ile Leu Lys Met Arg Leu Tyr Tyr Gln Gln Asn Ala Lys Cys Leu Tyr
545                 550                 555                 560

Ser Gly Lys Pro Leu Glu Leu His Arg Leu Phe Glu Gln Lys Tyr Val
                565                 570                 575

Glu Val Asp His Ala Leu Pro Leu Ser Arg Thr Trp Asp Asp Ser Phe
            580                 585                 590

Asn Asn Lys Val Leu Val Leu Ala Asn Glu Asn Gln Asn Lys Gly Asn
            595                 600                 605

Leu Thr Pro Phe Glu Trp Leu Asp Gly Lys Asn Asn Ser Glu Arg Trp
    610                 615                 620

Arg Thr Phe Lys Ala Leu Val Glu Thr Ser Ala Phe Pro Tyr Ala Lys
625                 630                 635                 640

Lys Gln Arg Ile Leu Ser Gln Lys Leu Asp Glu Lys Gly Phe Ile Glu
                645                 650                 655

Arg Asn Leu Asn Asp Thr Arg Tyr Val Ala Arg Phe Leu Cys Asn Phe
            660                 665                 670

Ile Ala Asp Asn Met His Leu Thr Gly Glu Gly Lys Arg Lys Val Phe
            675                 680                 685

Ala Ser Asn Gly Gln Ile Thr Ala Leu Leu Arg Arg Arg Trp Gly Leu
690                 695                 700

Ala Lys Ser Arg Glu Asp Asn Asp Arg His His Ala Leu Asp Ala Val
705                 710                 715                 720

Leu Val Ala Cys Ser Thr Val Ala Met Gln Gln Lys Ile Thr Arg Phe
                725                 730                 735

Val Arg Phe Lys Ala Gly Asp Val Phe Thr Gly Glu Arg Ile Asp Arg
            740                 745                 750

Glu Thr Gly Glu Ile Ile Pro Leu His Phe Pro Thr Pro Trp Gln Phe
    755                 760                 765

Phe Lys Gln Glu Val Glu Ile Arg Ile Phe Ser Asp Asn Pro Lys Leu
```

```
                770                 775                 780
Glu Leu Glu Asn Arg Leu Pro Asp Arg Pro Gln Ala Asn His Glu Phe
785                 790                 795                 800

Val Gln Pro Leu Phe Val Ser Arg Met Pro Thr Arg Lys Met Thr Gly
                805                 810                 815

Gln Gly His Met Glu Thr Val Lys Ser Ala Lys Arg Leu Asn Glu Gly
                820                 825                 830

Ile Ser Met Ile Lys Met Pro Leu Thr Lys Leu Lys Leu Lys Asp Leu
                835                 840                 845

Glu Leu Met Val Asn Arg Glu Arg Glu Lys Asp Leu Tyr Asp Ala Leu
                850                 855                 860

Lys Thr Arg Leu Glu Ala Phe Asn Asp Asp Pro Ala Lys Ala Phe Ala
865                 870                 875                 880

Glu Pro Phe Met Lys Lys Gly Ala Ile Val Lys Ser Val Arg Val
                885                 890                 895

Glu Gln Val Gln Lys Ser Gly Val Leu Val Arg Gln Gly Asn Gly Val
                900                 905                 910

Ala Asp Asn Ala Ser Met Val Arg Val Asp Val Phe Thr Lys Asp Gly
                915                 920                 925

Lys Tyr Phe Leu Val Pro Ile Tyr Thr Trp Gln Val Ala Lys Gly Ile
                930                 935                 940

Leu Pro Asn Lys Ala Val Ile Gln Gly Lys Asp Glu Glu Asp Trp Glu
945                 950                 955                 960

Asp Ile Asp Asp Ala Thr Phe Gln Phe Ser Leu His Pro Asn Asp Leu
                965                 970                 975

Ile Ser Val Lys Thr Lys Lys Asp Glu Phe Leu Gly Tyr Phe Asn Gly
                980                 985                 990

Leu Asn Arg His Thr Gly Gly Ile Asn Ile Arg Thr His Asp Leu Glu
                995                 1000                1005

Lys Ser Lys Gly Lys Gln Gly Ile Phe Glu Gly Ile Gly Val Lys
                1010                1015                1020

Ile Ala Leu Ser Phe Glu Lys Tyr Gln Ile Asp Glu Leu Gly Lys
                1025                1030                1035

Asn Ile Arg Leu Cys Lys Pro Ser Lys Arg Gln Pro Val Arg
                1040                1045                1050

<210> SEQ ID NO 37
<211> LENGTH: 1082
<212> TYPE: PRT
<213> ORGANISM: Neisseria meningitidis

<400> SEQUENCE: 37

Met Ala Ala Phe Lys Pro Asn Pro Ile Asn Tyr Ile Leu Gly Leu Asp
1               5                   10                  15

Ile Gly Ile Ala Ser Val Gly Trp Ala Met Val Glu Ile Asp Glu Asp
                20                  25                  30

Glu Asn Pro Ile Cys Leu Ile Asp Leu Gly Val Arg Val Phe Glu Arg
                35                  40                  45

Ala Glu Val Pro Lys Thr Gly Asp Ser Leu Ala Met Ala Arg Arg Leu
        50                  55                  60

Ala Arg Ser Val Arg Arg Leu Thr Arg Arg Ala His Arg Leu Leu
65                  70                  75                  80

Arg Ala Arg Arg Leu Leu Lys Arg Glu Gly Val Leu Gln Ala Ala Asp
                85                  90                  95
```

-continued

```
Phe Asp Glu Asn Gly Leu Ile Lys Ser Leu Pro Asn Thr Pro Trp Gln
                100                 105                 110

Leu Arg Ala Ala Ala Leu Asp Arg Lys Leu Thr Pro Leu Glu Trp Ser
            115                 120                 125

Ala Val Leu Leu His Leu Ile Lys His Arg Gly Tyr Leu Ser Gln Arg
130                 135                 140

Lys Asn Glu Gly Glu Thr Ala Asp Lys Glu Leu Gly Ala Leu Leu Lys
145                 150                 155                 160

Gly Val Ala Asp Asn Ala His Ala Leu Gln Thr Gly Asp Phe Arg Thr
                165                 170                 175

Pro Ala Glu Leu Ala Leu Asn Lys Phe Glu Lys Glu Ser Gly His Ile
            180                 185                 190

Arg Asn Gln Arg Gly Asp Tyr Ser His Thr Phe Ser Arg Lys Asp Leu
        195                 200                 205

Gln Ala Glu Leu Ile Leu Leu Phe Glu Lys Gln Lys Glu Phe Gly Asn
210                 215                 220

Pro His Val Ser Gly Gly Leu Lys Glu Gly Ile Glu Thr Leu Leu Met
225                 230                 235                 240

Thr Gln Arg Pro Ala Leu Ser Gly Asp Ala Val Gln Lys Met Leu Gly
                245                 250                 255

His Cys Thr Phe Glu Pro Ala Glu Pro Lys Ala Ala Lys Asn Thr Tyr
            260                 265                 270

Thr Ala Glu Arg Phe Ile Trp Leu Thr Lys Leu Asn Asn Leu Arg Ile
        275                 280                 285

Leu Glu Gln Gly Ser Glu Arg Pro Leu Thr Asp Thr Glu Arg Ala Thr
290                 295                 300

Leu Met Asp Glu Pro Tyr Arg Lys Ser Lys Leu Thr Tyr Ala Gln Ala
305                 310                 315                 320

Arg Lys Leu Leu Gly Leu Glu Asp Thr Ala Phe Phe Lys Gly Leu Arg
                325                 330                 335

Tyr Gly Lys Asp Asn Ala Glu Ala Ser Thr Leu Met Glu Met Lys Ala
            340                 345                 350

Tyr His Ala Ile Ser Arg Ala Leu Glu Lys Glu Gly Leu Lys Asp Lys
        355                 360                 365

Lys Ser Pro Leu Asn Leu Ser Pro Glu Leu Gln Asp Glu Ile Gly Thr
370                 375                 380

Ala Phe Ser Leu Phe Lys Thr Asp Glu Asp Ile Thr Gly Arg Leu Lys
385                 390                 395                 400

Asp Arg Ile Gln Pro Glu Ile Leu Glu Ala Leu Leu Lys His Ile Ser
                405                 410                 415

Phe Asp Lys Phe Val Gln Ile Ser Leu Lys Ala Leu Arg Arg Ile Val
            420                 425                 430

Pro Leu Met Glu Gln Gly Lys Arg Tyr Asp Glu Ala Cys Ala Glu Ile
        435                 440                 445

Tyr Gly Asp His Tyr Gly Lys Lys Asn Thr Glu Lys Ile Tyr Leu
450                 455                 460

Pro Pro Ile Pro Ala Asp Glu Ile Arg Asn Pro Val Val Leu Arg Ala
465                 470                 475                 480

Leu Ser Gln Ala Arg Lys Val Ile Asn Gly Val Val Arg Arg Tyr Gly
                485                 490                 495

Ser Pro Ala Arg Ile His Ile Glu Thr Ala Arg Glu Val Gly Lys Ser
            500                 505                 510

Phe Lys Asp Arg Lys Glu Ile Glu Lys Arg Gln Glu Glu Asn Arg Lys
```

```
                515                 520                 525
Asp Arg Glu Lys Ala Ala Lys Phe Arg Glu Tyr Phe Pro Asn Phe
            530                 535                 540
Val Gly Glu Pro Lys Ser Lys Asp Ile Leu Lys Leu Arg Leu Tyr Glu
545                 550                 555                 560
Gln Gln His Gly Lys Cys Leu Tyr Ser Gly Lys Glu Ile Asn Leu Gly
                565                 570                 575
Arg Leu Asn Glu Lys Gly Tyr Val Glu Ile Asp His Ala Leu Pro Phe
            580                 585                 590
Ser Arg Thr Trp Asp Asp Ser Phe Asn Asn Lys Val Leu Val Leu Gly
            595                 600                 605
Ser Glu Asn Gln Asn Lys Gly Asn Gln Thr Pro Tyr Glu Tyr Phe Asn
            610                 615                 620
Gly Lys Asp Asn Ser Arg Glu Trp Gln Glu Phe Lys Ala Arg Val Glu
625                 630                 635                 640
Thr Ser Arg Phe Pro Arg Ser Lys Lys Gln Arg Ile Leu Leu Gln Lys
                645                 650                 655
Phe Asp Glu Asp Gly Phe Lys Glu Arg Asn Leu Asn Asp Thr Arg Tyr
            660                 665                 670
Val Asn Arg Phe Leu Cys Gln Phe Val Ala Asp Arg Met Arg Leu Thr
            675                 680                 685
Gly Lys Gly Lys Lys Arg Val Phe Ala Ser Asn Gly Gln Ile Thr Asn
            690                 695                 700
Leu Leu Arg Gly Phe Trp Gly Leu Arg Lys Val Arg Ala Glu Asn Asp
705                 710                 715                 720
Arg His His Ala Leu Asp Ala Val Val Val Ala Cys Ser Thr Val Ala
                725                 730                 735
Met Gln Gln Lys Ile Thr Arg Phe Val Arg Tyr Lys Glu Met Asn Ala
                740                 745                 750
Phe Asp Gly Lys Thr Ile Asp Lys Glu Thr Gly Glu Val Leu His Gln
                755                 760                 765
Lys Thr His Phe Pro Gln Pro Trp Glu Phe Phe Ala Gln Glu Val Met
            770                 775                 780
Ile Arg Val Phe Gly Lys Pro Asp Gly Lys Pro Glu Phe Glu Glu Ala
785                 790                 795                 800
Asp Thr Pro Glu Lys Leu Arg Thr Leu Leu Ala Glu Lys Leu Ser Ser
                805                 810                 815
Arg Pro Glu Ala Val His Glu Tyr Val Thr Pro Leu Phe Val Ser Arg
            820                 825                 830
Ala Pro Asn Arg Lys Met Ser Gly Gln Gly His Met Glu Thr Val Lys
            835                 840                 845
Ser Ala Lys Arg Leu Asp Glu Gly Val Ser Val Leu Arg Val Pro Leu
            850                 855                 860
Thr Gln Leu Lys Leu Lys Asp Leu Glu Lys Met Val Asn Arg Glu Arg
865                 870                 875                 880
Glu Pro Lys Leu Tyr Glu Ala Leu Lys Ala Arg Leu Glu Ala His Lys
                885                 890                 895
Asp Asp Pro Ala Lys Ala Phe Ala Glu Pro Phe Tyr Lys Tyr Asp Lys
            900                 905                 910
Ala Gly Asn Arg Thr Gln Gln Val Lys Ala Val Arg Val Glu Gln Val
            915                 920                 925
Gln Lys Thr Gly Val Trp Val Arg Asn His Asn Gly Ile Ala Asp Asn
            930                 935                 940
```

Ala Thr Met Val Arg Val Asp Val Phe Glu Lys Gly Asp Lys Tyr Tyr
945                 950                 955                 960

Leu Val Pro Ile Tyr Ser Trp Gln Val Ala Lys Gly Ile Leu Pro Asp
            965                 970                 975

Arg Ala Val Val Gln Gly Lys Asp Glu Glu Asp Trp Gln Leu Ile Asp
            980                 985                 990

Asp Ser Phe Asn Phe Lys Phe Ser Leu His Pro Asn Asp Leu Val Glu
        995                 1000                1005

Val Ile Thr Lys Lys Ala Arg Met Phe Gly Tyr Phe Ala Ser Cys
1010                1015                1020

His Arg Gly Thr Gly Asn Ile Asn Ile Arg Ile His Asp Leu Asp
    1025                1030                1035

His Lys Ile Gly Lys Asn Gly Ile Leu Glu Gly Ile Gly Val Lys
    1040                1045                1050

Thr Ala Leu Ser Phe Gln Lys Tyr Gln Ile Asp Glu Leu Gly Lys
    1055                1060                1065

Glu Ile Arg Pro Cys Arg Leu Lys Lys Arg Pro Pro Val Arg
    1070                1075                1080

<210> SEQ ID NO 38
<211> LENGTH: 338
<212> TYPE: PRT
<213> ORGANISM: Homo sapiens

<400> SEQUENCE: 38

Met Gly Lys Lys Gln Asn Arg Lys Thr Gly Asn Ser Lys Thr Gln Ser
1               5                   10                  15

Ala Ser Pro Pro Lys Glu Arg Ser Ser Pro Ala Thr Glu Gln
            20                  25                  30

Ser Trp Met Glu Asn Asp Phe Asp Glu Leu Arg Glu Glu Gly Phe Arg
        35                  40                  45

Arg Ser Asn Tyr Ser Glu Leu Arg Glu Asp Ile Gln Thr Lys Gly Lys
    50                  55                  60

Glu Val Glu Asn Phe Glu Lys Asn Leu Glu Glu Cys Ile Thr Arg Ile
65                  70                  75                  80

Thr Asn Thr Glu Lys Cys Leu Lys Glu Leu Met Glu Leu Lys Thr Lys
                85                  90                  95

Ala Arg Glu Leu Arg Glu Glu Cys Arg Ser Leu Arg Ser Arg Cys Asp
            100                 105                 110

Gln Leu Glu Glu Arg Val Ser Ala Met Glu Asp Glu Met Asn Glu Met
        115                 120                 125

Lys Arg Glu Gly Lys Phe Arg Glu Lys Arg Ile Lys Arg Asn Glu Gln
    130                 135                 140

Ser Leu Gln Glu Ile Trp Asp Tyr Val Lys Arg Pro Asn Leu Arg Leu
145                 150                 155                 160

Ile Gly Val Pro Glu Ser Asp Val Glu Asn Gly Thr Lys Leu Glu Asn
                165                 170                 175

Thr Leu Gln Asp Ile Ile Gln Glu Asn Phe Pro Asn Leu Ala Arg Gln
            180                 185                 190

Ala Asn Val Gln Ile Gln Glu Ile Gln Arg Thr Pro Gln Arg Tyr Ser
        195                 200                 205

Ser Arg Arg Ala Thr Pro Arg His Ile Ile Val Arg Phe Thr Lys Val
    210                 215                 220

Glu Met Lys Glu Lys Met Leu Arg Ala Ala Arg Glu Lys Gly Arg Val

```
            225                 230                 235                 240

Thr Leu Lys Gly Lys Pro Ile Arg Leu Thr Ala Asp Leu Ser Ala Glu
                        245                 250                 255

Thr Leu Gln Ala Arg Arg Glu Trp Gly Pro Ile Phe Asn Ile Leu Lys
                    260                 265                 270

Glu Lys Asn Phe Gln Pro Arg Ile Ser Tyr Pro Ala Lys Leu Ser Phe
                275                 280                 285

Ile Ser Glu Gly Glu Ile Lys Tyr Phe Ile Asp Lys Gln Met Leu Arg
            290                 295                 300

Asp Phe Val Thr Thr Arg Pro Ala Leu Lys Glu Leu Leu Lys Glu Ala
        305                 310                 315                 320

Leu Asn Met Glu Arg Asn Asn Arg Tyr Gln Pro Leu Gln Asn His Ala
                        325                 330                 335

Lys Met

<210> SEQ ID NO 39
<211> LENGTH: 357
<212> TYPE: PRT
<213> ORGANISM: Mus sp.

<400> SEQUENCE: 39

Met Ala Lys Gly Lys Arg Lys Asn Pro Thr Asn Arg Asn Gln Asp His
        1               5                   10                  15

Ser Pro Ser Ser Glu Arg Ser Thr Pro Thr Pro Ser Pro Gly His
                    20                  25                  30

Pro Asn Thr Thr Glu Asn Leu Asp Pro Asp Leu Lys Thr Phe Leu Met
                    35                  40                  45

Met Met Ile Glu Asp Ile Lys Lys Asp Phe His Lys Ser Leu Lys Asp
            50                  55                  60

Leu Gln Glu Ser Thr Ala Lys Glu Leu Gln Ala Leu Lys Glu Lys Gln
        65                  70                  75                  80

Glu Asn Thr Ala Lys Gln Val Met Glu Met Asn Lys Thr Ile Leu Glu
                        85                  90                  95

Leu Lys Gly Glu Val Asp Thr Ile Lys Lys Thr Gln Ser Glu Ala Thr
                    100                 105                 110

Leu Glu Ile Glu Thr Leu Gly Lys Arg Ser Gly Thr Ile Asp Ala Ser
                    115                 120                 125

Ile Ser Asn Arg Ile Gln Glu Met Glu Glu Arg Ile Ser Gly Ala Glu
            130                 135                 140

Asp Ser Ile Glu Asn Ile Asp Thr Thr Val Lys Glu Asn Thr Lys Cys
        145                 150                 155                 160

Lys Arg Ile Leu Thr Gln Asn Ile Gln Val Ile Gln Asp Thr Met Arg
                        165                 170                 175

Arg Pro Asn Leu Arg Ile Ile Gly Ile Asp Glu Asn Glu Asp Phe Gln
                    180                 185                 190

Leu Lys Gly Pro Ala Asn Ile Phe Asn Lys Ile Ile Glu Glu Asn Phe
                    195                 200                 205

Pro Asn Ile Lys Lys Glu Met Pro Met Ile Ile Gln Glu Ala Tyr Arg
            210                 215                 220

Thr Pro Asn Arg Leu Asp Gln Lys Arg Asn Ser Ser Arg His Ile Ile
        225                 230                 235                 240

Ile Arg Thr Thr Asn Ala Leu Asn Lys Asp Arg Ile Leu Lys Ala Val
                        245                 250                 255

Arg Glu Lys Gly Gln Val Thr Tyr Lys Gly Arg Pro Ile Arg Ile Thr
```

```
                    260                 265                 270
Pro Asp Phe Ser Pro Glu Thr Met Lys Ala Arg Arg Ala Trp Thr Asp
                275                 280                 285
Val Ile Gln Thr Leu Arg Glu His Lys Cys Gln Pro Arg Leu Leu Tyr
            290                 295                 300
Pro Ala Lys Leu Ser Ile Thr Ile Asp Gly Glu Thr Lys Val Phe His
305                 310                 315                 320
Asp Lys Thr Lys Phe Thr Gln Tyr Leu Ser Thr Asn Pro Ala Leu Gln
                325                 330                 335
Arg Ile Ile Thr Glu Lys Lys Gln Tyr Lys Asp Gly Asn His Ala Leu
            340                 345                 350
Glu Gln Pro Arg Lys
            355

<210> SEQ ID NO 40
<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Met Thr Leu Asn Ile Glu Asp Glu Tyr Arg Leu His Glu Thr Ser Lys
1               5                   10                  15
Glu Pro Asp Val Ser Leu Gly Ser Thr Trp Leu Ser Asp Phe Pro Gln
            20                  25                  30
Ala Trp Ala Glu Thr Gly Gly Met Gly Leu Ala Val Arg Gln Ala Pro
        35                  40                  45
Leu Ile Ile Pro Leu Lys Ala Thr Ser Thr Pro Val Ser Ile Lys Gln
    50                  55                  60
Tyr Pro Met Ser Gln Glu Ala Arg Leu Gly Ile Lys Pro His Ile Gln
65                  70                  75                  80
Arg Leu Leu Asp Gln Gly Ile Leu Val Pro Cys Gln Ser Pro Trp Asn
                85                  90                  95
Thr Pro Leu Leu Pro Val Lys Lys Pro Gly Thr Asn Asp Tyr Arg Pro
            100                 105                 110
Val Gln Asp Leu Arg Glu Val Asn Lys Arg Val Glu Asp Ile His Pro
        115                 120                 125
Thr Val Pro Asn Pro Tyr Asn Leu Leu Ser Gly Leu Pro Pro Ser His
    130                 135                 140
Gln Trp Tyr Thr Val Leu Asp Leu Lys Asp Ala Phe Phe Cys Leu Arg
145                 150                 155                 160
Leu His Pro Thr Ser Gln Pro Leu Phe Ala Phe Glu Trp Arg Asp Pro
                165                 170                 175
Glu Met Gly Ile Ser Gly Gln Leu Thr Trp Thr Arg Leu Pro Gln Gly
            180                 185                 190
Phe Lys Asn Ser Pro Thr Leu Phe Asn Glu Ala Leu His Arg Asp Leu
        195                 200                 205
Ala Asp Phe Arg Ile Gln His Pro Asp Leu Ile Leu Leu Gln Tyr Val
    210                 215                 220
Asp Asp Leu Leu Leu Ala Ala Thr Ser Glu Leu Asp Cys Gln Gln Gly
225                 230                 235                 240
Thr Arg Ala Leu Leu Gln Thr Leu Gly Asn Leu Gly Tyr Arg Ala Ser
                245                 250                 255
```

```
Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Arg Glu Phe
    290                 295                 300

Leu Gly Lys Ala Gly Phe Cys Arg Leu Phe Ile Pro Gly Phe Ala Glu
305                 310                 315                 320

Met Ala Ala Pro Leu Tyr Pro Leu Thr Lys Pro Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Asp Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
                565                 570                 575

Lys Lys Leu Asn Val Tyr Thr Asp Ser Arg Tyr Ala Phe Ala Thr Ala
            580                 585                 590

His Ile His Gly Glu Ile Tyr Arg Arg Arg Gly Trp Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro
```

<210> SEQ ID NO 41
<211> LENGTH: 678
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 41

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asn Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Arg Glu Phe
    290                 295                 300

Leu Gly Lys Ala Gly Phe Cys Arg Leu Phe Ile Pro Gly Phe Ala Glu
305                 310                 315                 320

Met Ala Ala Pro Leu Tyr Pro Leu Thr Lys Pro Gly Thr Leu Phe Asn
                325                 330                 335

Trp Gly Pro Asp Gln Gln Lys Ala Tyr Gln Glu Ile Lys Gln Ala Leu
            340                 345                 350

```
Leu Thr Ala Pro Ala Leu Gly Leu Pro Asp Leu Thr Lys Pro Phe Glu
            355                 360                 365

Leu Phe Val Asp Glu Lys Gln Gly Tyr Ala Lys Gly Val Leu Thr Gln
370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Lys Leu Thr Met Gly Gln Pro
            420                 425                 430

Leu Val Ile Leu Ala Pro His Ala Val Glu Ala Leu Val Lys Gln Pro
            435                 440                 445

Pro Asp Arg Trp Leu Ser Asn Ala Arg Met Thr His Tyr Gln Ala Leu
            450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Asp Gly Ser Ser
            515                 520                 525

Leu Leu Gln Glu Gly Gln Arg Lys Ala Gly Ala Ala Val Thr Thr Glu
            530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
                565                 570                 575

Lys Lys Leu Asn Val Tyr Thr Asp Ser Arg Tyr Ala Phe Ala Thr Ala
            580                 585                 590

His Ile His Gly Glu Ile Tyr Arg Arg Gly Trp Leu Thr Ser Glu
            595                 600                 605

Gly Lys Glu Ile Lys Asn Lys Asp Glu Ile Leu Ala Leu Leu Lys Ala
610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro
            675

<210> SEQ ID NO 42
<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Thr Leu Asn Ile Glu Asp Glu Tyr Arg Leu His Glu Thr Ser Lys
1               5                   10                  15

Glu Pro Asp Val Ser Leu Gly Ser Thr Trp Leu Ser Asp Phe Pro Gln
            20                  25                  30
```

```
Ala Trp Ala Glu Thr Gly Gly Met Gly Leu Ala Val Arg Gln Ala Pro
         35                  40                  45

Leu Ile Ile Leu Leu Lys Ala Thr Ser Thr Pro Val Ser Ile Lys Gln
 50                  55                  60

Tyr Pro Met Ser Gln Glu Ala Arg Leu Gly Ile Lys Pro His Ile Gln
 65                  70                  75                  80

Arg Leu Leu Asp Gln Gly Ile Leu Val Pro Cys Gln Ser Pro Trp Asn
                 85                  90                  95

Thr Pro Leu Leu Pro Val Lys Lys Pro Gly Thr Asn Asp Tyr Arg Pro
             100                 105                 110

Val Gln Asp Leu Arg Glu Val Asn Lys Arg Val Glu Asp Ile His Pro
         115                 120                 125

Thr Val Pro Asn Pro Tyr Asn Leu Leu Ser Gly Leu Pro Pro Ser His
     130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                 165                 170                 175

Glu Met Gly Ile Ser Gly Gln Leu Thr Trp Thr Arg Leu Pro Gln Gly
             180                 185                 190

Phe Lys Asn Ser Pro Thr Leu Phe Asn Glu Ala Leu His Arg Asp Leu
         195                 200                 205

Ala Asp Phe Arg Ile Gln His Pro Asp Leu Ile Leu Leu Gln Tyr Val
     210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                 245                 250                 255

Ala Lys Lys Ala Gln Ile Cys Gln Lys Gln Val Lys Tyr Leu Gly Tyr
             260                 265                 270

Leu Leu Lys Glu Gly Gln Arg Trp Leu Thr Glu Ala Arg Lys Glu Thr
         275                 280                 285

Val Met Gly Gln Pro Thr Pro Lys Thr Pro Arg Gln Leu Arg Glu Phe
     290                 295                 300

Leu Gly Lys Ala Gly Phe Cys Arg Leu Phe Ile Pro Gly Phe Ala Glu
305                 310                 315                 320

Met Ala Ala Pro Leu Tyr Pro Leu Thr Lys Pro Gly Thr Leu Phe Asn
                 325                 330                 335

Trp Gly Pro Asp Gln Gln Lys Ala Tyr Gln Glu Ile Lys Gln Ala Leu
             340                 345                 350

Leu Thr Ala Pro Ala Leu Gly Leu Pro Asp Leu Thr Lys Pro Phe Glu
         355                 360                 365

Leu Phe Val Asp Glu Lys Gln Gly Tyr Ala Lys Gly Val Leu Thr Gln
     370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                 405                 410                 415

Ile Ala Val Leu Thr Lys Asp Ala Gly Lys Leu Thr Met Gly Gln Pro
             420                 425                 430

Leu Val Ile Leu Ala Pro His Ala Val Glu Ala Leu Val Lys Gln Pro
         435                 440                 445
```

Pro Asp Arg Trp Leu Ser Asn Ala Arg Met Thr His Tyr Gln Ala Leu
450                 455                 460

Leu Leu Asp Thr Asp Arg Val Gln Phe Gly Pro Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Asp Gly Ser Ser
            515                 520                 525

Leu Leu Gln Glu Gly Gln Arg Lys Ala Gly Ala Ala Val Thr Thr Glu
530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
                565                 570                 575

Lys Lys Leu Asn Val Tyr Thr Asp Ser Arg Tyr Ala Phe Ala Thr Ala
            580                 585                 590

His Ile His Gly Glu Ile Tyr Arg Arg Arg Gly Trp Leu Thr Ser Glu
            595                 600                 605

Gly Lys Glu Ile Lys Asn Lys Asp Glu Ile Leu Ala Leu Leu Lys Ala
610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro
            675

<210> SEQ ID NO 43
<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Met Thr Leu Asn Ile Glu Asp Glu Tyr Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ala Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

```
Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
                180                 185                 190

Phe Lys Asn Ser Pro Thr Leu Phe Asn Glu Ala Leu His Arg Asp Leu
                195                 200                 205

Ala Asp Phe Arg Ile Gln His Pro Asp Leu Ile Leu Leu Gln Tyr Val
210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
                260                 265                 270

Leu Leu Lys Glu Gly Gln Arg Trp Leu Thr Glu Ala Arg Lys Glu Thr
                275                 280                 285

Val Met Gly Gln Pro Thr Pro Lys Thr Pro Arg Gln Leu Arg Glu Phe
290                 295                 300

Leu Gly Lys Ala Gly Phe Cys Arg Leu Phe Ile Pro Gly Phe Ala Glu
305                 310                 315                 320

Met Ala Ala Pro Leu Tyr Pro Leu Thr Lys Pro Gly Thr Leu Phe Asn
                325                 330                 335

Trp Gly Pro Asp Gln Gln Lys Ala Tyr Gln Glu Ile Lys Gln Ala Leu
                340                 345                 350

Leu Thr Ala Pro Ala Leu Gly Leu Pro Asp Leu Thr Lys Pro Phe Glu
                355                 360                 365

Leu Phe Val Asp Glu Lys Gln Gly Tyr Ala Lys Gly Val Leu Thr Gln
                370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
                420                 425                 430

Leu Val Ile Leu Ala Pro His Ala Val Glu Ala Leu Val Lys Gln Pro
                435                 440                 445

Pro Asp Arg Trp Leu Ser Asn Ala Arg Met Thr His Tyr Gln Ala Leu
450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
                500                 505                 510

Gln Pro Leu Pro Asp Ala Asp His Thr Trp Tyr Thr Asp Gly Ser Ser
                515                 520                 525

Leu Leu Gln Glu Gly Gln Arg Lys Ala Gly Ala Ala Val Thr Thr Glu
530                 535                 540
```

```
Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
                565                 570                 575

Lys Lys Leu Asn Val Tyr Thr Asp Ser Arg Tyr Ala Phe Ala Thr Ala
                580                 585                 590

His Ile His Gly Glu Ile Tyr Arg Arg Gly Trp Leu Thr Ser Glu
                595                 600                 605

Gly Lys Glu Ile Lys Asn Lys Asp Glu Ile Leu Ala Leu Leu Lys Ala
        610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
                660                 665                 670

Ile Glu Asn Ser Ser Pro
                675

<210> SEQ ID NO 44
<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Met Thr Leu Asn Ile Glu Asp Glu Tyr Arg Leu His Glu Thr Ser Lys
1               5                   10                  15

Glu Pro Asp Val Ser Leu Gly Ser Thr Trp Leu Ser Asp Phe Pro Gln
                20                  25                  30

Ala Trp Ala Glu Thr Gly Gly Met Gly Leu Ala Val Arg Gln Ala Pro
            35                  40                  45

Leu Ile Ile Pro Leu Lys Ala Thr Ser Thr Pro Val Ser Ile Lys Gln
    50                  55                  60

Tyr Pro Met Arg Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asn Glu Ala Leu His Arg Asp Leu
        195                 200                 205

Ala Asp Phe Arg Ile Gln His Pro Asp Leu Ile Leu Leu Gln Tyr Val
    210                 215                 220
```

```
Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
            245                 250                 255

Ala Lys Lys Ala Gln Ile Cys Gln Lys Gln Val Lys Tyr Leu Gly Tyr
        260                 265                 270

Leu Leu Lys Glu Gly Gln Arg Trp Leu Thr Glu Ala Arg Lys Glu Thr
    275                 280                 285

Val Met Gly Gln Pro Thr Pro Lys Thr Pro Arg Gln Leu Arg Glu Phe
290                 295                 300

Leu Gly Lys Ala Gly Phe Cys Arg Leu Phe Ile Pro Gly Phe Ala Glu
305                 310                 315                 320

Met Ala Ala Pro Leu Tyr Pro Leu Thr Lys Pro Gly Thr Leu Phe Asn
            325                 330                 335

Trp Gly Pro Asp Gln Gln Lys Ala Tyr Gln Glu Ile Lys Gln Ala Leu
        340                 345                 350

Leu Thr Ala Pro Ala Leu Gly Leu Pro Asp Leu Thr Lys Pro Phe Glu
    355                 360                 365

Leu Phe Val Asp Glu Lys Gln Gly Tyr Ala Lys Gly Val Leu Thr Gln
370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
            405                 410                 415

Ile Ala Val Leu Thr Lys Asp Ala Gly Lys Leu Thr Met Gly Gln Pro
        420                 425                 430

Leu Val Ile Leu Ala Pro His Ala Val Glu Ala Leu Val Lys Gln Pro
    435                 440                 445

Pro Asp Arg Trp Leu Ser Asn Ala Arg Met Thr His Tyr Gln Ala Leu
450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
            485                 490                 495

Leu Asp Ile Leu Ala Glu Ala His Gly Thr Arg Pro Asp Leu Thr Asp
        500                 505                 510

Gln Pro Leu Pro Asp Ala Asp His Thr Trp Tyr Thr Asp Gly Ser Ser
    515                 520                 525

Leu Leu Gln Glu Gly Gln Arg Lys Ala Gly Ala Ala Val Thr Thr Glu
530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
            565                 570                 575

Lys Lys Leu Asn Val Tyr Thr Asp Ser Arg Tyr Ala Phe Ala Thr Ala
        580                 585                 590

His Ile His Gly Glu Ile Tyr Arg Arg Arg Gly Trp Leu Thr Ser Glu
    595                 600                 605

Gly Lys Glu Ile Lys Asn Lys Asp Glu Ile Leu Ala Leu Leu Lys Ala
610                 615                 620

Leu Phe Leu Pro Lys Arg Leu Ser Ile Ile His Cys Pro Gly His Gln
625                 630                 635                 640
```

```
Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro
        675
```

```
<210> SEQ ID NO 45
<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45
```

```
Met Thr Leu Asn Ile Glu Asp Glu Tyr Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
 50                  55                  60

Tyr Pro Met Ser Gln Lys Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asn Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Arg Glu Phe
    290                 295                 300

Leu Gly Lys Ala Gly Phe Cys Arg Leu Phe Ile Pro Gly Phe Ala Glu
305                 310                 315                 320
```

```
Met Ala Ala Pro Leu Tyr Pro Leu Thr Lys Pro Gly Thr Leu Phe Asn
            325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
            355                 360                 365

Leu Phe Val Asp Glu Lys Gln Gly Tyr Ala Lys Gly Val Leu Thr Gln
        370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
        450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Asp Gly Ser Ser
        515                 520                 525

Leu Leu Gln Glu Gly Gln Arg Lys Ala Gly Ala Ala Val Thr Thr Glu
        530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
                565                 570                 575

Lys Lys Leu Asn Val Tyr Thr Asp Ser Arg Tyr Ala Phe Ala Thr Ala
            580                 585                 590

His Ile His Gly Glu Ile Tyr Arg Arg Arg Gly Trp Leu Thr Ser Glu
        595                 600                 605

Gly Lys Glu Ile Lys Asn Lys Asp Glu Ile Leu Ala Leu Leu Lys Ala
        610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro
            675

<210> SEQ ID NO 46
<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 46

```
Met Thr Leu Asn Ile Glu Asp Glu Tyr Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Ala Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asn Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Arg Glu Phe
    290                 295                 300

Leu Gly Lys Ala Gly Phe Cys Arg Leu Phe Ile Pro Gly Phe Ala Glu
305                 310                 315                 320

Met Ala Ala Pro Leu Tyr Pro Leu Thr Lys Pro Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415
```

```
Ile Ala Val Leu Thr Lys Asp Ala Gly Lys Leu Thr Met Gly Gln Pro
                420                 425                 430

Leu Val Ile Leu Ala Pro His Ala Val Glu Ala Leu Val Lys Gln Pro
            435                 440                 445

Pro Asp Arg Trp Leu Ser Asn Ala Arg Met Thr His Tyr Gln Ala Leu
        450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Asp Gly Ser Ser
        515                 520                 525

Leu Leu Gln Glu Gly Gln Arg Lys Ala Gly Ala Ala Val Thr Thr Glu
530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
                565                 570                 575

Lys Lys Leu Asn Val Tyr Thr Asp Ser Arg Tyr Ala Phe Ala Thr Ala
            580                 585                 590

His Ile His Gly Glu Ile Tyr Arg Arg Arg Gly Trp Leu Thr Ser Glu
        595                 600                 605

Gly Lys Glu Ile Lys Asn Lys Asp Glu Ile Leu Ala Leu Leu Lys Ala
610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro
            675

<210> SEQ ID NO 47
<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Met Thr Leu Asn Ile Glu Asp Glu Tyr Arg Leu His Glu Thr Ser Lys
1               5                   10                  15

Glu Pro Asp Val Ser Leu Gly Ser Thr Trp Leu Ser Asp Phe Pro Gln
                20                  25                  30

Ala Trp Ala Glu Thr Gly Gly Met Gly Leu Ala Val Arg Gln Ala Pro
            35                  40                  45

Leu Ile Ile Pro Leu Lys Ala Thr Ser Thr Pro Val Ser Ile Lys Gln
        50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
```

-continued

```
                85                  90                  95
Thr Pro Leu Leu Pro Val Lys Lys Pro Gly Thr Asn Asp Tyr Arg Pro
            100                 105                 110
Val Gln Asp Leu Arg Glu Val Asn Lys Arg Val Glu Asp Ile His Pro
            115                 120                 125
Thr Val Pro Asn Pro Tyr Asn Leu Leu Ser Gly Leu Pro Pro Ser His
            130                 135                 140
Gln Trp Tyr Thr Val Leu Asp Leu Lys Asp Ala Tyr Phe Cys Leu Arg
145                 150                 155                 160
Leu His Pro Thr Ser Gln Pro Leu Phe Ala Phe Glu Trp Arg Asp Pro
                165                 170                 175
Glu Met Gly Ile Ser Gly Gln Leu Thr Trp Thr Arg Leu Pro Gln Gly
                180                 185                 190
Phe Lys Asn Ser Pro Thr Leu Phe Asn Glu Ala Leu His Arg Asp Leu
                195                 200                 205
Ala Asp Phe Arg Ile Gln His Pro Asp Leu Ile Leu Leu Gln Tyr Val
            210                 215                 220
Asp Asp Leu Leu Leu Ala Ala Thr Ser Glu Leu Asp Cys Gln Gln Gly
225                 230                 235                 240
Thr Arg Ala Leu Leu Gln Thr Leu Gly Asn Leu Gly Tyr Arg Ala Ser
                245                 250                 255
Ala Lys Lys Ala Gln Ile Cys Gln Lys Gln Val Lys Tyr Leu Gly Tyr
                260                 265                 270
Leu Leu Lys Glu Gly Gln Arg Trp Leu Thr Glu Ala Arg Lys Glu Thr
            275                 280                 285
Val Met Gly Gln Pro Thr Pro Lys Thr Pro Arg Gln Leu Arg Glu Phe
            290                 295                 300
Leu Gly Lys Ala Gly Phe Cys Arg Leu Phe Ile Pro Gly Phe Ala Glu
305                 310                 315                 320
Met Ala Ala Pro Leu Tyr Pro Leu Thr Lys Pro Gly Thr Leu Phe Asn
                325                 330                 335
Trp Gly Pro Asp Gln Gln Lys Ala Tyr Gln Glu Ile Lys Gln Ala Leu
                340                 345                 350
Leu Thr Ala Pro Ala Leu Gly Leu Pro Asp Leu Thr Lys Pro Phe Glu
            355                 360                 365
Leu Phe Val Asp Glu Lys Gln Gly Tyr Ala Lys Gly Val Leu Thr Gln
            370                 375                 380
Lys Leu Gly Pro Trp Arg Arg Pro Val Ala Tyr Leu Ser Lys Lys Leu
385                 390                 395                 400
Asp Pro Val Ala Ala Gly Trp Pro Pro Cys Leu Arg Met Val Ala Ala
                405                 410                 415
Ile Ala Val Leu Thr Lys Asp Ala Gly Lys Leu Thr Met Gly Gln Pro
            420                 425                 430
Leu Val Ile Leu Ala Pro His Ala Val Glu Ala Leu Val Lys Gln Pro
            435                 440                 445
Pro Asp Arg Trp Leu Ser Asn Ala Arg Met Thr His Tyr Gln Ala Leu
450                 455                 460
Leu Leu Asp Thr Asp Arg Val Gln Phe Gly Pro Val Val Ala Leu Asn
465                 470                 475                 480
Pro Ala Thr Leu Leu Pro Leu Pro Glu Glu Gly Leu Gln His Asn Cys
                485                 490                 495
Leu Asp Ile Leu Ala Glu Ala His Gly Thr Arg Pro Asp Leu Thr Asp
                500                 505                 510
```

-continued

```
Gln Pro Leu Pro Asp Ala Asp His Thr Trp Tyr Thr Asp Gly Ser Ser
            515                 520                 525

Leu Leu Gln Glu Gly Gln Arg Lys Ala Gly Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
                565                 570                 575

Lys Lys Leu Asn Val Tyr Thr Asp Ser Arg Tyr Ala Phe Ala Thr Ala
                580                 585                 590

His Ile His Gly Glu Ile Tyr Arg Arg Arg Gly Trp Leu Thr Ser Glu
            595                 600                 605

Gly Lys Glu Ile Lys Asn Lys Asp Glu Ile Leu Ala Leu Leu Lys Ala
        610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro
            675

<210> SEQ ID NO 48
<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Met Thr Leu Asn Ile Glu Asp Glu Tyr Arg Leu His Glu Thr Ser Lys
1               5                  10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
```

```
            180                 185                 190
Phe Lys Asn Ser Pro Ala Leu Phe Asn Glu Ala Leu His Arg Asp Leu
            195                 200                 205
Ala Asp Phe Arg Ile Gln His Pro Asp Leu Ile Leu Leu Gln Tyr Val
            210                 215                 220
Asp Asp Leu Leu Leu Ala Ala Thr Ser Glu Leu Asp Cys Gln Gln Gly
225                 230                 235                 240
Thr Arg Ala Leu Leu Gln Thr Leu Gly Asn Leu Gly Tyr Arg Ala Ser
                245                 250                 255
Ala Lys Lys Ala Gln Ile Cys Gln Lys Gln Val Lys Tyr Leu Gly Tyr
            260                 265                 270
Leu Leu Lys Glu Gly Gln Arg Trp Leu Thr Glu Ala Arg Lys Glu Thr
            275                 280                 285
Val Met Gly Gln Pro Thr Pro Lys Thr Pro Arg Gln Leu Arg Glu Phe
            290                 295                 300
Leu Gly Lys Ala Gly Phe Cys Arg Leu Phe Ile Pro Gly Phe Ala Glu
305                 310                 315                 320
Met Ala Ala Pro Leu Tyr Pro Leu Thr Lys Pro Gly Thr Leu Phe Asn
                325                 330                 335
Trp Gly Pro Asp Gln Gln Lys Ala Tyr Gln Glu Ile Lys Gln Ala Leu
                340                 345                 350
Leu Thr Ala Pro Ala Leu Gly Leu Pro Asp Leu Thr Lys Pro Phe Glu
                355                 360                 365
Leu Phe Val Asp Glu Lys Gln Gly Tyr Ala Lys Gly Val Leu Thr Gln
            370                 375                 380
Lys Leu Gly Pro Trp Arg Arg Pro Val Ala Tyr Leu Ser Lys Lys Leu
385                 390                 395                 400
Asp Pro Val Ala Ala Gly Trp Pro Pro Cys Leu Arg Met Val Ala Ala
                405                 410                 415
Ile Ala Val Leu Thr Lys Asp Ala Gly Lys Leu Thr Met Gly Gln Pro
                420                 425                 430
Leu Val Ile Leu Ala Pro His Ala Val Glu Ala Leu Val Lys Gln Pro
            435                 440                 445
Pro Asp Arg Trp Leu Ser Asn Ala Arg Met Thr His Tyr Gln Ala Leu
    450                 455                 460
Leu Leu Asp Thr Asp Arg Val Gln Phe Gly Pro Val Val Ala Leu Asn
465                 470                 475                 480
Pro Ala Thr Leu Leu Pro Leu Pro Glu Glu Gly Leu Gln His Asn Cys
                485                 490                 495
Leu Asp Ile Leu Ala Glu Ala His Gly Thr Arg Pro Asp Leu Thr Asp
            500                 505                 510
Gln Pro Leu Pro Asp Ala Asp His Thr Trp Tyr Thr Asp Gly Ser Ser
            515                 520                 525
Leu Leu Gln Glu Gly Gln Arg Lys Ala Gly Ala Ala Val Thr Thr Glu
            530                 535                 540
Thr Glu Val Ile Trp Ala Lys Ala Leu Pro Ala Gly Thr Ser Ala Gln
545                 550                 555                 560
Arg Ala Glu Leu Ile Ala Leu Thr Gln Ala Leu Lys Met Ala Glu Gly
                565                 570                 575
Lys Lys Leu Asn Val Tyr Thr Asp Ser Arg Tyr Ala Phe Ala Thr Ala
            580                 585                 590
His Ile His Gly Glu Ile Tyr Arg Arg Arg Gly Trp Leu Thr Ser Glu
            595                 600                 605
```

```
Gly Lys Glu Ile Lys Asn Lys Asp Glu Ile Leu Ala Leu Leu Lys Ala
            610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
            645                 650                 655

Ala Arg Lys Ala Ala Ile Thr Glu Thr Pro Asp Thr Ser Thr Leu Leu
            660                 665                 670

Ile Glu Asn Ser Ser Pro
            675

<210> SEQ ID NO 49
<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Met Thr Leu Asn Ile Glu Asp Glu Tyr Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
            85                  90                  95

Thr Pro Leu Leu Pro Val Lys Lys Pro Gly Thr Asn Asp Tyr Arg Pro
        100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
            165                 170                 175

Glu Met Gly Ile Ser Gly Gln Leu Thr Trp Thr Arg Leu Pro Gln Gly
        180                 185                 190

Phe Lys Asn Ser Pro Thr Leu Phe Asn Glu Ala Leu Arg Arg Asp Leu
    195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
            245                 250                 255

Ala Lys Lys Ala Gln Ile Cys Gln Lys Gln Val Lys Tyr Leu Gly Tyr
        260                 265                 270

Leu Leu Lys Glu Gly Gln Arg Trp Leu Thr Glu Ala Arg Lys Glu Thr
```

```
            275                 280                 285
Val Met Gly Gln Pro Thr Pro Lys Thr Pro Arg Gln Leu Arg Glu Phe
    290                 295                 300

Leu Gly Lys Ala Gly Phe Cys Arg Leu Phe Ile Pro Gly Phe Ala Glu
305                 310                 315                 320

Met Ala Ala Pro Leu Tyr Pro Leu Thr Lys Pro Gly Thr Leu Phe Asn
                325                 330                 335

Trp Gly Pro Asp Gln Gln Lys Ala Tyr Gln Glu Ile Lys Gln Ala Leu
                340                 345                 350

Leu Thr Ala Pro Ala Leu Gly Leu Pro Asp Leu Thr Lys Pro Phe Glu
                355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
                420                 425                 430

Leu Val Ile Leu Ala Pro His Ala Val Glu Ala Leu Val Lys Gln Pro
                435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
                500                 505                 510

Gln Pro Leu Pro Asp Ala Asp His Thr Trp Tyr Thr Asp Gly Ser Ser
                515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
                565                 570                 575

Lys Lys Leu Asn Val Tyr Thr Asp Ser Arg Tyr Ala Phe Ala Thr Ala
                580                 585                 590

His Ile His Gly Glu Ile Tyr Arg Arg Arg Gly Trp Leu Thr Ser Glu
    595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
                660                 665                 670

Ile Glu Asn Ser Ser Pro
                675

<210> SEQ ID NO 50
```

<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Met Thr Leu Asn Ile Glu Asp Glu Tyr Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asn Glu Ala Leu His Arg Asp Leu
        195                 200                 205

Ala Asp Phe Arg Ile Gln His Pro Asp Leu Ile Leu Leu Gln Tyr Val
210                 215                 220

Asp Asp Leu Leu Leu Ala Ala Thr Ser Glu Leu Asp Cys Gln Gln Gly
225                 230                 235                 240

Thr Arg Ala Leu Leu Gln Glu Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Arg Glu Phe
290                 295                 300

Leu Gly Lys Ala Gly Phe Cys Arg Leu Phe Ile Pro Gly Phe Ala Glu
305                 310                 315                 320

Met Ala Ala Pro Leu Tyr Pro Leu Thr Lys Pro Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln

```
                370                 375                 380
Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
                420                 425                 430

Leu Val Ile Leu Ala Pro His Ala Val Glu Ala Leu Val Lys Gln Pro
            435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
                500                 505                 510

Gln Pro Leu Pro Asp Ala Asp His Thr Trp Tyr Thr Asp Gly Ser Ser
            515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
                565                 570                 575

Lys Lys Leu Asn Val Tyr Thr Asp Ser Arg Tyr Ala Phe Ala Thr Ala
                580                 585                 590

His Ile His Gly Glu Ile Tyr Arg Arg Gly Trp Leu Thr Ser Glu
            595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
                660                 665                 670

Ile Glu Asn Ser Ser Pro
            675

<210> SEQ ID NO 51
<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Met Thr Leu Asn Ile Glu Asp Glu Tyr Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45
```

```
Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asn Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asp Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Arg Glu Phe
    290                 295                 300

Leu Gly Lys Ala Gly Phe Cys Arg Leu Phe Ile Pro Gly Phe Ala Glu
305                 310                 315                 320

Met Ala Ala Pro Leu Tyr Pro Leu Thr Lys Pro Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
```

```
465                 470                 475                 480
Pro Ala Thr Leu Leu Pro Leu Pro Glu Glu Gly Leu Gln His Asn Cys
            485                 490                 495
Leu Asp Ile Leu Ala Glu Ala His Gly Thr Arg Pro Asp Leu Thr Asp
            500                 505                 510
Gln Pro Leu Pro Asp Ala Asp His Thr Trp Tyr Thr Asp Gly Ser Ser
            515                 520                 525
Leu Leu Gln Glu Gly Gln Arg Lys Ala Gly Ala Val Thr Thr Glu
            530                 535                 540
Thr Glu Val Ile Trp Ala Lys Ala Leu Pro Ala Gly Thr Ser Ala Gln
545                 550                 555                 560
Arg Ala Glu Leu Ile Ala Leu Thr Gln Ala Leu Lys Met Ala Glu Gly
            565                 570                 575
Lys Lys Leu Asn Val Tyr Thr Asp Ser Arg Tyr Ala Phe Ala Thr Ala
            580                 585                 590
His Ile His Gly Glu Ile Tyr Arg Arg Arg Gly Trp Leu Thr Ser Glu
            595                 600                 605
Gly Lys Glu Ile Lys Asn Lys Asp Glu Ile Leu Ala Leu Leu Lys Ala
            610                 615                 620
Leu Phe Leu Pro Lys Arg Leu Ser Ile Ile His Cys Pro Gly His Gln
625                 630                 635                 640
Lys Gly His Ser Ala Glu Ala Arg Gly Asn Arg Met Ala Asp Gln Ala
            645                 650                 655
Ala Arg Lys Ala Ala Ile Thr Glu Thr Pro Asp Thr Ser Thr Leu Leu
            660                 665                 670
Ile Glu Asn Ser Ser Pro
            675

<210> SEQ ID NO 52
<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Met Thr Leu Asn Ile Glu Asp Glu Tyr Arg Leu His Glu Thr Ser Lys
1               5                   10                  15
Glu Pro Asp Val Ser Leu Gly Ser Thr Trp Leu Ser Asp Phe Pro Gln
            20                  25                  30
Ala Trp Ala Glu Thr Gly Gly Met Gly Leu Ala Val Arg Gln Ala Pro
        35                  40                  45
Leu Ile Ile Pro Leu Lys Ala Thr Ser Thr Pro Val Ser Ile Lys Gln
    50                  55                  60
Tyr Pro Met Ser Gln Glu Ala Arg Leu Gly Ile Lys Pro His Ile Gln
65                  70                  75                  80
Arg Leu Leu Asp Gln Gly Ile Leu Val Pro Cys Gln Ser Pro Trp Asn
            85                  90                  95
Thr Pro Leu Leu Pro Val Lys Lys Pro Gly Thr Asn Asp Tyr Arg Pro
            100                 105                 110
Val Gln Asp Leu Arg Glu Val Asn Lys Arg Val Glu Asp Ile His Pro
        115                 120                 125
Thr Val Pro Asn Pro Tyr Asn Leu Leu Ser Gly Leu Pro Pro Ser His
    130                 135                 140
```

```
Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asn Glu Ala Leu His Arg Asp Leu
        195                 200                 205

Ala Asp Phe Arg Ile Gln His Pro Asp Leu Ile Leu Leu Gln Tyr Val
210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Arg Thr
        275                 280                 285

Val Met Gly Gln Pro Thr Pro Lys Thr Pro Arg Gln Leu Arg Glu Phe
290                 295                 300

Leu Gly Lys Ala Gly Phe Cys Arg Leu Phe Ile Pro Gly Phe Ala Glu
305                 310                 315                 320

Met Ala Ala Pro Leu Tyr Pro Leu Thr Lys Pro Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Asp Gly Ser Ser
        515                 520                 525

Leu Leu Gln Glu Gly Gln Arg Lys Ala Gly Ala Ala Val Thr Thr Glu
530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
```

565                 570                 575
Lys Lys Leu Asn Val Tyr Thr Asp Ser Arg Tyr Ala Phe Ala Thr Ala
            580                 585                 590

His Ile His Gly Glu Ile Tyr Arg Arg Gly Trp Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro
                675

<210> SEQ ID NO 53
<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Met Thr Leu Asn Ile Glu Asp Glu Tyr Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asn Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

-continued

```
Thr Arg Ala Leu Leu Gln Thr Leu Gly Asn Leu Gly Tyr Arg Ala Ser
                245                 250                 255
Ala Lys Lys Ala Gln Ile Cys Gln Lys Gln Val Lys Tyr Leu Gly Tyr
            260                 265                 270
Leu Leu Lys Glu Gly Gln Arg Trp Leu Thr Glu Ala Arg Lys Glu Thr
        275                 280                 285
Val Met Gly Ile Pro Thr Pro Lys Thr Pro Arg Gln Leu Arg Glu Phe
    290                 295                 300
Leu Gly Lys Ala Gly Phe Cys Arg Leu Phe Ile Pro Gly Phe Ala Glu
305                 310                 315                 320
Met Ala Ala Pro Leu Tyr Pro Leu Thr Lys Pro Gly Thr Leu Phe Asn
                325                 330                 335
Trp Gly Pro Asp Gln Gln Lys Ala Tyr Gln Glu Ile Lys Gln Ala Leu
            340                 345                 350
Leu Thr Ala Pro Ala Leu Gly Leu Pro Asp Leu Thr Lys Pro Phe Glu
        355                 360                 365
Leu Phe Val Asp Glu Lys Gln Gly Tyr Ala Lys Gly Val Leu Thr Gln
    370                 375                 380
Lys Leu Gly Pro Trp Arg Arg Pro Val Ala Tyr Leu Ser Lys Lys Leu
385                 390                 395                 400
Asp Pro Val Ala Ala Gly Trp Pro Pro Cys Leu Arg Met Val Ala Ala
                405                 410                 415
Ile Ala Val Leu Thr Lys Asp Ala Gly Lys Leu Thr Met Gly Gln Pro
            420                 425                 430
Leu Val Ile Leu Ala Pro His Ala Val Glu Ala Leu Val Lys Gln Pro
        435                 440                 445
Pro Asp Arg Trp Leu Ser Asn Ala Arg Met Thr His Tyr Gln Ala Leu
    450                 455                 460
Leu Leu Asp Thr Asp Arg Val Gln Phe Gly Pro Val Val Ala Leu Asn
465                 470                 475                 480
Pro Ala Thr Leu Leu Pro Leu Pro Glu Glu Gly Leu Gln His Asn Cys
                485                 490                 495
Leu Asp Ile Leu Ala Glu Ala His Gly Thr Arg Pro Asp Leu Thr Asp
            500                 505                 510
Gln Pro Leu Pro Asp Ala Asp His Thr Trp Tyr Thr Asp Gly Ser Ser
        515                 520                 525
Leu Leu Gln Glu Gly Gln Arg Lys Ala Gly Ala Ala Val Thr Thr Glu
    530                 535                 540
Thr Glu Val Ile Trp Ala Lys Ala Leu Pro Ala Gly Thr Ser Ala Gln
545                 550                 555                 560
Arg Ala Glu Leu Ile Ala Leu Thr Gln Ala Leu Lys Met Ala Glu Gly
                565                 570                 575
Lys Lys Leu Asn Val Tyr Thr Asp Ser Arg Tyr Ala Phe Ala Thr Ala
            580                 585                 590
His Ile His Gly Glu Ile Tyr Arg Arg Arg Gly Trp Leu Thr Ser Glu
        595                 600                 605
Gly Lys Glu Ile Lys Asn Lys Asp Glu Ile Leu Ala Leu Leu Lys Ala
    610                 615                 620
Leu Phe Leu Pro Lys Arg Leu Ser Ile Ile His Cys Pro Gly His Gln
625                 630                 635                 640
Lys Gly His Ser Ala Glu Ala Arg Gly Asn Arg Met Ala Asp Gln Ala
                645                 650                 655
Ala Arg Lys Ala Ala Ile Thr Glu Thr Pro Asp Thr Ser Thr Leu Leu
```

```
                        660                 665                 670
Ile Glu Asn Ser Ser Pro
                675

<210> SEQ ID NO 54
<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Met Thr Leu Asn Ile Glu Asp Glu Tyr Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asn Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Leu Glu Phe
    290                 295                 300

Leu Gly Lys Ala Gly Phe Cys Arg Leu Phe Ile Pro Gly Phe Ala Glu
305                 310                 315                 320

Met Ala Ala Pro Leu Tyr Pro Leu Thr Lys Pro Gly Thr Leu Phe Asn
                325                 330                 335
```

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Asp Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
                565                 570                 575

Lys Lys Leu Asn Val Tyr Thr Asp Ser Arg Tyr Ala Phe Ala Thr Ala
            580                 585                 590

His Ile His Gly Glu Ile Tyr Arg Arg Arg Gly Trp Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro
            675

<210> SEQ ID NO 55
<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Met Thr Leu Asn Ile Glu Asp Glu Tyr Arg Leu His Glu Thr Ser Lys
1               5                   10                  15

```
Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asn Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Arg Lys Phe
    290                 295                 300

Leu Gly Lys Ala Gly Phe Cys Arg Leu Phe Ile Pro Gly Phe Ala Glu
305                 310                 315                 320

Met Ala Ala Pro Leu Tyr Pro Leu Thr Lys Pro Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430
```

```
Leu Val Ile Leu Ala Pro His Ala Val Glu Ala Leu Val Lys Gln Pro
            435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Asp Gly Ser Ser
    515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
                565                 570                 575

Lys Lys Leu Asn Val Tyr Thr Asp Ser Arg Tyr Ala Phe Ala Thr Ala
            580                 585                 590

His Ile His Gly Glu Ile Tyr Arg Arg Arg Gly Trp Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro
        675

<210> SEQ ID NO 56
<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Met Thr Leu Asn Ile Glu Asp Glu Tyr Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110
```

```
Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
                180                 185                 190

Phe Lys Asn Ser Pro Thr Leu Phe Asn Glu Ala Leu His Arg Asp Leu
            195                 200                 205

Ala Asp Phe Arg Ile Gln His Pro Asp Leu Ile Leu Leu Gln Tyr Val
            210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
                260                 265                 270

Leu Leu Lys Glu Gly Gln Arg Trp Leu Thr Glu Ala Arg Lys Glu Thr
            275                 280                 285

Val Met Gly Gln Pro Thr Pro Lys Thr Pro Arg Gln Leu Arg Glu Phe
            290                 295                 300

Leu Gly Lys Ala Gly Asn Cys Arg Leu Phe Ile Pro Gly Phe Ala Glu
305                 310                 315                 320

Met Ala Ala Pro Leu Tyr Pro Leu Thr Lys Pro Gly Thr Leu Phe Asn
                325                 330                 335

Trp Gly Pro Asp Gln Gln Lys Ala Tyr Gln Glu Ile Lys Gln Ala Leu
                340                 345                 350

Leu Thr Ala Pro Ala Leu Gly Leu Pro Asp Leu Thr Lys Pro Phe Glu
            355                 360                 365

Leu Phe Val Asp Glu Lys Gln Gly Tyr Ala Lys Gly Val Leu Thr Gln
            370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
                420                 425                 430

Leu Val Ile Leu Ala Pro His Ala Val Glu Ala Leu Val Lys Gln Pro
            435                 440                 445

Pro Asp Arg Trp Leu Ser Asn Ala Arg Met Thr His Tyr Gln Ala Leu
450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
                500                 505                 510

Gln Pro Leu Pro Asp Ala Asp His Thr Trp Tyr Thr Asp Gly Ser Ser
            515                 520                 525
```

Leu Leu Gln Glu Gly Gln Arg Lys Ala Gly Ala Ala Val Thr Thr Glu
530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
                565                 570                 575

Lys Lys Leu Asn Val Tyr Thr Asp Ser Arg Tyr Ala Phe Ala Thr Ala
                580                 585                 590

His Ile His Gly Glu Ile Tyr Arg Arg Gly Trp Leu Thr Ser Glu
            595                 600                 605

Gly Lys Glu Ile Lys Asn Lys Asp Glu Ile Leu Ala Leu Leu Lys Ala
610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
                660                 665                 670

Ile Glu Asn Ser Ser Pro
            675

<210> SEQ ID NO 57
<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Met Thr Leu Asn Ile Glu Asp Glu Tyr Arg Leu His Glu Thr Ser Lys
1               5                   10                  15

Glu Pro Asp Val Ser Leu Gly Ser Thr Trp Leu Ser Asp Phe Pro Gln
                20                  25                  30

Ala Trp Ala Glu Thr Gly Gly Met Gly Leu Ala Val Arg Gln Ala Pro
            35                  40                  45

Leu Ile Ile Pro Leu Lys Ala Thr Ser Thr Pro Val Ser Ile Lys Gln
50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
                100                 105                 110

Val Gln Asp Leu Arg Glu Val Asn Lys Arg Val Glu Asp Ile His Pro
            115                 120                 125

Thr Val Pro Asn Pro Tyr Asn Leu Leu Ser Gly Leu Pro Pro Ser His
130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asn Glu Ala Leu His Arg Asp Leu
                195                 200                 205

```
Ala Asp Phe Arg Ile Gln His Pro Asp Leu Ile Leu Leu Gln Tyr Val
    210                 215                 220
Asp Asp Leu Leu Leu Ala Ala Thr Ser Glu Leu Asp Cys Gln Gln Gly
225                 230                 235                 240
Thr Arg Ala Leu Leu Gln Thr Leu Gly Asn Leu Gly Tyr Arg Ala Ser
                245                 250                 255
Ala Lys Lys Ala Gln Ile Cys Gln Lys Gln Val Lys Tyr Leu Gly Tyr
            260                 265                 270
Leu Leu Lys Glu Gly Gln Arg Trp Leu Thr Glu Ala Arg Lys Glu Thr
        275                 280                 285
Val Met Gly Gln Pro Thr Pro Lys Thr Pro Arg Gln Leu Arg Glu Phe
290                 295                 300
Leu Gly Lys Ala Gly Phe Cys Arg Leu Phe Ile Pro Gly Phe Ala Glu
305                 310                 315                 320
Leu Ala Ala Pro Leu Tyr Pro Leu Thr Lys Pro Gly Thr Leu Phe Asn
                325                 330                 335
Trp Gly Pro Asp Gln Gln Lys Ala Tyr Gln Glu Ile Lys Gln Ala Leu
            340                 345                 350
Leu Thr Ala Pro Ala Leu Gly Leu Pro Asp Leu Thr Lys Pro Phe Glu
        355                 360                 365
Leu Phe Val Asp Glu Lys Gln Gly Tyr Ala Lys Gly Val Leu Thr Gln
370                 375                 380
Lys Leu Gly Pro Trp Arg Arg Pro Val Ala Tyr Leu Ser Lys Lys Leu
385                 390                 395                 400
Asp Pro Val Ala Ala Gly Trp Pro Pro Cys Leu Arg Met Val Ala Ala
                405                 410                 415
Ile Ala Val Leu Thr Lys Asp Ala Gly Lys Leu Thr Met Gly Gln Pro
            420                 425                 430
Leu Val Ile Leu Ala Pro His Ala Val Glu Ala Leu Val Lys Gln Pro
        435                 440                 445
Pro Asp Arg Trp Leu Ser Asn Ala Arg Met Thr His Tyr Gln Ala Leu
450                 455                 460
Leu Leu Asp Thr Asp Arg Val Gln Phe Gly Pro Val Val Ala Leu Asn
465                 470                 475                 480
Pro Ala Thr Leu Leu Pro Leu Pro Glu Glu Gly Leu Gln His Asn Cys
                485                 490                 495
Leu Asp Ile Leu Ala Glu Ala His Gly Thr Arg Pro Asp Leu Thr Asp
            500                 505                 510
Gln Pro Leu Pro Asp Ala Asp His Thr Trp Tyr Thr Asp Gly Ser Ser
        515                 520                 525
Leu Leu Gln Glu Gly Gln Arg Lys Ala Gly Ala Ala Val Thr Thr Glu
530                 535                 540
Thr Glu Val Ile Trp Ala Lys Ala Leu Pro Ala Gly Thr Ser Ala Gln
545                 550                 555                 560
Arg Ala Glu Leu Ile Ala Leu Thr Gln Ala Leu Lys Met Ala Glu Gly
                565                 570                 575
Lys Lys Leu Asn Val Tyr Thr Asp Ser Arg Tyr Ala Phe Ala Thr Ala
            580                 585                 590
His Ile His Gly Glu Ile Tyr Arg Arg Arg Gly Trp Leu Thr Ser Glu
        595                 600                 605
Gly Lys Glu Ile Lys Asn Lys Asp Glu Ile Leu Ala Leu Leu Lys Ala
610                 615                 620
```

```
Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro
            675

<210> SEQ ID NO 58
<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Met Thr Leu Asn Ile Glu Asp Glu Tyr Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asn Glu Ala Leu His Arg Asp Leu
        195                 200                 205

Ala Asp Phe Arg Ile Gln His Pro Asp Leu Ile Leu Leu Gln Tyr Val
210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Arg Glu Phe
290                 295                 300
```

```
Leu Gly Lys Ala Gly Phe Cys Arg Leu Phe Ile Pro Gly Phe Ala Glu
305                 310                 315                 320

Met Ala Ala Pro Leu Tyr Pro Leu Thr Lys Pro Gly Thr Leu Phe Asn
            325                 330                 335

Trp Gly Pro Asp Gln Gln Lys Ala Tyr Gln Glu Ile Lys Gln Ala Leu
        340                 345                 350

Leu Thr Ala Pro Ala Leu Gly Leu Pro Asp Leu Thr Lys Pro Phe Glu
    355                 360                 365

Leu Phe Val Asp Glu Lys Gln Gly Tyr Ala Lys Gly Val Leu Thr Gln
370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Gly Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Asp Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
                565                 570                 575

Lys Lys Leu Asn Val Tyr Thr Asp Ser Arg Tyr Ala Phe Ala Thr Ala
            580                 585                 590

His Ile His Gly Glu Ile Tyr Arg Arg Arg Gly Trp Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro
            675

<210> SEQ ID NO 59
<211> LENGTH: 678
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 59

Met Thr Leu Asn Ile Glu Asp Glu Tyr Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asn Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Arg Glu Phe
    290                 295                 300

Leu Gly Lys Ala Gly Phe Cys Arg Leu Phe Ile Pro Gly Phe Ala Glu
305                 310                 315                 320

Met Ala Ala Pro Leu Tyr Pro Leu Thr Lys Pro Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

```
Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Ala Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
                565                 570                 575

Lys Lys Leu Asn Val Tyr Thr Asp Ser Arg Tyr Ala Phe Ala Thr Ala
            580                 585                 590

His Ile His Gly Glu Ile Tyr Arg Arg Gly Trp Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro
        675

<210> SEQ ID NO 60
<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Met Thr Leu Asn Ile Glu Asp Glu Tyr Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Gln
```

```
            65                  70                  75                  80
        Arg Leu Leu Asp Gln Gly Ile Leu Val Pro Cys Gln Ser Pro Trp Asn
                        85                  90                  95
        Thr Pro Leu Leu Pro Val Lys Lys Pro Gly Thr Asn Asp Tyr Arg Pro
                        100                 105                 110
        Val Gln Asp Leu Arg Glu Val Asn Lys Arg Val Glu Asp Ile His Pro
                        115                 120                 125
        Thr Val Pro Asn Pro Tyr Asn Leu Leu Ser Gly Leu Pro Pro Ser His
                130                 135                 140
        Gln Trp Tyr Thr Val Leu Asp Leu Lys Asp Ala Phe Phe Cys Leu Arg
        145                 150                 155                 160
        Leu His Pro Thr Ser Gln Pro Leu Phe Ala Phe Glu Trp Arg Asp Pro
                        165                 170                 175
        Glu Met Gly Ile Ser Gly Gln Leu Thr Trp Thr Arg Leu Pro Gln Gly
                        180                 185                 190
        Phe Lys Asn Ser Pro Thr Leu Phe Asn Glu Ala Leu His Arg Asp Leu
                        195                 200                 205
        Ala Asp Phe Arg Ile Gln His Pro Asp Leu Ile Leu Leu Gln Tyr Val
                210                 215                 220
        Asp Asp Leu Leu Leu Ala Ala Thr Ser Glu Leu Asp Cys Gln Gln Gly
        225                 230                 235                 240
        Thr Arg Ala Leu Leu Gln Thr Leu Gly Asn Leu Gly Tyr Arg Ala Ser
                        245                 250                 255
        Ala Lys Lys Ala Gln Ile Cys Gln Lys Gln Val Lys Tyr Leu Gly Tyr
                        260                 265                 270
        Leu Leu Lys Glu Gly Gln Arg Trp Leu Thr Glu Ala Arg Lys Glu Thr
                        275                 280                 285
        Val Met Gly Gln Pro Thr Pro Lys Thr Pro Arg Gln Leu Arg Glu Phe
                290                 295                 300
        Leu Gly Lys Ala Gly Phe Cys Arg Leu Phe Ile Pro Gly Phe Ala Glu
        305                 310                 315                 320
        Met Ala Ala Pro Leu Tyr Pro Leu Thr Lys Pro Gly Thr Leu Phe Asn
                        325                 330                 335
        Trp Gly Pro Asp Gln Gln Lys Ala Tyr Gln Glu Ile Lys Gln Ala Leu
                        340                 345                 350
        Leu Thr Ala Pro Ala Leu Gly Leu Pro Asp Leu Thr Lys Pro Phe Glu
                        355                 360                 365
        Leu Phe Val Asp Glu Lys Gln Gly Tyr Ala Lys Gly Val Leu Thr Gln
                370                 375                 380
        Lys Leu Gly Pro Trp Arg Arg Pro Val Ala Tyr Leu Ser Lys Lys Leu
        385                 390                 395                 400
        Asp Pro Val Ala Ala Gly Trp Pro Pro Cys Leu Arg Met Val Ala Ala
                        405                 410                 415
        Ile Ala Val Leu Thr Lys Asp Ala Gly Lys Leu Thr Met Gly Gln Pro
                        420                 425                 430
        Leu Val Ile Leu Ala Pro His Ala Val Glu Ala Leu Val Lys Gln Pro
                        435                 440                 445
        Pro Asp Arg Trp Leu Ser Asn Ala Arg Met Thr His Tyr Gln Ala Leu
                450                 455                 460
        Leu Leu Asp Thr Asp Arg Val Gln Phe Gly Pro Val Val Ala Leu Asn
        465                 470                 475                 480
        Pro Ala Thr Leu Leu Pro Leu Pro Glu Glu Gly Leu Gln His Asn Cys
                        485                 490                 495
```

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Gly Gly Ser Ser
            515                 520                 525

Leu Leu Gln Glu Gly Gln Arg Lys Ala Gly Ala Ala Val Thr Thr Glu
        530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
            565                 570                 575

Lys Lys Leu Asn Val Tyr Thr Asp Ser Arg Tyr Ala Phe Ala Thr Ala
            580                 585                 590

His Ile His Gly Glu Ile Tyr Arg Arg Arg Gly Trp Leu Thr Ser Glu
            595                 600                 605

Gly Lys Glu Ile Lys Asn Lys Asp Glu Ile Leu Ala Leu Leu Lys Ala
        610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
            645                 650                 655

Ala Arg Lys Ala Ala Ile Thr Glu Thr Pro Asp Thr Ser Thr Leu Leu
            660                 665                 670

Ile Glu Asn Ser Ser Pro
        675

<210> SEQ ID NO 61
<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Met Thr Leu Asn Ile Glu Asp Glu Tyr Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
            85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro

-continued

```
                165                 170                 175
Glu Met Gly Ile Ser Gly Gln Leu Thr Trp Thr Arg Leu Pro Gln Gly
            180                 185                 190
Phe Lys Asn Ser Pro Thr Leu Phe Asn Glu Ala Leu His Arg Asp Leu
        195                 200                 205
Ala Asp Phe Arg Ile Gln His Pro Asp Leu Ile Leu Leu Gln Tyr Val
210                 215                 220
Asp Asp Leu Leu Leu Ala Ala Thr Ser Glu Leu Asp Cys Gln Gln Gly
225                 230                 235                 240
Thr Arg Ala Leu Leu Gln Thr Leu Gly Asn Leu Gly Tyr Arg Ala Ser
                245                 250                 255
Ala Lys Lys Ala Gln Ile Cys Gln Lys Gln Val Lys Tyr Leu Gly Tyr
            260                 265                 270
Leu Leu Lys Glu Gly Gln Arg Trp Leu Thr Glu Ala Arg Lys Glu Thr
        275                 280                 285
Val Met Gly Gln Pro Thr Pro Lys Thr Pro Arg Gln Leu Arg Glu Phe
        290                 295                 300
Leu Gly Lys Ala Gly Phe Cys Arg Leu Phe Ile Pro Gly Phe Ala Glu
305                 310                 315                 320
Met Ala Ala Pro Leu Tyr Pro Leu Thr Lys Pro Gly Thr Leu Phe Asn
                325                 330                 335
Trp Gly Pro Asp Gln Gln Lys Ala Tyr Gln Glu Ile Lys Gln Ala Leu
            340                 345                 350
Leu Thr Ala Pro Ala Leu Gly Leu Pro Asp Leu Thr Lys Pro Phe Glu
        355                 360                 365
Leu Phe Val Asp Glu Lys Gln Gly Tyr Ala Lys Gly Val Leu Thr Gln
        370                 375                 380
Lys Leu Gly Pro Trp Arg Arg Pro Val Ala Tyr Leu Ser Lys Lys Leu
385                 390                 395                 400
Asp Pro Val Ala Ala Gly Trp Pro Pro Cys Leu Arg Met Val Ala Ala
                405                 410                 415
Ile Ala Val Leu Thr Lys Asp Ala Gly Lys Leu Thr Met Gly Gln Pro
            420                 425                 430
Leu Val Ile Leu Ala Pro His Ala Val Glu Ala Leu Val Lys Gln Pro
        435                 440                 445
Pro Asp Arg Trp Leu Ser Asn Ala Arg Met Thr His Tyr Gln Ala Leu
        450                 455                 460
Leu Leu Asp Thr Asp Arg Val Gln Phe Gly Pro Val Val Ala Leu Asn
465                 470                 475                 480
Pro Ala Thr Leu Leu Pro Leu Pro Glu Glu Gly Leu Gln His Asn Cys
                485                 490                 495
Leu Asp Ile Leu Ala Glu Ala His Gly Thr Arg Pro Asp Leu Thr Asp
            500                 505                 510
Gln Pro Leu Pro Asp Ala Asp His Thr Trp Tyr Thr Asn Gly Ser Ser
        515                 520                 525
Leu Leu Gln Glu Gly Gln Arg Lys Ala Gly Ala Ala Val Thr Thr Glu
        530                 535                 540
Thr Glu Val Ile Trp Ala Lys Ala Leu Pro Ala Gly Thr Ser Ala Gln
545                 550                 555                 560
Arg Ala Glu Leu Ile Ala Leu Thr Gln Ala Leu Lys Met Ala Glu Gly
                565                 570                 575
Lys Lys Leu Asn Val Tyr Thr Asp Ser Arg Tyr Ala Phe Ala Thr Ala
            580                 585                 590
```

```
His Ile His Gly Glu Ile Tyr Arg Arg Gly Trp Leu Thr Ser Glu
            595                 600                 605

Gly Lys Glu Ile Lys Asn Lys Asp Glu Ile Leu Ala Leu Leu Lys Ala
610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro
            675

<210> SEQ ID NO 62
<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Met Thr Leu Asn Ile Glu Asp Glu Tyr Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asn Glu Ala Leu His Arg Asp Leu
        195                 200                 205

Ala Asp Phe Arg Ile Gln His Pro Asp Leu Ile Leu Leu Gln Tyr Val
210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
```

-continued

```
                260                 265                 270
Leu Leu Lys Glu Gly Gln Arg Trp Leu Thr Glu Ala Arg Lys Glu Thr
            275                 280                 285
Val Met Gly Gln Pro Thr Pro Lys Thr Pro Arg Gln Leu Arg Glu Phe
            290                 295                 300
Leu Gly Lys Ala Gly Phe Cys Arg Leu Phe Ile Pro Gly Phe Ala Glu
305                 310                 315                 320
Met Ala Ala Pro Leu Tyr Pro Leu Thr Lys Pro Gly Thr Leu Phe Asn
                325                 330                 335
Trp Gly Pro Asp Gln Gln Lys Ala Tyr Gln Glu Ile Lys Gln Ala Leu
                340                 345                 350
Leu Thr Ala Pro Ala Leu Gly Leu Pro Asp Leu Thr Lys Pro Phe Glu
                355                 360                 365
Leu Phe Val Asp Glu Lys Gln Gly Tyr Ala Lys Gly Val Leu Thr Gln
                370                 375                 380
Lys Leu Gly Pro Trp Arg Arg Pro Val Ala Tyr Leu Ser Lys Lys Leu
385                 390                 395                 400
Asp Pro Val Ala Ala Gly Trp Pro Pro Cys Leu Arg Met Val Ala Ala
                405                 410                 415
Ile Ala Val Leu Thr Lys Asp Ala Gly Lys Leu Thr Met Gly Gln Pro
                420                 425                 430
Leu Val Ile Leu Ala Pro His Ala Val Glu Ala Leu Val Lys Gln Pro
                435                 440                 445
Pro Asp Arg Trp Leu Ser Asn Ala Arg Met Thr His Tyr Gln Ala Leu
                450                 455                 460
Leu Leu Asp Thr Asp Arg Val Gln Phe Gly Pro Val Val Ala Leu Asn
465                 470                 475                 480
Pro Ala Thr Leu Leu Pro Leu Pro Glu Glu Gly Leu Gln His Asn Cys
                485                 490                 495
Leu Asp Ile Leu Ala Glu Ala His Gly Thr Arg Pro Asp Leu Thr Asp
                500                 505                 510
Gln Pro Leu Pro Asp Ala Asp His Thr Trp Tyr Thr Asp Gly Ser Ser
                515                 520                 525
Leu Leu Gln Glu Gly Gln Arg Lys Ala Gly Ala Ala Val Thr Thr Glu
                530                 535                 540
Thr Glu Val Ile Trp Ala Lys Ala Leu Pro Ala Gly Thr Ser Ala Gln
545                 550                 555                 560
Arg Ala Asp Leu Ile Ala Leu Thr Gln Ala Leu Lys Met Ala Glu Gly
                565                 570                 575
Lys Lys Leu Asn Val Tyr Thr Asp Ser Arg Tyr Ala Phe Ala Thr Ala
                580                 585                 590
His Ile His Gly Glu Ile Tyr Arg Arg Arg Gly Trp Leu Thr Ser Glu
                595                 600                 605
Gly Lys Glu Ile Lys Asn Lys Asp Glu Ile Leu Ala Leu Leu Lys Ala
                610                 615                 620
Leu Phe Leu Pro Lys Arg Leu Ser Ile Ile His Cys Pro Gly His Gln
625                 630                 635                 640
Lys Gly His Ser Ala Glu Ala Arg Gly Asn Arg Met Ala Asp Gln Ala
                645                 650                 655
Ala Arg Lys Ala Ala Ile Thr Glu Thr Pro Asp Thr Ser Thr Leu Leu
                660                 665                 670
Ile Glu Asn Ser Ser Pro
                675
```

<210> SEQ ID NO 63
<211> LENGTH: 678
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 63

Met Thr Leu Asn Ile Glu Asp Glu Tyr Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asn Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Arg Glu Phe
    290                 295                 300

Leu Gly Lys Ala Gly Phe Cys Arg Leu Phe Ile Pro Gly Phe Ala Glu
305                 310                 315                 320

Met Ala Ala Pro Leu Tyr Pro Leu Thr Lys Pro Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu

```
                355                 360                 365
Leu Phe Val Asp Glu Lys Gln Gly Tyr Ala Lys Gly Val Leu Thr Gln
370                 375                 380
Lys Leu Gly Pro Trp Arg Arg Pro Val Ala Tyr Leu Ser Lys Lys Leu
385                 390                 395                 400
Asp Pro Val Ala Ala Gly Trp Pro Pro Cys Leu Arg Met Val Ala Ala
                405                 410                 415
Ile Ala Val Leu Thr Lys Asp Ala Gly Lys Leu Thr Met Gly Gln Pro
            420                 425                 430
Leu Val Ile Leu Ala Pro His Ala Val Glu Ala Leu Val Lys Gln Pro
                435                 440                 445
Pro Asp Arg Trp Leu Ser Asn Ala Arg Met Thr His Tyr Gln Ala Leu
            450                 455                 460
Leu Leu Asp Thr Asp Arg Val Gln Phe Gly Pro Val Val Ala Leu Asn
465                 470                 475                 480
Pro Ala Thr Leu Leu Pro Leu Pro Glu Glu Gly Leu Gln His Asn Cys
                485                 490                 495
Leu Asp Ile Leu Ala Glu Ala His Gly Thr Arg Pro Asp Leu Thr Asp
            500                 505                 510
Gln Pro Leu Pro Asp Ala Asp His Thr Trp Tyr Thr Asp Gly Ser Ser
            515                 520                 525
Leu Leu Gln Glu Gly Gln Arg Lys Ala Gly Ala Ala Val Thr Thr Glu
            530                 535                 540
Thr Glu Val Ile Trp Ala Lys Ala Leu Pro Ala Gly Thr Ser Ala Gln
545                 550                 555                 560
Arg Ala Glu Leu Ile Ala Leu Thr Gln Ala Leu Arg Met Ala Glu Gly
                565                 570                 575
Lys Lys Leu Asn Val Tyr Thr Asp Ser Arg Tyr Ala Phe Ala Thr Ala
            580                 585                 590
His Ile His Gly Glu Ile Tyr Arg Arg Arg Gly Trp Leu Thr Ser Glu
            595                 600                 605
Gly Lys Glu Ile Lys Asn Lys Asp Glu Ile Leu Ala Leu Leu Lys Ala
            610                 615                 620
Leu Phe Leu Pro Lys Arg Leu Ser Ile Ile His Cys Pro Gly His Gln
625                 630                 635                 640
Lys Gly His Ser Ala Glu Ala Arg Gly Asn Arg Met Ala Asp Gln Ala
                645                 650                 655
Ala Arg Lys Ala Ala Ile Thr Glu Thr Pro Asp Thr Ser Thr Leu Leu
            660                 665                 670
Ile Glu Asn Ser Ser Pro
            675

<210> SEQ ID NO 64
<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Met Thr Leu Asn Ile Glu Asp Glu Tyr Arg Leu His Glu Thr Ser Lys
1               5                   10                  15
Glu Pro Asp Val Ser Leu Gly Ser Thr Trp Leu Ser Asp Phe Pro Gln
                20                  25                  30
```

-continued

```
Ala Trp Ala Glu Thr Gly Gly Met Gly Leu Ala Val Arg Gln Ala Pro
         35                   40                  45

Leu Ile Ile Pro Leu Lys Ala Thr Ser Thr Pro Val Ser Ile Lys Gln
 50                  55                  60

Tyr Pro Met Ser Gln Glu Ala Arg Leu Gly Ile Lys Pro His Ile Gln
 65                  70                  75                  80

Arg Leu Leu Asp Gln Gly Ile Leu Val Pro Cys Gln Ser Pro Trp Asn
                 85                  90                  95

Thr Pro Leu Leu Pro Val Lys Lys Pro Gly Thr Asn Asp Tyr Arg Pro
                100                 105                 110

Val Gln Asp Leu Arg Glu Val Asn Lys Arg Val Glu Asp Ile His Pro
            115                 120                 125

Thr Val Pro Asn Pro Tyr Asn Leu Leu Ser Gly Leu Pro Pro Ser His
130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
                180                 185                 190

Phe Lys Asn Ser Pro Thr Leu Phe Asn Glu Ala Leu His Arg Asp Leu
            195                 200                 205

Ala Asp Phe Arg Ile Gln His Pro Asp Leu Ile Leu Leu Gln Tyr Val
210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
                260                 265                 270

Leu Leu Lys Glu Gly Gln Arg Trp Leu Thr Glu Ala Arg Lys Glu Thr
            275                 280                 285

Val Met Gly Gln Pro Thr Pro Lys Thr Pro Arg Gln Leu Arg Glu Phe
290                 295                 300

Leu Gly Lys Ala Gly Phe Cys Arg Leu Phe Ile Pro Gly Phe Ala Glu
305                 310                 315                 320

Met Ala Ala Pro Leu Tyr Pro Leu Thr Lys Pro Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
            355                 360                 365

Leu Phe Val Asp Glu Lys Gln Gly Tyr Ala Lys Gly Val Leu Thr Gln
370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
            435                 440                 445

Pro Asp Arg Trp Leu Ser Asn Ala Arg Met Thr His Tyr Gln Ala Leu
```

450                 455                 460
Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
                500                 505                 510

Gln Pro Leu Pro Asp Ala Asp His Thr Trp Tyr Thr Asp Gly Ser Ser
                515                 520                 525

Leu Leu Gln Glu Gly Gln Arg Lys Ala Gly Ala Ala Val Thr Thr Glu
                530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
                580                 585                 590

His Ile His Gly Glu Ile Tyr Arg Arg Arg Gly Trp Leu Thr Ser Glu
                595                 600                 605

Gly Lys Glu Ile Lys Asn Lys Asp Glu Ile Leu Ala Leu Leu Lys Ala
                610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
                660                 665                 670

Ile Glu Asn Ser Ser Pro
                675

<210> SEQ ID NO 65
<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Met Thr Leu Asn Ile Glu Asp Glu Tyr Arg Leu His Glu Thr Ser Lys
1               5                   10                  15

Glu Pro Asp Val Ser Leu Gly Ser Thr Trp Leu Ser Asp Phe Pro Gln
                20                  25                  30

Ala Trp Ala Glu Thr Gly Gly Met Gly Leu Ala Val Arg Gln Ala Pro
            35                  40                  45

Leu Ile Ile Pro Leu Lys Ala Thr Ser Thr Pro Val Ser Ile Lys Gln
        50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
                100                 105                 110

Val Gln Asp Leu Arg Glu Val Asn Lys Arg Val Glu Asp Ile His Pro
            115                 120                 125

```
Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
                180                 185                 190

Phe Lys Asn Ser Pro Thr Leu Phe Asn Glu Ala Leu His Arg Asp Leu
            195                 200                 205

Ala Asp Phe Arg Ile Gln His Pro Asp Leu Ile Leu Leu Gln Tyr Val
210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
                260                 265                 270

Leu Leu Lys Glu Gly Gln Arg Trp Leu Thr Glu Ala Arg Lys Glu Thr
            275                 280                 285

Val Met Gly Gln Pro Thr Pro Lys Thr Pro Arg Gln Leu Arg Glu Phe
290                 295                 300

Leu Gly Lys Ala Gly Phe Cys Arg Leu Phe Ile Pro Gly Phe Ala Glu
305                 310                 315                 320

Met Ala Ala Pro Leu Tyr Pro Leu Thr Lys Pro Gly Thr Leu Phe Asn
                325                 330                 335

Trp Gly Pro Asp Gln Gln Lys Ala Tyr Gln Glu Ile Lys Gln Ala Leu
                340                 345                 350

Leu Thr Ala Pro Ala Leu Gly Leu Pro Asp Leu Thr Lys Pro Phe Glu
            355                 360                 365

Leu Phe Val Asp Glu Lys Gln Gly Tyr Ala Lys Gly Val Leu Thr Gln
            370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
                420                 425                 430

Leu Val Ile Leu Ala Pro His Ala Val Glu Ala Leu Val Lys Gln Pro
            435                 440                 445

Pro Asp Arg Trp Leu Ser Asn Ala Arg Met Thr His Tyr Gln Ala Leu
450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
                500                 505                 510

Gln Pro Leu Pro Asp Ala Asp His Thr Trp Tyr Thr Asp Gly Ser Ser
            515                 520                 525

Leu Leu Gln Glu Gly Gln Arg Lys Ala Gly Ala Ala Val Thr Thr Glu
530                 535                 540

Thr Glu Val Ile Trp Ala Lys Ala Leu Pro Ala Gly Thr Ser Ala Gln
```

```
                545                 550                 555                 560
Arg Ala Glu Leu Ile Ala Leu Thr Gln Ala Leu Lys Met Ala Glu Gly
                565                 570                 575

Lys Lys Leu Asn Val Tyr Thr Asp Ser Arg Ser Ala Phe Ala Thr Ala
                580                 585                 590

His Ile His Gly Glu Ile Tyr Arg Arg Arg Gly Trp Leu Thr Ser Glu
                595                 600                 605

Gly Lys Glu Ile Lys Asn Lys Asp Glu Ile Leu Ala Leu Leu Lys Ala
                610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
                660                 665                 670

Ile Glu Asn Ser Ser Pro
                675

<210> SEQ ID NO 66
<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Met Thr Leu Asn Ile Glu Asp Glu Tyr Arg Leu His Glu Thr Ser Lys
1               5                   10                  15

Glu Pro Asp Val Ser Leu Gly Ser Thr Trp Leu Ser Asp Phe Pro Gln
                20                  25                  30

Ala Trp Ala Glu Thr Gly Gly Met Gly Leu Ala Val Arg Gln Ala Pro
            35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
                100                 105                 110

Val Gln Asp Leu Arg Glu Val Asn Lys Arg Val Glu Asp Ile His Pro
            115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
                180                 185                 190

Phe Lys Asn Ser Pro Thr Leu Phe Asn Glu Ala Leu His Arg Asp Leu
            195                 200                 205

Ala Asp Phe Arg Ile Gln His Pro Asp Leu Ile Leu Leu Gln Tyr Val
    210                 215                 220
```

```
Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
            245                 250                 255

Ala Lys Lys Ala Gln Ile Cys Gln Lys Gln Val Lys Tyr Leu Gly Tyr
        260                 265                 270

Leu Leu Lys Glu Gly Gln Arg Trp Leu Thr Glu Ala Arg Lys Glu Thr
    275                 280                 285

Val Met Gly Gln Pro Thr Pro Lys Thr Pro Arg Gln Leu Arg Glu Phe
290                 295                 300

Leu Gly Lys Ala Gly Phe Cys Arg Leu Phe Ile Pro Gly Phe Ala Glu
305                 310                 315                 320

Met Ala Ala Pro Leu Tyr Pro Leu Thr Lys Pro Gly Thr Leu Phe Asn
            325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
    355                 360                 365

Leu Phe Val Asp Glu Lys Gln Gly Tyr Ala Lys Gly Val Leu Thr Gln
370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
    435                 440                 445

Pro Asp Arg Trp Leu Ser Asn Ala Arg Met Thr His Tyr Gln Ala Leu
450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
            485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Asp Gly Ser Ser
    515                 520                 525

Leu Leu Gln Glu Gly Gln Arg Lys Ala Gly Ala Ala Val Thr Thr Glu
530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
            565                 570                 575

Lys Lys Leu Asn Val Tyr Thr Asp Ser Arg Tyr Ala Phe Ala Thr Ala
            580                 585                 590

His Ile Gln Gly Glu Ile Tyr Arg Arg Arg Gly Trp Leu Thr Ser Glu
    595                 600                 605

Gly Lys Glu Ile Lys Asn Lys Asp Glu Ile Leu Ala Leu Leu Lys Ala
610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
```

```
                        645                 650                 655
Ala Arg Lys Ala Ala Ile Thr Glu Thr Pro Asp Thr Ser Thr Leu Leu
                660                 665                 670
Ile Glu Asn Ser Ser Pro
        675

<210> SEQ ID NO 67
<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Met Thr Leu Asn Ile Glu Asp Glu Tyr Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asn Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Arg Glu Phe
    290                 295                 300

Leu Gly Lys Ala Gly Phe Cys Arg Leu Phe Ile Pro Gly Phe Ala Glu
305                 310                 315                 320
```

Met Ala Ala Pro Leu Tyr Pro Leu Thr Lys Pro Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Asp Gly Ser Ser
        515                 520                 525

Leu Leu Gln Glu Gly Gln Arg Lys Ala Gly Ala Ala Val Thr Thr Glu
530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
                565                 570                 575

Lys Lys Leu Asn Val Tyr Thr Asp Ser Arg Tyr Ala Phe Ala Thr Ala
            580                 585                 590

His Ile His Gly Glu Ile Tyr Arg Arg Arg Gly Trp Leu Thr Ser Glu
        595                 600                 605

Gly Lys Glu Ile Lys Asn Lys Asp Glu Ile Leu Ala Leu Leu Lys Ala
610                 615                 620

Leu Phe Leu Pro Lys Arg Leu Ser Ile Ile His Cys Pro Gly Gly Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro
            675

<210> SEQ ID NO 68
<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

```
Met Thr Leu Asn Ile Glu Asp Glu Tyr Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asn Glu Ala Leu His Arg Asp Leu
        195                 200                 205

Ala Asp Phe Arg Ile Gln His Pro Asp Leu Ile Leu Leu Gln Tyr Val
210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Arg Glu Phe
290                 295                 300

Leu Gly Lys Ala Gly Phe Cys Arg Leu Phe Ile Pro Gly Phe Ala Glu
305                 310                 315                 320

Met Ala Ala Pro Leu Tyr Pro Leu Thr Lys Pro Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415
```

Ile Ala Val Leu Thr Lys Asp Ala Gly Lys Leu Thr Met Gly Gln Pro
                420                 425                 430

Leu Val Ile Leu Ala Pro His Ala Val Glu Ala Leu Val Lys Gln Pro
                435                 440                 445

Pro Asp Arg Trp Leu Ser Asn Ala Arg Met Thr His Tyr Gln Ala Leu
            450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Asp Gly Ser Ser
        515                 520                 525

Leu Leu Gln Glu Gly Gln Arg Lys Ala Gly Ala Ala Val Thr Thr Glu
530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
                565                 570                 575

Lys Lys Leu Asn Val Tyr Thr Asp Ser Arg Tyr Ala Phe Ala Thr Ala
                580                 585                 590

His Ile His Gly Glu Ile Tyr Arg Arg Arg Gly Trp Leu Thr Ser Glu
                595                 600                 605

Gly Lys Glu Ile Lys Asn Lys Asp Glu Ile Leu Ala Leu Leu Lys Ala
            610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asn Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro
        675

<210> SEQ ID NO 69
<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Met Thr Leu Asn Ile Glu Asp Glu Tyr Arg Leu His Glu Thr Ser Lys
1               5                   10                  15

Glu Pro Asp Val Ser Leu Gly Ser Thr Trp Leu Ser Asp Phe Pro Gln
                20                  25                  30

Ala Trp Ala Glu Thr Gly Gly Met Gly Leu Ala Val Arg Gln Ala Pro
            35                  40                  45

Leu Ile Ile Pro Leu Lys Ala Thr Ser Thr Pro Val Ser Ile Lys Gln
        50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

```
Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asn Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Arg Glu Phe
    290                 295                 300

Leu Gly Lys Ala Gly Phe Cys Arg Leu Phe Ile Pro Gly Phe Ala Glu
305                 310                 315                 320

Met Ala Ala Pro Leu Tyr Pro Leu Thr Lys Pro Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510
```

```
Gln Pro Leu Pro Asp Ala Asp His Thr Trp Tyr Thr Asp Gly Ser Ser
        515                 520                 525

Leu Leu Gln Glu Gly Gln Arg Lys Ala Gly Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
                565                 570                 575

Lys Lys Leu Asn Val Tyr Thr Asp Ser Arg Tyr Ala Phe Ala Thr Ala
            580                 585                 590

His Ile His Gly Glu Ile Tyr Arg Arg Gly Trp Leu Thr Ser Glu
        595                 600                 605

Gly Lys Glu Ile Lys Asn Lys Asp Glu Ile Leu Ala Leu Leu Lys Ala
        610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Asn Pro Asp Thr Ser Thr Leu Leu
            660                 665                 670

Ile Glu Asn Ser Ser Pro
        675

<210> SEQ ID NO 70
<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Met Thr Leu Asn Ile Glu Asp Glu Tyr Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190
```

-continued

```
Phe Lys Asn Ser Pro Thr Leu Phe Asn Glu Ala Leu His Arg Asp Leu
    195                 200                 205

Ala Asp Phe Arg Ile Gln His Pro Asp Leu Ile Leu Leu Gln Tyr Val
210                 215                 220

Asp Asp Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Arg Glu Phe
    290                 295                 300

Leu Gly Lys Ala Gly Phe Cys Arg Leu Phe Ile Pro Gly Phe Ala Glu
305                 310                 315                 320

Met Ala Ala Pro Leu Tyr Pro Leu Thr Lys Pro Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Asp Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
                565                 570                 575

Lys Lys Leu Asn Val Tyr Thr Asp Ser Arg Tyr Ala Phe Ala Thr Ala
            580                 585                 590

His Ile His Gly Glu Ile Tyr Arg Arg Arg Gly Trp Leu Thr Ser Glu
        595                 600                 605
```

```
Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Pro
            660                 665                 670

Ile Glu Asn Ser Ser Pro
            675

<210> SEQ ID NO 71
<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Met Thr Leu Asn Ile Glu Asp Glu Tyr Arg Leu His Glu Thr Ser Lys
1               5                   10                  15

Glu Pro Asp Val Ser Leu Gly Ser Thr Trp Leu Ser Asp Phe Pro Gln
                20                  25                  30

Ala Trp Ala Glu Thr Gly Gly Met Gly Leu Ala Val Arg Gln Ala Pro
            35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Ala Leu Phe Asn Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285
```

Val Met Gly Gln Pro Thr Pro Lys Thr Pro Arg Gln Leu Arg Glu Phe
    290                 295                 300

Leu Gly Lys Ala Gly Phe Cys Arg Leu Phe Ile Pro Gly Phe Ala Glu
305                 310                 315                 320

Met Ala Ala Pro Leu Tyr Pro Leu Thr Lys Pro Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Asp Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
                565                 570                 575

Lys Lys Leu Asn Val Tyr Thr Asp Ser Arg Tyr Ala Phe Ala Thr Ala
            580                 585                 590

His Ile His Gly Glu Ile Tyr Arg Arg Gly Trp Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asn Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro
        675

<210> SEQ ID NO 72
<211> LENGTH: 678

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 72

Met Thr Leu Asn Ile Glu Asp Glu Tyr Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Ala Leu Phe Asn Glu Ala Leu His Arg Asp Leu
        195                 200                 205

Ala Asp Phe Arg Ile Gln His Pro Asp Leu Ile Leu Leu Gln Tyr Val
210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Arg Glu Phe
290                 295                 300

Leu Gly Lys Ala Gly Phe Cys Arg Leu Phe Ile Pro Gly Phe Ala Glu
305                 310                 315                 320

Met Ala Ala Pro Leu Tyr Pro Leu Thr Lys Pro Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
370                 375                 380

```
Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
            405                 410                 415

Ile Ala Val Leu Thr Lys Asp Ala Gly Lys Leu Thr Met Gly Gln Pro
        420                 425                 430

Leu Val Ile Leu Ala Pro His Ala Val Glu Ala Leu Val Lys Gln Pro
            435                 440                 445

Pro Asp Arg Trp Leu Ser Asn Ala Arg Met Thr His Tyr Gln Ala Leu
        450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
                500                 505                 510

Gln Pro Leu Pro Asp Ala Asp His Thr Trp Tyr Thr Asp Gly Ser Ser
            515                 520                 525

Leu Leu Gln Glu Gly Gln Arg Lys Ala Gly Ala Ala Val Thr Thr Glu
530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
                565                 570                 575

Lys Lys Leu Asn Val Tyr Thr Asp Ser Arg Tyr Ala Phe Ala Thr Ala
            580                 585                 590

His Ile His Gly Glu Ile Tyr Arg Arg Arg Gly Trp Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Asn Pro Asp Thr Ser Thr Leu Leu
            660                 665                 670

Ile Glu Asn Ser Ser Pro
        675

<210> SEQ ID NO 73
<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Met Thr Leu Asn Ile Glu Asp Glu Tyr Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
```

```
            50                  55                  60
Tyr Pro Met Ser Gln Glu Ala Arg Leu Gly Ile Lys Pro His Ile Gln
 65                  70                  75                  80

Arg Leu Leu Asp Gln Gly Ile Leu Val Pro Cys Gln Ser Pro Trp Asn
                 85                  90                  95

Thr Pro Leu Leu Pro Val Lys Lys Pro Gly Thr Asn Asp Tyr Arg Pro
                100                 105                 110

Val Gln Asp Leu Arg Glu Val Asn Lys Arg Val Glu Asp Ile His Pro
                115                 120                 125

Thr Val Pro Asn Pro Tyr Asn Leu Leu Ser Gly Leu Pro Pro Ser His
                130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
                180                 185                 190

Phe Lys Asn Ser Pro Ala Leu Phe Asn Glu Ala Leu His Arg Asp Leu
                195                 200                 205

Ala Asp Phe Arg Ile Gln His Pro Asp Leu Ile Leu Leu Gln Tyr Val
                210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
                260                 265                 270

Leu Leu Lys Glu Gly Gln Arg Trp Leu Thr Glu Ala Arg Lys Glu Thr
                275                 280                 285

Val Met Gly Gln Pro Thr Pro Lys Thr Pro Arg Gln Leu Arg Glu Phe
                290                 295                 300

Leu Gly Lys Ala Gly Phe Cys Arg Leu Phe Ile Pro Gly Phe Ala Glu
305                 310                 315                 320

Met Ala Ala Pro Leu Tyr Pro Leu Thr Lys Pro Gly Thr Leu Phe Asn
                325                 330                 335

Trp Gly Pro Asp Gln Gln Lys Ala Tyr Gln Glu Ile Lys Gln Ala Leu
                340                 345                 350

Leu Thr Ala Pro Ala Leu Gly Leu Pro Asp Leu Thr Lys Pro Phe Glu
                355                 360                 365

Leu Phe Val Asp Glu Lys Gln Gly Tyr Ala Lys Gly Val Leu Thr Gln
                370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
                420                 425                 430

Leu Val Ile Leu Ala Pro His Ala Val Glu Ala Leu Val Lys Gln Pro
                435                 440                 445

Pro Asp Arg Trp Leu Ser Asn Ala Arg Met Thr His Tyr Gln Ala Leu
                450                 455                 460

Leu Leu Asp Thr Asp Arg Val Gln Phe Gly Pro Val Val Ala Leu Asn
465                 470                 475                 480
```

```
Pro Ala Thr Leu Leu Pro Leu Pro Glu Glu Gly Leu Gln His Asn Cys
            485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Asp Gly Ser Ser
            515                 520                 525

Leu Leu Gln Glu Gly Gln Arg Lys Ala Gly Ala Val Thr Thr Glu
            530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
                565                 570                 575

Lys Lys Leu Asn Val Tyr Thr Asp Ser Arg Tyr Ala Phe Ala Thr Ala
            580                 585                 590

His Ile His Gly Glu Ile Tyr Arg Arg Arg Gly Trp Leu Thr Ser Glu
            595                 600                 605

Gly Lys Glu Ile Lys Asn Lys Asp Glu Ile Leu Ala Leu Leu Lys Ala
            610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Pro
            660                 665                 670

Ile Glu Asn Ser Ser Pro
            675

<210> SEQ ID NO 74
<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Met Thr Leu Asn Ile Glu Asp Glu Tyr Arg Leu His Glu Thr Ser Lys
1               5                   10                  15

Glu Pro Asp Val Ser Leu Gly Ser Thr Trp Leu Ser Asp Phe Pro Gln
                20                  25                  30

Ala Trp Ala Glu Thr Gly Gly Met Gly Leu Ala Val Arg Gln Ala Pro
            35                  40                  45

Leu Ile Ile Pro Leu Lys Ala Thr Ser Thr Pro Val Ser Ile Lys Gln
        50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
```

```
            145                 150                 155                 160
Leu His Pro Thr Ser Gln Pro Leu Phe Ala Phe Glu Trp Arg Asp Pro
                    165                 170                 175
Glu Met Gly Ile Ser Gly Gln Leu Thr Trp Thr Arg Leu Pro Gln Gly
                180                 185                 190
Phe Lys Asn Ser Pro Ala Leu Phe Asn Glu Ala Leu His Arg Asp Leu
            195                 200                 205
Ala Asp Phe Arg Ile Gln His Pro Asp Leu Ile Leu Leu Gln Tyr Val
        210                 215                 220
Asp Asp Leu Leu Leu Ala Ala Thr Ser Glu Leu Asp Cys Gln Gln Gly
225                 230                 235                 240
Thr Arg Ala Leu Leu Gln Thr Leu Gly Asn Leu Gly Tyr Arg Ala Ser
                    245                 250                 255
Ala Lys Lys Ala Gln Ile Cys Gln Lys Gln Val Lys Tyr Leu Gly Tyr
                260                 265                 270
Leu Leu Lys Glu Gly Gln Arg Trp Leu Thr Glu Ala Arg Lys Glu Thr
            275                 280                 285
Val Met Gly Gln Pro Thr Pro Lys Thr Pro Arg Gln Leu Arg Glu Phe
        290                 295                 300
Leu Gly Lys Ala Gly Phe Cys Arg Leu Phe Ile Pro Gly Phe Ala Glu
305                 310                 315                 320
Met Ala Ala Pro Leu Tyr Pro Leu Thr Lys Pro Gly Thr Leu Phe Asn
                    325                 330                 335
Trp Gly Pro Asp Gln Gln Lys Ala Tyr Gln Glu Ile Lys Gln Ala Leu
                340                 345                 350
Leu Thr Ala Pro Ala Leu Gly Leu Pro Asp Leu Thr Lys Pro Phe Glu
            355                 360                 365
Leu Phe Val Asp Glu Lys Gln Gly Tyr Ala Lys Gly Val Leu Thr Gln
        370                 375                 380
Lys Leu Gly Pro Trp Arg Arg Pro Val Ala Tyr Leu Ser Lys Lys Leu
385                 390                 395                 400
Asp Pro Val Ala Ala Gly Trp Pro Pro Cys Leu Arg Met Val Ala Ala
                    405                 410                 415
Ile Ala Val Leu Thr Lys Asp Ala Gly Lys Leu Thr Met Gly Gln Pro
                420                 425                 430
Leu Val Ile Leu Ala Pro His Ala Val Glu Ala Leu Val Lys Gln Pro
            435                 440                 445
Pro Asp Arg Trp Leu Ser Asn Ala Arg Met Thr His Tyr Gln Ala Leu
        450                 455                 460
Leu Leu Asp Thr Asp Arg Val Gln Phe Gly Pro Val Val Ala Leu Asn
465                 470                 475                 480
Pro Ala Thr Leu Leu Pro Leu Pro Glu Glu Gly Leu Gln His Asn Cys
                    485                 490                 495
Leu Asp Ile Leu Ala Glu Ala His Gly Thr Arg Pro Asp Leu Thr Asp
                500                 505                 510
Gln Pro Leu Pro Asp Ala Asp His Thr Trp Tyr Thr Asp Gly Ser Ser
            515                 520                 525
Leu Leu Gln Glu Gly Gln Arg Lys Ala Gly Ala Ala Val Thr Thr Glu
        530                 535                 540
Thr Glu Val Ile Trp Ala Lys Ala Leu Pro Ala Gly Thr Ser Ala Gln
545                 550                 555                 560
Arg Ala Glu Leu Ile Ala Leu Thr Gln Ala Leu Lys Met Ala Glu Gly
                    565                 570                 575
```

```
Lys Lys Leu Asn Val Tyr Thr Asp Ser Arg Tyr Ala Phe Ala Thr Ala
            580                 585                 590

His Ile His Gly Glu Ile Tyr Arg Arg Gly Trp Leu Thr Ser Glu
            595                 600                 605

Gly Lys Glu Ile Lys Asn Lys Asp Glu Ile Leu Ala Leu Leu Lys Ala
            610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asn Gln Ala
                    645                 650                 655

Ala Arg Lys Ala Ala Ile Thr Glu Asn Pro Asp Thr Ser Thr Leu Pro
                    660                 665                 670

Ile Glu Asn Ser Ser Pro
                675

<210> SEQ ID NO 75
<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Met Thr Leu Asn Ile Glu Asp Glu Tyr Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Leu Leu Lys Ala Thr Ser Thr Pro Val Ser Ile Lys Gln
    50                  55                  60

Tyr Pro Met Arg Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Ala Leu Phe Asn Glu Ala Leu Arg Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
```

```
                     245                 250                 255
Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
            275                 280                 285

Val Met Gly Gln Pro Thr Pro Lys Thr Pro Arg Gln Leu Arg Glu Phe
            290                 295                 300

Leu Gly Lys Ala Gly Phe Cys Arg Leu Phe Ile Pro Gly Phe Ala Glu
305                 310                 315                 320

Met Ala Ala Pro Leu Tyr Pro Leu Thr Lys Pro Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
            355                 360                 365

Leu Phe Val Asp Glu Lys Gln Gly Tyr Ala Lys Gly Val Leu Thr Gln
        370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                    405                 410                 415

Ile Ala Val Leu Thr Lys Asp Ala Gly Lys Leu Thr Met Gly Gln Pro
                420                 425                 430

Leu Val Ile Gly Ala Pro His Ala Val Glu Ala Leu Val Lys Gln Pro
                435                 440                 445

Pro Asp Arg Trp Leu Ser Asn Ala Arg Met Thr His Tyr Gln Ala Leu
        450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
                500                 505                 510

Gln Pro Leu Pro Asp Ala Asp His Thr Trp Tyr Thr Ala Gly Ser Ser
        515                 520                 525

Leu Leu Gln Glu Gly Gln Arg Lys Ala Gly Ala Ala Val Thr Thr Glu
        530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
                565                 570                 575

Lys Lys Leu Asn Val Tyr Thr Asp Ser Arg Tyr Ala Phe Ala Thr Ala
            580                 585                 590

His Ile His Gly Glu Ile Tyr Arg Arg Arg Gly Trp Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asn Gln Ala
                645                 650                 655

Ala Arg Lys Ala Ala Ile Thr Glu Asn Pro Asp Thr Ser Thr Leu Pro
            660                 665                 670
```

Ile Glu Asn Ser Ser Pro
        675

<210> SEQ ID NO 76
<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Met Thr Leu Asn Ile Glu Asp Glu Tyr Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asn Glu Ala Leu His Arg Asp Leu
        195                 200                 205

Ala Asp Phe Arg Ile Gln His Pro Asp Leu Ile Leu Leu Arg Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Arg Glu Phe
    290                 295                 300

Leu Gly Lys Ala Gly Phe Cys Arg Leu Phe Ile Pro Gly Phe Ala Glu
305                 310                 315                 320

Met Ala Ala Pro Leu Tyr Pro Leu Thr Lys Pro Gly Thr Leu Phe Asn
                325                 330                 335

Trp Gly Pro Asp Gln Gln Lys Ala Tyr Gln Glu Ile Lys Gln Ala Leu 340                 345                 350
Leu Thr Ala Pro Ala Leu Gly Leu Pro Asp Leu Thr Lys Pro Phe Glu
            355                 360                 365

Leu Phe Val Asp Glu Lys Gln Gly Tyr Ala Lys Gly Val Leu Thr Gln
        370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Asp Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
                565                 570                 575

Lys Lys Leu Asn Val Tyr Thr Asp Ser Arg Tyr Ala Phe Ala Thr Ala
            580                 585                 590

His Ile His Gly Glu Ile Tyr Arg Arg Arg Gly Trp Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro
            675

<210> SEQ ID NO 77
<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Met Thr Leu Asn Ile Glu Asp Glu Tyr Arg Leu His Glu Thr Ser Lys
1               5                   10                  15

```
Glu Pro Asp Val Ser Leu Gly Ser Thr Trp Leu Ser Asp Phe Pro Gln
             20                  25                  30

Ala Trp Ala Glu Thr Gly Gly Met Gly Leu Ala Val Arg Gln Ala Pro
         35                  40                  45

Leu Ile Ile Pro Leu Lys Ala Thr Ser Thr Pro Val Ser Ile Lys Gln
 50                  55                  60

Tyr Pro Met Ser Gln Glu Ala Arg Leu Gly Ile Lys Pro His Ile Gln
 65                  70                  75                  80

Arg Leu Leu Asp Gln Gly Ile Leu Val Pro Cys Gln Ser Pro Trp Asn
                 85                  90                  95

Thr Pro Leu Leu Pro Val Lys Lys Pro Gly Thr Asn Asp Tyr Arg Pro
             100                 105                 110

Val Gln Asp Leu Arg Glu Val Asn Lys Arg Val Glu Asp Ile His Pro
         115                 120                 125

Thr Val Pro Asn Pro Tyr Asn Leu Leu Ser Gly Leu Pro Pro Ser His
130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                 165                 170                 175

Glu Met Gly Ile Ser Gly Gln Leu Thr Trp Thr Arg Leu Pro Gln Gly
             180                 185                 190

Phe Lys Asn Ser Pro Thr Leu Phe Asn Glu Ala Leu His Arg Asp Leu
         195                 200                 205

Ala Asp Phe Arg Ile Gln His Pro Asp Leu Ile Leu Leu Gln Tyr Ala
 210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                 245                 250                 255

Ala Lys Lys Ala Gln Ile Cys Gln Lys Gln Val Lys Tyr Leu Gly Tyr
             260                 265                 270

Leu Leu Lys Glu Gly Gln Arg Trp Leu Thr Glu Ala Arg Lys Glu Thr
         275                 280                 285

Val Met Gly Gln Pro Thr Pro Lys Thr Pro Arg Gln Leu Arg Glu Phe
 290                 295                 300

Leu Gly Lys Ala Gly Phe Cys Arg Leu Phe Ile Pro Gly Phe Ala Glu
305                 310                 315                 320

Met Ala Ala Pro Leu Tyr Pro Leu Thr Lys Pro Gly Thr Leu Phe Asn
                 325                 330                 335

Trp Gly Pro Asp Gln Gln Lys Ala Tyr Gln Glu Ile Lys Gln Ala Leu
             340                 345                 350

Leu Thr Ala Pro Ala Leu Gly Leu Pro Asp Leu Thr Lys Pro Phe Glu
         355                 360                 365

Leu Phe Val Asp Glu Lys Gln Gly Tyr Ala Lys Gly Val Leu Thr Gln
 370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                 405                 410                 415

Ile Ala Val Leu Thr Lys Asp Ala Gly Lys Leu Thr Met Gly Gln Pro
             420                 425                 430

Leu Val Ile Leu Ala Pro His Ala Val Glu Ala Leu Val Lys Gln Pro
```

```
                       435                 440                 445

Pro Asp Arg Trp Leu Ser Asn Ala Arg Met Thr His Tyr Gln Ala Leu
450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Asp Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
                565                 570                 575

Lys Lys Leu Asn Val Tyr Thr Asp Ser Arg Tyr Ala Phe Ala Thr Ala
            580                 585                 590

His Ile His Gly Glu Ile Tyr Arg Arg Gly Trp Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro
        675

<210> SEQ ID NO 78
<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Met Thr Leu Asn Ile Glu Asp Glu Tyr Arg Leu His Glu Thr Ser Lys
1               5                   10                  15

Glu Pro Asp Val Ser Leu Gly Ser Thr Trp Leu Ser Asp Phe Pro Gln
                20                  25                  30

Ala Trp Ala Glu Thr Gly Gly Met Gly Leu Ala Val Arg Gln Ala Pro
            35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110
```

-continued

Val Gln Asp Leu Arg Glu Val Asn Lys Arg Val Glu Asp Ile His Pro
         115                 120                 125

Thr Val Pro Asn Pro Tyr Asn Leu Leu Ser Gly Leu Pro Pro Ser His
130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                 165                 170                 175

Glu Met Gly Ile Ser Gly Gln Leu Thr Trp Thr Arg Leu Pro Gln Gly
             180                 185                 190

Phe Lys Asn Ser Pro Thr Leu Phe Asn Glu Ala Leu His Arg Asp Leu
         195                 200                 205

Ala Asp Phe Arg Ile Gln His Pro Asp Leu Ile Leu Leu Gln Tyr Met
210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                 245                 250                 255

Ala Lys Lys Ala Gln Ile Cys Gln Lys Gln Val Lys Tyr Leu Gly Tyr
             260                 265                 270

Leu Leu Lys Glu Gly Gln Arg Trp Leu Thr Glu Ala Arg Lys Glu Thr
         275                 280                 285

Val Met Gly Gln Pro Thr Pro Lys Thr Pro Arg Gln Leu Arg Glu Phe
         290                 295                 300

Leu Gly Lys Ala Gly Phe Cys Arg Leu Phe Ile Pro Gly Phe Ala Glu
305                 310                 315                 320

Met Ala Ala Pro Leu Tyr Pro Leu Thr Lys Pro Gly Thr Leu Phe Asn
                 325                 330                 335

Trp Gly Pro Asp Gln Gln Lys Ala Tyr Gln Glu Ile Lys Gln Ala Leu
             340                 345                 350

Leu Thr Ala Pro Ala Leu Gly Leu Pro Asp Leu Thr Lys Pro Phe Glu
         355                 360                 365

Leu Phe Val Asp Glu Lys Gln Gly Tyr Ala Lys Gly Val Leu Thr Gln
370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                 405                 410                 415

Ile Ala Val Leu Thr Lys Asp Ala Gly Lys Leu Thr Met Gly Gln Pro
             420                 425                 430

Leu Val Ile Leu Ala Pro His Ala Val Glu Ala Leu Val Lys Gln Pro
         435                 440                 445

Pro Asp Arg Trp Leu Ser Asn Ala Arg Met Thr His Tyr Gln Ala Leu
450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                 485                 490                 495

Leu Asp Ile Leu Ala Glu Ala His Gly Thr Arg Pro Asp Leu Thr Asp
             500                 505                 510

Gln Pro Leu Pro Asp Ala Asp His Thr Trp Tyr Thr Asp Gly Ser Ser
         515                 520                 525

Leu Leu Gln Glu Gly Gln Arg Lys Ala Gly Ala Ala Val Thr Thr Glu

```
                530              535              540
Thr Glu Val Ile Trp Ala Lys Ala Leu Pro Ala Gly Thr Ser Ala Gln
545                 550              555              560

Arg Ala Glu Leu Ile Ala Leu Thr Gln Ala Leu Lys Met Ala Glu Gly
                565              570              575

Lys Lys Leu Asn Val Tyr Thr Asp Ser Arg Tyr Ala Phe Ala Thr Ala
                580              585              590

His Ile His Gly Glu Ile Tyr Arg Arg Arg Gly Trp Leu Thr Ser Glu
                595              600              605

Gly Lys Glu Ile Lys Asn Lys Asp Glu Ile Leu Ala Leu Leu Lys Ala
                610              615              620

Leu Phe Leu Pro Lys Arg Leu Ser Ile Ile His Cys Pro Gly His Gln
625              630              635              640

Lys Gly His Ser Ala Glu Ala Arg Gly Asn Arg Met Ala Asp Gln Ala
                645              650              655

Ala Arg Lys Ala Ala Ile Thr Glu Thr Pro Asp Thr Ser Thr Leu Leu
                660              665              670

Ile Glu Asn Ser Ser Pro
                675

<210> SEQ ID NO 79
<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Met Thr Leu Asn Ile Glu Asp Glu Tyr Arg Leu His Glu Thr Ser Lys
1               5                   10                  15

Glu Pro Asp Val Ser Leu Gly Ser Thr Trp Leu Ser Asp Phe Pro Gln
                20                  25                  30

Ala Trp Ala Glu Thr Gly Gly Met Gly Leu Ala Val Arg Gln Ala Pro
            35                  40                  45

Leu Ile Ile Pro Leu Lys Ala Thr Ser Thr Pro Val Ser Ile Lys Gln
        50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
                100                 105                 110

Val Gln Asp Leu Arg Glu Val Asn Lys Arg Val Glu Asp Ile His Pro
            115                 120                 125

Thr Val Pro Asn Pro Tyr Asn Leu Leu Ser Gly Leu Pro Pro Ser His
        130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
                180                 185                 190

Phe Lys Asn Ser Pro Thr Leu Phe Asn Glu Ala Leu His Arg Asp Leu
            195                 200                 205
```

```
Ala Asp Phe Arg Ile Gln His Pro Asp Leu Ile Leu Leu Arg Tyr Ala
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
            245                 250                 255

Ala Lys Lys Ala Gln Ile Cys Gln Lys Gln Val Lys Tyr Leu Gly Tyr
        260                 265                 270

Leu Leu Lys Glu Gly Gln Arg Trp Leu Thr Glu Ala Arg Lys Glu Thr
    275                 280                 285

Val Met Gly Gln Pro Thr Pro Lys Thr Pro Arg Gln Leu Arg Glu Phe
290                 295                 300

Leu Gly Lys Ala Gly Phe Cys Arg Leu Phe Ile Pro Gly Phe Ala Glu
305                 310                 315                 320

Met Ala Ala Pro Leu Tyr Pro Leu Thr Lys Pro Gly Thr Leu Phe Asn
            325                 330                 335

Trp Gly Pro Asp Gln Gln Lys Ala Tyr Gln Glu Ile Lys Gln Ala Leu
        340                 345                 350

Leu Thr Ala Pro Ala Leu Gly Leu Pro Asp Leu Thr Lys Pro Phe Glu
    355                 360                 365

Leu Phe Val Asp Glu Lys Gln Gly Tyr Ala Lys Gly Val Leu Thr Gln
370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
            405                 410                 415

Ile Ala Val Leu Thr Lys Asp Ala Gly Lys Leu Thr Met Gly Gln Pro
        420                 425                 430

Leu Val Ile Leu Ala Pro His Ala Val Glu Ala Leu Val Lys Gln Pro
    435                 440                 445

Pro Asp Arg Trp Leu Ser Asn Ala Arg Met Thr His Tyr Gln Ala Leu
450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
            485                 490                 495

Leu Asp Ile Leu Ala Glu Ala His Gly Thr Arg Pro Asp Leu Thr Asp
        500                 505                 510

Gln Pro Leu Pro Asp Ala Asp His Thr Trp Tyr Thr Asp Gly Ser Ser
    515                 520                 525

Leu Leu Gln Glu Gly Gln Arg Lys Ala Gly Ala Ala Val Thr Thr Glu
530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
            565                 570                 575

Lys Lys Leu Asn Val Tyr Thr Asp Ser Arg Tyr Ala Phe Ala Thr Ala
        580                 585                 590

His Ile His Gly Glu Ile Tyr Arg Arg Gly Trp Leu Thr Ser Glu
    595                 600                 605

Gly Lys Glu Ile Lys Asn Lys Asp Glu Ile Leu Ala Leu Leu Lys Ala
610                 615                 620

Leu Phe Leu Pro Lys Arg Leu Ser Ile Ile His Cys Pro Gly His Gln
```

-continued

```
             625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
                660                 665                 670

Ile Glu Asn Ser Ser Pro
            675

<210> SEQ ID NO 80
<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Met Thr Leu Asn Ile Glu Asp Glu Tyr Arg Leu His Glu Thr Ser Lys
1               5                   10                  15

Glu Pro Asp Val Ser Leu Gly Ser Thr Trp Leu Ser Asp Phe Pro Gln
                20                  25                  30

Ala Trp Ala Glu Thr Gly Gly Met Gly Leu Ala Val Arg Gln Ala Pro
            35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asn Glu Ala Leu His Arg Asp Leu
        195                 200                 205

Ala Asp Phe Arg Ile Gln His Pro Asp Leu Ile Leu Leu Arg Tyr Met
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Arg Glu Phe
    290                 295                 300
```

```
Leu Gly Lys Ala Gly Phe Cys Arg Leu Phe Ile Pro Gly Phe Ala Glu
305                 310                 315                 320

Met Ala Ala Pro Leu Tyr Pro Leu Thr Lys Pro Gly Thr Leu Phe Asn
            325                 330                 335

Trp Gly Pro Asp Gln Gln Lys Ala Tyr Gln Glu Ile Lys Gln Ala Leu
        340                 345                 350

Leu Thr Ala Pro Ala Leu Gly Leu Pro Asp Leu Thr Lys Pro Phe Glu
    355                 360                 365

Leu Phe Val Asp Glu Lys Gln Gly Tyr Ala Lys Gly Val Leu Thr Gln
370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
            405                 410                 415

Ile Ala Val Leu Thr Lys Asp Ala Gly Lys Leu Thr Met Gly Gln Pro
        420                 425                 430

Leu Val Ile Leu Ala Pro His Ala Val Glu Ala Leu Val Lys Gln Pro
    435                 440                 445

Pro Asp Arg Trp Leu Ser Asn Ala Arg Met Thr His Tyr Gln Ala Leu
450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
            485                 490                 495

Leu Asp Ile Leu Ala Glu Ala His Gly Thr Arg Pro Asp Leu Thr Asp
        500                 505                 510

Gln Pro Leu Pro Asp Ala Asp His Thr Trp Tyr Thr Asp Gly Ser Ser
    515                 520                 525

Leu Leu Gln Glu Gly Gln Arg Lys Ala Gly Ala Ala Val Thr Thr Glu
530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
            565                 570                 575

Lys Lys Leu Asn Val Tyr Thr Asp Ser Arg Tyr Ala Phe Ala Thr Ala
        580                 585                 590

His Ile His Gly Glu Ile Tyr Arg Arg Gly Trp Leu Thr Ser Glu
    595                 600                 605

Gly Lys Glu Ile Lys Asn Lys Asp Glu Ile Leu Ala Leu Leu Lys Ala
610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
            645                 650                 655

Ala Arg Lys Ala Ala Ile Thr Glu Thr Pro Asp Thr Ser Thr Leu Leu
        660                 665                 670

Ile Glu Asn Ser Ser Pro
        675

<210> SEQ ID NO 81
<211> LENGTH: 677
<212> TYPE: PRT
<213> ORGANISM: Murine leukemia virus

<400> SEQUENCE: 81
```

```
Thr Leu Asn Ile Glu Asp Glu Tyr Arg Leu His Glu Thr Ser Lys Glu
1               5                   10                  15

Pro Asp Val Ser Leu Gly Ser Thr Trp Leu Ser Asp Phe Pro Gln Ala
            20                  25                  30

Trp Ala Glu Thr Gly Gly Met Gly Leu Ala Val Arg Gln Ala Pro Leu
        35                  40                  45

Ile Ile Pro Leu Lys Ala Thr Ser Thr Pro Val Ser Ile Lys Gln Tyr
50                  55                  60

Pro Met Ser Gln Glu Ala Arg Leu Gly Ile Lys Pro His Ile Gln Arg
65                  70                  75                  80

Leu Leu Asp Gln Gly Ile Leu Val Pro Cys Gln Ser Pro Trp Asn Thr
                85                  90                  95

Pro Leu Leu Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
        115                 120                 125

Val Pro Asn Pro Tyr Asn Leu Leu Ser Gly Leu Pro Pro Ser His Gln
130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
            180                 185                 190

Lys Asn Ser Pro Thr Leu Phe Asp Glu Ala Leu His Arg Asp Leu Ala
        195                 200                 205

Asp Phe Arg Ile Gln His Pro Asp Leu Ile Leu Leu Gln Tyr Val Asp
210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
            260                 265                 270

Leu Lys Glu Gly Gln Arg Trp Leu Thr Glu Ala Arg Lys Glu Thr Val
        275                 280                 285

Met Gly Gln Pro Thr Pro Lys Thr Pro Arg Gln Leu Arg Glu Phe Leu
290                 295                 300

Gly Thr Ala Gly Phe Cys Arg Leu Trp Ile Pro Gly Phe Ala Glu Met
305                 310                 315                 320

Ala Ala Pro Leu Tyr Pro Leu Thr Lys Thr Gly Thr Leu Phe Asn Trp
                325                 330                 335

Gly Pro Asp Gln Gln Lys Ala Tyr Gln Glu Ile Lys Gln Ala Leu Leu
            340                 345                 350

Thr Ala Pro Ala Leu Gly Leu Pro Asp Leu Thr Lys Pro Phe Glu Leu
        355                 360                 365

Phe Val Asp Glu Lys Gln Gly Tyr Ala Lys Gly Val Leu Thr Gln Lys
370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415
```

```
Ala Val Leu Thr Lys Asp Ala Gly Lys Leu Thr Met Gly Gln Pro Leu
            420                 425                 430

Val Ile Leu Ala Pro His Ala Val Glu Ala Leu Val Lys Gln Pro Pro
            435                 440                 445

Asp Arg Trp Leu Ser Asn Ala Arg Met Thr His Tyr Gln Ala Leu Leu
            450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
            500                 505                 510

Pro Leu Pro Asp Ala Asp His Thr Trp Tyr Thr Asp Gly Ser Ser Leu
            515                 520                 525

Leu Gln Glu Gly Gln Arg Lys Ala Gly Ala Ala Val Thr Thr Glu Thr
            530                 535                 540

Glu Val Ile Trp Ala Lys Ala Leu Pro Ala Gly Thr Ser Ala Gln Arg
545                 550                 555                 560

Ala Glu Leu Ile Ala Leu Thr Gln Ala Leu Lys Met Ala Glu Gly Lys
                565                 570                 575

Lys Leu Asn Val Tyr Thr Asp Ser Arg Tyr Ala Phe Ala Thr Ala His
            580                 585                 590

Ile His Gly Glu Ile Tyr Arg Arg Arg Gly Ile Leu Thr Ser Glu Gly
            595                 600                 605

Lys Glu Ile Lys Asn Lys Asp Glu Ile Leu Ala Leu Leu Lys Ala Leu
            610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
                645                 650                 655

Arg Lys Ala Ala Ile Thr Glu Thr Pro Asp Thr Ser Thr Leu Leu Ile
            660                 665                 670

Glu Asn Ser Ser Pro
            675

<210> SEQ ID NO 82
<211> LENGTH: 112
<212> TYPE: PRT
<213> ORGANISM: Human immunodeficiency virus 2

<400> SEQUENCE: 82

Met Thr Asp Pro Arg Glu Thr Val Pro Pro Gly Asn Ser Gly Glu Glu
1               5                   10                  15

Thr Ile Gly Glu Ala Phe Ala Trp Leu Asn Arg Thr Val Glu Ala Ile
            20                  25                  30

Asn Arg Glu Ala Val Asn His Leu Pro Arg Glu Leu Ile Phe Gln Val
            35                  40                  45

Trp Gln Arg Ser Trp Arg Tyr Trp His Asp Glu Gln Gly Met Ser Glu
            50                  55                  60

Ser Tyr Thr Lys Tyr Arg Tyr Leu Cys Ile Ile Gln Lys Ala Val Tyr
65                  70                  75                  80

Met His Val Arg Lys Gly Cys Thr Cys Leu Gly Arg Gly His Gly Pro
                85                  90                  95

Gly Gly Trp Arg Pro Gly Pro Pro Pro Pro Pro Pro Gly Leu Val
            100                 105                 110
```

<210> SEQ ID NO 83
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Gly Ser Gly Ala Thr Asn Phe Ser Leu Leu Lys Gln Ala Gly Asp Val
1               5                   10                  15

Glu Glu Asn Pro Gly Pro Met Thr Asp Pro Arg Glu Thr Val Pro Pro
            20                  25                  30

Gly Asn Ser Gly Glu Glu Thr Ile Gly Glu Ala Phe Ala Trp Leu Asn
        35                  40                  45

Arg Thr Val Glu Ala Ile Asn Arg Glu Ala Val Asn His Leu Pro Arg
    50                  55                  60

Glu Leu Ile Phe Gln Val Trp Gln Arg Ser Trp Arg Tyr Trp His Asp
65                  70                  75                  80

Glu Gln Gly Met Ser Glu Ser Tyr Thr Lys Tyr Arg Tyr Leu Cys Ile
                85                  90                  95

Ile Gln Lys Ala Val Tyr Met His Val Arg Lys Gly Cys Thr Cys Leu
            100                 105                 110

Gly Arg Gly His Gly Pro Gly Gly Trp Arg Pro Gly Pro Pro Pro Pro
        115                 120                 125

Pro Pro Pro Gly Leu Val
    130

<210> SEQ ID NO 84
<211> LENGTH: 1368
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

-continued

```
Met Ile Lys Phe Arg Gly His Phe Leu Ile Glu Gly Asp Leu Asn Pro
            165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
            195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
            245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
            290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
            325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Gly Lys Met Asp
            370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
            405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
            450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
            485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
            565                 570                 575
```

-continued

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe

```
                995              1000             1005
Val Tyr Gly Asp Tyr Lys Val Tyr Asp Val Arg Lys Met Ile Ala
        1010             1015             1020

Lys Ser Glu Gln Glu Ile Gly Lys Ala Thr Ala Lys Tyr Phe Phe
        1025             1030             1035

Tyr Ser Asn Ile Met Asn Phe Phe Lys Thr Glu Ile Thr Leu Ala
        1040             1045             1050

Asn Gly Glu Ile Arg Lys Arg Pro Leu Ile Glu Thr Asn Gly Glu
        1055             1060             1065

Thr Gly Glu Ile Val Trp Asp Lys Gly Arg Asp Phe Ala Thr Val
        1070             1075             1080

Arg Lys Val Leu Ser Met Pro Gln Val Asn Ile Val Lys Lys Thr
        1085             1090             1095

Glu Val Gln Thr Gly Gly Phe Ser Lys Glu Ser Ile Leu Pro Lys
        1100             1105             1110

Arg Asn Ser Asp Lys Leu Ile Ala Arg Lys Lys Asp Trp Asp Pro
        1115             1120             1125

Lys Lys Tyr Gly Gly Phe Asp Ser Pro Thr Val Ala Tyr Ser Val
        1130             1135             1140

Leu Val Val Ala Lys Val Glu Lys Gly Lys Ser Lys Lys Leu Lys
        1145             1150             1155

Ser Val Lys Glu Leu Leu Gly Ile Thr Ile Met Glu Arg Ser Ser
        1160             1165             1170

Phe Glu Lys Asn Pro Ile Asp Phe Leu Glu Ala Lys Gly Tyr Lys
        1175             1180             1185

Glu Val Lys Lys Asp Leu Ile Ile Lys Leu Pro Lys Tyr Ser Leu
        1190             1195             1200

Phe Glu Leu Glu Asn Gly Arg Lys Arg Met Leu Ala Ser Ala Gly
        1205             1210             1215

Glu Leu Gln Lys Gly Asn Glu Leu Ala Leu Pro Ser Lys Tyr Val
        1220             1225             1230

Asn Phe Leu Tyr Leu Ala Ser His Tyr Glu Lys Leu Lys Gly Ser
        1235             1240             1245

Pro Glu Asp Asn Glu Gln Lys Gln Leu Phe Val Glu Gln His Lys
        1250             1255             1260

His Tyr Leu Asp Glu Ile Ile Glu Gln Ile Ser Glu Phe Ser Lys
        1265             1270             1275

Arg Val Ile Leu Ala Asp Ala Asn Leu Asp Lys Val Leu Ser Ala
        1280             1285             1290

Tyr Asn Lys His Arg Asp Lys Pro Ile Arg Glu Gln Ala Glu Asn
        1295             1300             1305

Ile Ile His Leu Phe Thr Leu Thr Asn Leu Gly Ala Pro Ala Ala
        1310             1315             1320

Phe Lys Tyr Phe Asp Thr Thr Ile Asp Arg Lys Arg Tyr Thr Ser
        1325             1330             1335

Thr Lys Glu Val Leu Asp Ala Thr Leu Ile His Gln Ser Ile Thr
        1340             1345             1350

Gly Leu Tyr Glu Thr Arg Ile Asp Leu Ser Gln Leu Gly Gly Asp
        1355             1360             1365

<210> SEQ ID NO 85
<211> LENGTH: 1368
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 85

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65              70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
```

-continued

```
            385                 390                 395                 400
Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
                435                 440                 445

Pro Tyr Tyr Val Gly Pro Leu Ala Arg Gly Asn Ser Arg Phe Ala Trp
            450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
                515                 520                 525

Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
                595                 600                 605

Asn Glu Glu Asn Glu Asp Ile Leu Glu Asp Ile Val Leu Thr Leu Thr
            610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
            770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815
```

-continued

```
Gln Asn Gly Arg Asp Met Tyr Val Asp Gln Glu Leu Asp Ile Asn Arg
            820                 825                 830
Leu Ser Asp Tyr Asp Val Asp Ala Ile Val Pro Gln Ser Phe Leu Lys
            835                 840                 845
Asp Asp Ser Ile Asp Asn Lys Val Leu Thr Arg Ser Lys Asn Arg
850                 855                 860
Gly Lys Ser Asp Asn Val Pro Ser Glu Glu Val Val Lys Lys Met Lys
865                 870                 875                 880
Asn Tyr Trp Arg Gln Leu Leu Asn Ala Lys Leu Ile Thr Gln Arg Lys
            885                 890                 895
Phe Asp Asn Leu Thr Lys Ala Glu Arg Gly Gly Leu Ser Glu Leu Asp
            900                 905                 910
Lys Ala Gly Phe Ile Lys Arg Gln Leu Val Glu Thr Arg Gln Ile Thr
            915                 920                 925
Lys His Val Ala Gln Ile Leu Asp Ser Arg Met Asn Thr Lys Tyr Asp
            930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
            965                 970                 975
Glu Ile Asn Asn Tyr His His Ala His Asp Ala Tyr Leu Asn Ala Val
            980                 985                 990
Val Gly Thr Ala Leu Ile Lys Lys Tyr Pro Lys Leu Glu Ser Glu Phe
            995                 1000                1005
Val Tyr Gly Asp Tyr Lys Val Tyr Asp Val Arg Lys Met Ile Ala
            1010                1015                1020
Lys Ser Glu Gln Glu Ile Gly Lys Ala Thr Ala Lys Tyr Phe Phe
            1025                1030                1035
Tyr Ser Asn Ile Met Asn Phe Phe Lys Thr Glu Ile Thr Leu Ala
            1040                1045                1050
Asn Gly Glu Ile Arg Lys Arg Pro Leu Ile Glu Thr Asn Gly Glu
            1055                1060                1065
Thr Gly Glu Ile Val Trp Asp Lys Gly Arg Cys Phe Ala Thr Val
            1070                1075                1080
Arg Lys Val Leu Ser Met Pro Gln Val Asn Ile Val Lys Lys Thr
            1085                1090                1095
Glu Val Gln Thr Gly Gly Phe Ser Lys Glu Ser Ile Leu Pro Lys
            1100                1105                1110
Arg Asn Ser Asp Lys Leu Ile Ala Arg Lys Lys Asp Trp Asp Pro
            1115                1120                1125
Lys Lys Tyr Gly Gly Phe Asp Ser Pro Thr Val Ala Tyr Ser Val
            1130                1135                1140
Leu Val Val Ala Lys Val Glu Lys Gly Lys Ser Lys Lys Leu Lys
            1145                1150                1155
Ser Val Lys Glu Leu Leu Gly Ile Thr Ile Met Glu Arg Ser Ser
            1160                1165                1170
Phe Glu Lys Asn Pro Ile Asp Phe Leu Glu Ala Lys Gly Tyr Lys
            1175                1180                1185
Glu Val Lys Lys Asp Leu Ile Ile Lys Leu Pro Lys Tyr Ser Leu
            1190                1195                1200
Phe Glu Leu Glu Asn Gly Arg Lys Arg Met Leu Ala Ser Ala Gly
            1205                1210                1215
```

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 86
<211> LENGTH: 1368
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

```
Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
    610                 615                 620
```

-continued

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
        645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
            725                 730                 735

Ile Leu Gln Thr Val Lys Val Val Asp Glu Leu Val Lys Val Met Gly
        740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
        820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
        900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
        980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala

```
              1040                1045                1050

Asn Gly Glu Ile Arg Lys Arg Pro Leu Ile Glu Thr Asn Gly Glu
         1055                1060                1065

Thr Gly Glu Ile Val Trp Asp Lys Gly Arg Asp Phe Ala Thr Val
         1070                1075                1080

Arg Lys Val Leu Ser Met Pro Gln Val Asn Ile Val Lys Lys Thr
         1085                1090                1095

Glu Val Gln Thr Gly Gly Phe Ser Lys Glu Ser Ile Leu Pro Lys
         1100                1105                1110

Arg Asn Ser Asp Lys Leu Ile Ala Arg Lys Lys Asp Trp Asp Pro
         1115                1120                1125

Lys Lys Tyr Gly Gly Phe Asp Ser Pro Thr Val Ala Tyr Ser Val
         1130                1135                1140

Leu Val Val Ala Lys Val Glu Lys Gly Lys Ser Lys Lys Leu Lys
         1145                1150                1155

Ser Val Lys Glu Leu Leu Gly Ile Thr Ile Met Glu Arg Ser Cys
         1160                1165                1170

Phe Glu Lys Asn Pro Ile Asp Phe Leu Glu Ala Lys Gly Tyr Lys
         1175                1180                1185

Glu Val Lys Lys Asp Leu Ile Ile Lys Leu Pro Lys Tyr Ser Leu
         1190                1195                1200

Phe Glu Leu Glu Asn Gly Arg Lys Arg Met Leu Ala Ser Ala Gly
         1205                1210                1215

Glu Leu Gln Lys Gly Asn Glu Leu Ala Leu Pro Ser Lys Tyr Val
         1220                1225                1230

Asn Phe Leu Tyr Leu Ala Ser His Tyr Glu Lys Leu Lys Gly Ser
         1235                1240                1245

Pro Glu Asp Asn Glu Gln Lys Gln Leu Phe Val Glu Gln His Lys
         1250                1255                1260

His Tyr Leu Asp Glu Ile Ile Glu Gln Ile Ser Glu Phe Ser Lys
         1265                1270                1275

Arg Val Ile Leu Ala Asp Ala Asn Leu Asp Lys Val Leu Ser Ala
         1280                1285                1290

Tyr Asn Lys His Arg Asp Lys Pro Ile Arg Glu Gln Ala Glu Asn
         1295                1300                1305

Ile Ile His Leu Phe Thr Leu Thr Asn Leu Gly Ala Pro Ala Ala
         1310                1315                1320

Phe Lys Tyr Phe Asp Thr Thr Ile Asp Arg Lys Arg Tyr Thr Ser
         1325                1330                1335

Thr Lys Glu Val Leu Asp Ala Thr Leu Ile His Gln Ser Ile Thr
         1340                1345                1350

Gly Leu Tyr Glu Thr Arg Ile Asp Leu Ser Gln Leu Gly Gly Asp
         1355                1360                1365

<210> SEQ ID NO 87
<211> LENGTH: 1368
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Met Asp Lys Lys Tyr Ser Ile Gly Leu Asp Ile Gly Thr Asn Ser Val
1               5                   10                  15
```

```
Gly Trp Ala Val Ile Thr Asp Glu Tyr Lys Val Pro Ser Lys Lys Phe
                20                  25                  30

Lys Val Leu Gly Asn Thr Asp Arg His Ser Ile Lys Lys Asn Leu Ile
            35                  40                  45

Gly Ala Leu Leu Phe Asp Ser Gly Glu Thr Ala Glu Ala Thr Arg Leu
        50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
        130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
        370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
```

```
                    435             440             445
        Pro Tyr Tyr Val Gly Pro Leu Ala Arg Gly Asn Ser Arg Phe Ala Trp
        450                     455                     460
        Met Thr Arg Lys Ser Glu Glu Thr Ile Thr Pro Trp Asn Phe Glu Glu
        465                     470                     475                     480
        Val Val Asp Lys Gly Ala Ser Ala Gln Ser Phe Ile Glu Arg Met Thr
                                485                     490                     495
        Asn Phe Asp Lys Asn Leu Pro Asn Glu Lys Val Leu Pro Lys His Ser
                        500                     505                     510
        Leu Leu Tyr Glu Tyr Phe Thr Val Tyr Asn Glu Leu Thr Lys Val Lys
                        515                     520                     525
        Tyr Val Thr Glu Gly Met Arg Lys Pro Ala Phe Leu Ser Gly Glu Gln
        530                     535                     540
        Lys Lys Ala Ile Val Asp Leu Leu Phe Lys Thr Asn Arg Lys Val Thr
        545                     550                     555                     560
        Val Lys Gln Leu Lys Glu Asp Tyr Phe Lys Lys Ile Glu Cys Phe Asp
                        565                     570                     575
        Ser Val Glu Ile Ser Gly Val Glu Asp Arg Phe Asn Ala Ser Leu Gly
                        580                     585                     590
        Thr Tyr His Asp Leu Leu Lys Ile Ile Lys Asp Lys Asp Phe Leu Asp
                        595                     600                     605
        Asn Glu Glu Asn Glu Asp Ile Leu Glu Asp Ile Val Leu Thr Leu Thr
        610                     615                     620
        Leu Phe Glu Asp Arg Glu Met Ile Glu Glu Arg Leu Lys Thr Tyr Ala
        625                     630                     635                     640
        His Leu Phe Asp Asp Lys Val Met Lys Gln Leu Lys Arg Arg Arg Tyr
                        645                     650                     655
        Thr Gly Trp Gly Arg Leu Ser Arg Lys Leu Ile Asn Gly Ile Arg Asp
                        660                     665                     670
        Lys Gln Ser Gly Lys Thr Ile Leu Asp Phe Leu Lys Ser Asp Gly Phe
                        675                     680                     685
        Ala Asn Arg Asn Phe Met Gln Leu Ile His Asp Asp Ser Leu Thr Phe
        690                     695                     700
        Lys Glu Asp Ile Gln Lys Ala Gln Val Ser Gly Gln Gly Asp Ser Leu
        705                     710                     715                     720
        His Glu His Ile Ala Asn Leu Ala Gly Ser Pro Ala Ile Lys Lys Gly
                        725                     730                     735
        Ile Leu Gln Thr Val Lys Val Val Asp Glu Leu Val Lys Val Met Gly
                        740                     745                     750
        Arg His Lys Pro Glu Asn Ile Val Ile Glu Met Ala Arg Glu Asn Gln
                        755                     760                     765
        Thr Thr Gln Lys Gly Gln Lys Asn Ser Arg Glu Arg Met Lys Arg Ile
        770                     775                     780
        Glu Glu Gly Ile Lys Glu Leu Gly Ser Gln Ile Leu Lys Glu His Pro
        785                     790                     795                     800
        Val Glu Asn Thr Gln Leu Gln Asn Glu Lys Leu Tyr Leu Tyr Tyr Leu
                        805                     810                     815
        Gln Asn Gly Arg Asp Met Tyr Val Asp Gln Glu Leu Asp Ile Asn Arg
                        820                     825                     830
        Leu Ser Asp Tyr Asp Val Asp Ala Ile Val Pro Gln Ser Phe Leu Lys
                        835                     840                     845
        Asp Asp Ser Ile Asp Asn Lys Val Leu Thr Arg Ser Asp Lys Asn Arg
        850                     855                     860
```

```
Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Cys Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260
```

His Tyr Leu Asp Glu Ile Ile Glu Gln Ile Ser Glu Phe Ser Lys
        1265                1270                1275

Arg Val Ile Leu Ala Asp Ala Asn Leu Asp Lys Val Leu Ser Ala
        1280                1285                1290

Tyr Asn Lys His Arg Asp Lys Pro Ile Arg Glu Gln Ala Glu Asn
        1295                1300                1305

Ile Ile His Leu Phe Thr Leu Thr Asn Leu Gly Ala Pro Ala Ala
        1310                1315                1320

Phe Lys Tyr Phe Asp Thr Thr Ile Asp Arg Lys Arg Tyr Thr Ser
        1325                1330                1335

Thr Lys Glu Val Leu Asp Ala Thr Leu Ile His Gln Ser Ile Thr
        1340                1345                1350

Gly Leu Tyr Glu Thr Arg Ile Asp Leu Ser Gln Leu Gly Gly Asp
        1355                1360                1365

<210> SEQ ID NO 88
<211> LENGTH: 102
<212> TYPE: PRT
<213> ORGANISM: Unknown
<220> FEATURE:
<223> OTHER INFORMATION: Description of Unknown:
    Npu N Intein sequence

<400> SEQUENCE: 88

Cys Leu Ser Tyr Glu Thr Glu Ile Leu Thr Val Glu Tyr Gly Leu Leu
1               5                   10                  15

Pro Ile Gly Lys Ile Val Glu Lys Arg Ile Glu Cys Thr Val Tyr Ser
                20                  25                  30

Val Asp Asn Asn Gly Asn Ile Tyr Thr Gln Pro Val Ala Gln Trp His
            35                  40                  45

Asp Arg Gly Glu Gln Glu Val Phe Glu Tyr Cys Leu Glu Asp Gly Ser
        50                  55                  60

Leu Ile Arg Ala Thr Lys Asp His Lys Phe Met Thr Val Asp Gly Gln
65                  70                  75                  80

Met Leu Pro Ile Asp Glu Ile Phe Glu Arg Glu Leu Asp Leu Met Arg
                85                  90                  95

Val Asp Asn Leu Pro Asn
            100

<210> SEQ ID NO 89
<211> LENGTH: 35
<212> TYPE: PRT
<213> ORGANISM: Unknown
<220> FEATURE:
<223> OTHER INFORMATION: Description of Unknown:
    Npu C Intein sequence

<400> SEQUENCE: 89

Ile Lys Ile Ala Thr Arg Lys Tyr Leu Gly Lys Gln Asn Val Tyr Asp
1               5                   10                  15

Ile Gly Val Glu Arg Asp His Asn Phe Ala Leu Lys Asn Gly Phe Ile
                20                  25                  30

Ala Ser Asn
        35

<210> SEQ ID NO 90
<211> LENGTH: 1292
<212> TYPE: PRT
<213> ORGANISM: Artificial Sequence
<220> FEATURE:

<223> OTHER INFORMATION: Description of Artificial Sequence: Synthetic polypeptide

<400> SEQUENCE: 90

| | | | | | | | | | | | | | | |
|---|---|---|---|---|---|---|---|---|---|---|---|---|---|---|
| Met<br>1 | Lys | Arg | Thr | Ala<br>5 | Asp | Gly | Ser | Glu | Phe<br>10 | Glu | Ser | Pro | Lys | Lys<br>15 |
| Arg | Lys | Val | Asp<br>20 | Lys | Lys | Tyr | Ser | Ile<br>25 | Gly | Leu | Asp | Ile | Gly<br>30 | Thr | Asn |
| Ser | Val | Gly<br>35 | Trp | Ala | Val | Ile | Thr<br>40 | Asp | Glu | Tyr | Lys | Val<br>45 | Pro | Ser | Lys |
| Lys | Phe<br>50 | Lys | Val | Leu | Gly | Asn<br>55 | Thr | Asp | Arg | His | Ser<br>60 | Ile | Lys | Lys | Asn |
| Leu<br>65 | Ile | Gly | Ala | Leu | Leu<br>70 | Phe | Asp | Ser | Gly | Glu<br>75 | Thr | Ala | Glu | Ala | Thr<br>80 |
| Arg | Leu | Lys | Arg | Thr<br>85 | Ala | Arg | Arg | Arg | Tyr<br>90 | Thr | Arg | Arg | Lys | Asn<br>95 | Arg |
| Ile | Cys | Tyr | Leu<br>100 | Gln | Glu | Ile | Phe | Ser<br>105 | Asn | Glu | Met | Ala | Lys<br>110 | Val | Asp |
| Asp | Ser | Phe<br>115 | Phe | His | Arg | Leu | Glu<br>120 | Glu | Ser | Phe | Leu | Val<br>125 | Glu | Glu | Asp |
| Lys | Lys<br>130 | His | Glu | Arg | His | Pro<br>135 | Ile | Phe | Gly | Asn | Ile<br>140 | Val | Asp | Glu | Val |
| Ala<br>145 | Tyr | His | Glu | Lys | Tyr<br>150 | Pro | Thr | Ile | Tyr | His<br>155 | Leu | Arg | Lys | Lys | Leu<br>160 |
| Val | Asp | Ser | Thr | Asp<br>165 | Lys | Ala | Asp | Leu | Arg<br>170 | Leu | Ile | Tyr | Leu | Ala<br>175 | Leu |
| Ala | His | Met | Ile<br>180 | Lys | Phe | Arg | Gly | His<br>185 | Phe | Leu | Ile | Glu | Gly<br>190 | Asp | Leu |
| Asn | Pro | Asp<br>195 | Asn | Ser | Asp | Val | Asp<br>200 | Lys | Leu | Phe | Ile | Gln<br>205 | Leu | Val | Gln |
| Thr | Tyr<br>210 | Asn | Gln | Leu | Phe | Glu<br>215 | Glu | Asn | Pro | Ile | Asn<br>220 | Ala | Ser | Gly | Val |
| Asp<br>225 | Ala | Lys | Ala | Ile | Leu<br>230 | Ser | Ala | Arg | Leu | Ser<br>235 | Lys | Ser | Arg | Arg | Leu<br>240 |
| Glu | Asn | Leu | Ile | Ala<br>245 | Gln | Leu | Pro | Gly | Glu<br>250 | Lys | Lys | Asn | Gly | Leu<br>255 | Phe |
| Gly | Asn | Leu | Ile<br>260 | Ala | Leu | Ser | Leu | Gly<br>265 | Leu | Thr | Pro | Asn | Phe<br>270 | Lys | Ser |
| Asn | Phe | Asp<br>275 | Leu | Ala | Glu | Asp | Ala<br>280 | Lys | Leu | Gln | Leu | Ser<br>285 | Lys | Asp | Thr |
| Tyr | Asp<br>290 | Asp | Asp | Leu | Asp | Asn<br>295 | Leu | Leu | Ala | Gln | Ile<br>300 | Gly | Asp | Gln | Tyr |
| Ala<br>305 | Asp | Leu | Phe | Leu | Ala<br>310 | Ala | Lys | Asn | Leu | Ser<br>315 | Asp | Ala | Ile | Leu | Leu<br>320 |
| Ser | Asp | Ile | Leu | Arg<br>325 | Val | Asn | Thr | Glu | Ile<br>330 | Thr | Lys | Ala | Pro | Leu<br>335 | Ser |
| Ala | Ser | Met | Ile<br>340 | Lys | Arg | Tyr | Asp | Glu<br>345 | His | His | Gln | Asp | Leu<br>350 | Thr | Leu |
| Leu | Lys | Ala<br>355 | Leu | Val | Arg | Gln | Gln<br>360 | Leu | Pro | Glu | Lys | Tyr<br>365 | Lys | Glu | Ile |
| Phe | Phe<br>370 | Asp | Gln | Ser | Lys | Asn<br>375 | Gly | Tyr | Ala | Gly | Tyr<br>380 | Ile | Asp | Gly | Gly |
| Ala<br>385 | Ser | Gln | Glu | Glu | Phe<br>390 | Tyr | Lys | Phe | Ile | Lys<br>395 | Pro | Ile | Leu | Glu | Lys<br>400 |

```
Met Asp Gly Thr Glu Glu Leu Leu Val Lys Leu Asn Arg Glu Asp Leu
                405                 410                 415

Leu Arg Lys Gln Arg Thr Phe Asp Asn Gly Ser Ile Pro His Gln Ile
            420                 425                 430

His Leu Gly Glu Leu His Ala Ile Leu Arg Arg Gln Glu Asp Phe Tyr
            435                 440                 445

Pro Phe Leu Lys Asp Asn Arg Glu Lys Ile Glu Lys Ile Leu Thr Phe
        450                 455                 460

Arg Ile Pro Tyr Tyr Val Gly Pro Leu Ala Arg Gly Asn Ser Arg Phe
465                 470                 475                 480

Ala Trp Met Thr Arg Lys Ser Glu Glu Thr Ile Thr Pro Trp Asn Phe
                485                 490                 495

Glu Glu Val Val Asp Lys Gly Ala Ser Ala Gln Ser Phe Ile Glu Arg
                500                 505                 510

Met Thr Asn Phe Asp Lys Asn Leu Pro Asn Glu Lys Val Leu Pro Lys
            515                 520                 525

His Ser Leu Leu Tyr Glu Tyr Phe Thr Val Tyr Asn Glu Leu Thr Lys
            530                 535                 540

Val Lys Tyr Val Thr Glu Gly Met Arg Lys Pro Ala Phe Leu Ser Gly
545                 550                 555                 560

Glu Gln Lys Lys Ala Ile Val Asp Leu Leu Phe Lys Thr Asn Arg Lys
                565                 570                 575

Val Thr Val Lys Gln Leu Lys Glu Asp Tyr Phe Lys Lys Ile Glu Cys
                580                 585                 590

Phe Asp Ser Val Glu Ile Ser Gly Val Glu Asp Arg Phe Asn Ala Ser
            595                 600                 605

Leu Gly Thr Tyr His Asp Leu Leu Lys Ile Ile Lys Asp Lys Asp Phe
        610                 615                 620

Leu Asp Asn Glu Glu Asn Glu Asp Ile Leu Glu Asp Ile Val Leu Thr
625                 630                 635                 640

Leu Thr Leu Phe Glu Asp Arg Glu Met Ile Glu Glu Arg Leu Lys Thr
                645                 650                 655

Tyr Ala His Leu Phe Asp Asp Lys Val Met Lys Gln Leu Lys Arg Arg
                660                 665                 670

Arg Tyr Thr Gly Trp Gly Arg Leu Ser Arg Lys Leu Ile Asn Gly Ile
            675                 680                 685

Arg Asp Lys Gln Ser Gly Lys Thr Ile Leu Asp Phe Leu Lys Ser Asp
        690                 695                 700

Gly Phe Ala Asn Arg Asn Phe Met Gln Leu Ile His Asp Asp Ser Leu
705                 710                 715                 720

Thr Phe Lys Glu Asp Ile Gln Lys Ala Gln Val Ser Gly Gln Gly Asp
                725                 730                 735

Ser Leu His Glu His Ile Ala Asn Leu Ala Gly Ser Pro Ala Ile Lys
            740                 745                 750

Lys Gly Ile Leu Gln Thr Val Lys Val Val Asp Glu Leu Val Lys Val
            755                 760                 765

Met Gly Arg His Lys Pro Glu Asn Ile Val Ile Glu Met Ala Arg Glu
        770                 775                 780

Asn Gln Thr Thr Gln Lys Gly Gln Lys Asn Ser Arg Glu Arg Met Lys
785                 790                 795                 800

Arg Ile Glu Glu Gly Ile Lys Glu Leu Gly Ser Gln Ile Leu Lys Glu
                805                 810                 815
```

```
His Pro Val Glu Asn Thr Gln Leu Gln Asn Glu Lys Leu Tyr Leu Tyr
            820                 825                 830

Tyr Leu Gln Asn Gly Arg Asp Met Tyr Val Asp Gln Glu Leu Asp Ile
            835                 840                 845

Asn Arg Leu Ser Asp Tyr Asp Val Asp Ala Ile Val Pro Gln Ser Phe
850                 855                 860

Leu Lys Asp Asp Ser Ile Asp Asn Lys Val Leu Thr Arg Ser Asp Lys
865                 870                 875                 880

Asn Arg Gly Lys Ser Asp Asn Val Pro Ser Glu Glu Val Val Lys Lys
                885                 890                 895

Met Lys Asn Tyr Trp Arg Gln Leu Leu Asn Ala Lys Leu Ile Thr Gln
            900                 905                 910

Arg Lys Phe Asp Asn Leu Thr Lys Ala Glu Arg Gly Gly Leu Ser Glu
            915                 920                 925

Leu Asp Lys Ala Gly Phe Ile Lys Arg Gln Leu Val Glu Thr Arg Gln
            930                 935                 940

Ile Thr Lys His Val Ala Gln Ile Leu Asp Ser Arg Met Asn Thr Lys
945                 950                 955                 960

Tyr Asp Glu Asn Asp Lys Leu Ile Arg Glu Val Lys Val Ile Thr Leu
                965                 970                 975

Lys Ser Lys Leu Val Ser Asp Phe Arg Lys Asp Phe Gln Phe Tyr Lys
            980                 985                 990

Val Arg Glu Ile Asn Asn Tyr His His Ala His Asp Ala Tyr Leu Asn
            995                 1000                1005

Ala Val Val Gly Thr Ala Leu Ile Lys Lys Tyr Pro Lys Leu Glu
    1010                1015                1020

Ser Glu Phe Val Tyr Gly Asp Tyr Lys Val Tyr Asp Val Arg Lys
    1025                1030                1035

Met Ile Ala Lys Ser Glu Gln Glu Ile Gly Lys Ala Thr Ala Lys
    1040                1045                1050

Tyr Phe Phe Tyr Ser Asn Ile Met Asn Phe Phe Lys Thr Glu Ile
    1055                1060                1065

Thr Leu Ala Asn Gly Glu Ile Arg Lys Arg Pro Leu Ile Glu Thr
    1070                1075                1080

Asn Gly Glu Thr Gly Glu Ile Val Trp Asp Lys Gly Arg Asp Phe
    1085                1090                1095

Ala Thr Val Arg Lys Val Leu Ser Met Pro Gln Val Asn Ile Val
    1100                1105                1110

Lys Lys Thr Glu Val Gln Thr Gly Gly Phe Ser Lys Glu Ser Ile
    1115                1120                1125

Leu Pro Lys Arg Asn Ser Asp Lys Leu Ile Ala Arg Lys Lys Asp
    1130                1135                1140

Trp Asp Pro Lys Lys Tyr Gly Gly Phe Asp Ser Pro Thr Val Ala
    1145                1150                1155

Tyr Ser Val Leu Val Val Ala Lys Val Glu Lys Gly Lys Ser Lys
    1160                1165                1170

Lys Leu Lys Ser Val Lys Glu Leu Leu Gly Ile Thr Ile Met Glu
    1175                1180                1185

Arg Ser Cys Leu Ser Tyr Glu Thr Glu Ile Leu Thr Val Glu Tyr
    1190                1195                1200

Gly Leu Leu Pro Ile Gly Lys Ile Val Glu Lys Arg Ile Glu Cys
    1205                1210                1215

Thr Val Tyr Ser Val Asp Asn Asn Gly Asn Ile Tyr Thr Gln Pro
```

-continued

```
                1220                1225                1230
Val Ala Gln Trp His Asp Arg Gly Glu Gln Val Phe Glu Tyr
        1235                1240                1245

Cys Leu Glu Asp Gly Ser Leu Ile Arg Ala Thr Lys Asp His Lys
    1250                1255                1260

Phe Met Thr Val Asp Gly Gln Met Leu Pro Ile Asp Glu Ile Phe
    1265                1270                1275

Glu Arg Glu Leu Asp Leu Met Arg Val Asp Asn Leu Pro Asn
    1280                1285                1290

<210> SEQ ID NO 91
<211> LENGTH: 953
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Ile Lys Ile Ala Thr Arg Lys Tyr Leu Gly Lys Gln Asn Val Tyr Asp
1               5                   10                  15

Ile Gly Val Glu Arg Asp His Asn Phe Ala Leu Lys Asn Gly Phe Ile
            20                  25                  30

Ala Ser Asn Cys Phe Glu Lys Asn Pro Ile Asp Phe Leu Glu Ala Lys
        35                  40                  45

Gly Tyr Lys Glu Val Lys Lys Asp Leu Ile Ile Lys Leu Pro Lys Tyr
    50                  55                  60

Ser Leu Phe Glu Leu Glu Asn Gly Arg Lys Arg Met Leu Ala Ser Ala
65                  70                  75                  80

Gly Glu Leu Gln Lys Gly Asn Glu Leu Ala Leu Pro Ser Lys Tyr Val
                85                  90                  95

Asn Phe Leu Tyr Leu Ala Ser His Tyr Glu Lys Leu Lys Gly Ser Pro
            100                 105                 110

Glu Asp Asn Glu Gln Lys Gln Leu Phe Val Glu Gln His Lys His Tyr
        115                 120                 125

Leu Asp Glu Ile Ile Glu Gln Ile Ser Glu Phe Ser Lys Arg Val Ile
    130                 135                 140

Leu Ala Asp Ala Asn Leu Asp Lys Val Leu Ser Ala Tyr Asn Lys His
145                 150                 155                 160

Arg Asp Lys Pro Ile Arg Glu Gln Ala Glu Asn Ile Ile His Leu Phe
                165                 170                 175

Thr Leu Thr Asn Leu Gly Ala Pro Ala Ala Phe Lys Tyr Phe Asp Thr
            180                 185                 190

Thr Ile Asp Arg Lys Arg Tyr Thr Ser Thr Lys Glu Val Leu Asp Ala
        195                 200                 205

Thr Leu Ile His Gln Ser Ile Thr Gly Leu Tyr Glu Thr Arg Ile Asp
    210                 215                 220

Leu Ser Gln Leu Gly Gly Asp Gly Ser Glu Thr Pro Gly Thr Ser Glu
225                 230                 235                 240

Ser Ala Thr Pro Glu Ser Ser Gly Gly Ser Ser Gly Gly Ser Ser Thr
                245                 250                 255

Leu Asn Ile Glu Asp Glu Tyr Arg Leu His Glu Thr Ser Lys Glu Pro
            260                 265                 270

Asp Val Ser Leu Gly Ser Thr Trp Leu Ser Asp Phe Pro Gln Ala Trp
        275                 280                 285
```

```
Ala Glu Thr Gly Gly Met Gly Leu Ala Val Arg Gln Ala Pro Leu Ile
    290             295                 300
Ile Pro Leu Lys Ala Thr Ser Thr Pro Val Ser Ile Lys Gln Tyr Pro
305                 310                 315                 320
Met Ser Gln Glu Ala Arg Leu Gly Ile Lys Pro His Ile Gln Arg Leu
                325                 330                 335
Leu Asp Gln Gly Ile Leu Val Pro Cys Gln Ser Pro Trp Asn Thr Pro
            340                 345                 350
Leu Leu Pro Val Lys Lys Pro Gly Thr Asn Asp Tyr Arg Pro Val Gln
        355                 360                 365
Asp Leu Arg Glu Val Asn Lys Arg Val Glu Asp Ile His Pro Thr Val
    370                 375                 380
Pro Asn Pro Tyr Asn Leu Leu Ser Gly Leu Pro Pro Ser His Gln Trp
385                 390                 395                 400
Tyr Thr Val Leu Asp Leu Lys Asp Ala Phe Phe Cys Leu Arg Leu His
                405                 410                 415
Pro Thr Ser Gln Pro Leu Phe Ala Phe Glu Trp Arg Asp Pro Glu Met
            420                 425                 430
Gly Ile Ser Gly Gln Leu Thr Trp Thr Arg Leu Pro Gln Gly Phe Lys
        435                 440                 445
Asn Ser Pro Thr Leu Phe Asn Glu Ala Leu His Arg Asp Leu Ala Asp
    450                 455                 460
Phe Arg Ile Gln His Pro Asp Leu Ile Leu Leu Gln Tyr Val Asp Asp
465                 470                 475                 480
Leu Leu Leu Ala Ala Thr Ser Glu Leu Asp Cys Gln Gln Gly Thr Arg
                485                 490                 495
Ala Leu Leu Gln Thr Leu Gly Asn Leu Gly Tyr Arg Ala Ser Ala Lys
            500                 505                 510
Lys Ala Gln Ile Cys Gln Lys Gln Val Lys Tyr Leu Gly Tyr Leu Leu
        515                 520                 525
Lys Glu Gly Gln Arg Trp Leu Thr Glu Ala Arg Lys Glu Thr Val Met
    530                 535                 540
Gly Gln Pro Thr Pro Lys Thr Pro Arg Gln Leu Arg Glu Phe Leu Gly
545                 550                 555                 560
Lys Ala Gly Phe Cys Arg Leu Phe Ile Pro Gly Phe Ala Glu Met Ala
                565                 570                 575
Ala Pro Leu Tyr Pro Leu Thr Lys Pro Gly Thr Leu Phe Asn Trp Gly
            580                 585                 590
Pro Asp Gln Gln Lys Ala Tyr Gln Glu Ile Lys Gln Ala Leu Leu Thr
    595                 600                 605
Ala Pro Ala Leu Gly Leu Pro Asp Leu Thr Lys Pro Phe Glu Leu Phe
610                 615                 620
Val Asp Glu Lys Gln Gly Tyr Ala Lys Gly Val Leu Thr Gln Lys Leu
625                 630                 635                 640
Gly Pro Trp Arg Arg Pro Val Ala Tyr Leu Ser Lys Lys Leu Asp Pro
                645                 650                 655
Val Ala Ala Gly Trp Pro Pro Cys Leu Arg Met Val Ala Ala Ile Ala
            660                 665                 670
Val Leu Thr Lys Asp Ala Gly Lys Leu Thr Met Gly Gln Pro Leu Val
        675                 680                 685
Ile Leu Ala Pro His Ala Val Glu Ala Leu Val Lys Gln Pro Pro Asp
    690                 695                 700
Arg Trp Leu Ser Asn Ala Arg Met Thr His Tyr Gln Ala Leu Leu Leu
```

```
                        705                 710                 715                 720
Asp Thr Asp Arg Val Gln Phe Gly Pro Val Val Ala Leu Asn Pro Ala
                    725                 730                 735

Thr Leu Leu Pro Leu Pro Glu Glu Gly Leu Gln His Asn Cys Leu Asp
                740                 745                 750

Ile Leu Ala Glu Ala His Gly Thr Arg Pro Asp Leu Thr Asp Gln Pro
            755                 760                 765

Leu Pro Asp Ala Asp His Thr Trp Tyr Thr Asp Gly Ser Ser Leu Leu
        770                 775                 780

Gln Glu Gly Gln Arg Lys Ala Gly Ala Ala Val Thr Thr Glu Thr Glu
785                 790                 795                 800

Val Ile Trp Ala Lys Ala Leu Pro Ala Gly Thr Ser Ala Gln Arg Ala
                805                 810                 815

Glu Leu Ile Ala Leu Thr Gln Ala Leu Lys Met Ala Glu Gly Lys Lys
            820                 825                 830

Leu Asn Val Tyr Thr Asp Ser Arg Tyr Ala Phe Ala Thr Ala His Ile
        835                 840                 845

His Gly Glu Ile Tyr Arg Arg Arg Gly Trp Leu Thr Ser Glu Gly Lys
    850                 855                 860

Glu Ile Lys Asn Lys Asp Glu Ile Leu Ala Leu Leu Lys Ala Leu Phe
865                 870                 875                 880

Leu Pro Lys Arg Leu Ser Ile Ile His Cys Pro Gly His Gln Lys Gly
                885                 890                 895

His Ser Ala Glu Ala Arg Gly Asn Arg Met Ala Asp Gln Ala Ala Arg
            900                 905                 910

Lys Ala Ala Ile Thr Glu Thr Pro Asp Thr Ser Thr Leu Leu Ile Glu
        915                 920                 925

Asn Ser Ser Pro Ser Gly Gly Ser Lys Arg Thr Ala Asp Gly Ser Glu
    930                 935                 940

Phe Glu Pro Lys Lys Lys Arg Lys Val
945                 950

<210> SEQ ID NO 92
<211> LENGTH: 2108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Met Lys Arg Thr Ala Asp Gly Ser Glu Phe Glu Ser Pro Lys Lys Lys
1               5                   10                  15

Arg Lys Val Asp Lys Lys Tyr Ser Ile Gly Leu Asp Ile Gly Thr Asn
                20                  25                  30

Ser Val Gly Trp Ala Val Ile Thr Asp Glu Tyr Lys Val Pro Ser Lys
            35                  40                  45

Lys Phe Lys Val Leu Gly Asn Thr Asp Arg His Ser Ile Lys Lys Asn
        50                  55                  60

Leu Ile Gly Ala Leu Leu Phe Asp Ser Gly Glu Thr Ala Glu Ala Thr
65                  70                  75                  80

Arg Leu Lys Arg Thr Ala Arg Arg Tyr Thr Arg Arg Lys Asn Arg
                85                  90                  95

Ile Cys Tyr Leu Gln Glu Ile Phe Ser Asn Glu Met Ala Lys Val Asp
        100                 105                 110
```

-continued

```
Asp Ser Phe Phe His Arg Leu Glu Glu Ser Phe Leu Val Glu Glu Asp
            115                 120                 125
Lys Lys His Glu Arg His Pro Ile Phe Gly Asn Ile Val Asp Glu Val
130                 135                 140
Ala Tyr His Glu Lys Tyr Pro Thr Ile Tyr His Leu Arg Lys Lys Leu
145                 150                 155                 160
Val Asp Ser Thr Asp Lys Ala Asp Leu Arg Leu Ile Tyr Leu Ala Leu
                165                 170                 175
Ala His Met Ile Lys Phe Arg Gly His Phe Leu Ile Glu Gly Asp Leu
            180                 185                 190
Asn Pro Asp Asn Ser Asp Val Asp Lys Leu Phe Ile Gln Leu Val Gln
            195                 200                 205
Thr Tyr Asn Gln Leu Phe Glu Glu Asn Pro Ile Asn Ala Ser Gly Val
210                 215                 220
Asp Ala Lys Ala Ile Leu Ser Ala Arg Leu Ser Lys Ser Arg Arg Leu
225                 230                 235                 240
Glu Asn Leu Ile Ala Gln Leu Pro Gly Glu Lys Lys Asn Gly Leu Phe
                245                 250                 255
Gly Asn Leu Ile Ala Leu Ser Leu Gly Leu Thr Pro Asn Phe Lys Ser
            260                 265                 270
Asn Phe Asp Leu Ala Glu Asp Ala Lys Leu Gln Leu Ser Lys Asp Thr
            275                 280                 285
Tyr Asp Asp Asp Leu Asp Asn Leu Leu Ala Gln Ile Gly Asp Gln Tyr
        290                 295                 300
Ala Asp Leu Phe Leu Ala Ala Lys Asn Leu Ser Asp Ala Ile Leu Leu
305                 310                 315                 320
Ser Asp Ile Leu Arg Val Asn Thr Glu Ile Thr Lys Ala Pro Leu Ser
                325                 330                 335
Ala Ser Met Ile Lys Arg Tyr Asp Glu His His Gln Asp Leu Thr Leu
            340                 345                 350
Leu Lys Ala Leu Val Arg Gln Gln Leu Pro Glu Lys Tyr Lys Glu Ile
            355                 360                 365
Phe Phe Asp Gln Ser Lys Asn Gly Tyr Ala Gly Tyr Ile Asp Gly Gly
370                 375                 380
Ala Ser Gln Glu Glu Phe Tyr Lys Phe Ile Lys Pro Ile Leu Glu Lys
385                 390                 395                 400
Met Asp Gly Thr Glu Glu Leu Leu Val Lys Leu Asn Arg Glu Asp Leu
                405                 410                 415
Leu Arg Lys Gln Arg Thr Phe Asp Asn Gly Ser Ile Pro His Gln Ile
            420                 425                 430
His Leu Gly Glu Leu His Ala Ile Leu Arg Arg Gln Glu Asp Phe Tyr
            435                 440                 445
Pro Phe Leu Lys Asp Asn Arg Glu Lys Ile Glu Lys Ile Leu Thr Phe
450                 455                 460
Arg Ile Pro Tyr Tyr Val Gly Pro Leu Ala Arg Gly Asn Ser Arg Phe
465                 470                 475                 480
Ala Trp Met Thr Arg Lys Ser Glu Glu Thr Ile Thr Pro Trp Asn Phe
                485                 490                 495
Glu Glu Val Val Asp Lys Gly Ala Ser Ala Gln Ser Phe Ile Glu Arg
            500                 505                 510
Met Thr Asn Phe Asp Lys Asn Leu Pro Asn Glu Lys Val Leu Pro Lys
            515                 520                 525
His Ser Leu Leu Tyr Glu Tyr Phe Thr Val Tyr Asn Glu Leu Thr Lys
```

-continued

```
              530                 535                 540
Val Lys Tyr Val Thr Glu Gly Met Arg Lys Pro Ala Phe Leu Ser Gly
545                 550                 555                 560

Glu Gln Lys Lys Ala Ile Val Asp Leu Leu Phe Lys Thr Asn Arg Lys
                    565                 570                 575

Val Thr Val Lys Gln Leu Lys Glu Asp Tyr Phe Lys Lys Ile Glu Cys
                580                 585                 590

Phe Asp Ser Val Glu Ile Ser Gly Val Glu Asp Arg Phe Asn Ala Ser
                595                 600                 605

Leu Gly Thr Tyr His Asp Leu Leu Lys Ile Ile Lys Asp Lys Asp Phe
            610                 615                 620

Leu Asp Asn Glu Glu Asn Glu Asp Ile Leu Glu Asp Ile Val Leu Thr
625                 630                 635                 640

Leu Thr Leu Phe Glu Asp Arg Glu Met Ile Glu Glu Arg Leu Lys Thr
                645                 650                 655

Tyr Ala His Leu Phe Asp Asp Lys Val Met Lys Gln Leu Lys Arg Arg
                660                 665                 670

Arg Tyr Thr Gly Trp Gly Arg Leu Ser Arg Lys Leu Ile Asn Gly Ile
                675                 680                 685

Arg Asp Lys Gln Ser Gly Lys Thr Ile Leu Asp Phe Leu Lys Ser Asp
690                 695                 700

Gly Phe Ala Asn Arg Asn Phe Met Gln Leu Ile His Asp Asp Ser Leu
705                 710                 715                 720

Thr Phe Lys Glu Asp Ile Gln Lys Ala Gln Val Ser Gly Gln Gly Asp
                725                 730                 735

Ser Leu His Glu His Ile Ala Asn Leu Ala Gly Ser Pro Ala Ile Lys
                740                 745                 750

Lys Gly Ile Leu Gln Thr Val Lys Val Val Asp Glu Leu Val Lys Val
                755                 760                 765

Met Gly Arg His Lys Pro Glu Asn Ile Val Ile Glu Met Ala Arg Glu
770                 775                 780

Asn Gln Thr Thr Gln Lys Gly Gln Lys Asn Ser Arg Glu Arg Met Lys
785                 790                 795                 800

Arg Ile Glu Glu Gly Ile Lys Glu Leu Gly Ser Gln Ile Leu Lys Glu
                805                 810                 815

His Pro Val Glu Asn Thr Gln Leu Gln Asn Glu Lys Leu Tyr Leu Tyr
                820                 825                 830

Tyr Leu Gln Asn Gly Arg Asp Met Tyr Val Asp Gln Glu Leu Asp Ile
                835                 840                 845

Asn Arg Leu Ser Asp Tyr Asp Val Asp Ala Ile Val Pro Gln Ser Phe
850                 855                 860

Leu Lys Asp Asp Ser Ile Asp Asn Lys Val Leu Thr Arg Ser Asp Lys
865                 870                 875                 880

Asn Arg Gly Lys Ser Asp Asn Val Pro Ser Glu Glu Val Val Lys Lys
                885                 890                 895

Met Lys Asn Tyr Trp Arg Gln Leu Leu Asn Ala Lys Leu Ile Thr Gln
                900                 905                 910

Arg Lys Phe Asp Asn Leu Thr Lys Ala Glu Arg Gly Gly Leu Ser Glu
                915                 920                 925

Leu Asp Lys Ala Gly Phe Ile Lys Arg Gln Leu Val Glu Thr Arg Gln
930                 935                 940

Ile Thr Lys His Val Ala Gln Ile Leu Asp Ser Arg Met Asn Thr Lys
945                 950                 955                 960
```

```
Tyr Asp Glu Asn Asp Lys Leu Ile Arg Glu Val Lys Val Ile Thr Leu
            965                 970                 975
Lys Ser Lys Leu Val Ser Asp Phe Arg Lys Asp Phe Gln Phe Tyr Lys
            980                 985                 990
Val Arg Glu Ile Asn Asn Tyr His His Ala His Asp Ala Tyr Leu Asn
            995                 1000                1005
Ala Val Val Gly Thr Ala Leu Ile Lys Lys Tyr Pro Lys Leu Glu
        1010                1015                1020
Ser Glu Phe Val Tyr Gly Asp Tyr Lys Val Tyr Asp Val Arg Lys
        1025                1030                1035
Met Ile Ala Lys Ser Glu Gln Glu Ile Gly Lys Ala Thr Ala Lys
        1040                1045                1050
Tyr Phe Phe Tyr Ser Asn Ile Met Asn Phe Phe Lys Thr Glu Ile
        1055                1060                1065
Thr Leu Ala Asn Gly Glu Ile Arg Lys Arg Pro Leu Ile Glu Thr
        1070                1075                1080
Asn Gly Glu Thr Gly Glu Ile Val Trp Asp Lys Gly Arg Asp Phe
        1085                1090                1095
Ala Thr Val Arg Lys Val Leu Ser Met Pro Gln Val Asn Ile Val
        1100                1105                1110
Lys Lys Thr Glu Val Gln Thr Gly Gly Phe Ser Lys Glu Ser Ile
        1115                1120                1125
Leu Pro Lys Arg Asn Ser Asp Lys Leu Ile Ala Arg Lys Lys Asp
        1130                1135                1140
Trp Asp Pro Lys Lys Tyr Gly Gly Phe Asp Ser Pro Thr Val Ala
        1145                1150                1155
Tyr Ser Val Leu Val Val Ala Lys Val Glu Lys Gly Lys Ser Lys
        1160                1165                1170
Lys Leu Lys Ser Val Lys Glu Leu Leu Gly Ile Thr Ile Met Glu
        1175                1180                1185
Arg Ser Cys Phe Glu Lys Asn Pro Ile Asp Phe Leu Glu Ala Lys
        1190                1195                1200
Gly Tyr Lys Glu Val Lys Lys Asp Leu Ile Ile Lys Leu Pro Lys
        1205                1210                1215
Tyr Ser Leu Phe Glu Leu Glu Asn Gly Arg Lys Arg Met Leu Ala
        1220                1225                1230
Ser Ala Gly Glu Leu Gln Lys Gly Asn Glu Leu Ala Leu Pro Ser
        1235                1240                1245
Lys Tyr Val Asn Phe Leu Tyr Leu Ala Ser His Tyr Glu Lys Leu
        1250                1255                1260
Lys Gly Ser Pro Glu Asp Asn Glu Gln Lys Gln Leu Phe Val Glu
        1265                1270                1275
Gln His Lys His Tyr Leu Asp Glu Ile Ile Glu Gln Ile Ser Glu
        1280                1285                1290
Phe Ser Lys Arg Val Ile Leu Ala Asp Ala Asn Leu Asp Lys Val
        1295                1300                1305
Leu Ser Ala Tyr Asn Lys His Arg Asp Lys Pro Ile Arg Glu Gln
        1310                1315                1320
Ala Glu Asn Ile Ile His Leu Phe Thr Leu Thr Asn Leu Gly Ala
        1325                1330                1335
Pro Ala Ala Phe Lys Tyr Phe Asp Thr Thr Ile Asp Arg Lys Arg
        1340                1345                1350
```

Tyr Thr Ser Thr Lys Glu Val Leu Asp Ala Thr Leu Ile His Gln
1355             1360                 1365

Ser Ile Thr Gly Leu Tyr Glu Thr Arg Ile Asp Leu Ser Gln Leu
1370             1375                 1380

Gly Gly Asp Gly Ser Glu Thr Pro Gly Thr Ser Glu Ser Ala Thr
1385             1390                 1395

Pro Glu Ser Ser Gly Gly Ser Ser Gly Gly Ser Ser Thr Leu Asn
1400             1405                 1410

Ile Glu Asp Glu Tyr Arg Leu His Glu Thr Ser Lys Glu Pro Asp
1415             1420                 1425

Val Ser Leu Gly Ser Thr Trp Leu Ser Asp Phe Pro Gln Ala Trp
1430             1435                 1440

Ala Glu Thr Gly Gly Met Gly Leu Ala Val Arg Gln Ala Pro Leu
1445             1450                 1455

Ile Ile Pro Leu Lys Ala Thr Ser Thr Pro Val Ser Ile Lys Gln
1460             1465                 1470

Tyr Pro Met Ser Gln Glu Ala Arg Leu Gly Ile Lys Pro His Ile
1475             1480                 1485

Gln Arg Leu Leu Asp Gln Gly Ile Leu Val Pro Cys Gln Ser Pro
1490             1495                 1500

Trp Asn Thr Pro Leu Leu Pro Val Lys Lys Pro Gly Thr Asn Asp
1505             1510                 1515

Tyr Arg Pro Val Gln Asp Leu Arg Glu Val Asn Lys Arg Val Glu
1520             1525                 1530

Asp Ile His Pro Thr Val Pro Asn Pro Tyr Asn Leu Leu Ser Gly
1535             1540                 1545

Leu Pro Pro Ser His Gln Trp Tyr Thr Val Leu Asp Leu Lys Asp
1550             1555                 1560

Ala Phe Phe Cys Leu Arg Leu His Pro Thr Ser Gln Pro Leu Phe
1565             1570                 1575

Ala Phe Glu Trp Arg Asp Pro Glu Met Gly Ile Ser Gly Gln Leu
1580             1585                 1590

Thr Trp Thr Arg Leu Pro Gln Gly Phe Lys Asn Ser Pro Thr Leu
1595             1600                 1605

Phe Asn Glu Ala Leu His Arg Asp Leu Ala Asp Phe Arg Ile Gln
1610             1615                 1620

His Pro Asp Leu Ile Leu Leu Gln Tyr Val Asp Asp Leu Leu Leu
1625             1630                 1635

Ala Ala Thr Ser Glu Leu Asp Cys Gln Gln Gly Thr Arg Ala Leu
1640             1645                 1650

Leu Gln Thr Leu Gly Asn Leu Gly Tyr Arg Ala Ser Ala Lys Lys
1655             1660                 1665

Ala Gln Ile Cys Gln Lys Gln Val Lys Tyr Leu Gly Tyr Leu Leu
1670             1675                 1680

Lys Glu Gly Gln Arg Trp Leu Thr Glu Ala Arg Lys Glu Thr Val
1685             1690                 1695

Met Gly Gln Pro Thr Pro Lys Thr Pro Arg Gln Leu Arg Glu Phe
1700             1705                 1710

Leu Gly Lys Ala Gly Phe Cys Arg Leu Phe Ile Pro Gly Phe Ala
1715             1720                 1725

Glu Met Ala Ala Pro Leu Tyr Pro Leu Thr Lys Pro Gly Thr Leu
1730             1735                 1740

Phe Asn Trp Gly Pro Asp Gln Gln Lys Ala Tyr Gln Glu Ile Lys

```
            1745                1750                1755

Gln Ala Leu Leu Thr Ala Pro Ala Leu Gly Leu Pro Asp Leu Thr
    1760                1765                1770

Lys Pro Phe Glu Leu Phe Val Asp Glu Lys Gln Gly Tyr Ala Lys
    1775                1780                1785

Gly Val Leu Thr Gln Lys Leu Gly Pro Trp Arg Arg Pro Val Ala
    1790                1795                1800

Tyr Leu Ser Lys Lys Leu Asp Pro Val Ala Ala Gly Trp Pro Pro
    1805                1810                1815

Cys Leu Arg Met Val Ala Ala Ile Ala Val Leu Thr Lys Asp Ala
    1820                1825                1830

Gly Lys Leu Thr Met Gly Gln Pro Leu Val Ile Leu Ala Pro His
    1835                1840                1845

Ala Val Glu Ala Leu Val Lys Gln Pro Pro Asp Arg Trp Leu Ser
    1850                1855                1860

Asn Ala Arg Met Thr His Tyr Gln Ala Leu Leu Leu Asp Thr Asp
    1865                1870                1875

Arg Val Gln Phe Gly Pro Val Val Ala Leu Asn Pro Ala Thr Leu
    1880                1885                1890

Leu Pro Leu Pro Glu Glu Gly Leu Gln His Asn Cys Leu Asp Ile
    1895                1900                1905

Leu Ala Glu Ala His Gly Thr Arg Pro Asp Leu Thr Asp Gln Pro
    1910                1915                1920

Leu Pro Asp Ala Asp His Thr Trp Tyr Thr Asp Gly Ser Ser Leu
    1925                1930                1935

Leu Gln Glu Gly Gln Arg Lys Ala Gly Ala Ala Val Thr Thr Glu
    1940                1945                1950

Thr Glu Val Ile Trp Ala Lys Ala Leu Pro Ala Gly Thr Ser Ala
    1955                1960                1965

Gln Arg Ala Glu Leu Ile Ala Leu Thr Gln Ala Leu Lys Met Ala
    1970                1975                1980

Glu Gly Lys Lys Leu Asn Val Tyr Thr Asp Ser Arg Tyr Ala Phe
    1985                1990                1995

Ala Thr Ala His Ile His Gly Glu Ile Tyr Arg Arg Arg Gly Trp
    2000                2005                2010

Leu Thr Ser Glu Gly Lys Glu Ile Lys Asn Lys Asp Glu Ile Leu
    2015                2020                2025

Ala Leu Leu Lys Ala Leu Phe Leu Pro Lys Arg Leu Ser Ile Ile
    2030                2035                2040

His Cys Pro Gly His Gln Lys Gly His Ser Ala Glu Ala Arg Gly
    2045                2050                2055

Asn Arg Met Ala Asp Gln Ala Ala Arg Lys Ala Ala Ile Thr Glu
    2060                2065                2070

Thr Pro Asp Thr Ser Thr Leu Leu Ile Glu Asn Ser Ser Pro Ser
    2075                2080                2085

Gly Gly Ser Lys Arg Thr Ala Asp Gly Ser Glu Phe Glu Pro Lys
    2090                2095                2100

Lys Lys Arg Lys Val
    2105

<210> SEQ ID NO 93
<211> LENGTH: 112
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 93

Met Ala Asp Pro Arg Glu Ile Ile Pro Pro Gly Asn Ser Gly Glu Glu
1               5                   10                  15

Thr Val Gly Glu Ala Phe Ala Trp Leu Glu Arg Thr Val Glu Ala Ile
            20                  25                  30

Asn Arg Glu Ala Val Asn His Leu Pro Arg Glu Leu Ile Phe Gln Val
        35                  40                  45

Trp Gln Arg Ser Trp Arg Tyr Trp His Asp Glu Gln Gly Met Ser Ser
    50                  55                  60

Ser Tyr Thr Lys Tyr Arg Tyr Leu Cys Leu Met Gln Lys Ala Met Phe
65                  70                  75                  80

Ile His Phe Thr Arg Gly Cys Thr Cys Leu Gly Gly His Gly Pro
                85                  90                  95

Gly Gly Trp Gly Pro Gly Pro Pro Pro Pro Pro Gly Leu Val
            100                 105                 110

<210> SEQ ID NO 94
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
ggtcccatgg tgtaatggtt agcactctgg actttgaatc cagcgatccg agttcaaatc      60
tcggtgggac ct                                                         72

<210> SEQ ID NO 95
<211> LENGTH: 698
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Thr Leu Asn Ile Glu Asp Glu Tyr Arg Leu His Glu Thr Ser Lys Glu
1               5                   10                  15

Pro Asp Val Ser Leu Gly Ser Thr Trp Leu Ser Asp Phe Pro Gln Ala
            20                  25                  30

Trp Ala Glu Thr Gly Gly Met Gly Leu Ala Val Arg Gln Ala Pro Leu
        35                  40                  45

Ile Ile Pro Leu Lys Ala Thr Ser Thr Pro Val Ser Ile Lys Gln Tyr
    50                  55                  60

Pro Met Ser Gln Glu Ala Arg Leu Gly Ile Lys Pro His Ile Gln Arg
65                  70                  75                  80

Leu Leu Asp Gln Gly Ile Leu Val Pro Cys Gln Ser Pro Trp Asn Thr
                85                  90                  95

Pro Leu Leu Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
        115                 120                 125

Val Pro Asn Pro Tyr Asn Leu Leu Ser Gly Leu Pro Pro Ser His Gln
    130                 135                 140
```

```
Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
            165                 170                 175

Met Gly Ile Ser Gly Gln Leu Thr Trp Thr Arg Leu Pro Gln Gly Phe
        180                 185                 190

Lys Asn Ser Pro Thr Leu Phe Asn Glu Ala Leu His Arg Asp Leu Ala
        195                 200                 205

Asp Phe Arg Ile Gln His Pro Asp Leu Ile Leu Leu Gln Tyr Val Asp
        210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
            260                 265                 270

Leu Lys Glu Gly Gln Arg Trp Leu Thr Glu Ala Arg Lys Glu Thr Val
        275                 280                 285

Met Gly Gln Pro Thr Pro Lys Thr Pro Arg Gln Leu Arg Glu Phe Leu
290                 295                 300

Gly Lys Ala Gly Phe Cys Arg Leu Phe Ile Pro Gly Phe Ala Glu Met
305                 310                 315                 320

Ala Ala Pro Leu Tyr Pro Leu Thr Lys Pro Gly Thr Leu Phe Asn Trp
                325                 330                 335

Gly Pro Asp Gln Gln Lys Ala Tyr Gln Glu Ile Lys Gln Ala Leu Leu
            340                 345                 350

Thr Ala Pro Ala Leu Gly Leu Pro Asp Leu Thr Lys Pro Phe Glu Leu
        355                 360                 365

Phe Val Asp Glu Lys Gln Gly Tyr Ala Lys Gly Val Leu Thr Gln Lys
370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
            420                 425                 430

Val Ile Leu Ala Pro His Ala Val Glu Ala Leu Val Lys Gln Pro Pro
        435                 440                 445

Asp Arg Trp Leu Ser Asn Ala Arg Met Thr His Tyr Gln Ala Leu Leu
        450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
            500                 505                 510

Pro Leu Pro Asp Ala Asp His Thr Trp Tyr Thr Asp Gly Ser Ser Leu
        515                 520                 525

Leu Gln Glu Gly Gln Arg Lys Ala Gly Ala Ala Val Thr Thr Glu Thr
        530                 535                 540

Glu Val Ile Trp Ala Lys Ala Leu Pro Ala Gly Thr Ser Ala Gln Arg
545                 550                 555                 560
```

```
Ala Glu Leu Ile Ala Leu Thr Gln Ala Leu Lys Met Ala Glu Gly Lys
            565                 570                 575

Lys Leu Asn Val Tyr Thr Asp Ser Arg Tyr Ala Phe Ala Thr Ala His
        580                 585                 590

Ile His Gly Glu Ile Tyr Arg Arg Gly Trp Leu Thr Ser Glu Gly
    595                 600                 605

Lys Glu Ile Lys Asn Lys Asp Glu Ile Leu Ala Leu Leu Lys Ala Leu
610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
            645                 650                 655

Arg Lys Ala Ala Ile Thr Glu Thr Pro Asp Thr Ser Thr Leu Leu Ile
            660                 665                 670

Glu Asn Ser Ser Pro Ser Gly Gly Ser Lys Arg Thr Ala Asp Gly Ser
            675                 680                 685

Glu Phe Glu Pro Lys Lys Lys Arg Lys Val
    690                 695

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
tctgtatcta tattcatcat                                                 20

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
accattaaag aaaatatcat                                                 20

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
ggagaactgg agccttcaga                                                 20

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
gaaggtggaa tcacactgag                                                 20
```

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
cttgctcgtt gacctccact                                              20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
gtttgcagag aaagacaata                                              20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
aggacatctc caagtttgca                                              20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
cacctgtggt atcactccaa                                              20

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
caataacttt gcaacagtga                                              20

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
gaaggagaaa tccagatcga                                              20

```
<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
ggtgtcacac tgaagtcctt                                                   20

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
aattctgcaa tcctcactct                                                   20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
aggcacctcc agcccagcag                                                   20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
gcagagtacc cacctctcca                                                   20

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
tcttgtagaa gaaagtacca                                                   20

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
aagaaagtac caaggaagtg                                                   20

<210> SEQ ID NO 112
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
ttggtgactg ccacgcccaa                                                     20

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
tctggctgtg gtggggactg                                                     20

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
ctctttgtgt tcattgccct                                                     20

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
ttgccaagtg ttccagccac                                                     20

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
agtccctcaa gtccttccag                                                     20

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
gaccctggaa aagctgatga                                                     20

<210> SEQ ID NO 118
<211> LENGTH: 20
```

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
ggcggctgag gaagctgagg                                              20

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
ggcggcggct gaggaagctg                                              20

<210> SEQ ID NO 120
<211> LENGTH: 57
<212> TYPE: DNA
<213> ORGANISM: Unknown
<220> FEATURE:
<223> OTHER INFORMATION: Description of Unknown:
      Reference sequence

<400> SEQUENCE: 120
ctctgggcag tgtgagtgca aaaagaagc caaaggactt cagtgtgaca cctgcag      57

<210> SEQ ID NO 121
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
ctctgggcag tgcgagtgca aaaagaagc aaaggactt cagtgtgaca cctgcag       57

<210> SEQ ID NO 122
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
ctctgggcag tgtgagtgca aaaagaagc aaaggactt cagtgtgaca cctgcag       57

<210> SEQ ID NO 123
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
ctctgggcag tgcgagtgca aaaagaagc caaaggactt cagtgtgaca cctgcag      57

<210> SEQ ID NO 124
<211> LENGTH: 58
<212> TYPE: DNA

-continued

```
<213> ORGANISM: Artificial Sequence
<220> FEATURE:
<223> OTHER INFORMATION: Description of Artificial Sequence: Synthetic
      oligonucleotide

<400> SEQUENCE: 124
ctctgggcag tgcgagtgca aaaaagaagc aaaaaggact tcagtgtgac acctgcag      58

<210> SEQ ID NO 125
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
ctctgggcag tgcgagtgca aaaaagaag caaaaggact tcagtgtgac acctgcag       58

<210> SEQ ID NO 126
<211> LENGTH: 57
<212> TYPE: DNA
<213> ORGANISM: Unknown
<220> FEATURE:
<223> OTHER INFORMATION: Description of Unknown:
      Reference sequence

<400> SEQUENCE: 126
ctctgggcag tgtgagtgca aaaagaagc caaaggactt cagtgtgaca cctgcag        57

<210> SEQ ID NO 127
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
ctctgggcag tgcgagtgca aaaagaagc aaaaggactt cagtgtgaca cctgcag        57

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
ggtgtcacac tgaagtcctt                                                20

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
aattctgcaa tcctcactct                                                20

<210> SEQ ID NO 130
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 130
gaaggtggaa tcacactgag                                                    20

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
aagaaagtac caaggaagtg                                                    20

<210> SEQ ID NO 132
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
aggcacctcc agcccagcag                                                    20

<210> SEQ ID NO 133
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
gcagagtacc cacctctcca                                                    20

<210> SEQ ID NO 134
<211> LENGTH: 57
<212> TYPE: DNA
<213> ORGANISM: Unknown
<220> FEATURE:
<223> OTHER INFORMATION: Description of Unknown:
      Reference sequence

<400> SEQUENCE: 134
ctctgggcag tgtgagtgca aaaagaagc caaaggactt cagtgtgaca cctgcag            57

<210> SEQ ID NO 135
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
ctctgggcag tgcgagtgca aaaagaagc aaaag                                    35

<210> SEQ ID NO 136
<211> LENGTH: 35
<212> TYPE: DNA
<213> ORGANISM: Artificial Sequence
<220> FEATURE:
```

<223> OTHER INFORMATION: Description of Artificial Sequence: Synthetic
    oligonucleotide

<400> SEQUENCE: 136
ctctgggcag tgcgagtgca agaaagaagc aaaag                                    35

<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 137
agtccctcaa gtccttccag                                                     20

<210> SEQ ID NO 138
<211> LENGTH: 1386
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 138

```
Met Lys Arg Thr Ala Asp Gly Ser Glu Phe Glu Ser Pro Lys Lys Lys
1               5                   10                  15

Arg Lys Val Asp Lys Lys Tyr Ser Ile Gly Leu Asp Ile Gly Thr Asn
            20                  25                  30

Ser Val Gly Trp Ala Val Ile Thr Asp Glu Tyr Lys Val Pro Ser Lys
        35                  40                  45

Lys Phe Lys Val Leu Gly Asn Thr Asp Arg His Ser Ile Lys Lys Asn
    50                  55                  60

Leu Ile Gly Ala Leu Leu Phe Asp Ser Gly Glu Thr Ala Glu Ala Thr
65                  70                  75                  80

Arg Leu Lys Arg Thr Ala Arg Arg Arg Tyr Thr Arg Arg Lys Asn Arg
                85                  90                  95

Ile Cys Tyr Leu Gln Glu Ile Phe Ser Asn Glu Met Ala Lys Val Asp
            100                 105                 110

Asp Ser Phe Phe His Arg Leu Glu Glu Ser Phe Leu Val Glu Glu Asp
        115                 120                 125

Lys Lys His Glu Arg His Pro Ile Phe Gly Asn Ile Val Asp Glu Val
    130                 135                 140

Ala Tyr His Glu Lys Tyr Pro Thr Ile Tyr His Leu Arg Lys Lys Leu
145                 150                 155                 160

Val Asp Ser Thr Asp Lys Ala Asp Leu Arg Leu Ile Tyr Leu Ala Leu
                165                 170                 175

Ala His Met Ile Lys Phe Arg Gly His Phe Leu Ile Glu Gly Asp Leu
            180                 185                 190

Asn Pro Asp Asn Ser Asp Val Asp Lys Leu Phe Ile Gln Leu Val Gln
        195                 200                 205

Thr Tyr Asn Gln Leu Phe Glu Glu Asn Pro Ile Asn Ala Ser Gly Val
    210                 215                 220

Asp Ala Lys Ala Ile Leu Ser Ala Arg Leu Ser Lys Ser Arg Arg Leu
225                 230                 235                 240

Glu Asn Leu Ile Ala Gln Leu Pro Gly Glu Lys Lys Asn Gly Leu Phe
                245                 250                 255
```

```
Gly Asn Leu Ile Ala Leu Ser Leu Gly Leu Thr Pro Asn Phe Lys Ser
            260                 265                 270

Asn Phe Asp Leu Ala Glu Asp Ala Lys Leu Gln Leu Ser Lys Asp Thr
        275                 280                 285

Tyr Asp Asp Asp Leu Asp Asn Leu Leu Ala Gln Ile Gly Asp Gln Tyr
    290                 295                 300

Ala Asp Leu Phe Leu Ala Ala Lys Asn Leu Ser Asp Ala Ile Leu Leu
305                 310                 315                 320

Ser Asp Ile Leu Arg Val Asn Thr Glu Ile Thr Lys Ala Pro Leu Ser
                325                 330                 335

Ala Ser Met Ile Lys Arg Tyr Asp Glu His His Gln Asp Leu Thr Leu
            340                 345                 350

Leu Lys Ala Leu Val Arg Gln Gln Leu Pro Glu Lys Tyr Lys Glu Ile
        355                 360                 365

Phe Phe Asp Gln Ser Lys Asn Gly Tyr Ala Gly Tyr Ile Asp Gly Gly
    370                 375                 380

Ala Ser Gln Glu Glu Phe Tyr Lys Phe Ile Lys Pro Ile Leu Glu Lys
385                 390                 395                 400

Met Asp Gly Thr Glu Glu Leu Leu Val Lys Leu Asn Arg Glu Asp Leu
                405                 410                 415

Leu Arg Lys Gln Arg Thr Phe Asp Asn Gly Ser Ile Pro His Gln Ile
            420                 425                 430

His Leu Gly Glu Leu His Ala Ile Leu Arg Arg Gln Glu Asp Phe Tyr
        435                 440                 445

Pro Phe Leu Lys Asp Asn Arg Glu Lys Ile Glu Lys Ile Leu Thr Phe
    450                 455                 460

Arg Ile Pro Tyr Tyr Val Gly Pro Leu Ala Arg Gly Asn Ser Arg Phe
465                 470                 475                 480

Ala Trp Met Thr Arg Lys Ser Glu Glu Thr Ile Thr Pro Trp Asn Phe
                485                 490                 495

Glu Glu Val Val Asp Lys Gly Ala Ser Ala Gln Ser Phe Ile Glu Arg
            500                 505                 510

Met Thr Asn Phe Asp Lys Asn Leu Pro Asn Glu Lys Val Leu Pro Lys
        515                 520                 525

His Ser Leu Leu Tyr Glu Tyr Phe Thr Val Tyr Asn Glu Leu Thr Lys
    530                 535                 540

Val Lys Tyr Val Thr Glu Gly Met Arg Lys Pro Ala Phe Leu Ser Gly
545                 550                 555                 560

Glu Gln Lys Lys Ala Ile Val Asp Leu Leu Phe Lys Thr Asn Arg Lys
                565                 570                 575

Val Thr Val Lys Gln Leu Lys Glu Asp Tyr Phe Lys Lys Ile Glu Cys
            580                 585                 590

Phe Asp Ser Val Glu Ile Ser Gly Val Glu Asp Arg Phe Asn Ala Ser
        595                 600                 605

Leu Gly Thr Tyr His Asp Leu Leu Lys Ile Ile Lys Asp Lys Asp Phe
    610                 615                 620

Leu Asp Asn Glu Glu Asn Glu Asp Ile Leu Glu Asp Ile Val Leu Thr
625                 630                 635                 640

Leu Thr Leu Phe Glu Asp Arg Glu Met Ile Glu Glu Arg Leu Lys Thr
                645                 650                 655

Tyr Ala His Leu Phe Asp Asp Lys Val Met Lys Gln Leu Lys Arg Arg
            660                 665                 670

Arg Tyr Thr Gly Trp Gly Arg Leu Ser Arg Lys Leu Ile Asn Gly Ile
```

-continued

```
                675                 680                 685
Arg Asp Lys Gln Ser Gly Lys Thr Ile Leu Asp Phe Leu Lys Ser Asp
690                 695                 700
Gly Phe Ala Asn Arg Asn Phe Met Gln Leu Ile His Asp Asp Ser Leu
705                 710                 715                 720
Thr Phe Lys Glu Asp Ile Gln Lys Ala Gln Val Ser Gly Gln Gly Asp
                725                 730                 735
Ser Leu His Glu His Ile Ala Asn Leu Ala Gly Ser Pro Ala Ile Lys
                740                 745                 750
Lys Gly Ile Leu Gln Thr Val Lys Val Val Asp Glu Leu Val Lys Val
                755                 760                 765
Met Gly Arg His Lys Pro Glu Asn Ile Val Ile Glu Met Ala Arg Glu
                770                 775                 780
Asn Gln Thr Thr Gln Lys Gly Gln Lys Asn Ser Arg Glu Arg Met Lys
785                 790                 795                 800
Arg Ile Glu Glu Gly Ile Lys Glu Leu Gly Ser Gln Ile Leu Lys Glu
                805                 810                 815
His Pro Val Glu Asn Thr Gln Leu Gln Asn Glu Lys Leu Tyr Leu Tyr
                820                 825                 830
Tyr Leu Gln Asn Gly Arg Asp Met Tyr Val Asp Gln Glu Leu Asp Ile
                835                 840                 845
Asn Arg Leu Ser Asp Tyr Asp Val Asp Ala Ile Val Pro Gln Ser Phe
850                 855                 860
Leu Lys Asp Asp Ser Ile Asp Asn Lys Val Leu Thr Arg Ser Asp Lys
865                 870                 875                 880
Asn Arg Gly Lys Ser Asp Asn Val Pro Ser Glu Glu Val Val Lys Lys
                885                 890                 895
Met Lys Asn Tyr Trp Arg Gln Leu Leu Asn Ala Lys Leu Ile Thr Gln
                900                 905                 910
Arg Lys Phe Asp Asn Leu Thr Lys Ala Glu Arg Gly Gly Leu Ser Glu
                915                 920                 925
Leu Asp Lys Ala Gly Phe Ile Lys Arg Gln Leu Val Glu Thr Arg Gln
                930                 935                 940
Ile Thr Lys His Val Ala Gln Ile Leu Asp Ser Arg Met Asn Thr Lys
945                 950                 955                 960
Tyr Asp Glu Asn Asp Lys Leu Ile Arg Glu Val Lys Val Ile Thr Leu
                965                 970                 975
Lys Ser Lys Leu Val Ser Asp Phe Arg Lys Asp Phe Gln Phe Tyr Lys
                980                 985                 990
Val Arg Glu Ile Asn Asn Tyr His His Ala His Asp Ala Tyr Leu Asn
                995                 1000                1005
Ala Val Val Gly Thr Ala Leu Ile Lys Lys Tyr Pro Lys Leu Glu
                1010                1015                1020
Ser Glu Phe Val Tyr Gly Asp Tyr Lys Val Tyr Asp Val Arg Lys
                1025                1030                1035
Met Ile Ala Lys Ser Glu Gln Glu Ile Gly Lys Ala Thr Ala Lys
                1040                1045                1050
Tyr Phe Phe Tyr Ser Asn Ile Met Asn Phe Phe Lys Thr Glu Ile
                1055                1060                1065
Thr Leu Ala Asn Gly Glu Ile Arg Lys Arg Pro Leu Ile Glu Thr
                1070                1075                1080
Asn Gly Glu Thr Gly Glu Ile Val Trp Asp Lys Gly Arg Asp Phe
                1085                1090                1095
```

-continued

```
Ala Thr Val Arg Lys Val Leu Ser Met Pro Gln Val Asn Ile Val
    1100            1105                1110
Lys Lys Thr Glu Val Gln Thr Gly Gly Phe Ser Lys Glu Ser Ile
    1115            1120                1125
Leu Pro Lys Arg Asn Ser Asp Lys Leu Ile Ala Arg Lys Lys Asp
    1130            1135                1140
Trp Asp Pro Lys Lys Tyr Gly Gly Phe Asp Ser Pro Thr Val Ala
    1145            1150                1155
Tyr Ser Val Leu Val Val Ala Lys Val Glu Lys Gly Lys Ser Lys
    1160            1165                1170
Lys Leu Lys Ser Val Lys Glu Leu Leu Gly Ile Thr Ile Met Glu
    1175            1180                1185
Arg Ser Ser Phe Glu Lys Asn Pro Ile Asp Phe Leu Glu Ala Lys
    1190            1195                1200
Gly Tyr Lys Glu Val Lys Lys Asp Leu Ile Ile Lys Leu Pro Lys
    1205            1210                1215
Tyr Ser Leu Phe Glu Leu Glu Asn Gly Arg Lys Arg Met Leu Ala
    1220            1225                1230
Ser Ala Gly Glu Leu Gln Lys Gly Asn Glu Leu Ala Leu Pro Ser
    1235            1240                1245
Lys Tyr Val Asn Phe Leu Tyr Leu Ala Ser His Tyr Glu Lys Leu
    1250            1255                1260
Lys Gly Ser Pro Glu Asp Asn Glu Gln Lys Gln Leu Phe Val Glu
    1265            1270                1275
Gln His Lys His Tyr Leu Asp Glu Ile Ile Glu Gln Ile Ser Glu
    1280            1285                1290
Phe Ser Lys Arg Val Ile Leu Ala Asp Ala Asn Leu Asp Lys Val
    1295            1300                1305
Leu Ser Ala Tyr Asn Lys His Arg Asp Lys Pro Ile Arg Glu Gln
    1310            1315                1320
Ala Glu Asn Ile Ile His Leu Phe Thr Leu Thr Asn Leu Gly Ala
    1325            1330                1335
Pro Ala Ala Phe Lys Tyr Phe Asp Thr Thr Ile Asp Arg Lys Arg
    1340            1345                1350
Tyr Thr Ser Thr Lys Glu Val Leu Asp Ala Thr Leu Ile His Gln
    1355            1360                1365
Ser Ile Thr Gly Leu Tyr Glu Thr Arg Ile Asp Leu Ser Gln Leu
    1370            1375                1380
Gly Gly Asp
    1385
```

<210> SEQ ID NO 139
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
gtttaagagc tatgctggaa acagcatagc aagtttaaat aaggctagtc cgttatcaac    60
ttgaaaaagt ggcaccgagt cggtgc                                         86

<210> SEQ ID NO 140
<211> LENGTH: 113

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 140
agcggctgtg cctgcggcgg cggctgagga agctgaggag gcggcggcgg cggcggcggc      60
ggtggcggct gttgctgttg ctgctgttgc tggaaggact tgagggatt ttt             113

<210> SEQ ID NO 141
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 141
agcggctgtg cctgcggcgg cggctgagga agctgaggag gcggcggcgg cggcggcggc      60
ggtggcggct gttgctgttg ctgctgttgc tggaaggact tgagggaccg ccgcaggcac     120
agccgctttt ttt                                                        133

<210> SEQ ID NO 142
<211> LENGTH: 4570
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 142
gacattgatt attgactagt tattaatagt aatcaattac ggggtcatta gttcatagcc      60
catatatgga gttccgcgtt acataactta cggtaaatgg cccgcctggc tgaccgccca     120
acgaccccg cccattgacg tcaataatga cgtatgttcc catagtaacg ccaatagga      180
ctttccattg acgtcaatgg gtggagtatt tacggtaaac tgcccacttg gcagtacatc     240
aagtgtatca tatgccaagt acgcccccta ttgacgtcaa tgacggtaaa tggcccgcct     300
ggcattatgc ccagtacatg accttatggg actttcctac ttggcagtac atctacgtat     360
tagtcatcgc tattaccatg gtgatgcggt tttggcagta catcaatggg cgtggatagc     420
ggtttgactc acggggattt ccaagtctcc accccattga cgtcaatggg agtttgtttt     480
ggcaccaaaa tcaacgggac tttccaaaat gtcgtaacaa ctccgcccca ttgacgcaaa     540
tgggcggtag gcgtgtacgg tgggaggtct atataagcag agctctctgg ctaactaccg     600
gtgccaccat gaaacggaca gccgacgaaa gcgagttcga gtcaccaaag aagaagcgga     660
aagtcgacaa gaagtacagc atcggcctgg acatcggcac caactctgtg ggctgggccg     720
tgatcaccga cgagtacaag gtgcccagca gaaattcaa ggtgctgggc aacaccgacc     780
ggcacagcat caagaagaac ctgatcggag ccctgctgtt cgacagcggc gaaacagccg     840
aggccacccg gctgaagaga accgccagaa gaagatacac cagacggaag aaccggatct     900
gctatctgca agagatcttc agcaacgaga tggccaaggt ggacgacagc ttcttccaca     960
gactggaaga gtccttcctg gtggaagagg ataagaagca cgagcggcac cccatcttcg    1020
gcaacatcgt ggacgaggtg gcctaccacg agaagtaccc caccatctac cacctgagaa    1080
agaaactggt ggacagcacc gacaaggccg acctgcggct gatctatctg gccctggccc    1140
acatgatcaa gttccggggc cacttcctga tcgagggcga cctgaacccc gacaacagcg    1200

-continued

```
acgtggacaa gctgttcatc cagctggtgc agacctacaa ccagctgttc gaggaaaacc    1260
ccatcaacgc cagcggcgtg gacgccaagg ccatcctgtc tgccagactg agcaagagca    1320
gacggctgga aaatctgatc gcccagctgc ccggcgagaa gaagaatggc ctgttcggaa    1380
acctgattgc cctgagcctg ggcctgaccc ccaacttcaa gagcaacttc gacctggccg    1440
aggatgccaa actgcagctg agcaaggaca cctacgacga cgacctggac aacctgctgg    1500
cccagatcgg cgaccagtac gccgacctgt ttctggccgc caagaacctg tccgacgcca    1560
tcctgctgag cgacatcctg agagtgaaca ccgagatcac caaggccccc ctgagcgcct    1620
ctatgatcaa gagatacgac gagcaccacc aggacctgac cctgctgaaa gctctcgtgc    1680
ggcagcagct gcctgagaag tacaaagaga ttttcttcga ccagagcaag aacggctacg    1740
ccggctacat tgacggcgga gccagccagg aagagttcta caagttcatc aagcccatcc    1800
tggaaaagat ggacggcacc gaggaactgc tcgtgaagct gaacagagag gacctgctgc    1860
ggaagcagcg gaccttcgac aacggcagca tccccaccca gatccacctg ggagagctgc    1920
acgccattct gcggcggcag gaagattttt acccattcct gaaggacaac cgggaaaaga    1980
tcgagaagat cctgaccttc cgcatcccct actacgtggg ccctctggcc aggggaaaca    2040
gcagattcgc ctggatgacc agaaagagcg aggaaaccat cacccctgg aacttcgagg    2100 aagtggtgga caagggcgct tccgcccaga gcttcatcga gcggatgacc aacttcgata    2160
agaacctgcc caacgagaag gtgctgccca gcacagcct gctgtacgag tacttcaccg    2220
tgtataacga gctgaccaaa gtgaaatacg tgaccgaggg aatgagaaag cccgccttcc    2280
tgagcggcga gcagaaaaag gccatcgtgg acctgctgtt caagaccaac cggaaagtga    2340
ccgtgaagca gctgaaagag gactacttca gaaaatcga gtgcttcgac tccgtggaaa    2400
tctccggcgt ggaagatcgg ttcaacgcct ccctgggcac ataccacgat ctgctgaaaa    2460
ttatcaagga caaggacttc ctggacaatg aggaaacga ggacattctg gaagatatcg    2520 tgctgacccct gacactgttt gaggacagag agatgatcga ggaacggctg aaaacctatg    2580
cccacctgtt cgacgacaaa gtgatgaagc agctgaagcg gcggagatac accggctggg    2640
gcaggctgag ccggaagctg atcaacggca tccgggacaa gcagtccggc aagacaatcc    2700
tggatttcct gaagtccgac ggcttcgcca acagaaactt catgcagctg atccacgacg    2760
acagcctgac ctttaaagag gacatccaga agcccaggt gtccggccag ggcgatagcc    2820
tgcacgagca cattgccaat ctggccggca gccccgccat taagaagggc atcctgcaga    2880
cagtgaaggt ggtggacgag ctcgtgaaag tgatgggccg gcacaagccc gagaacatcg    2940
tgatcgaaat ggccagagag aaccagacca cccagaaggg acagaagaac agccgcgaga    3000
gaatgaagcg gatcgaagag ggcatcaaag agctgggcag ccagatcctg aaagaacacc    3060
ccgtggaaaa cacccagctg cagaacgaga agctgtacct gtactacctg cagaatgggc    3120
gggatatgta cgtggaccag gaactggaca tcaaccggct gtccgactac gatgtggacg    3180
ctatcgtgcc tcagagcttt ctgaaggacg actccatcga caacaaggtg ctgaccagaa    3240
gcgacaagaa ccggggcaag agcgacaacg tgccctccga agaggtcgtg aagaagatga    3300
agaactactg gcggcagctg ctgaacgcca agctgattac cagagaaag ttcgacaatc    3360 tgaccaaggc cgagagaggc ggcctgagcg aactggataa ggccggcttc atcaagagac    3420
agctggtgga aacccggcag atcacaaagc acgtggcaca gatcctggac tcccggatga    3480
acactaagta cgacgagaat gacaagctga tccgggaagt gaaagtgatc accctgaagt    3540
```

```
ccaagctggt gtccgatttc cggaaggatt tccagtttta caaagtgcgc gagatcaaca    3600
actaccacca cgcccacgac gcctacctga acgccgtcgt gggaaccgcc ctgatcaaaa    3660
agtaccctaa gctggaaagc gagttcgtgt acggcgacta caaggtgtac gacgtgcgga    3720
agatgatcgc caagagcgag caggaaatcg gcaaggctac cgccaagtac ttcttctaca    3780
gcaacatcat gaacttttc aagaccgaga ttaccctggc caacggcgag atccggaagc    3840
ggcctctgat cgagacaaac ggcgaaaccg gggagatcgt gtgggataag gcccgggatt    3900
ttgccaccgt gcggaaagtg ctgagcatgc cccaagtgaa tatcgtgaaa aagaccgagg    3960
tgcagacagg cggcttcagc aaagagtcta tcctgcccaa gaggaacagc gataagctga    4020
tcgccagaaa gaaggactgg gaccctaaga agtacggcgg cttcgacagc cccaccgtgg    4080
cctattctgt gctggtggtg gccaaagtgg aaaagggcaa gtccaagaaa ctgaagagtg    4140
tgaaagagct gctgggatc accatcatgg aaagaagctg cctgtcctac gagacagaga    4200
tcctgacagt ggagtatggc ctgctgccaa tcggcaagat cgtggagaag aggatcgagt    4260
gtaccgtgta ctctgtggat aacaatggca acatctatac acagcccgtg gcacagtggc    4320 acgataggg agagcaggag gtgttcgagt attgcctgga ggacggcagc ctgatcaggg    4380
caaccaagga ccacaagttc atgacagtgg atggccagat gctgcccatc gacgagattt    4440
tcgagcggga gctggacctg atgagagtgg ataacctgcc taatccagct gcgaaaagag    4500
tgaaactcga ttaataagaa ttcaataaaa gatctttatt tcattagat ctgtgtgttg    4560 gttttttgtg                                                            4570
```

<210> SEQ ID NO 143  
<211> LENGTH: 4483  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 143

```
gacattgatt attgactagt tattaatagt aatcaattac ggggtcatta gttcatagcc      60
catatatgga gttccgcgtt acataactta cggtaaatgg cccgcctggc tgaccgccca    120 acgaccccg cccattgacg tcaataatga cgtatgttcc catagtaacg ccaatagga    180 ctttccattg acgtcaatgg gtggagtatt tacggtaaac tgcccacttg gcagtacatc    240
aagtgtatca tatgccaagt acgccccta ttgacgtcaa tgacggtaaa tggcccgcct    300
ggcattatgc ccagtacatg accttatggg actttcctac ttggcagtac atctacgtat    360
tagtcatcgc tattaccatg gtgatgcggt tttggcagta catcaatggg cgtggatagc    420
ggtttgactc acggggattt ccaagtctcc accccattga cgtcaatggg agtttgtttt    480
ggcaccaaaa tcaacgggac tttccaaaat gtcgtaacaa ctccgcccca ttgacgcaaa    540
tgggcggtag gcgtgtacgg tgggaggtct atataagcag agctggttta gtgaaccgtc    600
agatccgcta gagatccgcg ccgctaata cgactcacta tagggagagc cgccaccatg    660
atcaagattg ctacacggaa atacctggga aagcagaacg tgtacgacat cggcgtggag    720
cgggatcaca acttcgccct gaagaatggc tttatcgcca gcaattgttt cgagaagaat    780
cccatcgact ttctggaagc caagggctac aaagaagtga aaaggacct gatcatcaag    840 ctgcctaagt actccctgtt cgagctggaa acggccgga agagaatgct ggcctctgcc    900
ggcgaactgc agaagggaaa cgaactggcc ctgccctcca aatatgtgaa cttcctgtac    960
```

```
ctggccagcc actatgagaa gctgaagggc tcccccgagg ataatgagca gaaacagctg    1020
tttgtggaac agcacaagca ctacctggac gagatcatcg agcagatcag cgagttctcc    1080
aagagagtga tcctggccga cgctaatctg acaaagtgc tgtccgccta caacaagcac    1140
cgggataagc ccatcagaga gcaggccgag aatatcatcc acctgtttac cctgaccaat    1200
ctgggagccc ctgccgcctt caagtacttt gacaccacca tcgaccggaa gaggtacacc    1260
agcaccaaag aggtgctgga cgccacccctg atccaccaga gcatcaccgg cctgtacgag    1320
acacggatcg acctgtctca gctgggaggt gacggcagcg agacaccagg aacaagcgag    1380
tcagcaacac cagagagcag tggcggcagc agcggcggca gcagcaccct aaatatagaa    1440
gatgagtatc ggctacatga gacctcaaaa gagccagatg tttctctagg gtccacatgg    1500
ctgtctgatt ttcctcaggc ctgggcgaaa accgggggca tgggactggc agttcgccaa    1560
gctcctctga tcatactcct gaaagcaacc tctaccccccg tgtccataaa acaataccccc    1620 atgcgccaag aagccagact ggggatcaag ccccacatac agagactgtt ggaccaggga    1680
atactggtac cctgccagtc cccctggaac acgcccctgc tacccgttaa gaaaccaggg    1740
actaatgatt ataggcctgt ccaggatctg agagaagtca caagcgggt ggaagacatc    1800 cacccccaccg tgcccaaccc ttacaacctc ttgagcgggc tcccaccgtc ccaccagtgg    1860
tacactgtgc ttgatttaaa ggatgccttt ttctgcctga actccacccc caccagtcag    1920
cctctcttcg cctttgagtg gagagatcca gagatgggaa tctcaggaca attgacctgg    1980
accagactcc cacagggttt caaaaacagt cccgctctgt ttaatgaggc actgcggaga    2040
gacctagcag acttccggat ccagcaccca gacttgatcc tgctacagta cgtggatgac    2100
ttactgctgg ccgccacttc tgagctagac tgccaacaag gtactcgggc cctgttacaa    2160
accctaggga acctcgggta tcgggcctcg gccaagaaag cccaaatttg ccagaaacag    2220
gtcaagtatc tggggtatct tctaaaagag ggtcagagat ggctgactga ggccagaaaa    2280
gagactgtga tggggcagcc tactccgaag acccctcgac aactaaggga gttcctaggg    2340
aaggcaggct tctgtcgcct cttcatccct gggtttgcag aaatggcagc cccccctgtac    2400 cctctcacca aaccggggac tctgtttaat tggggcccag accaacaaaa ggcctatcaa    2460
gaaatcaagc aagctcttct aactgcccca gccctggggt tgccagattt gactaagccc    2520
tttgaactct ttgtcgacga aagcagggc tacgccaaag tgtcctaac gcaaaaactg    2580 ggaccttggc gtcggccggt ggcctacctg tccaaaaagc tagacccagt agcagctggg    2640 tggcccccctt gcctacggat ggtagcagcc attgccgtac tgacaaagga tgcaggcaag    2700
ctaaccatgg gacagccact agtcattggc gccccccatg cagtagaggc actagtcaaa    2760
caaccccccg accgctggct ttccaacgcc cggatgactc actatcaggc cttgcttttg    2820
gacacggacc gggtccagtt cggaccggtg gtagccctga acccggctac gctgctccca    2880
ctgcctgagg aagggctgca acacaactgc cttgatatcc tggccgaagc ccacggaacc    2940
cgacccgacc taacgaccaa gccgctccca gacgccgacc acacctggta cacggccgga    3000
agcagtctct acaagagggg acagcgtaag gcgggagctg cggtgaccac cgagaccgag    3060
gtaatctggg ctaaagccct gccagccggg acatccgctc agcggctga actgataagca    3120 ctcacccagg ccctaaagat ggcagaaggt aagaagctaa atgtttatac tgatagccgt    3180
tatgcttttg ctactgccca tatccatgga gaaatataca gaaggcgtgg gtggctcaca    3240
tcagaaggca aagagatcaa aaataaagac gagatcttgg ccctactaaa agccctcttt    3300
ctgcccaaaa gacttagcat aatccattgt ccaggacatc aaaagggaca cagcgccgag    3360
```

```
gctagaggca accggatggc taaccaagcg gcccgaaagg cagccatcac agagaaccca    3420
gacacctcta ccctccccat agaaaattca tcaccctctg gcggctcaaa aagaaccgcc    3480
gacggcagcg aattcgagcc caagaagaag aggaaagtcg gaagcggagg atccggcgca    3540
acaaacttct ctctgctgaa acaagccgga gatgtcgaag agaatcctgg accgggaagc    3600
ggaatggccg atccacgaga aatcatccca cctggaaaca gtggagagga gacagttggt    3660
gaagccttcg catggctgga aagaacggtt gaggctatta atcgagaagc ggtcaatcac    3720
ttgccgcgcg aactcatctt tcaagtgtgg caacgatcct ggcggtattg gcacgacgaa    3780
caaggcatga gttctagtta tacaaaatac agatatctct gtctcatgca gaaagccatg    3840
tttatccact tcaccagagg ctgcacatgt ctcggggcg gacacggacc aggtggatgg     3900
ggccctggac caccacctcc tccaccacct ggacttgttt aagaattcaa taaaagatct    3960
ttattttcat tagatctgtg tgttggtttt ttgtgaacca aaaaaaaaat tctgcaatcc    4020
tcactctgtc acactgaagt cctttttgctt cttttttgca ctcgcactgc ccagagtgag   4080
gattgcagaa tttgcaccga ctcggtgcca cttttcaag ttgataacgg actagcctta    4140
tttaaacttg ctatgctgtt tccagcatag ctcttaaaca aggacttcag tgtgacaccg    4200
gtgtttcgtc ctttccacaa gatatataaa gccaagaaat cgaaatactt tcaagttacg    4260
gtaagcatat gatagtccat tttaaaacat aattttaaaa ctgcaaacta cccaagaaat    4320
tattactttc tacgtcacgt attttgtact aatatctttg tgtttacagt caaattaatt    4380
ctaattatct ctctaacagc cttgtatcgt atatgcaaat atgaaggaat catgggaaat    4440
aggccctctt cctgcccgac cttggtaccg gatccagtcg act                      4483

<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
caccctcgtg accaccctga                                                   20
```